United States Patent
Mihara et al.

(10) Patent No.: US 9,375,000 B2
(45) Date of Patent: Jun. 28, 2016

(54) PESTICIDAL ARYLPYRROLIDINES

(75) Inventors: Jun Mihara, Osaka (JP); Mamoru Hatazawa, Ibaraki (JP); Daiei Yamazaki, Yamaguchi (JP); Hidetoshi Kishikawa, Shiga (JP); Kei Domon, Shizuoka (JP); Hidekazu Watanabe, Tokyo (JP); Norio Sasaki, Ibaraki (JP); Tetsuya Murata, Osaka (JP); Koichi Araki, Ibaraki (JP); Eiichi Shimojo, Osaka (JP); Teruyuki Ichihara, Tochigi (JP); Tadashi Ishikawa, Kanagawa (JP); Katsuhiko Shibuya, Shimotsuke (JP); Ulrich Görgens, Ratingen (DE); Peter Bruechner, Düsseldorf (DE); Reiner Fischer, Monheim (DE); Johannes-Rudolf Jansen, Monheim (DE); Tobias Kapferer, Düsseldorf (DE); Simon Maechling, Lyons (DE); Michael Maue, Langenfeld (DE); Arnd Voerste, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 21 days.

(21) Appl. No.: 13/818,291

(22) PCT Filed: Sep. 13, 2011

(86) PCT No.: PCT/EP2011/065849
§ 371 (c)(1),
(2), (4) Date: Oct. 8, 2013

(87) PCT Pub. No.: WO2012/035011
PCT Pub. Date: Mar. 22, 2012

(65) Prior Publication Data
US 2014/0046069 A1    Feb. 13, 2014

(51) Int. Cl.
| | | |
|---|---|---|
| *C07D 207/08* | (2006.01) |
| *A01N 43/36* | (2006.01) |
| *C07D 207/12* | (2006.01) |
| *C07D 207/26* | (2006.01) |
| *C07D 401/04* | (2006.01) |
| *C07D 403/04* | (2006.01) |
| *C07D 403/10* | (2006.01) |
| *C07D 403/14* | (2006.01) |
| *C07D 409/12* | (2006.01) |
| *C07D 409/14* | (2006.01) |
| *C07D 417/04* | (2006.01) |
| *A01N 43/40* | (2006.01) |
| *A01N 43/56* | (2006.01) |
| *A01N 43/653* | (2006.01) |
| *A01N 43/713* | (2006.01) |

(52) U.S. Cl.
CPC ........... *A01N 43/36* (2013.01); *A01N 43/40* (2013.01); *A01N 43/56* (2013.01); *A01N 43/653* (2013.01); *A01N 43/713* (2013.01); *C07D 207/12* (2013.01); *C07D 207/26* (2013.01); *C07D 401/04* (2013.01); *C07D 403/04* (2013.01); *C07D 403/10* (2013.01); *C07D 403/14* (2013.01); *C07D 409/12* (2013.01); *C07D 409/14* (2013.01); *C07D 417/04* (2013.01)

(58) Field of Classification Search
CPC .................................................... C07D 207/08
USPC .......................................... 548/568; 514/428
See application file for complete search history.

(56) References Cited

U.S. PATENT DOCUMENTS

| | | | |
|---|---|---|---|
| 5,084,082 | A | 1/1992 | Sebastian |
| 5,187,185 | A | 2/1993 | Outcalt et al. |
| 5,198,599 | A | 3/1993 | Thill |
| 5,773,702 | A | 6/1998 | Penner et al. |
| 6,245,968 | B1 | 6/2001 | Boudec et al. |
| 6,268,549 | B1 | 7/2001 | Sailland et al. |
| 6,768,044 | B1 | 7/2004 | Boudec et al. |
| 6,812,010 | B1 | 11/2004 | Derose et al. |
| 7,253,343 | B2 | 8/2007 | Carozzi et al. |
| 7,355,099 | B2 | 4/2008 | Carozzi et al. |

(Continued)

FOREIGN PATENT DOCUMENTS

| | | |
|---|---|---|
| CN | 102057925 A | 5/2012 |
| EP | 372982 A2 | 6/1990 |

(Continued)

OTHER PUBLICATIONS

English translation of Iwata et al. JP 2008-110971 May 15, 2008.*
Saccomani, G., et al., "Synthesis and Beta-Blocking Activity of (R,S)-(E)-Oximeethers of 2,3-Dihydro-1,8-naphthyridine and 2,3-Dihydrothiopyrano[2,3-b]pyridine: Identification of Beta3-Antagonists," Bioorganic & Medicinal Chemistry 11:4921-4931 (2003).
Okano, K., et al., "Silica Gel-Catalyzed Air Oxidation of Cyclopentenones," Chem. Pharm. Bull 38(2): 532-533 (1990).

(Continued)

*Primary Examiner* — Patricia L Morris
(74) *Attorney, Agent, or Firm* — McBee Moore Woodward Vanik IP, LLC

(57) ABSTRACT

Arylpyrrolidines of Formula (I): wherein each substituent is as defined in the specification, and use thereof as pesticides and animal parasite-controlling agents.

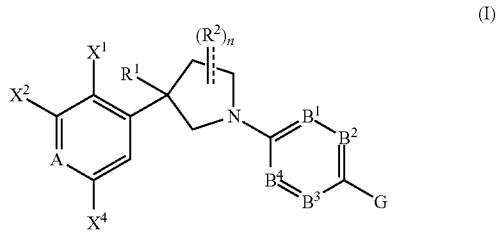

(I)

13 Claims, No Drawings

(56) References Cited

U.S. PATENT DOCUMENTS

| | | |
|---|---|---|
| 7,482,432 B2 | 1/2009 | Carozzi et al. |
| 7,674,959 B2 | 3/2010 | Carozzi et al. |
| 7,692,068 B2 | 4/2010 | Carozzi et al. |
| 7,803,391 B2 | 9/2010 | Carozzi et al. |
| 7,803,925 B2 | 9/2010 | Carozzi et al. |
| 7,811,598 B2 | 10/2010 | Carozzi et al. |
| 7,923,602 B2 | 4/2011 | Carozzi et al. |
| 8,147,856 B2 | 4/2012 | Carozzi et al. |
| 8,173,590 B2 | 5/2012 | Carozzi et al. |
| 8,188,122 B2 | 5/2012 | Mihara et al. |
| 8,314,292 B2 | 11/2012 | Carozzi et al. |
| 8,334,431 B2 | 12/2012 | Sampson et al. |
| 8,536,201 B2 * | 9/2013 | Mihara et al. ............ 514/336 |
| 8,785,647 B2 * | 7/2014 | Gorgens et al. .......... 546/276.4 |
| 2004/0116744 A1 | 6/2004 | Furuya et al. |
| 2004/0210964 A1 | 10/2004 | Carozzi et al. |
| 2004/0216186 A1 | 10/2004 | Carozzi et al. |
| 2005/0257283 A1 | 11/2005 | Matringe et al. |
| 2007/0240239 A1 | 10/2007 | Carozzi et al. |
| 2008/0070829 A1 | 3/2008 | Carozzi et al. |
| 2009/0099081 A1 | 4/2009 | Carozzi et al. |
| 2009/0100543 A1 | 4/2009 | Carozzi et al. |
| 2009/0111847 A1 | 4/2009 | Li et al. |
| 2009/0126044 A1 | 5/2009 | Carozzi et al. |
| 2009/0144852 A1 | 6/2009 | Tomso et al. |
| 2009/0247551 A1 | 10/2009 | Jeschke et al. |
| 2009/0313717 A1 | 12/2009 | Hernandez et al. |
| 2010/0005543 A1 | 1/2010 | Sampson et al. |
| 2010/0048646 A1 | 2/2010 | Jeschke et al. |
| 2010/0216792 A1 | 8/2010 | Goergens et al. |
| 2010/0240705 A1 | 9/2010 | Jeschke et al. |
| 2010/0256195 A1 | 10/2010 | Fischer et al. |
| 2011/0082175 A1 | 4/2011 | Mihara et al. |
| 2011/0190493 A1 | 8/2011 | Bretschneider et al. |
| 2011/0195998 A1 | 8/2011 | Goto et al. |
| 2011/0212949 A1 | 9/2011 | Bretschneider et al. |
| 2011/0257231 A1 | 10/2011 | Koyanagi et al. |
| 2011/0257389 A1 | 10/2011 | Hamamoto et al. |
| 2011/0306499 A1 | 12/2011 | Bretschneider et al. |
| 2012/0124698 A1 | 5/2012 | Zink et al. |
| 2012/0157498 A1 | 6/2012 | Jeschke et al. |
| 2012/0172615 A1 | 7/2012 | Mita et al. |
| 2012/0232278 A1 | 9/2012 | Mihara et al. |

FOREIGN PATENT DOCUMENTS

| | | |
|---|---|---|
| EP | 0539588 A1 | 5/1993 |
| EP | 1999141 B1 | 12/2008 |
| JP | 2005-500986 A | 1/2005 |
| JP | 2008110971 | 5/2008 |
| JP | 2010-526035 A | 7/2010 |
| WO | 9421795 A1 | 9/1994 |
| WO | 9638567 A2 | 12/1996 |
| WO | 9741218 A1 | 11/1997 |
| WO | 9924585 A1 | 5/1999 |
| WO | 9924586 A1 | 5/1999 |
| WO | 9934008 A1 | 7/1999 |
| WO | 9957965 A1 | 11/1999 |
| WO | 0165922 A2 | 9/2001 |
| WO | 0166704 A2 | 9/2001 |
| WO | 0236787 A2 | 5/2002 |
| WO | 0246387 A2 | 6/2002 |
| WO | 02096882 A1 | 12/2002 |
| WO | 03106457 A1 | 12/2003 |
| WO | 2004024928 A2 | 3/2004 |
| WO | 2004099160 A1 | 11/2004 |
| WO | 2005035486 A1 | 4/2005 |
| WO | 2005063094 A1 | 7/2005 |
| WO | 2005077934 A1 | 8/2005 |
| WO | 2005085216 A1 | 9/2005 |
| WO | 2006056433 A2 | 6/2006 |
| WO | 2006089633 A2 | 8/2006 |
| WO | 2006100288 A2 | 9/2006 |
| WO | 2007027777 A2 | 3/2007 |
| WO | 2007040280 A1 | 4/2007 |
| WO | 2007057407 A2 | 5/2007 |
| WO | 2007075459 A2 | 7/2007 |
| WO | 2007101369 A1 | 9/2007 |
| WO | 2007103567 A2 | 9/2007 |
| WO | 2007107302 A2 | 9/2007 |
| WO | 2007115643 A1 | 10/2007 |
| WO | 2007115644 A1 | 10/2007 |
| WO | 2007115646 A1 | 10/2007 |
| WO | 2007149134 A1 | 12/2007 |
| WO | 2008009360 A2 | 1/2008 |
| WO | 2008066153 A1 | 6/2008 |
| WO | 2008067911 A1 | 6/2008 |
| WO | 2008104503 A1 | 9/2008 |
| WO | 2008128711 | 10/2008 |
| WO | 2008150473 A2 | 12/2008 |
| WO | 2009049851 A1 | 4/2009 |
| WO | 2009144079 A1 | 12/2009 |
| WO | 2010005692 A2 | 1/2010 |
| WO | 2010006713 A2 | 1/2010 |
| WO | 2010020522 A1 | 2/2010 |
| WO | 2010043315 | 4/2010 |
| WO | 2010069502 A2 | 6/2010 |
| WO | 2010074747 A1 | 7/2010 |
| WO | 2010074751 A1 | 7/2010 |
| WO | 2011049233 A1 | 4/2011 |
| WO | 2011/080211 * | 7/2011 |

OTHER PUBLICATIONS

Barry, G., et al., "Inhibitors of Amino Acid Biosynthesis: Strategies for Imparting Glyphosate Tolerance to Crop Plants," in Biosynthesis and Molecular Regulation of Amino Acids in Plants, BK Sing et al., eds, vol. 7, pp. 139-145 (1992).

Kawano, Y., et al., "Synthesis of a 2-Pyrrolidinol Metabolite of OPC-51803, A Vasopressin V2 Receptor Agonist," Heterocycles 61:551-555 (2003).

Gasser, C., et al., "Structure, Expression, and Evolution of the 5-Enolpyruvylshikirnate-3-phosphate Synthase Genes of Petunia and Tomato," JBC 263(9):4280-4289 (1988).

Markgraf, J.H. and Carolyn Stickney, "A New Synthesis of N-Phenyl Lactams," J. Heterocyclic. Chem. 37:109-110 (2000).

Watterson, S., et al., "Acridone-Based Inhibitors of Inosine 5'-Monophosphate Dehydrogenase: Discovery and SAR Leading to the Identification of N-(2-(6-(4-Ethylpiperazin-1-yl)pyridin-3-yl)propan-2-yl)-2-fluoro-9-oxo-9, 10-dihydroacridine-3-carboxamide (BMS-566419)," J. Med. Chem. 50:3730-3742 (2007).

Kurusu, Y. and D.C. Neckers, "Functionalization of Silica Gel: Application for the Catalytic Oxidation of Alkanes," J. Org. Chem. 56:1981-1983 (1991).

Medina, J., et al., "Benzyl 2-Cyano-3,3-Dimethyl-1-pyrrolidinecarboxylate, a Versatile Intermediate for the Synthesis of 3,3-Dimethylproline Derivatives," J. Org. Chem. 73: 3946-3949 (2008).

Crickmore, N., et al., "Revision of the Nomenclature for the *Bacillus thuringiensis* Pesticidal Crystal Proteins," Microbiology and Molecular Biology Reviews 62(3): 807-813 (Sep. 1998).

Schnepf, H.E., et al., "Characterization of Cry34/Cry35 Binary Insecticidal Proteins from Diverse *Bacillus thuringiensis* Strain Collections," Applied and Environmental Microbiology 71(4):1765-1774 (Apr. 2005).

Moellenbeck, D., et al., "Insecticidal proteins from Bacillus thuringiensis protect corn from corn rootworms," Nat. Biotechnol. 19:668-672 (Jul. 2001).

Schumacher, R., et al., "Synthesis of 2,3-Dihydroselenophene and Selenophene Derivatives by Electrophilic Cyclization of Homopropargyl Selenides," Organic Letters 12(9): 1952-1955 (2010).

Baur, P., et al., "Polydisperse Ethoxylated Fatty Alcohol Surfactants as Accelerators of Cuticular Penetration. 1. Effects of Ethoxy Chain Length and the Size of the Penetrants," Pestic. Sci. 51:131-152 (1997).

(56) References Cited

OTHER PUBLICATIONS

Comai, L., et al., "An Altered aroA Gene Product Confers Resistance to the Herbicide Glyphosate," Science 221:370-371 (1983).

Shah, D., et al., "Engineering Herbicide Tolerance in Transgenic Plants," Science 233:478-481 (Jul. 1986).

Kienzle, F., "A Facile Synthesis of 1,4-Dihydro-1-Alkyl-2H-3,1-Benzoxazines and Related Compounds," Tetrahedron Letters 24(21): 2213-2216 (1983).

Conti, P., et al., "Synthesis of New Bicyclic Analogues of Glutamic Acid," Tetrahedron 55: 5623-5634 (1999).

Kato, Y., et al., "Asymmetric synthesis of a selective endothelin a receptor antagonist," Tetrahedron 58:3409-3415 (2002).

Kaname, M., et al., "Ruthenium tetroxide oxidation of cyclic N-acylamines by a single layer method: formation of gamma-amino acids," Tetrahedron Letters 49:2786-2788 (2008).

Tranel, P. and Terry Wright, "Resistance of weeds to ALS-inhibiting herbicides: what have we learned?[Review]," Weed Science 50:700-712 (2002).

"Glossary of Common Names and Abbreviations of Herbicides," Weed Research, vol. 26, pp. 441-445 (1986).

Japanese Patent Application Publication No. 2010-018586; Date of publication: Jan. 28, 2010; Applicant: Meiji Seika Kaisha Ltd.

International Search Report of PCT/EP2011/065849 Mailed Nov. 17, 2011.

\* cited by examiner

PESTICIDAL ARYLPYRROLIDINES

CROSS REFERENCE TO RELATED APPLICATIONS

This application is a §371 National Stage Application of PCT/EP2011/056972, filed Sep. 13, 2011, which claims priority from JP 2010-206992 filed Sep. 15, 2010 and JP 2010-291998 filed Dec. 28, 2010.

BACKGROUND OF THE INVENTION

1. Field of the Invention

The present invention relates to novel arylpyrrolidines and use thereof as pesticides.

2. Description of Related Art

Several arylpyrrolidine compounds have been described in WO 2008/128711, WO 2010/043315 which can be used as pest-controlling agents. Moreover, from JP 2008-110971 several nitrogen-containing heterocyclic compounds are known to be useful as pest-controlling agents.

Since ecological and economic demands on modern plant treatment agents are continually increasing, particularly in respect to the amount applied, residue formation, selectivity, toxicity and favourable production methodology, and also because, for example, resistance problems can occur, there is the on-going task to develop new plant treatment agents that at least in certain areas are able to demonstrate advantages over known agents.

Inventors of the present invention extensively studied to develop novel compounds which are highly effective as pesticides and have a broad spectrum of use. As a result, the inventors found that the novel arylpyrrolidines represented by the following Formula (I) have a high activity, a broad spectrum of use and safety, and also are effective against pests that are resistant to an organic phosphorous agent or a carbamate agent.

SUMMARY

Thus, this invention is directed to arylpyrrolidine compounds of Formula (I):

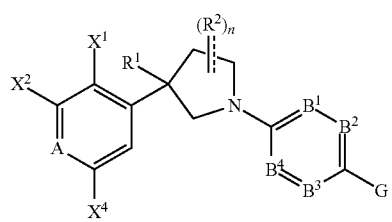

(I)

wherein
in Formula (I), the dotted line stands for a bond, or has no meaning, which means that $R^2$ can be bound via a double or a single bond to the pyrrolidine ring;
if the dotted line stands for a bond, so that $R^2$ is bound through a double bond to the pyrrolidine ring, then $R^2$ is oxo and/or thioxo and n is 1 or 2; preferably $R^2$ is oxo and n is 1;
if the dotted line has no meaning, so that $R^2$ is bound through a single bond to the pyrrolidine ring, then $R^2$ independently is halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, sulfur pentafluoride, $C_{1-12}$ alkoxy-carbonyl, $C_{1-12}$ haloalkoxy-carbonyl, $C_{1-12}$ alkoxy-carbonyloxy or $C_{1-12}$ haloalkoxy-carbonyloxy;

preferably $R^2$ is hydroxy, chloro, bromo or iodo and n is 1 or 2; more preferably $R^2$ is hydroxyl and n is 1 or 2 (preferably n is 1);

$R^1$ is $C_{1-12}$ alkyl, $C_{3-8}$ cycloalkyl, $C_{1-12}$ haloalkyl, $C_{3-8}$ halocycloalkyl; $R^1$ is preferably $C_{1-4}$ haloalkyl; more preferably $R^1$ is $CF_3$;

A is C—$X^3$ or nitrogen;

$X^1, X^2, X^3$ and $X^4$ each independently are hydrogen, halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{H2}$ haloalkyl)amino, ($C_{1-12}$ alkyl)($C_{1-12}$ haloalkyl)amino or sulfur pentafluoride; preferably $X^1, X^2, X^3$ and $X^4$ each independently are hydrogen, fluoro, chloro, bromo or iodo or $C_{1-4}$ haloalkyl; more preferably $X^1, X^2, X^3$ and $X^4$ each independently are hydrogen, fluoro, chloro, bromo or trifluoromethyl;

$B^1$ is C—$Y^1$ or nitrogen; $B^1$ preferably is C—H, C—F or nitrogen;

$B^2$ is C—$Y^2$ or nitrogen; $B^2$ preferably is C—H, C—F, C—Cl, C—Br, C—I, C—$CH_3$, C—$CH_2CH_3$, C—$CF_2H$, C—$CF_3$, C—$OCF_2H$, C—$OCF_3$ or nitrogen;

$B^3$ is C—$Y^3$ or nitrogen; $B^3$ preferably is C—H;

$B^4$ is C—$Y^4$ or nitrogen; $B^4$ preferably is C—H, or C—F or nitrogen; or $B^3, B^4$ and a bond between $B^3$ and $B^4$ together represent sulfur, thus giving a thiophenyl or a thiazolyl moiety (the latter if $B^1$ is nitrogen)

$Y^1, Y^2, Y^3$, and $Y^4$ each independently are hydrogen, halogen, nitro, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl) amino, sulfur pentafluoride, aryl or heterocyclyl;

$Y^1, Y^2, Y^3$ and $Y^4$ each independently are preferably hydrogen, halogen, $C_{1-4}$ alkyl, $C_{1-4}$ haloalkyl, $C_{1-4}$ haloalkoxy, phenyl, pyridyl, $C_{1-4}$ alkoxy, cyano, cyclopropyl; more preferably $Y^1$ is hydrogen or fluoro and/or $Y^2$ is hydrogen, halogen (fluoro, chloro, bromo, iodo), methyl, ethyl, difluoromethyl, trifluoromethyl, pentafluoroethyl, chlorodifluoromethyl, methoxy, cyano, cyclopropyl, pyridyl, phenyl, difluoromethoxy and trifluoromethoxy and/or $Y^3$ is hydrogen and/or $Y^4$ is hydrogen, fluoro; or wherein the chemical moiety (a) in Formula (I) represented by the following Formula:

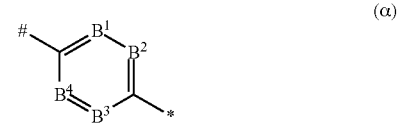

(α)

stands for one of the following chemical moieties (β) or (γ);

(β)

(γ)

wherein
B⁴ and B³ are as defined before;
Y⁵ is hydrogen, halogen, nitro, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino or sulfur pentafluoride; $Y^5$ preferably is hydrogen, halogen, $C_{1-4}$ alkyl or $C_{1-4}$ haloalkyl; $Y^5$ more preferably is hydrogen, fluoro, chloro, methyl, or trifluoromethyl; and
n' is 1, 2, 3 or 4; preferably n' is 1 or 2; more preferably n' is 1;
G is chemical moiety (δ) or (ε)

(δ)

(ε)

or is an optionally substituted heterocyclyl group selected from G1 to G9:

G1

G2

G3

-continued

G4

G5

G6

G7

G8

G9 wherein
(Z) is hydrogen, halogen, nitro, cyano, hydroxy, mercapto, amino, $C_{1-12}$ alkyl, $C_{1-12}$ haloalkyl, $C_{1-12}$ alkoxy, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl or sulfur pentafluoride; (Z) preferably is cyano hydrogen, halogen, $C_{1-4}$ alkyl or $C_{1-4}$ haloalkyl; (Z) more preferably is cyano hydrogen, fluoro, chloro, methyl, or trifluoromethyl; and
l is 1, 2 or 3; preferably 1 is for 2; more preferably 1 is 1;
$R^3$ is hydrogen, cyano, hydroxy, mercapto, amino, $C_{1-12}$ alkyl, $C_{1-12}$ haloalkyl, $C_{2-12}$ alkenyl, $C_{2-12}$ haloalkenyl, $C_{2-12}$ alkynyl, $C_{2-12}$ haloalkynyl, $C_{1-12}$ alkyl-carbonyl, $C_{1-12}$ haloalkyl-carbonyl, $C_{1-12}$ alkoxy-carbonyl or $C_{1-12}$ haloalkoxy-carbonyl; preferably $R^3$ is hydrogen, $C_{1-4}$ alkyl, $C_{1-4}$ haloalkyl, $C_{3-4}$ alkenyl, $C_{1-6}$ alkyl-carbonyl, $C_{1-6}$ alkoxy-carbonyl; more preferably $R^3$ is hydrogen; or
$R^3$ is $C_{1-12}$ alkoxy-$C_{1-12}$ alkyl, or cyano-$C_{1-12}$ alkyl; preferably $R^3$ is $C_{1-6}$alkoxy-$C_{1-6}$alkyl, or cyano-$C_{1-6}$ alkyl; more preferably $R^3$ is methoxy-methyl, methoxy-ethyl, ethoxy-methyl, ethoxy-ethyl or cyanomethyl;
$R^4$ is hydrogen, cyano, hydroxy, mercapto, amino, $C_{1-12}$ alkyl, $C_{1-12}$ haloalkyl, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, $C_{1-12}$ alkylsulfonyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl) amino, cyano$C_{1-12}$ alkyl, cyano$C_{3-8}$cycloalkyl, aryl, aryl-$C_{1-12}$ alkyl, a heterocyclic group, $C_{1-12}$ alkyl substituted with a heterocyclic group, $C_{1-12}$ alkyl-O—N=CH—, $C_{1-12}$ haloalkyl-O—N=CH— or $(R^8)(R^9)$N—CO—$C_{1-12}$ alkyl;

$R^5$ and $R^6$ each independently are hydrogen, cyano, $C_{1-12}$ alkyl, $C_{1-12}$ haloalkyl, $C_{3-8}$ cycloalkyl, $C_{3-8}$ halocycloalkyl, $C_{1-12}$ alkoxy-carbonyl or $C_{1-12}$ haloalkoxy-carbonyl; preferably $R^5$ and $R^6$ each independently are hydrogen, cyano, $C_{1-4}$ alkyl, $C_{1-4}$ haloalkyl or cyclopropyl more preferably $R^5$ and $R^6$ each independently are hydrogen, trifluoromethyl or methyl;

$R^7$ is hydrogen, or optionally substituted $C_{1-12}$ alkyl, $C_{1-12}$ cyanoalkyl, and $C_{1-12}$ haloalkyl, optionally substituted $C_{3-8}$ cycloalkyl, $C_{3-8}$ halocycloalkyl, $C_{3-8}$ cycloalkyl-$C_{1-12}$ alkyl, and $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, amino, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl) ($C_{1-12}$ haloalkyl)amino, optionally substituted aryl and aryl-$C_{1-12}$ alkyl, an optionally substituted heterocyclic group, $C_{1-12}$ alkyl substituted with a heterocyclic group, $C_{1-12}$alkylcarbonyl, $C_{1-12}$haloalkylcarbonyl or $(R^8)(R^9)N$—CO—; preferably $R^7$ is optionally substituted $C_{1-6}$ alkyl, $C_{1-6}$ cyanoalkyl, and $C_{1-6}$ haloalkyl, optionally substituted $C_{3-6}$ cycloalkyl, $C_{3-6}$ halocycloalkyl, $C_{3-6}$ cycloalkyl-$C_{1-4}$ alkyl, and $C_{3-6}$ halocycloalkyl-$C_{1-6}$ alkyl, $C_{2-6}$ alkenyl, $C_{2-6}$ haloalkenyl, $C_{1-4}$ alkoxy, $C_{1-4}$ haloalkoxy, $C_{1-4}$ alkoxy-$C_{1-4}$ alkyl, $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl, optionally substituted phenyl and phenyl-$C_{1-6}$ alkyl, methylamino, dimethylamino, ethylamino, cyclopropylamino, prop-2-yn-1-ylamino, optionally substituted heterocyclic group; more preferably $R^7$ is optionally substituted $C_{1-6}$ alkyl (in particular methyl, ethyl, propyl, isopropyl, butyl, iso-butyl or tert.-butyl), $C_{1-6}$ cyanoalkyl (in particular cyanomethyl), $C_{1-6}$ haloalkyl (in particular ethyl, propyl, iso-propyl, butyl, iso-butyl, tert.-butyl any of which is substituted with 1 to 5 fluorine atoms and/or chlorine atoms), $C_{1-4}$ alkoxy (in particular methoxy, ethoxy, propoxy, isopropoxy, butoxy, isobutoxy, tert.-butoxy), $C_{1-4}$ haloalkoxy (in particular methoxy, ethoxy, propoxy, isopropoxy, butoxy, isobutoxy, tert.-butoxy any of which is substituted with 1 to 5 fluorine atoms and/or chlorine atoms), $C_{1-4}$ alkoxy-$C_{1-4}$ alkyl (in particular methoxy-methyl, methoxy-ethyl, ethoxy-methyl, ethoxy-ethyl), $C_{1-4}$ alkoxy-$C_{1-4}$ haloalkyl (in particular methoxy-methyl, methoxy-ethyl, ethoxy-methyl, ethoxy-ethyl any of the alkyl group is optionally substituted with 1 to 5 fluorine atoms and/or chlorine atoms), optionally fluorine or chlorine substituted $C_{1-4}$ alkyl-S—$C_{1-4}$ alkyl, $C_{1-4}$ alkyl-S(O)—$C_{1-4}$ alkyl or $C_{1-4}$ alkyl-S(O)$_2$—$C_{1-4}$ alkyl (in particular (methylsulfanyl)methyl, (methylsulfinyl)methyl, (methylsulfonyl)methyl any of which is optionally substituted with 1 to 5 fluorine atoms and/or chlorine atoms), optionally with 1 to 5 fluorine or chlorine substituted methylamino, dimethylamino, ethylamino, cyclopropylamino, and prop-2-yn-1-ylamino, optionally with 1 to 5 fluorine, chlorine, or $C_{1-4}$ haloalkyl substituted $C_{3-6}$ cycloalkyl (in particular cyclopropyl, cyclobutyl any of which is optionally substituted with 1 to 5 fluorine atoms and/or chlorine atoms and/or $C_{1-4}$ haloalkyl (e.g. $CF_3$), optionally with 1 to 5 fluorine or chlorine substituted $C_{3-6}$ cycloalkyl-$C_{1-4}$ alkyl (in particular cyclopropyl-methyl, cyclopropyl-ethyl cyclobutyl-methyl, cyclobutyl-ethyl any of which is optionally substituted with 1 to 5 fluorine atoms and/or chlorine atoms), or optionally with 1 to 5 fluorine or chlorine substituted heterocyclic group such as $C_{3-6}$ heterocycloalkyl (in particular oxetan-3-yl, thietan-3-yl, 1-oxidothietan-3-yl, 1,1-dioxidothietan-3-yl any of which is optionally substituted with 1 to 5 fluorine atoms and/or chlorine atoms), optionally with 1 to 4 halogen atoms or $C_{1-4}$ haloalkyl substituted phenyl or phenyl —$C_{1-4}$ alkyl;

$R^8$ and $R^9$ each independently are hydrogen, cyano, hydroxy, amino, $C_{1-12}$ alkyl, $C_{1-12}$ haloalkyl, $C_{3-8}$ cycloalkyl, $C_{3-8}$ halocycloalkyl, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ alkoxy, $C_{1-12}$ haloalkoxy, $C_{1-12}$ alkoxy-$C_{1-12}$ alkyl, $C_{1-12}$ haloalkoxy-$C_{1-12}$ alkyl, $C_{1-12}$ alkyl-S—$C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, $C_{1-12}$ alkylsulfonyl, $C_{1-12}$ haloalkylsulfonyl, $C_{1-12}$ alkylamino, di($C_{1-12}$ alkyl)amino, $C_{1-12}$ haloalkylamino, di($C_{1-12}$ haloalkyl) amino, ($C_{1-12}$ alkyl) ($C_{1-12}$ haloalkyl)amino, cyano $C_{1-12}$ alkyl, cyano-$C_{3-8}$ cycloalkyl, aryl, aryl-$C_{1-12}$ alkyl, a heterocyclic group or $C_{1-12}$ alkyl substituted with a heterocyclic group;

W is oxygen or sulfur, preferably oxygen;

m is 1 or 2, preferably 1;

when $B^2$ is C—$Y^2$ then either one of the pair $Y^2$ and $R^5$ or the pair $Y^2$ and $R^6$ may form, together with the carbon atoms to which they are bound and further together with the carbon atom(s) between said carbon atoms, a 5- to 7-membered hydrocarbon ring, which may be unsaturated, and preferably both are hydrogen or one is hydrogen and the other is $C_{1-4}$ alkyl, more preferably one is hydrogen and the other is $C_{1-4}$ alkyl, and when one is hydrogen and the other is $C_{1-4}$ alkyl, the stereo configuration of the carbon to which $R^5$ and $R^6$ are bonded preferably in the (S) form; in particular if in the compounds of Formula (I), G is the chemical moiety (ϵ), with m being 1, $B^2$ being C—$Y^2$, then $R^5$ and $Y^2$ together with the carbon atoms, to which they are attached to together with the chemical moiety (α), may form the following cyclic chemical moiety (κ)

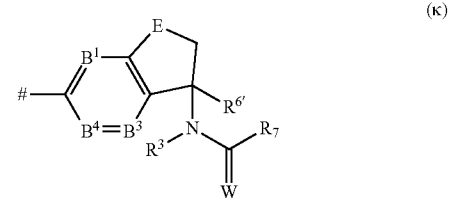

(κ)

wherein

E is oxygen, sulfur or a $C_{1-3}$ alkandiyl-group which group can be optionally substituted by 1 or 2 $C_1$-$C_6$ alkyl groups; and $R^{6'}$ is hydrogen or $C_1$-$C_6$ alkyl.

DETAILED DESCRIPTION OF A PREFERRED EMBODIMENT

If in the compounds of Formula (I), G is the chemical moiety (ϵ), with $R^5$ being methyl, $R^6$ being hydrogen and m being 1, then the stereo configuration of the carbon to which $R^5$ and $R^6$ are bonded preferably represents an (S) form or a mixture of (S) form and (R) form wherein preferably the (S) form is present in a higher proportion.

The respective compounds of the Formula (I) of the invention contain an asymmetric carbon atom, and therefore the compounds of the present invention encompass their respective optical isomers. The nitrogen atom on the pyrrolidine skeleton of the compounds of the Formula (I) of the invention may be substituted with oxygen, alkyl which may be substituted or haloalkyl which may be substituted. It may also form other salts.

In an [embodiment A], the invention is directed to compounds of the following Formula (I-B) and (I-C)

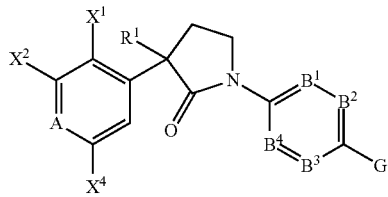
(I-B)

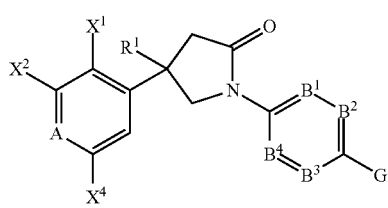
(I-C)

wherein A, $X^1$, $X^2$, $X^4$, $R^1$, $B^1$, $B^2$, $B^3$, $B^4$, and the moiety α are as defined herein for the compounds of Formula (I), and to the use of such compounds as intermediates, preferably in Step 2 of the Preparation method (a) according to the invention for the preparation of the compounds of Formula (I-A) or (I-A'),

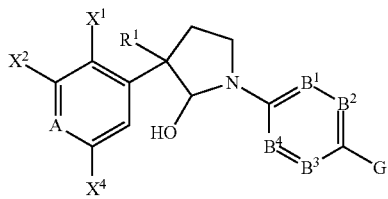
(I-A)

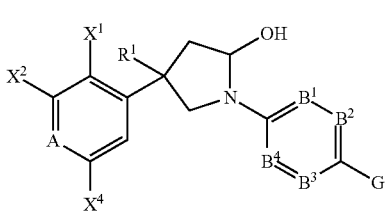
(I-A')

wherein A, $X^1$, $X^2$, $X^4$, $R^1$, $B^1$, $B^2$, $B^3$, $B^4$, and the moiety a are as defined herein for the compounds of Formula (I).

In an embodiment [B], the invention is directed to compounds of the following Formula (I-s-A) or (I-s-A')

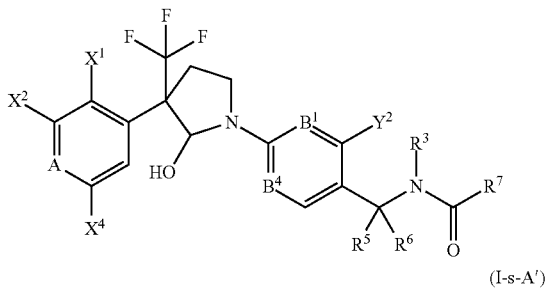
(I-s-A)

(I-s-A')

wherein $X^1$, $X^2$, A, $X^4$, $B^1$, $B^4$, $Y^2$, $R^3$, $R^5$, $R^6$ and $R^7$ are as defined herein for the compounds of Formula (I).

In an embodiment [C], the invention is directed to compounds of the following Formula (I-s-A1)

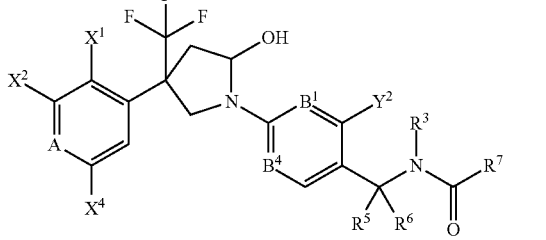
(I-s-A1)

wherein $X^1$, $X^2$, A, $X^4$, $Y^1$, $Y^2$, $Y^4$, $R^3$ and $R^7$ are as defined herein for the compounds of Formula (I).

In an embodiment [D], the invention is directed to compounds of the following Formula (I-s-A2)

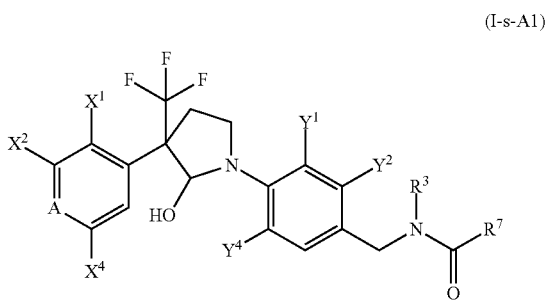
(I-s-A2)

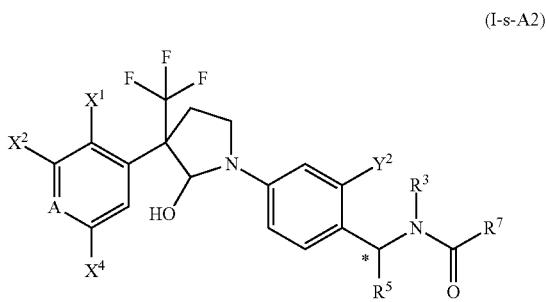

wherein $X^1$, $X^2$, A, $X^4$, $Y^2$, $R^3$, $R^5$ and $R^7$ are as defined herein for the compounds of Formula (I), provided that $R^5$ is not hydrogen, and the stereo configuration of the carbon atom to which R⁵ is bound is in the (S)-form, (R)-form or a racemate of (S)-form and (R)-form.

In an embodiment [E], the invention is directed to compounds of the following Formula (I-s-A3) or (I-s-A'3)

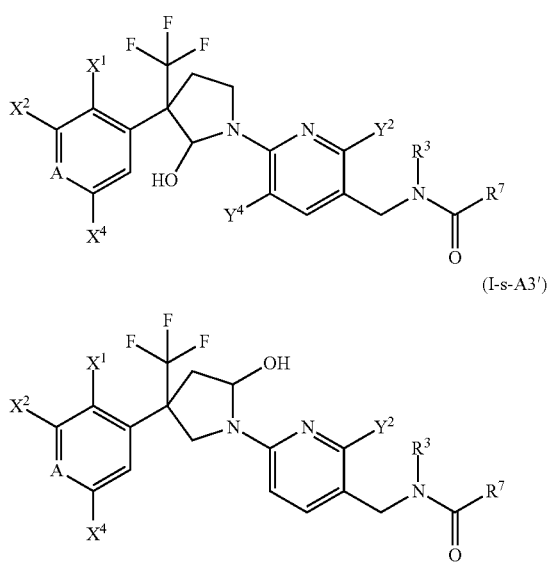

wherein $X^1, X^2, A, X^4, Y^2, Y^4, R^3$ and $R^7$ are as defined herein for the compounds of Formula (I).

In an embodiment [F], the invention is directed to compounds of the following Formula (I-s-A4)

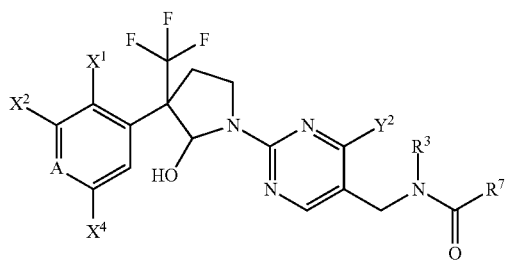

wherein $X^1, X^2, A, X^4, Y^2, R^3$ and $R^7$ are as defined herein for the compounds of Formula (I).

In an embodiment [G], the invention is directed to compounds of the following Formula (I-s-A5)

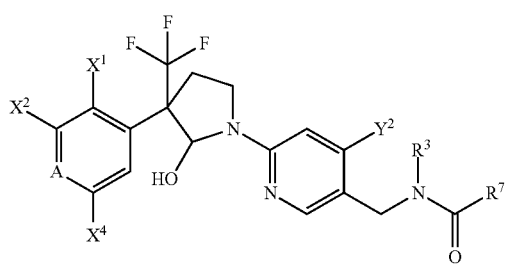

wherein $X^1, X^2, A, X^4, Y^2, R^3$ and $R^7$ are as defined herein for the compounds of Formula (I).

In an embodiment [H], the invention is directed to compounds of the following Formula (I-s-A6)

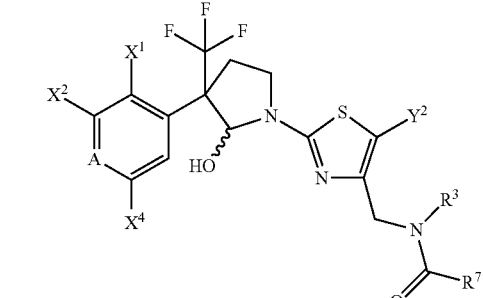

wherein $X^1, X^2, A, X^4, Y^2, R^3$ and $R^7$ are as defined herein for the compounds of Formula (I).

In an embodiment [I], the invention is directed to compounds of the following Formula (I-s-A7)

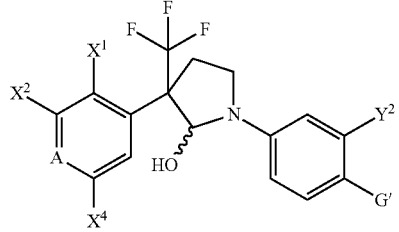

wherein $X^1, X^2, A, X^4, Y^2, R^3$ and $R^7$ are as defined herein for the compounds of Formula (I) and G' represents G1-G9.

In an embodiment [J], the invention is directed to compounds of the following Formula (I-s-B)

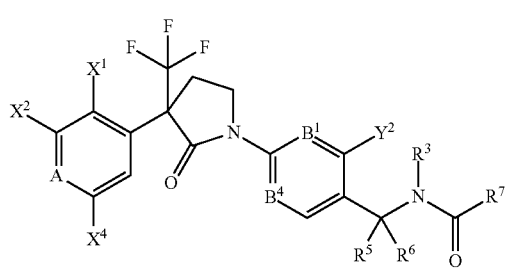

wherein $X^1, X^2, A, X^4, B^1, B^4, Y^2, R^3, R^5, R^6$ and $R^7$ are as defined herein for the compounds of Formula (I).

In an embodiment [K], the invention is directed to compounds of the following Formula (I-s-B1)

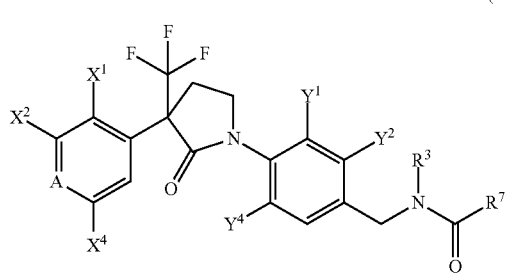

wherein $X^1$, $X^2$, A, $X^4$, $Y^1$, $Y^2$, $Y^4$, $R^3$ and $R^7$ are as defined herein for the compounds of Formula (I).

In an embodiment [L], the invention is directed to compounds of the following Formula (I-s-B2)

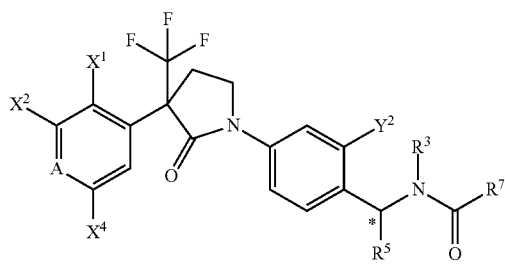

(I-s-B2)

wherein $X^1$, $X^2$, A, $X^4$, $Y^2$, $R^3$, $R^5$ and $R^7$ are as defined herein for the compounds of Formula (I), provided that $R^5$ is not hydrogen, and the stereo configuration of the carbon atom to which $R^5$ is bonded is (S)-form, (R)-form or a racemate of (S)-form and (R)-form.

In an embodiment [M], the invention is directed to compounds of the following Formula (I-s-B3)

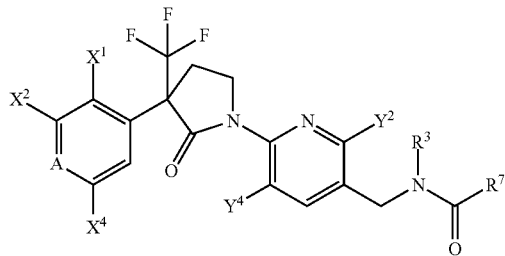

(I-s-B3)

wherein $X^1$, $X^2$, A, $X^4$, $Y^2$, $Y^4$, $R^3$ and $R^7$ are as defined herein for the compounds of Formula (I).

In an embodiment [N], the invention is directed to compounds of the following Formula (I-s-C)

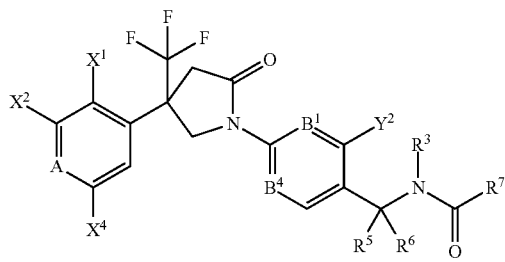

(I-s-C)

wherein $X^1$, $X^2$, A, $X^4$, $B^1$, $B^4$, $Y^2$, $R^3$, $R^5$, $R^6$ and $R^7$ are as defined herein for the compounds of Formula (I).

In an embodiment [O], the invention is directed to compounds of the following Formula (I-s-C1)

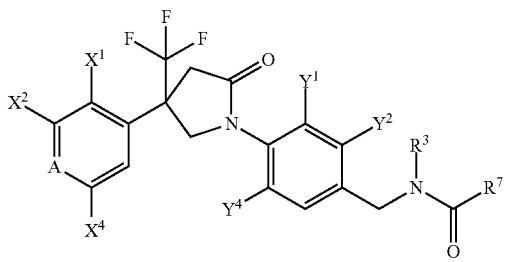

(I-s-C1)

wherein $X^1$, $X^2$, A, $X^4$, $Y^1$, $Y^2$, $Y^4$, $R^3$ and $R^7$ are as defined herein for the compounds of Formula (I).

In an embodiment [P], the invention is directed to compounds of the following Formula (I-s-C2)

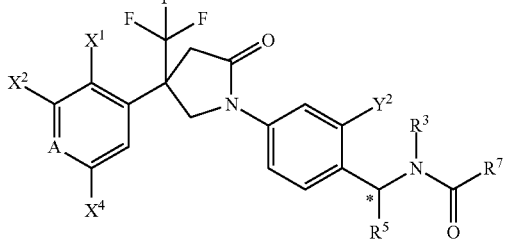

(I-s-C2)

wherein $X^1$, $X^2$, A, $X^4$, $Y^2$, $R^3$, $R^5$ and $R^7$ are as defined herein for the compounds of Formula (I), provided that $R^5$ is not hydrogen, and the stereo configuration of the carbon atom to which $R^5$ is bonded is (S)-form, (R)-form or a racemate of (S)-form and (R)-form.

In an embodiment [Q], the invention is directed to compounds of the following Formula (I-s-C3)

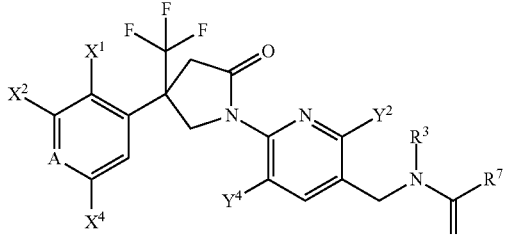

(I-s-C3)

wherein $X^1$, $X^2$, A, $X^4$, $Y^2$, $Y^4$, $R^3$ and $R^7$ are as defined herein for the compounds of Formula (I).

The arylpyrrolidines of the Formula (I) and those of the embodiments [A] to [Q] as given herein exhibit a potent pesticidal effect. It is understood that terms like "compounds according to the invention" or "active compounds" refer to all compounds which can be summarized under Formula (I), and thus include all compounds as defined in the embodiments [A] to [Q].

Each of the above mentioned chemical groups such as $C_{1-12}$ alkyl, $C_{1-12}$ haloalkyl, $C_{1-12}$ alkoxy, $C_{1-12}$ alkoxy-$C_1$-

$C_{12}$ alkyl, $C_{1-12}$ haloalkoxy, $C_{1-12}$ alkylsulfenyl, $C_{1-12}$ alkylsulfinyl, $C_{1-12}$ alkylsulfonyl, $C_{1-12}$ haloalkylsulfenyl, $C_{1-12}$ haloalkylsulfinyl, $C_{1-12}$ haloalkylsulfonyl, $C_{1-12}$ alkoxy-carbonyl, $C_{1-12}$ haloalkoxy-carbonyl, $C_{1-12}$ alkoxy-carbonyloxy, $C_{1-12}$ haloalkoxy-carbonyloxy, $C_{3-8}$ cycloalkyl, $C_{3-8}$ halocycloalkyl, sulfur pentafluoride, $C_{3-8}$ cycloalkyl-$C_{1-12}$ alkyl, $C_{3-8}$ halocycloalkyl-$C_{1-12}$ alkyl, $C_{2-12}$ alkenyl, $C_{2-12}$ haloalkenyl, $C_{2-12}$ alkynyl, $C_{2-12}$ haloalkynyl, $C_{1-12}$ haloalkoxy-$C_{1-12}$ alkyl, $C_{1-12}$ alkyl, $C_{1-12}$ haloalkyl-S—$C_{1-12}$ alkyl, $C_{1-12}$ alkyl-S(O)—$C_{1-12}$ alkyl, $C_{1-12}$ haloalkyl-S(O)—$C_{1-12}$ alkyl, $C_{1-12}$ alkyl-S(O)$_2$—$C_{1-12}$ alkyl, $C_{1-12}$ haloalkyl-S(O)$_2$—$C_{1-12}$ alkyl, amino, $C_{1-12}$ alkylamino, di($C_{1-12}$ alkyl)amino, $C_{1-12}$ haloalkylamino, di($C_{1-12}$ haloalkyl)amino, ($C_{1-12}$ alkyl)($C_{1-12}$ haloalkyl)amino, aryl, aryl-$C_{1-12}$ alkyl, heterocyclic groups (such as hetoraryls or heteroalkyl), $C_{1-12}$ alkyl substituted with a heterocyclic group, $C_{1-12}$alkylcarbonyl, $C_{1-12}$haloalkylcarbonyl etc. may be substituted with a suitable substituent.

For example, $C_{1-12}$ alkyl, $C_{1-12}$ alkoxy, $C_{1-12}$ haloalkyl, $C_{1-12}$ haloalkoxy, $C_{1-12}$ alkoxy-$C_{1-12}$ alkyl and $C_{1-12}$ alkylthio-$C_{1-12}$ alkyl moieties any of which may be substituted by 1 or 2 cyano (preferably 1 cyano); or aryl and heteroaryl groups any of which may independently be substituted by 1 or 2 cyano, $C_{1-4}$ alkyl, $C_{1-4}$ haloalkyl, $C_{1-4}$ alkoxy and/or $C_{1-4}$ haloalkoxy groups and/or fluorine, chlorine, bromine (preferably independently by 1 or 2 cyano, methyl, trifluoromethyl, methoxy, difluoromethoxy or trifluoromethoxy groups, or fluorine chlorine, bromine); or $C_{3-8}$ cycloalkyl (saturated or unsaturated) may be substituted by 1 or 2 cyano, $C_{1-4}$ alkyl, $C_{1-4}$ haloalkyl and/or $C_{1-4}$ alkoxy groups and/or fluorine, chlorine; or a heterocyclic group, in particular a $C_{3-8}$ heterocycloalkyl group which preferably contains 1 or 2 oxygen and/or sulphur atoms, a SO— or SO$_2$-group and/or may optionally independently be substituted by 1 or 2 cyano, methyl, trifluoromethyl or methoxy groups, or fluorine or chlorine;

If not defined otherwise, "alkyl" represents linear or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl or n-dodecyl, preferably $C_{1-6}$ alkyl, and more preferably $C_{1-4}$ alkyl. Alkyl may be optionally substituted, preferably by 1 or 2 cyano groups.

In addition, examples of an alkyl moiety included in other groups as a part of their constitution, can be those described above for the "alkyl".

Accordingly, for example, "alkoxy" means linear or branched $C_{1-12}$ alkoxy, preferably $C_{1-6}$ alkoxy, such as methoxy, ethoxy, n-propoxy, i-propoxy, n-, iso-, sec- or tert-butoxy, pentyloxy or hexyloxy, and more preferably $C_{1-4}$ alkoxy. The alkoxy may be further substituted with a substituent, preferably with cyano.

If not defined otherwise, "haloalkyl" represents a linear or branched $C_{1-12}$ alkyl, preferably $C_{1-6}$ alkyl, more preferably $C_{1-4}$ alkyl, wherein at least one hydrogen atom of which is substituted by a halogen atom (preferably a fluorine or chlorine), such as for example CH$_2$F, CHF$_2$, CF$_3$, CF$_2$Cl, CFCl$_2$, CF$_2$Br, CF$_2$CF$_3$, CFHCF$_3$, CH$_2$CF$_3$, CH$_2$CHF$_2$, CFClCF$_3$, CCl$_2$CF$_3$, CF$_2$CH$_3$, CF$_2$CH$_2$F, CF$_2$CHF$_2$, CF$_2$CF$_2$Cl, CF$_2$CF$_2$Br, CFHCH$_3$, CFHCHF$_2$, CFHCHF$_2$, CHFCF$_3$, CHFCF$_2$Cl, CHFCF$_2$Br, CFClCF$_3$, CCl$_2$CF$_3$, CF$_2$CF$_2$CF$_3$, CH$_2$CF$_2$CF$_3$, CF$_2$CH$_2$CF$_3$, CF$_2$CF$_2$CH$_3$, CHFCF$_2$CF$_3$, CF$_2$CHFCF$_3$, CF$_2$CF$_2$CHF$_2$, CF$_2$CF$_2$CH$_2$F, CF$_2$CF$_2$CF$_2$Cl and CF$_2$CF$_2$Br.

If not defined otherwise, in the present specification "acylamino" represents, for example, alkylcarbonylamino, cyclopropylcarbonylamino or benzoylamino, wherein examples of the alkyl moiety can also be those described above for the "alkyl".

If not defined otherwise, "halogen" and a halogen moiety included in each group substituted with a halogen represent fluorine, chlorine, bromine or iodine, preferably fluorine, chlorine or bromine.

If not defined otherwise, "cycloalkyl" represents $C_{3-8}$ cycloalkyl, such as cyclopropyl, cyclobutyl, cyclopentyl, cyclohexyl, cycloheptyl or cyclooctyl, preferably $C_{3-7}$ cycloalkyl, and more preferably $C_{3-6}$ cycloalkyl.

If not defined otherwise, "alkenyl" represents $C_{2-12}$ alkenyl, preferably $C_{2-5}$ alkenyl, such as vinyl, allyl, 1-propenyl, 1-(or 2- or 3-)butenyl or 1-pentenyl, more preferably $C_{2-5}$ alkenyl.

If not defined otherwise, "alkynyl" represents $C_{2-12}$ alkynyl, preferably $C_{2-5}$ alkynyl, such as ethynyl, propargyl, 1-propynyl, butan-3-ynyl or pentan-4-ynyl, more preferably $C_{2-4}$ alkynyl.

If not defined otherwise, "aryl" represents a $C_{6-12}$ aromatic hydrocarbon group, for example, phenyl, naphthyl or biphenyl, preferably a $C_{6-10}$ aromatic hydrocarbon group, and more preferably phenyl.

If not defined otherwise, in the present specification "heterocycle" or "heterocyclic group" represents a 3- to 6-membered heterocyclic ring group comprising at least one of N, O and S as a hetero atom, and also represents a fused heterocyclic ring group which may be benzo-fused. Further, the heterocycle may have oxide on its N atom, if possible. According to the invention, the term "heterocycle" or "heterocyclic group" preferably stands for a $C_{3-8}$ heterocycloalkyl group which preferably contains 1 or 2 oxygen and/or sulphur atoms, a SO— or SO$_2$-group and/or may optionally independently be substituted by 1 or 2 cyano, methyl, trifluoromethyl or methoxy groups, or fluorine or chlorine atoms.

Examples of the heterocycle include oxiranyl, thiranyl, 1-oxide thiranyl, 1,1-dioxide thiranyl, aziridinyl, oxetanyl, thietanyl, 1-oxide thietanyl, 1,1-dioxide thietanyl, azetidinyl, tetrahydrofuranyl, tetrahydrothienyl, 1-oxide tetrahydrothienyl, 1,1-dioxide tetrahydrothienyl, pyrrolidinyl, tetrahydropyranyl, piperidinyl, tetrahydrothiopyranyl, 1-oxide tetrahydrothiopyranyl, 1,1-dioxide tetrahydrothiopyranyl, furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl.

Even if not mentioned specifically, it is understood that all chemical groupings mentioned in the present application can be substituted. Suitable substituents are known to the skilled person and include among others amino, hydroxy, halogen, nitro, cyano, isocyano, mercapto, isothiocyanate, carboxy, carbamide, SF$_5$, aminosulfonyl, alkyl, cycloalkyl, alkenyl, cycloalkenyl, alkynyl, monoalkylamino, dialkylamino, N-alkylcarbonyl-amino, alkoxy, alkenyloxy, alkynyloxy, cycloalkyloxy, cycloalkenyloxy, alkoxycarbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfenyl, alkylsulfinyl, alkylsulfinyl including isomers, alkylsulfonyl, monoalkylaminosulfonyl, dialkylaminosulfonyl, alkylphosphinyl, alkylphosphonyl, alkylphosphinyl including isomers, alkylphosphonyl including isomers, N-alkyl-aminocarbonyl, N,N-dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, arylamino, benzylamino, heterocycle, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl or haloalkoxyalkyl, and preferably chloro, fluoro, bromo, iodo, amino, nitro, cyano, hydroxy, thio or carboxy.

If not defined otherwise or mentioned expressly in the present application, the term "in the agricultural field" refers to the protection of plants or plant parts. Livestock farming is not included.

If not defined otherwise or mentioned expressly in the present application, the term "controlling" or "combating" means that the active compounds according to the invention are effective in reducing the incidence of the respective agricultural pests on plants, or plant parts (such as seeds). More specifically, "controlling" or "combating" as used herein, means that the active compound is effective in killing the respective pest, inhibiting its growth, or inhibiting its proliferation.

The expression "active compound" or "compounds according to the invention" are used synonymously herein.

The invention is further directed to a Preparation method (c) for the preparation of a compound of Formula (I-A), (I-A'), (I-B) or (I-C)

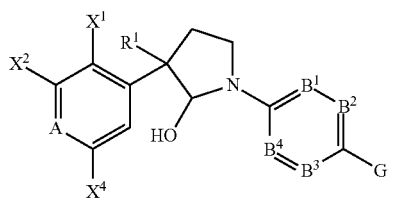
(I-A)

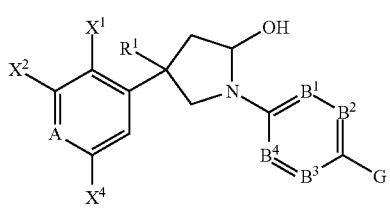
(I-A')

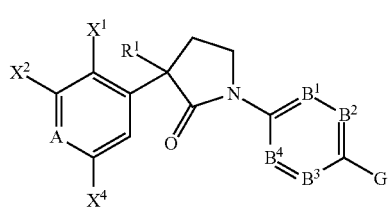
(I-B)

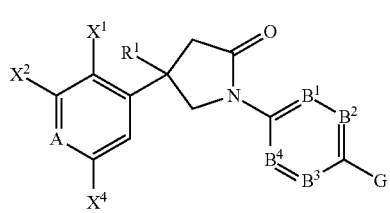
(I-C)

comprising the oxidation of a compound of Formula (II)

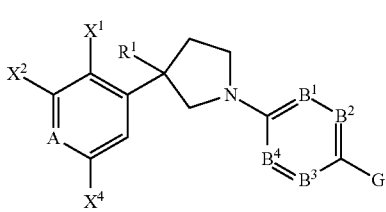
(II)

wherein in the compound of Formula (I-A), (I-A'), (I-B), (I-C) and (II) $X^1, X^2, A, X^4, R^1, B^1$ to $B^4$ and G are as defined herein for compounds of Formula (I), with an oxidation agent, under appropriate reaction conditions, optionally in the presence of a catalyst.

Suitable oxidation agents comprise $H_2O_2$, $MnO_2$, $KMnO_4$, $RuO_4$, peracids (e.g. m-chloroperbenzoic acid (MCPBA)), quinones (e.g. 2,3-dichloro-5,6-dicyano-1,4-benzoquinone (DDQ), tetrachloro-1,2-benzoquinone (o-Chloranil), tetrachloro-1,4-benzoquinone (Chloranil)), cerium(IV) salts (e.g. ceric(IV)ammonium nitrate (CAN)) or silver(II) salts (such as inorganic or organic silver(II) salts (e.g. silver(II)fluoride, bis(α,α'-bipyridine)silver(II)nitrate, bis(α,α'-bipyridine)silver(II)peroxydisulfate, silver(II)picolinate, and tetrakis(pyridine)silver(II)), hypervalent iodine compounds (e.g. [bis(trifluoroacetoxy)iodo]benzene, [bis(acetoxy)iodo]benzene, iodosobenzene, 2-iodoxybenzoic acid, pentafluoroiodosobenzene) and air (oxygen).

Suitable catalysts are transition metal catalyst (e.g. N',N'-bis(salicylidene)ethylenediamine iron (II)), an acid catalyst (e.g. acetic acid, trifluoroacetic acid, silica gel) or a phase transfer catalyst (e.g. benzyltriethylammonium chloride, tetrabutylammonium bromide, crown ether).

In an embodiment of before mentioned Preparation method (c), the compound of Formula (I-B) or (I-C) can be converted into the respective compound of Formula (I-A) or (I-A'). For this conversion, the compound of Formula (I-B) or (I-C) is isolated using routine methods and then reacted with a reducing agent, such as e.g. sodium tetrahydroborate, lithium tetrahydroborate, lithium aluminum hydride, diisobutylaluminum hydride, or super hydride), if necessary, in the presence of an appropriate diluent. This embodiment which includes Preparation method (c) as Step 1 and a reduction as Step 2 will be further summarized under "Preparation method (a)".

An oxidation reaction of pyrrolidine ring by using $KMnO_4$ and benzyltriethylammonium chloride as a phase transfer catalyst in dichloromethan is described by Markgraf and Stickney in Journal of Heterocyclic Chemistry, 2000 (37), 109-110.

Mamoru et al. describes in Tetrahedron Letters, 2008(49), 2786-2788, an oxidation reaction to oxidize N-acyl pyrrolidine with $RuO_2$ and using $NaII_4$ as co-oxidant and ethyl acetate system.

Preparation Method (a)

A method in which, in a Step 1, the compounds represented by the following Formula (II):

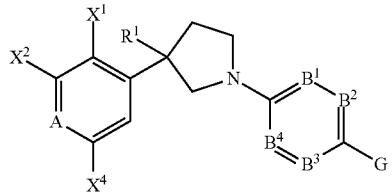

(II)

wherein $X^1$, $X^2$, A, $X^4$, $R^1$, $B^1$ to $B^4$ and G are as defined above,
are reacted with an oxidizing agent, such as e.g. manganese dioxide, potassium permanganate, ruthenium tetraoxide, if necessary, in the presence of an appropriate diluent to give the compounds represented by the following Formula (I-B):

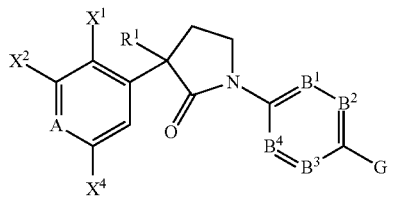

(I-B)

and/or the compounds represented by the following Formula (I-C):

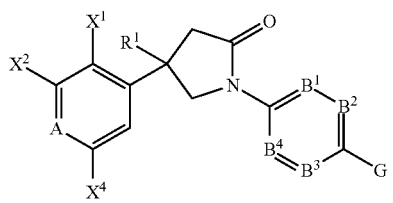

(I-C)

wherein $X^1$, $X^2$, A, $X^4$, $R^1$, $B^1$ to $B^4$ and G are as defined above for the compounds of Formula (I), and subsequently,
in a Step 2, they are reacted with a reducing agent, such as e.g. sodium tetrahydroborate, lithium tetrahydroborate, lithium aluminum hydride, diisobutylaluminum hydride, or super hydride, if necessary, in the presence of an appropriate diluent, to give the compounds represented by the following Formula (I-A):

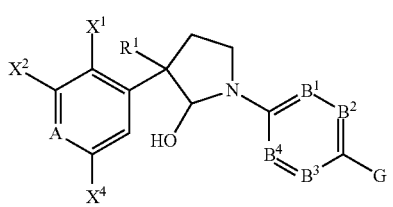

(I-A)

and/or the compounds represented by the following Formula (I-A'):

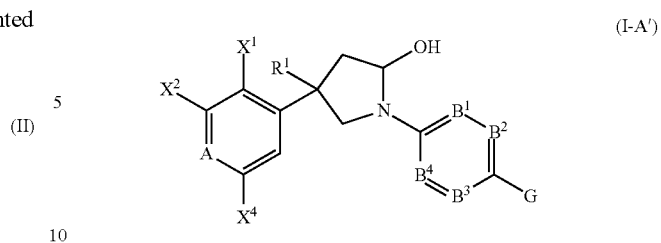

(I-A')

wherein $X^1$, $X^2$, A, $X^4$, $R^1$, $B^1$ to $B^4$ and G are as defined above.

The reaction of Step 1 in the Preparation method (a) can be carried out in the presence of a catalyst, such as e.g. transition metal catalyst (e.g. N',N'-bis(salicylidene)ethylenediamine iron (II)), an acid catalyst (e.g. acetic acid, trifluoroacetic acid, silica gel) or a phase transfer catalyst (e.g. bennzyltriethylammonium chloride, tetrabutylammonium bromide, crown ether) (cf. Journal of Heterocyclic Chemistry, 2000 (37), 109-110 and Tetrahedron Letters, 2008(49), 2786-2788).

Compounds of the above Formula (I-A), Formula (I-B), Formula (I-C), Formula (I-A'), Formula (Int. 1-2) and Formula (Int. 1-4) are encompassed by the compounds of the Formula (I) of the invention.

The diluent which can be used in the reaction of Step 1 in the Preparation method (a) are for example a aliphatic hydrocarbons (e.g. hexane, cyclohexane, heptane), aliphatic halogenated hydrocarbons (e.g. dichloromethane, chloroform, carbon tetrachloride, dichloroethane), aromatic hydrocarbons (e.g. benzene, toluene, xylene, chlorobenzene), ethers [e.g. diethyl ether, dibutyl ether, dimethoxyethane (DME), tetrahydrofuran, dioxane], esters (e.g. ethyl acetate, ethyl propionate), acid amides [e.g. dimethylformamide (DMF), dimethylacetamide (DMA), N-methylpyrrolidone], nitriles (e.g. acetonitrile, propionitrile), dimethylsulfoxide (DMSO), water or a mixture of the diluents.

The diluent which can be used in Preparation method (c) are for example a aliphatic hydrocarbons (e.g. hexane, cyclohexane, heptane), aliphatic halogenated hydrocarbons (e.g. dichloromethane, chloroform, carbon tetrachloride, dichloroethane), aromatic hydrocarbons (e.g. benzene, toluene, xylene, chlorobenzene), esters (e.g. ethyl acetate, ethyl propionate), acid amides [e.g. dimethylformamide (DMF), dimethylacetamide (DMA), N-methylpyrrolidone], nitriles (e.g. acetonitrile, propionitrile), dimethylsulfoxide (DMSO), water or a mixture of the diluents.

The Preparation method (c) and the reaction of Step 1 in the Preparation method (a) can be carried out over a substantially wide range of temperatures. It may be generally carried out at the temperature ranging from about −78° C. to about 200° C., preferably from about −10° C. to about 150° C. Furthermore, the reaction is preferably carried out under normal pressure. However, it may be carried out under reduced or elevated pressure. The reaction time is 0.1 to 72 hours, preferably 0.1 to 24 hours.

In carrying out the Preparation method (c) and Step 1 of the Preparation method (a), for example, a compound of the Formula (I-B) and/or Formula (I-C) can be obtained by reacting relative to 1 mole of a compound of the Formula (II) with 1 to 5 molar amounts of an oxidizing agent, such as potassium permanganate, in the presence of 1 to 5 molar amounts of a phase transfer catalyst, such as benzyltriethylammonium chloride, in a diluent, such as dichloromethane.

The diluent which can be used in the reaction of Step 2 in the Preparation method (a) are for example aliphatic hydrocarbons (e.g. hexane, cyclohexane, heptane), aliphatic halogenated hydrocarbons (e.g. dichloromethane, chloroform, carbon tetrachloride, dichloroethane), aromatic hydrocarbons (e.g. benzene, toluene, xylene, chlorobenzene), ethers (e.g. diethyl ether, dibutyl ether, dimethoxyethane (DME), tetrahydrofuran, dioxane), alcohols (e.g. methanol, ethanol, isopropanol, tert-butyl alcohol), water or a mixture of the diluents.

The reaction of Step 2 of the Preparation method (a) can be carried out over a substantially wide range of temperatures. It may be generally carried out at the temperature ranging from about −100° C. to about 200° C., preferably from −78° C. to 100° C. Furthermore, the reaction is preferably carried out under normal pressure. However, it may be carried out under reduced or elevated pressure. The reaction time is 0.1 to 72 hours, and preferably 0.1 to 24 hours.

In carrying out Step 2 of the Preparation method (a), for example, a compound of the Formula (I-A) or Formula (I-A') can be obtained by reacting relative to 1 mole of the compound of the Formula (I-B) or the Formula (I-C) with 1 to 10 molar amounts of a reducing agent, such as diisobutylaluminum hydride, in a diluent, such as dichloromethane.

Similar reactions are described in Organic Letters, 2010, 1252-1254; Tetrahedron, 1999, 5623-5634, and Journal of the Organic Chemistry, 2008, 3946-3949.

The invention is further directed to a method wherein compounds of the Formula (II) are oxidized in one step to obtain compounds of the Formula (I-A) and/or Formula (I-A'). This method will be further summarized under "Preparation method (b)".

The reaction of the Preparation method (b) can be carried out in the presence of an appropriate diluent, and examples of the diluent which can be used include aliphatic hydrocarbons (hexane, cyclohexane, heptane), halogenated aliphatic hydrocarbons (dichloromethane, chloroform, carbon tetrachloride, dichloroethane), aromatic hydrocarbons (benzene, toluene, xylene, chlorobenzene), ethers (diethyl ether, dibutyl ether, dimethoxyethane (DME), tetrahydrofuran, dioxane), esters (ethyl acetate, ethyl propionate, etc.), acid amides (dimethylformamide (DMF), dimethylacetamide (DMA), N-methylpyrrolidone), nitriles (acetonitrile, propionitrile), dimethyl sulfoxide (DMSO), tert-butyl alcohol, carboxylic acids (acetic acid, propionic acid, trifluoroacetic acid), water or a mixture of the diluents.

Similar to the Preparation method (c), the oxidation reaction in Preparation method (b) can be carried out by using an oxidizing agent such as manganese dioxide, cerium ammonium nitrate (IV) (CAN), 2,3-dichloro-5,6-dicyano-1,4-benzoquinone (DDQ), tetrachloro-1,2-benzoquinone (o-Chloranil), tetrachloro-1,4-benzoquinone (Chloranil), iodosobenzene, pentafluoroiodosobenzene, hydrogen peroxide, air (oxygen).

Similar to the Preparation method (c), the reaction of the Preparation method (b) can be also carried out, if necessary, by using a catalyst, such as a transition metal catalyst (e.g. N',N'-bis(salicylidene)ethylenediamine iron (II)), or an acid catalyst (e.g. acetic acid, trifluoroacetic acid, silica gel).

Similar reactions are described in Heterocycles, 2003, 551-555; Tetrahedron letters, 1983, 2213-2216; Journal of the Organic Chemistry, 1991, 1981-1983 and Chemical & Pharmaceutical Bulletin, 1990, 532-533.

The reaction of the Preparation method (b) can be carried out over a substantially wide range of temperatures. It may be generally carried out at the temperature ranging from about −78° C. to about 200° C., preferably from about −10° C. to about 150° C. Furthermore, the reaction is preferably carried out under normal pressure. However, it may be carried out under reduced or elevated pressure. The reaction time is 0.1 to 72 hours, and preferably 0.1 to 24 hours.

For carrying out the Preparation method (b), for example, a compound of the Formula (I-A) which is within the compounds of the Formula (I) of the invention can be obtained by reacting relative to 1 mole of the compound of the Formula (II) with 1 to 5 molar amounts of an oxidizing agent, such as iodosobenzene, in a diluent, such as dichloromethane, in the presence of 0.01 to 1 molar amounts of N',N'-bis(salicylidene)ethylenediamine iron (II).

Preferred compounds of Formula (II) to be used for the Preparation method (a) or (b) according to the invention are compounds having one of the following Formula (II-a) to (II-e), wherein $X^1$, $X^2$, $X^4$, and $Y^2$, $R^3$, $R^4$, $R^5$, $R^7$ are as defined herein for the compounds of Formula (I).

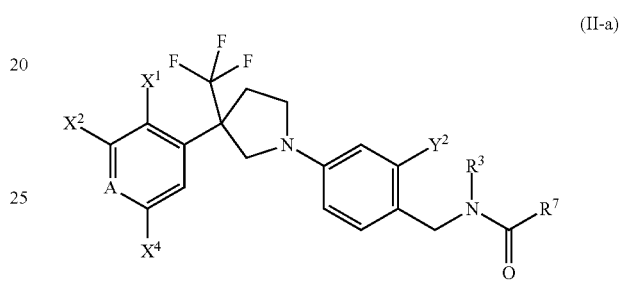

(II-a)

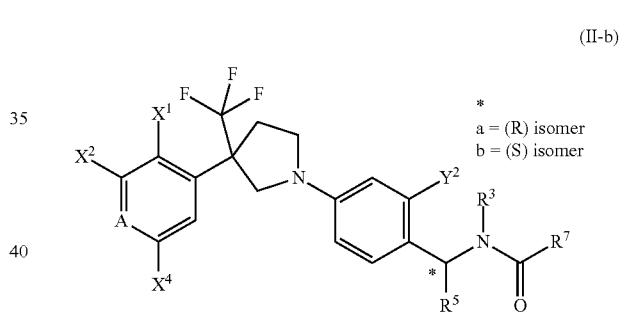

(II-b)

a = (R) isomer
b = (S) isomer

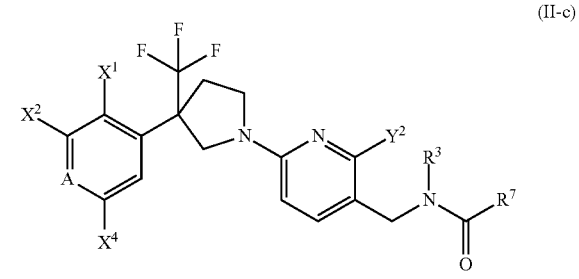

(II-c)

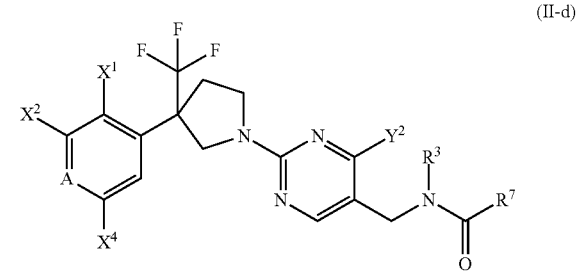

(II-d)

(II-e)

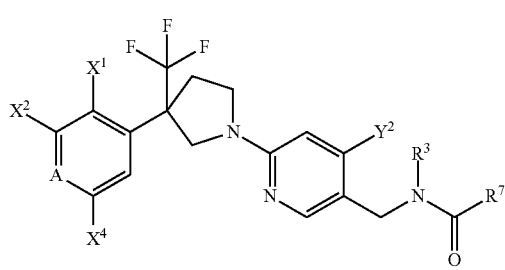

Precursors for the preparation of compounds of Formula (II) are compounds having one of the following Formula (p-II-a) to (p-II-d), wherein $X^1$, $X^2$, A and $Y^2$, $R^3$, $R^4$, $R^5$, $R^7$ and T are as defined herein for the compounds or Formula (I) and for the compound of Formula (Int.).

(p-II-a)

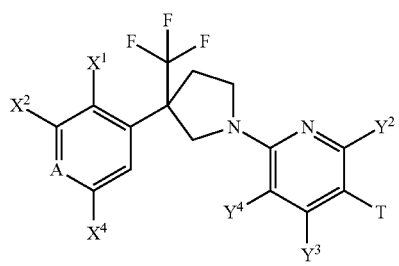

(p-II-b)

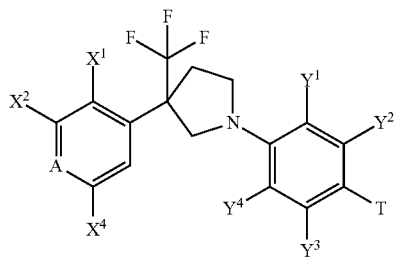

(p-II-c)

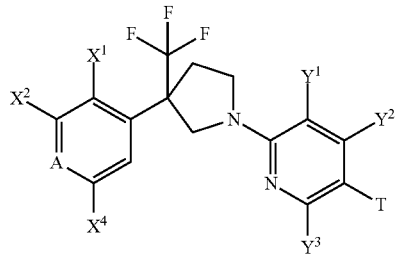

(p-II-d)

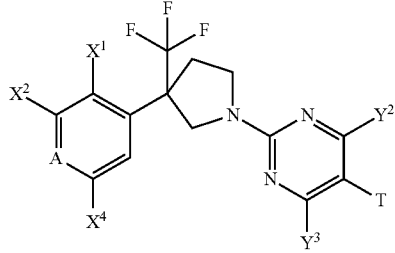

The invention is also directed to the use of compounds of Formula (Int.) for the preparation of compounds according to the invention as well as to a intermediate compound of Formula (Int.)

(Int.)

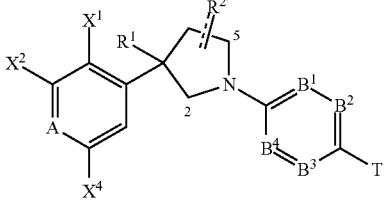

wherein $X^1$, $X^2$, A, $X^4$, $R^1$, $B^1$ to $B^4$ and the dotted line are as defined herein for the compounds of Formula (I), $R^{2'}$ is hydroxy or oxo; $R^{2'}$ preferably is 2-hydroxy, 5-hydroxy, 2-oxo or 5-oxo ("2-" and "5-" marks the positions at pyrrolidine ring); and T is hydrogen, halogen, cyano or is one of the following chemical moieties T-1, T-2, T-3, or T-4:

(T-1)

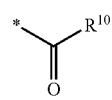

(T-2)

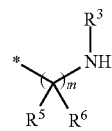

(T-3)

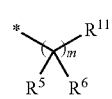

(T-3)

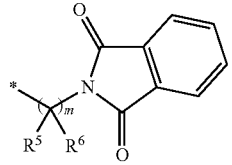

wherein

* marks the binding site to the chemical moiety (a);

$R^3$, $R^5$, $R^6$, and m are as defined herein for the compounds of Formula (I);

$R^{10}$ is hydrogen, hydroxy, fluorine, chlorine, bromine, $C_{1-4}$ alkoxy or $C_{1-4}$ haloalkoxy; and $R^{11}$ is hydroxyl, azide, $C_{1-4}$ alkylsulfonyloxy, $C_{1-4}$ haloalkylsulfonyloxy or optionally substituted arylsulfonyloxy; T preferably is cyano, hydrogen, fluorine, chlorine, bromine, or is a chemical moiety T-1 wherein $R^{10}$ is hydroxy, methoxy, ethoxy, or hydrogen; or is a chemical moiety T-2 wherein $R^3$, $R^5$, and $R^6$ are hydrogen and m is 1.

Compounds having one of the following Formula (Int-a) to (Int-p), wherein $X^1$, $X^2$, A, $X^4$, $R^1$, $B^1$ to $B^4$ and the dotted line, $R^{2'}$, T, $R^{10}$ and $R^{11}$ are as defined herein for the compounds of Formula (I) are preferably used for the preparation of compounds according to the invention and are therefore preferred intermediates.

(Int-a)
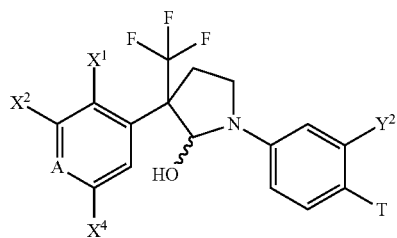
(Int-b)
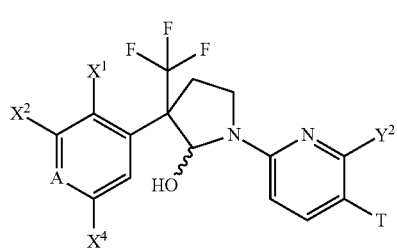
(Int-c)
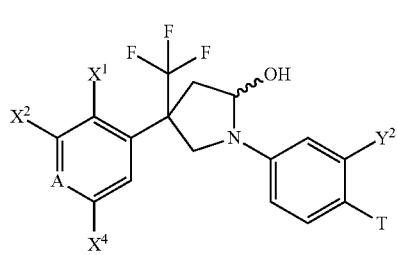
(Int-d)
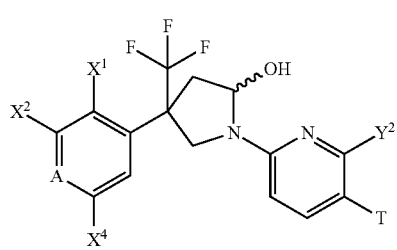
(Int-e)
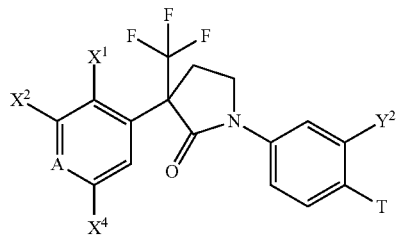
(Int-f)
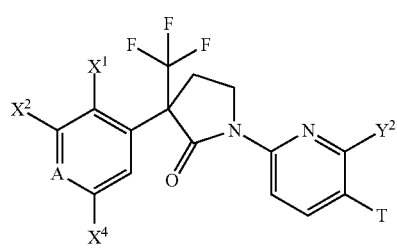
-continued
(Int-g)
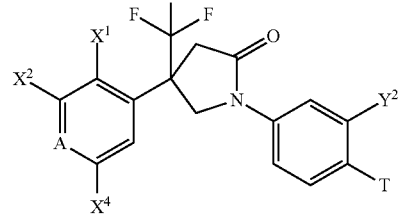
(Int-h)
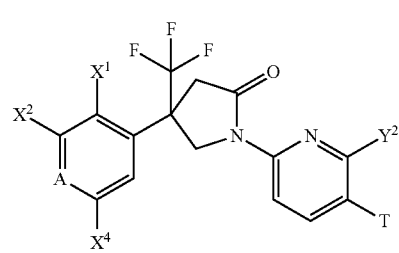
(Int-i)
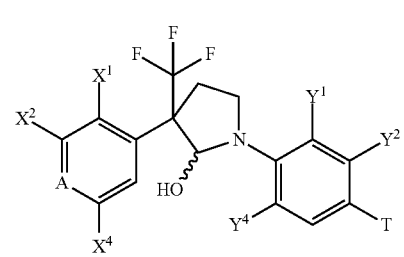
(Int-j)
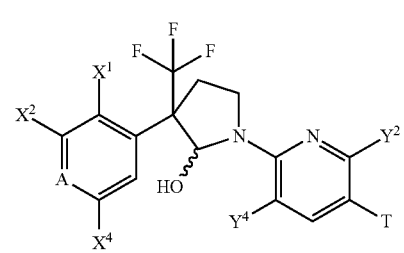
(Int-k)
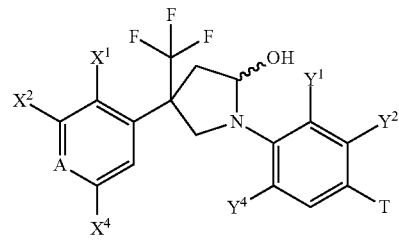
(Int-l)
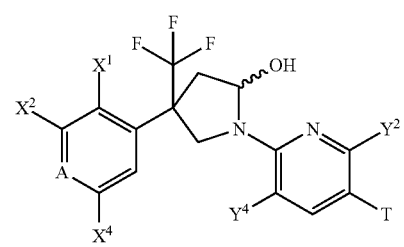

(Int-m)
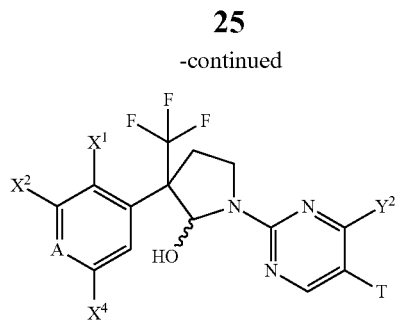
(Int-n)
(Int-o)
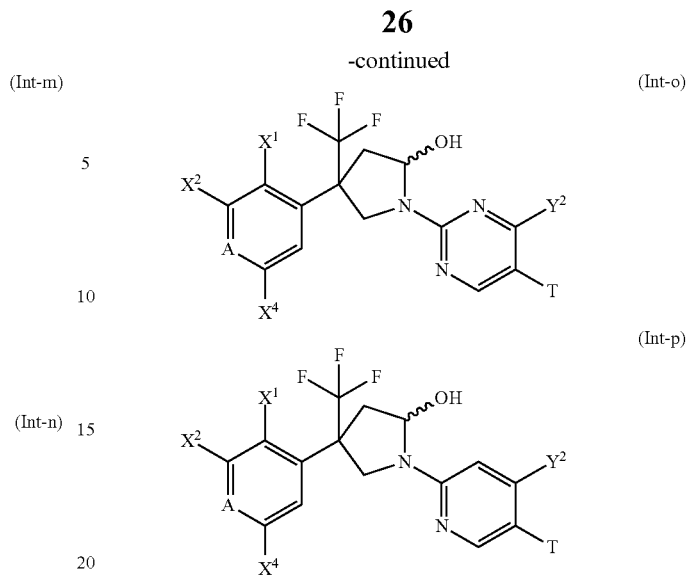
(Int-p)
The use of the compounds of Formula (Int.) is exemplified in the following Reaction Schemes 1 and 2 and is summarized under "Preparation method (b)"
Reaction Scheme 1:
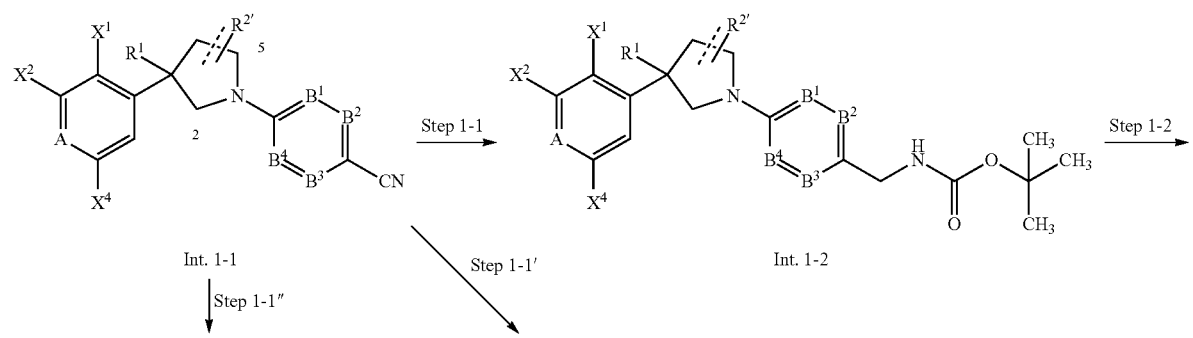
Int. 1-1    Step 1-1′    Int. 1-2
Step 1-1″
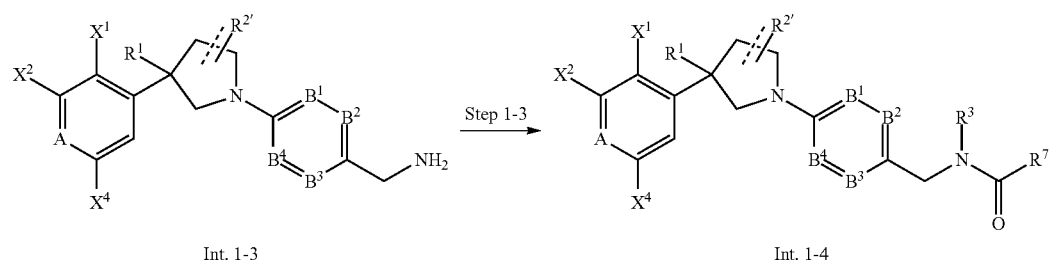
Int. 1-3    Int. 1-4 wherein in the respective Formula $X^1$, $X^2$, A, $X^4$, $R^1$, $B^1$ to $B^4$, $R^3$, $R^7$ and the dotted line are as defined herein for the compounds of Formula (I), and wherein $R^{2'}$ is hydrogen, 2-hydroxy, 5-hydroxy, 2-oxo, or 5-oxo.

Reaction Scheme 2:

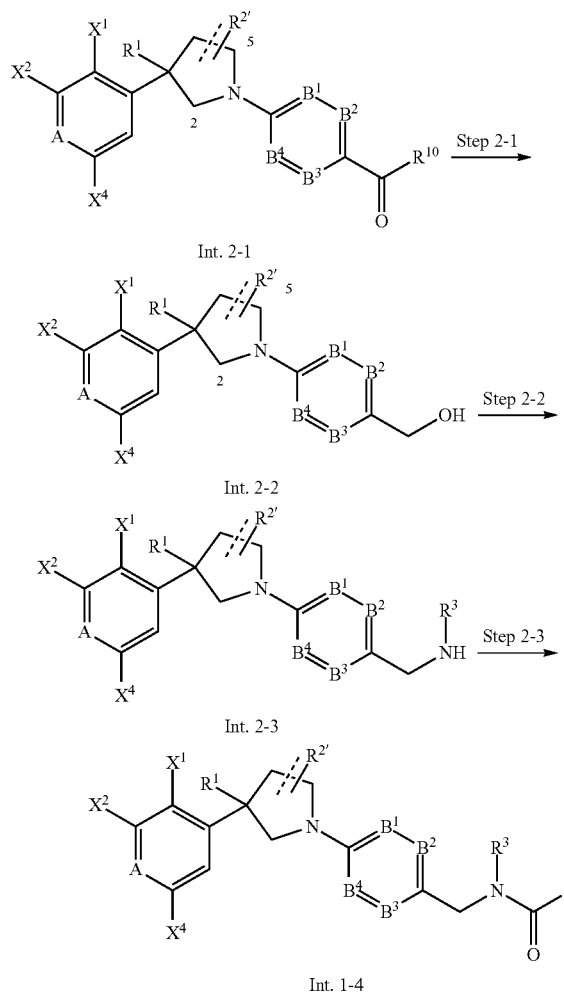

wherein in the respective Formula $X^1$, $X^2$, A, $X^4$, $R^1$, $R^{2'}$, $R^7$, $B^1$ to $B^4$, $R^3$ and the dotted line are as defined herein, and wherein $R^{10}$ is hydrogen, hydroxy, fluoro, chloro, bromo, $C_{1-4}$ alkoxy or $C_{1-4}$ haloalkoxy.

In Reaction Scheme 1 and 2, the reductive acylation of Steps 1-1 or Step 1-1', the reduction in Step 1-1'', the deprotection in Step 1-2, and the acylation and/or alkylation in Step 1-3, as well as the reduction of Step 2-1, the amination of Step 2-2 and the acylation and/or alkylation of Step 2-3 can be carried out according to the methods described in WO 2010/043315.

Any intermediate which are named in Reaction Scheme 1 as Int. 1-1, Int. 1-2, or Int. 1-4 or in Reaction Scheme 2 as Int. 2-1, Int. 2-2, Int. 2-3 and Int. 1-4 can be either oxidized and subsequently reduced or oxidized.

For example: The intermediate Int. 1-1 wherein $R^{2'}$ is hydrogen can be oxidized to give Int. 1-1 wherein $R^{2'}$ is 2-oxo, followed by the reduction of Step 1-1 to give Int. 1-2 wherein $R^{2'}$ represents 2-oxo. Int. 1-2 is then further reduced to give Int. 1-2 wherein $R^{2'}$ represents 2-hydroxy. The compound is then subjected to the reaction of Step 1-2, followed by the reaction of Step 1-3.

For example, the intermediate Int. 2-1 wherein $R^{2'}$ represents hydrogen is oxidized to give Int. 2-1 wherein $R^{2'}$ is 2-hydroxy, and then this compound is subjected to the reaction of Step 2-2 followed by the reaction of Step 2-3 are carried out.

Int. 2-1 wherein $R^{2'}$ is hydrogen and $R^{10}$ is hydrogen, and which is the starting material in Reaction Scheme 2, can also be synthesized according to the methods described Tetrahedron, 2002, 58, 3409-3415.

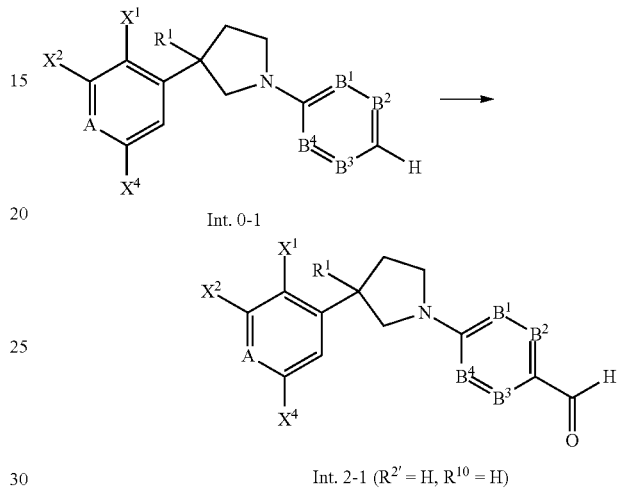

Int. 0-1 can be synthesized according to WO 2010/043315.

Int. 1-1 wherein $R^{2'}$ is hydrogen, which is the starting material in Reaction Scheme 1, can also be synthesized according to the methods described in Journal of Medicinal Chemistry, 2007, 50, 3730-3742.

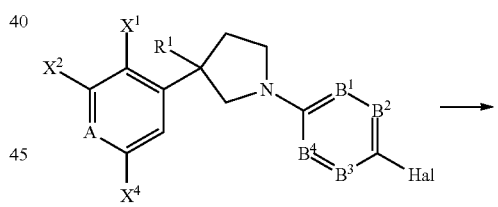

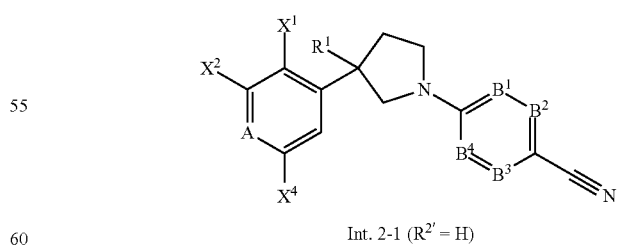

wherein Hal is halogen.

Int. 0-2 can be obtained according to the methods described in Bioorganic & Medicinal Chemistry, 2003, 11, 4921-4931 or Journal of Medicinal Chemistry, 2007, 50, 3730-3742, namely by reacting Int. 0-1 with a halogenating agent.

The methods according to the invention are further exemplified below without limiting the methods to the examples.

Example of Step 1 of the Preparation Method (a)

Oxidation of N-{4-[3-(3,4,5-trichlorophenyl)-3-(trifluoromethyl)pyrrolidin-1-yl]-2-(trifluoromethyl)-benzyl}propanamide with KMnO₄ permanganate

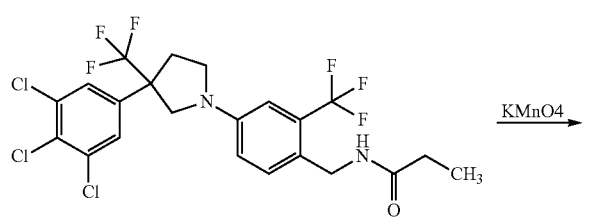

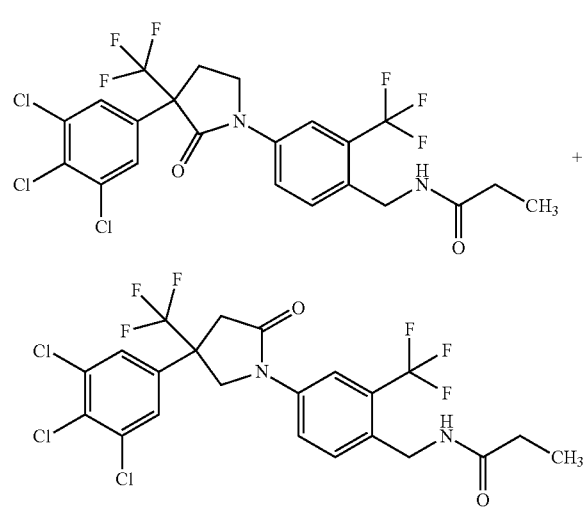

Example of Step 2 of the Preparation Method (a)

Reduction of tert-butyl (4-{3-[3,5-bis-(trifluoromethyl)phenyl]-2-oxo-3-(trifluoromethyl)pyrrolidin-1-yl}-2-chlorobenzyl)-carbamate with diisobutylaluminum hydride

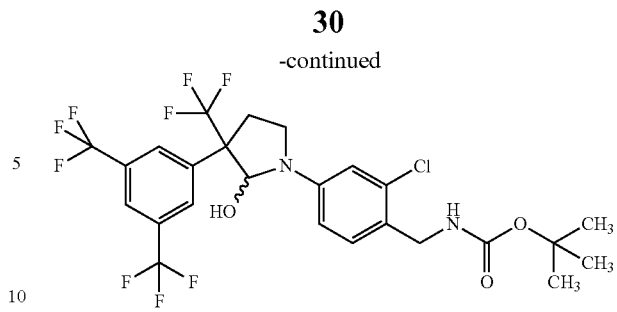

Example of the Preparation Method (b) and Preparation Method (c)

Reacting N-[(1S)-1-(4-{3-[3,5-bis(trifluoromethyl)phenyl]-3-(trifluoromethyl)pyrrolidin-1-yl}phenyl)-ethyl]cyclopropanecarboxamide, with a reducing agent, namely N',N'-bis(salicylidene)ethylenediamine iron(II) and iodosobenzene

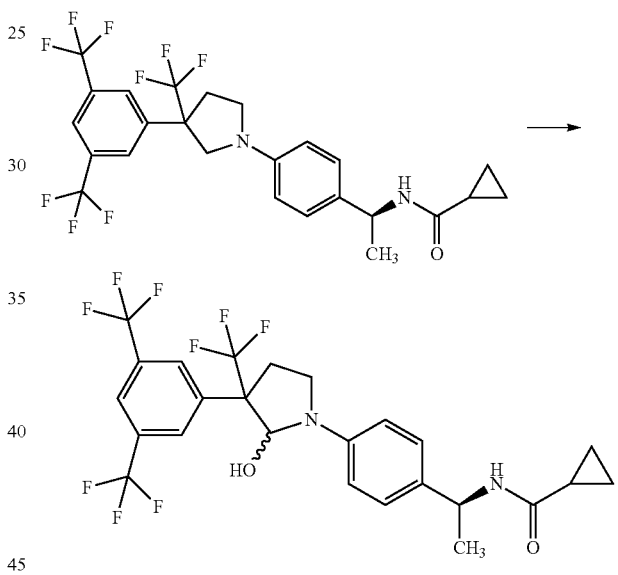

Compounds of the Formula (II) which are used as starting materials in the Preparation methods according to the invention (in particular Preparation methods (a), (b) and (c)) are known and can be prepared according to the method described in WO 2008/128711, WO 2010/020522, WO 2010/043315, JP 2008-110971A.

Examples of compounds of Formula (II) include N-{2-chloro-4-[3-(3,5-dichlorophenyl)-3-(trifluoromethyl)pyrrolidin-1-yl]benzyl}acetamide, N-{2-chloro-4-[3-(3,5-dichlorophenyl)-3-(trifluoromethyl)pyrrolidin-1-yl]benzyl}propanamide, N-{2-chloro-4-[3-(3,5-dichlorophenyl)-3-(trifluoromethyl)pyrrolidin-1-yl]benzyl}-cyclopropanecarboxamide, N-{2-chloro-4-[3-(3,4,5-trichlorophenyl)-3-(trifluoromethyl)pyrrolidin-1-yl]benzyl}acetamide, N-{2-chloro-4-[3-(3,4,5-trichlorophenyl)-3-(trifluoromethyl)pyrrolidin-1-yl]benzyl}propanamide, N-{2-chloro-4-[3-(3,4,5-trichlorophenyl)-3-(trifluoromethyl)pyrrolidin-1-yl]benzyl}cyclopropanecarboxamide, N-(4-{3-[3,5-bis(trifluoromethyl)phenyl]-3-(trifluoromethyl)pyrrolidin-1-yl}-2-chlorobenzyl)acetamide, N-(4-{3-[3,5-bis (trifluoromethyl)phenyl]-3-(trifluoromethyl)pyrrolidin-1-yl}-2-chlorobenzyl)propanamide, N-(4-{3-[3,5-bis(trifluoromethyl)phenyl]-3-(trifluoromethyl)pyrrolidin-1-yl}-2-chlorobenzyl)cyclopropanecarboxamide, N-{2-chloro-4-[3-(3,5-dichloro-2,4-difluorophenyl)-3-(trifluoromethyl)pyrrolidin-1-yl]benzyl}acetamide, N-{2-chloro-4-[3-(3,5-dichloro-2,4-difluorophenyl)-3-(trifluoromethyl)pyrrolidin-1-yl]benzyl}propanamide, N-{2-bromo-4-[3-(3,5-dichloro-2,4-difluorophenyl)-3-(trifluoromethyl)pyrrolidin-1-yl]benzyl}cyclopropanecarboxamide, N-{2-bromo-4-[3-(3,5-dichlorophenyl)-3-(trifluoromethyl)pyrrolidin-1-yl]benzyl}acetamide, N-{2-bromo-4-[3-(3,5-dichlorophenyl)-3-(trifluoromethyl)pyrrolidin-1-yl]benzyl}propanamide, N-{2-bromo-4-[3-(3,5-dichlorophenyl)-3-(trifluoromethyl)pyrrolidin-1-yl]benzyl}-cyclopropanecarboxamide, N-{2-bromo-4-[3-(3,4,5-trichlorophenyl)-3-(trifluoromethyl)pyrrolidin-1-yl]benzyl}acetamide, N-{2-bromo-4-[3-(3,4,5-trichlorophenyl)-3-(trifluoromethyl)pyrrolidin-1-yl]benzyl}-propanamide, N-{2-bromo-4-[3-(3,4,5-trichlorophenyl)-3-(trifluoromethyl)pyrrolidin-1-yl]benzyl}-cyclopropanecarboxamide, N-(4-{3-[3,5-bis(trifluoromethyl)phenyl]-3-(trifluoromethyl)pyrrolidin-1-yl}-2-chlorobenzyl)acetamide, N-(4-{3-[3,5-bis(trifluoromethyl)phenyl]-3-(trifluoromethyl)pyrrolidin-1-yl}-2-bromobenzyl)propanamide, N-(4-{3-[3,5-bis(trifluoromethyl)phenyl]-3-(trifluoromethyl)pyrrolidin-1-yl}-2-bromo-benzyl)cyclopropane carboxamide, N-{2-bromo-4-[3-(3,5-dichloro-2,4-difluorophenyl)-3-(trifluoromethyl)pyrrolidin-1-yl]benzyl}acetamide, N-{2-bromo-4-[3-(3,5-dichloro-2,4-difluorophenyl)-3-(trifluoromethyl)pyrrolidin-1-yl]benzyl}propanamide, N-{2-bromo-4-[3-(3,5-dichloro-2,4-difluorophenyl)-3-(trifluoromethyl)pyrrolidin-1-yl]benzyl}cyclopropanecarboxamide, N-{4-[3-3,5-dichlorophenyl)-3-(trifluoromethyl)pyrrolidin-1-yl]-2-(trifluoromethyl)-benzyl}acetamide, N-{4-[3-(3,5-dichlorophenyl)-3-(trifluoromethyl)pyrrolidin-1-yl]-2-(trifluoromethyl)benzyl}propanamide, N-{4-[3-(3,5-dichlorophenyl)-3-(trifluoromethyl)pyrrolidin-1-yl]-2-(trifluoromethyl)benzyl}cyclopropanecarboxamide, N-{4-[3-(3,4,5-trichlorophenyl)-3-(trifluoromethyl)pyrrolidin-1-yl]-2-(trifluoro-methyl)benzyl}acetamide, N-{4-[3-(3,4,5-trichlorophenyl)-3-(trifluoromethyl)pyrrolidin-1-yl]-2-(trifluoromethyl)benzyl}propanamide, N-{4-[3-(3,4,5-trichlorophenyl)-3-(trifluoromethyl)pyrrolidin-1-yl]-2-(trifluoromethyl)benzyl}cyclopropanecarboxamide, N-[4-{3-[3,5-bis(trifluoromethyl)phenyl]-3-(trifluoromethyl)pyrrolidin-1-yl}-2-(trifluoromethyl)benzyl]acetamide, N-[4-{3-[3,5-bis(trifluoromethyl)phenyl]-3-(trifluoromethyl)pyrrolidin-1-yl}-2-(trifluoromethyl)benzyl}propanamide, N-[4-{3-[3,5-bis(trifluoromethyl)phenyl]-3-(trifluoromethyl)pyrrolidin-1-yl}-2-(trifluoromethyl)benzyl]cyclopropanecarboxamide, N-{4-[3-(3,5-dichloro-2,4-difluorophenyl)-3-(trifluoromethyl)pyrrolidin-1-yl]-2-(trifluoromethyl)benzyl}acetamide, N-{4-[3-(3,5-dichloro-2,4-difluorophenyl)-3-(trifluoromethyl)pyrrolidin-1-yl]-2-(trifluoromethyl)benzyl}propanamide, N-{4-[3-(3,5-dichloro-2,4-difluorophenyl)-3-(trifluoromethyl)pyrrolidin-1-yl]-2-(trifluoromethyl)benzyl}cyclopropanecarboxamide, N-(1-{4-[3-(3,5-dichlorophenyl)-3-(trifluoromethyl)pyrrolidin-1-yl]phenyl}ethyl)acetamide, N-(1-{4-[3-(3,5-dichlorophenyl)-3-(trifluoromethyl)pyrrolidin-1-yl]phenyl}ethyl)propanamide, N-(1-{4-[3-(3,5-dichlorophenyl)-3-(trifluoromethyl)pyrrolidin-1-yl]phenyl}ethyl)cyclopropanecarboxamide, N-(1-{4-[3-(3,4,5-trichlorophenyl)-3-(trifluoromethyl)pyrrolidin-1-yl]phenyl}ethyl)acetamide, N-(1-{4-[3-(3,4,5-trichlorophenyl)-3-(trifluoromethyl)pyrrolidin-1-yl]phenyl}ethyl)propanamide, N-(1-{4-[3-(3,4,5-trichlorophenyl)-3-(trifluoromethyl)pyrrolidin-1-yl]phenyl}ethyl)cyclopropanecarboxamide, N-[1-(4-{3-[3,5-bis(trifluoromethyl)phenyl]-3-(trifluoromethyl)pyrrolidin-1-yl}phenyl)ethyl]acetamide, N-[1-(4-{3-[3,5-bis(trifluoromethyl)phenyl]-3-(trifluoromethyl)pyrrolidin-1-yl}phenyl)ethyl]propanamide, N-[1-(4-{3-[3,5-bis(trifluoromethyl)phenyl]-3-(trifluoromethyl)pyrrolidin-1-yl}phenyl)ethyl]cyclopropanecarboxamide, N-[(1S)-1-(4-{3-[3,5-bis(trifluoromethyl)phenyl]-3-(trifluoromethyl)pyrrolidin-1-yl}phenyl)ethyl]cyclopropanecarboxamide, N-[(1S)-1-(4-{3-[2,6-bis(trifluoromethyl)pyridin-4-yl]-3-(trifluoromethyl)pyrrolidin-1-yl}phenyl)ethyl]cyclopropanecarboxamide, N-({6-[3-(3,5-dichlorophenyl)-3-(trifluoromethyl)pyrrolidin-1-yl]-2-(trifluoromethyl)pyridin-3-yl}methyl)acetamide, N-({6-[3-(3,5-dichlorophenyl)-3-(trifluoromethyl)pyrrolidin-1-yl]-2-(trifluoromethyl)pyridin-3-yl}methyl)propanamide, N-({6-[3-(3,5-dichlorophenyl)-3-(trifluoromethyl)pyrrolidin-1-yl]-2-(trifluoromethyl)pyridin-3-yl}methyl)cyclopropane carboxamide, N-({6-[3-(3,4,5-trichlorophenyl)-3-(trifluoromethyl)pyrrolidin-1-yl]-2-(trifluoromethyl)pyridin-3-yl}methyl)acetamide, N-({6-[3-(3,4,5-trichlorophenyl)-3-(trifluoromethyl)pyrrolidin-1-yl]-2-(trifluoromethyl)pyridin-3-yl}methyl)propanamide, N-({6-[3-(3,4,5-trichlorophenyl)-3-(trifluoromethyl)pyrrolidin-1-yl]-2-(trifluoromethyl)pyridin-3-yl}methyl)cyclopropane carboxamide, N-{[6-{3-[3,5-bis(trifluoromethyl)phenyl]-3-(trifluoromethyl)pyrrolidin-1-yl]-2-(trifluoromethyl)pyridin-3-yl]methyl}acetamide, N-{[6-[3-[3,5-bis(trifluoromethyl)phenyl]-3-(trifluoromethyl)pyrrolidin-1-yl]-2-(trifluoromethyl)pyridin-3-yl]methyl}propanamide, N-{[6-[3-[3,5-bis(trifluoromethyl)phenyl]-3-(trifluoromethyl)pyrrolidin-1-yl]-2-(trifluoromethyl)pyridin-3-yl]methyl}cyclopropanecarboxamide, N-({6-[3-(3,5-dichloro-2,4-difluorophenyl)-3-(trifluoromethyl)pyrrolidin-1-yl]-2-(trifluoromethyl)pyridin-3-yl}methyl)acetamide, N-({6-[3-(3,5-dichloro-2,4-difluorophenyl)-3-(trifluoromethyl)pyrrolidin-1-yl]-2-(trifluoromethyl)pyridin-3-yl}methyl)propanamide, N-({6-[3-(3,5-dichloro-2,4-difluorophenyl)-3-(trifluoromethyl)pyrrolidin-1-yl]-2-(trifluoromethyl)pyridin-3-yl}methyl)cyclopropanecarboxamide, N-({2-[3-(3,5-dichlorophenyl)-3-(trifluoromethyl)pyrrolidin-1-yl]-4-(difluoromethyl)pyrimidin-5-yl}methyl)acetamide, N-({2-[3-(3,5-dichlorophenyl)-3-(trifluoromethyl)pyrrolidin-1-yl]-4-(difluoromethyl)pyrimidin-5-yl}methyl)propanamide, N-({2-[3-(3,5-dichlorophenyl)-3-(trifluoromethyl)pyrrolidin-1-yl]-4-(difluoromethyl)pyrimidin-5-yl}methyl)cyclopropanecarboxamide, N-({2-[3-(3,4,5-trichlorophenyl)-3-(trifluoromethyl)pyrrolidin-1-yl]-4-(difluoromethyl)pyrimidin-5-yl}methyl)acetamide, N-({2-[3-(3,4,5-trichlorophenyl)-3-(trifluoromethyl)pyrrolidin-1-yl]-4-(difluoromethyl)pyrimidin-5-yl}methyl)propanamide, N-({2-[3-(3,4,5-trichlorophenyl)-3-(trifluoromethyl)pyrrolidin-1-yl]-4-(difluoromethyl)pyrimidin-5-yl}methyl)cyclopropanecarboxamide, N-{[2-{3-[3,5-bis(trifluoromethyl)phenyl]-3-(trifluoromethyl)pyrrolidin-1-yl]-4-(difluoromethyl)pyrimidin-5-yl]methyl}acetamide, N-{[2-{3-[3,5-bis(trifluoromethyl)phenyl]-3-(trifluoro-methyl)pyrrolidin-1-yl]-4-(difluoromethyl)pyrimidin-5-yl]methyl}propanamide, N-{[2-{3-[3,5-bis(trifluoromethyl)phenyl]-3-(trifluoromethyl)pyrrolidin-1-yl]-4-(difluoromethyl)pyrimidin-5-yl]methyl}cyclopropanecarboxamide, N-({2-[3-(3,5-dichloro-2,4-difluorophenyl)-3-(trifluoromethyl)pyrrolidin-1-yl]-4-

(difluoromethyl)pyrimidin-5-yl}methyl)acetamide, N-({2-[3-(3,5-dichloro-2,4-difluorophenyl)-3-(trifluoromethyl)pyrrolidin-1-yl]-4-(difluoromethyl)pyrimidin-5-yl}methyl)propanamide, N-({2-[3-(3,5-dichloro-2,4-difluorophenyl)-3-(trifluoromethyl)pyrrolidin-1-yl]-4-(difluoromethyl)pyrimidin-5-yl}methyl)cyclopropanecarboxamide, N-({2-[3-(3,5-dichlorophenyl)-3-(trifluoromethyl)pyrrolidin-1-yl]-4-(trifluoromethyl)pyrimidin-5-yl}methyl)acetamide, N-({2-[3-(3,5-dichlorophenyl)-3-(trifluoromethyl)pyrrolidin-1-yl]-4-(trifluoromethyl)pyrimidin-5-yl}methyl)propanamide, N-({2-[3-(3,5-dichlorophenyl)-3-(trifluoromethyl)pyrrolidin-1-yl]-4-(trifluoromethyl)pyrimidin-5-yl}methyl)cyclopropanecarboxamide, N-({2-[3-(3,4,5-trichlorophenyl)-3-(trifluoromethyl)pyrrolidin-1-yl]-4-(trifluoromethyl)pyrimidin-5-yl}methyl)acetamide, N-({2-[3-(3,4,5-trichlorophenyl)-3-(trifluoromethyl)pyrrolidin-1-yl]-4-(trifluoro-methyl)pyrimidin-5-yl}methyl)propanamide, N-({2-[3-(3,4,5-trichlorophenyl)-3-(trifluoromethyl)pyrrolidin-1-yl]-4-(trifluoromethyl)pyrimidin-5-yl}methyl)cyclopropanecarboxamide, N-({2-{3-[3,5-bis(trifluoromethyl)phenyl]-3-(trifluoromethyl)pyrrolidin-1-yl}-4-(trifluoromethyl)pyrimidin-5-yl]methyl}acetamide, N-{[2-{3-[3,5-bis(trifluoromethyl)phenyl]-3-(trifluoromethyl)pyrrolidin-1-yl}-4-(trifluoromethyl)pyrimidin-5-yl]methyl}propanamide, N-{[2-[3-[3,5-bis(trifluoromethyl)phenyl]-3-(trifluoromethyl)pyrrolidin-1-yl]-4-(trifluoromethyl)pyrimidin-5-yl]methyl}cyclopropanecarboxamide, N-({2-[3-(3,5-dichloro-2,4-difluorophenyl)-3-(trifluoromethyl)pyrrolidin-1-yl]-4-(trifluoromethyl)pyrimidin-5-yl}methyl)acetamide, N-({2-[3-(3,5-dichloro-2,4-difluorophenyl)-3-(trifluoromethyl)pyrrolidin-1-yl]-4-(trifluoromethyl)pyrimidin-5-yl}methyl)propanamide, N-({2-[3-(3,5-dichloro-2,4-difluorophenyl)-3-(trifluoromethyl)pyrrolidin-1-yl]-4-(trifluoromethyl)pyrimidin-5-yl}methyl)cyclopropanecarboxamide, N-({6-[3-(3,5-dichlorophenyl)-3-(trifluoromethyl)pyrrolidin-1-yl]-4-(trifluoromethyl)pyridin-3-yl}methyl)acetamide, N-({6-[3-(3,5-dichlorophenyl)-3-(trifluoro-methyl)pyrrolidin-1-yl]-4-(trifluoromethyl)pyridin-3-yl}methyl)propanamide, N-({6-[3-(3,5-di-chlorophenyl)-3-(trifluoromethyl)pyrrolidin-1-yl]-4-(trifluoromethyl)pyridin-3-yl}methyl)cyclopropanecarboxamide, N-({6-[3-(3,4,5-trichlorophenyl)-3-(trifluoromethyl)pyrrolidin-1-yl]-4-(trifluoromethyl)pyridin-3-yl}methyl)acetamide, N-({6-[3-(3,4,5-trichlorophenyl)-3-(trifluoromethyl)pyrrolidin-1-yl]-4-(trifluoromethyl)pyridin-3-yl}methyl)propanamide, N-({6-[3-(3,4,5-trichlorophenyl)-3-(trifluoromethyl)pyrrolidin-1-yl]-4-(trifluoromethyl)pyridin-3-yl}methyl)cyclopropanecarboxamide, N-{[6-[3-[3,5-bis(trifluoromethyl)phenyl]-3-(trifluoromethyl)pyrrolidin-1-yl]-4-(trifluoromethyl)pyridin-3-yl]methyl}acetamide, N-{[6-{3-[3,5-bis(trifluoromethyl)phenyl]-3-(trifluoromethyl)pyrrolidin-1-yl]-4-(trifluoromethyl)pyridin-3-yl}methyl}propanamide, N-{[6-{3-[3,5-bis(trifluoromethyl)phenyl]-3-(trifluoromethyl)pyrrolidin-1-yl]-4-(trifluoromethyl)pyridin-3-yl]methyl}cyclopropanecarboxamide, N-({6-[3-(3,5-dichloro-2,4-difluorophenyl)-3-(trifluoromethyl)pyrrolidin-1-yl]-4-(trifluoromethyl)pyridin-3-yl}methyl)acetamide, N-({6-[3-(3,5-dichloro-2,4-difluorophenyl)-3-(trifluoromethyl)pyrrolidin-1-yl]-4-(trifluoromethyl)pyridin-3-yl}methyl)propanamide, N-({6-[3-(3,5-dichloro-2,4-difluorophenyl)-3-(trifluoromethyl)pyrrolidin-1-yl]-4-(trifluoromethyl)pyridin-3-yl}methyl)cyclopropanecarboxamide, N-({2-[3-(3,4,5-trichlorophenyl)-3-(trifluoromethyl)pyrrolidin-1-yl]-4-(trifluoromethyl)-1,3-thiazol-5-yl}methyl)acetamide, N-({2-[3-(3,4,5-trichlorophenyl)-3-(trifluoromethyl)pyrrolidin-1-yl]-4-(trifluoromethyl)-1,3-thiazol-5-yl}methyl)propanamide, N-({2-[3-(3,4,5-trichlorophenyl)-3-(trifluoromethyl)pyrrolidin-1-yl]-4-(trifluoromethyl)-1,3-thiazol-5-yl}methyl)cyclopropanecarboxamide, 5-[3-(3,5-dichlorophenyl)-3-(trifluoromethyl)pyrrolidin-1-yl]-2-(1H-1,2,4-triazol-1-yl)benzonitrile, 2-(1H-1,2,4-triazol-1-yl)-5-[3-(3,4,5-trichlorophenyl)-3-(trifluoromethyl)pyrrolidin-1-yl]benzonitrile.

The compounds of the Formula (I) of the invention exhibit a potent pesticidal effect, and therefore can be used as pesticides. Furthermore, the compounds of the invention exhibit a potent controlling effect against noxious insects without causing any damages on crop plants that are cultivated. Therefore, the compounds of the invention can be used for controlling a wide variety of pests including, for example, harmful sucking insects, chewing insects and other plant parasitic pests, stored grain insects, hygienic pests, etc., and can be applied to control and eradicate these pests. Examples of animal pests are as follows:

As an insect, Coleoptera, for example *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus* and *Aulacophora femoralis*; Lepidoptera, for example, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotisfucosa, Galleria mellonella, Plutella maculipennis, Heliothis virescens* and *Phyllocnistis citrella*; Hemiptera, for example, *Nephotettix cincticeps, Nilaparvata lugens, Pseudococcus comstocki, Unapsis yanonensis, Myzus persicas, Aphis pomi, Aphis gossypii, Rhopalosiphum pseudobrassicas, Stephanitis nashi, Nezara* spp., *Trialeurodes vaporariorm* and *Psylla* spp.; Thysanoptera, for example, *Thrips palmi* and *Franklinella occidental*; Orthoptera, for example, *Blatella germanica, Periplaneta americana, Gryllotalpa Africana* and *Locusta migratoria* migratoriodes; Isoptera, for example, *Reticulitermes speratus* and *Coptotermes formosanus*; Diptera, for example, *Musca domestica, Aedes aegypti, Hylemia platura, Culex pipiens, Anopheles sinensis, Culex tritaeniorhynchus* and *Liriomyza torifolii*. As acarina, for example, *Tetranychus cinnabarinus, Tetranychus urticae, Panonychus citri, Aculops pelekassi* and *Tarsonemus* spp. As nematodes, for example, *Meloidogyne incognita, Bursaphelenchus lignicolus Mamiya et Kiyohara, Aphelenchoides besseyi, Heterodera glycines* and *Pratylenchus* spp.

Further, the compounds of the present invention have good tolerance in plants and low toxicity to warm-blooded animals, as well as being well received by an environment, and accordingly, the compounds of the present invention are appropriate for the protection of plants and plant parts. With application of the compounds of the present invention, both crop yield and quality of harvested products may be improved. In addition, the compounds of the present invention are suitable for protection of preserved products and materials and for a hygiene field, in terms of controlling harmful animals, in particular insects, spider-like animals, helminth, nematodes and mollusks that are encountered in agriculture, horticulture, veterinary medicine, forest, garden and entertainment facilities. The compounds of the present invention can be preferably used as agents for protecting plants. The compounds of the present invention have an activity for normal sensitive species or resistant species, and for all over or several growth stages thereof. In particular, the harmful organisms mentioned above include the followings. From Anoplura (Phthiraptera), for example, *Damalinia* spp., *Haematopinus*, *Linognathus* spp., *Pediculus* spp. and *Trichodectes* spp. From Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranyctus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp. and *Vasates lycopersici*. From Bivalva, for example, *Dreissena* spp. From Chilopoda, for example, *Geophilus* spp. and *Scutigera* spp. From Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp. and *Zabrus* spp. From Collembola, for example, *Onychiurus armatus*). From Dermaptera, for example, *Forficula auricularia*). From Diplopoda, for example, *Blaniulus guttulatus*). From Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus* oleae, *Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa* and *Wohlfahrtia* spp. From Gastropoda, for example, *Anion* spp., *Biomphalaria* spp., *Bulinus* spp., *Deroceras* spp., *Galba* spp., *Lymnaea* spp., *Oncomelania* spp. and *Succinea* spp. From helminthes, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medeinensis, Echinococcus granulosus, Echinococcus multiocularis, Enterobius vermicularis, Faciola* spp., *Haemonchus* spp., *Heterakis* spp., *Hymenolepis nana, Hyostrongulus* spp., *Loa loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria*) and *Wuchereria bancrofti*. Further, Protozoa, such as Eimeria, can be controlled by the compound of the present invention. From Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus*, spp., *Euschistus* spp., *Eurygaster* spp., *Heliopeltis* spp., *Horchias nobiellus, Leptocorisa* spp., *Leptoglossus phyllopus, Lygus* spp., *Macropes excavatus, Miridae, Nezara* spp., *Oebalus* spp., Pentomidae, *Piesma quadrata, Piezodorus* spp., *Psallus seriatus, Pseudacysta persea, Rhodonius* spp., *Sahlbergella singularis, Scotinophora* spp., *Stephanitis nashi, Tibraca* spp. and *Triatoma* spp. From Homoptera, for example, *Acyrthosipon* spp., *Aeneolamia* spp., gonoscena spp., *Aleurodes* spp., *Aleurolobus barodensis*), *Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Chryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratorioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesda gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp. and *Viteus vitifolii*. From Hymenoptera, for example, *Diprion* spp., *Hoplocampa* spp., *Lasius* spp., *Monomorium pharaonis*) and *Vespa* spp. From Isopoda, for example, *Armadillidium vulgare, Oniscus asellus* and *Porcellio scaber*. From Isoptera, for example, *Reticulitermes* spp. and *Odontotermes* spp. From Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flam-* mea, *Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana* and *Trichoplusia* spp. From Orthoptera, for example, *Acheta domesticus, Blatta orientalis, Blattella germanica, Gryllotalpa* spp., *Leucophaea maderae, Locusta* spp., *Melanoplus* spp., *Periplaneta Americana* and *Schistocerca gregaria*. From Siphonaptera, for example, *Ceratophyllus* spp. and *Xenopsylla* cheopis. From Symphyla, for example, *Scutigerella immaculate*. From Thynsanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp. From Thysanura, for example, *Lepisma saccharina*. As plant parasitic nematodes, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Thlenchulus semipenetrans* and *Xiphinema* spp. are included.

Additionally to above mentioned, the active compounds according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in protection of stored products and of materials, and in the hygiene sector. They can be preferably employed as plant protection agents. They are active against normally sensitive and resistant species and against all or some stages of development. The abovementioned pests include:

pests from the phylum Arthropoda, especially from the class Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia graminum, Bryobia praetiosa, Centruroides* spp., *Choriopres* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Glycyphagus domesticus, Halotydeus destructor, Hemitarsonemus* spp., *Hyalomma* spp., *Ixodes* spp., *Latrodectus* spp., *Loxosceles* spp., *Metatetranychus* spp., *Neutrombicula autumnalis, Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., *Tetranychus* spp., *Trombicula alfreddugesi, Vaejovis* spp., *Vasates lycopersici;*
from the class Chilopoda, for example, *Geophilus* spp., *Scutigera* spp.;

from the order or the class Collembola, for example, *Onychiurus armatus;* from the class Diplopoda, for example, *Blaniulus guttulatus;* from the class Insecta, e.g. from the order Blattodea, for example, *Blattella asahinai, Blattella germanica, Blatta orientalis, Leucophaea maderae, Panchlora* spp., *Parcoblatta* spp., *Periplaneta* spp., *Supella longipalpa;* from the order Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptolestes ferrugineus, Cryptorhynchus lapathi, Cylindrocopturus* spp., *Dermestes* spp., *Diabrotica* spp., *Dichocrocis* spp., *Dicladispa armigera, Diloboderus* spp., *Epilachna* spp., *Epitrix* spp., *Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *Lachnosterna consanguinea, Lasioderma serricorne, Latheticus oryzae, Lathridius* spp., *Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllophaga helleri, Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sitophilus oryzae, Sphenophorus* spp., *Stegobium paniceum, Sternechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.;

from the order Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit, Paratanytarsus* spp., *Paralauterborniella subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.;

from the order Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptocorisa varicornis, Leptoglossus phyllopus, Lygus* spp., *Macropes excavatus, Miridae, Monalonion atratum, Nezara* spp., *Oebalus* spp., Pentomidae, *Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order Homoptera, for example, *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis,*

*Amrasca* spp., *Anuraphis cardui*, *Aonidiella* spp., *Aphanostigma piri*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order Isopoda, for example, *Armadillidium vulgare*, *Oniscus asellus*, *Porcellio scaber*;

from the order Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.;

from the order Lepidoptera, for example, *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria*;

from the order Phthiraptera, for example, *Damalinia* spp., *Haematopinus* spp., *Linognathus* spp., *Pediculus* spp., *Ptirus pubis*, *Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans*, *Tunga penetrans*, *Xenopsylla cheopsis*;

from the order Thysanoptera, for example, *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.;

from the order Zygentoma (=Thysanura), for example, *Ctenolepisma* spp., *Lepisma saccharina*, *Lepismodes inquilinus*, *Thermobia domestica*;

from the class Symphyla, for example, *Scutigerella* spp.;

pests from the phylum Mollusca, especially from the class Bivalvia, for example, *Dreissena* spp., and from the class Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests from the phylums Plathelminthes and Nematoda, for example, *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*;

phytoparasitic pests from the phylum Nematoda, for example, *Aphelenchoides* spp., *Bursaphelenchus* spp., *Dity-*

*lenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

It is furthermore possible to control organisms from the subphylum Protozoa, especially from the order Coccidia, such as *Eimeria* spp.

Any kind of plant and plant part can be treated according to the present invention. In the present invention, a plant should be understood as all plants and plant populations including desirable and undesirable wild plants or crop plants (including naturally-occurring crop plants) and the like. As for the crop plants, they can be plants which are obtainable by conventional methods of breeding modified varieties and optimization methods, or biotechnological methods and genetic engineering methods, or by combination of these methods, and they include transgenic plants. In addition, plant varieties which are either protected or not protected by a plant breeder are also included. Plant parts should be understood as all parts and organs of a plant that are present above or under ground. Examples thereof include shoots, leaves, flowers and roots, etc. Specific examples thereof include a leaf, a needle, a stem, a trunk, a flower, a fruit, a fruit body, a seed, a root, a tuber and an underground tuber, etc. The plant parts also include a harvested material and a material which propagates sexually or asexually, for example, a cutting, a tuber, an underground tuber, a side branch and a seed.

Treatment of plants and plant parts with the active compounds according to the present invention can be carried out directly or by using conventional methods such as impregnation, spray, evaporation, particularization, dispersion, coating and injection, or for a propagating material, especially for a seed, by coating it with one or more of the compounds, so that the compounds are applied to their surroundings, habitat environment, or preservation place.

The compounds of the present invention have a penetrating activity and this means that the compounds can penetrate a plant body and can migrate from the underground part to the above-ground part of a plant.

As it has been described above, according to the present invention, all plants and parts thereof can be treated. According to a preferred embodiment for carrying out the invention, wild plant species and plant mutants, or those obtained by traditional plant breeding methods such as hybridization or protoplast fusion, and parts thereof are treated. According to a more preferred embodiment for carrying out the invention, transgenic plants and plant varieties (genetically modified organisms) obtained by conventional methods in appropriate combination with genetic engineering methods, and parts thereof are treated. The terms "parts", "parts of a plant" and "plant parts" are as defined above. Still more preferably, for each specific case, plants of plant varieties that are commercially available or currently in use are treated according to the present invention. Plant varieties are understood as plants having new characteristics ("traits") obtained by conventional breed improvements, introduction of mutation or recombinant DNA techniques. They can be plant varieties, biotypes or genotypes. Depending on plant species or plant varieties, their habitat and growth condition (soil, weather, growth period, nutrition, etc.), the treatment according to the present invention may have a supra-additive ("synergy") effect. Thus, for example, exceeding an expected effect, it is possible to obtain several effects including reduction of application rate and/or broadening of an activity spectrum, and/or increased activity of the material and composition that can be used according to the present invention, improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products. The preferable transgenic plants or plant varieties (obtainable by genetic engineering methods) treated according to the present invention include all kinds of plant having genetic materials that can provide the plants with very advantageous and useful traits based on genetic modifications. Examples of such traits include improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products. Further examples in which such traits are particularly more emphasized include improved protection of plants against harmful animals and harmful microorganisms such as insect, tick, plant pathogenic fungus, bacteria and/or virus, and improved tolerance of plants against compounds having certain type of herbicidal activities. Examples of the transgenic plant include grain crops (barley, rice), corn, soybean, potato, sugar beet, tomato, bean and other modified plant species, useful plants such as cotton, tobacco, rape seed, and fruit plants (fruits like an apple, a pear, a citrus fruit and other fruit-bearing plants like a grape). In particular, corn, soybean, potato, cotton, tobacco and rape seed are important. As for the traits considered to be important, improved plant defense based on toxins produced by plants, in particular based on the toxins produced by plants with an action of genetic materials derived from *Bacillus thuringiensis* (for example, genes including CryIA (a), CryIA(b), CryIA(c), CryIIA, CryIIIA, CryIIIB2, Cry9c, Cry2Ab, Cry3Bb and CryIF, and combination thereof), against insects, spider-like animals, nematodes, slugs, and snails (herein below, referred to as "Bt plant") can be mentioned. Other traits considered to be important include improved plant defense against fungus, bacteria and virus, based on systemic acquired resistance (SAR), systemin, phytoallexin, elicitor, resistance gene and the corresponding protein and toxin expressed from the gene. Further, particularly important traits are improved tolerance of plants to a certain kind of an active compound having a herbicidal activity, such as imidazolinone, sulfonyl urea, glyphosate or phosphinotricine (e.g., "PTA" gene). Genes which can endow desired traits to a subject can also be present in combination each other in a transgenic plant. Examples of the "Bt plant" include modified varieties of corn, modified varieties of cotton and modified varieties of potato that are commercially available under the trade names of YIELD GARD® (for example, corn, cotton, soybean), KnockOut® (for example, corn), StarLink® (for example, corn), Bollgard® (cotton), Nucotn® (cotton) and New Leaf® (potato), respectively. Examples of the plant having resistance to herbicides include modified varieties of corn, modified varieties of cotton and modified varieties of potato that are commercially available under the trade names of Roundup Ready® (resistance to glyphosate, for example, corn, cotton, soybean), Liberty Link® (resistance to phosphinotricine, for example rape seed), IMI® (resistance to imidazolinones) and STS® (resistance to sulfonylurea, for example, corn), respectively. Examples of the plant having resistance to herbicides (i.e., the plant obtained by conventional breeding methods to have resistance to herbicides) also include modified varieties, for example those that are commercially available under the trade name of Clearfield® (for example, corn). Of course, these descriptions are also applied to plant varieties which have already had genetic traits or will have genetic traits to be developed in future. Such plant varieties will be developed and/or on the market in future.

Additionally to above mentioned, according to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance mangold, spinach beet, spinach, beetroots), Malvaceae (for instance okra), Asparagaceae (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782, 096, 11/657,964, 12/192,904, 11/396,808, 12/166,253, 12/166,239, 12/166,124, 12/166,209, 11/762,886, 12/364, 335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes. Plants expressing EPSPS genes that confer glyphosate tolerance are described. Plants comprising other genes that confer glyphosate tolerance, such as decarboxylase genes, are described.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). HPPD is an enzyme that catalyzes the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712). The production of sulfonylurea-tolerant plants and imidazolinone-tolerant plants is described. Other imidazolinone-tolerant plants are also described. Further sulfonylurea- and imidazolinone-tolerant plants are also described.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants.

2) plants which contain a stress tolerance enhancing transgene capable of reducing the expression and/or the activity of the PARG encoding genes of the plants or plants cells.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha-1,4-glucans, plants producing alpha-1,6 branched alpha-1,4-glucans, plants producing alternan.

3) transgenic plants which produce hyaluronan 4) transgenic plants or hybrid plants, such as onions with characteristics such as 'high soluble solids content', 'low pungency' (LP) and/or 'long storage' (LS).

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes
b) Plants, such as cotton plants, containing an altered form of rsw2 or rsw3 homologous nucleic acids Plants, such as cotton plants, with increased expression of sucrose phosphate synthase
c) Plants, such as cotton plants, with increased expression of sucrose Plants, such as cotton plants, wherein the timing of the plasmodesmatal gating at the basis of the fiber cell is altered, e.g. through downregulation of fiber-selective β-1,3-glucanase
d) Plants, such as cotton plants, having fibers with altered reactivity, e.g. through the expression of N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content
b) Plants such as oilseed rape plants, producing oil having a low linolenic acid content
c) Plant such as oilseed rape plants, producing oil having a low level of saturated fatty acids Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those containing the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://cera-gm-c.org/index.php?evidcode=&hstIDXCode=&gType=& AbbrCode=&atCode=&stCode=&coIDCode=& action=gm_crop_database&mode=Submit).

With the compounds of the present invention at appropriate concentration, the plants mentioned above can be advantageously treated, in particular.

In particular, the following conventional or GMO-plants as well as their seeds or their propargation material can be treated with the compound according to the invention: cotton, corn, maize, soybean, wheat, barley, oil seed rape, tobacco, banana, vine, rice, cereals, fruits and vegetables (such as aubergine, pome fruit, stone fruit, soft fruit, cucumber, pear, bell pepper, melons, cabbage, potato, apple) and turf.

Further, in a veterinary medicine field, the novel compounds of the present invention can be effectively used against various harmful animal parasites (endo- and ectoparasites), for example, insects and helminths. Examples of such harmful animal parasites include the harmful organisms as follows. As insects, there are for example, *Gasterophilus* spp., *Stomoxys* spp., *Trichodectes* spp., *Rhodnius* spp., *Ctenocephalides canis, Cimx lectularius, Ctenocephalides felis, Lucilia cuprina* and the like. As Acarina, there are for example, *Ornithodoros* spp., *Ixodes* spp., *Boophilus* spp. and the like.

In a field of veterinary, i.e., in a veterinary medicine field, the active compounds of the present invention show an activity against parasites, in particular endoparasites and ectoparasites. The term "endoparasites" especially include helminths such as tapeworms, nematodes, and trematodes and protozoas such as coccidian. Ectoparasites include, typically and also preferably, arthropods, in particular, insects such as fly (biting fly and sucking fly), larva of parasitic fly, louse, pubic louse, bird louse, and flea, and mites of Acarina such as hard tick or soft tick, sarcoptic mite, chigger mite and bird mite.

These parasites include the followings:

From Anoplurida, for example, *Haematopinus* spp., *Linognathus* spp., *Pediculus* spp., *Phtirus* spp. and *Solenopotes* spp., and specific examples thereof include *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis* and *Solenopotes capillatus.*

From Mallophagida, Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp., and specific examples include *Bovicola bovis, Bovicola ovis, Bovicola limbata, Damalina bovis, Trichodectes canis, Felicola subrostratus, Bovicola caprae, Lepikentron ovis*) and *Werneckiella equi.*

From Diptera, Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitora* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.) and *Rhinoestrus* spp., *Tipula* spp. and specific examples include *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melphagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis*), *Gasterophilus pecorum*) and *Braulra coeca.*

From Siphonapterida, for example, *Pulex* spp., *Ctenocephalides* spp., *Tunga* spp., *Xenopsylla* spp. and *Ceratophyllus* spp., and specific examples include *Ctenocephalides canis, Ctenocephalides felis, Pulex* irritans, *Tunga penetrans* and *Xenopsylla* cheopsis.

From Heteropterida, for example, *Cimex* spp., *Triatoma* spp., *Rhodnius* spp. and *Panstrongylus* spp.

From Blattarida, for example, *Blatta orientalis, Periplaneta americana, Blattela germanica*) and *Supella* spp., for example, *Supella longipalpa.*

From Acari (Acarina), and Metastigmata and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp.)(original genus of heteroxenous mites), *Ornithonyssus* spp., *Pneumonyssus* spp., *Raillietia* spp., *Pneumonyssus* spp., *Sternostoma* spp., *Varroa* spp. and *Acarapis* spp., and specific examples include *Argas persicus, Argas reflexus, Ornithodorus moubata, Otobius megnini, Rhipicephalus*(*Boophilus*)*microplus, Rhipicephalus*(*Boophilus*)*decoloratus, Rhipicephalus*(*Boophilus*)*annulatus, Rhipicephalus*(*Boophilus*)*calceratus, Hyalomma annatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum and Varroa jacobsoni*).

From Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp.) and *Laminosioptes* spp., and examples thereof include *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae*(=*S. caprae, Sarcoptes equi, Sarcoptes suis, Psoroptes ovis, Psoroptes cuniculi, Psoroptes equi, Chorioptes bovis, Psoergates ovis, Pneumonyssoidic* mange, *Pneumonyssoides caninum* and *Acarapis woodi.*

The active compounds of the present invention are also suitable for controlling arthropods, helminths and protozoas which attack an animal. The animal includes an agricultural livestock like a cow, a sheep, a goat, a horse, a pig, a donkey, a camel, a buffalo, a rabbit, a chicken, a turkey, a duck, a goose, a nursery fish, a honey bee and the like. In addition, the animal also includes a pet (i.e., companion animal) like a dog, a cat, a pet bird, an aquarium fish and the like and an animal known as a test animal like a hamster, a guinea pig, a rat, a mouse and the like.

With the control of these arthropods, helminths and/or protozoas by using the active compounds of the present invention, death ratio of the host animal is reduced, productivity (for obtaining meat, milk, wool, leather, eggs and honey, etc.) and health of the host animal are expected to be improved, and also economically more favorable and convenient breeding of the animal can be achieved.

For example, (when applicable) it is preferable that blood mixing from a host via parasites is inhibited or interrupted. In addition, control of parasite can be useful for inhibiting transfer of infectious factors.

The term "control" used in the present specification in relation to a veterinary field means that the active compounds of the present invention are effective for reducing the occurrence of parasites in the animal infected with each parasite to a harmless level. More specifically, the term "control" used in the present specification means that the active compounds of the present invention are effective for eradicating each parasite or for inhibiting its growth or proliferation.

In general, when used for an animal treatment, the compounds of the present invention can be directly applied. Preferably, the compounds of the present invention are applied as pharmaceutical compositions which may contain vehicles and/or auxiliary agents that are known in the field and pharmaceutically acceptable.

In a veterinary medicine field and livestock farming, the active compounds can be applied (administered) in various known ways, such as via enteral administration in form of a tablet, a capsule, a drink, a syrup, a granule, a paste, a bolus and a feed stuff, or a suppository; via parenteral administration based on injection (intramuscular, subcutaneous, intravenous, intraperitoneal, etc.), implant, intranasal administration, etc.; by administration on skin in form of impregnation, liquid impregnation, spray, pouring on, spotting on, washing and powder spray; or with an aid of an molded article containing the active compounds, such as a neck tag, an ear tag, a tail tag, a leg tag, a horse rein, an identification tag, etc. The active compounds also can be prepared as shampoo, an appropriate preparation usable in aerosol, or as an unpressurized spray, for example a pump spray and a sprayer.

When used for livestock, poultry, pet and the like, the active compounds of the present invention can be prepared as a formulation containing them in an amount of 1 to 80% of weight (for example, powder, wettable preparation (WP), an emulsion, an emulsified concentrate (EC), a flowable, a homogenous solution and a suspension concentrate (SC)), and then can be applied directly or after dilution (for example, 100 to 10,000 times dilution), or they can be also applied as impregnation solution.

When used in a field of veterinary medicine, the active compounds of the present invention can be used in combination with appropriate synergists such as acaricides, pesticides, anti-helminth agents or anti-protozoa agents or with other active compounds.

In the present invention, the compounds which have a pesticidal activity against the harmful pests encompassing all of above are also referred to as insecticides.

When used as insecticides, the active compounds of the present invention can be prepared in a common preparation form. Such a preparation form may include, for example, a solution, an emulsion, wettable powder, granulated wettable powder, a suspension, powder, a foam, a paste, a tablet, a granule, an aerosol, a natural or synthetic agent impregnated with the active compounds, a microcapsule, a coating agent for seeds, a formulation equipped with a combustion device (the combustion device can be a smoke or fog cartridge, a can or a coil, etc.) and ULV (cold mist, warm mist), and the like. These formulations may be prepared by methods known per se. For example, they can be prepared by mixing the active compounds together with spreading agents, i.e. liquid diluents or carriers; liquefied gas diluents or carriers; solid diluents or carriers, and, optionally, with surfactants i.e. emulsifiers and/or dispersants and/or foam-forming agents.

When water is used as a spreading agent, for example, organic solvents may be used as auxiliary solvents. The liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes) or paraffins (e.g. mineral oil fractions), alcohols (e.g. butanol, glycol and ethers or esters thereof, etc.), ketones (e.g. acetone, methyl ethyl ketone, methyl isobutyl ketone, cyclohexanone etc.), strong polar solvents (e.g. dimethylformamide, dimethylsulfoxide etc.), water and the like. The liquefied gas dilution agents or carriers may include those present as gas at atmospheric temperature and by evaporation, for example, butane, propane, nitrogen gas, carbon dioxide, and an aerosol propellant such as halogenated hydrocarbons. Examples of the solid dilution agents include ground natural minerals (for example, kaolins, clay, talc, chalk, quartz, attapulgite, montmorillonite, diatomaceous earth, etc.) and finely-ground synthetic minerals (for example, highly dispersed silicic acid, alumina and silicate, etc.) and the like. Examples of the solid carriers for granules may include finely pulverized and sifted rocks (for example, calcite, marble, pumice, sepiolite and dolomite, etc.), synthetic granules of inorganic or organic powders, and fine granules of organic materials (for example, sawdust, coconut shells, corn cobs and tobacco stalks, etc.) and the like. Examples of the emulsifiers and/or foam formers may include nonionic and anionic emulsifiers, for example, polyoxyethylene fatty acid esters, polyoxyethylene fatty acid alcohol ethers (for example, alkylaryl polyglycol ether), alkyl sulfonates, alkyl sulfates and aryl sulfonates, and albumin hydrolysates and the like. Examples of the dispersants include lignin sulfite waste liquor and methylcellulose. Binders may also be used in the formulation (powder, granule and emulsion). Examples of the binders may include carboxymethyl cellulose, natural or synthetic polymers (for example, gum arabic, polyvinyl alcohol and polyvinyl acetate, etc.). Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc. In general, the formulation may include the above active components in an amount of 0.1 to 95% by weight, preferably 0.5 to 90% by weight.

The active compounds represented by the Formula (I) of the present invention can be provided as mixtures with other active compounds such as pesticides, poison baits, sterilizing agents, acaricidal agents, nematocides, fungicides, growth regulating agents, and herbicides in a form of commercially useful formulation or an application form modified from formulation thereof. Herein, examples of the insecticide include organic phosphorus agents, carbamate agents, carboxylate agents, chlorinated hydrocarbon agents, neonicotinoide insecticides and insecticidal substances produced from organisms.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

(1) Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, and Vamidothion.

(2) GABA-gated chloride channel antagonists, for example cyclodiene organochlorines, e.g. Chlordane and Endosulfan; or phenylpyrazoles (fiproles), e.g. Ethiprole and Fipronil.

(3) Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers], Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer], Prallethrin, Pyrethrine (pyrethrum), Resmethrin, Silafluofen, Tefluthrin, Tetramethrin, Tetramethrin [(1R) isomers)], Tralomethrin, and Transfluthrin; or DDT; or Methoxychlor.

(4) Nicotinic acetylcholine receptor (nAChR) agonists, for example neonicotinoids, e.g. Acetamiprid, Clothianidin, Dinotefuran, Imidacloprid, Nitenpyram, Thiacloprid, and Thiamethoxam; or Nicotine.

(5) Nicotinic acetylcholine receptor (nAChR) allosteric activators, for example spinosyns, e.g. Spinetoram and Spinosad.

(6) Chloride channel activators, for example avermectins/milbemycins, e.g. Abamectin, Emamectin benzoate, Lepimectin, and Milbemectin.

(7) Juvenile hormone mimics, for example juvenile hormon analogues, e.g. Hydroprene, Kinoprene, and Methoprene; or Fenoxycarb; or Pyriproxyfen.

(8) Miscellaneous non-specific (multi-site) inhibitors, for example alkyl halides, e.g. Methyl bromide and other alkyl halides; or Chloropicrin; or Sulfuryl fluoride; or Borax; or Tartar emetic.

(9) Selective homopteran feeding blockers, e.g. Pymetrozine; or Flonicamid.

(10) Mite growth inhibitors, e.g. Clofentezine, Hexythiazox, and Diflovidazin; or Etoxazole.

(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example Diafenthiuron; or organotin miticides, e.g. Azocyclotin, Cyhexatin, and Fenbutatin oxide; or Propargite; or Tetradifon.

(13) Uncouplers of oxidative phoshorylation via disruption of the proton gradient, for example Chlorfenapyr, DNOC, and Sulfluramid.

(14) Nicotinic acetylcholine receptor (nAChR) channel blockers, for example Bensultap, Cartap hydrochloride, Thiocyclam, and Thiosultap-sodium.

(15) Inhibitors of chitin biosynthesis, type 0, for example Bistrifluoron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide, and Tebufenozide.

(19) Octopamine receptor agonists, for example Amitraz.

(20) Mitochondrial complex III electron transport inhibitors, for example Hydramethylnon; or Acequinocyl; or Fluacrypyrim.

(21) Mitochondrial complex I electron transport inhibitors, for example METI acaricides, e.g. Fenazaquin, Fenpyroximate, Pyrimidifen, Pyridaben, Tebufenpyrad, and Tolfenpyrad; or Rotenone (Derris).

(22) Voltage-dependent sodium channel blockers, e.g. Indoxacarb; or Metaflumizone.

(23) Inhibitors of acetyl CoA carboxylase, for example tetronic and tetramic acid derivatives, e.g. Spirodiclofen, Spiromesifen, and Spirotetramat.

(24) Mitochondrial complex IV electron transport inhibitors, for example phosphines, e.g. Aluminium phosphide, Calcium phosphide, Phosphine, and Zinc phosphide; or Cyanide.

(25) Mitochondrial complex II electron transport inhibitors, for example Cyenopyrafen.

(28) Ryanodine receptor modulators, for example diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl] phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl] (2,2-difluoroethyl)amino}furan-2(5H)-one (known from WO2007/115644), 4-{[(2-chloro-1,3-thiazol-5-yl)methyl] (2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl](cyclopropyl)amino}furan-2(5H)-one (known from WO 2007/115643), 4-{-[(6-chloropyridin-3-yl)methyl](cyclopropyl)amino}furan-2(5H)-one (known from EP-A-0 539 588), 4-{[(6-chlorpyridin-3-yl)methyl](methyl)amino}furan-2(5H)-one (known from EP-A-0 539 588), {1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-$\lambda^4$-sulfanylidene]cyanamide (A1) and [(S)-methyl(oxido) {(1S)-1-[6-(trifluoromethyl)pyridin-3-yl]ethyl}-$\lambda^4$-sulfanylidene]cyanamide (A2), referred to as group of diastereomers A (known from WO2010/074747, WO2010/074751), [(R)-methyl(oxido){(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a, 12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1 (2H)-yl}(2-chloropyridin-4-yl)methanone (known from WO 2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-O-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazine carboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N-cyano-N-(2,2-difluoroethyl)ethanimidamide (known from WO2008/009360), N-[2-(5-amino-1,3,4-thiadiazol-2-O-4-chloro-6-methylphenyl]-3-bromo-1-(3-chloropyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

Fungicides which can be used in a combination according to the invention are the following:
(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-)trimethylsilyl)propoxy]-phenyl}-N-ethyl-N-methylimidoformamide, N-ethyl-N-methyl-N'-{2-methyl-5-(trifluoromethyl)-4-[3-(trimethylsilyl)propoxy] phenyl}imidoformamide and O-[1-(4-methoxyphenoxy)-3,3-dimethylbutan-2-yl]1H-imidazole-1-carbothioate.

(2) inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl) ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy] methyl}phenyl)-2,4-dihydro-3H-1,2,4-triazol-3-one, methyl (2E)-2-{2-[({cyclopropyl[(4-methoxyphenyl)imino] methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl] phenyl}-2-methoxy-N-methylacetamide and (2R)-2-{2-[(2,5-dimethylphenoxy)methyl]phenyl}-2-methoxy-N-methylacetamide.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds capable to have a multisite action, for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(6) Compounds capable to induce a host defence, for example acibenzolar-5-methyl, isotianil, probenazole and tiadinil.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon, tricyclazole and 2,2,2-trifluoroethyl {3-methyl-1-[(4-methylbenzoyl)amino]butan-2-yl}carbamate.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarbfosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl) prop-2-en-1-one, pyrrolnitrine, tebufloquin, tecloftalam, tolnifanide, triazoxide, trichlamide, zarilamid, (3S,6 S,7R, 8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4 (3H)-one, 2,6-dimethyl-1H,5H-[1,4]dithiino[2,3-c:5,6-c'] dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1, 3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3, 4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1, 2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl] propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylmidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl) (phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl) pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl) prop-2-yn-1-yl]oxy}-3-methoxyphenyl)ethyl]-N2-(methylsulfonyl)valinamide, 4-oxo-4-[(2-phenylethyl) amino/butanoic acid and but-3-yn-1-yl{6-[({[(Z)-(1-methyl-1H-tetrazol-5-yl)(phenyl)methylene]amino}oxy)methyl] pyridin-2-yl]carbamate.

All named mixing partners of the classes (1) to (16) can, if their functional groups enable this, optionally form salts with suitable bases or acids.

Herbicidal components which can be used in combination with the active compounds according to the invention in mixed formulations or in tank mix are, for example, known active compounds as they are described in, for example, Weed Research 26, 441-445 (1986), or "The Pesticide Manual", 15th edition, The British Crop Protection Council and the Royal Soc. of Chemistry, 2006, and the literature cited therein, and which for example act as inhibitor of acetolactate synthase, acetyl-CoA-carboxylase, cellulose-synthase, enolpyruvylshikimat-3-phosphat-synthase, glutamin-synthetase, p-hydroxyphenylpyruvat-dioxygenase, phytoendesaturase, photosystem I, photosystem II and/or protoporphyrinogen-oxidase.

Examples of active compounds which may be mentioned as herbicides or plant growth regulators which are known from the literature and which can be combined with the compounds according to the invention are the following (compounds are either described by "common name" in accordance with the International Organization for Standardization (ISO) or by chemical name or by a customary code number), and always comprise all applicable forms such as acids, salts, ester, or modifications such as isomers, like stereoisomers and optical isomers. As an example at least one applicable from and/or modifications can be mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-methyl, aminocyclopyrachlor-potassium, aminopyralid, amitrole, ammoniumsulfamat, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chlorid, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]-ethansulfonamide, F-7967, i.e. 3-[7-chloro-5-fluoro-2-(trifluoromethyl)-1H-benzimidazol-4-yl]-1-methyl-6-(trifluoromethyl)pyrimidin-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellinic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl)-O-ethyl-isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)-ethyl-(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indol-3-ylacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl, and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chlorid, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropen, methylisothiocyanat, metobenzuron, metobromuron, metolachlor, S-metolachlor, metosulam, metoxuron, metribuzin, metsulfuron, metsulfuron-methyl, molinate, monalide, monocarbamide, monocarbamide-dihydrogensulphate, monolinuron, monosulfuron, monosulfuron ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (mixture of isomers), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl-(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl-5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidin-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, as well as the following compounds:

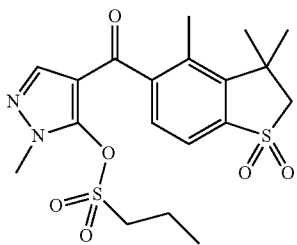

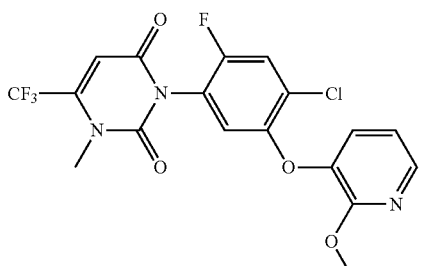

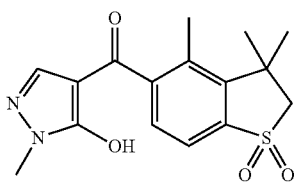

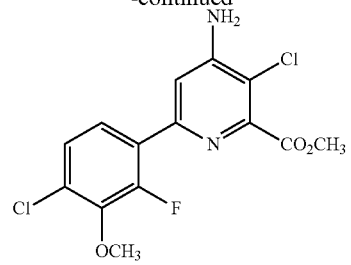

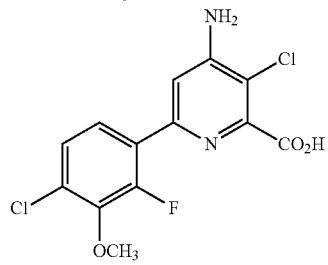

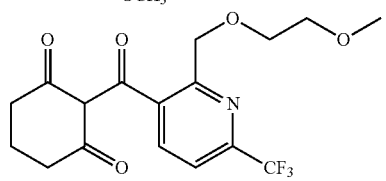

Further, the active compounds of Formula (I) of the present invention can be present in a formulation or use form as a mixed agent with synergists. Examples of the formulation or use form are those commercially useful. The synergists per se need not be active but can enhance the activity of the active compounds. The amount of the compounds of the present invention in commercially useful application form may vary over a broad range. The concentration of the active compounds of the Formula (I) of the present invention for actual use may be, for example, between 0.0000001 and 100% by weight, preferably between 0.00001 and 1% by weight. The compounds of the Formula (I) of the present invention can be used according to any common methods suitable for each application form.

Additionally to above mentioned, the present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

The active compounds of the present invention have stability that is effective for alkaline substances present on lime materials when the compounds are used against hygienic pests and other stored product pests. In addition, they exhibit excellent residual effectiveness on woods and soils.

In general, when used for an animal treatment, the compounds of the present invention can be directly applied. Preferably, the compounds of the present invention are applied as pharmaceutical compositions which may contain vehicles and/or auxiliary agents that are known in the field and pharmaceutically acceptable.

In a veterinary medicine field and livestock farming, the active compounds can be applied (administered) in various known ways, such as via enteral administration in form of a tablet, a capsule, a drink, a syrup, a granule, a paste, a bolus and a feed stuff, or a suppository; via parenteral administration based on injection (intramuscular, subcutaneous, intravenous, intraperitoneal, etc.), implant, intranasal administration, etc.; by administration on skin in form of impregnation, liquid impregnation, spray, pouring on, spotting on, washing and powder spray; or with an aid of an molded article containing the active compounds, such as a neck tag, an ear tag, a tail tag, a leg tag, a horse rein, an identification tag, etc. The active compounds also can be prepared as shampoo, an appropriate preparation usable in aerosol, or as an unpressurized spray, for example a pump spray and a sprayer.

When used for livestock, poultry, pet and the like, the active compounds of the present invention can be prepared as a formulation containing them in an amount of 1 to 80% of weight [for example, powder, wettable preparation (WP), an emulsion, an emulsified concentrate (EC), a flowable, a homogenous solution and a suspension concentrate (SC)], and then can be applied directly or after dilution (for example, 100 to 10,000 times dilution), or they can be also applied as impregnation solution.

When used in a field of veterinary medicine, the active compounds of the present invention can be used in combination with appropriate synergists or other active compounds such as acaricides, pesticides, anti-helminth agents or anti-protozoa agents.

The compounds of the present invention have low toxicity against worm-blooded animals, and therefore can be used safely.

Herein below, the present invention will be exemplified by the following examples. However, the present invention should not be construed as being limit to these examples.

SYNTHETIC EXAMPLES

A: Synthesis of N-{4-[2-oxo-3-(3,4,5-trichlorophenyl)-3-(trifluoromethyl)pyrrolidin-1-yl]-2-(tri-fluoromethyl)benzyl}propanamide (B1-46) and N-{4-[2-oxo-4-(3,4,5-trichlorophenyl)-4-(trifluoro-methyl)pyrrolidin-1-yl]-2-(trifluoromethyl)benzyl}propanamide (C1-46)

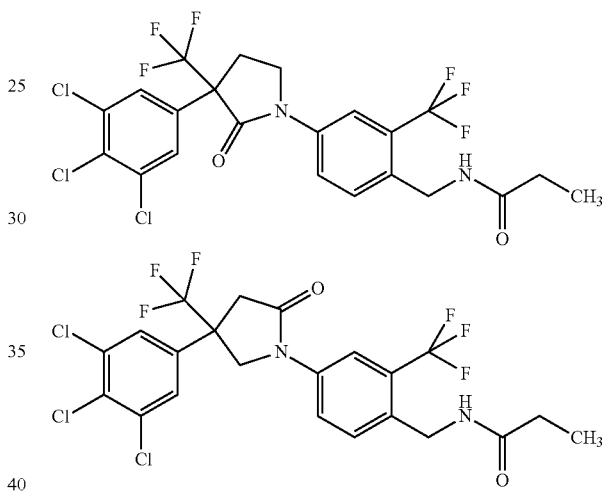

Step 1: Synthesis of tert-butyl {4-[3-(3,4,5-trichlorophenyl)-3-(trifluoromethyl)pyrrolidin-1-yl]-2-(trifluoromethyl)benzyl}carbamate

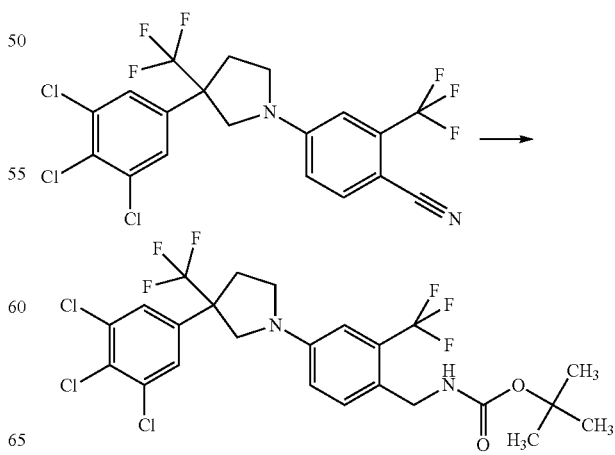

4-[3-(3,4,5-Trichlorophenyl)-3-(trifluoromethyl)pyrrolidin-1-yl]-2-(trifluoromethyl)-benzonitrile (cf. WO 2010/043315) (1.4 g) was dissolved in methanol (20 mL) and 1,4-dioxane (10 mL).

In the resulting solution, di-tert-butyl bicarbonate (1.3 g) and nickel (II) chloride hexahydrate (0.68 g) were dissolved. While being cooled with ice water, to the reaction solution was slowly added sodium tetrahydroborate (0.51 g) followed by stirring for 30 minutes.

Further, sodium tetrahydroborate (0.51 g) was slowly added followed by stirring for 30 minutes. Then, diethylenetriamine (6.2 mL) was added, the ice bath was removed, and the stirring was continued for 30 minutes.

The resultant was diluted with ethyl acetate and water. The organic layer was separated and the aqueous layer was extracted with ethyl acetate. The organic layers were combined, washed with brine, and dried over sodium sulfate. The drying agent was filtered off and the solvent was distilled off under reduced pressure to obtain a crude product.

This crude product was separated and purified by column chromatography to obtain tert-butyl {4-[3-(3,4,5-trichlorophenyl)-3-(trifluoromethyl)pyrrolidin-1-yl]-2-(trifluoromethyl)benzyl}carbamate (1.2 g).

$^1$H-NMR (CDCl$_3$) δ: 1.44 (9H, s), 2.49-2.59 (1H, m), 2.82-2.90 (1H, m), 3.46-3.61 (2H, m), 3.77 (1H, d), 4.05 (1H, d), 4.38 (2H, d), 4.82 (1H, br s), 6.71 (1H, dd), 6.79 (1H, d), 7.43-7.46 (3H, m).

Step 2: Synthesis of 1-{4-[3-(3,4,5-trichlorophenyl)-3-(trifluoromethyl)pyrrolidin-1-yl]-2-(tri-fluoromethyl)phenyl}methanamine

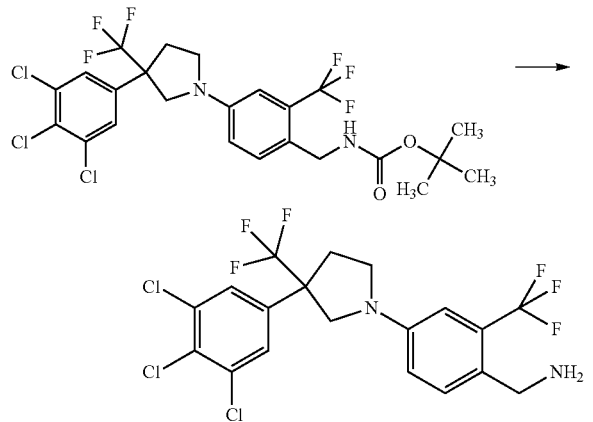

Tert-butyl {4-[3-(3,4,5-trichlorophenyl)-3-{trifluoromethyl}pyrrolidin-1-yl]-2-(trifluoromethyl)benzyl}-carbamate (1.2 g) was dissolved in ethanol (20 mL). To the solution was added conc. hydrochloric acid (4 mL) and then stirred and heated at 50° C. for 3 hours. After cooling to room temperature, the mixture was diluted with ethyl acetate and water, and under vigorous stirring, potassium carbonate was added until no longer effervescent.

The organic layer was separated and the aqueous layer was extracted with ethyl acetate. The organic layers were combined, washed with water, and dried over sodium sulfate. The drying agent was filtered off and the solvent was distilled off under reduced pressure to obtain 1-{4-[3-(3,4,5-trichlorophenyl)-3-(trifluoromethyl)pyrrolidin-1-yl]-2-(trifluoromethyl)phenyl}methanamine (0.98 g).

$^1$H-NMR (CDCl$_3$) δ: 2.49-2.59 (1H, m), 2.82-2.90 (1H, m), 3.49-3.62 (2H, m), 3.78 (1H, d), 3.91 (2H, s), 4.05 (1H, d), 6.73 (1H, dd), 6.80 (1H, d), 7.40-7.43 (3H, m).

Step 3: Synthesis of N-{4-[3-(3,4,5-trichlorophenyl)-3-(trifluoromethyl)pyrrolidin-1-yl]-2-(trifluoro-methyl)benzyl}propanamide

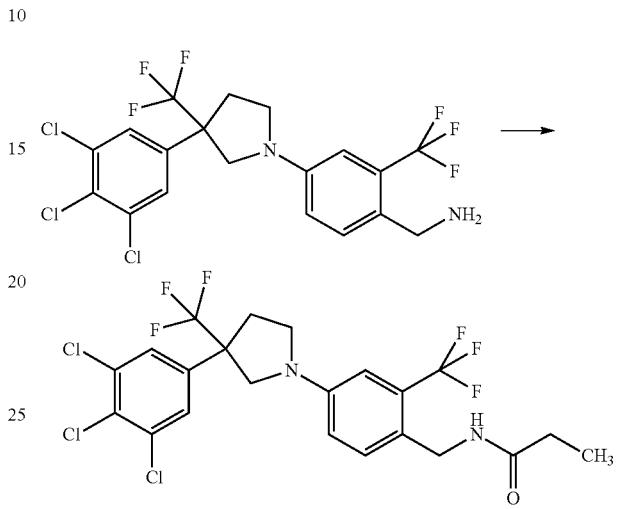

1-{4-[3-(3,4,5-Trichlorophenyl)-3-(trifluoromethyl)pyrrolidin-1-yl]-2-(trifluoromethyl)phenyl}-methanamine (0.20 g) was dissolved in tetrahydrofuran (5 mL). To the resulting solution was added propionic acid anhydride (0.06 g) at room temperature and stirred for 2 hours. The reaction solution was diluted with water and extracted twice with ethyl acetate. The organic layers were combined, washed with water, and dried over magnesium sulfate. The drying agent was filtered off and the solvent was distilled off under reduced pressure to obtain a crude product. This crude product was purified by silica gel column chromatography to obtain N-{4-[3-(3,4,5-trichlorophenyl)-3-(trifluoromethyl)-pyrrolidin-1-yl]-2-(trifluoromethyl)benzyl}propanamide (0.18 g).

$^1$H-NMR (CDCl$_3$) δ: 1.15 (3H, t), 2.20 (3H, q), 2.49-2.59 (1H, m), 2.82-2.91 (1H, m), 3.46-3.61 (2H, m), 3.78 (1H, d), 4.05 (1H, d), 4.50 (2H, d), 5.72 (1H, br s), 6.70 (1H, dd), 6.79 (1H, d), 7.43-7.47 (3H, m).

Step 4: Synthesis of N-{4-[2,-oxo-3-(3,4,5-trichlorophenyl)-3-(trifluoromethyl)pyrrolidin-1-yl]-2-(trifluoromethyl)benzyl}propanamide (B1-46) and N-{4-[2-oxo-4-(3,4,5-trichlorophenyl)-4-(trifluoromethyl)pyrrolidin-1-yl]-2-(trifluoromethyl)benzyl}propanamide (C1-46)

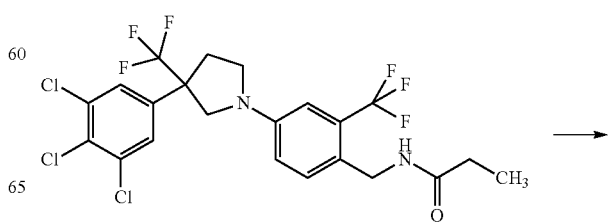

-continued

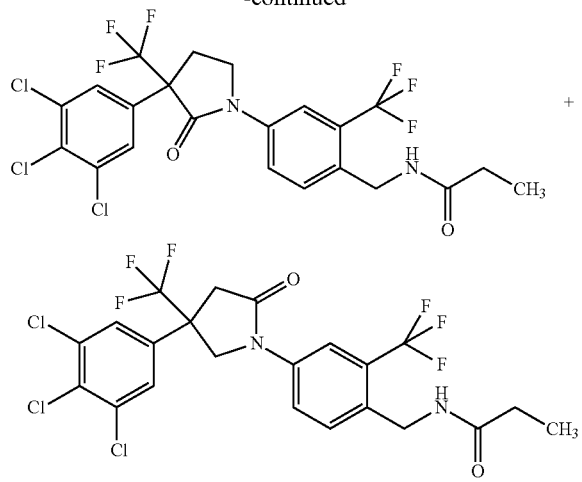

N-{4-[3-(3,4,5-Trichlorophenyl)-3-(trifluoromethyl)pyrrolidin-1-yl]-2-(trifluoromethyl)benzyl}-propanamide (0.33 g) and benzyltriethylammonium chloride (0.41 g) were dissolved in dichloromethane (10 mL).

To the resulting solution was added potassium permanganate (0.28 g) at room temperature and stirred for 4 hours. To the reaction mixture was slowly added an aqueous solution (12 mL) of sodium hydrogen sulfite (1.2 g) while cooling with ice water.

The ice bath was removed and the stirring was continued for 1 hour. 2 N hydrochloric acid was slowly added until the precipitates disappeared. The organic layer was separated and the aqueous layer was extracted with dichloromethane. The organic layers were combined, washed with water, and dried over sodium sulfate. The drying agent was filtered off and the solvent was distilled off under reduced pressure to obtain a crude product.

This crude product was purified by silica gel column chromatography to obtain N-{4-[2-oxo-3-(3,4,5-trichlorophenyl)-3-(trifluoromethyl)pyrrolidin-1-yl]-2-(trifluoromethyl)benzyl}propanamide (B1-46) (0.15 g) and N-{4-[2-oxo-4-(3,4,5-trichlorophenyl)-4-(trifluoromethyl)pyrrolidin-1-yl]-2-(trifluoromethyl)benzyl}propanamide (C1-46) (0.03 g).

$^1$H-NMR: see the table below.

B: Synthesis of N-(4-{3-[3,5-bis(trifluoromethyl)phenyl]-2-hydroxy-3-(trifluoromethyl)pyrrolidin-1-yl}-2-chlorobenzyl)cyclopropanecarboxamide (A1-27)

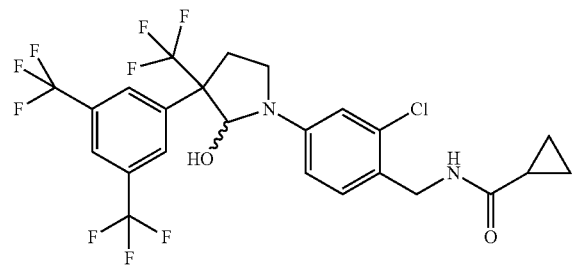 [SMILES: O=C(NCc1ccc(N2CCC(c3cc(C(F)(F)F)cc(C(F)(F)F)c3)(C(F)(F)F)C2O)cc1Cl)C1CC1]

Step 1: Synthesis of 4-{3-[3,5-bis(trifluoromethyl)phenyl]-2-oxo-3-(trifluoromethyl)-pyrrolidin-1-yl}-2-chlorobenzonitrile (b1-5)

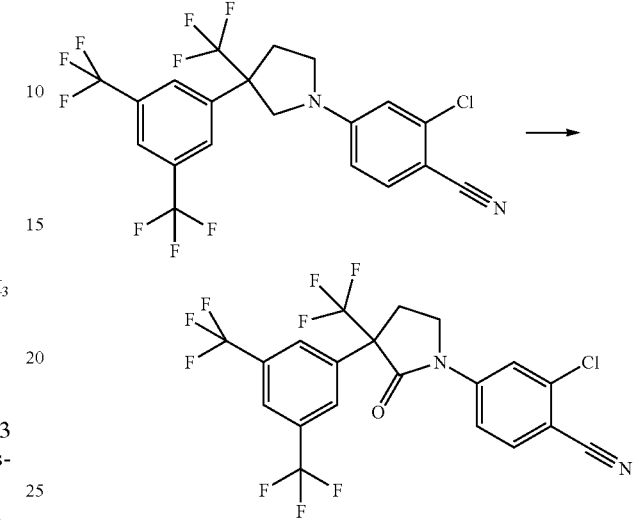

4-{3-[3,5-Bis(trifluoromethyl)phenyl]-3-(trifluoromethyl)pyrrolidin-1-yl}-2-chlorobenzonitrile (reference document: WO 2010/043315) (1.0 g) and benzyltriethylammonium chloride (1.4 g) were dissolved in dichloromethane (22 mL).

To the resulting solution was added potassium permanganate (0.97 g) at room temperature and stirred for 18 hours. While being cooled with ice water, to the reaction mixture was slowly added an aqueous solution (22 mL) of sodium hydrogen sulfite (4.3 g). The ice bath was removed and the stirring was continued for 1 hour. 2 N hydrochloric acid was slowly added until the precipitates disappeared. The organic layer was separated and the aqueous layer was extracted with dichloromethane. The organic layers were combined, washed with water, and dried over sodium sulfate. The drying agent was filtered off and the solvent was distilled off under reduced pressure to obtain a crude product.

This crude product was purified by column chromatography to obtain 4-{3-[3,5-bis(tri-fluoromethyl)phenyl]-2-oxo-3-(trifluoromethyl)pyrrolidin-1-yl}-2-chlorobenzonitrile (0.44 g).

$^1$H-NMR: see the table below.

Step 2: Synthesis of tert-butyl (4-{3-[3,5-bis(trifluoromethyl)phenyl]-2-oxo-3-(trifluoro-methyl)pyrrolidin-1-yl}-2-chlorobenzyl)carbamate (B1-69)

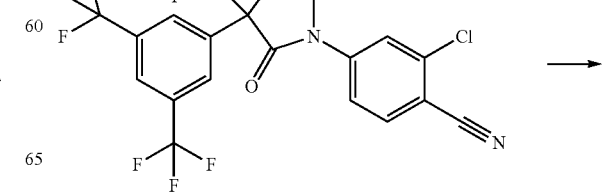

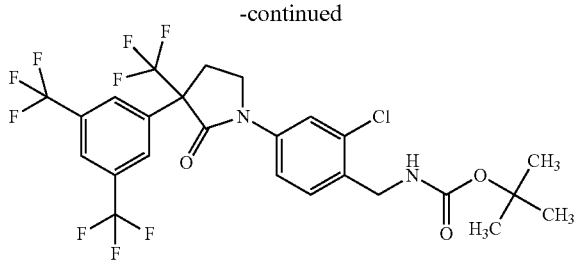

4-{3-[3,5-Bis(trifluoromethyl)phenyl]-2-oxo-3-(trifluoromethyl)pyrrolidin-1-yl}-2-chlorobenzonitrile (0.39 g) was dissolved in methanol (10 mL) and 1,4-dioxane (5 mL). In the resulting solution, di-tert-butyl bicarbonate (0.68 g) and nickel (II) chloride hexahydrate (0.19 g) were dissolved.

While being cooled with ice water, to the reaction solution was slowly added sodium tetrahydroborate (0.14 g). The ice bath was removed and stirring was continued for 1 hour. Then, diethylenetriamine (0.84 mL) was added and the stirring was continued for 30 minutes. The resultant was diluted with ethyl acetate and water. The organic layer was separated and the aqueous layer was extracted with ethyl acetate. The organic layers were combined, washed with brine, and dried over sodium sulfate. The drying agent was filtered off and the solvent was distilled off under reduced pressure to obtain a crude product.

This crude product was purified by silica gel column chromatography to obtain tert-butyl (4-{3-[3,5-bis(trifluoromethyl)phenyl]-2-oxo-3-(trifluoromethyl)-pyrrolidin-1-yl}-2-chlorobenzyl)carbamate (0.36 g).

$^1$H-NMR: see the table below.

Step 3: Synthesis of tert-butyl (4-{3-[3,5-bis(trifluoromethyl)phenyl]-2-hydroxy-3-(trifluoro-methyl)pyrrolidin-1-yl}-2-chlorobenzyl)carbamate (A1-69)

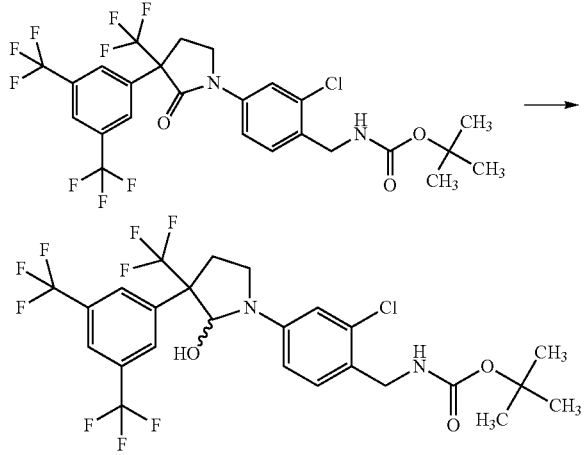

Tert-butyl (4-{3-[3,5-bis(trifluoromethyl)phenyl]-2-oxo-3-(trifluoro-methyl)-pyrrolidin-1-yl}-2-chloro-benzyl)carbamate (0.36 g) was dissolved in dichloromethane (6 mL). To the resulting solution was slowly added n-hexane solution (1.8 mL) of 1 mol/l diisobutylaluminum hydride while being cooled with ethanol-dry ice under argon atmosphere, and stirring was continued for 30 minutes at the same temperature. Then, n-hexane solution (0.6 mL) of 1 mol/l diisobutylaluminum hydride was further added thereto, and stirring was continued for 30 minutes at the same temperature. Ethyl acetate (1.2 mL) was added, the ethanol-dry ice bath was removed, and stirring was continued for 1 hour. Sodium sulfate decahydrate (3.8 g) was added and stirring was continued for 30 minutes. The precipitates were filtered using Celite and washed with ethyl acetate. The collected filtrate was concentrated under reduced pressure to obtain a crude product. The crude product was separated and purified by column chromatography to obtain tert-butyl (4-{3-[3,5-bis(trifluoromethyl)phenyl]-2-hydroxy-3-(trifluoromethyl)pyrrolidin-1-yl}-2-chlorobenzyl)carbamate (0.30 g).

$^1$H-NMR see the table below.

Step 4: Synthesis of N-(4-{3-[3,5-bis(trifluoromethyl)phenyl]-2-hydroxy-3-(trifluoromethyl)pyrrolidin-1-yl}-2-chlorobenzyl)cyclopropanecarboxamide (A1-27)

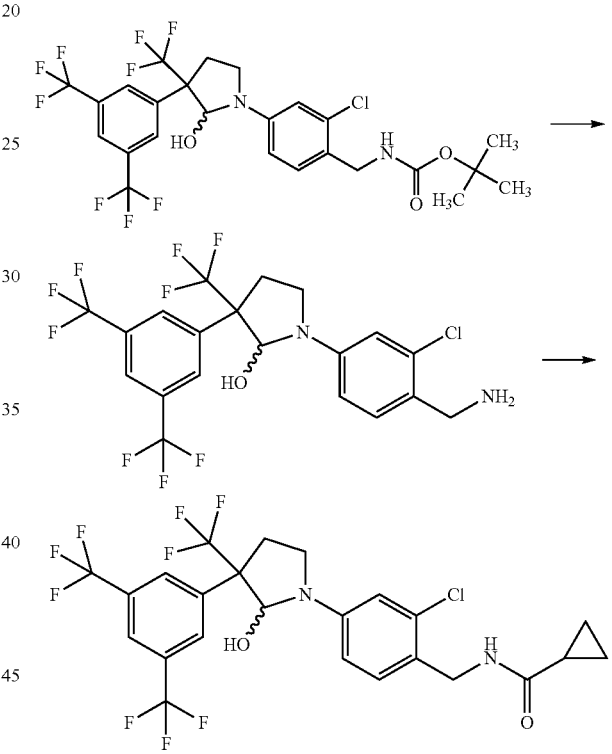

tert-Butyl (4-{3-[3,5-bis(trifluoromethyl)phenyl]-2-hydroxy-3-(trifluoromethyl)-pyrrolidin-1-yl}-2-chlorobenzyl)carbamate (0.3 g) was dissolved in ethanol (10 mL).

To the resulting solution was added conc. hydrochloric acid (1 mL) and then stirred at 60° C. for 30 minutes. After cooling to room temperature, the mixture was diluted with ethyl acetate and water, and under vigorous stirring, sodium hydrogen carbonate was added until no longer effervescent. The organic layer was separated and the aqueous layer was extracted with ethyl acetate. The organic layers were combined, washed with water, and dried over sodium sulfate. The drying agent was filtered off and the solvent was distilled off under reduced pressure to obtain 1-[4-(aminomethyl)-3-chlorophenyl]-3-[3,5-bis(trifluoromethyl)phenyl]-3-(trifluoromethyl)pyrrolidin-2-ol (0.23 g) as a crude product.

Part of the crude product (0.11 g) and pyridine (24 mg) were dissolved in tetrahydrofuran (3 mL). To the resulting solution was added cyclopropanecarbonyl chloride (26 mg)

and stirred at room temperature for 2 hours. The resultant was diluted with ethyl acetate and water. The organic layer was separated and the aqueous layer was extracted with ethyl acetate. The organic layers were combined, washed with a saturated sodium bicarbonate solution, and dried over sodium sulfate. The drying agent was filtered off and the solvent was distilled off under reduced pressure to obtain a crude product. This crude product was separated and purified by column chromatography to obtain N-(4-{3-[3,5-bis(trifluoromethyl) phenyl]-2-hydroxy-3-(trifluoromethyl)pyrrolidin-1-yl}-2-chlorobenzyl)-cyclopropanecarboxamide (90 mg).

$^1$H-NMR: see the table below.

C: Synthesis of N-[(1S)-1-(4-{3-[3,5-bis(trifluoromethyl)phenyl]-2-hydroxy-3-(trifluoro-methyl)pyrrolidin-1-yl}phenyl)ethyl]cyclopropanecarboxamide (A2-27-b)

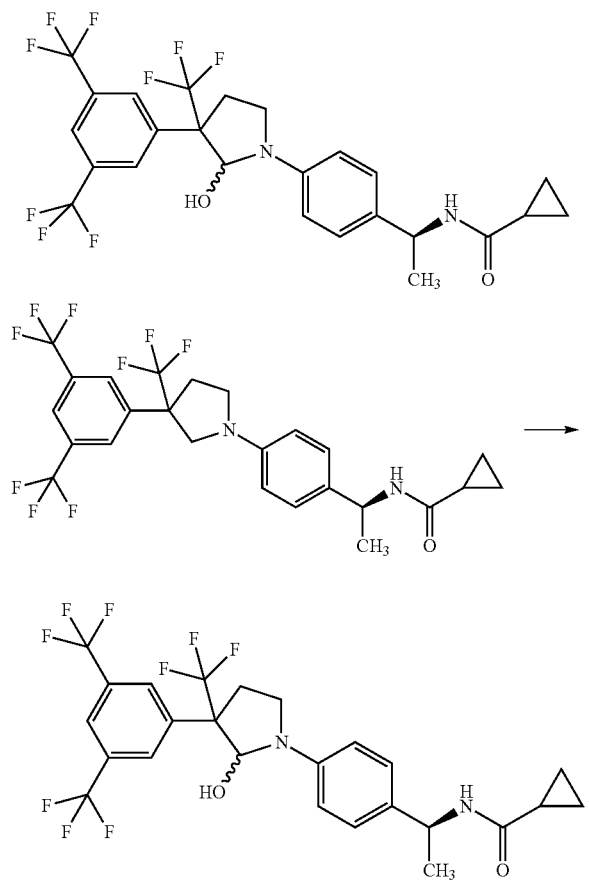

N-[(1S)-1-(4-{3-[3,5-bis(trifluoromethyl)phenyl]-3-(trifluoromethyl)pyrrolidin-1-yl)phenyl)-ethyl]cyclopropanecarboxamide (cf. Japanese Patent Application No. 2009-296889) (200 mg) was dissolved in dichloromethane (10 mL), and to the reaction solution was added Fe(salen) (12 mg) and iodosobenzene (98 mg). The resulting mixture was stirred at room temperature for 20 hours. Under reduced pressure, the solvent was distilled off and the residues were purified by silica gel column chromatography to obtain N-[(1S)-1-(4-{3-[3,5-bis(trifluoromethyl)-phenyl]-2-hydroxy-3-(trifluoromethyl)pyrrolidin-1-yl}phenyl)ethyl]cyclopropane-carboxamide (24 mg).

$^1$H-NMR: see the table below.

D: Synthesis of N-({6-[2-hydroxy-3-(3,4,5-trichlorophenyl)-3-(trifluoromethyl)-pyrrolidin-1-yl]-2-(trifluoromethyl)pyridin-3-yl}methyl)propanamide (A3-13)

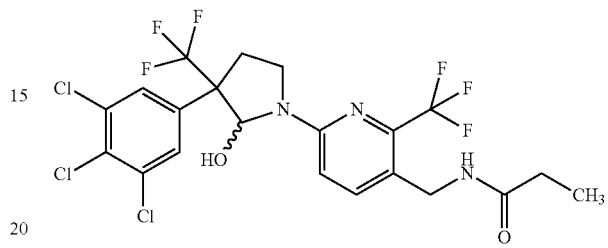

Step 1: Synthesis of 1-{6-[3-(3,4,5-trichlorophenyl)-3-(trifluoromethyl)pyrrolidin-1-yl]-2-(tri-fluoromethyl)pyridin-3-yl}methanamine

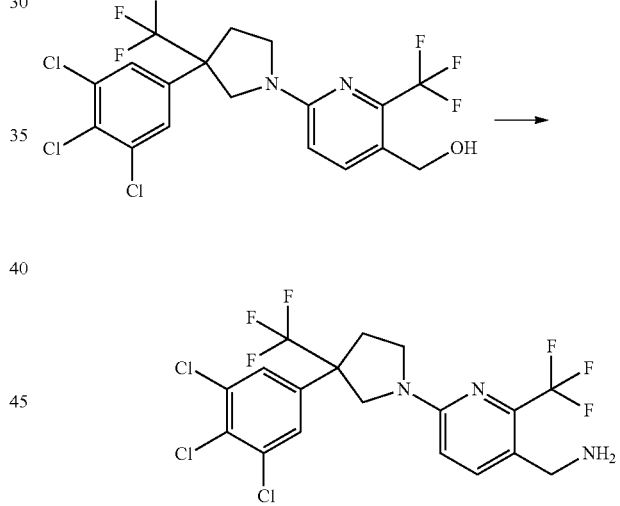

{6-[3-(3,4,5-Trichlorophenyl)-3-(trifluoromethyl)pyrrolidin-1-yl]-2-(trifluoromethyl)pyridin-3-yl}methanol (Reference document: WO2010/043315) (1.8 g) and triethylamine (0.5 g) were dissolved in acetonitrile (30 mL), and an acetonitrile (10 mL) solution of methanesulfonyl chloride (0.5 g) was added dropwise thereto under ice cooling. Upon the completion of the dropwise addition, the reaction solution was stirred at room temperature for 1 hour, and then the resulting solution was added dropwise to a mixture solution containing 28% ammonia water (50 mL) and acetonitrile (200 mL), which had been prepared separately, under ice cooling. After stirring at room temperature for 12 hours, the reaction solution was poured into ice water and extracted with ethyl acetate. The organic layer was dried over magnesium sulfate. The solvent was distilled off and the purification was carried out by silica gel chromatography to obtain the title compound (1.25 g).

¹H-NMR (CDCl₃) δ: 2.51-2.89 (2H, m), 3.60-3.66 (2H, m), 3.88-3.91 (2H, m), 3.98 (1H, d), 4.37 (1H, d), 6.55 (1H, d), 7.44 (2H, s), 7.68 (1H, d).

Step 2: Synthesis of N-{6-[3-(3,4,5-trichlorophenyl)-3-(trifluoromethyl)pyrrolidin-1-yl]-2-(tri-fluoromethyl)pyridin-3-yl}methyl)propanamide

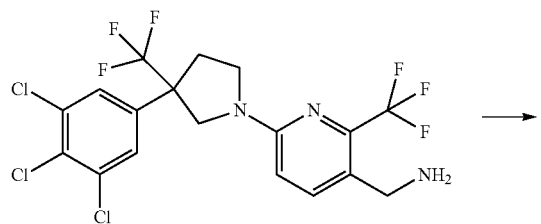

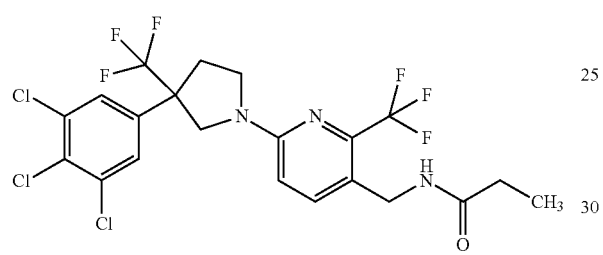

1-{6-[3-(3,4,5-Trichlorophenyl)-3-(trifluoromethyl)pyrrolidin-1-yl]-2-(trifluoromethyl)pyridine-3-yl}methanamine (0.2 g) and triethylamine (0.1 g) were dissolved in dichloromethane (20 mL), and to the solution was added dropwise a dichloromethane (10 mL) solution of propionic acid anhydride (0.1 g) under ice cooling.

Upon the completion of the dropwise addition, the reaction solution was stirred at room temperature for 1 hour, the solvent was distilled off, and the purification was carried out by silica gel chromatography to obtain the title compound (0.2 g).

¹H-NMR (CDCl₃) δ: 1.15 (3H, t), 2.20 (2H, qz), 2.48-2.58 (1H, m), 2.82-2.91 (1H, m), 3.56-3.70 (2H, m), 3.96 (1H, d), 4.37 (1H, d), 4.46 (2H, d), 5.74-5.78 (1H, m), 6.51 (1H, d), 7.44 (2H, s), 7.73 (1H, d).

Step 3: Synthesis of N-({6-[2-hydroxy-3-(3,4,5-trichlorophenyl)-3-(trifluoromethyl)-pyrrolidin-1-yl]-2-(trifluoromethyl)pyridin-3-yl}methyl)propanamide (A3-13)

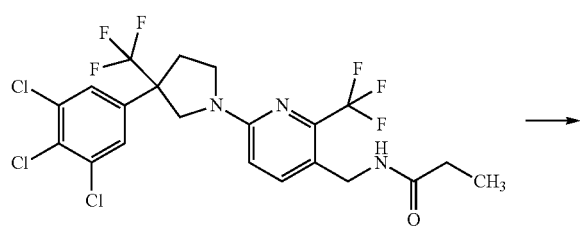

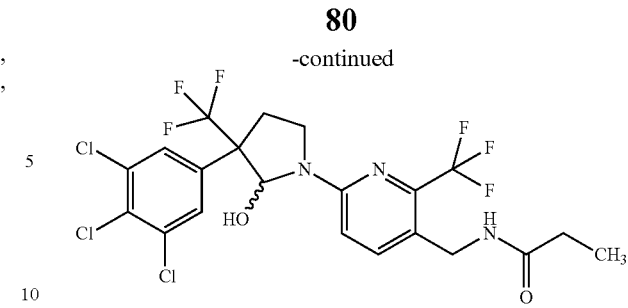

N-{6-[3-(3,4,5-Trichlorophenyl)-3-(trifluoromethyl)pyrrolidin-1-yl]-2-(trifluoromethyl)pyridin-3-yl}methyl)propanamide (0.1 g) was dissolved in acetic acid (5 mL).

To the solution was added an aqueous 30% hydrogen peroxide (0.5 g) and silica gel [Wakogel® C-300] (2.0 g), stirred for 2 hours at room temperature, and then allowed to stand at room temperature for 3 days. To the reaction mixture was added ethyl acetate (50 mL) and filtered using Celite.

The filtrate was washed with a saturated aqueous solution of sodium hydrogen carbonate. The organic layer was dried over magnesium sulfate. The solvent was distilled off and the purification was carried out by silica gel chromatography to obtain the title compound (0.04 g).

¹H-NMR: see the table below.

E: Synthesis of N-{4-[3-(3,5-dichlorophenyl)-2-hydroxy-3-(trichloromethyl)pyrrolidin-1-yl]-2-(trifluoromethyl)benzyl}propanamide (A1-35)

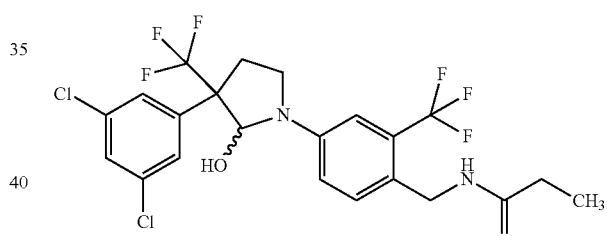

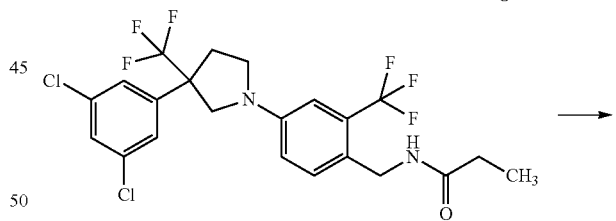

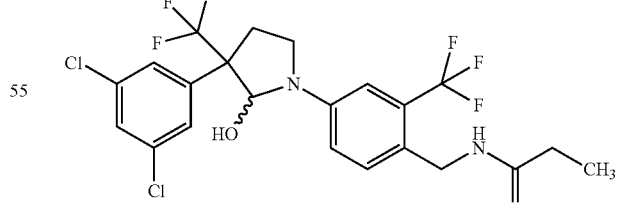

To an acetonitrile (5 ml) and water (0.5 ml) solution of N-{4-[3-(3,5-dichlorophenyl)-3-(trifluormethyl)pyrrolidin-1-yl]-2-(trifluoromethyl)benzyl}propanamide (Reference Document: WO 2010/043315) (100 mg), 2,3-dichloro-5,6-dicyano-1,4-benzoquinone (48.6 mg) was added at room temperature and stirred for 16 hours.

To the reaction mixture, ethyl acetate and water were added. The organic layer was washed with a sodium bicarbonate aqueous solution and water, and dried over anhydrous magnesium sulfate. The drying agent was filtered off, the solvent was distilled off under reduced pressure, and the residue was purified by silica gel chromatography to obtain N-{4-[3-(3,5-dichlorophenyl)-2-hydroxy-3-(trifluoromethyl)pyrrolidin-1-yl]-2-(trifluoromethyl)benzyl}propanamide (55 mg).

¹H-NMR: see the table below.

F: Synthesis of N-{4-[3-(3,5-dichloro-2,4-difluorophenyl)-2-hydroxy-3-(trifluoromethyl)pyrrolidin-1-yl]-2-(trifluoromethyl)benzyl}propanamide (A1-283)

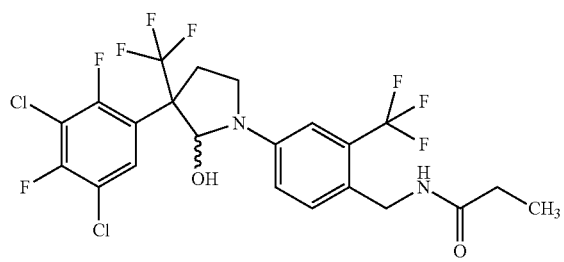 [SMILES: CCC(=O)NCc1ccc(N2CCC(c3cc(Cl)c(F)c(Cl)c3F)(C(F)(F)F)C2O)cc1C(F)(F)F]

Step 1: Synthesis of 1,3-dichloro-2,4-difluoro-5-iodobenzene

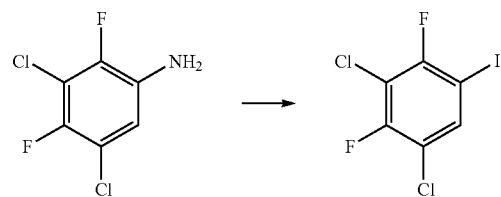 [SMILES: Nc1cc(Cl)c(F)c(Cl)c1F ; Fc1c(Cl)cc(I)c(F)c1Cl]

To a mixture of 3,5-dichloro-2,4-difluoroaniline (5.0 g), an aqueous 57% solution of hydroiodic acid (20 ml) and water (20 ml), copper iodide (1.92 g) was added. The reaction liquid was maintained at 30° C. or less in a water bath.

To the reaction mixture was added dropwise a water solution (2 mL) of sodium nitrite (1.74 g). The reaction mixture was stirred for 10 minutes, maintained at 30° C. or less in a water bath. To the reaction mixture was added dropwise a water solution (2 mL) of sodium nitrite (1.74 g), again. The reaction mixture was further stirred for 10 minutes, maintained at 30° C. or less in a water bath. To the reaction mixture was added dropwise a water solution (2 mL) of sodium nitrite (1.74 g), again. t-Butyl methyl ether was added and the mixture was washed with water and with an aqueous solution of sodium sulfite and brine, and dried over anhydrous magnesium sulfate. The drying agent was filtered off, the solvent was distilled off under reduced pressure and the residue was purified by silica gel chromatography (n-hexane) to obtain 1,3-dichloro-2,4-difluoro-5-iodobenzene (6.0 g).

¹H-NMR (CDCl₃) δ: 7.6-7.75 (1H, m).

Step 2: Synthesis of 1,3-dichloro-2,4-difluoro-5-(3,3,3-trifluoroprop-1-en-2-yl)benzene

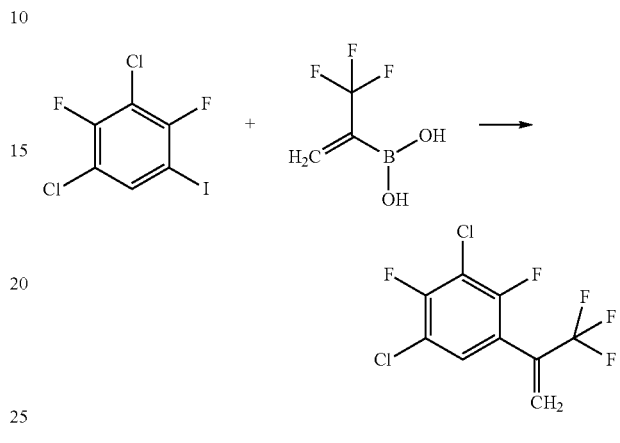

1,3-Dichloro-2,4-difluoro-5-iodobenzene (9.7 g), (3,3,3-trifluoroprop-1-en-2-yl)-boronic acid (10.5 g: 50% tetrahydrofuran solution) and potassium carbonate (10.4 g) were dissolved in tetrahydrofuran (44 ml) and water (22 ml), and then deaerated.

Dichlorobis(triphenylphosphine)palladium (II) (1.1 g) was added thereto and the mixture was stirred for 3 hours under reflux under argon atmosphere. After cooling the mixture to the room temperature, water and n-hexane were added, and the organic layer was washed with water and dried over anhydrous magnesium sulfate. The drying agent was filtered off, the solvent was distilled off under reduced pressure, and the residue was purified by silica gel chromatography (n-hexane) to obtain a mixture containing 1,3-dichloro-2,4-difluoro-5-(3,3,3-trifluoroprop-1-en-2-yl)benzene.

¹H-NMR (CDCl₃) δ: 5.81 (1H, s), 6.27 (1H, s), 7.3 (1H, t).

Step 3: Synthesis of 1-benzyl-3-(3,5-dichloro-2,4-difluorophenyl)-3-(trifluoromethyl)-pyrrolidine

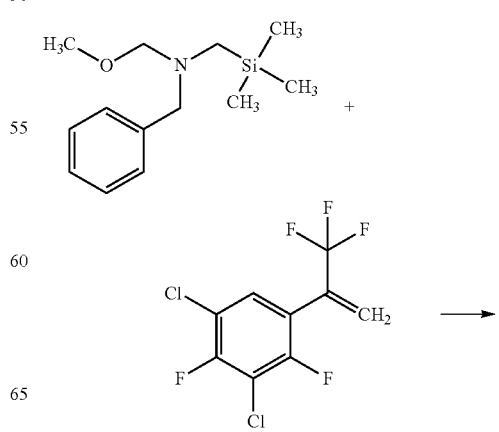

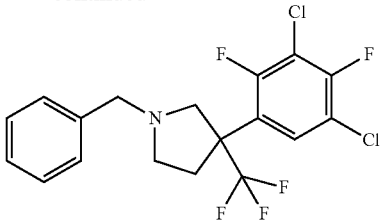

1,3-Dichloro-2,4-difluoro-5-(3,3,3-trifluoroprop-1-en-2-yl)benzene (2.8 g) and N-(methoxymethyl)-N-(trimethylsilylmethyl)benzylamine (2.0 g) were dissolved in dichloromethane (50 ml) and to the solution was slowly added dropwise a dichloromethane solution (0.8 ml) of anhydrous trifluoroacetic acid (0.065 ml) under ice cooling.

Upon the completion of the dropwise addition, the reaction temperature was raised to the room temperature and stirred overnight. The reaction solution was concentrated under reduced pressure, and the residue was purified by silica gel column chromatography to obtain 1-benzyl-3-(3,5-dichloro-2,4-difluorophenyl)-3-(trifluoromethyl)pyrrolidine (1.9 g).

$^1$H-NMR (CDCl$_3$) δ: 2.34-2.43 (1H, m), 2.57-2.70 (2H, m), 2.79-2.90 (1H, m), 3.01 (1H, dd), 3.38 (1H, dd), 3.67 (2H, s), 7.22-7.33 (6H, m).

Step 4: Synthesis of 3-(3,5-dichloro-2,4-difluorophenyl)-3-(trifluoromethyl)pyrrolidine

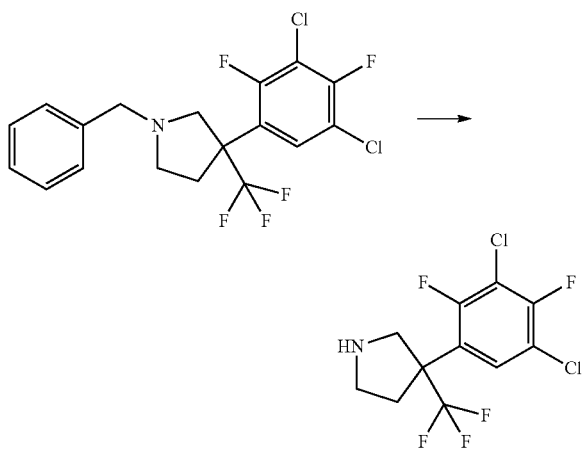

1-Benzyl-3-(3,5-dichloro-2,4-difluorophenyl)-3-(trifluoromethyl)pyrrolidine (1.9 g) was dissolved in 1,2-dichloroethane (20 ml) and to the solution was added 1-chloroethyl chloroformate (1.3 g) at room temperature, and then refluxed under heating for 3 hours.

The reaction solution was concentrated under reduced pressure, and to the residue obtained was added methanol (30 ml) and further refluxed under heating for 2 hours. The reaction solution was concentrated under reduced pressure and to the residue obtained was added t-butyl methyl ether and water to separate the aqueous layer. After that, the organic layer was again washed with a 1 M aqueous solution of hydrochloric acid, and the aqueous layers were combined. To the mixture was added a saturated aqueous solution of potassium carbonate to make it alkaline, and extracted with t-butyl methyl ether. The aqueous phase was extracted again with t-butyl methyl ether, and the organic layers were combined, dried over magnesium sulfate, filtered and concentrated under reduced pressure to obtain 3-(3,5-dichloro-2,4-difluorophenyl)-3-(trifluoromethyl)pyrrolidine (1.3 g).

$^1$H-NMR (CDCl$_3$) δ: 1.85 (1H, br s), 2.25-2.34 (1H, m), 2.60-2.69 (1H, m), 2.96-3.09 (1H, m), 3.16-3.31 (2H, m), 3.94 (1H, dd), 7.29 (1H, t).

Step 5: Synthesis of 4-[3-(3,5-dichloro-2,4-difluorophenyl)-3-(trifluoromethyl)pyrrolidin-1-yl]-2-(trifluoromethyl)benzonitrile

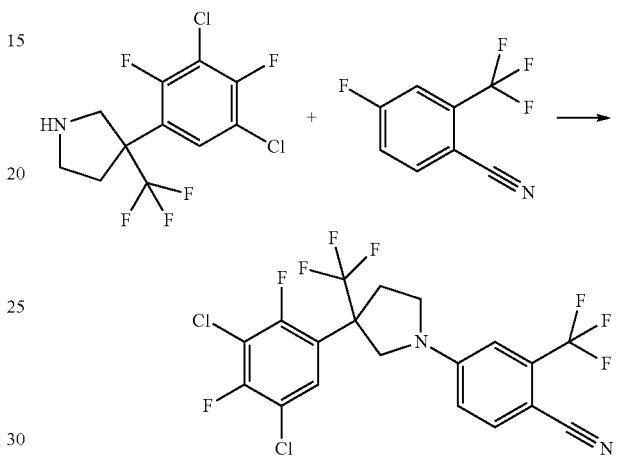

3-(3,5-Dichloro-2,4-difluorophenyl)-3-(trifluoromethyl)pyrrolidine (430 mg) and 4-fluoro-2-(trifluoromethyl)benzonitrile (254 mg) were weighed, dissolved in N,N-dimethylacetamide (10 ml) and to the solution was added N,N-diisopropylethylamine (0.468 ml) at room temperature and reacted for 1 hour using a microwave reactor (trade name: INITIATOR™, manufactured by Biotage).

The reaction mixture was diluted by adding t-butyl methyl ether, and the organic layer was washed three times with water and then saturated brine in that order. The organic layer was dried over magnesium sulfate, filtered and concentrated under reduced pressure and the residue obtained was purified by silicsa gel column chromatography to obtain 4-[3-(3,5-dichloro-2,4-difluorophenyl)-3-(trifluoromethyl)pyrrolidin-1-yl]-2-(trifluoromethyl)benzonitrile (500 mg).

$^1$H-NMR (CDCl$_3$) δ: 2.53-2.66 (1H, m), 3.06-3.13 (1H, m), 3.68-3.61 (2H, m), 3.85-3.79 (1H, m), 4.35 (1H, dd), 6.73 (1H, dd), 6.87 (1H, d), 7.32 (1H, t), 7.66 (1H, d).

Step 6: Synthesis of 4-[3-(3,5-dichloro-2,4-difluorophenyl)-2-hydroxy-3-(trifluoromethyl)-pyrrolidin-1-yl]-2-(trifluoromethyl)benzonitrile (a1-48)

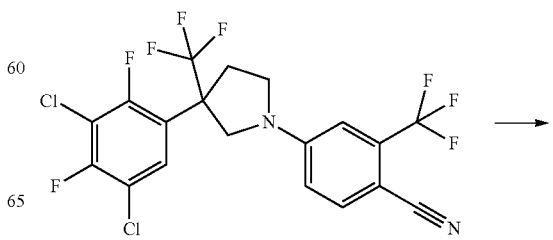

-continued

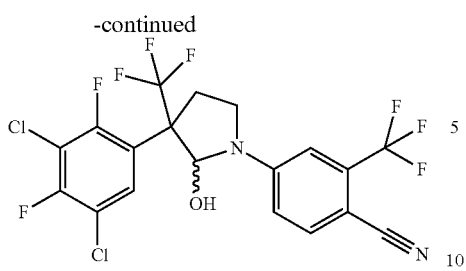

4-[3-(3,5-Dichloro-2,4-difluorophenyl)-3-(trifluoromethyl)pyrrolidin-1-yl]-2-(trifluoro-methyl)benzonitrile (350 mg) was dissolved in acetonitrile (15 ml), cooled by using an ice bath, and then stirred.

To the solution, a 1 M aqueous solution of cerium ammonium nitrate (IV) (1.42 ml) was added dropwise and stirred in an ice bath for 5 minutes. After that, t-butyl methyl ether was added for dilution and the organic layer was washed with water, an aqueous solution of sodium thiosulfate and saturated brine in that order. The organic layer was dried over magnesium sulfate, filtered and concentrated under reduced pressure, and the residue obtained was purified by column chromatography to obtain 4-[3-(3,5-dichloro-2,4-difluorophenyl)-2-hydroxy-3-(trifluoromethyl)pyrrolidin-1-yl]-2-(trifluoromethyl)benzonitrile (285 mg).

$^1$H-NMR: see the table below.

Step 7: Synthesis of N-{4-[3-(3,5-dichloro-2,4-difluorophenyl)-2-hydroxy-3-(trifluoro-methyl)pyrrolidin-1-yl]-2-(trifluoromethyl)benzyl}propanamide (A1-283)

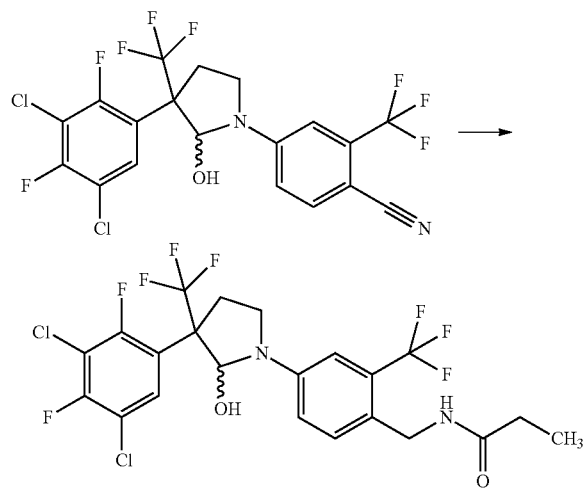

4-[3-(3,5-Dichloro-2,4-difluorophenyl)-2-hydroxy-3-(trifluoromethyl)pyrrolidin-1-yl]-2-(trifluoromethyl)benzonitrile (124 mg) was dissolved in 1,4-dioxane (5 ml) and methanol (10 ml), cooled by using an ice bath, and stirred.

To the resulting solution, propionic anhydride (0.157 ml) and nickel (II) chloride hexahydrate (58 mg) were added and thoroughly dissolved. After that, sodium borohydride (46 mg) was added thereto in three divided portions. The mixture was brought back to the room temperature and stirred for 30 minutes. After that, diethylenetriamine (1 ml) was added and the mixture was stirred until the solution became transparent.

The reaction solution was diluted with t-butyl methyl ether and washed with water and saturated brine. The organic layer was dried over magnesium sulfate, filtered and concentrated under reduced pressure and the residue obtained was purified by silica gel column chromatography to obtain N-{4-[3-(3,5-dichloro-2,4-difluorophenyl)-2-hydroxy-3-(trifluoromethyl)pyrrolidin-1-yl]-2-(tri-fluoromethyl)benzyl}propanamide (75 mg).

$^1$H-NMR see the table below.

G: N-{2-bromo-4-[2-hydroxy-3-(3,4,5-trichlorophenyl)-3-(trifluoromethyl)pyrrolidin-1-yl]benzyl}propanamide (A1-162)

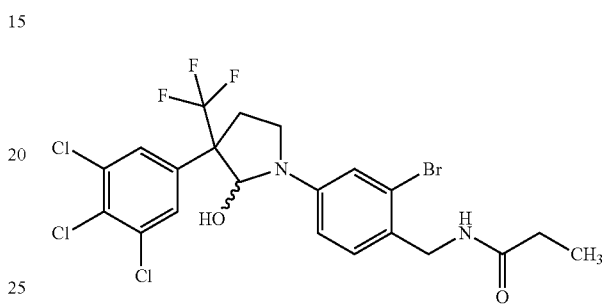

Step 1: Synthesis of 1-(3-bromophenyl)-3-(3,4,5-trichlorophenyl)-3-(trifluoromethyl)pyrrolidine (i-2)

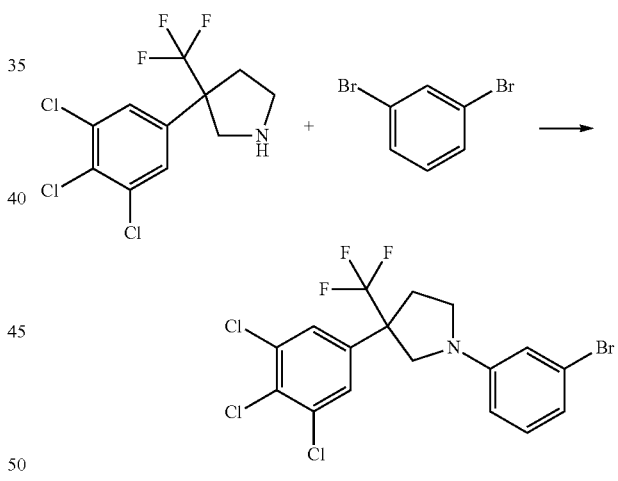

3-(3,4,5-Trichlorophenyl)-3-(trifluoromethyl)-pyrrolidine (2.0 g) and 1,3-dibromobenzene were dissolved in toluene (20 ml) and to the solution was added sodium t-butoxide (1.21 g), tris(dibenzylideneacetone)dipalladium (0)-chloroform adduct (0.130 g) and 4,5-bis(diphenylphosphino)-9,9-dimethylxanthene (0.218 g).

The mixture was sealed off under argon atmosphere and reacted for 10 minutes at 120° C. using a microwave reactor (trade name: INITIATOR™, manufactured by Biotage). The reaction mixture was diluted with ethyl acetate (20 ml), washed with water and then saturated brine and dried over anhydrous magnesium sulfate. After the filtration, the solvent was distilled off under reduced pressure and the residue was purified by silica gel chromatography to obtain 1-(3-bromophenyl)-3-(3,4,5-trichlorophenyl)-3-(trifluoromethyl)pyrrolidine (2.83 g).

Step 2: Synthesis of 2-bromo-4-[3-(3,4,5-trichlorophenyl)-3-(trifluoromethyl)pyrrolidin-1-yl]benzaldehyde (i-8)

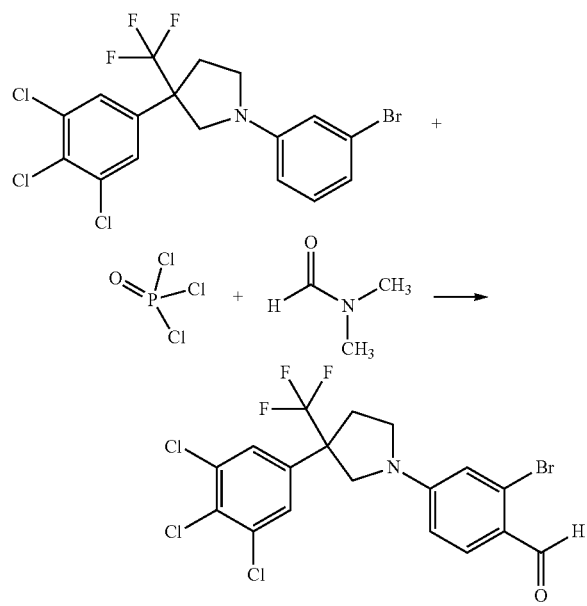

Under ice cooling, phosphoryl chloride (0.48 g) was slowly added dropwise to N,N-dimethylformamide (0.534 g) and the reaction solution was brought back to the room temperature and reacted for 20 minutes. To the reaction solution, a solution in which 1-(3-bromophenyl)-3-(3,4,5-trichlorophenyl)-3-(trifluoromethyl)pyrrolidine (0.988 g) is dissolved in N,N-dimethylformamide (4.58 g) was slowly added dropwise, and the reaction solution was stirred for 5 hours at 90° C.

The reaction solution was cooled to the room temperature, neutralized by adding an aqueous solution of sodium hydrogen carbonate, and then extracted twice with ethyl acetate (100 ml). The combined extracts were washed with water, and dried over anhydrous magnesium sulfate. After the filtration, the solvent was distilled off under reduced pressure, and the residue was purified by silica gel chromatography to obtain 2-bromo-4-[3-(3,4,5-trichlorophenyl)-3-(trifluoromethyl)-pyrrolidin-1-yl]benzaldehyde (0.809 g).

$^1$H-NMR: see the table below.

Step 3: Synthesis of {2-bromo-4-[3-(3,4,5-trichlorophenyl)-3-(trifluoromethyl)pyrrolidin-1-yl]phenyl}methanol

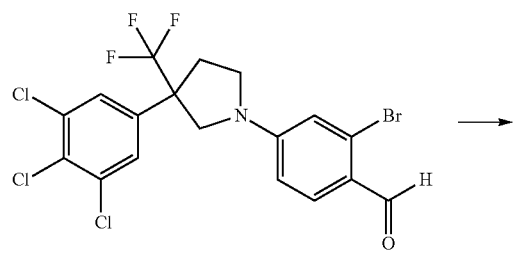

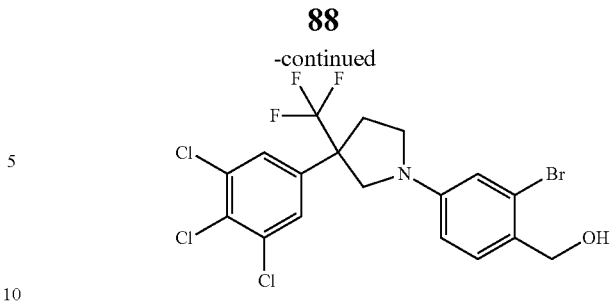

2-Bromo-4-[3-(3,4,5-trichlorophenyl)-3-(trifluoromethyl)pyrrolidin-1-yl]benzaldehyde (1.128 g) was dissolved in mixed solvents of methanol (10 ml) and tetrahydrofuran (10 ml), and to the solution was slowly added dropwise sodium borohydride (0.085 g) under ice cooling.

The reaction mixture was brought back to the room temperature and stirred overnight. Water (100 ml) was added to the reaction mixture for dilution, and extracted twice with ethyl acetate (50 ml). The combined extracts were washed with water, and dried over anhydrous magnesium sulfate. After the filtration, the solvent was distilled off under reduced pressure and the residue was purified by silica gel chromatography to obtain {2-bromo-4-[3-(3,4,5-trichlorophenyl)-3-(trifluoromethyl)pyrrolidin-1-yl]phenyl}methanol (1.069 g).

$^1$H-NMR (CDCl$_3$) δ: 1.96-2.16 (1H, m), 2.41-2.51 (1H, m), 2.79-2.87 (1H, m), 3.43-3.56 (2H, m), 3.73 (1H, d), 4.01 (1H, d), 4.64 (2H, d), 6.52 (1H, dd), 6.77 (1H, d), 7.28 (1H, d), 7.42 (2H, s).

Step 4: Synthesis of 1-[4-(azidomethyl)-3-bromophenyl]-3-(3,4,5-trichlorophenyl)-3-(trifluoromethyl)pyrrolidine

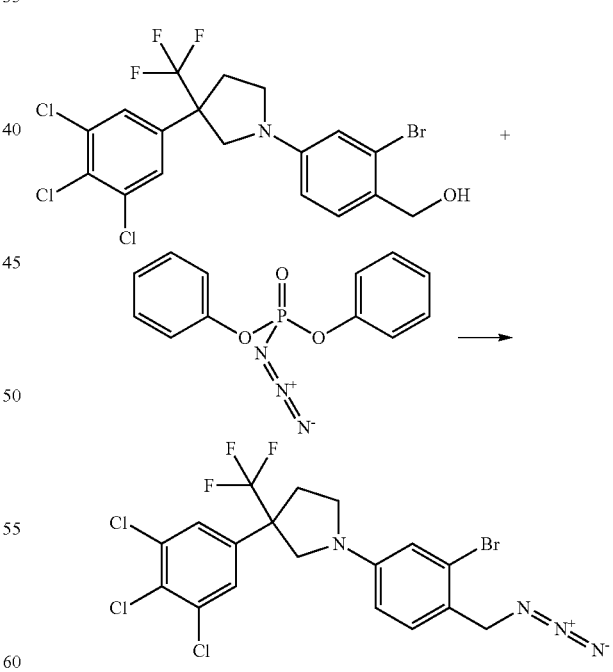

{2-Bromo-4-[3-(3,4,5-trichlorophenyl)-3-(trifluoromethyl)pyrrolidin-1-yl]phenyl}-methanol (1.069 g) was dissolved in mixed solvents of toluene (11.6 ml) and tetrahydrofuran (5.8 ml), and to the solution was slowly added dropwise diphenylphosphoryl azide (1.168 g) and 1,8-diazabicyclo[5.4.0]-7-undecene under ice cooling.

The reaction mixture was brought back to the room temperature and stirred overnight. Ethyl acetate (100 ml) was added to the reaction mixture for dilution, washed with water and then saturated brine, and dried over anhydrous magnesium sulfate. After the filtration, the solvent was distilled off under reduced pressure, and the residue was purified by silica gel chromatography to obtain 1-[4-(azidomethyl)-3-bromophenyl]-3-(3,4,5-trichlorophenyl)-3-(trifluororomethyl)-pyrrolidine (0.834 g).

$^{1}$H-NMR (CDCl$_{3}$) δ: 2.48-2.57 (1H, m), 2.81-2.89 (1H, m), 3.46-3.59 (2H, m), 3.57 (1H, d), 4.03 (1H, d), 4.39 (2H, s), 6.53 (1H, dd), 6.82 (1H, d), 7.14-7.28 (1H, m), 7.42 (2H, s).

Step 5: Synthesis of 1-{2-bromo-4-[3-(3,4,5-trichlorophenyl)-3-(trifluoromethyl)pyrrolidin-1-yl]phenyl}methanamine

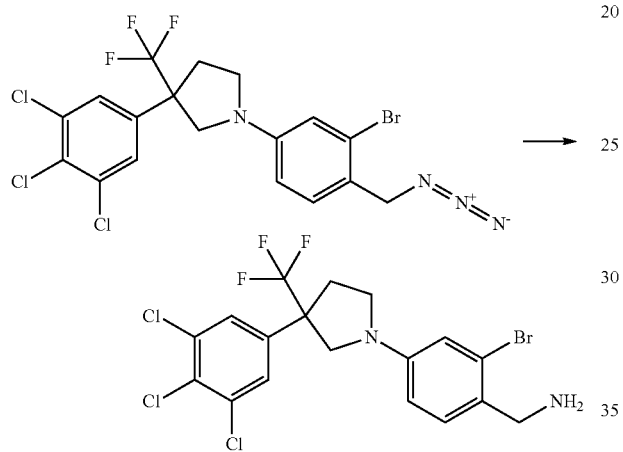

1-[4-(Azidomethyl)-3-bromophenyl]-3-(3,4,5-trichlorophenyl)-3-(trifluoromethyl)-pyrrolidine (0.634 g) was dissolved in tetrahydrofuran (10 ml), to the solution was added a 1 M toluene solution (1.37 ml) of trimethylphosphine, and stirred for 10 minutes. To the reaction solution, water (0.09 ml) was added and stirred overnight at room temperature. The volatile compound was distilled off under reduced pressure to obtain almost pure 1-{2-bromo-4-[3-(3,4,5-trichlorophenyl)-3-(trifluoromethyl)pyrrolidin-1-yl]phenyl}methanamine (0.520 g).

$^{1}$H-NMR (CDCl$_{3}$) δ: 2.46-2.56 (1H, m), 2.79-2.88 (1H, m), 3.44-3.54 (2H, m), 3.74 (1H, d), 3.82 (2H, s), 4.01 (1H, d), 6.52 (1H, dd), 6.79 (1H, d), 7.22 (1H, d), 7.42 (2H, s).

Step 6: Synthesis of N-{2-bromo-4-[3-(3,4,5-trichlorophenyl)-3-(trifluoromethyl)pyrrolidin-1-yl]benzyl}propanamide

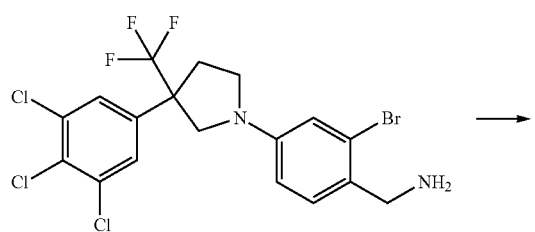

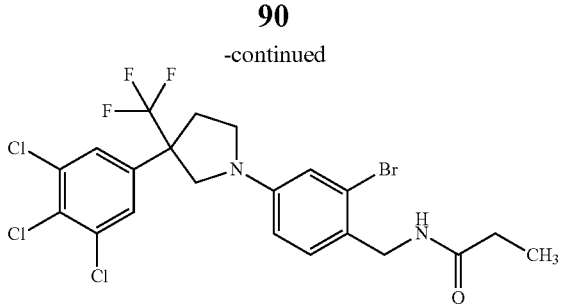

1-{2-Bromo-4-[3-(3,4,5-trichlorophenyl)-3-(trifluoromethyl)pyrrolidin-1-yl]phenyl}-methanamine (0.213 g) was dissolved in tetrahydrofuran (10 ml), to the solution was added propionic anhydride (0.052 g) at room temperature, and the reaction mixture was stirred for 2 hours. Water (70 ml) was added to the reaction mixture for dilution and extracted twice with ethyl acetate (50 ml).

The combined extracts were washed with water and then saturated brine, and dried over anhydrous magnesium sulfate. After the filtration, the solvent was distilled off under reduced pressure, and the residue was purified by silica gel chromatography to obtain N-{2-bromo-4-[3-(3,4,5-trichlorophenyl)-3-(trifluoromethyl)-pyrrolidin-1-yl]benzyl}propanamide (0.176 g).

$^{1}$H-NMR (CDCl$_{3}$) δ: 1.16 (3H, td), 2.21 (2H, q), 2.46-2.56 (1H, m), 2.80-2.88 (1H, m), 3.44-3.54 (2H, m), 3.73 (1H, d), 4.01 (1H, d), 4.43 (2H, d), 5.81 (1H, br s), 6.50 (1H, dd), 6.77 (1H, d), 7.27-7.29 (1H, m), 7.42 (2H, s).

Step 7: Synthesis of N-{2-bromo-4-[2-hydroxy-3-(3,4,5-trichlorophenyl)-3-(trifluoromethyl)pyrrolidin-1-yl]benzyl}propanamide (A1-162)

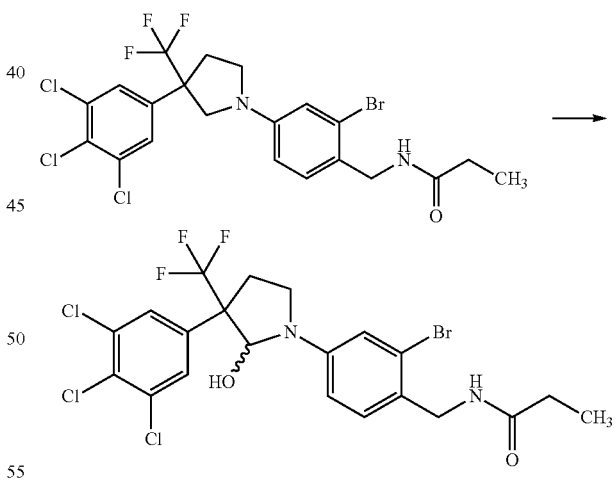

N-{2-Bromo-4-[3-(3,4,5-trichlorophenyl)-3-(trifluoromethyl)pyrrolidin-1-yl]-benzyl}propanamide (0.088 g) was dissolved in acetonitrile (5 ml) and cooled to −10° C. by using an ethanol-ice refrigerant.

To an acetonitrile solution, a 1 M aqueous solution of cerium ammonium nitrate (IV) (0.31 ml) was added and stirred at −10° C. for 5 minutes. t-Butyl methyl ether (30 ml) was added to the reaction mixture for dilution, which was then washed twice with water (10 ml) and dried over anhydrous magnesium sulfate. After the filtration, the solvent was distilled off under reduced pressure and the residue was purified by silica gel chromatography to obtain N-{2-bromo-4-[2-hydroxy-3-(3,4,5-trichlorophenyl)-3-(trifluoromethyl)pyrrolidin-1-yl]benzyl}propanamide (0.046 g).

¹H-NMR: see the table below.

H: Synthesis of N-[(6-{3-[3,5-bis(trifluoromethyl)phenyl]-2-hydroxy-3-(trifluoromethyl)pyrrolidin-1-yl}-2-bromopyridin-3-yl)methyl]-3,3,3-trifluoropropanamide (A3-161)

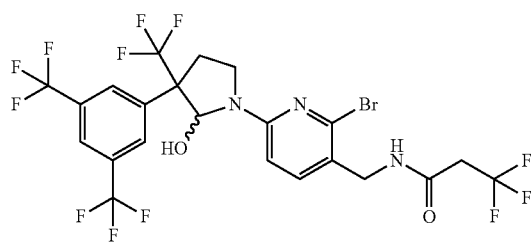 [SMILES: O=C(CC(F)(F)F)NCc1ccc(N2CCC(c3cc(C(F)(F)F)cc(C(F)(F)F)c3)(C(F)(F)F)C2O)nc1Br]

Step 1: Synthesis of 2-{3-[3,5-bis(trifluoromethyl)phenyl]-3-(trifluoromethyl)pyrrolidin-1-yl}-6-bromo-pyridine (iii-9)

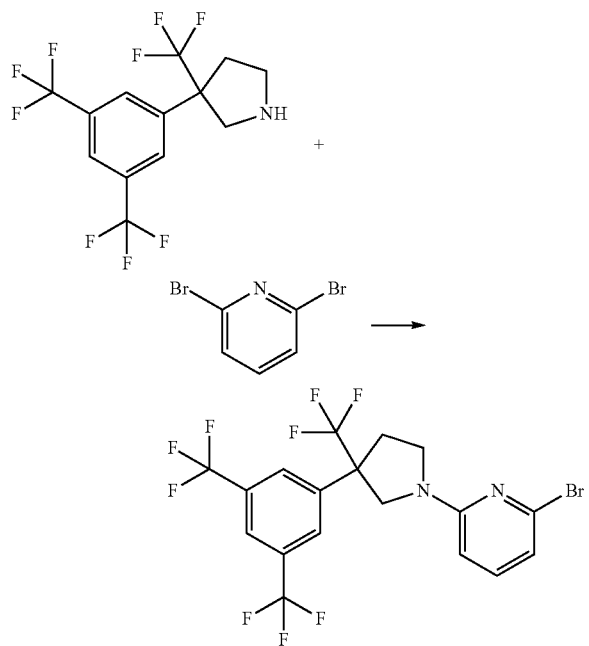

A mixture of 3-[3,5-bis(trifluoromethyl)phenyl]-3-(trifluoromethyl)pyrrolidine (3.0 g), 2,6-dibromopyridine (2.22 g), N,N-diisopropylethylamine (2.2 g) and dimethylacetamide (15 ml) was reacted at 160° C. in a sealed tube for 1 hour. Upon the completion of the reaction, the mixture was added with ethyl acetate, washed with water and then saturated brine, dried over anhydrous magnesium sulfate, and the solvent was distilled off under reduced pressure. The residue was purified by silica gel chromatography to obtain 2-{3-[3,5-bis(trifluoromethyl)phenyl]-3-(trifluoromethyl)pyrrolidin-1-yl}-6-bromopyridine (4.0 g).

¹H-NMR: see the table below.

Step 2: Synthesis of 6-{3-[3,5-bis(trifluoromethyl)phenyl]-3-(trifluoromethyl)pyrrolidin-1-yl}-2-bromo-nicotinealdehyde (iii-18)

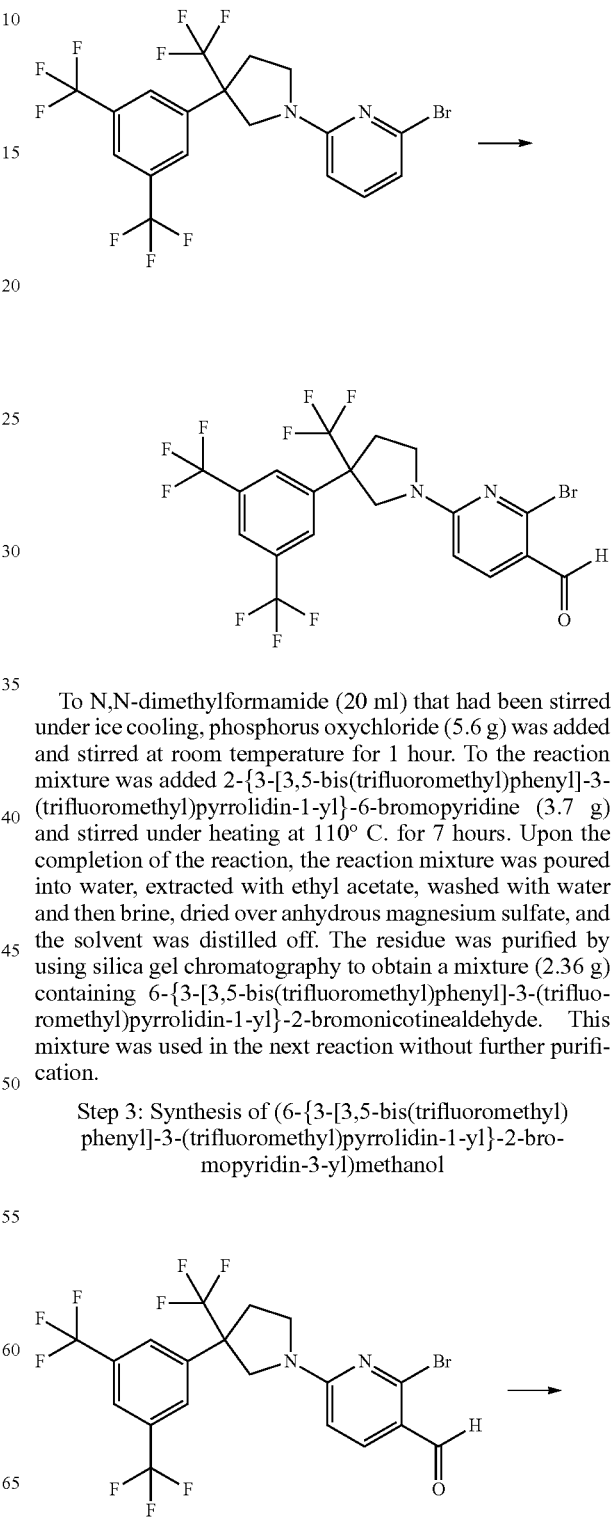

To N,N-dimethylformamide (20 ml) that had been stirred under ice cooling, phosphorus oxychloride (5.6 g) was added and stirred at room temperature for 1 hour. To the reaction mixture was added 2-{3-[3,5-bis(trifluoromethyl)phenyl]-3-(trifluoromethyl)pyrrolidin-1-yl}-6-bromopyridine (3.7 g) and stirred under heating at 110° C. for 7 hours. Upon the completion of the reaction, the reaction mixture was poured into water, extracted with ethyl acetate, washed with water and then brine, dried over anhydrous magnesium sulfate, and the solvent was distilled off. The residue was purified by using silica gel chromatography to obtain a mixture (2.36 g) containing 6-{3-[3,5-bis(trifluoromethyl)phenyl]-3-(trifluoromethyl)pyrrolidin-1-yl}-2-bromonicotinealdehyde. This mixture was used in the next reaction without further purification.

Step 3: Synthesis of (6-{3-[3,5-bis(trifluoromethyl)phenyl]-3-(trifluoromethyl)pyrrolidin-1-yl}-2-bromopyridin-3-yl)methanol

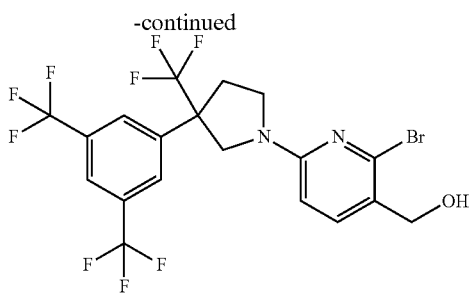

To a mixture of (6-{3-[3,5-bis(trifluoromethyl)phenyl]-3-(trifluoromethyl)pyrrolidin-1-yl}-2-bromonicotinealdehyde (1.54 g), methanol (30 ml) and THF (20 ml), which had been stirred at room temperature, sodium borohydride (0.22 g) was added in small portions over approximately 30 minutes, and stirred for 1 hour at room temperature. Upon the completion of the reaction, the solvent was distilled off under reduced pressure, to the residue was added water, extracted with ethyl acetate, dried over anhydrous magnesium sulfate and the solvent was distilled off under reduced pressure. The residue was purified by silica gel chromatography to obtain (6-{3-[3,5-bis(trifluoromethyl)phenyl]-3-(trifluoromethyl)-pyrrolidin-1-yl}-2-bromopyridin-3-yl)methanol (1.55 g).

$^1$H-NMR (CDCl$_3$) δ: 2.56-2.67 (1H, m), 2.97-3.07 (1H, m), 3.57-3.72 (2H, m), 4.00 (1H, d), 4.56 (1H, d), 4.66 (2H, d), 6.32-7.92 (5H, m).

Step 4: Synthesis of 3-(azidomethyl)-6-{3-[3,5-bis(trifluoromethyl)phenyl]-3-(trifluoromethyl)pyrrolidin-1-yl}-2-bromopyridine

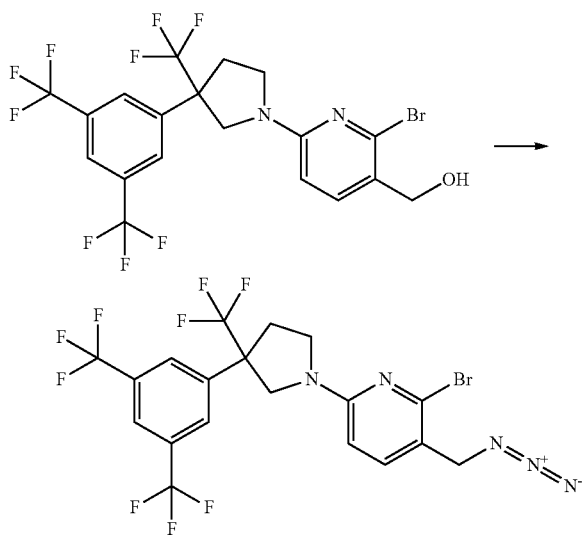

To a mixture of (6-{3-[3,5-bis(trifluoromethyl)phenyl]-3-(trifluoromethyl)pyrrolidin-1-yl}-2-bromopyridin-3-yl)methanol (1.55 g), toluene (10 ml) and THF (5 ml), which had been stirred under ice cooling, diphenylphosphoryl azide (1.59 g) and subsequently 1,8-diazabicyclo[5.4.0]-7-undecene (0.88 g) were added, and then stirred overnight at room temperature. The reaction mixture was poured into water, extracted with ethyl acetate, washed with water and dried over anhydrous magnesium sulfate. After filtration, the solvent was distilled off and the residue was purified by silica gel chromatography to obtain 3-(azidomethyl)-6-{3-[3,5-bis(trifluoromethyl)phenyl]-3-(trifluoromethyl)pyrrolidin-1-yl}-2-bromopyridine (1.35 g).

$^1$H-NMR (CDCl$_3$) δ: 2.57-2.67 (1H, m), 2.98-3.07 (1H, m), 3.58-3.74 (2H, m), 4.00 (1H, d), 4.42 (2H, s), 4.57 (1H, d), 6.33-7.92 (5H, m).

Step 5: Synthesis of 1-(6-{3-[3,5-bis(trifluoromethyl)phenyl]-3-(trifluoromethyl)pyrrolidin-1-yl}-2-bromopyridin-3-yl)methanamine

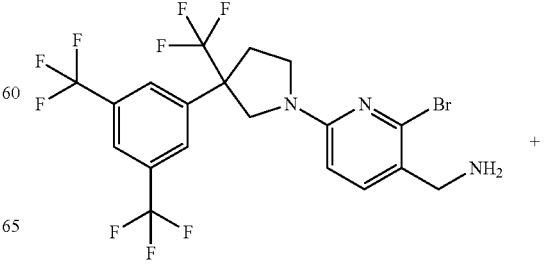

A mixture of 3-(azidomethyl)-6-{3-[3,5-bis(trifluoromethyl)phenyl]-3-(trifluoromethyl)pyrrolidin-1-yl}-2-bromopyridine (1.35 g), triphenylphosphine (0.95 g), tetrahydrofuran (30 ml) and water (200 mg) was stirred under heating for 2 hours at 60° C. Upon the completion of the reaction, the reaction mixture was poured into water, extracted with ethyl acetate, washed with water and dried over anhydrous magnesium sulfate. After filtration, the solvent was distilled off under reduced pressure to obtain a mixture (1.29 g) containing 1-(6-{3-[3,5-bis(trifluoromethyl)phenyl]-3-(trifluoromethyl)pyrrolidin-1-yl}-2-bromopyridin-3-yl)methanamine. This mixture was used in the next reaction without further purification.

Step 6: Synthesis of t-butyl[(6-{3-[3,5-bis(trifluoromethyl)phenyl]-3-(trifluoromethyl)-pyrrolidin-1-yl}-2-bromopyridin-3-yl)methyl]carbamate

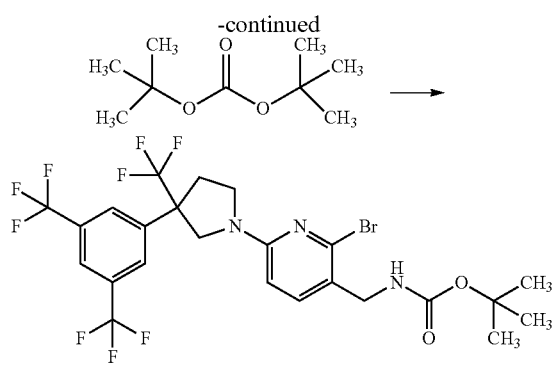

A mixture of the above-obtained mixture (1.29 g) containing 1-(6-{3-[3,5-bis-(trifluoromethyl)phenyl]-3-(trifluoromethyl)pyrrolidin-1-yl}-2-bromopyridin-3-yl)methanamine, di-t-butyl dicarbonate (0.73 g), tetrahydrofuran (50 ml) and triethylamine (0.34 g) was stirred overnight at room temperature. The reaction mixture was poured into water, extracted with ethyl acetate, washed with water and dried over anhydrous magnesium sulfate. After filtration, the solvent was distilled off under reduced pressure and the residue was purified by silica gel chromatography to obtain t-butyl[(6-{3-[3,5-bis-(trifluoromethyl)phenyl]-3-(trifluoromethyl)pyrrolidin-1-yl}-2-bromopyridin-3-yl)methyl]-carbamate (0.97 g).

$^1$H-NMR (CDCl$_3$) δ: 1.44 (9H, s), 2.55-2.66 (1H, m), 2.96-3.05 (1H, m), 3.58-3.68 (2H, m), 3.98 (1H, d), 4.26 (2H, d), 4.54 (1H, d), 5.00 (1H, b), 6.29-7.91 (5H, m).

Step 7: Synthesis of t-butyl[(6-{3-[3,5-bis(trifluoromethyl)phenyl]-2-hydroxy-3-(trifluoromethyl)pyrrolidin-1-yl}-2-bromopyridin-3-yl)methyl]carbamate (A3-321)

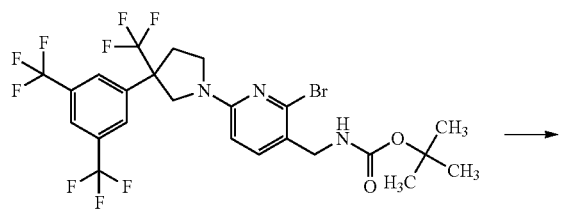

To a mixture of t-butyl[(6-{3-[3,5-bis(trifluoromethyl)phenyl]-3-(trifluoromethyl)-pyrrolidin-1-yl}-2-bromopyridin-3-yl)methyl]carbamate (0.5 g) and acetonitrile (30 ml), which had been stirred in ice water bath, a 1 M aqueous solution of cerium ammonium nitrate (IV) (1.6 ml) was added, stirred approximately for 10 minutes and the reaction mixture was diluted with ethyl acetate. After that, the mixture was washed with an aqueous solution of sodium thiosulfate and then an aqueous saturated brine solution and dried over anhydrous magnesium sulfate. The solvent was distilled off under reduced pressure and the residue was purified by silica gel chromatography to obtain t-butyl[(6-{3-[3,5-bis(trifluoromethyl)phenyl]-2-hydroxy-3-(trifluoromethyl)pyrrolidin-1-yl}-2-bromopyridin-3-yl)methyl]carbamate (0.35 g).

$^1$H-NMR: see the table below.

Step 8: Synthesis of 1-[5-(aminomethyl)-6-bromopyridin-2-yl]-3-[3,5-bis(trifluoromethyl)-phenyl]-3-(trifluoromethyl)pyrrolidin-2-ol (a3-6)

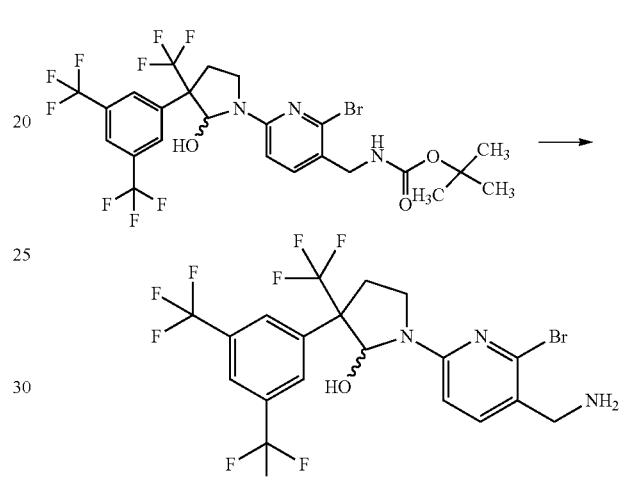

A mixture of t-butyl[(6-{3-[3,5-bis(trifluoromethyl)phenyl]-2-hydroxy-3-(trifluoromethyl)pyrrolidin-1-yl}-2-bromopyridin-3-yl)methyl]carbamate (0.63 g), ethyl acetate (20 ml) and conc. hydrochloric acid (2 ml) was stirred at 60° C. for 1 hour. After cooling, the mixture was neutralized with sodium carbonate, extracted with ethyl acetate and dried. The solvent was distilled off to obtain 1-[5-(aminomethyl)-6-bromopyridin-2-yl]-3-[3,5-bis-(trifluoromethyl)phenyl]-3-(trifluoromethyl)pyrrolidin-2-ol (0.43 g).

$^1$H-NMR: see the table below.

Step 9: Synthesis of N-[(6-{3-[3,5-bis(trifluoromethyl)phenyl]-2-hydroxy-3-(trifluoromethyl)pyrrolidin-1-yl}-2-bromopyridin-3-yl)methyl]-3,3,3-trifluoropropanamide (A3-161)

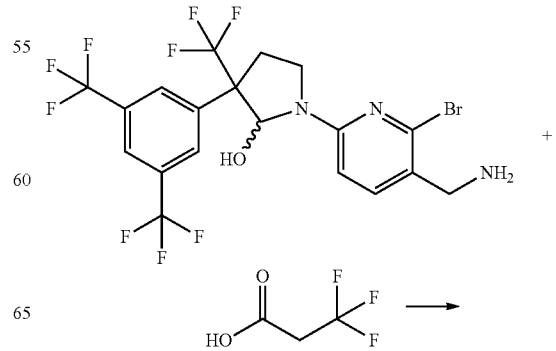

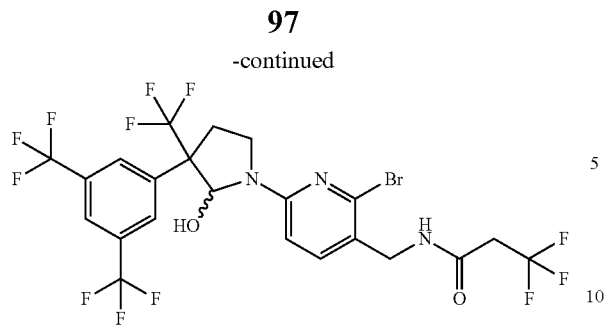

The mixture of 1-[5-(aminomethyl)-6-bromopyridin-2-yl]-3-[3,5-bis(trifluoromethyl)phenyl]-3-(trifluoromethyl)pyrrolidin-2-ol (90 mg), 3,3,3-trifluoropropionic acid (31 mg), 1-ethyl-3-(3-dimethylaminopropyl)carbodiimide hydrochloride (62 mg), dichloromethane (10 ml) and a catalytic amount of 4-dimethylaminopyridine was stirred overnight at room temperature. Upon the completion of the reaction, the solvent was distilled off and the residue was purified by silica gel chromatography to obtain N-[(6-{3-[3,5-bis(trifluoromethyl)phenyl]-2-hydroxy-3-(trifluoromethyl)pyrrolidin-1-yl}-2-bromopyridin-3-yl)methyl]-3,3,3-trifluoropropanamide (70 mg).

$^1$H-NMR: see the table below.

I: Synthesis of N-([6-[2-hydroxy-3-(3,4,5-trichlorophenyl)-(trifluoromethyl)-pyrrolidin-1-yl]-2-methylpyridin-3-yl]methyl)propanamide (A3-79)

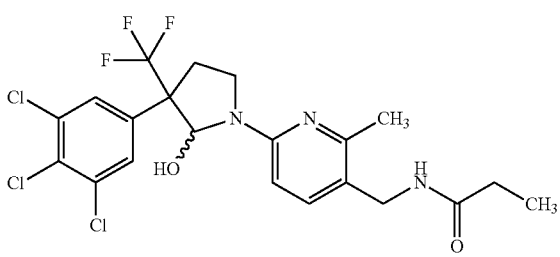 [SMILES: CCC(=O)NCc1ccc(N2CCC(c3cc(Cl)c(Cl)c(Cl)c3)(C(F)(F)F)C2O)nc1C]

Step 1: Synthesis of 2-methyl-6-[3-(3,4,5-trichlorophenyl)-3-(trifluoromethyl)pyrrolidin-1-yl]pyridine (iii-2)

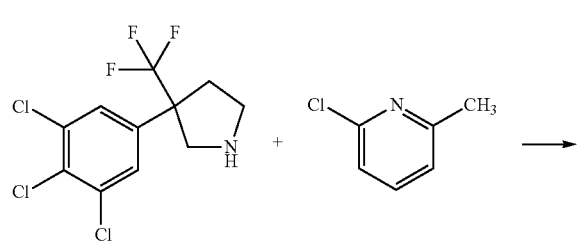

2-Chloro-6-methylpyridine (1.6 g), 3-(3,4,5-trichlorophenyl)-3-(trifluoromethyl)-pyrrolidine (4.0 g), sodium t-butoxide (1.5 g), tris(dibenzylideneacetone)dipalladium (0)-chloroform adduct (0.2 g) and 4,5-bis(diphenylphosphino)-9,9-dimethylxanthene (0.25 g) were added to toluene (15 ml), and heated for 1 hour at 120° C. using a microwave reactor (trade name: INITIATOR™, manufactured by Biotage). Upon the completion of the reaction, the reaction mixture was diluted with ethyl acetate, and the precipitate was filtered off through a short silica gel layer. The filtrate was distilled off under reduced pressure, and the residue was purified by column chromatography to obtain 2-methyl-6-[3-(3,4,5-trichlorophenyl)-3-(trifluoromethyl)pyrrolidin-1-yl]pyridine (3.4 g).

$^1$H-NMR: see the table below.

Step 2: Synthesis of 3-bromo-2-methyl-6-[3-(3,4,5-trichlorophenyl)-3-(trifluoromethyl)-pyrrolidin-1-yl]pyridine

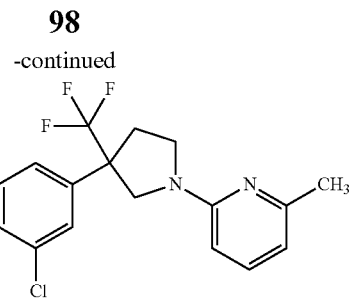

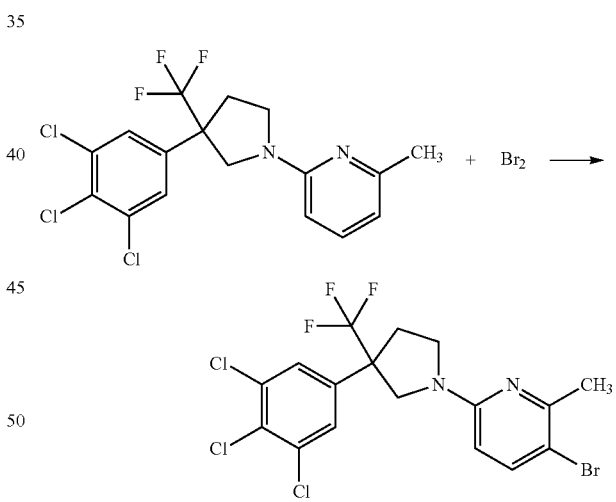

To a dichloromethane (200 ml) solution of 2-methyl-6-[3-(3,4,5-trichlorophenyl)-3-(trifluoro-methyl)pyrrolidin-1-yl]pyridine (3.4 g), an aqueous solution (100 ml) of sodium carbonate (1.2 g) was added. Under ice cooling, a dichloromethane solution of bromine (1.4 g) was added dropwise. Upon the completion of the dropwise addition, the stirring was continued for 1 hour at 0° C. The dichloromethane layer was separated and dried over magnesium sulfate. The solvent was distilled off under reduced pressure and the residue was purified by silica gel column chromatography to obtain 3-bromo-2-methyl-6-[3-(3,4,5-trichlorophenyl)-3-(trifluoromethyl)pyrrolidin-1-yl]pyridine (3.3 g).

¹H-NMR (CDCl₃) δ: 2.47-2.52 (4H, m), 2.80-2.88 (1H, m), 3.49-3.63 (2H, m), 3.92 (1H, d), 4.34 (1H, d), 6.11 (1H, d), 7.44 (2H, s), 7.52 (1H, d).

Step 3: Synthesis of 2-methyl-6-[3-(3,4,5-trichlorophenyl)-3-(trifluoromethyl)pyrrolidin-1-yl]nicotinonitrile

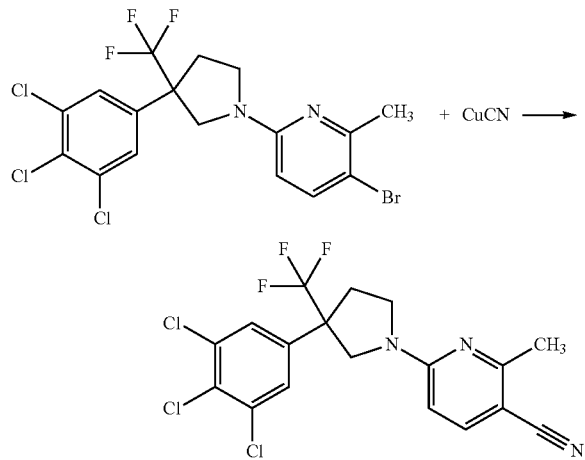

3-Bromo-2-methyl-6-[3-(3,4,5-trichlorophenyl)-3-(trifluoromethyl)pyrrolidin-1-yl]-pyridine (3.3 g) and copper cyanide (I) (0.65 g) were added to N-methyl-2-pyrrolidinone (10 ml). The mixture was heated for 4 hours at 200° C. using a microwave reactor (trade name: INITIATOR™, manufactured by Biotage). Upon the completion of the reaction, the reaction mixture was diluted with ethyl acetate and the precipitate was filtered off through a short silica gel layer. The filtrate was distilled off under reduced pressure, and the residue was purified by silica gel column chromatography to obtain 2-methyl-6-[3-(3,4,5-trichlorophenyl)-3-(trifluoromethyl)pyrrolidin-1-yl]nicotinonitrile (1.1 g).

¹H-NMR (CDCl₃) δ: 2.47-2.60 (4H, m), 2.85-2.91 (1H, m), 3.64-3.66 (2H, m), 3.97 (1H, d), 4.46 (1H, d), 6.24 (1H, d), 7.44 (2H, s), 7.59 (1H, d).

Step 4: Synthesis of t-butyl({2-methyl-6-[3-(3,4,5-trichlorophenyl)-3-(trifluoromethyl)-pyrrolidin-1-yl]pyridin-3-yl}methyl)carbamate

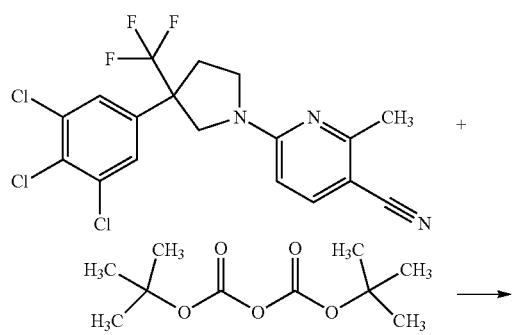

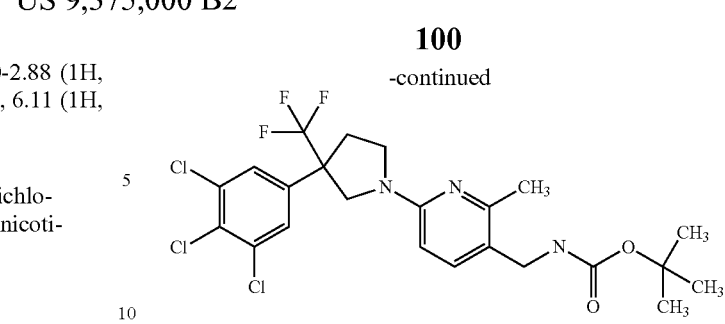

2-Methyl-6-[3-(3,4,5-trichlorophenyl)-3-(trifluoromethyl)pyrrolidin-1-yl]nicotinonitrile (1.1 g), di-t-butyl bicarbonate (1.2 g) and nickel (II) chloride hexahydrate (0.65 g) were added to mixed solvents of methanol (20 ml) and dioxane (40 ml). Under ice cooling, sodium borohydride (0.8 g) was added thereto in small portions. The reaction mixture was stirred for 2 hours at room temperature followed by addition of diethylenetriamine (5.0 g), and then further stirred for 30 minutes at room temperature. The reaction mixture was poured into ice water and extracted with ethyl acetate. The solvent was distilled off under reduced pressure and the residue was purified by silica gel column chromatography to obtain t-butyl({2-methyl-6-[3-(3,4,5-trichlorophenyl)-3-(trifluoromethyl)pyrrolidin-1-yl]pyridin-3-yl)methyl)carbamate (0.95 g).

¹H-NMR (CDCl₃) δ: 1.42 (9H, s), 2.37-2.55 (4H, m), 2.78-2.84 (1H, m), 3.51-3.64 (2H, m), 3.95 (1H, d), 4.20 (1H, d), 4.36 (1H, d), 4.59-4.62 (1H, m), 6.19 (1H, d), 7.34 (1H, d), 7.46 (2H, s)

Step 5: Synthesis of 1-{2-methyl-6-[3-(3,4,5-trichlorophenyl)-3-(trifluoromethyl)pyrrolidin-1-yl]pyridin-3-yl}methanamine

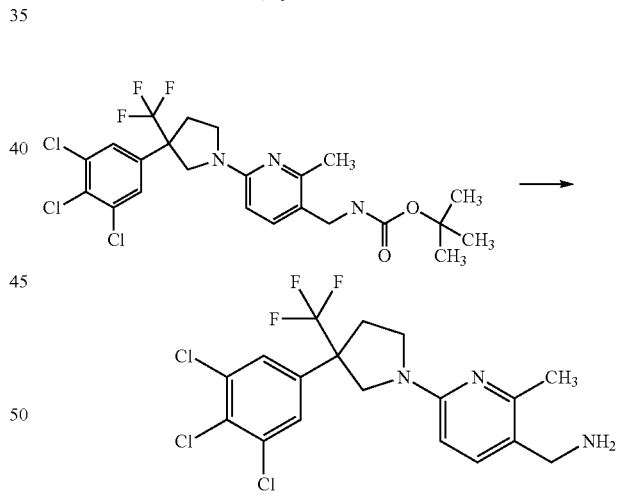

t-Butyl({2-methyl-6-[3-(3,4,5-trichlorophenyl)-3-(trifluoromethyl)pyrrolidin-1-yl]-pyridin-3-yl}methyl)carbamate (0.95 g) was added to ethanol (25 ml) and then to the solution was added conc. hydrochloric acid (5 ml) in small portions at room temperature, and then heated at 50° C. for 3 hours. After cooling the mixture to the room temperature, the reaction mixture was diluted with water (100 ml). The pH was adjusted to 11 by using an aqueous solution of sodium hydroxide and the solution was extracted with ethyl acetate. The solvent was distilled off under reduced pressure and the residue was purified by silica gel column chromatography to obtain 1-({2-methyl-6-[3-(3,4,5-trichlorophenyl)-3-(trifluoromethyl)pyrrolidin-1-yl]pyridin-3-yl}methanamine (0.6 g).

$^1$H-NMR (CDCl$_3$) δ: 2.41-2.59 (4H, m), 2.78-2.86 (1H, m), 3.51-3.77 (4H, m), 3.96 (1H, d), 4.36 (1H, d), 6.21 (1H, d), 7.38 (1H, d), 7.45 (2H, s).

Step 6: Synthesis of N-({2-methyl-6-[3-(3,4,5-trichlorophenyl)-3-(trifluoromethyl)-pyrrolidin-1-yl]pyridin-3-yl}methyl)propanamide

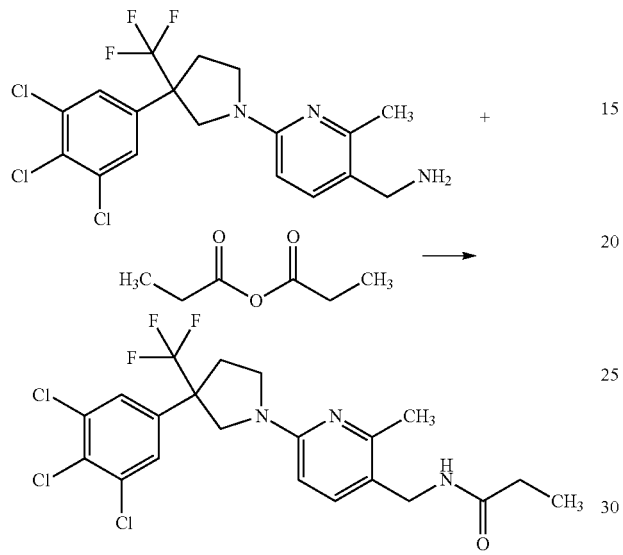

1-({2-Methyl-6-[3-(3,4,5-trichlorophenyl)-3-(trifluoromethyl)pyrrolidin-1-yl]pyridin-3-yl}methanamine (0.2 g) and triethylamine (0.1 g) were added to dichloromethane (20 ml), and to the solution was added dropwise a dichloromethane solution (10 ml) of propionic anhydride (0.1 g) under ice cooling. Upon the completion of the dropwise addition, the reaction mixture was stirred at room temperature for 1 hour, the solvent was distilled off under reduced pressure and the residue was purified by silica gel column chromatography to obtain N-({2-methyl-6-[3-(3,4,5-trichlorophenyl)-3-(trifluoromethyl)pyrrolidin-1-yl]pyridin-3-yl}methyl)propanamide (0.2 g).

$^1$H-NMR (CDCl$_3$) δ: 1.17 (3H, t), 2.22 (2H, q), 2.46-2.54 (4H, m), 2.81-2.86 (1H, m), 3.56-3.59 (2H, m), 3.95 (1H, d), 4.33-4.39 (3H, m), 5.41-5.45 (1H, m), 6.19 (1H, d), 7.35 (1H, d), 7.45 (2H, s).

Step 7: Synthesis of N-({6-[2-hydroxy-3-(3,4,5-trichlorophenyl)-3-(trifluoromethyl)-pyrrolidin-1-yl]-2-methylpyridin-3-yl}methyl)propanamide (A3-79)

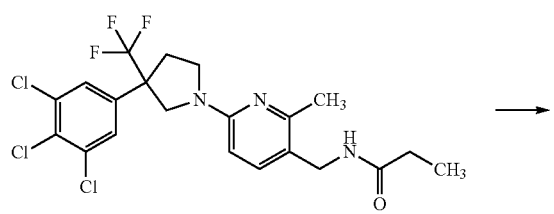

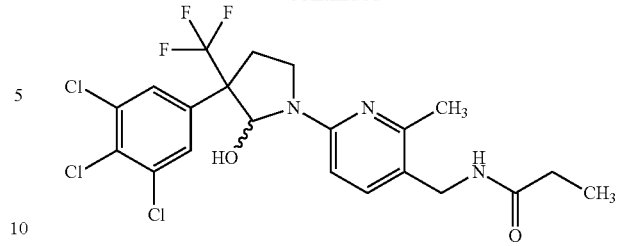

N-({2-Methyl-6-[3-(3,4,5-trichlorophenyl)-3-(trifluoromethyl)pyrrolidin-1-yl]-pyridin-3-yl}-methyl)propanamide (0.15 g) and manganese dioxide (1.2 g) were added to dichloromethane (20 ml), and acetic acid (2 ml) was added thereto in small portions at room temperature. The reaction mixture was stirred for 100 hours at room temperature, and filtered by suction on Celite. The filtrate was distilled off under reduced pressure and the residue was purified by silica gel column chromatography to obtain N-({6-[2-hydroxy-3-(3,4,5-trichlorophenyl)-3-(trifluoromethyl)pyrrolidin-1-yl]-2-methylpyridin-3-yl}methyl)propanamide (0.06 g).

$^1$H-NMR: see the table below.

J: Synthesis of N-({2-[2-hydroxy-3-(3,4,5-trichlorophenyl)-3-(trifluoromethyl)-pyrrolidin-1-yl]-4-(trifluoromethyl)pyrimidin-5-yl}methyl)cyclopropanecarboxamide (A4-16)

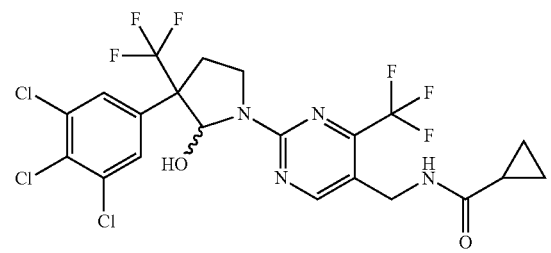 [SMILES: O=C(NCc1cnc(N2CCC(c3cc(Cl)c(Cl)c(Cl)c3)(C(F)(F)F)C2O)nc1C(F)(F)F)C1CC1]

Step 1: Synthesis of 2-({2-[3-(3,4,5-trichlorophenyl)-3-(trifluoromethyl)pyrrolidin-1-yl]-4-(trifluoromethyl)pyrimidin-5-yl}methyl)-1H-isoindole-1,3(2H)-dione

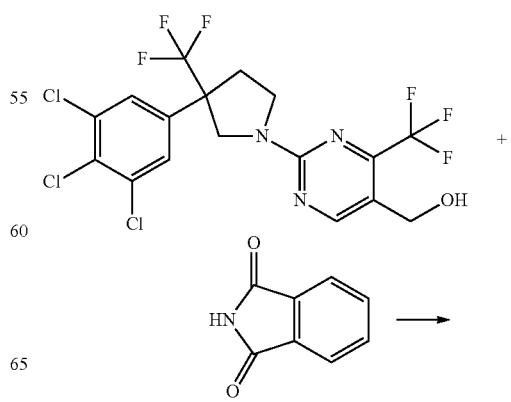

-continued

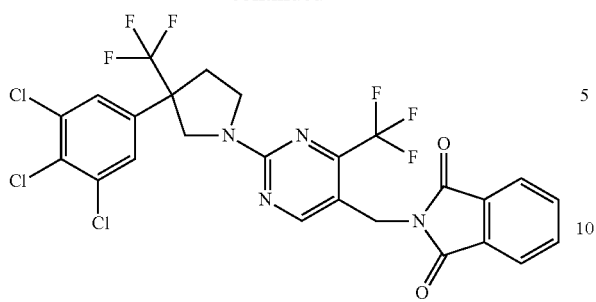

{2-({2-[3-(3,4,5-Trichlorophenyl)-3-(trifluoromethyl) pyrrolidin-1-yl]-4-(trifluoromethyl)pyrimidin-5-yl}methanol (Reference document: WO 2010/043315) (2.20 g), phthalimide (0.72 g) and triphenylphosphine (1.40 g) were dissolved in tetrahydrofuran (50 ml), and to the solution was added diethyl azodicarboxylate (40% toluene solution, 2.43 ml) at room temperature. After stirring the reaction solution for 3 hours, the solvent was distilled off under reduced pressure. The residue was purified by silica gel column chromatography to obtain the target compound (2.35 g).

$^1$H-NMR (CDCl$_3$) δ: 2.41-2.58 (m, 1H), 2.79-2.91 (m, 1H), 3.68-3.88 (m, 2H), 3.98 (d, 1H), 4.45 (d, 1H), 4.94 (s, 2H), 7.42 (s, 2H), 7.70-7.81 (m, 2H), 7.83-7.94 (m, 2H), 8.51 (s, 1H).

Step 2: Synthesis of 1-{2-[3-(3,4,5-trichlorophenyl)-3-(trifluoromethyl)pyrrolidin-1-yl]-4-(trifluoro-methyl)pyrimidin-5-yl}methanamine

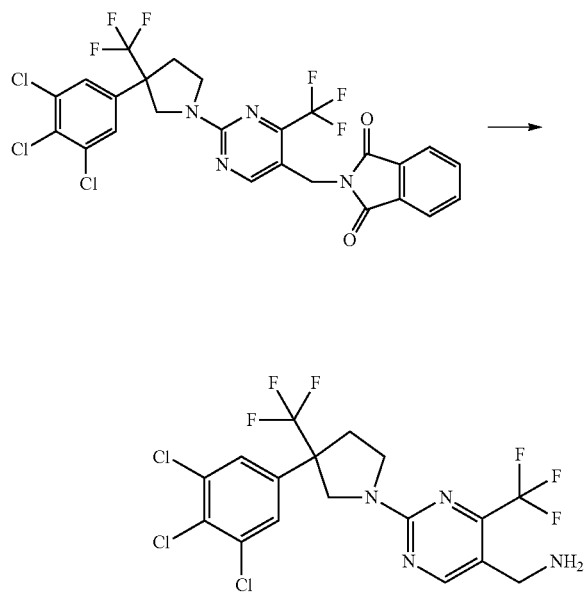

2-({2-[3-(3,4,5-Trichlorophenyl)-3-(trifluoromethyl)pyrrolidin-1-yl]-4-(trifluoromethyl)pyrimidin-5-yl}methyl)-1H-isoindole-1,3(2H)-dione (2.35 g) was added to ethanol (50 ml), followed by addition of hydrazine hydrate (0.37 ml) at room temperature. The reaction mixture was heated at 80° C. for 6 hours. The solvent was distilled off under reduced pressure, and then t-butyl methyl ether was added. The undissolved solids were removed by filtration, and the target compound was (1.71 g) obtained as a crude product after concentration under reduced pressure.

$^1$H-NMR (CDCl$_3$) δ: 1.91 (bs, 2H), 2.41-2.61 (m, 1H), 2.77-2.92 (m, 1H), 3.69-3.92 (m, 4H), 4.01 (d, 1H), 4.48 (d, 1H), 7.44 (s, 2H), 8.58 (s, 1H).

Step 3: Synthesis of 1-({2-[3-(3,4,5-trichlorophenyl)-3-(trifluoromethyl)pyrrolidin-1-yl]-4-(trifluoromethyl)pyrimidin-5-yl}methyl)cyclopropanecarboxamide

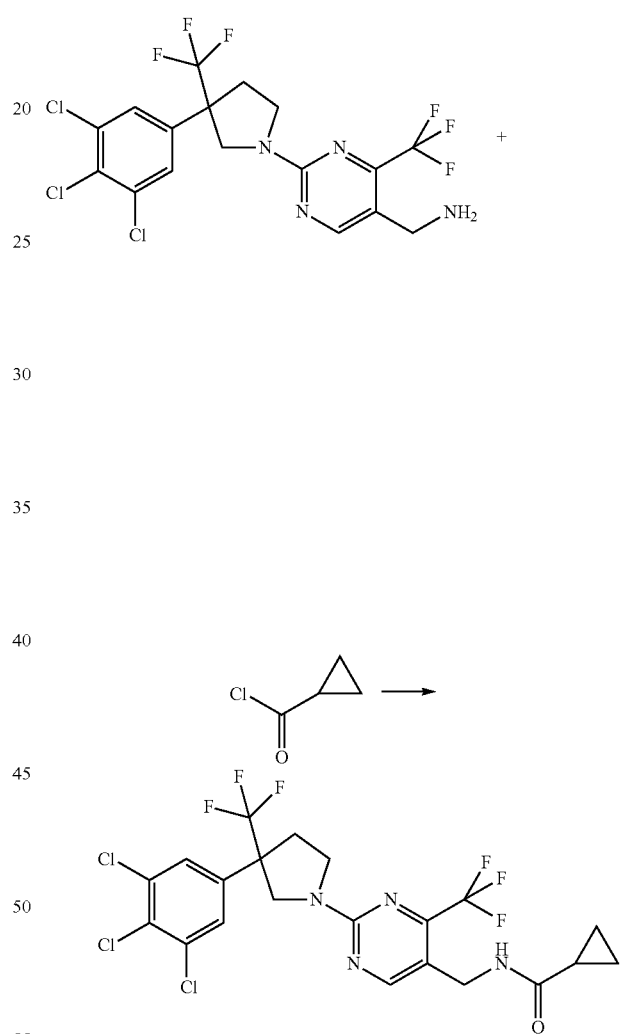

1-{2-[3-(3,4,5-Trichlorophenyl)-3-(trifluoromethyl)pyrrolidin-1-yl]-4-(trifluoromethyl)pyrimidin-5-yl}methanamine (0.15 g) and triethylamine (0.051 ml) were dissolved in methylene chloride (3 ml), and to the solution was added cyclopropane carbonyl chloride (0.033 ml, 0.37 mmol) at room temperature. The reaction mixture was stirred overnight and the solvent was distilled off under reduced pressure. The residue was purified by column chromatography to obtain the target compound (0.135 g).

$^1$H-NMR (CDCl$_3$) δ: 0.67-0.79 (m, 2H), 0.89-1.02 (m, 2H), 1.27-1.40 (m, 1H), 2.42-2.60 (m, 1H), 2.77-2.92 (m,

1H), 3.67-3.88 (m, 2H), 4.00 (d, 1H), 4.34-4.52 (m, 3H), 5.96-6.10 (m, 1H), 7.43 (s, 2H), 8.62 (s, 1H).

Step 4: Synthesis of N-({2-[2-hydroxy-3-(3,4,5-trichlorophenyl)-3-(trifluoromethyl)-pyrrolidin-1-yl]-4-(trifluoromethyl)pyrimidin-5-yl}methyl)cyclopropanecarboxamide (A4-16)

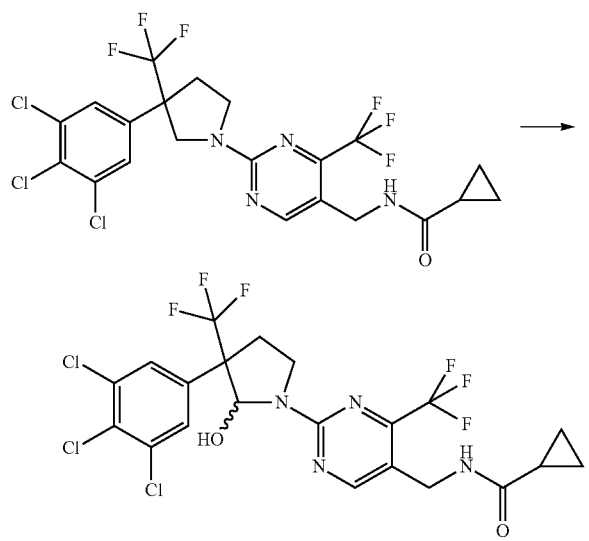

1-({2-[3-(3,4,5-Trichlorophenyl)-3-(trifluoromethyl)pyrrolidin-1-yl]-4-(trifluoromethyl)pyrimidin-5-yl}methyl)cyclopropanecarboxamide (0.13 g) was dissolved in acetonitrile (3 ml) and to the solution was added cerium ammonium nitrate (IV) (1 M aqueous solution, 0.46 ml) at 0° C. After stirring the mixture at 0° C. for 3 hours, cerium ammonium nitrate (IV) (1 M aqueous solution, 0.23 ml) was further added. After stirring the mixture at 0° C. for 1 hour, an aqueous solution of sodium sulfite was added. The solution was extracted with ethyl acetate, dried over magnesium sulfate, filtered and concentrated. The target compound (0.107 g) was obtained by purification with silica gel column chromatography.

¹H-NMR: see the table below.

K: Synthesis of N-{[6-{3-[3,5-bis(trifluoromethyl)phenyl]-2-hydroxy-3-(trifluoromethyl)pyrrolidin-1-yl}-4-(trifluoromethyl)pyridin-3-yl]methyl}cyclopropanecarboxamide (A5-27)

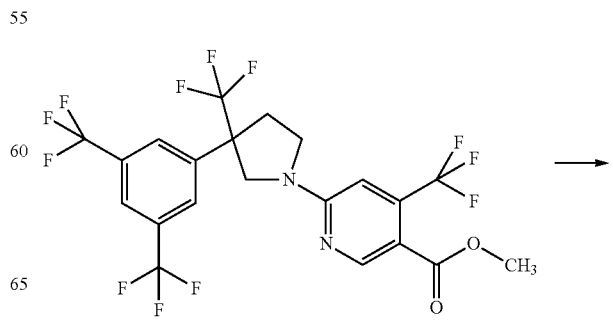

Step 1: Synthesis of methyl 6-{3-[3,5-bis(trifluoromethyl)phenyl]-3-(trifluoromethyl)-pyrrolidin-1-yl}-4-(trifluoromethyl)nicotinate

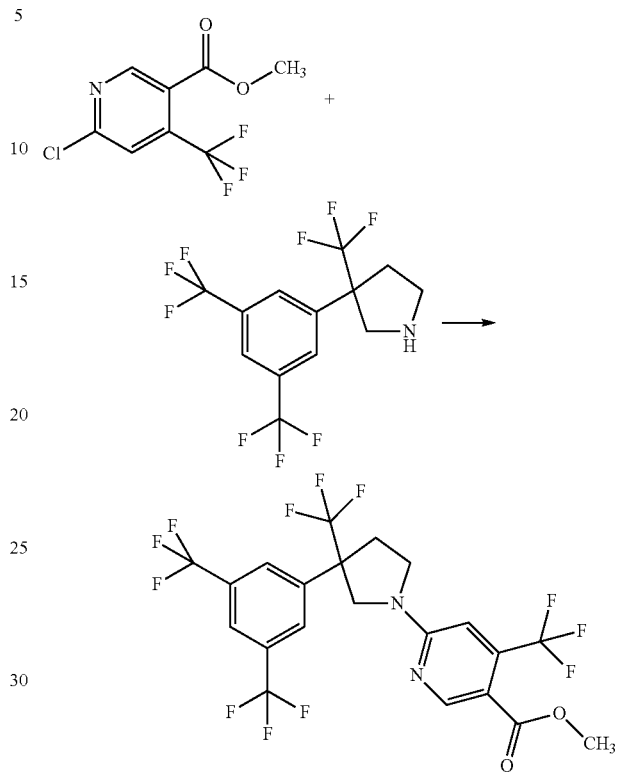

Methyl 6-chloro-4-(trifluoromethyl)nicotinate (2.39 g), 3-[3,5-bis(trifluoromethyl)-phenyl]-3-(tri-fluoromethyl)pyrrolidine (2.98 g) and potassium carbonate (1.8 g) were suspended in dimethylformamide (50 ml). The reaction mixture was heated for 8 hours at 80° C. Water and ethyl acetate were added and the extraction was carried out. The extract was dried over magnesium sulfate, filtered and concentrated under reduced pressure. The target compound (3.07 g) was obtained by purification with silica gel column chromatography.

¹H-NMR (CDCl₃) δ: 2.59-2.77 (m, 1H), 3.02-3.16 (m, 1H), 3.68-3.96 (m, 5H), 4.04-4.11 (m, 1H), 4.62-4.77 (m, 1H), 6.70 (s, 1H), 7.85 (s, 2H), 7.95 (s, 1H), 8.86 (s, 1H).

Step 2: Synthesis of 6-{3-[3,5-bis(trifluoromethyl)phenyl]-3-(trifluoromethyl)pyrrolidin-1-yl}-4-(trifluoromethyl)nicotinic acid

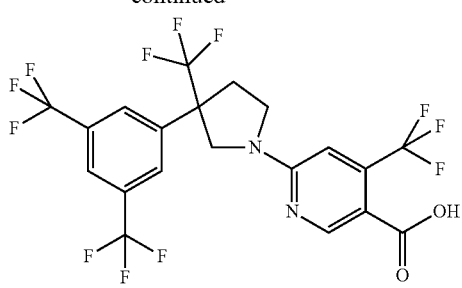

Methyl 6-{3-[3,5-bis(trifluoromethyl)phenyl]-3-(trifluoromethyl)pyrrolidin-1-yl}-4-(trifluoro-methyl)nicotinate (1.21 g), sodium hydroxide (0.26 g) and water (5 ml) were added to ethanol (40 ml) and stirred at room temperature for 1 day. The solvent was distilled off under reduced pressure, diluted hydrochloric acid and t-butyl methyl ether were added and then extracted. The target compound (1.11 g) was obtained by concentration under reduced pressure.

$^1$H-NMR (CDCl$_3$) δ: 2.78-2.55 (m, 1H), 3.18-3.04 (m, 1H), 3.87-3.67 (m, 2H), 4.08 (d, 1H), 4.70 (d, 1H), 6.71 (s, 1H), 7.87 (s, 2H), 7.93 (s, 1H), 8.91 (s, 1H).

Step 3: Synthesis of [6-{3-[3,5-bis(trifluoromethyl)phenyl]-3-(trifluoromethyl)pyrrolidin-1-yl}-4-(trifluoromethyl)pyridin-3-yl]methanol

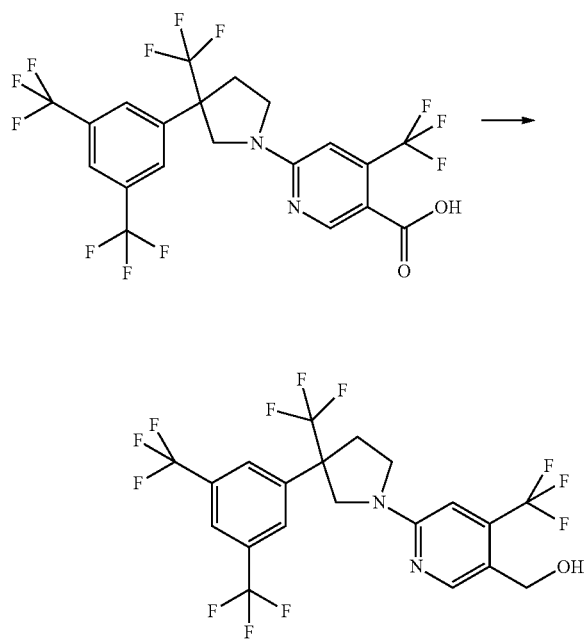

6-{3-[3,5-Bis(trifluoromethyl)phenyl]-3-(trifluoromethyl)pyrrolidin-1-yl}-4-(trifluoromethyl)nicotinic acid (1.11 g) was dissolved in methylene chloride (30 ml), and to the solution was added oxalyl chloride (0.54 ml, 6.16 mmol) and one drop of dimethylformamide at room temperature. After stirring for 5 hours, the solvent and excess oxalyl chloride were distilled off under reduced pressure. The residue was dissolved in dioxane, added with water, and then added with sodium borohydride (0.23 g) at 0° C. The mixture was stirred for 2 hours at room temperature and added with diluted hydrochloric acid. The mixture was extracted with ethyl acetate, dried over magnesium sulfate and filtered. After concentration under reduced pressure, the target compound (0.98 g) was obtained by purification with silica gel column chromatography.

$^1$H-NMR (CDCl$_3$) δ: 1.80 (t, 1H), 2.66-2.84 (m, 1H), 3.08-3.23 (m, 1H), 3.88-3.69 (m, 1H), 4.12 (d, 1H), 4.71 (d, 1H), 4.83 (d, 2H), 6.70 (s, 1H), 7.95 (s, 2H), 8.01 (s, 1H), 8.49 (s, 1H).

Step 4: Synthesis of 2-{[6-{3-[3,5-bis(trifluoromethyl)phenyl]-3-(trifluoromethyl)-pyrrolidin-1-yl}-4-(trifluoromethyl)pyridin-3-yl]methyl}-1H-isoindole-1,3(2H)-dione

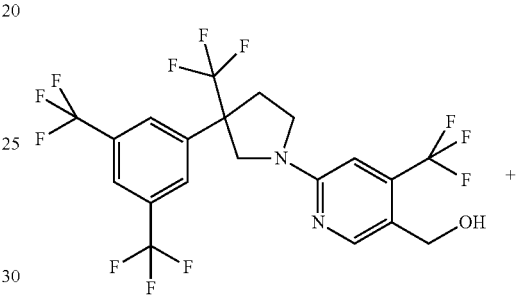

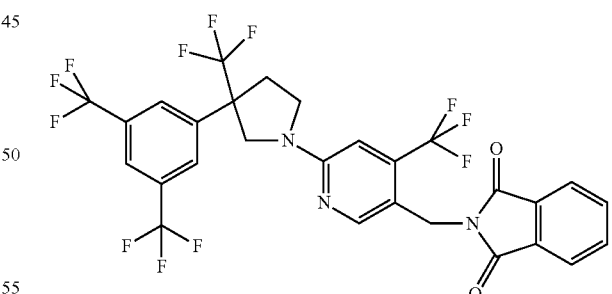

[6-{3-[3,5-Bis(trifluoromethyl)phenyl]-3-(trifluoromethyl)pyrrolidin-1-yl}-4-(trifluoromethyl)pyridin-3-yl]methanol (0.98 g), phthalimide (0.30 g, 2.04 mmol) and triphenylphosphine (0.58 g) were dissolved in tetrahydrofuran (50 ml), and to the solution was added diethyl azodicarboxylate (40% toluene solution, 1.0 ml) at room temperature. After stirring the mixture for 3 hours, the solvent was distilled off under reduced pressure. The residue was purified by silica gel column chromatography to obtain the target compound (0.60 g).

¹H-NMR (CDCl₃) δ: 2.54-2.73 (m, 1H), 2.98-3.14 (m, 1H), 3.56-3.80 (m, 2H), 3.97 (d, 1H), 4.57 (d, 1H), 4.99 (s, 2H), 6.64 (s, 1H), 7.70-7.99 (m, 7H), 8.20 (s, 1H).

Step 5: Synthesis of 1-[6-{3-[3,5-bis(trifluoromethyl)phenyl]-3-(trifluoromethyl)-pyrrolidin-1-yl}-4-(trifluoromethyl)pyridin-3-yl]methanamine

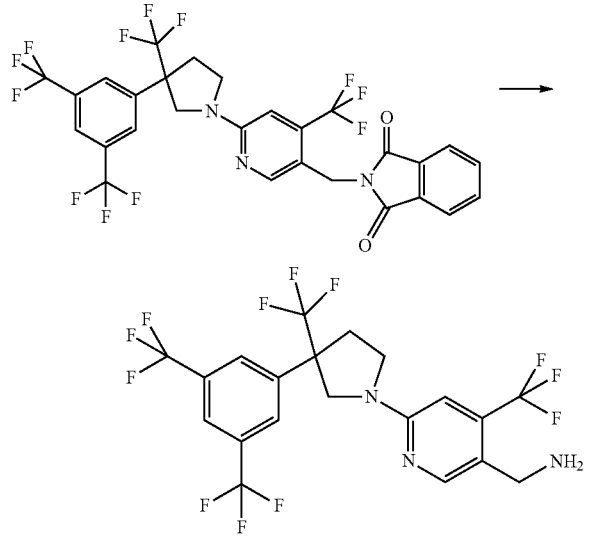

2-{[6-{3-[3,5-Bis(trifluoromethyl)phenyl]-3-(trifluoromethyl)pyrrolidin-1-yl}-4-(trifluoro-methyl)pyridin-3-yl]methyl}-1H-isoindole-1,3(2H)-dione (0.31 g) and hydrazine hydrate (0.035 ml) were added to ethanol (5 ml), and heated at 80° C. for 5 hours. The solvent was distilled off under reduced pressure, and then t-butyl methyl ether was added. The undissolved matters were removed by filtration, and the target compound (0.24 g) was obtained after concentration under reduced pressure.

¹H-NMR (CDCl₃) δ: 2.36 (br s, 2H), 2.57-2.73 (m, 1H), 2.98-3.13 (m, 1H), 3.79-3.57 (m, 2H), 3.91 (s, 2H), 4.03 (d, 1H), 4.60 (d, 1H), 6.60 (s, 1H), 7.86 (s, 2H), 7.92 (s, 1H), 8.34 (s, 1H).

Step 6: Synthesis of N-{[6-{3-[3,5-bis(trifluoromethyl)phenyl]-3-(trifluoromethyl)-pyrrolidin-1-yl}-4-(trifluoromethyl)pyridin-3-yl]methyl}cyclopropanecarboxamide

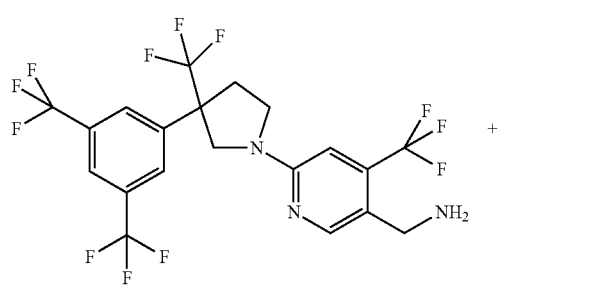

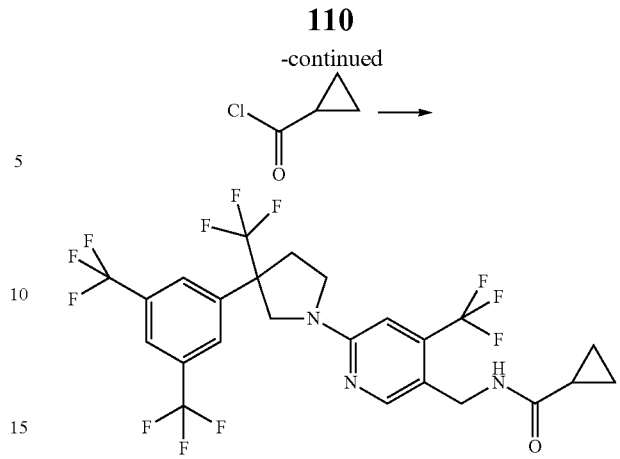

1-[6-{3-[3,5-Bis(trifluoromethyl)phenyl]-3-(trifluoromethyl)pyrrolidin-1-yl}-4-(trifluoromethyl)pyridin-3-yl]methanamine (0.18 g) was dissolved in methylene chloride (5 ml), and to the solution was added cyclopropane carbonyl chloride (0.036 ml) at room temperature. The reaction mixture was stirred overnight and the solvent was distilled off under reduced pressure. The residue was purified by silica gel column chromatography to obtain the target compound (0.15 g).

¹H-NMR (CDCl₃) δ: 0.69-0.82 (m, 2H), 0.93-1.05 (m, 2H), 1.28-1.41 (m, 1H), 2.56-2.75 (m, 1H), 2.98-3.13 (m, 1H), 3.60-3.79 (m, 2H), 4.02 (d, 2H), 4.51 (d, 2H), 4.60 (d, 1H), 5.81-5.91 (m, 1H), 6.60 (s, 1H), 7.86 (s, 2H), 7.92 (s, 1H), 8.39 (s, 1H).

Step 7: Synthesis of N-{[6-{3-[3,5-bis(trifluoromethyl)phenyl]-2-hydroxy-3-(trifluoromethyl)pyrrolidin-1-yl}-4-(trifluoromethyl)pyridin-3-yl]methyl}cyclopropanecarboxamide (A5-27)

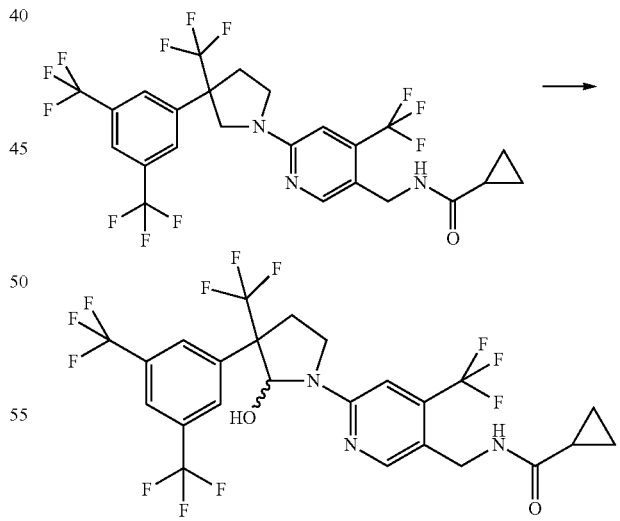

N-{[6-{3-[3,5-Bis(trifluoromethyl)phenyl]-3-(trifluoromethyl)pyrrolidin-1-yl-}-4-(trifluoro-methyl)pyridin-3-yl]methyl}cyclopropanecarboxamide (0.15 g) was dissolved in acetonitrile (3 ml) and to the solution was added cerium ammonium nitrate (IV) (1 M aqueous solution, 0.51 ml) at 0° C. After stirring at 0° C. for 3 hours, an aqueous solution of sodium sulfite was added, extracted with ethyl acetate, dried over magnesium sulfate, filtered and concentrated. The target compound (0.12 g) was obtained by purification with silica gel column chromatography.

¹H-NMR: see the table below.

L: Synthesis of N-{[6-{4-[3,5-bis(trifluoromethyl)phenyl]-2-hydroxy-4-(trifluoromethyl)pyrrolidin-1-yl}-2-(trifluoromethyl)pyridin-3-yl]methyl}propanamide (A'3-24)

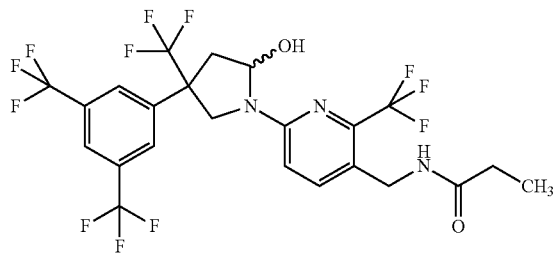 [SMILES: CCC(=O)NCc1ccc(N2CC(c3cc(C(F)(F)F)cc(C(F)(F)F)c3)(C(F)(F)F)CC2O)nc1C(F)(F)F]

Step 1: Synthesis of ethyl 6-{3-[3,5-bis(trifluoromethyl)phenyl]-3-(trifluoromethyl)-pyrrolidin-1-yl}-2-(trifluoromethyl)nicotinate

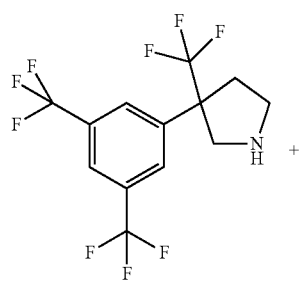

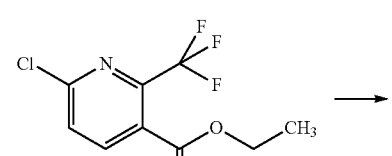

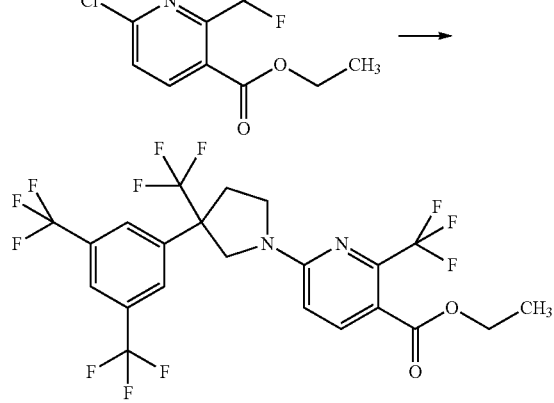

Ethyl 2-chloro-6-(trifluoromethyl)pyridin-5-carboxylate (0.95 g), 3-[3,5-bis(trifluoromethyl)phenyl]-3-(trifluoromethyl)pyrrolidine (1.4 g) and potassium carbonate (0.7 g) were added to N,N-dimethylformamide (30 ml), and heated for 5 hours at 100° C. After cooling, the reaction mixture was poured in ice water and extracted with ethyl acetate. The organic layer was dried over magnesium sulfate, the solvent was distilled off under reduced pressure, and purified by silica gel column chromatography to obtain ethyl 6-{3-[3,5-bis-(trifluoromethyl)phenyl]-3-(trifluoromethyl)pyrrolidin-1-yl}-2-(trifluoromethyl)nicotinate (1.7 g).

¹H-NMR (CDCl₃) δ: 1.38 (3H, t), 2.62-2.68 (1H, m), 3.01-3.09 (1H, m), 3.69-3.82 (2H, m), 4.08 (1H, d), 4.38 (2H, q), 4.59 (1H, d), 6.56 (1H, d), 7.90 (3H, m), 8.04 (1H, d).

Step 2: Synthesis of [6-{3-[3,5-bis(trifluoromethyl)phenyl]-3-(trifluoromethyl)pyrrolidin-1-yl}-2-(trifluoromethyl)pyridin-3-yl]methanol

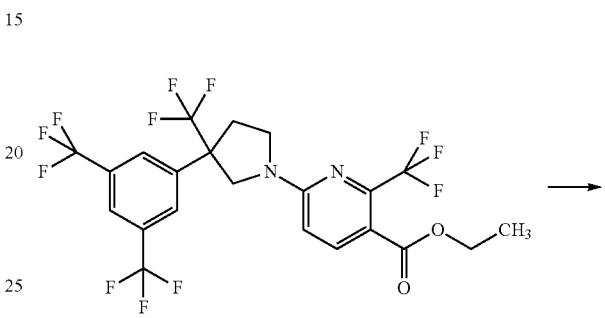

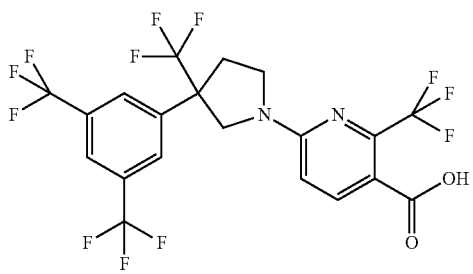

Ethyl 6-{3-[3,5-bis(trifluoromethyl)phenyl]-3-(trifluoromethyl)pyrrolidin-1-yl}-2-(trifluoro-methyl)nicotinate (1.7 g) was added to dichloromethane (50 ml). Then, 1.0 mol/l hexane solution (10 ml) of diisobutyl aluminum hydride was added dropwise thereto at −70° C. After continuing the stirring at −70° C. for 30 minutes, ethyl acetate (50 ml) and sodium sulfate decahydrate (3.0 g) were added. After further stirring at room temperature for 1 hour, the reaction liquid was filtered by suction on Celite. The filtrate was distilled off under reduced pressure and the purified by silica gel column chromatography to obtain [6-{3-[3,5-bis-(trifluoromethyl)phenyl]-3-(trifluoromethyl)pyrrolidin-1-yl}-2-(trifluoromethyl)pyridin-3-yl]-methanol (1.55 g).

¹H-NMR (CDCl₃) δ: 1.77 (1H, t), 2.60-2.65 (1H, m), 3.01-3.08 (1H, m), 3.60-3.77 (2H, m), 4.11 (1H, d), 4.52 (1H, d), 4.75 (2H, d), 6.59 (1H, d), 7.82-7.87 (4H, m).

Step 3: Synthesis of 1-[6-{3-[3,5-bis(trifluoromethyl)phenyl]-3-(trifluoromethyl)pyrrolidin-1-yl}-2-(tri-fluoromethyl)pyridin-3-yl]methanamine

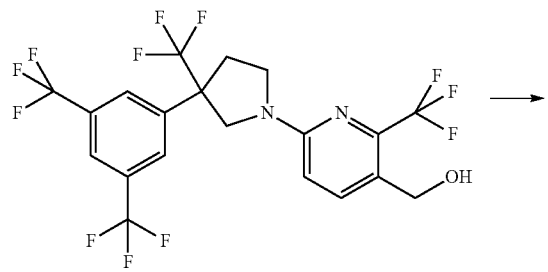

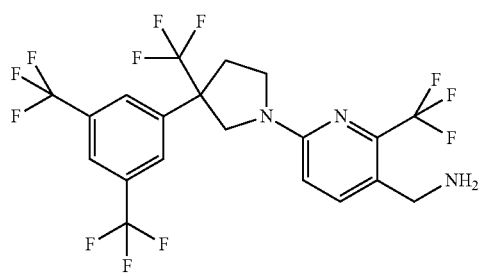

[6-{3-[3,5-Bis(trifluoromethyl)phenyl]-3-(trifluoromethyl)pyrrolidin-1-yl}-2-(trifluoromethyl)pyridin-3-yl]methanol (1.55 g) and triethylamine (0.4 g) were added to acetonitrile (30 ml), and an acetonitrile solution (10 ml) of methanesulfonyl chloride (0.4 g) was added dropwise thereto under ice cooling. Upon the completion of the dropwise addition, the reaction liquid was stirred at room temperature for 1 hour, and then the resulting solution was added dropwise to a mixture solution containing 28% ammonia water (30 ml) and acetonitrile (50 ml), which had been prepared separately, under ice cooling. After stirring at room temperature for 12 hours, the reaction mixture was poured into ice water and extracted with ethyl acetate. The organic layer was dried over magnesium sulfate, the solvent was distilled off under reduced pressure and the purified by silica gel chromatography to obtain 1-[6-{3-[3,5-bis(trifluoromethyl)phenyl]-3-(trifluoromethyl)pyrrolidin-1-yl}-2-(trifluoromethyl)pyridin-3-yl]methanamine (1.0 g).

¹H-NMR (CDCl₃) δ: 2.57-2.69 (1H, m), 3.00-3.07 (1H, m), 3.59-3.76 (2H, m), 3.84-3.89 (2H, m), 4.10 (1H, d), 4.55 (1H, d), 6.56 (1H, d), 7.72 (1H, d), 7.82-8.09 (3H, m).

Step 4: Synthesis of N-{[6-{3-[3,5-bis(trifluoromethyl)phenyl]-3-(trifluoromethyl)-pyrrolidin-1-yl}-2-(trifluoromethyl)pyridin-3-yl]methyl}propanamide

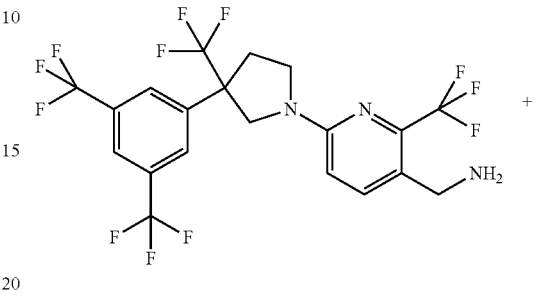

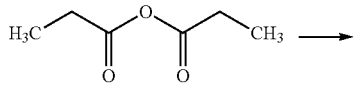

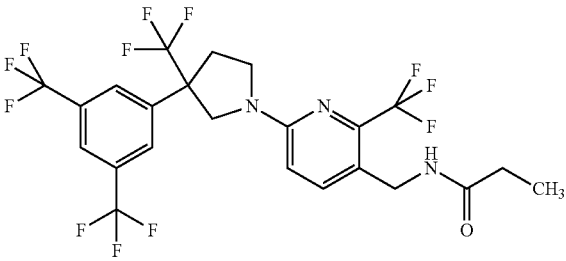

1-[6-{3-[3,5-Bis(trifluoromethyl)phenyl]-3-(trifluoromethyl)pyrrolidin-1-yl}-2-(trifluoromethyl)pyridin-3-yl]methanamine (0.6 g) and triethylamine (0.2 g) were added to dichloromethane (20 ml), and a dichloromethane solution (10 ml) of propionic anhydride (0.2 g) was added dropwise thereto under ice cooling. Upon the completion of the dropwise addition, the reaction mixture was stirred for 1 hour at room temperature, and the solvent was distilled off under reduced pressure. After purification by silica gel column chromatography, N-{[6-{3-[3,5-bis(trifluoromethyl)phenyl]-3-(trifluoromethyl)pyrrolidin-1-yl}-2-(trifluoromethyl)pyridin-3-yl]methyl}propanamide (0.6 g) was obtained.

¹H-NMR (CDCl₃) δ: 1.15 (3H, t), 2.20 (2H, q), 2.59-2.64 (1H, m), 3.00-3.06 (1H, m), 3.57-3.75 (2H, m), 4.06 (1H, d), 4.47-4.51 (3H, m), 5.76-5.78 (1H, m), 6.54 (1H, d), 7.75 (1H, d), 7.85-7.91 (3H, m).

Step 5: Synthesis of N-{[6-{4-[3,5-bis(trifluoromethyl)phenyl]-2-oxo-4-(trifluoromethyl)-pyrrolidin-1-yl}-2-(trifluoromethyl)pyridin-3-yl]methyl}propanamide (C3-24)

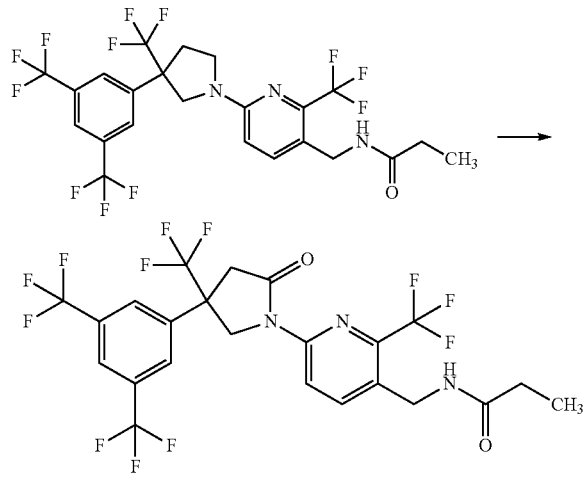

N-{[6-{3-[3,5-Bis(trifluoromethyl)phenyl]-3-(trifluoromethyl)pyrrolidin-1-yl}-2-(trifluoro-methyl)pyridin-3-yl]methyl}propanamide (0.3 g), benzyltriethylammonium chloride (0.35 g) and potassium permanganate (0.25 g) were added to dichloromethane (20 ml), and the mixture was stirred for 75 hours at room temperature. Upon the completion of the stirring, the reaction mixture was filtered through a short silica gel layer to remove precipitate. The filtrate was distilled off under reduced pressure and the purification was carried out by silica gel column chromatography to obtain N-{[6-{4-[3,5-bis(trifluoromethyl)phenyl]-2-oxo-4-(trifluoromethyl)pyrrolidin-1-yl}-2-(trifluoromethyl)pyridin-3-yl]methyl}propanamide (0.08 g).

¹H-NMR: see the table below.

Step 6: Synthesis of N-{[6-{4-[3,5-bis(trifluoromethyl)phenyl]-2-hydroxy-4-(trifluoro-methyl)pyrrolidin-1-yl}-2-(trifluoromethyl)pyridin-3-yl]methyl}propanamide (A'3-24)

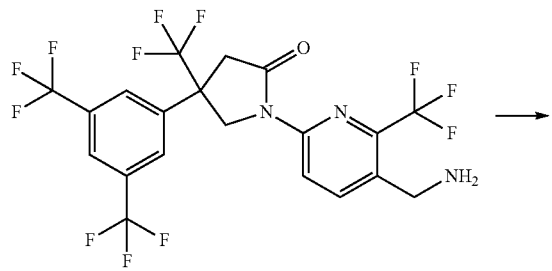

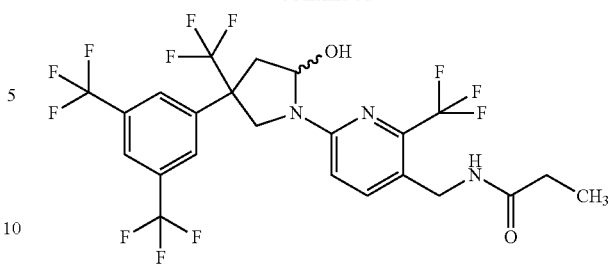

N-{[6-{4-[3,5-Bis(trifluoromethyl)phenyl]-2-oxo-4-(trifluoromethyl)pyrrolidin-1-yl}-2-(tri-fluoromethyl)pyridin-3-yl]methyl}propanamide (0.07 g) was added to dichloromethane (20 ml). Then, a 1.0 mol/l hexane solution (0.3 ml) of diisobutyl aluminum hydride was added dropwise thereto at −70° C. After continuing the stirring at −70° C. for 30 minutes, ethyl acetate (5 ml) and sodium sulfate decahydrate (0.5 g) were added. After further stirring at room temperature for 1 hour, the reaction mixture was filtered by suction on Celite. The filtrate was distilled off under reduced pressure and the purification was carried out by silica gel column chromatography to obtain N-{[6-{4-[3,5-bis(trifluoromethyl)phenyl]-2-hydroxy-4-(trifluoromethyl)pyrrolidin-1-yl]-2-(trifluoroethyl)pyridin-3-yl}methyl]-propanamide (0.02 g).

¹H-NMR: see the table below.

M: Synthesis of N-[(1S)-1-(4-{3-[2,6-bis(trifluoromethyl)pyridin-4-yl]-2-hydroxy-3-(trifluoro-methyl)pyrrolidin-1-yl}phenyl)ethyl]cyclopropanecarboxamide (A2-38-b)

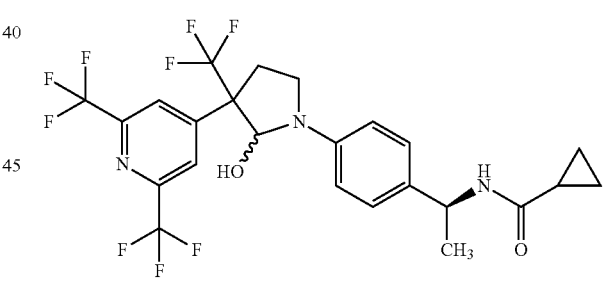

Step 1: Synthesis of 4-[1-benzyl-3-(trifluoromethyl)pyrrolidin-3-yl]-2,6-bis(trifluoromethyl)pyridine

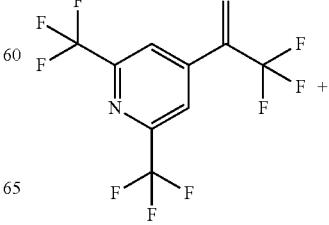

-continued

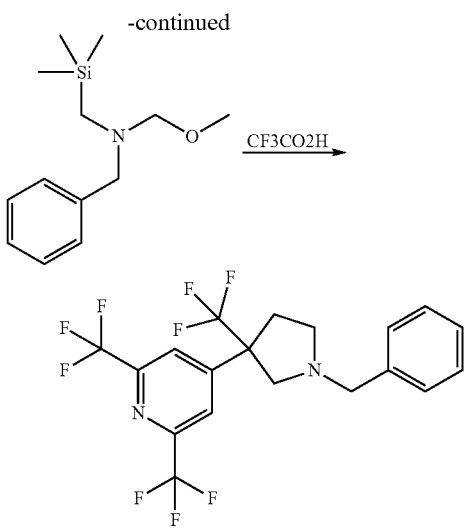

To the solution of 2,6-bis(trifluoromethyl)-4-(3,3,3-trifluoroprop-1-en-2-yl)pyridine (1.25 g) and N-benzyl-1-methoxy-N-[(trimethylsilyl)methyl]methanamine (5.0 g) in dichloromethane was added dropwise the solution of trifluoroacetic acid (0.038 g) in dichloromethane while cooling with ice. On completion of the dropwise addition, the mixture was warmed to room temperature and stirred over night. The mixture was washed with saturated sodium bicarbonate water and dried over anhydrous magnesium sulfate. After the drying agent was filtered off, the solvent was distilled away under the reduced pressure, and the residue was then purified by silica gel chromatography to yield 4-[1-benzyl-3-(trifluoromethyl)pyrrolidin-3-yl]-2,6-bis(trifluoromethyl)pyridine (1.52 g).

$^1$H-NMR (CDCl$_3$) δ: 2.23-2.29 (1H, m), 2.65-2.69 (2H, m), 2.96 (1H, d), 3.05-3.15 (2H, m), 3.58 (1H, d), 3.82 (1H, d), 7.26-7.37 (5H, m), 8.00 (2H, s).

Step 2: Synthesis of 2,6-bis(trifluoromethyl)-4-[3-(trifluoromethyl)pyrrolidin-3-yl]pyridine

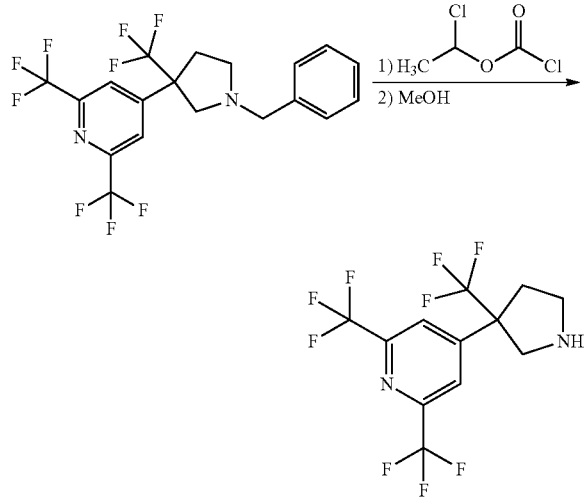

The solution of 4-[1-benzyl-3-(trifluoromethyl)pyrrolidin-3-yl]-2,6-bis(trifluoromethyl)pyridine (1.4 g) and 1-chloroethyl chloroformate (0.905 g) in dichloroethane was heated to reflux for 3 hours. The mixture was cooled to room temperature and then concentrated under the reduced pressure. Methanol was added to the resultant residue, which was then heated with stirring at 60° C. for two hours. The mixture was cooled to room temperature, to which was then added water. The solution was washed twice with the mixed solvent of hexane. The solution was neutralized with sodium hydroxide and then extracted with tert-butyl methyl ether three times. The organic layer was combined, which was then washed with brine and dried over anhydrous magnesium sulfate. After the drying agent was filtered off, the solvent was distilled away under the reduced pressure to yield 2,6-bis(trifluoromethyl)-4-[3-(trifluoromethyl)pyrrolidin-3-yl]pyridine (0.781 g).

$^1$H-NMR (CDCl$_3$) δ: 1.86 (1H, br s), 2.27-2.36 (1H, m), 2.63-2.69 (1H, m), 3.05-3.14 (1H, m), 3.26-3.33 (2H, m), 3.83 (1H, d), 7.87 (2H, s).

Step 3: Synthesis of N-[(1S)-1-(4-{3-[2,6-bis(triluoroethyl)pyridin-4-yl]-3-(trifluoromethyl)pyrrolidin-1-yl}phenyl)ethyl]cyclopropanecarboxamide

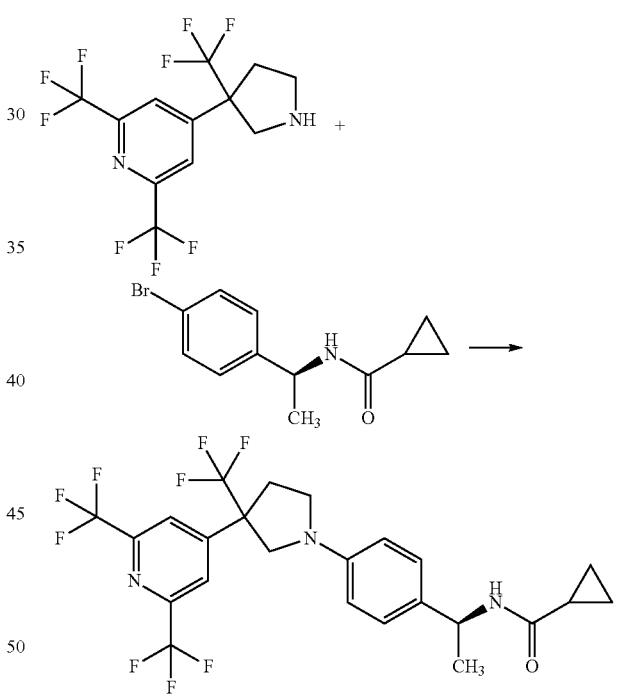

To the solution of N-[(1S)-1-(4-bromophenyl)ethyl]cyclopropanecarboxamide (0.134 g) and 2,6-bis(trifluoromethyl)-4-[3-(trifluoromethyl)pyrrolidin-3-yl]pyridine (0.195 g) in toluene was added sodium tert-butoxide (0.096 g), tris(dibenzylideneacetone)dipalladium chloroform complex (0.010 g) and xantphos (0.017 g) and the vessele was applied by Ar gas. The vessel was sealed and applied to microwave reactor at 120° C. for 10 min. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield N-[(1S)-1-(4-{3-[2,6-bis(triuoroethyl)pyridin-4-yl]-3-(trifluoromethyl)pyrrolidin-1-yl}phenyl)ethyl]cyclopropanecarboxamide (0.272 g).

¹H-NMR (CDCl₃) δ: 0.64-0.77 (2H, m), 0.86-1.01 (2H, m), 1.25-1.31 (1H, m), 1.48 (3H, d), 2.53-2.63 (1H, m), 2.91-3.00 (1H, m), 3.48-3.62 (2H, m), 3.85 (1H, d), 4.11 (1H, d), 5.03-5.13 (1H, m), 5.80 (1H, d), 6.62 (2H, d), 7.27 (2H, d), 7.90 (2H, s).

Step 4: Synthesis of N-[(1S)-1-(4-{3-[2,6-bis(triuoromethyl)pyridin-4-yl]-2-hydroxy-3-(trifluoromethyl)pyrrolidin-1-yl}phenyl)ethyl]cyclopropanecarboxamide N-[(1S)-1-(4-{3-[2,6-bis(trifluoromethyl)pyridin-4-yl]-3-(trifluoromethyl)pyrrolidin-1-yl}phenyl)ethyl]cyclopropanecarboxamide (0.26 g) was dissolved in chloroform and Wakogel C-200 (3 g) was added. The mixture was kept left 3 days. The reaction mixture was concentrated in vacuo and the residue was purified by silica gel chromatography to yield N-[(1S)-1-(4-{3-[2,6-bis(triuoromethyl)pyridin-4-yl]-2-hydroxy-3-(trifluoromethyl)pyrrolidin-1-yl}phenyl)ethyl]cyclopropanecarboxamide (0.12 g).

¹H-NMR: see the table below.

N: Synthesis of N-({2-[2-hydroxy-3-(3,4,5-trichlorophenyl)-3-(trifluoromethyl)pyrrolidin-1-yl]-4-(trifluoromethyl)-1,3-thiazol-5-yl}methyl)cyclopropanecarboxamide (A6-16)

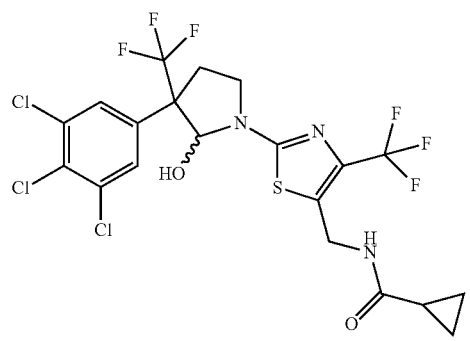 [SMILES: O=C(NCc1sc(N2CCC(c3cc(Cl)c(Cl)c(Cl)c3)(C(F)(F)F)C2O)nc1C(F)(F)F)C1CC1]

The title compound was obtained from N-({2-[3-(3,4,5-trichlorophenyl)-3-(trifluoromethyl)pyrrolidin-1-yl]-4-(trifluoromethyl)-1,3-thiazol-5-yl}methyl)cyclopropanearboxamide (WO2010/043315) according to the method of Step 6 of synthetic example 6.

¹H-NMR: see the table below.

O: Synthesis of 5-[3-(3,5-dichlorophenyl)-2-hydroxy-3-(trifluoromethyl)pyrrolidin-1-yl]-2-(1H-1,2,4-triazol-1-yl)benzonitrile (A7-4)

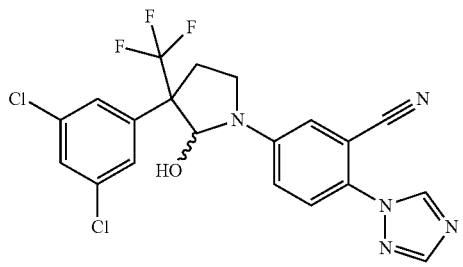 [SMILES: N#Cc1cc(N2CCC(c3cc(Cl)cc(Cl)c3)(C(F)(F)F)C2O)ccc1-n1cncn1]

The title compound was obtained from 5-[3-(3,5-dichlorophenyl)-3-(trifluoromethyl)pyrrolidin-1-yl]-2-(1H-1,2,4-triazol-1-yl)benzonitrile (WO2008/128711) according to the method of Step 6 of synthetic example 6.

¹H-NMR: see the table below.

P: Synthesis of N-{4-[3-(3,5-dichloro-2-fluorophenyl)-2-hydroxy-3-(trifluoromethyl)pyrrolidin-1-yl]-2-(trifluoromethyl)benzyl}cyclopropanecarboxamide (A1-409)

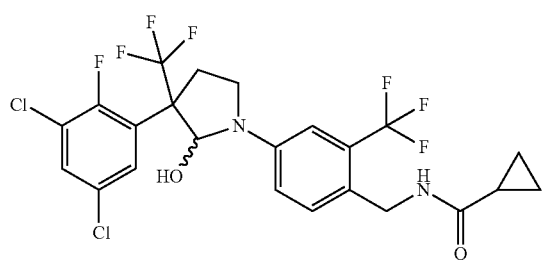 [SMILES: O=C(NCc1ccc(N2CCC(c3cc(Cl)cc(Cl)c3F)(C(F)(F)F)C2O)cc1C(F)(F)F)C1CC1]

Step 1: Synthesis of 1,5-dichloro-2-fluoro-3-(3,3,3-trifluoroprop-1-en-2-yl)benzene

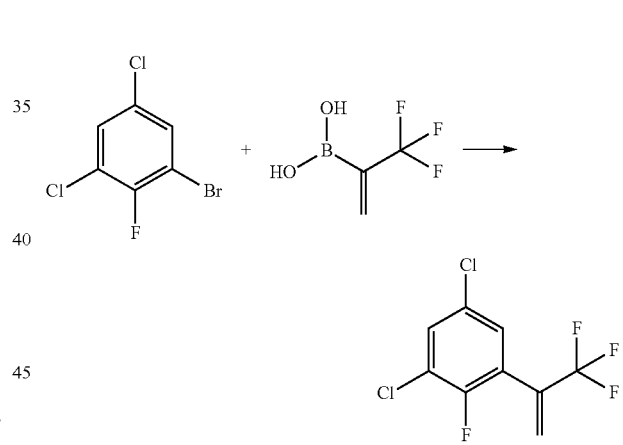

1-bromo-3,5-dichloro-2-fluorobenzene (10 g), (3,3,3-trifluoroprop-1-en-2-yl)-boronic acid (7.5 g) and potassium carbonate (13.6 g) were dissolved in tetrahydrofuran (41 ml) and water (20 ml), and then deaerated. Dichlorobis(triphenylphosphine)palladium (II) (1.4 g) was added thereto and the mixture was stirred for 3 hours under reflux under argon atomosphere. After cooling the mixture to the room temperature, water and n-hexane were added, and the organic layer was washed with water and dried over anhydrous magnesium sulfate. The drying agent was filtered off, the solvent was distilled off under reduced pressure, and the residue was roughly purified by silica gel chromatography (n-hexane) to obtain a mixture containing 1,3-dichloro-2,4-difluoro-5-(3,3,3-trifluoroprop-1-en-2-yl)benzene and hexane.

¹H-NMR (CDCl₃) δ: 5.82 (1H, s), 6.25 (1H, s), 7.21-7.26 (1H, m), 7.48-7.43 (1H, m).

Step 2: Synthesis of 1-benzyl-3-(3,5-dichloro-2-fluorophenyl)-3-(trifluoromethyl)pyrrolidine

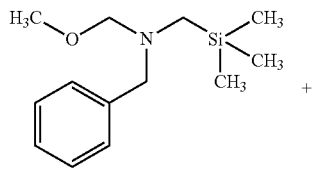

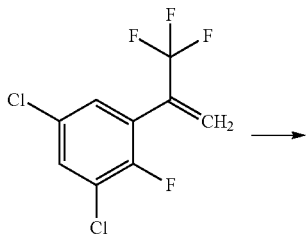

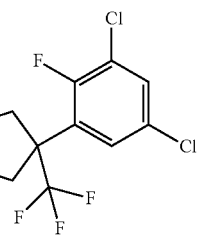

1,5-dichloro-2-fluoro-3-(3,3,3-trifluoroprop-1-en-2-yl)benzene (6.2 g) and N-(methoxymethyl)-N-(trimethylsilylmethyl)benzylamine (4.7 g) were dissolved in dichloromethane (100 ml) and slowly added dropwise with a dichloromethane solution (8 ml) of anhydrous trifluoroacetic acid (0.15 ml) under ice cooling. Upon the completion of the dropwise addition, the reaction temperature was raised to the room temperature and stirred overnight. The reaction solution was concentrated under reduced pressure, and the residue was purified by column chromatography to obtain 1-benzyl-3-(3,5-dichloro-2-fluorophenyl)-3-(trifluoromethyl)pyrrolidine (3.7 g).

$^1$H-NMR (CDCl$_3$) δ: 2.38-2.45 (1H, m), 2.56-2.70 (2H, m), 2.84-2.89 (1H, m), 3.02 (1H, d), 3.40 (1H, dd), 3.65 (1H, d), 3.70 (1H, d), 7.17 (1H, dd), 7.26-7.34 (5H, m), 7.40 (1H, dd).

Step 3: Synthesis of 3-(3,5-dichloro-4-fluorophenyl)-3-(trifluoromethyl)pyrrolidine

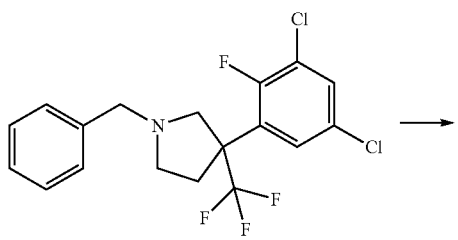

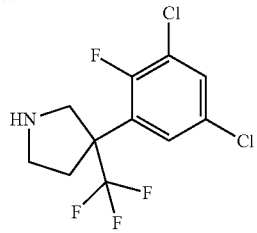

1-Benzyl-3-(3,5-dichloro-4-fluorophenyl)-3-(trifluoromethyl)pyrrolidine (3.7 g) was dissolved in 1,2-dichloroethane (20 ml), added with 1-chloroethyl chloroformate (2.7 g) at room temperature, and then refluxed under heating for 3 hours. The reaction solution was concentrated under reduced pressure, and the residue obtained was added with methanol (30 ml) and further refluxed under heating for 2 hours. The reaction solution was concentrated under reduced pressure and the residue obtained was added with t-butyl methyl ether and water to separate the aqueous layer. After that, the organic layer was again washed with a 1 M aqueous solution of hydrochloric acid, and the aqueous layers were combined, added with a saturated aqueous solution of potassium carbonate to make the liquid alkaline, and extracted with t-butyl methyl ether. The aqueous phase was extracted again with t-butyl methyl ether, and the organic layers were combined, dried over magnesium sulfate, filtered and concentrated under reduced pressure to obtain 3-(3,5-dichloro-4-fluorophenyl)-3-(trifluoromethyl)pyrrolidine (2.6 g).

$^1$H-NMR (CDCl$_3$) δ: 2.27-2.34 (1H, m), 2.61-2.68 (1H, m), 2.99-3.05 (1H, m), 3.29-3.17 (2H, m), 3.94 (1H, dd), 7.20 (1H, dd), 7.42 (1H, dd).

Step 4: Synthesis of 4-[3-(3,5-dichloro-4-fluorophenyl)-3-(trifluoromethyl)pyrrolidin-1-yl]-2-(trifluoromethyl)benzonitrile

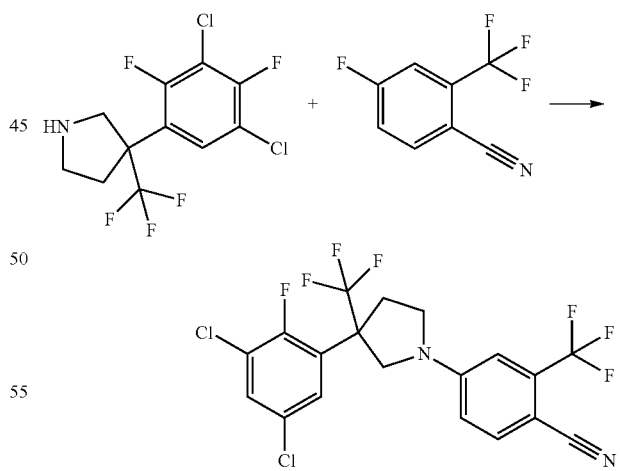

3-(3,5-Dichloro-4-fluorophenyl)-3-(trifluoromethyl)pyrrolidine (0.9 g) and 4-fluoro-2-(tri-fluoromethyl)benzonitrile (0.62 g) were weighed, dissolved in N,N-dimethylacetamide (10 ml), added with N,N-diisopropylethylamine (1.0 ml) at room temperature and reacted for 1 hour using a microwave reactor (trade name: INITIATOR™, manufactured by Biotage). The reaction solution was diluted by adding t-butyl methyl ether, and the organic layer was washed three times with water and then saturated brine in that order. The organic layer was dried over magnesium sulfate, filtered and concentrated under reduced pressure and the residue obtained was purified by column chromatography to obtain 4-[3-(3,5-dichloro-4-fluorophenyl)-3-(trifluoromethyl)pyrrolidin-1-yl]-2-(trifluoromethyl)benzonitrile (1.1 g).

¹H-NMR (CDCl₃) δ: 2.58-2.66 (1H, m), 3.07-3.12 (1H, m), 3.69-3.60 (2H, m), 3.83 (1H, d), 4.35 (1H, dd), 6.73 (1H, dd), 6.86 (1H, d), 7.22 (1H, dd), 7.51 (1H, dd), 7.65 (1H, d).

Step 5: Synthesis of N-{4-[3-(3,5-dichloro-2-fluorophenyl)-3-(trifluoromethyl)pyrrolidin-1-yl]-2-(trifluoromethyl)benzyl}cyclopropanecarboxamide

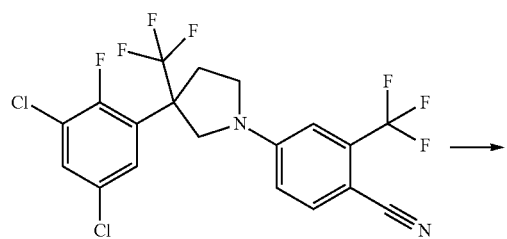

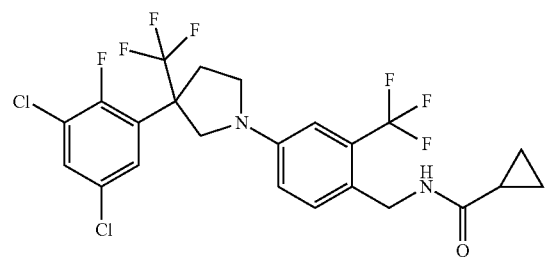

4-[3-(3,5-dichloro-4-fluorophenyl)-3-(trifluoromethyl)pyrrolidin-1-yl]-2-(trifluoromethyl)benzonitrile (0.36 g) was dissolved in 1,4-dioxane (7.5 ml) and methanol (15 ml), cooled by using an ice bath, and stirred. To the resulting solution, cyclopropanecarboxylic anhydride (0.59 g) and nickel (II) chloride hexahydrate (0.18 g) were added and thoroughly dissolved. After that, sodium borohydride (0.15 g) was added thereto in three divided portions. The mixture was brought back to the room temperature and stirred for 30 minutes. After that, diethylenetriamine (1.7 ml) was added and the mixture was stirred until the solution became transparent. The reaction solution was diluted with t-butyl methyl ether and washed with water and saturated brine. The organic layer was dried over magnesium sulfate, filtered and concentrated under reduced pressure and the residue obtained was purified by column chromatography to obtain N-{4-[3-(3,5-dichloro-2-fluorophenyl)-3-(trifluoromethyl)pyrrolidin-1-yl]-2-(trifluoromethyl)-benzyl}cyclopropanecarboxamide (0.28 g).

¹H-NMR (CDCl₃) δ: 0.70-0.75 (2H, m), 0.96-1.00 (2H, m), 1.28-1.34 (1H, m), 2.53-2.63 (1H, m), 3.01-3.06 (1H, m), 3.49-3.61 (2H, m), 3.77 (1H, d), 4.26 (1H, dd), 4.52 (2H, d), 5.87 (1H, t), 6.71 (1H, dd), 6.81 (1H, d), 7.23 (1H, dd), 7.44-7.49 (2H, m).

Step 6: Synthesis of N-{4-[3-(3,5-dichloro-2-fluorophenyl)-2-hydroxy-3-(trifluoromethyl)pyrrolidin-1-yl]-2-(trifluoromethyl)benzyl}cyclopropanecarboxamide

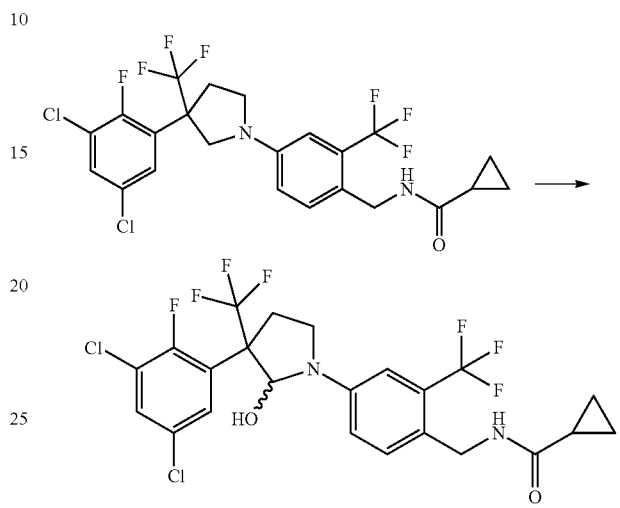

N-{4-[3-(3,5-dichloro-2-fluorophenyl)-3-(trifluoromethyl)pyrrolidin-1-yl]-2-(trifluoro-methyl)benzyl}cyclopropanecarboxamide (0.18 g) was dissolved in N,N-dimethylformamide (5 ml), cooled by using an ice bath, and then stirred. To the solution, a 1 M aqueous solution of cerium ammonium nitrate (IV) (0.72 ml) was added dropwise and stirred in an ice bath for 2 minutes. After that, t-butyl methyl ether was added for dilution and the organic layer was washed with water, an aqueous solution of sodium thiosulfate and saturated brine in that order. The organic layer was dried over magnesium sulfate, filtered and concentrated under reduced pressure, and the residue obtained was purified by column chromatography to obtain N-{4-[3-(3,5-dichloro-2-fluorophenyl)-2-hydroxy-3-(trifluoromethyl)pyrrolidin-1-yl]-2-(trifluoromethyl)benzyl}cyclopropanecarboxamide (0.08 g).

¹H-NMR: see the table below.

Q: Further Example 1,3-dichloro-2,4-difluoro-5-(3,3,3-trifluoroprop-1-en-2-yl)benzene (Synthetic example 6, step 2) can be also synthesized via 1-(3,5-dichloro-2,4-difluorophenyl)-2,2,2-trifluoroethanone from 1,3-dichloro-2,4-difluoro-5-iodobenzene (Synthetic example F, step 2) as shown below.

Step 1

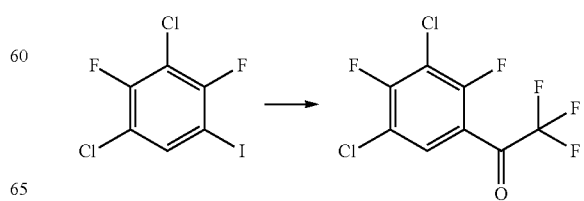

1,3-dichloro-2,4-difluoro-5-iodobenzene (4.0 g) was dissolved in tetrahydrofuran and cooled to −10 degree. A 2.0M solution of isopropylmagnesium chloride in tetrahydrofuran (10 ml) was added dropwise via a dropping funnel. The reaction mixture was stirred for 1 hour at same temperature. A solution of ethyl trifluoroacetae (2.76 g) in tetrahydrofuran (6 ml) was added dropwise and the reaction mixture was allowed to warm to abmient temperature. The reaction mixture was diluted with t-butyl methyl ether. and washed with 1 N NaOH and then brine. The combined extracts were dried over magnesium sulfate. After filtered off, the filtrate concentrated in vacuo to give crude product. A crude product was purified with Kugel-Rohr to give 1-(3,5-dichloro-2,4-difluorophenyl)-2,2,2-trifluoroethanone (2.5 g).

$^1$H-NMR (CDCl$_3$) δ: 7.90 (t)

Step 2

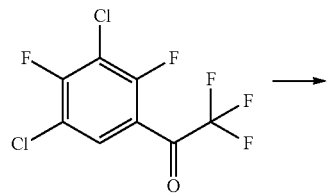

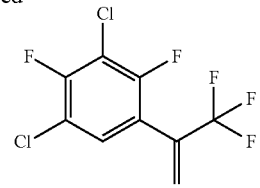

Synthesis of 1,3-dichloro-2,4-difluoro-5-(3,3,3-trifluoroprop-1-en-2-yl)benzene

To the suspension of methyl triphenylphosphonium iodide (1.92 g) in tetrahydrofuran (12 ml) was added potassium tert-butoxide (0.53 g) slowly at argon atomosphere below 0° C. on ice/water bath. The reaction mixture turned to yellow and stirred for 0.5 h. To the mixture was added a solution of 1-(3,5-dichloro-2,4-difluorophenyl)-2,2,2-trifluoroethanone (1.15 g) in tetrahydrofuran (3 ml) dropwise on ice/water bath. After addition, the reaction mixture was warmed to room temperature and stirred over night. The reaction mixture was diluted with pentane and water. The organic phase was separated and washed with water and dried over MgSO4. The crude residue was purified on silica-gel column chromatography (eluent: n-hexane) to give 1,3-dichloro-2,4-difluoro-5-(3,3,3-trifluoroprop-1-en-2-yl)benzene (0.80 g).

$^1$H-NMR (CDCl$_3$) δ: 7.32 (1H, t), 6.26 (1H, s), 5.80 (1H, s)

The compounds according to the invention which have been or can be prepared according to the invention as well as their intermediates are exemplified in the following tables.

TABLE A1

Compounds according to the invention

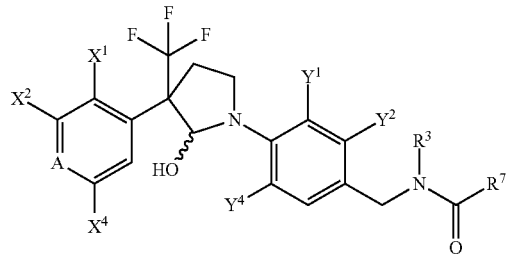

| Ex. No. | X$^1$ | X$^2$ | A | X$^4$ | Y$^1$ | Y$^2$ | Y$^4$ | R$^3$ | R$^7$ | log P |
|---|---|---|---|---|---|---|---|---|---|---|
| A1-1 | H | Cl | C—H | Cl | H | Cl | H | H | CH$_3$ | |
| A1-2 | H | Cl | C—H | Cl | H | Cl | H | H | ethyl | |
| A1-3 | H | Cl | C—H | Cl | H | Cl | H | H | n-propyl | |
| A1-4 | H | Cl | C—H | Cl | H | Cl | H | H | isopropyl | |
| A1-5 | H | Cl | C—H | Cl | H | Cl | H | H | cyclopropyl | |
| A1-6 | H | Cl | C—H | Cl | H | Cl | H | H | cyclopropylmethyl | |
| A1-7 | H | Cl | C—H | Cl | H | Cl | H | H | 2,2,2-trifluoroethyl | |
| A1-8 | H | Cl | C—H | Cl | H | Cl | H | H | 2-methoxyethyl | |
| A1-9 | H | Cl | C—H | Cl | H | Cl | H | H | (methylsulfanyl)methyl | |
| A1-10 | H | Cl | C—H | Cl | H | Cl | H | H | (methylsulfinyl)methyl | |
| A1-11 | H | Cl | C—H | Cl | H | Cl | H | H | (methylsulfonyl)methyl | |
| A1-12 | H | Cl | C—Cl | Cl | H | Cl | H | H | CH$_3$ | |
| A1-13 | H | Cl | C—Cl | Cl | H | Cl | H | H | ethyl | |
| A1-14 | H | Cl | C—Cl | Cl | H | Cl | H | H | n-propyl | |
| A1-15 | H | Cl | C—Cl | Cl | H | Cl | H | H | isopropyl | |
| A1-16 | H | Cl | C—Cl | Cl | H | Cl | H | H | cyclopropyl | |
| A1-17 | H | Cl | C—Cl | Cl | H | Cl | H | H | cyclopropylmethyl | |
| A1-18 | H | Cl | C—Cl | Cl | H | Cl | H | H | 2,2,2-trifluoroethyl | |
| A1-19 | H | Cl | C—Cl | Cl | H | Cl | H | H | 2-methoxyethyl | |
| A1-20 | H | Cl | C—Cl | Cl | H | Cl | H | H | (methylsulfanyl)methyl | |
| A1-21 | H | Cl | C—Cl | Cl | H | Cl | H | H | (methylsulfinyl)methyl | |
| A1-22 | H | Cl | C—Cl | Cl | H | Cl | H | H | (methylsulfonyl)methyl | |
| A1-23 | H | CF3 | C—H | CF3 | H | Cl | H | H | CH$_3$ | |
| A1-24 | H | CF3 | C—H | CF3 | H | Cl | H | H | ethyl | |
| A1-25 | H | CF3 | C—H | CF3 | H | Cl | H | H | n-propyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-26 | H | CF3 | C—H | CF3 | H | Cl | H | H | isopropyl | |
| A1-27 | H | CF3 | C—H | CF3 | H | Cl | H | H | cyclopropyl | |
| A1-28 | H | CF3 | C—H | CF3 | H | Cl | H | H | cyclopropylmethyl | |
| A1-29 | H | CF3 | C—H | CF3 | H | Cl | H | H | 2,2,2-trifluoroethyl | |
| A1-30 | H | CF3 | C—H | CF3 | H | Cl | H | H | 2-methoxyethyl | |
| A1-31 | H | CF3 | C—H | CF3 | H | Cl | H | H | (methylsulfanyl)methyl | |
| A1-32 | H | CF3 | C—H | CF3 | H | Cl | H | H | (methylsulfinyl)methyl | |
| A1-33 | H | CF3 | C—H | CF3 | H | Cl | H | H | (methylsulfonyl)methyl | |
| A1-34 | H | Cl | C—H | Cl | H | CF3 | H | H | CH₃ | |
| A1-35 | H | Cl | C—H | Cl | H | CF3 | H | H | ethyl | |
| A1-36 | H | Cl | C—H | Cl | H | CF3 | H | H | n-propyl | |
| A1-37 | H | Cl | C—H | Cl | H | CF3 | H | H | isopropyl | |
| A1-38 | H | Cl | C—H | Cl | H | CF3 | H | H | cyclopropyl | |
| A1-39 | H | Cl | C—H | Cl | H | CF3 | H | H | cyclopropylmethyl | |
| A1-40 | H | Cl | C—H | Cl | H | CF3 | H | H | 2,2,2-trifluoroethyl | |
| A1-41 | H | Cl | C—H | Cl | H | CF3 | H | H | 2-methoxyethyl | |
| A1-42 | H | Cl | C—H | Cl | H | CF3 | H | H | (methylsulfanyl)methyl | |
| A1-43 | H | Cl | C—H | Cl | H | CF3 | H | H | (methylsulfinyl)methyl | |
| A1-44 | H | Cl | C—H | Cl | H | CF3 | H | H | (methylsulfonyl)methyl | |
| A1-45 | H | Cl | C—Cl | Cl | H | CF3 | H | H | CH₃ | |
| A1-46 | H | Cl | C—Cl | Cl | H | CF3 | H | H | ethyl | |
| A1-47 | H | Cl | C—Cl | Cl | H | CF3 | H | H | n-propyl | |
| A1-48 | H | Cl | C—Cl | Cl | H | CF3 | H | H | isopropyl | |
| A1-49 | H | Cl | C—Cl | Cl | H | CF3 | H | H | cyclopropyl | |
| A1-50 | H | Cl | C—Cl | Cl | H | CF3 | H | H | cyclopropylmethyl | |
| A1-51 | H | Cl | C—Cl | Cl | H | CF3 | H | H | 2,2,2-trifluoroethyl | |
| A1-52 | H | Cl | C—Cl | Cl | H | CF3 | H | H | 2-methoxyethyl | |
| A1-53 | H | Cl | C—Cl | Cl | H | CF3 | H | H | (methylsulfanyl)methyl | |
| A1-54 | H | Cl | C—Cl | Cl | H | CF3 | H | H | (methylsulfinyl)methyl | |
| A1-55 | H | Cl | C—Cl | Cl | H | CF3 | H | H | (methylsulfonyl)methyl | |
| A1-56 | H | CF3 | C—H | CF3 | H | CF3 | H | H | CH₃ | |
| A1-57 | H | CF3 | C—H | CF3 | H | CF3 | H | H | ethyl | |
| A1-58 | H | CF3 | C—H | CF3 | H | CF3 | H | H | n-propyl | |
| A1-59 | H | CF3 | C—H | CF3 | H | CF3 | H | H | isopropyl | |
| A1-60 | H | CF3 | C—H | CF3 | H | CF3 | H | H | cyclopropyl | |
| A1-61 | H | CF3 | C—H | CF3 | H | CF3 | H | H | cyclopropylmethyl | |
| A1-62 | H | CF3 | C—H | CF3 | H | CF3 | H | H | 2,2,2-trifluoroethyl | |
| A1-63 | H | CF3 | C—H | CF3 | H | CF3 | H | H | 2-methoxyethyl | |
| A1-64 | H | CF3 | C—H | CF3 | H | CF3 | H | H | (methylsulfanyl)methyl | |
| A1-65 | H | CF3 | C—H | CF3 | H | CF3 | H | H | (methylsulfinyl)methyl | |
| A1-66 | H | CF3 | C—H | CF3 | H | CF3 | H | H | (methylsulfonyl)methyl | |
| A1-67 | H | Cl | C—H | Cl | H | Cl | H | H | tert-butoxy | |
| A1-68 | H | Cl | C—Cl | Cl | H | Cl | H | H | tert-butoxy | |
| A1-69 | H | CF3 | C—H | CF3 | H | Cl | H | H | tert-butoxy | |
| A1-70 | H | Cl | C—H | Cl | H | CF3 | H | H | tert-butoxy | |
| A1-71 | H | Cl | C—Cl | Cl | H | CF3 | H | H | tert-butoxy | |
| A1-72 | H | CF3 | C—H | CF3 | H | CF3 | H | H | tert-butoxy | |
| A1-73 | H | Cl | C—H | Cl | H | CH₃ | H | H | CH₃ | |
| A1-74 | H | Cl | C—H | Cl | H | CH₃ | H | H | ethyl | |
| A1-75 | H | Cl | C—H | Cl | H | CH₃ | H | H | n-propyl | |
| A1-76 | H | Cl | C—H | Cl | H | CH₃ | H | H | isopropyl | |
| A1-77 | H | Cl | C—H | Cl | H | CH₃ | H | H | cyclopropyl | 3.91 |
| A1-78 | H | Cl | C—H | Cl | H | CH₃ | H | H | cyclopropylmethyl | |
| A1-79 | H | Cl | C—H | Cl | H | CH₃ | H | H | 2,2,2-trifluoroethyl | 4.09 |
| A1-80 | H | Cl | C—H | Cl | H | CH₃ | H | H | 2-methoxyethyl | |
| A1-81 | H | Cl | C—H | Cl | H | CH₃ | H | H | (methylsulfanyl)methyl | |
| A1-82 | H | Cl | C—H | Cl | H | CH₃ | H | H | (methylsulfinyl)methyl | |
| A1-83 | H | Cl | C—H | Cl | H | CH₃ | H | H | (methylsulfonyl)methyl | |
| A1-84 | H | Cl | C—H | Cl | H | ethyl | H | H | CH₃ | |
| A1-85 | H | Cl | C—H | Cl | H | ethyl | H | H | ethyl | |
| A1-86 | H | Cl | C—H | Cl | H | ethyl | H | H | n-propyl | |
| A1-87 | H | Cl | C—H | Cl | H | ethyl | H | H | isopropyl | |
| A1-88 | H | Cl | C—H | Cl | H | ethyl | H | H | cyclopropyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-89 | H | Cl | C—H | Cl | H | ethyl | H | H | cyclopropylmethyl | |
| A1-90 | H | Cl | C—H | Cl | H | ethyl | H | H | 2,2,2-trifluoroethyl | |
| A1-91 | H | Cl | C—H | Cl | H | ethyl | H | H | 2-methoxyethyl | |
| A1-92 | H | Cl | C—H | Cl | H | ethyl | H | H | (methylsulfanyl)methyl | |
| A1-93 | H | Cl | C—H | Cl | H | ethyl | H | H | (methylsulfinyl)methyl | |
| A1-94 | H | Cl | C—H | Cl | H | ethyl | H | H | (methylsulfonyl)methyl | |
| A1-95 | H | Cl | C—H | Cl | H | F | H | H | CH₃ | |
| A1-96 | H | Cl | C—H | Cl | H | F | H | H | ethyl | |
| A1-97 | H | Cl | C—H | Cl | H | F | H | H | n-propyl | |
| A1-98 | H | Cl | C—H | Cl | H | F | H | H | isopropyl | |
| A1-99 | H | Cl | C—H | Cl | H | F | H | H | cyclopropyl | 3.47 |
| A1-100 | H | Cl | C—H | Cl | H | F | H | H | cyclopropylmethyl | |
| A1-101 | H | Cl | C—H | Cl | H | F | H | H | 2,2,2-trifluoroethyl | |
| A1-102 | H | Cl | C—H | Cl | H | F | H | H | 2-methoxyethyl | |
| A1-103 | H | Cl | C—H | Cl | H | F | H | H | (methylsulfanyl)methyl | |
| A1-104 | H | Cl | C—H | Cl | H | F | H | H | (methylsulfinyl)methyl | |
| A1-105 | H | Cl | C—H | Cl | H | F | H | H | (methylsulfonyl)methyl | |
| A1-106 | H | Cl | C—H | Cl | H | Br | H | H | CH₃ | |
| A1-107 | H | Cl | C—H | Cl | H | Br | H | H | ethyl | |
| A1-108 | H | Cl | C—H | Cl | H | Br | H | H | n-propyl | |
| A1-109 | H | Cl | C—H | Cl | H | Br | H | H | isopropyl | |
| A1-110 | H | Cl | C—H | Cl | H | Br | H | H | cyclopropyl | |
| A1-111 | H | Cl | C—H | Cl | H | Br | H | H | cyclopropylmethyl | |
| A1-112 | H | Cl | C—H | Cl | H | Br | H | H | 2,2,2-trifluoroethyl | |
| A1-113 | H | Cl | C—H | Cl | H | Br | H | H | 2-methoxyethyl | |
| A1-114 | H | Cl | C—H | Cl | H | Br | H | H | (methylsulfanyl)methyl | |
| A1-115 | H | Cl | C—H | Cl | H | Br | H | H | (methylsulfinyl)methyl | |
| A1-116 | H | Cl | C—H | Cl | H | Br | H | H | (methylsulfonyl)methyl | |
| A1-117 | H | Cl | C—H | Cl | H | I | H | H | CH₃ | |
| A1-118 | H | Cl | C—H | Cl | H | I | H | H | ethyl | |
| A1-119 | H | Cl | C—H | Cl | H | I | H | H | n-propyl | |
| A1-120 | H | Cl | C—H | Cl | H | I | H | H | isopropyl | |
| A1-121 | H | Cl | C—H | Cl | H | I | H | H | cyclopropyl | |
| A1-122 | H | Cl | C—H | Cl | H | I | H | H | cyclopropylmethyl | |
| A1-123 | H | Cl | C—H | Cl | H | I | H | H | 2,2,2-trifluoroethyl | |
| A1-124 | H | Cl | C—H | Cl | H | I | H | H | 2-methoxyethyl | |
| A1-125 | H | Cl | C—H | Cl | H | I | H | H | (methylsulfanyl)methyl | |
| A1-126 | H | Cl | C—H | Cl | H | I | H | H | (methylsulfinyl)methyl | |
| A1-127 | H | Cl | C—H | Cl | H | I | H | H | (methylsulfonyl)methyl | |
| A1-128 | H | Cl | C—Cl | Cl | H | CH₃ | H | H | CH₃ | |
| A1-129 | H | Cl | C—Cl | Cl | H | CH₃ | H | H | ethyl | |
| A1-130 | H | Cl | C—Cl | Cl | H | CH₃ | H | H | n-propyl | |
| A1-131 | H | Cl | C—Cl | Cl | H | CH₃ | H | H | isopropyl | |
| A1-132 | H | Cl | C—Cl | Cl | H | CH₃ | H | H | cyclopropyl | |
| A1-133 | H | Cl | C—Cl | Cl | H | CH₃ | H | H | cyclopropylmethyl | |
| A1-134 | H | Cl | C—Cl | Cl | H | CH₃ | H | H | 2,2,2-trifluoroethyl | |
| A1-135 | H | Cl | C—Cl | Cl | H | CH₃ | H | H | 2-methoxyethyl | |
| A1-136 | H | Cl | C—Cl | Cl | H | CH₃ | H | H | (methylsulfanyl)methyl | |
| A1-137 | H | Cl | C—Cl | Cl | H | CH₃ | H | H | (methylsulfinyl)methyl | |
| A1-138 | H | Cl | C—Cl | Cl | H | CH₃ | H | H | (methylsulfonyl)methyl | |
| A1-139 | H | Cl | C—Cl | Cl | H | ethyl | H | H | CH₃ | |
| A1-140 | H | Cl | C—Cl | Cl | H | ethyl | H | H | ethyl | |
| A1-141 | H | Cl | C—Cl | Cl | H | ethyl | H | H | n-propyl | |
| A1-142 | H | Cl | C—Cl | Cl | H | ethyl | H | H | isopropyl | |
| A1-143 | H | Cl | C—Cl | Cl | H | ethyl | H | H | cyclopropyl | |
| A1-144 | H | Cl | C—Cl | Cl | H | ethyl | H | H | cyclopropylmethyl | |
| A1-145 | H | Cl | C—Cl | Cl | H | ethyl | H | H | 2,2,2-trifluoroethyl | |
| A1-146 | H | Cl | C—Cl | Cl | H | ethyl | H | H | 2-methoxyethyl | |
| A1-147 | H | Cl | C—Cl | Cl | H | ethyl | H | H | (methylsulfanyl)methyl | |
| A1-148 | H | Cl | C—Cl | Cl | H | ethyl | H | H | (methylsulfinyl)methyl | |
| A1-149 | H | Cl | C—Cl | Cl | H | ethyl | H | H | (methylsulfonyl)methyl | |
| A1-150 | H | Cl | C—Cl | Cl | H | F | H | H | CH₃ | |
| A1-151 | H | Cl | C—Cl | Cl | H | F | H | H | ethyl | |

TABLE A1-continued

Compounds according to the invention

| Ex. No. | X$^1$ | X$^2$ | A | X$^4$ | Y$^1$ | Y$^2$ | Y$^4$ | R$^3$ | R$^7$ | log P |
|---|---|---|---|---|---|---|---|---|---|---|
| A1-152 | H | Cl | C—Cl | Cl | H | F | H | H | n-propyl | |
| A1-153 | H | Cl | C—Cl | Cl | H | F | H | H | isopropyl | |
| A1-154 | H | Cl | C—Cl | Cl | H | F | H | H | cyclopropyl | |
| A1-155 | H | Cl | C—Cl | Cl | H | F | H | H | cyclopropylmethyl | |
| A1-156 | H | Cl | C—Cl | Cl | H | F | H | H | 2,2,2-trifluoroethyl | |
| A1-157 | H | Cl | C—Cl | Cl | H | F | H | H | 2-methoxyethyl | |
| A1-158 | H | Cl | C—Cl | Cl | H | F | H | H | (methylsulfanyl)methyl | |
| A1-159 | H | Cl | C—Cl | Cl | H | F | H | H | (methylsulfinyl)methyl | |
| A1-160 | H | Cl | C—Cl | Cl | H | F | H | H | (methylsulfonyl)methyl | |
| A1-161 | H | Cl | C—Cl | Cl | H | Br | H | H | CH$_3$ | |
| A1-162 | H | Cl | C—Cl | Cl | H | Br | H | H | ethyl | |
| A1-163 | H | Cl | C—Cl | Cl | H | Br | H | H | n-propyl | |
| A1-164 | H | Cl | C—Cl | Cl | H | Br | H | H | isopropyl | |
| A1-165 | H | Cl | C—Cl | Cl | H | Br | H | H | cyclopropyl | |
| A1-166 | H | Cl | C—Cl | Cl | H | Br | H | H | cyclopropylmethyl | |
| A1-167 | H | Cl | C—Cl | Cl | H | Br | H | H | 2,2,2-trifluoroethyl | |
| A1-168 | H | Cl | C—Cl | Cl | H | Br | H | H | 2-methoxyethyl | |
| A1-169 | H | Cl | C—Cl | Cl | H | Br | H | H | (methylsulfanyl)methyl | |
| A1-170 | H | Cl | C—Cl | Cl | H | Br | H | H | (methylsulfinyl)methyl | |
| A1-171 | H | Cl | C—Cl | Cl | H | Br | H | H | (methylsulfonyl)methyl | |
| A1-172 | H | Cl | C—Cl | Cl | H | I | H | H | CH$_3$ | |
| A1-173 | H | Cl | C—Cl | Cl | H | I | H | H | ethyl | |
| A1-174 | H | Cl | C—Cl | Cl | H | I | H | H | n-propyl | |
| A1-175 | H | Cl | C—Cl | Cl | H | I | H | H | isopropyl | |
| A1-176 | H | Cl | C—Cl | Cl | H | I | H | H | cyclopropyl | |
| A1-177 | H | Cl | C—Cl | Cl | H | I | H | H | cyclopropylmethyl | |
| A1-178 | H | Cl | C—Cl | Cl | H | I | H | H | 2,2,2-trifluoroethyl | |
| A1-179 | H | Cl | C—Cl | Cl | H | I | H | H | 2-methoxyethyl | |
| A1-180 | H | Cl | C—Cl | Cl | H | I | H | H | (methylsulfanyl)methyl | |
| A1-181 | H | Cl | C—Cl | Cl | H | I | H | H | (methylsulfinyl)methyl | |
| A1-182 | H | Cl | C—Cl | Cl | H | I | H | H | (methylsulfonyl)methyl | |
| A1-183 | H | CF3 | C—H | CF3 | H | CH$_3$ | H | H | CH$_3$ | |
| A1-184 | H | CF3 | C—H | CF3 | H | CH$_3$ | H | H | ethyl | |
| A1-185 | H | CF3 | C—H | CF3 | H | CH$_3$ | H | H | n-propyl | |
| A1-186 | H | CF3 | C—H | CF3 | H | CH$_3$ | H | H | isopropyl | |
| A1-187 | H | CF3 | C—H | CF3 | H | CH$_3$ | H | H | cyclopropyl | |
| A1-188 | H | CF3 | C—H | CF3 | H | CH$_3$ | H | H | cyclopropylmethyl | |
| A1-189 | H | CF3 | C—H | CF3 | H | CH$_3$ | H | H | 2,2,2-trifluoroethyl | |
| A1-190 | H | CF3 | C—H | CF3 | H | CH$_3$ | H | H | 2-methoxyethyl | |
| A1-191 | H | CF3 | C—H | CF3 | H | CH$_3$ | H | H | (methylsulfanyl)methyl | |
| A1-192 | H | CF3 | C—H | CF3 | H | CH$_3$ | H | H | (methylsulfinyl)methyl | |
| A1-193 | H | CF3 | C—H | CF3 | H | CH$_3$ | H | H | (methylsulfonyl)methyl | |
| A1-194 | H | CF3 | C—H | CF3 | H | ethyl | H | H | CH$_3$ | |
| A1-195 | H | CF3 | C—H | CF3 | H | ethyl | H | H | ethyl | |
| A1-196 | H | CF3 | C—H | CF3 | H | ethyl | H | H | n-propyl | |
| A1-197 | H | CF3 | C—H | CF3 | H | ethyl | H | H | isopropyl | |
| A1-198 | H | CF3 | C—H | CF3 | H | ethyl | H | H | cyclopropyl | |
| A1-199 | H | CF3 | C—H | CF3 | H | ethyl | H | H | cyclopropylmethyl | |
| A1-200 | H | CF3 | C—H | CF3 | H | ethyl | H | H | 2,2,2-trifluoroethyl | |
| A1-201 | H | CF3 | C—H | CF3 | H | ethyl | H | H | 2-methoxyethyl | |
| A1-202 | H | CF3 | C—H | CF3 | H | ethyl | H | H | (methylsulfanyl)methyl | |
| A1-203 | H | CF3 | C—H | CF3 | H | ethyl | H | H | (methylsulfinyl)methyl | |
| A1-204 | H | CF3 | C—H | CF3 | H | ethyl | H | H | (methylsulfonyl)methyl | |
| A1-205 | H | CF3 | C—H | CF3 | H | F | H | H | CH$_3$ | |
| A1-206 | H | CF3 | C—H | CF3 | H | F | H | H | ethyl | |
| A1-207 | H | CF3 | C—H | CF3 | H | F | H | H | n-propyl | |
| A1-208 | H | CF3 | C—H | CF3 | H | F | H | H | isopropyl | |
| A1-209 | H | CF3 | C—H | CF3 | H | F | H | H | cyclopropyl | |
| A1-210 | H | CF3 | C—H | CF3 | H | F | H | H | cyclopropylmethyl | |
| A1-211 | H | CF3 | C—H | CF3 | H | F | H | H | 2,2,2-trifluoroethyl | |
| A1-212 | H | CF3 | C—H | CF3 | H | F | H | H | 2-methoxyethyl | |
| A1-213 | H | CF3 | C—H | CF3 | H | F | H | H | (methylsulfanyl)methyl | |
| A1-214 | H | CF3 | C—H | CF3 | H | F | H | H | (methylsulfinyl)methyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-215 | H | CF3 | C—H | CF3 | H | F | H | H | (methylsulfonyl)methyl | |
| A1-216 | H | CF3 | C—H | CF3 | H | Br | H | H | CH₃ | |
| A1-217 | H | CF3 | C—H | CF3 | H | Br | H | H | ethyl | |
| A1-218 | H | CF3 | C—H | CF3 | H | Br | H | H | n-propyl | |
| A1-219 | H | CF3 | C—H | CF3 | H | Br | H | H | isopropyl | |
| A1-220 | H | CF3 | C—H | CF3 | H | Br | H | H | cyclopropyl | |
| A1-221 | H | CF3 | C—H | CF3 | H | Br | H | H | cyclopropylmethyl | |
| A1-222 | H | CF3 | C—H | CF3 | H | Br | H | H | 2,2,2-trifluoroethyl | |
| A1-223 | H | CF3 | C—H | CF3 | H | Br | H | H | 2-methoxyethyl | |
| A1-224 | H | CF3 | C—H | CF3 | H | Br | H | H | (methylsulfanyl)methyl | |
| A1-225 | H | CF3 | C—H | CF3 | H | Br | H | H | (methylsulfinyl)methyl | |
| A1-226 | H | CF3 | C—H | CF3 | H | Br | H | H | (methylsulfonyl)methyl | |
| A1-227 | H | CF3 | C—H | CF3 | H | I | H | H | CH₃ | |
| A1-228 | H | CF3 | C—H | CF3 | H | I | H | H | ethyl | |
| A1-229 | H | CF3 | C—H | CF3 | H | I | H | H | n-propyl | |
| A1-230 | H | CF3 | C—H | CF3 | H | I | H | H | isopropyl | |
| A1-231 | H | CF3 | C—H | CF3 | H | I | H | H | cyclopropyl | |
| A1-232 | H | CF3 | C—H | CF3 | H | I | H | H | cyclopropylmethyl | |
| A1-233 | H | CF3 | C—H | CF3 | H | I | H | H | 2,2,2-trifluoroethyl | |
| A1-234 | H | CF3 | C—H | CF3 | H | I | H | H | 2-methoxyethyl | |
| A1-235 | H | CF3 | C—H | CF3 | H | I | H | H | (methylsulfanyl)methyl | |
| A1-236 | H | CF3 | C—H | CF3 | H | I | H | H | (methylsulfinyl)methyl | |
| A1-237 | H | CF3 | C—H | CF3 | H | I | H | H | (methylsulfonyl)methyl | |
| A1-238 | H | F | C—H | Cl | H | CF3 | H | H | CH₃ | |
| A1-239 | H | F | C—H | Cl | H | CF3 | H | H | ethyl | |
| A1-240 | H | F | C—H | Cl | H | CF3 | H | H | n-propyl | |
| A1-241 | H | F | C—H | Cl | H | CF3 | H | H | isopropyl | |
| A1-242 | H | F | C—H | Cl | H | CF3 | H | H | cyclopropyl | |
| A1-243 | H | F | C—H | Cl | H | CF3 | H | H | cyclopropylmethyl | |
| A1-244 | H | F | C—H | Cl | H | CF3 | H | H | 2,2,2-trifluoroethyl | |
| A1-245 | H | F | C—H | Cl | H | CF3 | H | H | 2-methoxyethyl | |
| A1-246 | H | F | C—H | Cl | H | CF3 | H | H | (methylsulfanyl)methyl | |
| A1-247 | H | F | C—H | Cl | H | CF3 | H | H | (methylsulfinyl)methyl | |
| A1-248 | H | F | C—H | Cl | H | CF3 | H | H | (methylsulfonyl)methyl | |
| A1-249 | H | Br | C—H | Br | H | CF3 | H | H | CH₃ | |
| A1-250 | H | Br | C—H | Br | H | CF3 | H | H | ethyl | |
| A1-251 | H | Br | C—H | Br | H | CF3 | H | H | n-propyl | |
| A1-252 | H | Br | C—H | Br | H | CF3 | H | H | isopropyl | |
| A1-253 | H | Br | C—H | Br | H | CF3 | H | H | cyclopropyl | |
| A1-254 | H | Br | C—H | Br | H | CF3 | H | H | cyclopropylmethyl | |
| A1-255 | H | Br | C—H | Br | H | CF3 | H | H | 2,2,2-trifluoroethyl | |
| A1-256 | H | Br | C—H | Br | H | CF3 | H | H | 2-methoxyethyl | |
| A1-257 | H | Br | C—H | Br | H | CF3 | H | H | (methylsulfanyl)methyl | |
| A1-258 | H | Br | C—H | Br | H | CF3 | H | H | (methylsulfinyl)methyl | |
| A1-259 | H | Br | C—H | Br | H | CF3 | H | H | (methylsulfonyl)methyl | |
| A1-260 | H | F | C—F | F | H | CF3 | H | H | CH₃ | |
| A1-261 | H | F | C—F | F | H | CF3 | H | H | ethyl | |
| A1-262 | H | F | C—F | F | H | CF3 | H | H | n-propyl | |
| A1-263 | H | F | C—F | F | H | CF3 | H | H | isopropyl | |
| A1-264 | H | F | C—F | F | H | CF3 | H | H | cyclopropyl | |
| A1-265 | H | F | C—F | F | H | CF3 | H | H | cyclopropylmethyl | |
| A1-266 | H | F | C—F | F | H | CF3 | H | H | 2,2,2-trifluoroethyl | |
| A1-267 | H | F | C—F | F | H | CF3 | H | H | 2-methoxyethyl | |
| A1-268 | H | F | C—F | F | H | CF3 | H | H | (methylsulfanyl)methyl | |
| A1-269 | H | F | C—F | F | H | CF3 | H | H | (methylsulfinyl)methyl | |
| A1-270 | H | F | C—F | F | H | CF3 | H | H | (methylsulfonyl)methyl | |
| A1-271 | H | Cl | C—F | Cl | H | CF3 | H | H | CH₃ | |
| A1-272 | H | Cl | C—F | Cl | H | CF3 | H | H | ethyl | |
| A1-273 | H | Cl | C—F | Cl | H | CF3 | H | H | n-propyl | |
| A1-274 | H | Cl | C—F | Cl | H | CF3 | H | H | isopropyl | |
| A1-275 | H | Cl | C—F | Cl | H | CF3 | H | H | cyclopropyl | |
| A1-276 | H | Cl | C—F | Cl | H | CF3 | H | H | cyclopropylmethyl | |
| A1-277 | H | Cl | C—F | Cl | H | CF3 | H | H | 2,2,2-trifluoroethyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-278 | H | Cl | C—F | Cl | H | CF3 | H | H | 2-methoxyethyl | |
| A1-279 | H | Cl | C—F | Cl | H | CF3 | H | H | (methylsulfanyl)methyl | |
| A1-280 | H | Cl | C—F | Cl | H | CF3 | H | H | (methylsulfinyl)methyl | |
| A1-281 | H | Cl | C—F | Cl | H | CF3 | H | H | (methylsulfonyl)methyl | |
| A1-282 | F | Cl | C—F | Cl | H | CF3 | H | H | CH₃ | |
| A1-283 | F | Cl | C—F | Cl | H | CF3 | H | H | ethyl | |
| A1-284 | F | Cl | C—F | Cl | H | CF3 | H | H | n-propyl | |
| A1-285 | F | Cl | C—F | Cl | H | CF3 | H | H | isopropyl | |
| A1-286 | F | Cl | C—F | Cl | H | CF3 | H | H | cyclopropyl | |
| A1-287 | F | Cl | C—F | Cl | H | CF3 | H | H | cyclopropylmethyl | |
| A1-288 | F | Cl | C—F | Cl | H | CF3 | H | H | 2,2,2-trifluoroethyl | |
| A1-289 | F | Cl | C—F | Cl | H | CF3 | H | H | 2-methoxyethyl | |
| A1-290 | F | Cl | C—F | Cl | H | CF3 | H | H | (methylsulfanyl)methyl | |
| A1-291 | F | Cl | C—F | Cl | H | CF3 | H | H | (methylsulfinyl)methyl | |
| A1-292 | F | Cl | C—F | Cl | H | CF3 | H | H | (methylsulfonyl)methyl | |
| A1-293 | H | CF3 | C—H | H | H | CF3 | H | H | CH₃ | |
| A1-294 | H | CF3 | C—H | H | H | CF3 | H | H | ethyl | |
| A1-295 | H | CF3 | C—H | H | H | CF3 | H | H | n-propyl | |
| A1-296 | H | CF3 | C—H | H | H | CF3 | H | H | isopropyl | |
| A1-297 | H | CF3 | C—H | H | H | CF3 | H | H | cyclopropyl | |
| A1-298 | H | CF3 | C—H | H | H | CF3 | H | H | cyclopropylmethyl | |
| A1-299 | H | CF3 | C—H | H | H | CF3 | H | H | 2,2,2-trifluoroethyl | |
| A1-300 | H | CF3 | C—H | H | H | CF3 | H | H | 2-methoxyethyl | |
| A1-301 | H | CF3 | C—H | H | H | CF3 | H | H | (methylsulfanyl)methyl | |
| A1-302 | H | CF3 | C—H | H | H | CF3 | H | H | (methylsulfinyl)methyl | |
| A1-303 | H | CF3 | C—H | H | H | CF3 | H | H | (methylsulfonyl)methyl | |
| A1-304 | H | CF3 | C—F | H | H | CF3 | H | H | CH₃ | |
| A1-305 | H | CF3 | C—F | H | H | CF3 | H | H | ethyl | |
| A1-306 | H | CF3 | C—F | H | H | CF3 | H | H | n-propyl | |
| A1-307 | H | CF3 | C—F | H | H | CF3 | H | H | isopropyl | |
| A1-308 | H | CF3 | C—F | H | H | CF3 | H | H | cyclopropyl | |
| A1-309 | H | CF3 | C—F | H | H | CF3 | H | H | cyclopropylmethyl | |
| A1-310 | H | CF3 | C—F | H | H | CF3 | H | H | 2,2,2-trifluoroethyl | |
| A1-311 | H | CF3 | C—F | H | H | CF3 | H | H | 2-methoxyethyl | |
| A1-312 | H | CF3 | C—F | H | H | CF3 | H | H | (methylsulfanyl)methyl | |
| A1-313 | H | CF3 | C—F | H | H | CF3 | H | H | (methylsulfinyl)methyl | |
| A1-314 | H | CF3 | C—F | H | H | CF3 | H | H | (methylsulfonyl)methyl | |
| A1-315 | H | CF3 | C—H | F | H | CF3 | H | H | CH₃ | |
| A1-316 | H | CF3 | C—H | F | H | CF3 | H | H | ethyl | |
| A1-317 | H | CF3 | C—H | F | H | CF3 | H | H | n-propyl | |
| A1-318 | H | CF3 | C—H | F | H | CF3 | H | H | isopropyl | |
| A1-319 | H | CF3 | C—H | F | H | CF3 | H | H | cyclopropyl | |
| A1-320 | H | CF3 | C—H | F | H | CF3 | H | H | cyclopropylmethyl | |
| A1-321 | H | CF3 | C—H | F | H | CF3 | H | H | 2,2,2-trifluoroethyl | |
| A1-322 | H | CF3 | C—H | F | H | CF3 | H | H | 2-methoxyethyl | |
| A1-323 | H | CF3 | C—H | F | H | CF3 | H | H | (methylsulfanyl)methyl | |
| A1-324 | H | CF3 | C—H | F | H | CF3 | H | H | (methylsulfinyl)methyl | |
| A1-325 | H | CF3 | C—H | F | H | CF3 | H | H | (methylsulfonyl)methyl | |
| A1-326 | H | CF3 | C—Cl | H | H | CF3 | H | H | CH₃ | |
| A1-327 | H | CF3 | C—Cl | H | H | CF3 | H | H | ethyl | |
| A1-328 | H | CF3 | C—Cl | H | H | CF3 | H | H | n-propyl | |
| A1-329 | H | CF3 | C—Cl | H | H | CF3 | H | H | isopropyl | |
| A1-330 | H | CF3 | C—Cl | H | H | CF3 | H | H | cyclopropyl | |
| A1-331 | H | CF3 | C—Cl | H | H | CF3 | H | H | cyclopropylmethyl | |
| A1-332 | H | CF3 | C—Cl | H | H | CF3 | H | H | 2,2,2-trifluoroethyl | |
| A1-333 | H | CF3 | C—Cl | H | H | CF3 | H | H | 2-methoxyethyl | |
| A1-334 | H | CF3 | C—Cl | H | H | CF3 | H | H | (methylsulfanyl)methyl | |
| A1-335 | H | CF3 | C—Cl | H | H | CF3 | H | H | (methylsulfinyl)methyl | |
| A1-336 | H | CF3 | C—Cl | H | H | CF3 | H | H | (methylsulfonyl)methyl | |
| A1-337 | H | CF3 | C—H | Cl | H | CF3 | H | H | CH₃ | |
| A1-338 | H | CF3 | C—H | Cl | H | CF3 | H | H | ethyl | |
| A1-339 | H | CF3 | C—H | Cl | H | CF3 | H | H | n-propyl | |
| A1-340 | H | CF3 | C—H | Cl | H | CF3 | H | H | isopropyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-341 | H | CF3 | C—H | Cl | H | CF3 | H | H | cyclopropyl | |
| A1-342 | H | CF3 | C—H | Cl | H | CF3 | H | H | cyclopropylmethyl | |
| A1-343 | H | CF3 | C—H | Cl | H | CF3 | H | H | 2,2,2-trifluoroethyl | |
| A1-344 | H | CF3 | C—H | Cl | H | CF3 | H | H | 2-methoxyethyl | |
| A1-345 | H | CF3 | C—H | Cl | H | CF3 | H | H | (methylsulfanyl)methyl | |
| A1-346 | H | CF3 | C—H | Cl | H | CF3 | H | H | (methylsulfinyl)methyl | |
| A1-347 | H | CF3 | C—H | Cl | H | CF3 | H | H | (methylsulfonyl)methyl | |
| A1-348 | H | CF3 | C—Cl | Cl | H | CF3 | H | H | CH₃ | |
| A1-349 | H | CF3 | C—Cl | Cl | H | CF3 | H | H | ethyl | |
| A1-350 | H | CF3 | C—Cl | Cl | H | CF3 | H | H | n-propyl | |
| A1-351 | H | CF3 | C—Cl | Cl | H | CF3 | H | H | isopropyl | |
| A1-352 | H | CF3 | C—Cl | Cl | H | CF3 | H | H | cyclopropyl | |
| A1-353 | H | CF3 | C—Cl | Cl | H | CF3 | H | H | cyclopropylmethyl | |
| A1-354 | H | CF3 | C—Cl | Cl | H | CF3 | H | H | 2,2,2-trifluoroethyl | |
| A1-355 | H | CF3 | C—Cl | Cl | H | CF3 | H | H | 2-methoxyethyl | |
| A1-356 | H | CF3 | C—Cl | Cl | H | CF3 | H | H | (methylsulfanyl)methyl | |
| A1-357 | H | CF3 | C—Cl | Cl | H | CF3 | H | H | (methylsulfinyl)methyl | |
| A1-358 | H | CF3 | C—Cl | Cl | H | CF3 | H | H | (methylsulfonyl)methyl | |
| A1-359 | H | Cl | C—H | Cl | H | CF3 | H | H | n-butyl | |
| A1-360 | H | Cl | C—H | Cl | H | CF3 | H | H | iso-butyl | |
| A1-361 | H | Cl | C—H | Cl | H | CF3 | H | H | cyclo-butyl | |
| A1-362 | H | Cl | C—H | Cl | H | CF3 | H | H | 2-chloroethyl | |
| A1-363 | H | Cl | C—H | Cl | H | CF3 | H | H | thietan-3-yl | |
| A1-364 | H | Cl | C—H | Cl | H | CF3 | H | H | 1-oxidothietan-3-yl | |
| A1-365 | H | Cl | C—H | Cl | H | CF3 | H | H | 1,1-dioxidothietan-3-yl | |
| A1-366 | H | Cl | C—H | Cl | H | CF3 | H | H | 2,4,6-trifluorophenyl | |
| A1-367 | H | Cl | C—H | Cl | H | CF3 | H | H | methylamino | |
| A1-368 | H | Cl | C—H | Cl | H | CF3 | H | H | dimethylamino | 3.81 |
| A1-369 | H | Cl | C—H | Cl | H | CF3 | H | H | ethylamino | 3.73 |
| A1-370 | H | Cl | C—H | Cl | H | CF3 | H | H | cyclopropylamino | |
| A1-371 | H | Cl | C—H | Cl | H | CF3 | H | H | prop-2-yn-1-ylamino | |
| A1-372 | H | Cl | C—H | Cl | H | H | H | H | CH₃ | |
| A1-373 | H | Cl | C—H | Cl | H | H | H | H | ethyl | |
| A1-374 | H | Cl | C—H | Cl | H | H | H | H | n-propyl | |
| A1-375 | H | Cl | C—H | Cl | H | H | H | H | isopropyl | |
| A1-376 | H | Cl | C—H | Cl | H | H | H | H | cyclopropyl | |
| A1-377 | H | Cl | C—H | Cl | H | H | H | H | cyclopropylmethyl | |
| A1-378 | H | Cl | C—H | Cl | H | H | H | H | 2,2,2-trifluoroethyl | |
| A1-379 | H | Cl | C—H | Cl | H | H | H | H | 2-methoxyethyl | |
| A1-380 | H | Cl | C—H | Cl | H | H | H | H | (methylsulfanyl)methyl | |
| A1-381 | H | Cl | C—H | Cl | H | H | H | H | (methylsulfinyl)methyl | |
| A1-382 | H | Cl | C—H | Cl | H | H | H | H | (methylsulfonyl)methyl | |
| A1-383 | H | Cl | C—Cl | Cl | H | H | H | H | CH₃ | |
| A1-384 | H | Cl | C—Cl | Cl | H | H | H | H | ethyl | |
| A1-385 | H | Cl | C—Cl | Cl | H | H | H | H | n-propyl | |
| A1-386 | H | Cl | C—Cl | Cl | H | H | H | H | isopropyl | |
| A1-387 | H | Cl | C—Cl | Cl | H | H | H | H | cyclopropyl | |
| A1-388 | H | Cl | C—Cl | Cl | H | H | H | H | cyclopropylmethyl | |
| A1-389 | H | Cl | C—Cl | Cl | H | H | H | H | 2,2,2-trifluoroethyl | |
| A1-390 | H | Cl | C—Cl | Cl | H | H | H | H | 2-methoxyethyl | |
| A1-391 | H | Cl | C—Cl | Cl | H | H | H | H | (methylsulfanyl)methyl | |
| A1-392 | H | Cl | C—Cl | Cl | H | H | H | H | (methylsulfinyl)methyl | |
| A1-393 | H | Cl | C—Cl | Cl | H | H | H | H | (methylsulfonyl)methyl | |
| A1-394 | H | CF3 | C—H | CF3 | H | H | H | H | CH₃ | |
| A1-395 | H | CF3 | C—H | CF3 | H | H | H | H | ethyl | |
| A1-396 | H | CF3 | C—H | CF3 | H | H | H | H | n-propyl | |
| A1-397 | H | CF3 | C—H | CF3 | H | H | H | H | isopropyl | |
| A1-398 | H | CF3 | C—H | CF3 | H | H | H | H | cyclopropyl | |
| A1-399 | H | CF3 | C—H | CF3 | H | H | H | H | cyclopropylmethyl | |
| A1-400 | H | CF3 | C—H | CF3 | H | H | H | H | 2,2,2-trifluoroethyl | |
| A1-401 | H | CF3 | C—H | CF3 | H | H | H | H | 2-methoxyethyl | |
| A1-402 | H | CF3 | C—H | CF3 | H | H | H | H | (methylsulfanyl)methyl | |
| A1-403 | H | CF3 | C—H | CF3 | H | H | H | H | (methylsulfinyl)methyl | |

TABLE A1-continued

Compounds according to the invention

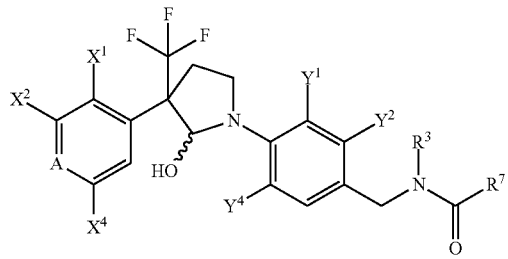

| Ex. No. | X¹ | X² | A | X⁴ | Y¹ | Y² | Y⁴ | R³ | R⁷ | log P |
|---|---|---|---|---|---|---|---|---|---|---|
| A1-404 | H | CF3 | C—H | CF3 | H | H | H | H | (methylsulfonyl)methyl | |
| A1-405 | F | Cl | C—H | Cl | H | CF3 | H | H | CH3 | |
| A1-406 | F | Cl | C—H | Cl | H | CF3 | H | H | ethyl | |
| A1-407 | F | Cl | C—H | Cl | H | CF3 | H | H | n-propyl | |
| A1-408 | F | Cl | C—H | Cl | H | CF3 | H | H | isopropyl | |
| A1-409 | F | Cl | C—H | Cl | H | CF3 | H | H | cyclopropyl | |
| A1-410 | F | Cl | C—H | Cl | H | CF3 | H | H | cyclopropylmethyl | |
| A1-411 | F | Cl | C—H | Cl | H | CF3 | H | H | 2,2,2-trifluoroethyl | |
| A1-412 | F | Cl | C—H | Cl | H | CF3 | H | H | 2-methoxyethyl | |
| A1-413 | F | Cl | C—H | Cl | H | CF3 | H | H | (methylsulfanyl)methyl | |
| A1-414 | F | Cl | C—H | Cl | H | CF3 | H | H | (methylsulfinyl)methyl | |
| A1-415 | F | Cl | C—H | Cl | H | CF3 | H | H | (methylsulfonyl)methyl | |
| A1-416 | F | Cl | C—H | Cl | H | CF3 | H | H | tert-butoxy | |
| A1-417 | F | Cl | C—F | Cl | H | Cl | H | H | CH3 | |
| A1-418 | F | Cl | C—F | Cl | H | Cl | H | H | ethyl | |
| A1-419 | F | Cl | C—F | Cl | H | Cl | H | H | n-propyl | |
| A1-420 | F | Cl | C—F | Cl | H | Cl | H | H | isopropyl | |
| A1-421 | F | Cl | C—F | Cl | H | Cl | H | H | cyclopropyl | |
| A1-422 | F | Cl | C—F | Cl | H | Cl | H | H | cyclopropylmethyl | |
| A1-423 | F | Cl | C—F | Cl | H | Cl | H | H | 2,2,2-trifluoroethyl | |
| A1-424 | F | Cl | C—F | Cl | H | Cl | H | H | 2-methoxyethyl | |
| A1-425 | F | Cl | C—F | Cl | H | Cl | H | H | (methylsulfanyl)methyl | |
| A1-426 | F | Cl | C—F | Cl | H | Cl | H | H | (methylsulfinyl)methyl | |
| A1-427 | F | Cl | C—F | Cl | H | Cl | H | H | (methylsulfonyl)methyl | |
| A1-428 | F | Cl | C—F | Cl | H | Cl | H | H | tert-butoxy | |
| A1-429 | F | Cl | C—F | Cl | H | Br | H | H | CH3 | |
| A1-430 | F | Cl | C—F | Cl | H | Br | H | H | ethyl | |
| A1-431 | F | Cl | C—F | Cl | H | Br | H | H | n-propyl | |
| A1-432 | F | Cl | C—F | Cl | H | Br | H | H | isopropyl | |
| A1-433 | F | Cl | C—F | Cl | H | Br | H | H | cyclopropyl | |
| A1-434 | F | Cl | C—F | Cl | H | Br | H | H | cyclopropylmethyl | |
| A1-435 | F | Cl | C—F | Cl | H | Br | H | H | 2,2,2-trifluoroethyl | |
| A1-436 | F | Cl | C—F | Cl | H | Br | H | H | 2-methoxyethyl | |
| A1-437 | F | Cl | C—F | Cl | H | Br | H | H | (methylsulfanyl)methyl | |
| A1-438 | F | Cl | C—F | Cl | H | Br | H | H | (methylsulfinyl)methyl | |
| A1-439 | F | Cl | C—F | Cl | H | Br | H | H | (methylsulfonyl)methyl | |
| A1-440 | F | Cl | C—F | Cl | H | Br | H | H | tert-butoxy | |
| A1-441 | H | Cl | C—Cl | Cl | F | F | H | H | CH3 | |
| A1-442 | H | Cl | C—Cl | Cl | F | F | H | H | ethyl | |
| A1-443 | H | Cl | C—Cl | Cl | F | F | H | H | n-propyl | |
| A1-444 | H | Cl | C—Cl | Cl | F | F | H | H | isopropyl | |
| A1-445 | H | Cl | C—Cl | Cl | F | F | H | H | cyclopropyl | |
| A1-446 | H | Cl | C—Cl | Cl | F | F | H | H | cyclopropylmethyl | |
| A1-447 | H | Cl | C—Cl | Cl | F | F | H | H | 2,2,2-trifluoroethyl | |
| A1-448 | H | Cl | C—Cl | Cl | F | F | H | H | 2-methoxyethyl | |
| A1-449 | H | Cl | C—Cl | Cl | F | F | H | H | (methylsulfanyl)methyl | |
| A1-450 | H | Cl | C—Cl | Cl | F | F | H | H | (methylsulfinyl)methyl | |
| A1-451 | H | Cl | C—Cl | Cl | F | F | H | H | (methylsulfonyl)methyl | |
| A1-452 | H | Cl | C—Cl | Cl | F | F | H | H | tert-butoxy | |
| A1-453 | H | Cl | C—Cl | Cl | H | F | F | H | CH3 | |
| A1-454 | H | Cl | C—Cl | Cl | H | F | F | H | ethyl | |
| A1-455 | H | Cl | C—Cl | Cl | H | F | F | H | n-propyl | |
| A1-456 | H | Cl | C—Cl | Cl | H | F | F | H | isopropyl | |
| A1-457 | H | Cl | C—Cl | Cl | H | F | F | H | cyclopropyl | |
| A1-458 | H | Cl | C—Cl | Cl | H | F | F | H | cyclopropylmethyl | |
| A1-459 | H | Cl | C—Cl | Cl | H | F | F | H | 2,2,2-trifluoroethyl | |
| A1-460 | H | Cl | C—Cl | Cl | H | F | F | H | 2-methoxyethyl | |
| A1-461 | H | Cl | C—Cl | Cl | H | F | F | H | (methylsulfanyl)methyl | |
| A1-462 | H | Cl | C—Cl | Cl | H | F | F | H | (methylsulfinyl)methyl | |
| A1-463 | H | Cl | C—Cl | Cl | H | F | F | H | (methylsulfonyl)methyl | |
| A1-464 | H | Cl | C—Cl | Cl | H | F | F | H | tert-butoxy | |
| A1-465 | H | Cl | C—Cl | Cl | F | Cl | H | H | CH3 | |
| A1-466 | H | Cl | C—Cl | Cl | F | Cl | H | H | ethyl | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-467 | H | Cl | C—Cl | Cl | F | Cl | H | H | n-propyl | |
| A1-468 | H | Cl | C—Cl | Cl | F | Cl | H | H | isopropyl | |
| A1-469 | H | Cl | C—Cl | Cl | F | Cl | H | H | cyclopropyl | |
| A1-470 | H | Cl | C—Cl | Cl | F | Cl | H | H | cyclopropylmethyl | |
| A1-471 | H | Cl | C—Cl | Cl | F | Cl | H | H | 2,2,2-trifluoroethyl | |
| A1-472 | H | Cl | C—Cl | Cl | F | Cl | H | H | 2-methoxyethyl | |
| A1-473 | H | Cl | C—Cl | Cl | F | Cl | H | H | (methylsulfanyl)methyl | |
| A1-474 | H | Cl | C—Cl | Cl | F | Cl | H | H | (methylsulfinyl)methyl | |
| A1-475 | H | Cl | C—Cl | Cl | F | Cl | H | H | (methylsulfonyl)methyl | |
| A1-476 | H | Cl | C—Cl | Cl | F | Cl | H | H | tert-butoxy | |
| A1-477 | H | Cl | C—Cl | Cl | H | Cl | F | H | CH3 | |
| A1-478 | H | Cl | C—Cl | Cl | H | Cl | F | H | ethyl | |
| A1-479 | H | Cl | C—Cl | Cl | H | Cl | F | H | n-propyl | |
| A1-480 | H | Cl | C—Cl | Cl | H | Cl | F | H | isopropyl | |
| A1-481 | H | Cl | C—Cl | Cl | H | Cl | F | H | cyclopropyl | |
| A1-482 | H | Cl | C—Cl | Cl | H | Cl | F | H | cyclopropylmethyl | |
| A1-483 | H | Cl | C—Cl | Cl | H | Cl | F | H | 2,2,2-trifluoroethyl | |
| A1-484 | H | Cl | C—Cl | Cl | H | Cl | F | H | 2-methoxyethyl | |
| A1-485 | H | Cl | C—Cl | Cl | H | Cl | F | H | (methylsulfanyl)methyl | |
| A1-486 | H | Cl | C—Cl | Cl | H | Cl | F | H | (methylsulfinyl)methyl | |
| A1-487 | H | Cl | C—Cl | Cl | H | Cl | F | H | (methylsulfonyl)methyl | |
| A1-488 | H | Cl | C—Cl | Cl | H | Cl | F | H | tert-butoxy | |
| A1-489 | H | Cl | C—Cl | Cl | F | CH3 | H | H | CH3 | |
| A1-490 | H | Cl | C—Cl | Cl | F | CH3 | H | H | ethyl | |
| A1-491 | H | Cl | C—Cl | Cl | F | CH3 | H | H | n-propyl | |
| A1-492 | H | Cl | C—Cl | Cl | F | CH3 | H | H | isopropyl | |
| A1-493 | H | Cl | C—Cl | Cl | F | CH3 | H | H | cyclopropyl | |
| A1-494 | H | Cl | C—Cl | Cl | F | CH3 | H | H | cyclopropylmethyl | |
| A1-495 | H | Cl | C—Cl | Cl | F | CH3 | H | H | 2,2,2-trifluoroethyl | |
| A1-496 | H | Cl | C—Cl | Cl | F | CH3 | H | H | 2-methoxyethyl | |
| A1-497 | H | Cl | C—Cl | Cl | F | CH3 | H | H | (methylsulfanyl)methyl | |
| A1-498 | H | Cl | C—Cl | Cl | F | CH3 | H | H | (methylsulfinyl)methyl | |
| A1-499 | H | Cl | C—Cl | Cl | F | CH3 | H | H | (methylsulfonyl)methyl | |
| A1-500 | H | Cl | C—Cl | Cl | F | CH3 | H | H | tert-butoxy | |
| A1-501 | H | Cl | C—Cl | Cl | H | CH3 | F | H | CH3 | |
| A1-502 | H | Cl | C—Cl | Cl | H | CH3 | F | H | ethyl | |
| A1-503 | H | Cl | C—Cl | Cl | H | CH3 | F | H | n-propyl | |
| A1-504 | H | Cl | C—Cl | Cl | H | CH3 | F | H | isopropyl | |
| A1-505 | H | Cl | C—Cl | Cl | H | CH3 | F | H | cyclopropyl | |
| A1-506 | H | Cl | C—Cl | Cl | H | CH3 | F | H | cyclopropylmethyl | |
| A1-507 | H | Cl | C—Cl | Cl | H | CH3 | F | H | 2,2,2-trifluoroethyl | |
| A1-508 | H | Cl | C—Cl | Cl | H | CH3 | F | H | 2-methoxyethyl | |
| A1-509 | H | Cl | C—Cl | Cl | H | CH3 | F | H | (methylsulfanyl)methyl | |
| A1-510 | H | Cl | C—Cl | Cl | H | CH3 | F | H | (methylsulfinyl)methyl | |
| A1-511 | H | Cl | C—Cl | Cl | H | CH3 | F | H | (methylsulfonyl)methyl | |
| A1-512 | H | Cl | C—Cl | Cl | H | CH3 | F | H | tert-butoxy | |
| A1-513 | H | Cl | C—Cl | Cl | F | CF3 | H | H | CH3 | |
| A1-514 | H | Cl | C—Cl | Cl | F | CF3 | H | H | ethyl | |
| A1-515 | H | Cl | C—Cl | Cl | F | CF3 | H | H | n-propyl | |
| A1-516 | H | Cl | C—Cl | Cl | F | CF3 | H | H | isopropyl | |
| A1-517 | H | Cl | C—Cl | Cl | F | CF3 | H | H | cyclopropyl | |
| A1-518 | H | Cl | C—Cl | Cl | F | CF3 | H | H | cyclopropylmethyl | |
| A1-519 | H | Cl | C—Cl | Cl | F | CF3 | H | H | 2,2,2-trifluoroethyl | |
| A1-520 | H | Cl | C—Cl | Cl | F | CF3 | H | H | 2-methoxyethyl | |
| A1-521 | H | Cl | C—Cl | Cl | F | CF3 | H | H | (methylsulfanyl)methyl | |
| A1-522 | H | Cl | C—Cl | Cl | F | CF3 | H | H | (methylsulfinyl)methyl | |
| A1-523 | H | Cl | C—Cl | Cl | F | CF3 | H | H | (methylsulfonyl)methyl | |
| A1-524 | H | Cl | C—Cl | Cl | F | CF3 | H | H | tert-butoxy | |
| A1-525 | H | Cl | C—Cl | Cl | H | Br | H | H | cyanomethyl | |
| A1-526 | H | Cl | C—Cl | Cl | H | CF3 | H | H | cyanomethyl | |
| A1-527 | H | CF3 | C—H | CF3 | H | Br | H | H | cyanomethyl | |
| A1-528 | H | CF3 | C—H | CF3 | H | CF3 | H | H | cyanomethyl | |
| A1-529 | H | Cl | C—Cl | Cl | H | OCF2H | H | H | CH3 | |

TABLE A1-continued

Compounds according to the invention

| Ex. No. | X¹ | X² | A | X⁴ | Y¹ | Y² | Y⁴ | R³ | R⁷ | log P |
|---|---|---|---|---|---|---|---|---|---|---|
| A1-530 | H | Cl | C—Cl | Cl | H | OCF2H | H | H | ethyl | |
| A1-531 | H | Cl | C—Cl | Cl | H | OCF2H | H | H | n-propyl | |
| A1-532 | H | Cl | C—Cl | Cl | H | OCF2H | H | H | isopropyl | |
| A1-533 | H | Cl | C—Cl | Cl | H | OCF2H | H | H | cyclopropyl | |
| A1-534 | H | Cl | C—Cl | Cl | H | OCF2H | H | H | cyclopropylmethyl | |
| A1-535 | H | Cl | C—Cl | Cl | H | OCF2H | H | H | 2,2,2-trifluoroethyl | |
| A1-536 | H | Cl | C—Cl | Cl | H | OCF2H | H | H | 2-methoxyethyl | |
| A1-537 | H | Cl | C—Cl | Cl | H | OCF2H | H | H | (methylsulfanyl)methyl | |
| A1-538 | H | Cl | C—Cl | Cl | H | OCF2H | H | H | (methylsulfinyl)methyl | |
| A1-539 | H | Cl | C—Cl | Cl | H | OCF2H | H | H | (methylsulfonyl)methyl | |
| A1-540 | H | Cl | C—Cl | Cl | H | OCF2H | H | H | tert-butoxy | |
| A1-541 | H | Cl | C—Cl | Cl | H | CF3 | H | H | CH3 | |
| A1-542 | H | Cl | C—Cl | Cl | H | CF3 | H | H | ethyl | |
| A1-543 | H | Cl | C—Cl | Cl | H | CF3 | H | H | n-propyl | |
| A1-544 | H | Cl | C—Cl | Cl | H | CF3 | H | H | isopropyl | |
| A1-545 | H | Cl | C—Cl | Cl | H | CF3 | H | H | cyclopropyl | |
| A1-546 | H | Cl | C—Cl | Cl | H | CF3 | H | H | cyclopropylmethyl | |
| A1-547 | H | Cl | C—Cl | Cl | H | CF3 | H | H | 2,2,2-trifluoroethyl | |
| A1-548 | H | Cl | C—Cl | Cl | H | CF3 | H | H | 2-methoxyethyl | |
| A1-549 | H | Cl | C—Cl | Cl | H | CF3 | H | H | (methylsulfanyl)methyl | |
| A1-550 | H | Cl | C—Cl | Cl | H | CF3 | H | H | (methylsulfinyl)methyl | |
| A1-551 | H | Cl | C—Cl | Cl | H | CF3 | H | H | (methylsulfonyl)methyl | |
| A1-552 | H | Cl | C—Cl | Cl | H | CF3 | H | H | tert-butoxy | |
| A1-553 | F | Cl | C—F | Cl | H | H | H | H | CH3 | |
| A1-554 | F | Cl | C—F | Cl | H | H | H | H | ethyl | |
| A1-555 | F | Cl | C—F | Cl | H | H | H | H | n-propyl | |
| A1-556 | F | Cl | C—F | Cl | H | H | H | H | isopropyl | |
| A1-557 | F | Cl | C—F | Cl | H | H | H | H | cyclopropyl | |
| A1-558 | F | Cl | C—F | Cl | H | H | H | H | cyclopropylmethyl | |
| A1-559 | F | Cl | C—F | Cl | H | H | H | H | 2,2,2-trifluoroethyl | |
| A1-560 | F | Cl | C—F | Cl | H | H | H | H | 2-methoxyethyl | |
| A1-561 | F | Cl | C—F | Cl | H | H | H | H | (methylsulfanyl)methyl | |
| A1-562 | F | Cl | C—F | Cl | H | H | H | H | (methylsulfinyl)methyl | |
| A1-563 | F | Cl | C—F | Cl | H | H | H | H | (methylsulfonyl)methyl | |
| A1-564 | F | Cl | C—H | Cl | H | H | H | H | CH3 | |
| A1-565 | F | Cl | C—H | Cl | H | H | H | H | ethyl | |
| A1-566 | F | Cl | C—H | Cl | H | H | H | H | n-propyl | |
| A1-567 | F | Cl | C—H | Cl | H | H | H | H | isopropyl | |
| A1-568 | F | Cl | C—H | Cl | H | H | H | H | cyclopropyl | |
| A1-569 | F | Cl | C—H | Cl | H | H | H | H | cyclopropylmethyl | |
| A1-570 | F | Cl | C—H | Cl | H | H | H | H | 2,2,2-trifluoroethyl | |
| A1-571 | F | Cl | C—H | Cl | H | H | H | H | 2-methoxyethyl | |
| A1-572 | F | Cl | C—H | Cl | H | H | H | H | (methylsulfanyl)methyl | |
| A1-573 | F | Cl | C—H | Cl | H | H | H | H | (methylsulfinyl)methyl | |
| A1-574 | F | Cl | C—H | Cl | H | H | H | H | (methylsulfonyl)methyl | |
| A1-575 | H | Cl | C—Cl | Cl | H | H | H | H | tert-butoxy | |

TABLE A2

Compounds according to the invention
As the compounds in this table A2 are diastereomers, the example number given in this table (for example A2-3) does imply the (R)-isomer and the (S)-isomer of the respective compound (e.g A2-1 implies compounds A2-1-a (the (R)-isomer and A2-1-b (the (S)-isomer)). The NMR data of the respective compounds given herein, do, however, distinguish between (R)-isomer and (S)-isomer (e.g. NMR data of the (S)-stereomer is given for compound A2-3 under the example number A2-3-b).

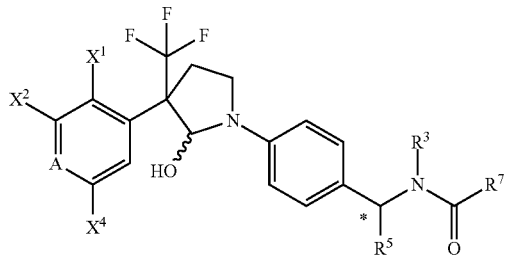

| Ex. No. | $X^1$ | $X^2$ | A | $X^4$ | $R^3$ | $R^5$ | $R^7$ |
|---|---|---|---|---|---|---|---|
| A2-1 | H | Cl | C—H | Cl | H | $CH_3$ | $CH_3$ |
| A2-2 | H | Cl | C—H | Cl | H | $CH_3$ | ethyl |
| A2-3 | H | Cl | C—H | Cl | H | $CH_3$ | n-propyl |
| A2-4 | H | Cl | C—H | Cl | H | $CH_3$ | isopropyl |
| A2-5 | H | Cl | C—H | Cl | H | $CH_3$ | cyclopropyl |
| A2-6 | H | Cl | C—H | Cl | H | $CH_3$ | cyclopropylmethyl |
| A2-7 | H | Cl | C—H | Cl | H | $CH_3$ | 2,2,2-trifluoroethyl |
| A2-8 | H | Cl | C—H | Cl | H | $CH_3$ | 2-methoxyethyl |
| A2-9 | H | Cl | C—H | Cl | H | $CH_3$ | (methylsulfanyl)methyl |
| A2-10 | H | Cl | C—H | Cl | H | $CH_3$ | (methylsulfinyl)methyl |
| A2-11 | H | Cl | C—H | Cl | H | $CH_3$ | (methylsulfonyl)methyl |
| A2-12 | H | Cl | C—Cl | Cl | H | $CH_3$ | $CH_3$ |
| A2-13 | H | Cl | C—Cl | Cl | H | $CH_3$ | ethyl |
| A2-14 | H | Cl | C—Cl | Cl | H | $CH_3$ | n-propyl |
| A2-15 | H | Cl | C—Cl | Cl | H | $CH_3$ | isopropyl |
| A2-16 | H | Cl | C—Cl | Cl | H | $CH_3$ | cyclopropyl |
| A2-17 | H | Cl | C—Cl | Cl | H | $CH_3$ | cyclopropylmethyl |
| A2-18 | H | Cl | C—Cl | Cl | H | $CH_3$ | 2,2,2-trifluoroethyl |
| A2-19 | H | Cl | C—Cl | Cl | H | $CH_3$ | 2-methoxyethyl |
| A2-20 | H | Cl | C—Cl | Cl | H | $CH_3$ | (methylsulfanyl)methyl |
| A2-21 | H | Cl | C—Cl | Cl | H | $CH_3$ | (methylsulfinyl)methyl |
| A2-22 | H | Cl | C—Cl | Cl | H | $CH_3$ | (methylsulfonyl)methyl |
| A2-23 | H | CF3 | C—H | CF3 | H | $CH_3$ | $CH_3$ |
| A2-24 | H | CF3 | C—H | CF3 | H | $CH_3$ | ethyl |
| A2-25 | H | CF3 | C—H | CF3 | H | $CH_3$ | n-propyl |
| A2-26 | H | CF3 | C—H | CF3 | H | $CH_3$ | isopropyl |
| A2-27 | H | CF3 | C—H | CF3 | H | $CH_3$ | cyclopropyl |
| A2-28 | H | CF3 | C—H | CF3 | H | $CH_3$ | cyclopropylmethyl |
| A2-29 | H | CF3 | C—H | CF3 | H | $CH_3$ | 2,2,2-trifluoroethyl |
| A2-30 | H | CF3 | C—H | CF3 | H | $CH_3$ | 2-methoxyethyl |
| A2-31 | H | CF3 | C—H | CF3 | H | $CH_3$ | (methylsulfanyl)methyl |
| A2-32 | H | CF3 | C—H | CF3 | H | $CH_3$ | (methylsulfinyl)methyl |
| A2-33 | H | CF3 | C—H | CF3 | H | $CH_3$ | (methylsulfonyl)methyl |
| A2-34 | H | CF3 | N | CF3 | H | $CH_3$ | $CH_3$ |
| A2-35 | H | CF3 | N | CF3 | H | $CH_3$ | ethyl |
| A2-36 | H | CF3 | N | CF3 | H | $CH_3$ | n-propyl |
| A2-37 | H | CF3 | N | CF3 | H | $CH_3$ | isopropyl |
| A2-38 | H | CF3 | N | CF3 | H | $CH_3$ | cyclopropyl |
| A2-39 | H | CF3 | N | CF3 | H | $CH_3$ | cyclopropylmethyl |
| A2-40 | H | CF3 | N | CF3 | H | $CH_3$ | 2,2,2-trifluoroethyl |
| A2-41 | H | CF3 | N | CF3 | H | $CH_3$ | 2-methoxyethyl |
| A2-42 | H | CF3 | N | CF3 | H | $CH_3$ | (methylsulfanyl)methyl |
| A2-43 | H | CF3 | N | CF3 | H | $CH_3$ | (methylsulfinyl)methyl |
| A2-44 | H | CF3 | N | CF3 | H | $CH_3$ | (methylsulfonyl)methyl |
| A2-45 | F | Cl | C—F | Cl | H | $CH_3$ | $CH_3$ |
| A2-46 | F | Cl | C—F | Cl | H | $CH_3$ | ethyl |
| A2-47 | F | Cl | C—F | Cl | H | $CH_3$ | n-propyl |
| A2-48 | F | Cl | C—F | Cl | H | $CH_3$ | isopropyl |
| A2-49 | F | Cl | C—F | Cl | H | $CH_3$ | cyclopropyl |
| A2-50 | F | Cl | C—F | Cl | H | $CH_3$ | cyclopropylmethyl |
| A2-51 | F | Cl | C—F | Cl | H | $CH_3$ | 2,2,2-trifluoroethyl |
| A2-52 | F | Cl | C—F | Cl | H | $CH_3$ | 2-methoxyethyl |
| A2-53 | F | Cl | C—F | Cl | H | $CH_3$ | (methylsulfanyl)methyl |
| A2-54 | F | Cl | C—F | Cl | H | $CH_3$ | (methylsulfinyl)methyl |
| A2-55 | F | Cl | C—F | Cl | H | $CH_3$ | (methylsulfonyl)methyl |
| A2-56 | F | Cl | C—H | Cl | H | CH3 | CH3 |
| A2-57 | F | Cl | C—H | Cl | H | CH3 | ethyl |
| A2-58 | F | Cl | C—H | Cl | H | CH3 | n-propyl |

TABLE A2-continued

Compounds according to the invention
As the compounds in this table A2 are diastereomers, the example number given in this table (for example A2-3) does imply the (R)-isomer and the (S)-isomer of the respective compound (e.g A2-1 implies compounds A2-1-a (the (R)-isomer and A2-1-b (the (S)-isomer)). The NMR data of the respective compounds given herein, do, however, distinguish between (R)-isomer and (S)-isomer (e.g. NMR data of the (S)-stereomer is given for compound A2-3 under the example number A2-3-b).

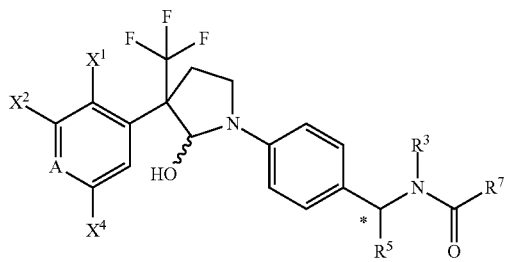

| Ex. No. | $X^1$ | $X^2$ | A | $X^4$ | $R^3$ | $R^5$ | $R^7$ |
|---|---|---|---|---|---|---|---|
| A2-59 | F | Cl | C—H | Cl | H | CH3 | isopropyl |
| A2-60 | F | Cl | C—H | Cl | H | CH3 | cyclopropyl |
| A2-61 | F | Cl | C—H | Cl | H | CH3 | cyclopropylmethyl |
| A2-62 | F | Cl | C—H | Cl | H | CH3 | 2,2,2-trifluoroethyl |
| A2-63 | F | Cl | C—H | Cl | H | CH3 | 2-methoxyethyl |
| A2-64 | F | Cl | C—H | Cl | H | CH3 | (methylsulfanyl)methyl |
| A2-65 | F | Cl | C—H | Cl | H | CH3 | (methylsulfinyl)methyl |
| A2-66 | F | Cl | C—H | Cl | H | CH3 | (methylsulfonyl)methyl |

\*
a = (R) isomer
b = (S) isomer

TABLE A3

Compounds according to the invention

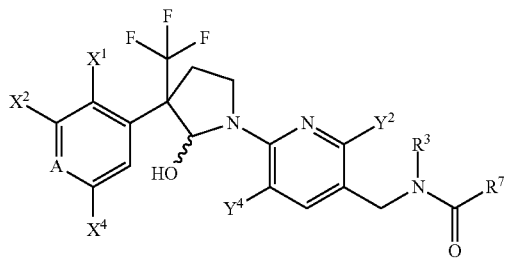

| Ex. No. | $X^1$ | $X^2$ | A | $X^4$ | $Y^2$ | $Y^4$ | $R^3$ | $R^7$ | logP |
|---|---|---|---|---|---|---|---|---|---|
| A3-1 | H | Cl | C—H | Cl | CF3 | H | H | $CH_3$ | |
| A3-2 | H | Cl | C—H | Cl | CF3 | H | H | ethyl | |
| A3-3 | H | Cl | C—H | Cl | CF3 | H | H | n-propyl | |
| A3-4 | H | Cl | C—H | Cl | CF3 | H | H | isopropyl | |
| A3-5 | H | Cl | C—H | Cl | CF3 | H | H | cyclopropyl | |
| A3-6 | H | Cl | C—H | Cl | CF3 | H | H | cyclopropylmethyl | |
| A3-7 | H | Cl | C—H | Cl | CF3 | H | H | 2,2,2-trifluoroethyl | |
| A3-8 | H | Cl | C—H | Cl | CF3 | H | H | 2-methoxyethyl | |
| A3-9 | H | Cl | C—H | Cl | CF3 | H | H | (methylsulfanyl)methyl | |
| A3-10 | H | Cl | C—H | Cl | CF3 | H | H | (methylsulfinyl)methyl | |
| A3-11 | H | Cl | C—H | Cl | CF3 | H | H | (methylsulfonyl)methyl | |
| A3-12 | H | Cl | C—Cl | Cl | CF3 | H | H | $CH_3$ | |
| A3-13 | H | Cl | C—Cl | Cl | CF3 | H | H | ethyl | |
| A3-14 | H | Cl | C—Cl | Cl | CF3 | H | H | n-propyl | |
| A3-15 | H | Cl | C—Cl | Cl | CF3 | H | H | isopropyl | |
| A3-16 | H | Cl | C—Cl | Cl | CF3 | H | H | cyclopropyl | |
| A3-17 | H | Cl | C—Cl | Cl | CF3 | H | H | cyclopropylmethyl | |
| A3-18 | H | Cl | C—Cl | Cl | CF3 | H | H | 2,2,2-trifluoroethyl | |
| A3-19 | H | Cl | C—Cl | Cl | CF3 | H | H | 2-methoxyethyl | |
| A3-20 | H | Cl | C—Cl | Cl | CF3 | H | H | (methylsulfanyl)methyl | |
| A3-21 | H | Cl | C—Cl | Cl | CF3 | H | H | (methylsulfinyl)methyl | |
| A3-22 | H | Cl | C—Cl | Cl | CF3 | H | H | (methylsulfonyl)methyl | |
| A3-23 | H | CF3 | C—H | CF3 | CF3 | H | H | $CH_3$ | |
| A3-24 | H | CF3 | C—H | CF3 | CF3 | H | H | ethyl | |

TABLE A3-continued

Compounds according to the invention

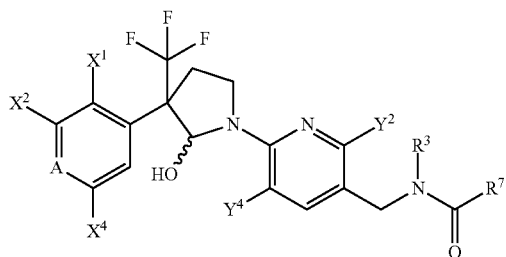

| Ex. No. | X¹ | X² | A | X⁴ | Y² | Y⁴ | R³ | R⁷ | logP |
|---|---|---|---|---|---|---|---|---|---|
| A3-25 | H | CF3 | C—H | CF3 | CF3 | H | H | n-propyl | |
| A3-26 | H | CF3 | C—H | CF3 | CF3 | H | H | isopropyl | |
| A3-27 | H | CF3 | C—H | CF3 | CF3 | H | H | cyclopropyl | |
| A3-28 | H | CF3 | C—H | CF3 | CF3 | H | H | cyclopropylmethyl | |
| A3-29 | H | CF3 | C—H | CF3 | CF3 | H | H | 2,2,2-trifluoroethyl | |
| A3-30 | H | CF3 | C—H | CF3 | CF3 | H | H | 2-methoxyethyl | |
| A3-31 | H | CF3 | C—H | CF3 | CF3 | H | H | (methylsulfanyl)methyl | |
| A3-32 | H | CF3 | C—H | CF3 | CF3 | H | H | (methylsulfinyl)methyl | |
| A3-33 | H | CF3 | C—H | CF3 | CF3 | H | H | (methylsulfonyl)methyl | |
| A3-34 | H | Cl | C—H | Cl | CH₃ | H | H | CH₃ | |
| A3-35 | H | Cl | C—H | Cl | CH₃ | H | H | ethyl | |
| A3-36 | H | Cl | C—H | Cl | CH₃ | H | H | n-propyl | |
| A3-37 | H | Cl | C—H | Cl | CH₃ | H | H | isopropyl | |
| A3-38 | H | Cl | C—H | Cl | CH₃ | H | H | cyclopropyl | |
| A3-39 | H | Cl | C—H | Cl | CH₃ | H | H | cyclopropylmethyl | |
| A3-40 | H | Cl | C—H | Cl | CH₃ | H | H | 2,2,2-trifluoroethyl | |
| A3-41 | H | Cl | C—H | Cl | CH₃ | H | H | 2-methoxyethyl | |
| A3-42 | H | Cl | C—H | Cl | CH₃ | H | H | (methylsulfanyl)methyl | |
| A3-43 | H | Cl | C—H | Cl | CH₃ | H | H | (methylsulfinyl)methyl | |
| A3-44 | H | Cl | C—H | Cl | CH₃ | H | H | (methylsulfonyl)methyl | |
| A3-45 | H | Cl | C—H | Cl | ethyl | H | H | CH₃ | |
| A3-46 | H | Cl | C—H | Cl | ethyl | H | H | ethyl | |
| A3-47 | H | Cl | C—H | Cl | ethyl | H | H | n-propyl | |
| A3-48 | H | Cl | C—H | Cl | ethyl | H | H | isopropyl | |
| A3-49 | H | Cl | C—H | Cl | ethyl | H | H | cyclopropyl | |
| A3-50 | H | Cl | C—H | Cl | ethyl | H | H | cyclopropylmethyl | |
| A3-51 | H | Cl | C—H | Cl | ethyl | H | H | 2,2,2-trifluoroethyl | |
| A3-52 | H | Cl | C—H | Cl | ethyl | H | H | 2-methoxyethyl | |
| A3-53 | H | Cl | C—H | Cl | ethyl | H | H | (methylsulfanyl)methyl | |
| A3-54 | H | Cl | C—H | Cl | ethyl | H | H | (methylsulfinyl)methyl | |
| A3-55 | H | Cl | C—H | Cl | ethyl | H | H | (methylsulfonyl)methyl | |
| A3-56 | H | Cl | C—H | Cl | Cl | H | H | CH₃ | |
| A3-57 | H | Cl | C—H | Cl | Cl | H | H | ethyl | |
| A3-58 | H | Cl | C—H | Cl | Cl | H | H | n-propyl | |
| A3-59 | H | Cl | C—H | Cl | Cl | H | H | isopropyl | |
| A3-60 | H | Cl | C—H | Cl | Cl | H | H | cyclopropyl | |
| A3-61 | H | Cl | C—H | Cl | Cl | H | H | cyclopropylmethyl | |
| A3-62 | H | Cl | C—H | Cl | Cl | H | H | 2,2,2-trifluoroethyl | |
| A3-63 | H | Cl | C—H | Cl | Cl | H | H | 2-methoxyethyl | |
| A3-64 | H | Cl | C—H | Cl | Cl | H | H | (methylsulfanyl)methyl | |
| A3-65 | H | Cl | C—H | Cl | Cl | H | H | (methylsulfinyl)methyl | |
| A3-66 | H | Cl | C—H | Cl | Cl | H | H | (methylsulfonyl)methyl | |
| A3-67 | H | Cl | C—H | Cl | Br | H | H | CH₃ | |
| A3-68 | H | Cl | C—H | Cl | Br | H | H | ethyl | |
| A3-69 | H | Cl | C—H | Cl | Br | H | H | n-propyl | |
| A3-70 | H | Cl | C—H | Cl | Br | H | H | isopropyl | |
| A3-71 | H | Cl | C—H | Cl | Br | H | H | cyclopropyl | |
| A3-72 | H | Cl | C—H | Cl | Br | H | H | cyclopropylmethyl | |
| A3-73 | H | Cl | C—H | Cl | Br | H | H | 2,2,2-trifluoroethyl | |
| A3-74 | H | Cl | C—H | Cl | Br | H | H | 2-methoxyethyl | |
| A3-75 | H | Cl | C—H | Cl | Br | H | H | (methylsulfanyl)methyl | |
| A3-76 | H | Cl | C—H | Cl | Br | H | H | (methylsulfinyl)methyl | |
| A3-77 | H | Cl | C—H | Cl | Br | H | H | (methylsulfonyl)methyl | |
| A3-78 | H | Cl | C—Cl | Cl | CH₃ | H | H | CH₃ | |
| A3-79 | H | Cl | C—Cl | Cl | CH₃ | H | H | ethyl | |
| A3-80 | H | Cl | C—Cl | Cl | CH₃ | H | H | n-propyl | |
| A3-81 | H | Cl | C—Cl | Cl | CH₃ | H | H | isopropyl | |
| A3-82 | H | Cl | C—Cl | Cl | CH₃ | H | H | cyclopropyl | |
| A3-83 | H | Cl | C—Cl | Cl | CH₃ | H | H | cyclopropylmethyl | |
| A3-84 | H | Cl | C—Cl | Cl | CH₃ | H | H | 2,2,2-trifluoroethyl | |
| A3-85 | H | Cl | C—Cl | Cl | CH₃ | H | H | 2-methoxyethyl | |
| A3-86 | H | Cl | C—Cl | Cl | CH₃ | H | H | (methylsulfanyl)methyl | |
| A3-87 | H | Cl | C—Cl | Cl | CH₃ | H | H | (methylsulfinyl)methyl | |

TABLE A3-continued

Compounds according to the invention

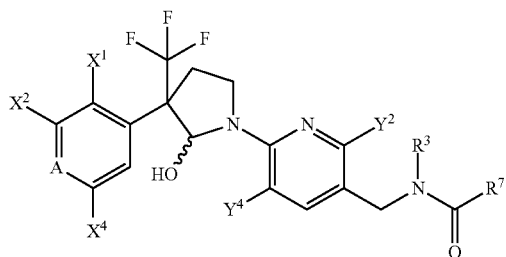

| Ex. No. | $X^1$ | $X^2$ | A | $X^4$ | $Y^2$ | $Y^4$ | $R^3$ | $R^7$ | logP |
|---|---|---|---|---|---|---|---|---|---|
| A3-88 | H | Cl | C—Cl | Cl | $CH_3$ | H | H | (methylsulfonyl)methyl | |
| A3-89 | H | Cl | C—Cl | Cl | ethyl | H | H | $CH_3$ | |
| A3-90 | H | Cl | C—Cl | Cl | ethyl | H | H | ethyl | |
| A3-91 | H | Cl | C—Cl | Cl | ethyl | H | H | n-propyl | |
| A3-92 | H | Cl | C—Cl | Cl | ethyl | H | H | isopropyl | |
| A3-93 | H | Cl | C—Cl | Cl | ethyl | H | H | cyclopropyl | |
| A3-94 | H | Cl | C—Cl | Cl | ethyl | H | H | cyclopropylmethyl | |
| A3-95 | H | Cl | C—Cl | Cl | ethyl | H | H | 2,2,2-trifluoroethyl | |
| A3-96 | H | Cl | C—Cl | Cl | ethyl | H | H | 2-methoxyethyl | |
| A3-97 | H | Cl | C—Cl | Cl | ethyl | H | H | (methylsulfanyl)methyl | |
| A3-98 | H | Cl | C—Cl | Cl | ethyl | H | H | (methylsulfinyl)methyl | |
| A3-99 | H | Cl | C—Cl | Cl | ethyl | H | H | (methylsulfonyl)methyl | |
| A3-100 | H | Cl | C—Cl | Cl | Cl | H | H | $CH_3$ | |
| A3-101 | H | Cl | C—Cl | Cl | Cl | H | H | ethyl | |
| A3-102 | H | Cl | C—Cl | Cl | Cl | H | H | n-propyl | |
| A3-103 | H | Cl | C—Cl | Cl | Cl | H | H | isopropyl | |
| A3-104 | H | Cl | C—Cl | Cl | Cl | H | H | cyclopropyl | |
| A3-105 | H | Cl | C—Cl | Cl | Cl | H | H | cyclopropylmethyl | |
| A3-106 | H | Cl | C—Cl | Cl | Cl | H | H | 2,2,2-trifluoroethyl | |
| A3-107 | H | Cl | C—Cl | Cl | Cl | H | H | 2-methoxyethyl | |
| A3-108 | H | Cl | C—Cl | Cl | Cl | H | H | (methylsulfanyl)methyl | |
| A3-109 | H | Cl | C—Cl | Cl | Cl | H | H | (methylsulfinyl)methyl | |
| A3-110 | H | Cl | C—Cl | Cl | Cl | H | H | (methylsulfonyl)methyl | |
| A3-111 | H | Cl | C—Cl | Cl | Br | H | H | $CH_3$ | |
| A3-112 | H | Cl | C—Cl | Cl | Br | H | H | ethyl | |
| A3-113 | H | Cl | C—Cl | Cl | Br | H | H | n-propyl | |
| A3-114 | H | Cl | C—Cl | Cl | Br | H | H | isopropyl | |
| A3-115 | H | Cl | C—Cl | Cl | Br | H | H | cyclopropyl | |
| A3-116 | H | Cl | C—Cl | Cl | Br | H | H | cyclopropylmethyl | |
| A3-117 | H | Cl | C—Cl | Cl | Br | H | H | 2,2,2-trifluoroethyl | |
| A3-118 | H | Cl | C—Cl | Cl | Br | H | H | 2-methoxyethyl | |
| A3-119 | H | Cl | C—Cl | Cl | Br | H | H | (methylsulfanyl)methyl | |
| A3-120 | H | Cl | C—Cl | Cl | Br | H | H | (methylsulfinyl)methyl | |
| A3-121 | H | Cl | C—Cl | Cl | Br | H | H | (methylsulfonyl)methyl | |
| A3-122 | H | CF3 | C—H | CF3 | $CH_3$ | H | H | $CH_3$ | |
| A3-123 | H | CF3 | C—H | CF3 | $CH_3$ | H | H | ethyl | |
| A3-124 | H | CF3 | C—H | CF3 | $CH_3$ | H | H | n-propyl | |
| A3-125 | H | CF3 | C—H | CF3 | $CH_3$ | H | H | isopropyl | |
| A3-126 | H | CF3 | C—H | CF3 | $CH_3$ | H | H | cyclopropyl | |
| A3-127 | H | CF3 | C—H | CF3 | $CH_3$ | H | H | cyclopropylmethyl | |
| A3-128 | H | CF3 | C—H | CF3 | $CH_3$ | H | H | 2,2,2-trifluoroethyl | |
| A3-129 | H | CF3 | C—H | CF3 | $CH_3$ | H | H | 2-methoxyethyl | |
| A3-130 | H | CF3 | C—H | CF3 | $CH_3$ | H | H | (methylsulfanyl)methyl | |
| A3-131 | H | CF3 | C—H | CF3 | $CH_3$ | H | H | (methylsulfinyl)methyl | |
| A3-132 | H | CF3 | C—H | CF3 | $CH_3$ | H | H | (methylsulfonyl)methyl | |
| A3-133 | H | CF3 | C—H | CF3 | ethyl | H | H | $CH_3$ | |
| A3-134 | H | CF3 | C—H | CF3 | ethyl | H | H | ethyl | |
| A3-135 | H | CF3 | C—H | CF3 | ethyl | H | H | n-propyl | |
| A3-136 | H | CF3 | C—H | CF3 | ethyl | H | H | isopropyl | |
| A3-137 | H | CF3 | C—H | CF3 | ethyl | H | H | cyclopropyl | |
| A3-138 | H | CF3 | C—H | CF3 | ethyl | H | H | cyclopropylmethyl | |
| A3-139 | H | CF3 | C—H | CF3 | ethyl | H | H | 2,2,2-trifluoroethyl | |
| A3-140 | H | CF3 | C—H | CF3 | ethyl | H | H | 2-methoxyethyl | |
| A3-141 | H | CF3 | C—H | CF3 | ethyl | H | H | (methylsulfanyl)methyl | |
| A3-142 | H | CF3 | C—H | CF3 | ethyl | H | H | (methylsulfinyl)methyl | |
| A3-143 | H | CF3 | C—H | CF3 | ethyl | H | H | (methylsulfonyl)methyl | |
| A3-144 | H | CF3 | C—H | CF3 | Cl | H | H | $CH_3$ | |
| A3-145 | H | CF3 | C—H | CF3 | Cl | H | H | ethyl | |
| A3-146 | H | CF3 | C—H | CF3 | Cl | H | H | n-propyl | |
| A3-147 | H | CF3 | C—H | CF3 | Cl | H | H | isopropyl | |
| A3-148 | H | CF3 | C—H | CF3 | Cl | H | H | cyclopropyl | 3.96 |
| A3-149 | H | CF3 | C—H | CF3 | Cl | H | H | cyclopropylmethyl | |
| A3-150 | H | CF3 | C—H | CF3 | Cl | H | H | 2,2,2-trifluoroethyl | |

TABLE A3-continued

Compounds according to the invention

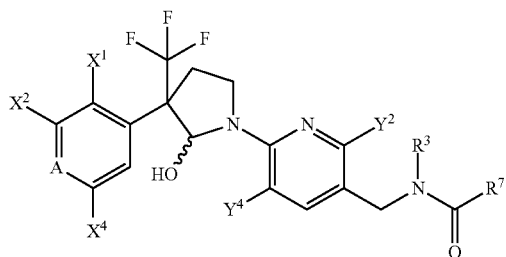

| Ex. No. | X¹ | X² | A | X⁴ | Y² | Y⁴ | R³ | R⁷ | logP |
|---|---|---|---|---|---|---|---|---|---|
| A3-151 | H | CF3 | C—H | CF3 | Cl | H | H | 2-methoxyethyl | |
| A3-152 | H | CF3 | C—H | CF3 | Cl | H | H | (methylsulfanyl)methyl | |
| A3-153 | H | CF3 | C—H | CF3 | Cl | H | H | (methylsulfinyl)methyl | |
| A3-154 | H | CF3 | C—H | CF3 | Cl | H | H | (methylsulfonyl)methyl | |
| A3-155 | H | CF3 | C—H | CF3 | Br | H | H | CH₃ | |
| A3-156 | H | CF3 | C—H | CF3 | Br | H | H | ethyl | |
| A3-157 | H | CF3 | C—H | CF3 | Br | H | H | n-propyl | |
| A3-158 | H | CF3 | C—H | CF3 | Br | H | H | isopropyl | |
| A3-159 | H | CF3 | C—H | CF3 | Br | H | H | cyclopropyl | |
| A3-160 | H | CF3 | C—H | CF3 | Br | H | H | cyclopropylmethyl | |
| A3-161 | H | CF3 | C—H | CF3 | Br | H | H | 2,2,2-trifluoroethyl | |
| A3-162 | H | CF3 | C—H | CF3 | Br | H | H | 2-methoxyethyl | 3.71 |
| A3-163 | H | CF3 | C—H | CF3 | Br | H | H | (methylsulfanyl)methyl | |
| A3-164 | H | CF3 | C—H | CF3 | Br | H | H | (methylsulfinyl)methyl | |
| A3-165 | H | CF3 | C—H | CF3 | Br | H | H | (methylsulfonyl)methyl | |
| A3-166 | H | F | C—H | Cl | CF3 | H | H | CH₃ | |
| A3-167 | H | F | C—H | Cl | CF3 | H | H | ethyl | |
| A3-168 | H | F | C—H | Cl | CF3 | H | H | n-propyl | |
| A3-169 | H | F | C—H | Cl | CF3 | H | H | isopropyl | |
| A3-170 | H | F | C—H | Cl | CF3 | H | H | cyclopropyl | |
| A3-171 | H | F | C—H | Cl | CF3 | H | H | cyclopropylmethyl | |
| A3-172 | H | F | C—H | Cl | CF3 | H | H | 2,2,2-trifluoroethyl | |
| A3-173 | H | F | C—H | Cl | CF3 | H | H | 2-methoxyethyl | |
| A3-174 | H | F | C—H | Cl | CF3 | H | H | (methylsulfanyl)methyl | |
| A3-175 | H | F | C—H | Cl | CF3 | H | H | (methylsulfinyl)methyl | |
| A3-176 | H | F | C—H | Cl | CF3 | H | H | (methylsulfonyl)methyl | |
| A3-177 | H | Br | C—H | Br | CF3 | H | H | CH₃ | |
| A3-178 | H | Br | C—H | Br | CF3 | H | H | ethyl | |
| A3-179 | H | Br | C—H | Br | CF3 | H | H | n-propyl | |
| A3-180 | H | Br | C—H | Br | CF3 | H | H | isopropyl | |
| A3-181 | H | Br | C—H | Br | CF3 | H | H | cyclopropyl | |
| A3-182 | H | Br | C—H | Br | CF3 | H | H | cyclopropylmethyl | |
| A3-183 | H | Br | C—H | Br | CF3 | H | H | 2,2,2-trifluoroethyl | |
| A3-184 | H | Br | C—H | Br | CF3 | H | H | 2-methoxyethyl | |
| A3-185 | H | Br | C—H | Br | CF3 | H | H | (methylsulfanyl)methyl | |
| A3-186 | H | Br | C—H | Br | CF3 | H | H | (methylsulfinyl)methyl | |
| A3-187 | H | Br | C—H | Br | CF3 | H | H | (methylsulfonyl)methyl | |
| A3-188 | H | F | C—F | F | CF3 | H | H | CH₃ | |
| A3-189 | H | F | C—F | F | CF3 | H | H | ethyl | |
| A3-190 | H | F | C—F | F | CF3 | H | H | n-propyl | |
| A3-191 | H | F | C—F | F | CF3 | H | H | isopropyl | |
| A3-192 | H | F | C—F | F | CF3 | H | H | cyclopropyl | |
| A3-193 | H | F | C—F | F | CF3 | H | H | cyclopropylmethyl | |
| A3-194 | H | F | C—F | F | CF3 | H | H | 2,2,2-trifluoroethyl | |
| A3-195 | H | F | C—F | F | CF3 | H | H | 2-methoxyethyl | |
| A3-196 | H | F | C—F | F | CF3 | H | H | (methylsulfanyl)methyl | |
| A3-197 | H | F | C—F | F | CF3 | H | H | (methylsulfinyl)methyl | |
| A3-198 | H | F | C—F | F | CF3 | H | H | (methylsulfonyl)methyl | |
| A3-199 | H | Cl | C—F | Cl | CF3 | H | H | CH₃ | |
| A3-200 | H | Cl | C—F | Cl | CF3 | H | H | ethyl | |
| A3-201 | H | Cl | C—F | Cl | CF3 | H | H | n-propyl | |
| A3-202 | H | Cl | C—F | Cl | CF3 | H | H | isopropyl | |
| A3-203 | H | Cl | C—F | Cl | CF3 | H | H | cyclopropyl | |
| A3-204 | H | Cl | C—F | Cl | CF3 | H | H | cyclopropylmethyl | |
| A3-205 | H | Cl | C—F | Cl | CF3 | H | H | 2,2,2-trifluoroethyl | |
| A3-206 | H | Cl | C—F | Cl | CF3 | H | H | 2-methoxyethyl | |
| A3-207 | H | Cl | C—F | Cl | CF3 | H | H | (methylsulfanyl)methyl | |
| A3-208 | H | Cl | C—F | Cl | CF3 | H | H | (methylsulfinyl)methyl | |
| A3-209 | H | Cl | C—F | Cl | CF3 | H | H | (methylsulfonyl)methyl | |
| A3-210 | F | Cl | C—F | Cl | CF3 | H | H | CH₃ | |
| A3-211 | F | Cl | C—F | Cl | CF3 | H | H | ethyl | |
| A3-212 | F | Cl | C—F | Cl | CF3 | H | H | n-propyl | |
| A3-213 | F | Cl | C—F | Cl | CF3 | H | H | isopropyl | |

TABLE A3-continued

Compounds according to the invention

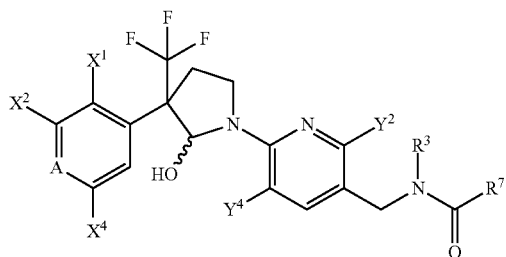

| Ex. No. | X¹ | X² | A | X⁴ | Y² | Y⁴ | R³ | R⁷ | logP |
|---|---|---|---|---|---|---|---|---|---|
| A3-214 | F | Cl | C—F | Cl | CF3 | H | H | cyclopropyl | |
| A3-215 | F | Cl | C—F | Cl | CF3 | H | H | cyclopropylmethyl | |
| A3-216 | F | Cl | C—F | Cl | CF3 | H | H | 2,2,2-trifluoroethyl | |
| A3-217 | F | Cl | C—F | Cl | CF3 | H | H | 2-methoxyethyl | |
| A3-218 | F | Cl | C—F | Cl | CF3 | H | H | (methylsulfanyl)methyl | |
| A3-219 | F | Cl | C—F | Cl | CF3 | H | H | (methylsulfinyl)methyl | |
| A3-220 | F | Cl | C—F | Cl | CF3 | H | H | (methylsulfonyl)methyl | |
| A3-221 | H | CF3 | C—H | H | CF3 | H | H | CH₃ | |
| A3-222 | H | CF3 | C—H | H | CF3 | H | H | ethyl | |
| A3-223 | H | CF3 | C—H | H | CF3 | H | H | n-propyl | |
| A3-224 | H | CF3 | C—H | H | CF3 | H | H | isopropyl | |
| A3-225 | H | CF3 | C—H | H | CF3 | H | H | cyclopropyl | |
| A3-226 | H | CF3 | C—H | H | CF3 | H | H | cyclopropylmethyl | |
| A3-227 | H | CF3 | C—H | H | CF3 | H | H | 2,2,2-trifluoroethyl | |
| A3-228 | H | CF3 | C—H | H | CF3 | H | H | 2-methoxyethyl | |
| A3-229 | H | CF3 | C—H | H | CF3 | H | H | (methylsulfanyl)methyl | |
| A3-230 | H | CF3 | C—H | H | CF3 | H | H | (methylsulfinyl)methyl | |
| A3-231 | H | CF3 | C—H | H | CF3 | H | H | (methylsulfonyl)methyl | |
| A3-232 | H | CF3 | C—F | H | CF3 | H | H | CH₃ | |
| A3-233 | H | CF3 | C—F | H | CF3 | H | H | ethyl | |
| A3-234 | H | CF3 | C—F | H | CF3 | H | H | n-propyl | |
| A3-235 | H | CF3 | C—F | H | CF3 | H | H | isopropyl | |
| A3-236 | H | CF3 | C—F | H | CF3 | H | H | cyclopropyl | |
| A3-237 | H | CF3 | C—F | H | CF3 | H | H | cyclopropylmethyl | |
| A3-238 | H | CF3 | C—F | H | CF3 | H | H | 2,2,2-trifluoroethyl | |
| A3-239 | H | CF3 | C—F | H | CF3 | H | H | 2-methoxyethyl | |
| A3-240 | H | CF3 | C—F | H | CF3 | H | H | (methylsulfanyl)methyl | |
| A3-241 | H | CF3 | C—F | H | CF3 | H | H | (methylsulfinyl)methyl | |
| A3-242 | H | CF3 | C—F | H | CF3 | H | H | (methylsulfonyl)methyl | |
| A3-243 | H | CF3 | C—H | F | CF3 | H | H | CH₃ | |
| A3-244 | H | CF3 | C—H | F | CF3 | H | H | ethyl | |
| A3-245 | H | CF3 | C—H | F | CF3 | H | H | n-propyl | |
| A3-246 | H | CF3 | C—H | F | CF3 | H | H | isopropyl | |
| A3-247 | H | CF3 | C—H | F | CF3 | H | H | cyclopropyl | |
| A3-248 | H | CF3 | C—H | F | CF3 | H | H | cyclopropylmethyl | |
| A3-249 | H | CF3 | C—H | F | CF3 | H | H | 2,2,2-trifluoroethyl | |
| A3-250 | H | CF3 | C—H | F | CF3 | H | H | 2-methoxyethyl | |
| A3-251 | H | CF3 | C—H | F | CF3 | H | H | (methylsulfanyl)methyl | |
| A3-252 | H | CF3 | C—H | F | CF3 | H | H | (methylsulfinyl)methyl | |
| A3-253 | H | CF3 | C—H | F | CF3 | H | H | (methylsulfonyl)methyl | |
| A3-254 | H | CF3 | C—Cl | H | CF3 | H | H | CH₃ | |
| A3-255 | H | CF3 | C—Cl | H | CF3 | H | H | ethyl | |
| A3-256 | H | CF3 | C—Cl | H | CF3 | H | H | n-propyl | |
| A3-257 | H | CF3 | C—Cl | H | CF3 | H | H | isopropyl | |
| A3-258 | H | CF3 | C—Cl | H | CF3 | H | H | cyclopropyl | |
| A3-259 | H | CF3 | C—Cl | H | CF3 | H | H | cyclopropylmethyl | |
| A3-260 | H | CF3 | C—Cl | H | CF3 | H | H | 2,2,2-trifluoroethyl | |
| A3-261 | H | CF3 | C—Cl | H | CF3 | H | H | 2-methoxyethyl | |
| A3-262 | H | CF3 | C—Cl | H | CF3 | H | H | (methylsulfanyl)methyl | |
| A3-263 | H | CF3 | C—Cl | H | CF3 | H | H | (methylsulfinyl)methyl | |
| A3-264 | H | CF3 | C—Cl | H | CF3 | H | H | (methylsulfonyl)methyl | |
| A3-265 | H | CF3 | C—H | Cl | CF3 | H | H | CH₃ | |
| A3-266 | H | CF3 | C—H | Cl | CF3 | H | H | ethyl | |
| A3-267 | H | CF3 | C—H | Cl | CF3 | H | H | n-propyl | |
| A3-268 | H | CF3 | C—H | Cl | CF3 | H | H | isopropyl | |
| A3-269 | H | CF3 | C—H | Cl | CF3 | H | H | cyclopropyl | |
| A3-270 | H | CF3 | C—H | Cl | CF3 | H | H | cyclopropylmethyl | |
| A3-271 | H | CF3 | C—H | Cl | CF3 | H | H | 2,2,2-trifluoroethyl | |
| A3-272 | H | CF3 | C—H | Cl | CF3 | H | H | 2-methoxyethyl | |
| A3-273 | H | CF3 | C—H | Cl | CF3 | H | H | (methylsulfanyl)methyl | |
| A3-274 | H | CF3 | C—H | Cl | CF3 | H | H | (methylsulfinyl)methyl | |
| A3-275 | H | CF3 | C—H | Cl | CF3 | H | H | (methylsulfonyl)methyl | |
| A3-276 | H | CF3 | C—Cl | Cl | CF3 | H | H | CH₃ | |

TABLE A3-continued

Compounds according to the invention

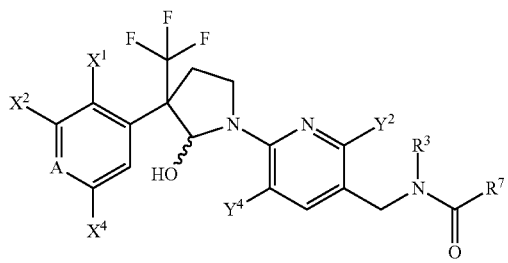

| Ex. No. | X¹ | X² | A | X⁴ | Y² | Y⁴ | R³ | R⁷ | logP |
|---|---|---|---|---|---|---|---|---|---|
| A3-277 | H | CF3 | C—Cl | Cl | CF3 | H | H | ethyl | |
| A3-278 | H | CF3 | C—Cl | Cl | CF3 | H | H | n-propyl | |
| A3-279 | H | CF3 | C—Cl | Cl | CF3 | H | H | isopropyl | |
| A3-280 | H | CF3 | C—Cl | Cl | CF3 | H | H | cyclopropyl | |
| A3-281 | H | CF3 | C—Cl | Cl | CF3 | H | H | cyclopropylmethyl | |
| A3-282 | H | CF3 | C—Cl | Cl | CF3 | H | H | 2,2,2-trifluoroethyl | |
| A3-283 | H | CF3 | C—Cl | Cl | CF3 | H | H | 2-methoxyethyl | |
| A3-284 | H | CF3 | C—Cl | Cl | CF3 | H | H | (methylsulfanyl)methyl | |
| A3-285 | H | CF3 | C—Cl | Cl | CF3 | H | H | (methylsulfinyl)methyl | |
| A3-286 | H | CF3 | C—Cl | Cl | CF3 | H | H | (methylsulfonyl)methyl | |
| A3-287 | H | Cl | C—Cl | Cl | CF3 | H | H | n-butyl | |
| A3-288 | H | Cl | C—Cl | Cl | CF3 | H | H | iso-butyl | |
| A3-289 | H | Cl | C—Cl | Cl | CF3 | H | H | cyclo-butyl | |
| A3-290 | H | Cl | C—Cl | Cl | CF3 | H | H | 2-chloroethyl | |
| A3-291 | H | Cl | C—Cl | Cl | CF3 | H | H | thietan-3-yl | |
| A3-292 | H | Cl | C—Cl | Cl | CF3 | H | H | 1-oxidothietan-3-yl | |
| A3-293 | H | Cl | C—Cl | Cl | CF3 | H | H | 1,1-dioxidothietan-3-yl | |
| A3-294 | H | Cl | C—Cl | Cl | CF3 | H | H | 2,4,6-trifluorophenyl | |
| A3-295 | H | Cl | C—Cl | Cl | CF3 | H | H | methylamino | |
| A3-296 | H | Cl | C—Cl | Cl | CF3 | H | H | dimethylamino | |
| A3-297 | H | Cl | C—Cl | Cl | CF3 | H | H | ethylamino | |
| A3-298 | H | Cl | C—Cl | Cl | CF3 | H | H | cyclopropylamino | |
| A3-299 | H | Cl | C—Cl | Cl | CF3 | H | H | prop-2-yn-1-ylamino | |
| A3-300 | H | CF3 | C—H | CF3 | CF3 | H | H | n-butyl | |
| A3-301 | H | CF3 | C—H | CF3 | CF3 | H | H | iso-butyl | |
| A3-302 | H | CF3 | C—H | CF3 | CF3 | H | H | cyclo-butyl | |
| A3-303 | H | CF3 | C—H | CF3 | CF3 | H | H | 2-Chloroethyl | |
| A3-304 | H | CF3 | C—H | CF3 | CF3 | H | H | thietan-3-yl | |
| A3-305 | H | CF3 | C—H | CF3 | CF3 | H | H | 1-oxidothietan-3-yl | |
| A3-306 | H | CF3 | C—H | CF3 | CF3 | H | H | 1,1-dioxidothietan-3-yl | |
| A3-307 | H | CF3 | C—H | CF3 | CF3 | H | H | 2,4,6-trifluorophenyl | |
| A3-308 | H | CF3 | C—H | CF3 | CF3 | H | H | methylamino | |
| A3-309 | H | CF3 | C—H | CF3 | CF3 | H | H | dimethylamino | |
| A3-310 | H | CF3 | C—H | CF3 | CF3 | H | H | ethylamino | |
| A3-311 | H | CF3 | C—H | CF3 | CF3 | H | H | cyclopropylamino | |
| A3-312 | H | CF3 | C—H | CF3 | CF3 | H | H | prop-2-yn-1-ylamino | |
| A3-313 | H | Cl | C—H | Cl | CF3 | H | H | tert-butoxy | |
| A3-314 | H | Cl | C—Cl | Cl | CF3 | H | H | tert-butoxy | |
| A3-315 | H | CF3 | C—H | CF3 | CF3 | H | H | tert-butoxy | |
| A3-316 | H | Cl | C—H | Cl | Cl | H | H | tert-butoxy | |
| A3-317 | H | Cl | C—Cl | Cl | Cl | H | H | tert-butoxy | |
| A3-318 | H | CF3 | C—H | CF3 | Cl | H | H | tert-butoxy | |
| A3-319 | H | Cl | C—H | Cl | Br | H | H | tert-butoxy | |
| A3-320 | H | Cl | C—Cl | Cl | Br | H | H | tert-butoxy | |
| A3-321 | H | CF3 | C—H | CF3 | Br | H | H | tert-butoxy | |
| A3-322 | F | Cl | C—F | Cl | Br | H | H | CH3 | |
| A3-323 | F | Cl | C—F | Cl | Br | H | H | ethyl | |
| A3-324 | F | Cl | C—F | Cl | Br | H | H | n-propyl | |
| A3-325 | F | Cl | C—F | Cl | Br | H | H | isopropyl | |
| A3-326 | F | Cl | C—F | Cl | Br | H | H | cyclopropyl | |
| A3-327 | F | Cl | C—F | Cl | Br | H | H | cyclopropylmethyl | |
| A3-328 | F | Cl | C—F | Cl | Br | H | H | 2,2,2-trifluoroethyl | |
| A3-329 | F | Cl | C—F | Cl | Br | H | H | 2-methoxyethyl | |
| A3-330 | F | Cl | C—F | Cl | Br | H | H | (methylsulfanyl)methyl | |
| A3-331 | F | Cl | C—F | Cl | Br | H | H | (methylsulfinyl)methyl | |
| A3-332 | F | Cl | C—F | Cl | Br | H | H | (methylsulfonyl)methyl | |
| A3-333 | F | Cl | C—H | Cl | Br | H | H | CH3 | |
| A3-334 | F | Cl | C—H | Cl | Br | H | H | ethyl | |
| A3-335 | F | Cl | C—H | Cl | Br | H | H | n-propyl | |
| A3-336 | F | Cl | C—H | Cl | Br | H | H | isopropyl | |
| A3-337 | F | Cl | C—H | Cl | Br | H | H | cyclopropyl | |
| A3-338 | F | Cl | C—H | Cl | Br | H | H | cyclopropylmethyl | |
| A3-339 | F | Cl | C—H | Cl | Br | H | H | 2,2,2-trifluoroethyl | |

TABLE A3-continued

Compounds according to the invention

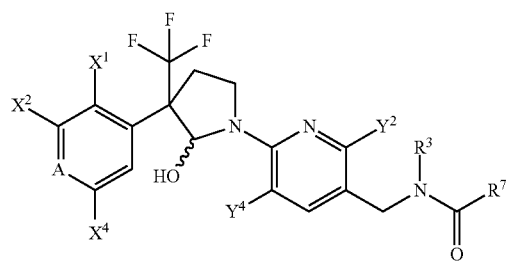

| Ex. No. | X¹ | X² | A | X⁴ | Y² | Y⁴ | R³ | R⁷ | logP |
|---|---|---|---|---|---|---|---|---|---|
| A3-340 | F | Cl | C—H | Cl | Br | H | H | 2-methoxyethyl | |
| A3-341 | F | Cl | C—H | Cl | Br | H | H | (methylsulfanyl)methyl | |
| A3-342 | F | Cl | C—H | Cl | Br | H | H | (methylsulfinyl)methyl | |
| A3-343 | F | Cl | C—H | Cl | Br | H | H | (methylsulfonyl)methyl | |
| A3-344 | F | Cl | C—H | Cl | CF3 | H | H | CH3 | |
| A3-345 | F | Cl | C—H | Cl | CF3 | H | H | ethyl | |
| A3-346 | F | Cl | C—H | Cl | CF3 | H | H | n-propyl | |
| A3-347 | F | Cl | C—H | Cl | CF3 | H | H | isopropyl | |
| A3-348 | F | Cl | C—H | Cl | CF3 | H | H | cyclopropyl | |
| A3-349 | F | Cl | C—H | Cl | CF3 | H | H | cyclopropylmethyl | |
| A3-350 | F | Cl | C—H | Cl | CF3 | H | H | 2,2,2-trifluoroethyl | |
| A3-351 | F | Cl | C—H | Cl | CF3 | H | H | 2-methoxyethyl | |
| A3-352 | F | Cl | C—H | Cl | CF3 | H | H | (methylsulfanyl)methyl | |
| A3-353 | F | Cl | C—H | Cl | CF3 | H | H | (methylsulfinyl)methyl | |
| A3-354 | F | Cl | C—H | Cl | CF3 | H | H | (methylsulfonyl)methyl | |
| A3-355 | H | Cl | C—H | Cl | Cl | F | H | CH₃ | |
| A3-356 | H | Cl | C—H | Cl | Cl | F | H | ethyl | 3.86 |
| A3-357 | H | Cl | C—H | Cl | Cl | F | H | n-propyl | |
| A3-358 | H | Cl | C—H | Cl | Cl | F | H | isopropyl | |
| A3-359 | H | Cl | C—H | Cl | Cl | F | H | cyclopropyl | |
| A3-360 | H | Cl | C—H | Cl | Cl | F | H | cyclopropylmethyl | |
| A3-361 | H | Cl | C—H | Cl | Cl | F | H | 2,2,2-trifluoroethyl | |
| A3-362 | H | Cl | C—H | Cl | Cl | F | H | 2-methoxyethyl | |
| A3-363 | H | Cl | C—H | Cl | Cl | F | H | (methylsulfanyl)methyl | |
| A3-364 | H | Cl | C—H | Cl | Cl | F | H | (methylsulfinyl)methyl | |
| A3-365 | H | Cl | C—H | Cl | Cl | F | H | (methylsulfonyl)methyl | |
| A3-366 | H | Cl | C—Cl | Cl | Cl | F | H | CH₃ | |
| A3-367 | H | Cl | C—Cl | Cl | Cl | F | H | ethyl | |
| A3-368 | H | Cl | C—Cl | Cl | Cl | F | H | n-propyl | |
| A3-369 | H | Cl | C—Cl | Cl | Cl | F | H | isopropyl | |
| A3-370 | H | Cl | C—Cl | Cl | Cl | F | H | cyclopropyl | |
| A3-371 | H | Cl | C—Cl | Cl | Cl | F | H | cyclopropylmethyl | |
| A3-372 | H | Cl | C—Cl | Cl | Cl | F | H | 2,2,2-trifluoroethyl | |
| A3-373 | H | Cl | C—Cl | Cl | Cl | F | H | 2-methoxyethyl | |
| A3-374 | H | Cl | C—Cl | Cl | Cl | F | H | (methylsulfanyl)methyl | |
| A3-375 | H | Cl | C—Cl | Cl | Cl | F | H | (methylsulfinyl)methyl | |
| A3-376 | H | Cl | C—Cl | Cl | Cl | F | H | (methylsulfonyl)methyl | |
| A3-377 | H | CF3 | C—H | CF3 | Cl | F | H | CH₃ | |
| A3-378 | H | CF3 | C—H | CF3 | Cl | F | H | ethyl | |
| A3-379 | H | CF3 | C—H | CF3 | Cl | F | H | n-propyl | |
| A3-380 | H | CF3 | C—H | CF3 | Cl | F | H | isopropyl | |
| A3-381 | H | CF3 | C—H | CF3 | Cl | F | H | cyclopropyl | |
| A3-382 | H | CF3 | C—H | CF3 | Cl | F | H | cyclopropylmethyl | |
| A3-383 | H | CF3 | C—H | CF3 | Cl | F | H | 2,2,2-trifluoroethyl | |
| A3-384 | H | CF3 | C—H | CF3 | Cl | F | H | 2-methoxyethyl | |
| A3-385 | H | CF3 | C—H | CF3 | Cl | F | H | (methylsulfanyl)methyl | |
| A3-386 | H | CF3 | C—H | CF3 | Cl | F | H | (methylsulfinyl)methyl | |
| A3-387 | H | CF3 | C—H | CF3 | Cl | F | H | (methylsulfonyl)methyl | |
| A3-388 | H | Cl | C—Cl | Cl | methoxy | H | H | CH₃ | |
| A3-389 | H | Cl | C—Cl | Cl | methoxy | H | H | ethyl | |
| A3-390 | H | Cl | C—Cl | Cl | methoxy | H | H | n-propyl | |
| A3-391 | H | Cl | C—Cl | Cl | methoxy | H | H | isopropyl | |
| A3-392 | H | Cl | C—Cl | Cl | methoxy | H | H | cyclopropyl | |
| A3-393 | H | Cl | C—Cl | Cl | methoxy | H | H | cyclopropylmethyl | |
| A3-394 | H | Cl | C—Cl | Cl | methoxy | H | H | 2,2,2-trifluoroethyl | |
| A3-395 | H | Cl | C—Cl | Cl | methoxy | H | H | 2-methoxyethyl | |
| A3-396 | H | Cl | C—Cl | Cl | methoxy | H | H | (methylsulfanyl)methyl | |
| A3-397 | H | Cl | C—Cl | Cl | methoxy | H | H | (methylsulfinyl)methyl | |
| A3-398 | H | Cl | C—Cl | Cl | methoxy | H | H | (methylsulfonyl)methyl | |
| A3-399 | H | Cl | C—Cl | Cl | difluoromethoxy | H | H | CH₃ | |
| A3-400 | H | Cl | C—Cl | Cl | difluoromethoxy | H | H | ethyl | |
| A3-401 | H | Cl | C—Cl | Cl | difluoromethoxy | H | H | n-propyl | |
| A3-402 | H | Cl | C—Cl | Cl | difluoromethoxy | H | H | isopropyl | |

TABLE A3-continued

Compounds according to the invention

| Ex. No. | X¹ | X² | A | X⁴ | Y² | Y⁴ | R³ | R⁷ | logP |
|---|---|---|---|---|---|---|---|---|---|
| A3-403 | H | Cl | C—Cl | Cl | difluoromethoxy | H | H | cyclopropyl | |
| A3-404 | H | Cl | C—Cl | Cl | difluoromethoxy | H | H | cyclopropylmethyl | |
| A3-405 | H | Cl | C—Cl | Cl | difluoromethoxy | H | H | 2,2,2-trifluoroethyl | |
| A3-406 | H | Cl | C—Cl | Cl | difluoromethoxy | H | H | 2-methoxyethyl | |
| A3-407 | H | Cl | C—Cl | Cl | difluoromethoxy | H | H | (methylsulfanyl)methyl | |
| A3-408 | H | Cl | C—Cl | Cl | difluoromethoxy | H | H | (methylsulfinyl)methyl | |
| A3-409 | H | Cl | C—Cl | Cl | difluoromethoxy | H | H | (methylsulfonyl)methyl | |
| A3-410 | H | Cl | C—Cl | Cl | trifluoromethoxy | H | H | CH₃ | |
| A3-411 | H | Cl | C—Cl | Cl | trifluoromethoxy | H | H | ethyl | |
| A3-412 | H | Cl | C—Cl | Cl | trifluoromethoxy | H | H | n-propyl | |
| A3-413 | H | Cl | C—Cl | Cl | trifluoromethoxy | H | H | isopropyl | |
| A3-414 | H | Cl | C—Cl | Cl | trifluoromethoxy | H | H | cyclopropyl | |
| A3-415 | H | Cl | C—Cl | Cl | trifluoromethoxy | H | H | cyclopropylmethyl | |
| A3-416 | H | Cl | C—Cl | Cl | trifluoromethoxy | H | H | 2,2,2-trifluoroethyl | |
| A3-417 | H | Cl | C—Cl | Cl | trifluoromethoxy | H | H | 2-methoxyethyl | |
| A3-418 | H | Cl | C—Cl | Cl | trifluoromethoxy | H | H | (methylsulfanyl)methyl | |
| A3-419 | H | Cl | C—Cl | Cl | trifluoromethoxy | H | H | (methylsulfinyl)methyl | |
| A3-420 | H | Cl | C—Cl | Cl | trifluoromethoxy | H | H | (methylsulfonyl)methyl | |
| A3-421 | H | Cl | C—Cl | Cl | CF3 | H | H | cyanomethyl | |
| A3-422 | F | Cl | C—F | Cl | CF3 | H | H | cyanomethyl | |
| A3-423 | H | Cl | C—Cl | Cl | CF3 | H | methyl | cyclopropyl | |
| A3-424 | H | Cl | C—Cl | Cl | CF3 | H | prop-1-en-2-yl | cyclopropyl | |

TABLE A4

Compounds according to the invention

| Ex. No. | X¹ | X² | A | X⁴ | Y² | R³ | R⁷ |
|---|---|---|---|---|---|---|---|
| A4-1 | H | Cl | C—H | Cl | CF3 | H | CH₃ |
| A4-2 | H | Cl | C—H | Cl | CF3 | H | ethyl |
| A4-3 | H | Cl | C—H | Cl | CF3 | H | n-propyl |
| A4-4 | H | Cl | C—H | Cl | CF3 | H | isopropyl |
| A4-5 | H | Cl | C—H | Cl | CF3 | H | cyclopropyl |
| A4-6 | H | Cl | C—H | Cl | CF3 | H | cyclopropylmethyl |
| A4-7 | H | Cl | C—H | Cl | CF3 | H | 2,2,2-trifluoroethyl |
| A4-8 | H | Cl | C—H | Cl | CF3 | H | 2-methoxyethyl |
| A4-9 | H | Cl | C—H | Cl | CF3 | H | (methylsulfanyl)methyl |
| A4-10 | H | Cl | C—H | Cl | CF3 | H | (methylsulfinyl)methyl |
| A4-11 | H | Cl | C—H | Cl | CF3 | H | (methylsulfonyl)methyl |
| A4-12 | H | Cl | C—Cl | Cl | CF3 | H | CH₃ |
| A4-13 | H | Cl | C—Cl | Cl | CF3 | H | ethyl |
| A4-14 | H | Cl | C—Cl | Cl | CF3 | H | n-propyl |
| A4-15 | H | Cl | C—Cl | Cl | CF3 | H | isopropyl |
| A4-16 | H | Cl | C—Cl | Cl | CF3 | H | cyclopropyl |
| A4-17 | H | Cl | C—Cl | Cl | CF3 | H | cyclopropylmethyl |
| A4-18 | H | Cl | C—Cl | Cl | CF3 | H | 2,2,2-trifluoroethyl |
| A4-19 | H | Cl | C—Cl | Cl | CF3 | H | 2-methoxyethyl |
| A4-20 | H | Cl | C—Cl | Cl | CF3 | H | (methylsulfanyl)methyl |

TABLE A4-continued

Compounds according to the invention

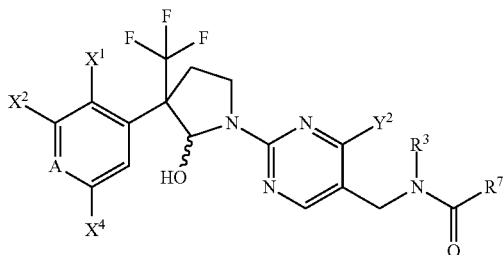

| Ex. No. | X$^1$ | X$^2$ | A | X$^4$ | Y$^2$ | R$^3$ | R$^7$ |
|---|---|---|---|---|---|---|---|
| A4-21 | H | Cl | C—Cl | Cl | CF3 | H | (methylsulfinyl)methyl |
| A4-22 | H | Cl | C—Cl | Cl | CF3 | H | (methylsulfonyl)methyl |
| A4-23 | H | CF3 | C—H | CF3 | CF3 | H | CH$_3$ |
| A4-24 | H | CF3 | C—H | CF3 | CF3 | H | ethyl |
| A4-25 | H | CF3 | C—H | CF3 | CF3 | H | n-propyl |
| A4-26 | H | CF3 | C—H | CF3 | CF3 | H | isopropyl |
| A4-27 | H | CF3 | C—H | CF3 | CF3 | H | cyclopropyl |
| A4-28 | H | CF3 | C—H | CF3 | CF3 | H | cyclopropylmethyl |
| A4-29 | H | CF3 | C—H | CF3 | CF3 | H | 2,2,2-trifluoroethyl |
| A4-30 | H | CF3 | C—H | CF3 | CF3 | H | 2-methoxyethyl |
| A4-31 | H | CF3 | C—H | CF3 | CF3 | H | (methylsulfanyl)methyl |
| A4-32 | H | CF3 | C—H | CF3 | CF3 | H | (methylsulfinyl)methyl |
| A4-33 | H | CF3 | C—H | CF3 | CF3 | H | (methylsulfonyl)methyl |
| A4-34 | H | Cl | C—H | Cl | CH$_3$ | H | CH$_3$ |
| A4-35 | H | Cl | C—H | Cl | CH$_3$ | H | ethyl |
| A4-36 | H | Cl | C—H | Cl | CH$_3$ | H | n-propyl |
| A4-37 | H | Cl | C—H | Cl | CH$_3$ | H | isopropyl |
| A4-38 | H | Cl | C—H | Cl | CH$_3$ | H | cyclopropyl |
| A4-39 | H | Cl | C—H | Cl | CH$_3$ | H | cyclopropylmethyl |
| A4-40 | H | Cl | C—H | Cl | CH$_3$ | H | 2,2,2-trifluoroethyl |
| A4-41 | H | Cl | C—H | Cl | CH$_3$ | H | 2-methoxyethyl |
| A4-42 | H | Cl | C—H | Cl | CH$_3$ | H | (methylsulfanyl)methyl |
| A4-43 | H | Cl | C—H | Cl | CH$_3$ | H | (methylsulfinyl)methyl |
| A4-44 | H | Cl | C—H | Cl | CH$_3$ | H | (methylsulfonyl)methyl |
| A4-45 | H | Cl | C—Cl | Cl | CH$_3$ | H | CH$_3$ |
| A4-46 | H | Cl | C—Cl | Cl | CH$_3$ | H | ethyl |
| A4-47 | H | Cl | C—Cl | Cl | CH$_3$ | H | n-propyl |
| A4-48 | H | Cl | C—Cl | Cl | CH$_3$ | H | isopropyl |
| A4-49 | H | Cl | C—Cl | Cl | CH$_3$ | H | cyclopropyl |
| A4-50 | H | Cl | C—Cl | Cl | CH$_3$ | H | cyclopropylmethyl |
| A4-51 | H | Cl | C—Cl | Cl | CH$_3$ | H | 2,2,2-trifluoroethyl |
| A4-52 | H | Cl | C—Cl | Cl | CH$_3$ | H | 2-methoxyethyl |
| A4-53 | H | Cl | C—Cl | Cl | CH$_3$ | H | (methylsulfanyl)methyl |
| A4-54 | H | Cl | C—Cl | Cl | CH$_3$ | H | (methylsulfinyl)methyl |
| A4-55 | H | Cl | C—Cl | Cl | CH$_3$ | H | (methylsulfonyl)methyl |
| A4-56 | H | CF3 | C—H | CF3 | CH$_3$ | H | CH$_3$ |
| A4-57 | H | CF3 | C—H | CF3 | CH$_3$ | H | ethyl |
| A4-58 | H | CF3 | C—H | CF3 | CH$_3$ | H | n-propyl |
| A4-59 | H | CF3 | C—H | CF3 | CH$_3$ | H | isopropyl |
| A4-60 | H | CF3 | C—H | CF3 | CH$_3$ | H | cyclopropyl |
| A4-61 | H | CF3 | C—H | CF3 | CH$_3$ | H | cyclopropylmethyl |
| A4-62 | H | CF3 | C—H | CF3 | CH$_3$ | H | 2,2,2-trifluoroethyl |
| A4-63 | H | CF3 | C—H | CF3 | CH$_3$ | H | 2-methoxyethyl |
| A4-64 | H | CF3 | C—H | CF3 | CH$_3$ | H | (methylsulfanyl)methyl |
| A4-65 | H | CF3 | C—H | CF3 | CH$_3$ | H | (methylsulfinyl)methyl |
| A4-66 | H | CF3 | C—H | CF3 | CH$_3$ | H | (methylsulfonyl)methyl |
| A4-67 | H | F | C—H | Cl | CF3 | H | CH$_3$ |
| A4-68 | H | F | C—H | Cl | CF3 | H | ethyl |
| A4-69 | H | F | C—H | Cl | CF3 | H | n-propyl |
| A4-70 | H | F | C—H | Cl | CF3 | H | isopropyl |
| A4-71 | H | F | C—H | Cl | CF3 | H | cyclopropyl |
| A4-72 | H | F | C—H | Cl | CF3 | H | cyclopropylmethyl |
| A4-73 | H | F | C—H | Cl | CF3 | H | 2,2,2-trifluoroethyl |
| A4-74 | H | F | C—H | Cl | CF3 | H | 2-methoxyethyl |
| A4-75 | H | F | C—H | Cl | CF3 | H | (methylsulfanyl)methyl |
| A4-76 | H | F | C—H | Cl | CF3 | H | (methylsulfinyl)methyl |
| A4-77 | H | F | C—H | Cl | CF3 | H | (methylsulfonyl)methyl |
| A4-78 | H | Br | C—H | Br | CF3 | H | CH$_3$ |
| A4-79 | H | Br | C—H | Br | CF3 | H | ethyl |
| A4-80 | H | Br | C—H | Br | CF3 | H | n-propyl |
| A4-81 | H | Br | C—H | Br | CF3 | H | isopropyl |
| A4-82 | H | Br | C—H | Br | CF3 | H | cyclopropyl |
| A4-83 | H | Br | C—H | Br | CF3 | H | cyclopropylmethyl |

TABLE A4-continued

Compounds according to the invention

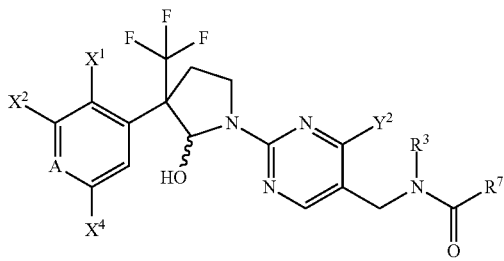

| Ex. No. | $X^1$ | $X^2$ | A | $X^4$ | $Y^2$ | $R^3$ | $R^7$ |
|---|---|---|---|---|---|---|---|
| A4-84 | H | Br | C—H | Br | CF3 | H | 2,2,2-trifluoroethyl |
| A4-85 | H | Br | C—H | Br | CF3 | H | 2-methoxyethyl |
| A4-86 | H | Br | C—H | Br | CF3 | H | (methylsulfanyl)methyl |
| A4-87 | H | Br | C—H | Br | CF3 | H | (methylsulfinyl)methyl |
| A4-88 | H | Br | C—H | Br | CF3 | H | (methylsulfonyl)methyl |
| A4-89 | H | F | C—F | F | CF3 | H | $CH_3$ |
| A4-90 | H | F | C—F | F | CF3 | H | ethyl |
| A4-91 | H | F | C—F | F | CF3 | H | n-propyl |
| A4-92 | H | F | C—F | F | CF3 | H | isopropyl |
| A4-93 | H | F | C—F | F | CF3 | H | cyclopropyl |
| A4-94 | H | F | C—F | F | CF3 | H | cyclopropylmethyl |
| A4-95 | H | F | C—F | F | CF3 | H | 2,2,2-trifluoroethyl |
| A4-96 | H | F | C—F | F | CF3 | H | 2-methoxyethyl |
| A4-97 | H | F | C—F | F | CF3 | H | (methylsulfanyl)methyl |
| A4-98 | H | F | C—F | F | CF3 | H | (methylsulfinyl)methyl |
| A4-99 | H | F | C—F | F | CF3 | H | (methylsulfonyl)methyl |
| A4-100 | H | Cl | C—F | Cl | CF3 | H | $CH_3$ |
| A4-101 | H | Cl | C—F | Cl | CF3 | H | ethyl |
| A4-102 | H | Cl | C—F | Cl | CF3 | H | n-propyl |
| A4-103 | H | Cl | C—F | Cl | CF3 | H | isopropyl |
| A4-104 | H | Cl | C—F | Cl | CF3 | H | cyclopropyl |
| A4-105 | H | Cl | C—F | Cl | CF3 | H | cyclopropylmethyl |
| A4-106 | H | Cl | C—F | Cl | CF3 | H | 2,2,2-trifluoroethyl |
| A4-107 | H | Cl | C—F | Cl | CF3 | H | 2-methoxyethyl |
| A4-108 | H | Cl | C—F | Cl | CF3 | H | (methylsulfanyl)methyl |
| A4-109 | H | Cl | C—F | Cl | CF3 | H | (methylsulfinyl)methyl |
| A4-110 | H | Cl | C—F | Cl | CF3 | H | (methylsulfonyl)methyl |
| A4-111 | F | Cl | C—F | Cl | CF3 | H | $CH_3$ |
| A4-112 | F | Cl | C—F | Cl | CF3 | H | ethyl |
| A4-113 | F | Cl | C—F | Cl | CF3 | H | n-propyl |
| A4-114 | F | Cl | C—F | Cl | CF3 | H | isopropyl |
| A4-115 | F | Cl | C—F | Cl | CF3 | H | cyclopropyl |
| A4-116 | F | Cl | C—F | Cl | CF3 | H | cyclopropylmethyl |
| A4-117 | F | Cl | C—F | Cl | CF3 | H | 2,2,2-trifluoroethyl |
| A4-118 | F | Cl | C—F | Cl | CF3 | H | 2-methoxyethyl |
| A4-119 | F | Cl | C—F | Cl | CF3 | H | (methylsulfanyl)methyl |
| A4-120 | F | Cl | C—F | Cl | CF3 | H | (methylsulfinyl)methyl |
| A4-121 | F | Cl | C—F | Cl | CF3 | H | (methylsulfonyl)methyl |
| A4-122 | H | CF3 | C—H | H | CF3 | H | $CH_3$ |
| A4-123 | H | CF3 | C—H | H | CF3 | H | ethyl |
| A4-124 | H | CF3 | C—H | H | CF3 | H | n-propyl |
| A4-125 | H | CF3 | C—H | H | CF3 | H | isopropyl |
| A4-126 | H | CF3 | C—H | H | CF3 | H | cyclopropyl |
| A4-127 | H | CF3 | C—H | H | CF3 | H | cyclopropylmethyl |
| A4-128 | H | CF3 | C—H | H | CF3 | H | 2,2,2-trifluoroethyl |
| A4-129 | H | CF3 | C—H | H | CF3 | H | 2-methoxyethyl |
| A4-130 | H | CF3 | C—H | H | CF3 | H | (methylsulfanyl)methyl |
| A4-131 | H | CF3 | C—H | H | CF3 | H | (methylsulfinyl)methyl |
| A4-132 | H | CF3 | C—H | H | CF3 | H | (methylsulfonyl)methyl |
| A4-133 | H | CF3 | C—F | H | CF3 | H | $CH_3$ |
| A4-134 | H | CF3 | C—F | H | CF3 | H | ethyl |
| A4-135 | H | CF3 | C—F | H | CF3 | H | n-propyl |
| A4-136 | H | CF3 | C—F | H | CF3 | H | isopropyl |
| A4-137 | H | CF3 | C—F | H | CF3 | H | cyclopropyl |
| A4-138 | H | CF3 | C—F | H | CF3 | H | cyclopropylmethyl |
| A4-139 | H | CF3 | C—F | H | CF3 | H | 2,2,2-trifluoroethyl |
| A4-140 | H | CF3 | C—F | H | CF3 | H | 2-methoxyethyl |
| A4-141 | H | CF3 | C—F | H | CF3 | H | (methylsulfanyl)methyl |
| A4-142 | H | CF3 | C—F | H | CF3 | H | (methylsulfinyl)methyl |
| A4-143 | H | CF3 | C—F | H | CF3 | H | (methylsulfonyl)methyl |
| A4-144 | H | CF3 | C—H | F | CF3 | H | $CH_3$ |
| A4-145 | H | CF3 | C—H | F | CF3 | H | ethyl |
| A4-146 | H | CF3 | C—H | F | CF3 | H | n-propyl |

TABLE A4-continued

Compounds according to the invention

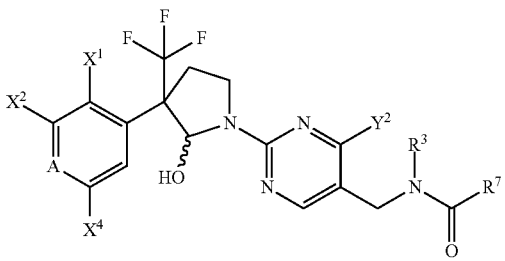

| Ex. No. | X¹ | X² | A | X⁴ | Y² | R³ | R⁷ |
|---|---|---|---|---|---|---|---|
| A4-147 | H | CF3 | C—H | F | CF3 | H | isopropyl |
| A4-148 | H | CF3 | C—H | F | CF3 | H | cyclopropyl |
| A4-149 | H | CF3 | C—H | F | CF3 | H | cyclopropylmethyl |
| A4-150 | H | CF3 | C—H | F | CF3 | H | 2,2,2-trifluoroethyl |
| A4-151 | H | CF3 | C—H | F | CF3 | H | 2-methoxyethyl |
| A4-152 | H | CF3 | C—H | F | CF3 | H | (methylsulfanyl)methyl |
| A4-153 | H | CF3 | C—H | F | CF3 | H | (methylsulfinyl)methyl |
| A4-154 | H | CF3 | C—H | F | CF3 | H | (methylsulfonyl)methyl |
| A4-155 | H | CF3 | C—Cl | H | CF3 | H | CH₃ |
| A4-156 | H | CF3 | C—Cl | H | CF3 | H | ethyl |
| A4-157 | H | CF3 | C—Cl | H | CF3 | H | n-propyl |
| A4-158 | H | CF3 | C—Cl | H | CF3 | H | isopropyl |
| A4-159 | H | CF3 | C—Cl | H | CF3 | H | cyclopropyl |
| A4-160 | H | CF3 | C—Cl | H | CF3 | H | cyclopropylmethyl |
| A4-161 | H | CF3 | C—Cl | H | CF3 | H | 2,2,2-trifluoroethyl |
| A4-162 | H | CF3 | C—Cl | H | CF3 | H | 2-methoxyethyl |
| A4-163 | H | CF3 | C—Cl | H | CF3 | H | (methylsulfanyl)methyl |
| A4-164 | H | CF3 | C—Cl | H | CF3 | H | (methylsulfinyl)methyl |
| A4-165 | H | CF3 | C—Cl | H | CF3 | H | (methylsulfonyl)methyl |
| A4-166 | H | CF3 | C—H | Cl | CF3 | H | CH₃ |
| A4-167 | H | CF3 | C—H | Cl | CF3 | H | ethyl |
| A4-168 | H | CF3 | C—H | Cl | CF3 | H | n-propyl |
| A4-169 | H | CF3 | C—H | Cl | CF3 | H | isopropyl |
| A4-170 | H | CF3 | C—H | Cl | CF3 | H | cyclopropyl |
| A4-171 | H | CF3 | C—H | Cl | CF3 | H | cyclopropylmethyl |
| A4-172 | H | CF3 | C—H | Cl | CF3 | H | 2,2,2-trifluoroethyl |
| A4-173 | H | CF3 | C—H | Cl | CF3 | H | 2-methoxyethyl |
| A4-174 | H | CF3 | C—H | Cl | CF3 | H | (methylsulfanyl)methyl |
| A4-175 | H | CF3 | C—H | Cl | CF3 | H | (methylsulfinyl)methyl |
| A4-176 | H | CF3 | C—H | Cl | CF3 | H | (methylsulfonyl)methyl |
| A4-177 | H | CF3 | C—Cl | Cl | CF3 | H | CH₃ |
| A4-178 | H | CF3 | C—Cl | Cl | CF3 | H | ethyl |
| A4-179 | H | CF3 | C—Cl | Cl | CF3 | H | n-propyl |
| A4-180 | H | CF3 | C—Cl | Cl | CF3 | H | isopropyl |
| A4-181 | H | CF3 | C—Cl | Cl | CF3 | H | cyclopropyl |
| A4-182 | H | CF3 | C—Cl | Cl | CF3 | H | cyclopropylmethyl |
| A4-183 | H | CF3 | C—Cl | Cl | CF3 | H | 2,2,2-trifluoroethyl |
| A4-184 | H | CF3 | C—Cl | Cl | CF3 | H | 2-methoxyethyl |
| A4-185 | H | CF3 | C—Cl | Cl | CF3 | H | (methylsulfanyl)methyl |
| A4-186 | H | CF3 | C—Cl | Cl | CF3 | H | (methylsulfinyl)methyl |
| A4-187 | H | CF3 | C—Cl | Cl | CF3 | H | (methylsulfonyl)methyl |
| A4-188 | H | Cl | C—Cl | Cl | CF3 | H | n-butyl |
| A4-189 | H | Cl | C—Cl | Cl | CF3 | H | iso-butyl |
| A4-190 | H | Cl | C—Cl | Cl | CF3 | H | cyclo-butyl |
| A4-191 | H | Cl | C—Cl | Cl | CF3 | H | 2-Chloroethyl |
| A4-192 | H | Cl | C—Cl | Cl | CF3 | H | thietan-3-yl |
| A4-193 | H | Cl | C—Cl | Cl | CF3 | H | 1-oxidothietan-3-yl |
| A4-194 | H | Cl | C—Cl | Cl | CF3 | H | 1,1-dioxidothietan-3-yl |
| A4-195 | H | Cl | C—Cl | Cl | CF3 | H | 2,4,6-trifluorophenyl |
| A4-196 | H | Cl | C—Cl | Cl | CF3 | H | methylamino |
| A4-197 | H | Cl | C—Cl | Cl | CF3 | H | dimethylamino |
| A4-198 | H | Cl | C—Cl | Cl | CF3 | H | ethylamino |
| A4-199 | H | Cl | C—Cl | Cl | CF3 | H | cyclopropylamino |
| A4-200 | H | Cl | C—Cl | Cl | CF3 | H | prop-2-yn-1-ylamino |
| A4-201 | H | Cl | C—H | Cl | CF3 | H | (dimethylamino)methyl |
| A4-202 | H | Cl | C—H | Cl | CF3 | H | pyrrolidin-2-yl |
| A4-203 | H | Cl | C—H | Cl | CF3 | H | 1-(tert-butoxycarbonyl)pyrrolidin-2-yl |
| A4-204 | H | Cl | C—H | Cl | difluoromethyl | H | CH₃ |
| A4-205 | H | Cl | C—H | Cl | difluoromethyl | H | ethyl |
| A4-206 | H | Cl | C—H | Cl | difluoromethyl | H | n-propyl |
| A4-207 | H | Cl | C—H | Cl | difluoromethyl | H | isopropyl |
| A4-208 | H | Cl | C—H | Cl | difluoromethyl | H | cyclopropyl |
| A4-209 | H | Cl | C—H | Cl | difluoromethyl | H | cyclopropylmethyl |

TABLE A4-continued

Compounds according to the invention

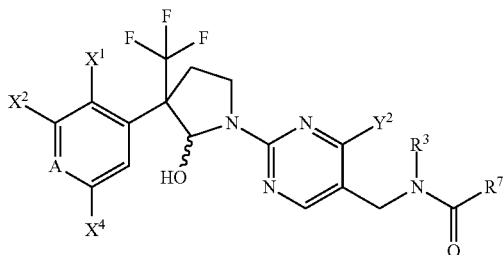

| Ex. No. | X¹ | X² | A | X⁴ | Y² | R³ | R⁷ |
|---|---|---|---|---|---|---|---|
| A4-210 | H | Cl | C—H | Cl | difluoromethyl | H | 2,2,2-trifluoroethyl |
| A4-211 | H | Cl | C—H | Cl | difluoromethyl | H | 2-methoxyethyl |
| A4-212 | H | Cl | C—H | Cl | difluoromethyl | H | (methylsulfanyl)methyl |
| A4-213 | H | Cl | C—H | Cl | difluoromethyl | H | (methylsulfinyl)methyl |
| A4-214 | H | Cl | C—H | Cl | difluoromethyl | H | (methylsulfonyl)methyl |
| A4-215 | H | Cl | C—Cl | Cl | difluoromethyl | H | CH₃ |
| A4-216 | H | Cl | C—Cl | Cl | difluoromethyl | H | ethyl |
| A4-217 | H | Cl | C—Cl | Cl | difluoromethyl | H | n-propyl |
| A4-218 | H | Cl | C—Cl | Cl | difluoromethyl | H | isopropyl |
| A4-219 | H | Cl | C—Cl | Cl | difluoromethyl | H | cyclopropyl |
| A4-220 | H | Cl | C—Cl | Cl | difluoromethyl | H | cyclopropylmethyl |
| A4-221 | H | Cl | C—Cl | Cl | difluoromethyl | H | 2,2,2-trifluoroethyl |
| A4-222 | H | Cl | C—Cl | Cl | difluoromethyl | H | 2-methoxyethyl |
| A4-223 | H | Cl | C—Cl | Cl | difluoromethyl | H | (methylsulfanyl)methyl |
| A4-224 | H | Cl | C—Cl | Cl | difluoromethyl | H | (methylsulfinyl)methyl |
| A4-225 | H | Cl | C—Cl | Cl | difluoromethyl | H | (methylsulfonyl)methyl |
| A4-226 | F | Cl | C—F | Cl | difluoromethyl | H | CH₃ |
| A4-227 | F | Cl | C—F | Cl | difluoromethyl | H | ethyl |
| A4-228 | F | Cl | C—F | Cl | difluoromethyl | H | n-propyl |
| A4-229 | F | Cl | C—F | Cl | difluoromethyl | H | isopropyl |
| A4-230 | F | Cl | C—F | Cl | difluoromethyl | H | cyclopropyl |
| A4-231 | F | Cl | C—F | Cl | difluoromethyl | H | cyclopropylmethyl |
| A4-232 | F | Cl | C—F | Cl | difluoromethyl | H | 2,2,2-trifluoroethyl |
| A4-233 | F | Cl | C—F | Cl | difluoromethyl | H | 2-methoxyethyl |
| A4-234 | F | Cl | C—F | Cl | difluoromethyl | H | (methylsulfanyl)methyl |
| A4-235 | F | Cl | C—F | Cl | difluoromethyl | H | (methylsulfinyl)methyl |
| A4-236 | F | Cl | C—F | Cl | difluoromethyl | H | (methylsulfonyl)methyl |
| A4-237 | H | Cl | C—Cl | Cl | Cl | H | CH₃ |
| A4-238 | H | Cl | C—Cl | Cl | Cl | H | ethyl |
| A4-239 | H | Cl | C—Cl | Cl | Cl | H | n-propyl |
| A4-240 | H | Cl | C—Cl | Cl | Cl | H | isopropyl |
| A4-241 | H | Cl | C—Cl | Cl | Cl | H | cyclopropyl |
| A4-242 | H | Cl | C—Cl | Cl | Cl | H | cyclopropylmethyl |
| A4-243 | H | Cl | C—Cl | Cl | Cl | H | 2,2,2-trifluoroethyl |
| A4-244 | H | Cl | C—Cl | Cl | Cl | H | 2-methoxyethyl |
| A4-245 | H | Cl | C—Cl | Cl | Cl | H | (methylsulfanyl)methyl |
| A4-246 | H | Cl | C—Cl | Cl | Cl | H | (methylsulfinyl)methyl |
| A4-247 | H | Cl | C—Cl | Cl | Cl | H | (methylsulfonyl)methyl |
| A4-248 | H | CF3 | C—H | CF3 | Cl | H | CH₃ |
| A4-249 | H | CF3 | C—H | CF3 | Cl | H | ethyl |
| A4-250 | H | CF3 | C—H | CF3 | Cl | H | n-propyl |
| A4-251 | H | CF3 | C—H | CF3 | Cl | H | isopropyl |
| A4-252 | H | CF3 | C—H | CF3 | Cl | H | cyclopropyl |
| A4-253 | H | CF3 | C—H | CF3 | Cl | H | cyclopropylmethyl |
| A4-254 | H | CF3 | C—H | CF3 | Cl | H | 2,2,2-trifluoroethyl |
| A4-255 | H | CF3 | C—H | CF3 | Cl | H | 2-methoxyethyl |
| A4-256 | H | CF3 | C—H | CF3 | Cl | H | (methylsulfanyl)methyl |
| A4-257 | H | CF3 | C—H | CF3 | Cl | H | (methylsulfinyl)methyl |
| A4-258 | H | CF3 | C—H | CF3 | Cl | H | (methylsulfonyl)methyl |
| A4-259 | H | Cl | C—H | Cl | chloro(difluoro)methyl | H | CH₃ |
| A4-260 | H | Cl | C—H | Cl | chloro(difluoro)methyl | H | ethyl |
| A4-261 | H | Cl | C—H | Cl | chloro(difluoro)methyl | H | n-propyl |
| A4-262 | H | Cl | C—H | Cl | chloro(difluoro)methyl | H | isopropyl |
| A4-263 | H | Cl | C—H | Cl | chloro(difluoro)methyl | H | cyclopropyl |
| A4-264 | H | Cl | C—H | Cl | chloro(difluoro)methyl | H | cyclopropylmethyl |
| A4-265 | H | Cl | C—H | Cl | chloro(difluoro)methyl | H | 2,2,2-trifluoroethyl |
| A4-266 | H | Cl | C—H | Cl | chloro(difluoro)methyl | H | 2-methoxyethyl |
| A4-267 | H | Cl | C—H | Cl | chloro(difluoro)methyl | H | (methylsulfanyl)methyl |
| A4-268 | H | Cl | C—H | Cl | chloro(difluoro)methyl | H | (methylsulfinyl)methyl |
| A4-269 | H | Cl | C—H | Cl | chloro(difluoro)methyl | H | (methylsulfonyl)methyl |
| A4-270 | H | Cl | C—Cl | Cl | chloro(difluoro)methyl | H | CH₃ |
| A4-271 | H | Cl | C—Cl | Cl | chloro(difluoro)methyl | H | ethyl |
| A4-272 | H | Cl | C—Cl | Cl | chloro(difluoro)methyl | H | n-propyl |

TABLE A4-continued

Compounds according to the invention

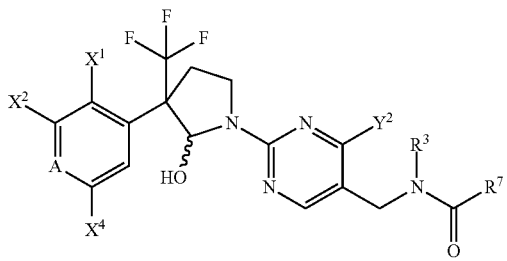

| Ex. No. | X¹ | X² | A | X⁴ | Y² | R³ | R⁷ |
|---|---|---|---|---|---|---|---|
| A4-273 | H | Cl | C—Cl | Cl | chloro(difluoro)methyl | H | isopropyl |
| A4-274 | H | Cl | C—Cl | Cl | chloro(difluoro)methyl | H | cyclopropyl |
| A4-275 | H | Cl | C—Cl | Cl | chloro(difluoro)methyl | H | cyclopropylmethyl |
| A4-276 | H | Cl | C—Cl | Cl | chloro(difluoro)methyl | H | 2,2,2-trifluoroethyl |
| A4-277 | H | Cl | C—Cl | Cl | chloro(difluoro)methyl | H | 2-methoxyethyl |
| A4-278 | H | Cl | C—Cl | Cl | chloro(difluoro)methyl | H | (methylsulfanyl)methyl |
| A4-279 | H | Cl | C—Cl | Cl | chloro(difluoro)methyl | H | (methylsulfinyl)methyl |
| A4-280 | H | Cl | C—Cl | Cl | chloro(difluoro)methyl | H | (methylsulfonyl)methyl |
| A4-281 | F | Cl | C—F | Cl | chloro(difluoro)methyl | H | CH₃ |
| A4-282 | F | Cl | C—F | Cl | chloro(difluoro)methyl | H | ethyl |
| A4-283 | F | Cl | C—F | Cl | chloro(difluoro)methyl | H | n-propyl |
| A4-284 | F | Cl | C—F | Cl | chloro(difluoro)methyl | H | isopropyl |
| A4-285 | F | Cl | C—F | Cl | chloro(difluoro)methyl | H | cyclopropyl |
| A4-286 | F | Cl | C—F | Cl | chloro(difluoro)methyl | H | cyclopropylmethyl |
| A4-287 | F | Cl | C—F | Cl | chloro(difluoro)methyl | H | 2,2,2-trifluoroethyl |
| A4-288 | F | Cl | C—F | Cl | chloro(difluoro)methyl | H | 2-methoxyethyl |
| A4-289 | F | Cl | C—F | Cl | chloro(difluoro)methyl | H | (methylsulfanyl)methyl |
| A4-290 | F | Cl | C—F | Cl | chloro(difluoro)methyl | H | (methylsulfinyl)methyl |
| A4-291 | F | Cl | C—F | Cl | chloro(difluoro)methyl | H | (methylsulfonyl)methyl |
| A4-292 | H | Cl | C—H | Cl | pentafluoroethyl | H | CH₃ |
| A4-293 | H | Cl | C—H | Cl | pentafluoroethyl | H | ethyl |
| A4-294 | H | Cl | C—H | Cl | pentafluoroethyl | H | n-propyl |
| A4-295 | H | Cl | C—H | Cl | pentafluoroethyl | H | isopropyl |
| A4-296 | H | Cl | C—H | Cl | pentafluoroethyl | H | cyclopropyl |
| A4-297 | H | Cl | C—H | Cl | pentafluoroethyl | H | cyclopropylmethyl |
| A4-298 | H | Cl | C—H | Cl | pentafluoroethyl | H | 2,2,2-trifluoroethyl |
| A4-299 | H | Cl | C—H | Cl | pentafluoroethyl | H | 2-methoxyethyl |
| A4-300 | H | Cl | C—H | Cl | pentafluoroethyl | H | (methylsulfanyl)methyl |
| A4-301 | H | Cl | C—H | Cl | pentafluoroethyl | H | (methylsulfinyl)methyl |
| A4-302 | H | Cl | C—H | Cl | pentafluoroethyl | H | (methylsulfonyl)methyl |
| A4-303 | H | Cl | C—Cl | Cl | pentafluoroethyl | H | CH₃ |
| A4-304 | H | Cl | C—Cl | Cl | pentafluoroethyl | H | ethyl |
| A4-305 | H | Cl | C—Cl | Cl | pentafluoroethyl | H | n-propyl |
| A4-306 | H | Cl | C—Cl | Cl | pentafluoroethyl | H | isopropyl |
| A4-307 | H | Cl | C—Cl | Cl | pentafluoroethyl | H | cyclopropyl |
| A4-308 | H | Cl | C—Cl | Cl | pentafluoroethyl | H | cyclopropylmethyl |
| A4-309 | H | Cl | C—Cl | Cl | pentafluoroethyl | H | 2,2,2-trifluoroethyl |
| A4-310 | H | Cl | C—Cl | Cl | pentafluoroethyl | H | 2-methoxyethyl |
| A4-311 | H | Cl | C—Cl | Cl | pentafluoroethyl | H | (methylsulfanyl)methyl |
| A4-312 | H | Cl | C—Cl | Cl | pentafluoroethyl | H | (methylsulfinyl)methyl |
| A4-313 | H | Cl | C—Cl | Cl | pentafluoroethyl | H | (methylsulfonyl)methyl |
| A4-314 | F | Cl | C—F | Cl | pentafluoroethyl | H | CH₃ |
| A4-315 | F | Cl | C—F | Cl | pentafluoroethyl | H | ethyl |
| A4-316 | F | Cl | C—F | Cl | pentafluoroethyl | H | n-propyl |
| A4-317 | F | Cl | C—F | Cl | pentafluoroethyl | H | isopropyl |
| A4-318 | F | Cl | C—F | Cl | pentafluoroethyl | H | cyclopropyl |
| A4-319 | F | Cl | C—F | Cl | pentafluoroethyl | H | cyclopropylmethyl |
| A4-320 | F | Cl | C—F | Cl | pentafluoroethyl | H | 2,2,2-trifluoroethyl |
| A4-321 | F | Cl | C—F | Cl | pentafluoroethyl | H | 2-methoxyethyl |
| A4-322 | F | Cl | C—F | Cl | pentafluoroethyl | H | (methylsulfanyl)methyl |
| A4-323 | F | Cl | C—F | Cl | pentafluoroethyl | H | (methylsulfinyl)methyl |
| A4-324 | F | Cl | C—F | Cl | pentafluoroethyl | H | (methylsulfonyl)methyl |
| A4-325 | H | Cl | C—H | Cl | phenyl | H | CH₃ |
| A4-326 | H | Cl | C—H | Cl | phenyl | H | ethyl |
| A4-327 | H | Cl | C—H | Cl | phenyl | H | n-propyl |
| A4-328 | H | Cl | C—H | Cl | phenyl | H | isopropyl |
| A4-329 | H | Cl | C—H | Cl | phenyl | H | cyclopropyl |
| A4-330 | H | Cl | C—H | Cl | phenyl | H | cyclopropylmethyl |
| A4-331 | H | Cl | C—H | Cl | phenyl | H | 2,2,2-trifluoroethyl |
| A4-332 | H | Cl | C—H | Cl | phenyl | H | 2-methoxyethyl |
| A4-333 | H | Cl | C—H | Cl | phenyl | H | (methylsulfanyl)methyl |
| A4-334 | H | Cl | C—H | Cl | phenyl | H | (methylsulfinyl)methyl |
| A4-335 | H | Cl | C—H | Cl | phenyl | H | (methylsulfonyl)methyl |

TABLE A4-continued

Compounds according to the invention

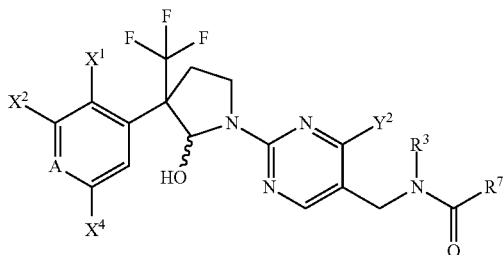

| Ex. No. | X¹ | X² | A | X⁴ | Y² | R³ | R⁷ |
|---|---|---|---|---|---|---|---|
| A4-336 | H | Cl | C—Cl | Cl | phenyl | H | CH₃ |
| A4-337 | H | Cl | C—Cl | Cl | phenyl | H | ethyl |
| A4-338 | H | Cl | C—Cl | Cl | phenyl | H | n-propyl |
| A4-339 | H | Cl | C—Cl | Cl | phenyl | H | isopropyl |
| A4-340 | H | Cl | C—Cl | Cl | phenyl | H | cyclopropyl |
| A4-341 | H | Cl | C—Cl | Cl | phenyl | H | cyclopropylmethyl |
| A4-342 | H | Cl | C—Cl | Cl | phenyl | H | 2,2,2-trifluoroethyl |
| A4-343 | H | Cl | C—Cl | Cl | phenyl | H | 2-methoxyethyl |
| A4-344 | H | Cl | C—Cl | Cl | phenyl | H | (methylsulfanyl)methyl |
| A4-345 | H | Cl | C—Cl | Cl | phenyl | H | (methylsulfinyl)methyl |
| A4-346 | H | Cl | C—Cl | Cl | phenyl | H | (methylsulfonyl)methyl |
| A4-347 | F | Cl | C—F | Cl | phenyl | H | CH₃ |
| A4-348 | F | Cl | C—F | Cl | phenyl | H | ethyl |
| A4-349 | F | Cl | C—F | Cl | phenyl | H | n-propyl |
| A4-350 | F | Cl | C—F | Cl | phenyl | H | isopropyl |
| A4-351 | F | Cl | C—F | Cl | phenyl | H | cyclopropyl |
| A4-352 | F | Cl | C—F | Cl | phenyl | H | cyclopropylmethyl |
| A4-353 | F | Cl | C—F | Cl | phenyl | H | 2,2,2-trifluoroethyl |
| A4-354 | F | Cl | C—F | Cl | phenyl | H | 2-methoxyethyl |
| A4-355 | F | Cl | C—F | Cl | phenyl | H | (methylsulfanyl)methyl |
| A4-356 | F | Cl | C—F | Cl | phenyl | H | (methylsulfinyl)methyl |
| A4-357 | F | Cl | C—F | Cl | phenyl | H | (methylsulfonyl)methyl |
| A4-358 | H | Cl | C—H | Cl | pyrid-2-yl | H | CH₃ |
| A4-359 | H | Cl | C—H | Cl | pyrid-2-yl | H | ethyl |
| A4-360 | H | Cl | C—H | Cl | pyrid-2-yl | H | n-propyl |
| A4-361 | H | Cl | C—H | Cl | pyrid-2-yl | H | isopropyl |
| A4-362 | H | Cl | C—H | Cl | pyrid-2-yl | H | cyclopropyl |
| A4-363 | H | Cl | C—H | Cl | pyrid-2-yl | H | cyclopropylmethyl |
| A4-364 | H | Cl | C—H | Cl | pyrid-2-yl | H | 2,2,2-trifluoroethyl |
| A4-365 | H | Cl | C—H | Cl | pyrid-2-yl | H | 2-methoxyethyl |
| A4-366 | H | Cl | C—H | Cl | pyrid-2-yl | H | (methylsulfanyl)methyl |
| A4-367 | H | Cl | C—H | Cl | pyrid-2-yl | H | (methylsulfinyl)methyl |
| A4-368 | H | Cl | C—H | Cl | pyrid-2-yl | H | (methylsulfonyl)methyl |
| A4-369 | H | Cl | C—Cl | Cl | pyrid-2-yl | H | CH₃ |
| A4-370 | H | Cl | C—Cl | Cl | pyrid-2-yl | H | ethyl |
| A4-371 | H | Cl | C—Cl | Cl | pyrid-2-yl | H | n-propyl |
| A4-372 | H | Cl | C—Cl | Cl | pyrid-2-yl | H | isopropyl |
| A4-373 | H | Cl | C—Cl | Cl | pyrid-2-yl | H | cyclopropyl |
| A4-374 | H | Cl | C—Cl | Cl | pyrid-2-yl | H | cyclopropylmethyl |
| A4-375 | H | Cl | C—Cl | Cl | pyrid-2-yl | H | 2,2,2-trifluoroethyl |
| A4-376 | H | Cl | C—Cl | Cl | pyrid-2-yl | H | 2-methoxyethyl |
| A4-377 | H | Cl | C—Cl | Cl | pyrid-2-yl | H | (methylsulfanyl)methyl |
| A4-378 | H | Cl | C—Cl | Cl | pyrid-2-yl | H | (methylsulfinyl)methyl |
| A4-379 | H | Cl | C—Cl | Cl | pyrid-2-yl | H | (methylsulfonyl)methyl |
| A4-380 | F | Cl | C—F | Cl | pyrid-2-yl | H | CH₃ |
| A4-381 | F | Cl | C—F | Cl | pyrid-2-yl | H | ethyl |
| A4-382 | F | Cl | C—F | Cl | pyrid-2-yl | H | n-propyl |
| A4-383 | F | Cl | C—F | Cl | pyrid-2-yl | H | isopropyl |
| A4-384 | F | Cl | C—F | Cl | pyrid-2-yl | H | cyclopropyl |
| A4-385 | F | Cl | C—F | Cl | pyrid-2-yl | H | cyclopropylmethyl |
| A4-386 | F | Cl | C—F | Cl | pyrid-2-yl | H | 2,2,2-trifluoroethyl |
| A4-387 | F | Cl | C—F | Cl | pyrid-2-yl | H | 2-methoxyethyl |
| A4-388 | F | Cl | C—F | Cl | pyrid-2-yl | H | (methylsulfanyl)methyl |
| A4-389 | F | Cl | C—F | Cl | pyrid-2-yl | H | (methylsulfinyl)methyl |
| A4-390 | F | Cl | C—F | Cl | pyrid-2-yl | H | (methylsulfonyl)methyl |
| A4-391 | H | Cl | C—H | Cl | cyclopropyl | H | CH₃ |
| A4-392 | H | Cl | C—H | Cl | cyclopropyl | H | ethyl |
| A4-393 | H | Cl | C—H | Cl | cyclopropyl | H | n-propyl |
| A4-394 | H | Cl | C—H | Cl | cyclopropyl | H | isopropyl |
| A4-395 | H | Cl | C—H | Cl | cyclopropyl | H | cyclopropyl |
| A4-396 | H | Cl | C—H | Cl | cyclopropyl | H | cyclopropylmethyl |
| A4-397 | H | Cl | C—H | Cl | cyclopropyl | H | 2,2,2-trifluoroethyl |
| A4-398 | H | Cl | C—H | Cl | cyclopropyl | H | 2-methoxyethyl |

TABLE A4-continued

Compounds according to the invention

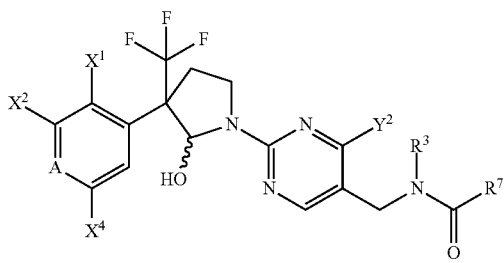

| Ex. No. | X¹ | X² | A | X⁴ | Y² | R³ | R⁷ |
|---|---|---|---|---|---|---|---|
| A4-399 | H | Cl | C—H | Cl | cyclopropyl | H | (methylsulfanyl)methyl |
| A4-400 | H | Cl | C—H | Cl | cyclopropyl | H | (methylsulfinyl)methyl |
| A4-401 | H | Cl | C—H | Cl | cyclopropyl | H | (methylsulfonyl)methyl |
| A4-402 | H | Cl | C—Cl | Cl | cyclopropyl | H | CH₃ |
| A4-403 | H | Cl | C—Cl | Cl | cyclopropyl | H | ethyl |
| A4-404 | H | Cl | C—Cl | Cl | cyclopropyl | H | n-propyl |
| A4-405 | H | Cl | C—Cl | Cl | cyclopropyl | H | isopropyl |
| A4-406 | H | Cl | C—Cl | Cl | cyclopropyl | H | cyclopropyl |
| A4-407 | H | Cl | C—Cl | Cl | cyclopropyl | H | cyclopropylmethyl |
| A4-408 | H | Cl | C—Cl | Cl | cyclopropyl | H | 2,2,2-trifluoroethyl |
| A4-409 | H | Cl | C—Cl | Cl | cyclopropyl | H | 2-methoxyethyl |
| A4-410 | H | Cl | C—Cl | Cl | cyclopropyl | H | (methylsulfanyl)methyl |
| A4-411 | H | Cl | C—Cl | Cl | cyclopropyl | H | (methylsulfinyl)methyl |
| A4-412 | H | Cl | C—Cl | Cl | cyclopropyl | H | (methylsulfonyl)methyl |
| A4-413 | F | Cl | C—F | Cl | cyclopropyl | H | CH₃ |
| A4-414 | F | Cl | C—F | Cl | cyclopropyl | H | ethyl |
| A4-415 | F | Cl | C—F | Cl | cyclopropyl | H | n-propyl |
| A4-416 | F | Cl | C—F | Cl | cyclopropyl | H | isopropyl |
| A4-417 | F | Cl | C—F | Cl | cyclopropyl | H | cyclopropyl |
| A4-418 | F | Cl | C—F | Cl | cyclopropyl | H | cyclopropylmethyl |
| A4-419 | F | Cl | C—F | Cl | cyclopropyl | H | 2,2,2-trifluoroethyl |
| A4-420 | F | Cl | C—F | Cl | cyclopropyl | H | 2-methoxyethyl |
| A4-421 | F | Cl | C—F | Cl | cyclopropyl | H | (methylsulfanyl)methyl |
| A4-422 | F | Cl | C—F | Cl | cyclopropyl | H | (methylsulfinyl)methyl |
| A4-423 | F | Cl | C—F | Cl | cyclopropyl | H | (methylsulfonyl)methyl |
| A4-424 | F | Cl | C—H | Cl | CF3 | H | CH₃ |
| A4-425 | F | Cl | C—H | Cl | CF3 | H | ethyl |
| A4-426 | F | Cl | C—H | Cl | CF3 | H | n-propyl |
| A4-427 | F | Cl | C—H | Cl | CF3 | H | isopropyl |
| A4-428 | F | Cl | C—H | Cl | CF3 | H | cyclopropyl |
| A4-429 | F | Cl | C—H | Cl | CF3 | H | cyclopropylmethyl |
| A4-430 | F | Cl | C—H | Cl | CF3 | H | 2,2,2-trifluoroethyl |
| A4-431 | F | Cl | C—H | Cl | CF3 | H | 2-methoxyethyl |
| A4-432 | F | Cl | C—H | Cl | CF3 | H | (methylsulfanyl)methyl |
| A4-433 | F | Cl | C—H | Cl | CF3 | H | (methylsulfinyl)methyl |
| A4-434 | F | Cl | C—H | Cl | CF3 | H | (methylsulfonyl)methyl |
| A4-435 | H | Cl | C—H | Cl | CF3 | H | cyanomethyl |
| A4-436 | H | Cl | C—Cl | Cl | CF3 | H | cyanomethyl |
| A4-437 | F | Cl | C—F | Cl | CF3 | H | cyanomethyl |
| A4-438 | F | Cl | C—H | Cl | difluoromethyl | H | CH₃ |
| A4-439 | F | Cl | C—H | Cl | difluoromethyl | H | ethyl |
| A4-440 | F | Cl | C—H | Cl | difluoromethyl | H | n-propyl |
| A4-441 | F | Cl | C—H | Cl | difluoromethyl | H | isopropyl |
| A4-442 | F | Cl | C—H | Cl | difluoromethyl | H | cyclopropyl |
| A4-443 | F | Cl | C—H | Cl | difluoromethyl | H | cyclopropylmethyl |
| A4-444 | F | Cl | C—H | Cl | difluoromethyl | H | 2,2,2-trifluoroethyl |
| A4-445 | F | Cl | C—H | Cl | difluoromethyl | H | 2-methoxyethyl |
| A4-446 | F | Cl | C—H | Cl | difluoromethyl | H | (methylsulfanyl)methyl |
| A4-447 | F | Cl | C—H | Cl | difluoromethyl | H | (methylsulfinyl)methyl |
| A4-448 | F | Cl | C—H | Cl | difluoromethyl | H | (methylsulfonyl)methyl |
| A4-449 | F | Cl | C—H | Cl | Cl | H | CH₃ |
| A4-450 | F | Cl | C—H | Cl | Cl | H | ethyl |
| A4-451 | F | Cl | C—H | Cl | Cl | H | n-propyl |
| A4-452 | F | Cl | C—H | Cl | Cl | H | isopropyl |
| A4-453 | F | Cl | C—H | Cl | Cl | H | cyclopropyl |
| A4-454 | F | Cl | C—H | Cl | Cl | H | cyclopropylmethyl |
| A4-455 | F | Cl | C—H | Cl | Cl | H | 2,2,2-trifluoroethyl |
| A4-456 | F | Cl | C—H | Cl | Cl | H | 2-methoxyethyl |
| A4-457 | F | Cl | C—H | Cl | Cl | H | (methylsulfanyl)methyl |

TABLE A4-continued

Compounds according to the invention

| Ex. No. | X$^1$ | X$^2$ | A | X$^4$ | Y$^2$ | R$^3$ | R$^7$ |
|---|---|---|---|---|---|---|---|
| A4-458 | F | Cl | C—H | Cl | Cl | H | (methylsulfinyl)methyl |
| A4-459 | F | Cl | C—H | Cl | Cl | H | (methylsulfonyl)methyl |

TABLE A5

Compounds according to the invention

| Ex. No. | X$^1$ | X$^2$ | A | X$^4$ | Y$^2$ | R$^3$ | R$^7$ |
|---|---|---|---|---|---|---|---|
| A5-1 | H | Cl | C—H | Cl | CF3 | H | CH$_3$ |
| A5-2 | H | Cl | C—H | Cl | CF3 | H | ethyl |
| A5-3 | H | Cl | C—H | Cl | CF3 | H | n-propyl |
| A5-4 | H | Cl | C—H | Cl | CF3 | H | isopropyl |
| A5-5 | H | Cl | C—H | Cl | CF3 | H | cyclopropyl |
| A5-6 | H | Cl | C—H | Cl | CF3 | H | cyclopropylmethyl |
| A5-7 | H | Cl | C—H | Cl | CF3 | H | 2,2,2-trifluoroethyl |
| A5-8 | H | Cl | C—H | Cl | CF3 | H | 2-methoxyethyl |
| A5-9 | H | Cl | C—H | Cl | CF3 | H | (methylsulfanyl)methyl |
| A5-10 | H | Cl | C—H | Cl | CF3 | H | (methylsulfinyl)methyl |
| A5-11 | H | Cl | C—H | Cl | CF3 | H | (methylsulfonyl)methyl |
| A5-12 | H | Cl | C—Cl | Cl | CF3 | H | CH$_3$ |
| A5-13 | H | Cl | C—Cl | Cl | CF3 | H | ethyl |
| A5-14 | H | Cl | C—Cl | Cl | CF3 | H | n-propyl |
| A5-15 | H | Cl | C—Cl | Cl | CF3 | H | isopropyl |
| A5-16 | H | Cl | C—Cl | Cl | CF3 | H | cyclopropyl |
| A5-17 | H | Cl | C—Cl | Cl | CF3 | H | cyclopropylmethyl |
| A5-18 | H | Cl | C—Cl | Cl | CF3 | H | 2,2,2-trifluoroethyl |
| A5-19 | H | Cl | C—Cl | Cl | CF3 | H | 2-methoxyethyl |
| A5-20 | H | Cl | C—Cl | Cl | CF3 | H | (methylsulfanyl)methyl |
| A5-21 | H | Cl | C—Cl | Cl | CF3 | H | (methylsulfinyl)methyl |
| A5-22 | H | Cl | C—Cl | Cl | CF3 | H | (methylsulfonyl)methyl |
| A5-23 | H | CF3 | C—H | CF3 | CF3 | H | CH$_3$ |
| A5-24 | H | CF3 | C—H | CF3 | CF3 | H | ethyl |
| A5-25 | H | CF3 | C—H | CF3 | CF3 | H | n-propyl |
| A5-26 | H | CF3 | C—H | CF3 | CF3 | H | isopropyl |
| A5-27 | H | CF3 | C—H | CF3 | CF3 | H | cyclopropyl |
| A5-28 | H | CF3 | C—H | CF3 | CF3 | H | cyclopropylmethyl |
| A5-29 | H | CF3 | C—H | CF3 | CF3 | H | 2,2,2-trifluoroethyl |
| A5-30 | H | CF3 | C—H | CF3 | CF3 | H | 2-methoxyethyl |
| A5-31 | H | CF3 | C—H | CF3 | CF3 | H | (methylsulfanyl)methyl |
| A5-32 | H | CF3 | C—H | CF3 | CF3 | H | (methylsulfinyl)methyl |
| A5-33 | H | CF3 | C—H | CF3 | CF3 | H | (methylsulfonyl)methyl |
| A5-34 | H | F | C—H | Cl | CF3 | H | CH$_3$ |
| A5-35 | H | F | C—H | Cl | CF3 | H | ethyl |
| A5-36 | H | F | C—H | Cl | CF3 | H | n-propyl |
| A5-37 | H | F | C—H | Cl | CF3 | H | isopropyl |
| A5-38 | H | F | C—H | Cl | CF3 | H | cyclopropyl |
| A5-39 | H | F | C—H | Cl | CF3 | H | cyclopropylmethyl |
| A5-40 | H | F | C—H | Cl | CF3 | H | 2,2,2-trifluoroethyl |
| A5-41 | H | F | C—H | Cl | CF3 | H | 2-methoxyethyl |
| A5-42 | H | F | C—H | Cl | CF3 | H | (methylsulfanyl)methyl |
| A5-43 | H | F | C—H | Cl | CF3 | H | (methylsulfinyl)methyl |
| A5-44 | H | F | C—H | Cl | CF3 | H | (methylsulfonyl)methyl |
| A5-45 | H | Br | C—H | Br | CF3 | H | CH$_3$ |
| A5-46 | H | Br | C—H | Br | CF3 | H | ethyl |
| A5-47 | H | Br | C—H | Br | CF3 | H | n-propyl |
| A5-48 | H | Br | C—H | Br | CF3 | H | isopropyl |
| A5-49 | H | Br | C—H | Br | CF3 | H | cyclopropyl |
| A5-50 | H | Br | C—H | Br | CF3 | H | cyclopropylmethyl |
| A5-51 | H | Br | C—H | Br | CF3 | H | 2,2,2-trifluoroethyl |
| A5-52 | H | Br | C—H | Br | CF3 | H | 2-methoxyethyl |
| A5-53 | H | Br | C—H | Br | CF3 | H | (methylsulfanyl)methyl |
| A5-54 | H | Br | C—H | Br | CF3 | H | (methylsulfinyl)methyl |
| A5-55 | H | Br | C—H | Br | CF3 | H | (methylsulfonyl)methyl |
| A5-56 | H | F | C—F | F | CF3 | H | CH$_3$ |
| A5-57 | H | F | C—F | F | CF3 | H | ethyl |
| A5-58 | H | F | C—F | F | CF3 | H | n-propyl |
| A5-59 | H | F | C—F | F | CF3 | H | isopropyl |
| A5-60 | H | F | C—F | F | CF3 | H | cyclopropyl |
| A5-61 | H | F | C—F | F | CF3 | H | cyclopropylmethyl |
| A5-62 | H | F | C—F | F | CF3 | H | 2,2,2-trifluoroethyl |
| A5-63 | H | F | C—F | F | CF3 | H | 2-methoxyethyl |
| A5-64 | H | F | C—F | F | CF3 | H | (methylsulfanyl)methyl |
| A5-65 | H | F | C—F | F | CF3 | H | (methylsulfinyl)methyl |
| A5-66 | H | F | C—F | F | CF3 | H | (methylsulfonyl)methyl |
| A5-67 | H | Cl | C—F | Cl | CF3 | H | CH$_3$ |
| A5-68 | H | Cl | C—F | Cl | CF3 | H | ethyl |
| A5-69 | H | Cl | C—F | Cl | CF3 | H | n-propyl |
| A5-70 | H | Cl | C—F | Cl | CF3 | H | isopropyl |
| A5-71 | H | Cl | C—F | Cl | CF3 | H | cyclopropyl |
| A5-72 | H | Cl | C—F | Cl | CF3 | H | cyclopropylmethyl |
| A5-73 | H | Cl | C—F | Cl | CF3 | H | 2,2,2-trifluoroethyl |
| A5-74 | H | Cl | C—F | Cl | CF3 | H | 2-methoxyethyl |
| A5-75 | H | Cl | C—F | Cl | CF3 | H | (methylsulfanyl)methyl |
| A5-76 | H | Cl | C—F | Cl | CF3 | H | (methylsulfinyl)methyl |

TABLE A5-continued

Compounds according to the invention

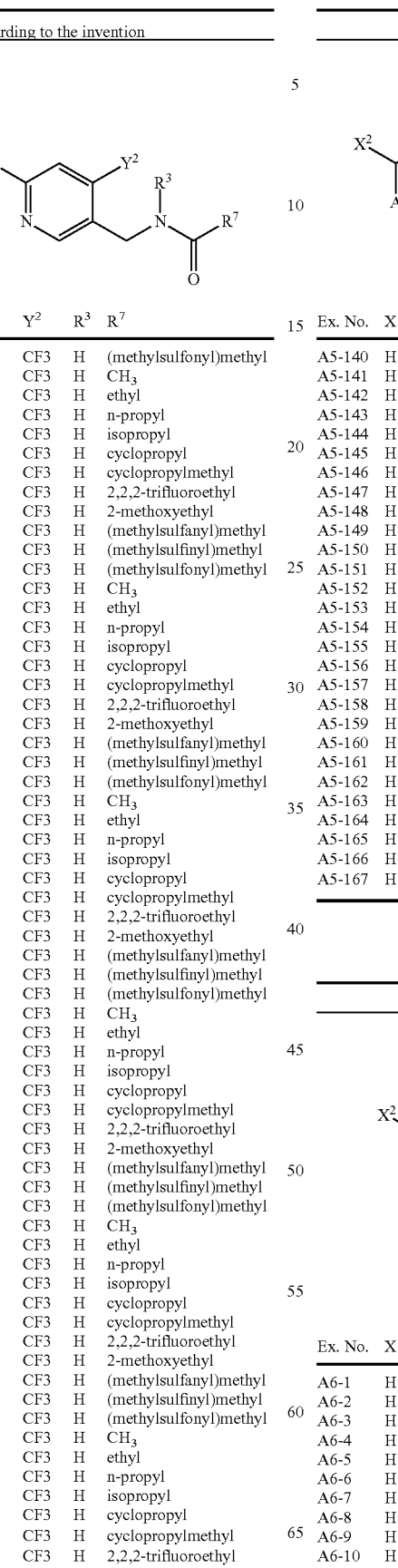

| Ex. No. | X¹ | X² | A | X⁴ | Y² | R³ | R⁷ |
|---|---|---|---|---|---|---|---|
| A5-77 | H | Cl | C—F | Cl | CF3 | H | (methylsulfonyl)methyl |
| A5-78 | F | Cl | C—F | Cl | CF3 | H | CH₃ |
| A5-79 | F | Cl | C—F | Cl | CF3 | H | ethyl |
| A5-80 | F | Cl | C—F | Cl | CF3 | H | n-propyl |
| A5-81 | F | Cl | C—F | Cl | CF3 | H | isopropyl |
| A5-82 | F | Cl | C—F | Cl | CF3 | H | cyclopropyl |
| A5-83 | F | Cl | C—F | Cl | CF3 | H | cyclopropylmethyl |
| A5-84 | F | Cl | C—F | Cl | CF3 | H | 2,2,2-trifluoroethyl |
| A5-85 | F | Cl | C—F | Cl | CF3 | H | 2-methoxyethyl |
| A5-86 | F | Cl | C—F | Cl | CF3 | H | (methylsulfanyl)methyl |
| A5-87 | F | Cl | C—F | Cl | CF3 | H | (methylsulfinyl)methyl |
| A5-88 | F | Cl | C—F | Cl | CF3 | H | (methylsulfonyl)methyl |
| A5-89 | H | CF3 | C—H | H | CF3 | H | CH₃ |
| A5-90 | H | CF3 | C—H | H | CF3 | H | ethyl |
| A5-91 | H | CF3 | C—H | H | CF3 | H | n-propyl |
| A5-92 | H | CF3 | C—H | H | CF3 | H | isopropyl |
| A5-93 | H | CF3 | C—H | H | CF3 | H | cyclopropyl |
| A5-94 | H | CF3 | C—H | H | CF3 | H | cyclopropylmethyl |
| A5-95 | H | CF3 | C—H | H | CF3 | H | 2,2,2-trifluoroethyl |
| A5-96 | H | CF3 | C—H | H | CF3 | H | 2-methoxyethyl |
| A5-97 | H | CF3 | C—H | H | CF3 | H | (methylsulfanyl)methyl |
| A5-98 | H | CF3 | C—H | H | CF3 | H | (methylsulfinyl)methyl |
| A5-99 | H | CF3 | C—H | H | CF3 | H | (methylsulfonyl)methyl |
| A5-100 | H | CF3 | C—F | H | CF3 | H | CH₃ |
| A5-101 | H | CF3 | C—F | H | CF3 | H | ethyl |
| A5-102 | H | CF3 | C—F | H | CF3 | H | n-propyl |
| A5-103 | H | CF3 | C—F | H | CF3 | H | isopropyl |
| A5-104 | H | CF3 | C—F | H | CF3 | H | cyclopropyl |
| A5-105 | H | CF3 | C—F | H | CF3 | H | cyclopropylmethyl |
| A5-106 | H | CF3 | C—F | H | CF3 | H | 2,2,2-trifluoroethyl |
| A5-107 | H | CF3 | C—F | H | CF3 | H | 2-methoxyethyl |
| A5-108 | H | CF3 | C—F | H | CF3 | H | (methylsulfanyl)methyl |
| A5-109 | H | CF3 | C—F | H | CF3 | H | (methylsulfinyl)methyl |
| A5-110 | H | CF3 | C—F | H | CF3 | H | (methylsulfonyl)methyl |
| A5-111 | H | CF3 | C—H | F | CF3 | H | CH₃ |
| A5-112 | H | CF3 | C—H | F | CF3 | H | ethyl |
| A5-113 | H | CF3 | C—H | F | CF3 | H | n-propyl |
| A5-114 | H | CF3 | C—H | F | CF3 | H | isopropyl |
| A5-115 | H | CF3 | C—H | F | CF3 | H | cyclopropyl |
| A5-116 | H | CF3 | C—H | F | CF3 | H | cyclopropylmethyl |
| A5-117 | H | CF3 | C—H | F | CF3 | H | 2,2,2-trifluoroethyl |
| A5-118 | H | CF3 | C—H | F | CF3 | H | 2-methoxyethyl |
| A5-119 | H | CF3 | C—H | F | CF3 | H | (methylsulfanyl)methyl |
| A5-120 | H | CF3 | C—H | F | CF3 | H | (methylsulfinyl)methyl |
| A5-121 | H | CF3 | C—H | F | CF3 | H | (methylsulfonyl)methyl |
| A5-122 | H | CF3 | C—Cl | H | CF3 | H | CH₃ |
| A5-123 | H | CF3 | C—Cl | H | CF3 | H | ethyl |
| A5-124 | H | CF3 | C—Cl | H | CF3 | H | n-propyl |
| A5-125 | H | CF3 | C—Cl | H | CF3 | H | isopropyl |
| A5-126 | H | CF3 | C—Cl | H | CF3 | H | cyclopropyl |
| A5-127 | H | CF3 | C—Cl | H | CF3 | H | cyclopropylmethyl |
| A5-128 | H | CF3 | C—Cl | H | CF3 | H | 2,2,2-trifluoroethyl |
| A5-129 | H | CF3 | C—Cl | H | CF3 | H | 2-methoxyethyl |
| A5-130 | H | CF3 | C—Cl | H | CF3 | H | (methylsulfanyl)methyl |
| A5-131 | H | CF3 | C—Cl | H | CF3 | H | (methylsulfinyl)methyl |
| A5-132 | H | CF3 | C—Cl | H | CF3 | H | (methylsulfonyl)methyl |
| A5-133 | H | CF3 | C—H | Cl | CF3 | H | CH₃ |
| A5-134 | H | CF3 | C—H | Cl | CF3 | H | ethyl |
| A5-135 | H | CF3 | C—H | Cl | CF3 | H | n-propyl |
| A5-136 | H | CF3 | C—H | Cl | CF3 | H | isopropyl |
| A5-137 | H | CF3 | C—H | Cl | CF3 | H | cyclopropyl |
| A5-138 | H | CF3 | C—H | Cl | CF3 | H | cyclopropylmethyl |
| A5-139 | H | CF3 | C—H | Cl | CF3 | H | 2,2,2-trifluoroethyl |
| A5-140 | H | CF3 | C—H | Cl | CF3 | H | 2-methoxyethyl |
| A5-141 | H | CF3 | C—H | Cl | CF3 | H | (methylsulfanyl)methyl |
| A5-142 | H | CF3 | C—H | Cl | CF3 | H | (methylsulfinyl)methyl |
| A5-143 | H | CF3 | C—H | Cl | CF3 | H | (methylsulfonyl)methyl |
| A5-144 | H | CF3 | C—Cl | Cl | CF3 | H | CH₃ |
| A5-145 | H | CF3 | C—Cl | Cl | CF3 | H | ethyl |
| A5-146 | H | CF3 | C—Cl | Cl | CF3 | H | n-propyl |
| A5-147 | H | CF3 | C—Cl | Cl | CF3 | H | isopropyl |
| A5-148 | H | CF3 | C—Cl | Cl | CF3 | H | cyclopropyl |
| A5-149 | H | CF3 | C—Cl | Cl | CF3 | H | cyclopropylmethyl |
| A5-150 | H | CF3 | C—Cl | Cl | CF3 | H | 2,2,2-trifluoroethyl |
| A5-151 | H | CF3 | C—Cl | Cl | CF3 | H | 2-methoxyethyl |
| A5-152 | H | CF3 | C—Cl | Cl | CF3 | H | (methylsulfanyl)methyl |
| A5-153 | H | CF3 | C—Cl | Cl | CF3 | H | (methylsulfinyl)methyl |
| A5-154 | H | CF3 | C—Cl | Cl | CF3 | H | (methylsulfonyl)methyl |
| A5-155 | H | Cl | C—Cl | Cl | CF3 | H | n-butyl |
| A5-156 | H | Cl | C—Cl | Cl | CF3 | H | iso-butyl |
| A5-157 | H | Cl | C—Cl | Cl | CF3 | H | cyclo-butyl |
| A5-158 | H | Cl | C—Cl | Cl | CF3 | H | 2-Chloroethyl |
| A5-159 | H | Cl | C—Cl | Cl | CF3 | H | thietan-3-yl |
| A5-160 | H | Cl | C—Cl | Cl | CF3 | H | 1-oxidothietan-3-yl |
| A5-161 | H | Cl | C—Cl | Cl | CF3 | H | 1,1-dioxidothietan-3-yl |
| A5-162 | H | Cl | C—Cl | Cl | CF3 | H | 2,4,6-trifluorophenyl |
| A5-163 | H | Cl | C—Cl | Cl | CF3 | H | methylamino |
| A5-164 | H | Cl | C—Cl | Cl | CF3 | H | dimethylamino |
| A5-165 | H | Cl | C—Cl | Cl | CF3 | H | ethylamino |
| A5-166 | H | Cl | C—Cl | Cl | CF3 | H | cyclopropylamino |
| A5-167 | H | Cl | C—Cl | Cl | CF3 | H | prop-2-yn-1-ylamino |

TABLE A6

Compounds according to the invention

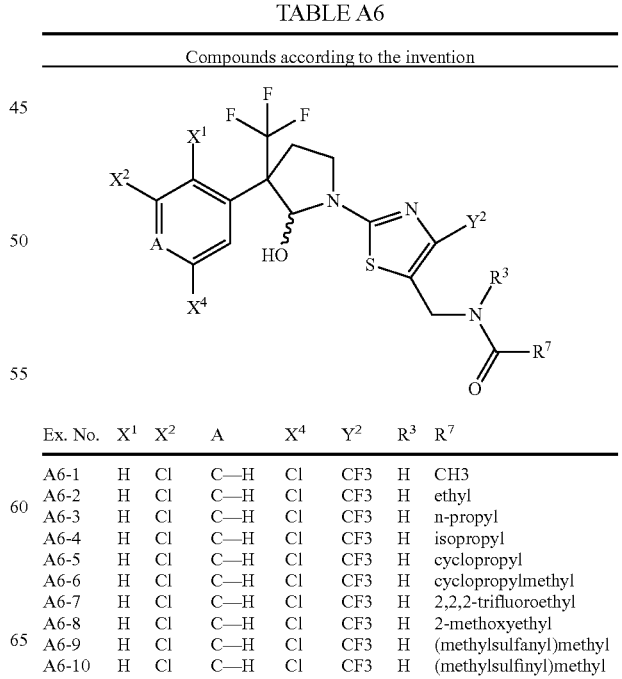

| Ex. No. | X¹ | X² | A | X⁴ | Y² | R³ | R⁷ |
|---|---|---|---|---|---|---|---|
| A6-1 | H | Cl | C—H | Cl | CF3 | H | CH3 |
| A6-2 | H | Cl | C—H | Cl | CF3 | H | ethyl |
| A6-3 | H | Cl | C—H | Cl | CF3 | H | n-propyl |
| A6-4 | H | Cl | C—H | Cl | CF3 | H | isopropyl |
| A6-5 | H | Cl | C—H | Cl | CF3 | H | cyclopropyl |
| A6-6 | H | Cl | C—H | Cl | CF3 | H | cyclopropylmethyl |
| A6-7 | H | Cl | C—H | Cl | CF3 | H | 2,2,2-trifluoroethyl |
| A6-8 | H | Cl | C—H | Cl | CF3 | H | 2-methoxyethyl |
| A6-9 | H | Cl | C—H | Cl | CF3 | H | (methylsulfanyl)methyl |
| A6-10 | H | Cl | C—H | Cl | CF3 | H | (methylsulfinyl)methyl |

TABLE A6-continued

Compounds according to the invention

| Ex. No. | X¹ | X² | A | X⁴ | Y² | R³ | R⁷ |
|---|---|---|---|---|---|---|---|
| A6-11 | H | Cl | C—H | Cl | CF3 | H | (methylsulfonyl)methyl |
| A6-12 | H | Cl | C—Cl | Cl | CF3 | H | CH3 |
| A6-13 | H | Cl | C—Cl | Cl | CF3 | H | ethyl |
| A6-14 | H | Cl | C—Cl | Cl | CF3 | H | n-propyl |
| A6-15 | H | Cl | C—Cl | Cl | CF3 | H | isopropyl |
| A6-16 | H | Cl | C—Cl | Cl | CF3 | H | cyclopropyl |
| A6-17 | H | Cl | C—Cl | Cl | CF3 | H | cyclopropylmethyl |
| A6-18 | H | Cl | C—Cl | Cl | CF3 | H | 2,2,2-trifluoroethyl |
| A6-19 | H | Cl | C—Cl | Cl | CF3 | H | 2-methoxyethyl |
| A6-20 | H | Cl | C—Cl | Cl | CF3 | H | (methylsulfanyl)methyl |
| A6-21 | H | Cl | C—Cl | Cl | CF3 | H | (methylsulfinyl)methyl |
| A6-22 | H | Cl | C—Cl | Cl | CF3 | H | (methylsulfonyl)methyl |
| A6-23 | H | CF3 | C—H | CF3 | CF3 | H | CH3 |
| A6-24 | H | CF3 | C—H | CF3 | CF3 | H | ethyl |
| A6-25 | H | CF3 | C—H | CF3 | CF3 | H | n-propyl |
| A6-26 | H | CF3 | C—H | CF3 | CF3 | H | isopropyl |
| A6-27 | H | CF3 | C—H | CF3 | CF3 | H | cyclopropyl |
| A6-28 | H | CF3 | C—H | CF3 | CF3 | H | cyclopropylmethyl |
| A6-29 | H | CF3 | C—H | CF3 | CF3 | H | 2,2,2-trifluoroethyl |
| A6-30 | H | CF3 | C—H | CF3 | CF3 | H | 2-methoxyethyl |
| A6-31 | H | CF3 | C—H | CF3 | CF3 | H | (methylsulfanyl)methyl |
| A6-32 | H | CF3 | C—H | CF3 | CF3 | H | (methylsulfinyl)methyl |
| A6-33 | H | CF3 | C—H | CF3 | CF3 | H | (methylsulfonyl)methyl |
| A6-34 | F | Cl | C—F | Cl | CF3 | H | CH3 |
| A6-35 | F | Cl | C—F | Cl | CF3 | H | ethyl |
| A6-36 | F | Cl | C—F | Cl | CF3 | H | n-propyl |
| A6-37 | F | Cl | C—F | Cl | CF3 | H | isopropyl |
| A6-38 | F | Cl | C—F | Cl | CF3 | H | cyclopropyl |
| A6-39 | F | Cl | C—F | Cl | CF3 | H | cyclopropylmethyl |
| A6-40 | F | Cl | C—F | Cl | CF3 | H | 2,2,2-trifluoroethyl |
| A6-41 | F | Cl | C—F | Cl | CF3 | H | 2-methoxyethyl |
| A6-42 | F | Cl | C—F | Cl | CF3 | H | (methylsulfanyl)methyl |
| A6-43 | F | Cl | C—F | Cl | CF3 | H | (methylsulfinyl)methyl |
| A6-44 | F | Cl | C—F | Cl | CF3 | H | (methylsulfonyl)methyl |

TABLE A7

Compounds according to the invention

| Ex. No. | X¹ | X² | A | X⁴ | Y² | G |
|---|---|---|---|---|---|---|
| A7-1 | H | Cl | C—H | Cl | cyano | 4-cyano-1H-pyrazol-1-yl |
| A7-2 | H | Cl | C—Cl | Cl | cyano | 4-cyano-1H-pyrazol-1-yl |
| A7-3 | H | CF3 | C—H | CF3 | cyano | 4-cyano-1H-pyrazol-1-yl |
| A7-4 | H | Cl | C—H | Cl | cyano | 1H-1,2,4-triazol-1-yl |
| A7-5 | H | Cl | C—Cl | Cl | cyano | 1H-1,2,4-triazol-1-yl |

TABLE A7-continued

Compounds according to the invention

| Ex. No. | X¹ | X² | A | X⁴ | Y² | G |
|---|---|---|---|---|---|---|
| A7-6 | H | CF3 | C—H | CF3 | cyano | 1H-1,2,4-triazol-1-yl |
| A7-7 | H | Cl | C—H | Cl | cyano | 1H-tetrazol-1-yl |
| A7-8 | H | Cl | C—Cl | Cl | cyano | 1H-tetrazol-1-yl |
| A7-9 | H | CF3 | C—H | CF3 | cyano | 1H-tetrazol-1-yl |
| A7-10 | F | Cl | C—F | Cl | cyano | 4-cyano-1H-pyrazol-1-yl |
| A7-11 | F | Cl | C—H | Cl | cyano | 4-cyano-1H-pyrazol-1-yl |
| A7-12 | H | Cl | C—Cl | CF3 | cyano | 4-cyano-1H-pyrazol-1-yl |
| A7-13 | F | Cl | C—F | Cl | cyano | 1H-1,2,4-triazol-1-yl |
| A7-14 | F | Cl | C—H | Cl | cyano | 1H-1,2,4-triazol-1-yl |
| A7-15 | H | Cl | C—Cl | CF3 | cyano | 1H-1,2,4-triazol-1-yl |
| A7-16 | F | Cl | C—F | Cl | cyano | 1H-tetrazol-1-yl |
| A7-17 | F | Cl | C—H | Cl | cyano | 1H-tetrazol-1-yl |
| A7-18 | H | Cl | C—Cl | CF3 | cyano | 1H-tetrazol-1-yl |

TABLE A'3

Compounds according to the invention

| Ex. No. | X¹ | X² | A | X⁴ | Y² | R³ | R⁷ |
|---|---|---|---|---|---|---|---|
| A'3-1 | H | Cl | C—H | Cl | CF3 | H | CH₃ |
| A'3-2 | H | Cl | C—H | Cl | CF3 | H | ethyl |
| A'3-3 | H | Cl | C—H | Cl | CF3 | H | n-propyl |
| A'3-4 | H | Cl | C—H | Cl | CF3 | H | isopropyl |
| A'3-5 | H | Cl | C—H | Cl | CF3 | H | cyclopropyl |
| A'3-6 | H | Cl | C—H | Cl | CF3 | H | cyclopropylmethyl |
| A'3-7 | H | Cl | C—H | Cl | CF3 | H | 2,2,2-trifluoroethyl |
| A'3-8 | H | Cl | C—H | Cl | CF3 | H | 2-methoxyethyl |
| A'3-9 | H | Cl | C—H | Cl | CF3 | H | (methylsulfanyl)methyl |
| A'3-10 | H | Cl | C—H | Cl | CF3 | H | (methylsulfinyl)methyl |
| A'3-11 | H | Cl | C—H | Cl | CF3 | H | (methylsulfonyl)methyl |
| A'3-12 | H | Cl | C—Cl | Cl | CF3 | H | CH₃ |
| A'3-13 | H | Cl | C—Cl | Cl | CF3 | H | ethyl |
| A'3-14 | H | Cl | C—Cl | Cl | CF3 | H | n-propyl |
| A'3-15 | H | Cl | C—Cl | Cl | CF3 | H | isopropyl |
| A'3-16 | H | Cl | C—Cl | Cl | CF3 | H | cyclopropyl |
| A'3-17 | H | Cl | C—Cl | Cl | CF3 | H | cyclopropylmethyl |
| A'3-18 | H | Cl | C—Cl | Cl | CF3 | H | 2,2,2-trifluoroethyl |
| A'3-19 | H | Cl | C—Cl | Cl | CF3 | H | 2-methoxyethyl |
| A'3-20 | H | Cl | C—Cl | Cl | CF3 | H | (methylsulfanyl)methyl |
| A'3-21 | H | Cl | C—Cl | Cl | CF3 | H | (methylsulfinyl)methyl |
| A'3-22 | H | Cl | C—Cl | Cl | CF3 | H | (methylsulfonyl)methyl |
| A'3-23 | H | CF3 | C—H | CF3 | CF3 | H | CH₃ |
| A'3-24 | H | CF3 | C—H | CF3 | CF3 | H | ethyl |
| A'3-25 | H | CF3 | C—H | CF3 | CF3 | H | n-propyl |
| A'3-26 | H | CF3 | C—H | CF3 | CF3 | H | isopropyl |
| A'3-27 | H | CF3 | C—H | CF3 | CF3 | H | cyclopropyl |
| A'3-28 | H | CF3 | C—H | CF3 | CF3 | H | cyclopropylmethyl |
| A'3-29 | H | CF3 | C—H | CF3 | CF3 | H | 2,2,2-trifluoroethyl |

TABLE A'3-continued

Compounds according to the invention

Structure: pyrrolidine with CF2 and OH substituents, attached to phenyl (X1, X2, A, X4) and pyridine-N-CH2-N(R3)-C(O)-R7 with Y2.

| Ex. No. | X¹ | X² | A | X⁴ | Y² | R³ | R⁷ |
|---|---|---|---|---|---|---|---|
| A'3-30 | H | CF3 | C—H | CF3 | CF3 | H | 2-methoxyethyl |
| A'3-31 | H | CF3 | C—H | CF3 | CF3 | H | (methylsulfanyl)methyl |
| A'3-32 | H | CF3 | C—H | CF3 | CF3 | H | (methylsulfinyl)methyl |
| A'3-33 | H | CF3 | C—H | CF3 | CF3 | H | (methylsulfonyl)methyl |

TABLE B1

Compounds according to the invention

Structure: pyrrolidinone with CF2, phenyl (X1, X2, A, X4), N-phenyl(Y2)-CH2-N(R3)-C(O)-R7.

| Ex. No. | X¹ | X² | A | X⁴ | Y² | R³ | R⁷ |
|---|---|---|---|---|---|---|---|
| B1-1 | H | Cl | C—H | Cl | Cl | H | CH₃ |
| B1-2 | H | Cl | C—H | Cl | Cl | H | ethyl |
| B1-3 | H | Cl | C—H | Cl | Cl | H | n-propyl |
| B1-4 | H | Cl | C—H | Cl | Cl | H | isopropyl |
| B1-5 | H | Cl | C—H | Cl | Cl | H | cyclopropyl |
| B1-6 | H | Cl | C—H | Cl | Cl | H | cyclopropylmethyl |
| B1-7 | H | Cl | C—H | Cl | Cl | H | 2,2,2-trifluoroethyl |
| B1-8 | H | Cl | C—H | Cl | Cl | H | 2-methoxyethyl |
| B1-9 | H | Cl | C—H | Cl | Cl | H | (methylsulfanyl)methyl |
| B1-10 | H | Cl | C—H | Cl | Cl | H | (methylsulfinyl)methyl |
| B1-11 | H | Cl | C—H | Cl | Cl | H | (methylsulfonyl)methyl |
| B1-12 | H | Cl | C—Cl | Cl | Cl | H | CH₃ |
| B1-13 | H | Cl | C—Cl | Cl | Cl | H | ethyl |
| B1-14 | H | Cl | C—Cl | Cl | Cl | H | n-propyl |
| B1-15 | H | Cl | C—Cl | Cl | Cl | H | isopropyl |
| B1-16 | H | Cl | C—Cl | Cl | Cl | H | cyclopropyl |
| B1-17 | H | Cl | C—Cl | Cl | Cl | H | cyclopropylmethyl |
| B1-18 | H | Cl | C—Cl | Cl | Cl | H | 2,2,2-trifluoroethyl |
| B1-19 | H | Cl | C—Cl | Cl | Cl | H | 2-methoxyethyl |
| B1-20 | H | Cl | C—Cl | Cl | Cl | H | (methylsulfanyl)methyl |
| B1-21 | H | Cl | C—Cl | Cl | Cl | H | (methylsulfinyl)methyl |
| B1-22 | H | Cl | C—Cl | Cl | Cl | H | (methylsulfonyl)methyl |
| B1-23 | H | CF3 | C—H | CF3 | Cl | H | CH₃ |
| B1-24 | H | CF3 | C—H | CF3 | Cl | H | ethyl |
| B1-25 | H | CF3 | C—H | CF3 | Cl | H | n-propyl |
| B1-26 | H | CF3 | C—H | CF3 | Cl | H | isopropyl |
| B1-27 | H | CF3 | C—H | CF3 | Cl | H | cyclopropyl |
| B1-28 | H | CF3 | C—H | CF3 | Cl | H | cyclopropylmethyl |
| B1-29 | H | CF3 | C—H | CF3 | Cl | H | 2,2,2-trifluoroethyl |
| B1-30 | H | CF3 | C—H | CF3 | Cl | H | 2-methoxyethyl |
| B1-31 | H | CF3 | C—H | CF3 | Cl | H | (methylsulfanyl)methyl |
| B1-32 | H | CF3 | C—H | CF3 | Cl | H | (methylsulfinyl)methyl |
| B1-33 | H | CF3 | C—H | CF3 | Cl | H | (methylsulfonyl)methyl |
| B1-34 | H | Cl | C—H | Cl | CF3 | H | CH₃ |
| B1-35 | H | Cl | C—H | Cl | CF3 | H | ethyl |
| B1-36 | H | Cl | C—H | Cl | CF3 | H | n-propyl |
| B1-37 | H | Cl | C—H | Cl | CF3 | H | isopropyl |
| B1-38 | H | Cl | C—H | Cl | CF3 | H | cyclopropyl |
| B1-39 | H | Cl | C—H | Cl | CF3 | H | cyclopropylmethyl |
| B1-40 | H | Cl | C—H | Cl | CF3 | H | 2,2,2-trifluoroethyl |
| B1-41 | H | Cl | C—H | Cl | CF3 | H | 2-methoxyethyl |
| B1-42 | H | Cl | C—H | Cl | CF3 | H | (methylsulfanyl)methyl |
| B1-43 | H | Cl | C—H | Cl | CF3 | H | (methylsulfinyl)methyl |
| B1-44 | H | Cl | C—H | Cl | CF3 | H | (methylsulfonyl)methyl |
| B1-45 | H | Cl | C—Cl | Cl | CF3 | H | CH₃ |
| B1-46 | H | Cl | C—Cl | Cl | CF3 | H | ethyl |
| B1-47 | H | Cl | C—Cl | Cl | CF3 | H | n-propyl |
| B1-48 | H | Cl | C—Cl | Cl | CF3 | H | isopropyl |
| B1-49 | H | Cl | C—Cl | Cl | CF3 | H | cyclopropyl |
| B1-50 | H | Cl | C—Cl | Cl | CF3 | H | cyclopropylmethyl |
| B1-51 | H | Cl | C—Cl | Cl | CF3 | H | 2,2,2-trifluoroethyl |
| B1-52 | H | Cl | C—Cl | Cl | CF3 | H | 2-methoxyethyl |
| B1-53 | H | Cl | C—Cl | Cl | CF3 | H | (methylsulfanyl)methyl |
| B1-54 | H | Cl | C—Cl | Cl | CF3 | H | (methylsulfinyl)methyl |
| B1-55 | H | Cl | C—Cl | Cl | CF3 | H | (methylsulfonyl)methyl |
| B1-56 | H | CF3 | C—H | CF3 | CF3 | H | CH₃ |
| B1-57 | H | CF3 | C—H | CF3 | CF3 | H | ethyl |
| B1-58 | H | CF3 | C—H | CF3 | CF3 | H | n-propyl |
| B1-59 | H | CF3 | C—H | CF3 | CF3 | H | isopropyl |
| B1-60 | H | CF3 | C—H | CF3 | CF3 | H | cyclopropyl |
| B1-61 | H | CF3 | C—H | CF3 | CF3 | H | cyclopropylmethyl |
| B1-62 | H | CF3 | C—H | CF3 | CF3 | H | 2,2,2-trifluoroethyl |
| B1-63 | H | CF3 | C—H | CF3 | CF3 | H | 2-methoxyethyl |
| B1-64 | H | CF3 | C—H | CF3 | CF3 | H | (methylsulfanyl)methyl |
| B1-65 | H | CF3 | C—H | CF3 | CF3 | H | (methylsulfinyl)methyl |
| B1-66 | H | CF3 | C—H | CF3 | CF3 | H | (methylsulfonyl)methyl |
| B1-67 | H | Cl | C—H | Cl | Cl | H | tert-butoxy |
| B1-68 | H | Cl | C—Cl | Cl | Cl | H | tert-butoxy |
| B1-69 | H | CF3 | C—H | CF3 | Cl | H | tert-butoxy |
| B1-70 | H | Cl | C—H | Cl | CF3 | H | tert-butoxy |
| B1-71 | H | Cl | C—Cl | Cl | CF3 | H | tert-butoxy |
| B1-72 | H | CF3 | C—H | CF3 | CF3 | H | tert-butoxy |
| B1-73 | H | Cl | C—H | Cl | H | H | CH₃ |
| B1-74 | H | Cl | C—H | Cl | H | H | ethyl |
| B1-75 | H | Cl | C—H | Cl | H | H | n-propyl |
| B1-76 | H | Cl | C—H | Cl | H | H | isopropyl |
| B1-77 | H | Cl | C—H | Cl | H | H | cyclopropyl |
| B1-78 | H | Cl | C—H | Cl | H | H | cyclopropylmethyl |
| B1-79 | H | Cl | C—H | Cl | H | H | 2,2,2-trifluoroethyl |
| B1-80 | H | Cl | C—H | Cl | H | H | 2-methoxyethyl |
| B1-81 | H | Cl | C—H | Cl | H | H | (methylsulfanyl)methyl |
| B1-82 | H | Cl | C—H | Cl | H | H | (methylsulfinyl)methyl |
| B1-83 | H | Cl | C—H | Cl | H | H | (methylsulfonyl)methyl |
| B1-84 | H | Cl | C—Cl | Cl | H | H | CH₃ |
| B1-85 | H | Cl | C—Cl | Cl | H | H | ethyl |
| B1-86 | H | Cl | C—Cl | Cl | H | H | n-propyl |
| B1-87 | H | Cl | C—Cl | Cl | H | H | isopropyl |
| B1-88 | H | Cl | C—Cl | Cl | H | H | cyclopropyl |
| B1-89 | H | Cl | C—Cl | Cl | H | H | cyclopropylmethyl |
| B1-90 | H | Cl | C—Cl | Cl | H | H | 2,2,2-trifluoroethyl |
| B1-91 | H | Cl | C—Cl | Cl | H | H | 2-methoxyethyl |
| B1-92 | H | Cl | C—Cl | Cl | H | H | (methylsulfanyl)methyl |
| B1-93 | H | Cl | C—Cl | Cl | H | H | (methylsulfinyl)methyl |
| B1-94 | H | Cl | C—Cl | Cl | H | H | (methylsulfonyl)methyl |
| B1-95 | H | CF3 | C—H | CF3 | H | H | CH₃ |
| B1-96 | H | CF3 | C—H | CF3 | H | H | ethyl |
| B1-97 | H | CF3 | C—H | CF3 | H | H | n-propyl |
| B1-98 | H | CF3 | C—H | CF3 | H | H | isopropyl |
| B1-99 | H | CF3 | C—H | CF3 | H | H | cyclopropyl |
| B1-100 | H | CF3 | C—H | CF3 | H | H | cyclopropylmethyl |
| B1-101 | H | CF3 | C—H | CF3 | H | H | 2,2,2-trifluoroethyl |
| B1-102 | H | CF3 | C—H | CF3 | H | H | 2-methoxyethyl |

TABLE B1-continued

Compounds according to the invention

| Ex. No. | X¹ | X² | A | X⁴ | Y² | R³ | R⁷ |
|---|---|---|---|---|---|---|---|
| B1-103 | H | CF3 | C—H | CF3 | H | H | (methylsulfanyl)methyl |
| B1-104 | H | CF3 | C—H | CF3 | H | H | (methylsulfinyl)methyl |
| B1-105 | H | CF3 | C—H | CF3 | H | H | (methylsulfonyl)methyl |

TABLE B2

Compounds according to the invention

| Ex. No. | X¹ | X² | A | X⁴ | R³ | R⁵ | R⁷ |
|---|---|---|---|---|---|---|---|
| B2-1 | H | Cl | C—H | Cl | H | CH₃ | CH₃ |
| B2-2 | H | Cl | C—H | Cl | H | CH₃ | ethyl |
| B2-3 | H | Cl | C—H | Cl | H | CH₃ | n-propyl |
| B2-4 | H | Cl | C—H | Cl | H | CH₃ | isopropyl |
| B2-5 | H | Cl | C—H | Cl | H | CH₃ | cyclopropyl |
| B2-6 | H | Cl | C—H | Cl | H | CH₃ | cyclopropylmethyl |
| B2-7 | H | Cl | C—H | Cl | H | CH₃ | 2,2,2-trifluoroethyl |
| B2-8 | H | Cl | C—H | Cl | H | CH₃ | 2-methoxyethyl |
| B2-9 | H | Cl | C—H | Cl | H | CH₃ | (methylsulfanyl)methyl |
| B2-10 | H | Cl | C—H | Cl | H | CH₃ | (methylsulfinyl)methyl |
| B2-11 | H | Cl | C—H | Cl | H | CH₃ | (methylsulfonyl)methyl |
| B2-12 | H | Cl | C—Cl | Cl | H | CH₃ | CH₃ |
| B2-13 | H | Cl | C—Cl | Cl | H | CH₃ | ethyl |
| B2-14 | H | Cl | C—Cl | Cl | H | CH₃ | n-propyl |
| B2-15 | H | Cl | C—Cl | Cl | H | CH₃ | isopropyl |
| B2-16 | H | Cl | C—Cl | Cl | H | CH₃ | cyclopropyl |
| B2-17 | H | Cl | C—Cl | Cl | H | CH₃ | cyclopropylmethyl |
| B2-18 | H | Cl | C—Cl | Cl | H | CH₃ | 2,2,2-trifluoroethyl |
| B2-19 | H | Cl | C—Cl | Cl | H | CH₃ | 2-methoxyethyl |
| B2-20 | H | Cl | C—Cl | Cl | H | CH₃ | (methylsulfanyl)methyl |
| B2-21 | H | Cl | C—Cl | Cl | H | CH₃ | (methylsulfinyl)methyl |
| B2-22 | H | Cl | C—Cl | Cl | H | CH₃ | (methylsulfonyl)methyl |
| B2-23 | H | CF3 | C—H | CF3 | H | CH₃ | CH₃ |
| B2-24 | H | CF3 | C—H | CF3 | H | CH₃ | ethyl |
| B2-25 | H | CF3 | C—H | CF3 | H | CH₃ | n-propyl |
| B2-26 | H | CF3 | C—H | CF3 | H | CH₃ | isopropyl |
| B2-27 | H | CF3 | C—H | CF3 | H | CH₃ | cyclopropyl |
| B2-27-b | H | CF3 | C—H | CF3 | H | CH₃ | cyclopropyl |
| B2-28 | H | CF3 | C—H | CF3 | H | CH₃ | cyclopropylmethyl |
| B2-29 | H | CF3 | C—H | CF3 | H | CH₃ | 2,2,2-trifluoroethyl |
| B2-30 | H | CF3 | C—H | CF3 | H | CH₃ | 2-methoxyethyl |
| B2-31 | H | CF3 | C—H | CF3 | H | CH₃ | (methylsulfanyl)methyl |
| B2-32 | H | CF3 | C—H | CF3 | H | CH₃ | (methylsulfinyl)methyl |
| B2-33 | H | CF3 | C—H | CF3 | H | CH₃ | (methylsulfonyl)methyl |

*
a = (R) isomer
b = (S) isomer

TABLE B3

Compounds according to the invention

| Ex. No. | X¹ | X² | A | X⁴ | Y² | R³ | R⁷ |
|---|---|---|---|---|---|---|---|
| B3-1 | H | Cl | C—H | Cl | CF3 | H | CH₃ |
| B3-2 | H | Cl | C—H | Cl | CF3 | H | ethyl |
| B3-3 | H | Cl | C—H | Cl | CF3 | H | n-propyl |
| B3-4 | H | Cl | C—H | Cl | CF3 | H | isopropyl |
| B3-5 | H | Cl | C—H | Cl | CF3 | H | cyclopropyl |
| B3-6 | H | Cl | C—H | Cl | CF3 | H | cyclopropylmethyl |
| B3-7 | H | Cl | C—H | Cl | CF3 | H | 2,2,2-trifluoroethyl |
| B3-8 | H | Cl | C—H | Cl | CF3 | H | 2-methoxyethyl |
| B3-9 | H | Cl | C—H | Cl | CF3 | H | (methylsulfanyl)methyl |
| B3-10 | H | Cl | C—H | Cl | CF3 | H | (methylsulfinyl)methyl |
| B3-11 | H | Cl | C—H | Cl | CF3 | H | (methylsulfonyl)methyl |
| B3-12 | H | Cl | C—Cl | Cl | CF3 | H | CH₃ |
| B3-13 | H | Cl | C—Cl | Cl | CF3 | H | ethyl |
| B3-14 | H | Cl | C—Cl | Cl | CF3 | H | n-propyl |
| B3-15 | H | Cl | C—Cl | Cl | CF3 | H | isopropyl |
| B3-16 | H | Cl | C—Cl | Cl | CF3 | H | cyclopropyl |
| B3-17 | H | Cl | C—Cl | Cl | CF3 | H | cyclopropylmethyl |
| B3-18 | H | Cl | C—Cl | Cl | CF3 | H | 2,2,2-trifluoroethyl |
| B3-19 | H | Cl | C—Cl | Cl | CF3 | H | 2-methoxyethyl |
| B3-20 | H | Cl | C—Cl | Cl | CF3 | H | (methylsulfanyl)methyl |
| B3-21 | H | Cl | C—Cl | Cl | CF3 | H | (methylsulfinyl)methyl |
| B3-22 | H | Cl | C—Cl | Cl | CF3 | H | (methylsulfonyl)methyl |
| B3-23 | H | CF3 | C—H | CF3 | CF3 | H | CH₃ |
| B3-24 | H | CF3 | C—H | CF3 | CF3 | H | ethyl |
| B3-25 | H | CF3 | C—H | CF3 | CF3 | H | n-propyl |
| B3-26 | H | CF3 | C—H | CF3 | CF3 | H | isopropyl |
| B3-27 | H | CF3 | C—H | CF3 | CF3 | H | cyclopropyl |
| B3-28 | H | CF3 | C—H | CF3 | CF3 | H | cyclopropylmethyl |
| B3-29 | H | CF3 | C—H | CF3 | CF3 | H | 2,2,2-trifluoroethyl |
| B3-30 | H | CF3 | C—H | CF3 | CF3 | H | 2-methoxyethyl |
| B3-31 | H | CF3 | C—H | CF3 | CF3 | H | (methylsulfanyl)methyl |
| B3-32 | H | CF3 | C—H | CF3 | CF3 | H | (methylsulfinyl)methyl |
| B3-33 | H | CF3 | C—H | CF3 | CF3 | H | (methylsulfonyl)methyl |
| B3-34 | H | CF3 | C—H | CF3 | CH₃ | H | CH₃ |
| B3-35 | H | CF3 | C—H | CF3 | CH₃ | H | ethyl |
| B3-36 | H | CF3 | C—H | CF3 | CH₃ | H | n-propyl |
| B3-37 | H | CF3 | C—H | CF3 | CH₃ | H | isopropyl |
| B3-38 | H | CF3 | C—H | CF3 | CH₃ | H | cyclopropyl |
| B3-39 | H | CF3 | C—H | CF3 | CH₃ | H | cyclopropylmethyl |
| B3-40 | H | CF3 | C—H | CF3 | CH₃ | H | 2,2,2-trifluoroethyl |
| B3-41 | H | CF3 | C—H | CF3 | CH₃ | H | 2-methoxyethyl |
| B3-42 | H | CF3 | C—H | CF3 | CH₃ | H | (methylsulfanyl)methyl |
| B3-43 | H | CF3 | C—H | CF3 | CH₃ | H | (methylsulfinyl)methyl |
| B3-44 | H | CF3 | C—H | CF3 | CH₃ | H | (methylsulfonyl)methyl |
| B3-45 | H | CF3 | C—H | CF3 | ethyl | H | CH₃ |
| B3-46 | H | CF3 | C—H | CF3 | ethyl | H | ethyl |
| B3-47 | H | CF3 | C—H | CF3 | ethyl | H | n-propyl |
| B3-48 | H | CF3 | C—H | CF3 | ethyl | H | isopropyl |
| B3-49 | H | CF3 | C—H | CF3 | ethyl | H | cyclopropyl |
| B3-50 | H | CF3 | C—H | CF3 | ethyl | H | cyclopropylmethyl |
| B3-51 | H | CF3 | C—H | CF3 | ethyl | H | 2,2,2-trifluoroethyl |
| B3-52 | H | CF3 | C—H | CF3 | ethyl | H | 2-methoxyethyl |
| B3-53 | H | CF3 | C—H | CF3 | ethyl | H | (methylsulfanyl)methyl |
| B3-54 | H | CF3 | C—H | CF3 | ethyl | H | (methylsulfinyl)methyl |
| B3-55 | H | CF3 | C—H | CF3 | ethyl | H | (methylsulfonyl)methyl |

TABLE C1

Compounds according to the invention

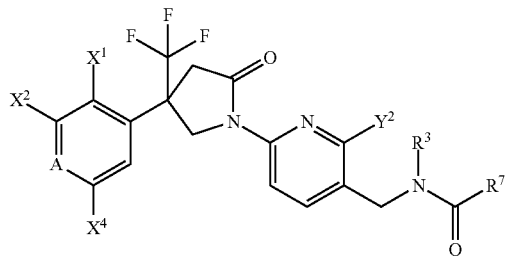

| Ex. No. | X¹ | X² | A | X⁴ | Y² | R³ | R⁷ |
|---|---|---|---|---|---|---|---|
| C1-1 | H | Cl | C—H | Cl | Cl | H | $CH_3$ |
| C1-2 | H | Cl | C—H | Cl | Cl | H | ethyl |
| C1-3 | H | Cl | C—H | Cl | Cl | H | n-propyl |
| C1-4 | H | Cl | C—H | Cl | Cl | H | isopropyl |
| C1-5 | H | Cl | C—H | Cl | Cl | H | cyclopropyl |
| C1-6 | H | Cl | C—H | Cl | Cl | H | cyclopropylmethyl |
| C1-7 | H | Cl | C—H | Cl | Cl | H | 2,2,2-trifluoroethyl |
| C1-8 | H | Cl | C—H | Cl | Cl | H | 2-methoxyethyl |
| C1-9 | H | Cl | C—H | Cl | Cl | H | (methylsulfanyl)methyl |
| C1-10 | H | Cl | C—H | Cl | Cl | H | (methylsulfinyl)methyl |
| C1-11 | H | Cl | C—H | Cl | Cl | H | (methylsulfonyl)methyl |
| C1-12 | H | Cl | C—Cl | Cl | Cl | H | $CH_3$ |
| C1-13 | H | Cl | C—Cl | Cl | Cl | H | ethyl |
| C1-14 | H | Cl | C—Cl | Cl | Cl | H | n-propyl |
| C1-15 | H | Cl | C—Cl | Cl | Cl | H | isopropyl |
| C1-16 | H | Cl | C—Cl | Cl | Cl | H | cyclopropyl |
| C1-17 | H | Cl | C—Cl | Cl | Cl | H | cyclopropylmethyl |
| C1-18 | H | Cl | C—Cl | Cl | Cl | H | 2,2,2-trifluoroethyl |
| C1-19 | H | Cl | C—Cl | Cl | Cl | H | 2-methoxyethyl |
| C1-20 | H | Cl | C—Cl | Cl | Cl | H | (methylsulfanyl)methyl |
| C1-21 | H | Cl | C—Cl | Cl | Cl | H | (methylsulfinyl)methyl |
| C1-22 | H | Cl | C—Cl | Cl | Cl | H | (methylsulfonyl)methyl |
| C1-23 | H | CF3 | C—H | CF3 | Cl | H | $CH_3$ |
| C1-24 | H | CF3 | C—H | CF3 | Cl | H | ethyl |
| C1-25 | H | CF3 | C—H | CF3 | Cl | H | n-propyl |
| C1-26 | H | CF3 | C—H | CF3 | Cl | H | isopropyl |
| C1-27 | H | CF3 | C—H | CF3 | Cl | H | cyclopropyl |
| C1-28 | H | CF3 | C—H | CF3 | Cl | H | cyclopropylmethyl |
| C1-29 | H | CF3 | C—H | CF3 | Cl | H | 2,2,2-trifluoroethyl |
| C1-30 | H | CF3 | C—H | CF3 | Cl | H | 2-methoxyethyl |
| C1-31 | H | CF3 | C—H | CF3 | Cl | H | (methylsulfanyl)methyl |
| C1-32 | H | CF3 | C—H | CF3 | Cl | H | (methylsulfinyl)methyl |
| C1-33 | H | CF3 | C—H | CF3 | Cl | H | (methylsulfonyl)methyl |
| C1-34 | H | Cl | C—H | Cl | CF3 | H | $CH_3$ |
| C1-35 | H | Cl | C—H | Cl | CF3 | H | ethyl |
| C1-36 | H | Cl | C—H | Cl | CF3 | H | n-propyl |
| C1-37 | H | Cl | C—H | Cl | CF3 | H | isopropyl |
| C1-38 | H | Cl | C—H | Cl | CF3 | H | cyclopropyl |
| C1-39 | H | Cl | C—H | Cl | CF3 | H | cyclopropylmethyl |
| C1-40 | H | Cl | C—H | Cl | CF3 | H | 2,2,2-trifluoroethyl |
| C1-41 | H | Cl | C—H | Cl | CF3 | H | 2-methoxyethyl |
| C1-42 | H | Cl | C—H | Cl | CF3 | H | (methylsulfanyl)methyl |
| C1-43 | H | Cl | C—H | Cl | CF3 | H | (methylsulfinyl)methyl |
| C1-44 | H | Cl | C—H | Cl | CF3 | H | (methylsulfonyl)methyl |
| C1-45 | H | Cl | C—Cl | Cl | CF3 | H | $CH_3$ |
| C1-46 | H | Cl | C—Cl | Cl | CF3 | H | ethyl |
| C1-47 | H | Cl | C—Cl | Cl | CF3 | H | n-propyl |
| C1-48 | H | Cl | C—Cl | Cl | CF3 | H | isopropyl |
| C1-49 | H | Cl | C—Cl | Cl | CF3 | H | cyclopropyl |
| C1-50 | H | Cl | C—Cl | Cl | CF3 | H | cyclopropylmethyl |
| C1-51 | H | Cl | C—Cl | Cl | CF3 | H | 2,2,2-trifluoroethyl |
| C1-52 | H | Cl | C—Cl | Cl | CF3 | H | 2-methoxyethyl |
| C1-53 | H | Cl | C—Cl | Cl | CF3 | H | (methylsulfanyl)methyl |
| C1-54 | H | Cl | C—Cl | Cl | CF3 | H | (methylsulfinyl)methyl |
| C1-55 | H | Cl | C—Cl | Cl | CF3 | H | (methylsulfonyl)methyl |
| C1-56 | H | CF3 | C—H | CF3 | CF3 | H | $CH_3$ |
| C1-57 | H | CF3 | C—H | CF3 | CF3 | H | ethyl |
| C1-58 | H | CF3 | C—H | CF3 | CF3 | H | n-propyl |
| C1-59 | H | CF3 | C—H | CF3 | CF3 | H | isopropyl |
| C1-60 | H | CF3 | C—H | CF3 | CF3 | H | cyclopropyl |
| C1-61 | H | CF3 | C—H | CF3 | CF3 | H | cyclopropylmethyl |
| C1-62 | H | CF3 | C—H | CF3 | CF3 | H | 2,2,2-trifluoroethyl |
| C1-63 | H | CF3 | C—H | CF3 | CF3 | H | 2-methoxyethyl |
| C1-64 | H | CF3 | C—H | CF3 | CF3 | H | (methylsulfanyl)methyl |
| C1-65 | H | CF3 | C—H | CF3 | CF3 | H | (methylsulfinyl)methyl |
| C1-66 | H | CF3 | C—H | CF3 | CF3 | H | (methylsulfonyl)methyl |
| C1-67 | H | Cl | C—H | Cl | Cl | H | tert-butoxy |
| C1-68 | H | Cl | C—Cl | Cl | Cl | H | tert-butoxy |
| C1-69 | H | CF3 | C—H | CF3 | Cl | H | tert-butoxy |
| C1-70 | H | Cl | C—H | Cl | CF3 | H | tert-butoxy |
| C1-71 | H | Cl | C—Cl | Cl | CF3 | H | tert-butoxy |
| C1-72 | H | CF3 | C—H | CF3 | CF3 | H | tert-butoxy |
| C1-73 | H | Cl | C—Cl | Cl | $CH_3$ | H | $CH_3$ |
| C1-74 | H | Cl | C—Cl | Cl | $CH_3$ | H | ethyl |
| C1-75 | H | Cl | C—Cl | Cl | $CH_3$ | H | n-propyl |
| C1-76 | H | Cl | C—Cl | Cl | $CH_3$ | H | isopropyl |
| C1-77 | H | Cl | C—Cl | Cl | $CH_3$ | H | cyclopropyl |
| C1-78 | H | Cl | C—Cl | Cl | $CH_3$ | H | cyclopropylmethyl |
| C1-79 | H | Cl | C—Cl | Cl | $CH_3$ | H | 2,2,2-trifluoroethyl |
| C1-80 | H | Cl | C—Cl | Cl | $CH_3$ | H | 2-methoxyethyl |
| C1-81 | H | Cl | C—Cl | Cl | $CH_3$ | H | (methylsulfanyl)methyl |
| C1-82 | H | Cl | C—Cl | Cl | $CH_3$ | H | (methylsulfinyl)methyl |
| C1-83 | H | Cl | C—Cl | Cl | $CH_3$ | H | (methylsulfonyl)methyl |
| C1-84 | H | CF3 | C—H | CF3 | $CH_3$ | H | $CH_3$ |
| C1-85 | H | CF3 | C—H | CF3 | $CH_3$ | H | ethyl |
| C1-86 | H | CF3 | C—H | CF3 | $CH_3$ | H | n-propyl |
| C1-87 | H | CF3 | C—H | CF3 | $CH_3$ | H | isopropyl |
| C1-88 | H | CF3 | C—H | CF3 | $CH_3$ | H | cyclopropyl |
| C1-89 | H | CF3 | C—H | CF3 | $CH_3$ | H | cyclopropylmethyl |
| C1-90 | H | CF3 | C—H | CF3 | $CH_3$ | H | 2,2,2-trifluoroethyl |
| C1-91 | H | CF3 | C—H | CF3 | $CH_3$ | H | 2-methoxyethyl |
| C1-92 | H | CF3 | C—H | CF3 | $CH_3$ | H | (methylsulfanyl)methyl |
| C1-93 | H | CF3 | C—H | CF3 | $CH_3$ | H | (methylsulfinyl)methyl |
| C1-94 | H | CF3 | C—H | CF3 | $CH_3$ | H | (methylsulfonyl)methyl |

TABLE C2

Compounds according to the invention

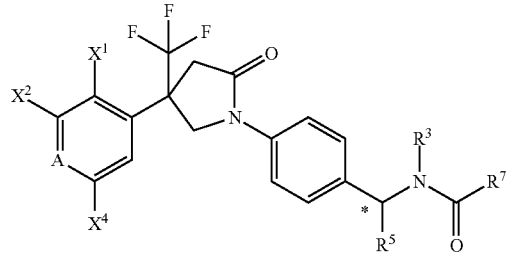

| Ex. No. | X¹ | X² | A | X⁴ | R³ | R⁵ | R⁷ |
|---|---|---|---|---|---|---|---|
| C2-1 | H | Cl | C—H | Cl | H | $CH_3$ | $CH_3$ |
| C2-2 | H | Cl | C—H | Cl | H | $CH_3$ | ethyl |
| C2-3 | H | Cl | C—H | Cl | H | $CH_3$ | n-propyl |
| C2-4 | H | Cl | C—H | Cl | H | $CH_3$ | isopropyl |
| C2-5 | H | Cl | C—H | Cl | H | $CH_3$ | cyclopropyl |
| C2-6 | H | Cl | C—H | Cl | H | $CH_3$ | cyclopropylmethyl |
| C2-7 | H | Cl | C—H | Cl | H | $CH_3$ | 2,2,2-trifluoroethyl |
| C2-8 | H | Cl | C—H | Cl | H | $CH_3$ | 2-methoxyethyl |
| C2-9 | H | Cl | C—H | Cl | H | $CH_3$ | (methylsulfanyl)methyl |
| C2-10 | H | Cl | C—H | Cl | H | $CH_3$ | (methylsulfinyl)methyl |

TABLE C2-continued

Compounds according to the invention

| Ex. No. | X¹ | X² | A | X⁴ | R³ | R⁵ | R⁷ |
|---|---|---|---|---|---|---|---|
| C2-11 | H | Cl | C—H | Cl | H | CH₃ | (methylsulfonyl)methyl |
| C2-12 | H | Cl | C—Cl | Cl | H | CH₃ | CH₃ |
| C2-13 | H | Cl | C—Cl | Cl | H | CH₃ | ethyl |
| C2-14 | H | Cl | C—Cl | Cl | H | CH₃ | n-propyl |
| C2-15 | H | Cl | C—Cl | Cl | H | CH₃ | isopropyl |
| C2-16 | H | Cl | C—Cl | Cl | H | CH₃ | cyclopropyl |
| C2-17 | H | Cl | C—Cl | Cl | H | CH₃ | cyclopropylmethyl |
| C2-18 | H | Cl | C—Cl | Cl | H | CH₃ | 2,2,2-trifluoroethyl |
| C2-19 | H | Cl | C—Cl | Cl | H | CH₃ | 2-methoxyethyl |
| C2-20 | H | Cl | C—Cl | Cl | H | CH₃ | (methylsulfanyl)methyl |
| C2-21 | H | Cl | C—Cl | Cl | H | CH₃ | (methylsulfinyl)methyl |
| C2-22 | H | Cl | C—Cl | Cl | H | CH₃ | (methylsulfonyl)methyl |
| C2-23 | H | CF3 | C—H | CF3 | H | CH₃ | CH₃ |
| C2-24 | H | CF3 | C—H | CF3 | H | CH₃ | ethyl |
| C2-25 | H | CF3 | C—H | CF3 | H | CH₃ | n-propyl |
| C2-26 | H | CF3 | C—H | CF3 | H | CH₃ | isopropyl |
| C2-27 | H | CF3 | C—H | CF3 | H | CH₃ | cyclopropyl |
| C2-27-b | H | CF3 | C—H | CF3 | H | CH₃ | cyclopropyl |
| C2-28 | H | CF3 | C—H | CF3 | H | CH₃ | cyclopropylmethyl |
| C2-29 | H | CF3 | C—H | CF3 | H | CH₃ | 2,2,2-trifluoroethyl |
| C2-30 | H | CF3 | C—H | CF3 | H | CH₃ | 2-methoxyethyl |
| C2-31 | H | CF3 | C—H | CF3 | H | CH₃ | (methylsulfanyl)methyl |
| C2-32 | H | CF3 | C—H | CF3 | H | CH₃ | (methylsulfinyl)methyl |
| C2-33 | H | CF3 | C—H | CF3 | H | CH₃ | (methylsulfonyl)methyl | a = (R)isomer
b = (S)isomer

TABLE C3

Compounds according to the invention

| Ex. No. | X¹ | X² | A | X⁴ | Y² | R³ | R⁷ |
|---|---|---|---|---|---|---|---|
| C3-1 | H | Cl | C—H | Cl | CF3 | H | CH₃ |
| C3-2 | H | Cl | C—H | Cl | CF3 | H | ethyl |
| C3-3 | H | Cl | C—H | Cl | CF3 | H | n-propyl |
| C3-4 | H | Cl | C—H | Cl | CF3 | H | isopropyl |
| C3-5 | H | Cl | C—H | Cl | CF3 | H | cyclopropyl |
| C3-6 | H | Cl | C—H | Cl | CF3 | H | cyclopropylmethyl |
| C3-7 | H | Cl | C—H | Cl | CF3 | H | 2,2,2-trifluoroethyl |
| C3-8 | H | Cl | C—H | Cl | CF3 | H | 2-methoxyethyl |
| C3-9 | H | Cl | C—H | Cl | CF3 | H | (methylsulfanyl)methyl |
| C3-10 | H | Cl | C—H | Cl | CF3 | H | (methylsulfinyl)methyl |
| C3-11 | H | Cl | C—H | Cl | CF3 | H | (methylsulfonyl)methyl |
| C3-12 | H | Cl | C—Cl | Cl | CF3 | H | CH₃ |
| C3-13 | H | Cl | C—Cl | Cl | CF3 | H | ethyl |
| C3-14 | H | Cl | C—Cl | Cl | CF3 | H | n-propyl |
| C3-15 | H | Cl | C—Cl | Cl | CF3 | H | isopropyl |

TABLE C3-continued

Compounds according to the invention

| Ex. No. | X¹ | X² | A | X⁴ | Y² | R³ | R⁷ |
|---|---|---|---|---|---|---|---|
| C3-16 | H | Cl | C—Cl | Cl | CF3 | H | cyclopropyl |
| C3-17 | H | Cl | C—Cl | Cl | CF3 | H | cyclopropylmethyl |
| C3-18 | H | Cl | C—Cl | Cl | CF3 | H | 2,2,2-trifluoroethyl |
| C3-19 | H | Cl | C—Cl | Cl | CF3 | H | 2-methoxyethyl |
| C3-20 | H | Cl | C—Cl | Cl | CF3 | H | (methylsulfanyl)methyl |
| C3-21 | H | Cl | C—Cl | Cl | CF3 | H | (methylsulfinyl)methyl |
| C3-22 | H | Cl | C—Cl | Cl | CF3 | H | (methylsulfonyl)methyl |
| C3-23 | H | CF3 | C—H | CF3 | CF3 | H | CH₃ |
| C3-24 | H | CF3 | C—H | CF3 | CF3 | H | ethyl |
| C3-25 | H | CF3 | C—H | CF3 | CF3 | H | n-propyl |
| C3-26 | H | CF3 | C—H | CF3 | CF3 | H | isopropyl |
| C3-27 | H | CF3 | C—H | CF3 | CF3 | H | cyclopropyl |
| C3-28 | H | CF3 | C—H | CF3 | CF3 | H | cyclopropylmethyl |
| C3-29 | H | CF3 | C—H | CF3 | CF3 | H | 2,2,2-trifluoroethyl |
| C3-30 | H | CF3 | C—H | CF3 | CF3 | H | 2-methoxyethyl |
| C3-31 | H | CF3 | C—H | CF3 | CF3 | H | (methylsulfanyl)methyl |
| C3-32 | H | CF3 | C—H | CF3 | CF3 | H | (methylsulfinyl)methyl |
| C3-33 | H | CF3 | C—H | CF3 | CF3 | H | (methylsulfonyl)methyl |

TABLE a1

Compounds of Formula (Int.)

| Ex. No. | X¹ | X² | A | X⁴ | Y² | T |
|---|---|---|---|---|---|---|
| a1-1 | H | Cl | C—H | Cl | Cl | aminomethyl |
| a1-2 | H | Cl | C—Cl | Cl | Cl | aminomethyl |
| a1-3 | H | CF3 | C—H | CF3 | Cl | aminomethyl |
| a1-4 | H | Cl | C—H | Cl | CF3 | aminomethyl |
| a1-5 | H | Cl | C—Cl | Cl | CF3 | aminomethyl |
| a1-6 | H | CF3 | C—H | CF3 | CF3 | aminomethyl |
| a1-7 | H | Cl | C—H | Cl | CH₃ | aminomethyl |
| a1-8 | H | Cl | C—H | Cl | ethyl | aminomethyl |
| a1-9 | H | Cl | C—H | Cl | F | aminomethyl |
| a1-10 | H | Cl | C—H | Cl | Br | aminomethyl |
| a1-11 | H | Cl | C—H | Cl | I | aminomethyl |
| a1-12 | H | Cl | C—Cl | Cl | CH₃ | aminomethyl |
| a1-13 | H | Cl | C—Cl | Cl | ethyl | aminomethyl |
| a1-14 | H | Cl | C—Cl | Cl | F | aminomethyl |
| a1-15 | H | Cl | C—Cl | Cl | Br | aminomethyl |
| a1-16 | H | Cl | C—Cl | Cl | I | aminomethyl |
| a1-17 | H | CF3 | C—H | CF3 | CH₃ | aminomethyl |
| a1-18 | H | CF3 | C—H | CF3 | ethyl | aminomethyl |
| a1-19 | H | CF3 | C—H | CF3 | F | aminomethyl |
| a1-20 | H | CF3 | C—H | CF3 | Br | aminomethyl |
| a1-21 | H | CF3 | C—H | CF3 | I | aminomethyl |
| a1-22 | H | F | C—H | Cl | CF3 | aminomethyl |
| a1-23 | H | Br | C—H | Br | CF3 | aminomethyl |

TABLE a1-continued

Compounds of Formula (Int.)

| Ex. No. | X¹ | X² | A | X⁴ | Y² | T |
|---|---|---|---|---|---|---|
| a1-24 | H | F | C—F | F | CF3 | aminomethyl |
| a1-25 | H | Cl | C—F | Cl | CF3 | aminomethyl |
| a1-26 | F | Cl | C—F | Cl | CF3 | aminomethyl |
| a1-27 | H | CF3 | C—H | H | CF3 | aminomethyl |
| a1-28 | H | CF3 | C—F | H | CF3 | aminomethyl |
| a1-29 | H | CF3 | C—H | F | CF3 | aminomethyl |
| a1-30 | H | CF3 | C—Cl | H | CF3 | aminomethyl |
| a1-31 | H | CF3 | C—H | Cl | CF3 | aminomethyl |
| a1-32 | H | CF3 | C—Cl | Cl | CF3 | aminomethyl |
| a1-33 | H | Cl | C—H | Cl | Cl | cyano |
| a1-34 | H | Cl | C—Cl | Cl | Cl | cyano |
| a1-35 | H | CF3 | C—H | CF3 | Cl | cyano |
| a1-36 | H | Cl | C—H | Cl | CF3 | cyano |
| a1-37 | H | Cl | C—Cl | Cl | CF3 | cyano |
| a1-38 | H | CF3 | C—H | CF3 | CF3 | cyano |
| a1-39 | H | Cl | C—H | Cl | CH3 | cyano |
| a1-40 | H | Cl | C—H | Cl | F | cyano |
| a1-41 | H | Cl | C—Cl | Cl | CH3 | cyano |
| a1-42 | H | Cl | C—Cl | Cl | F | cyano |
| a1-43 | H | CF3 | C—H | CF3 | CH3 | cyano |
| a1-44 | H | CF3 | C—H | CF3 | F | cyano |
| a1-45 | H | F | C—H | Cl | CF3 | cyano |
| a1-46 | H | F | C—F | F | CF3 | cyano |
| a1-47 | H | Cl | C—F | Cl | CF3 | cyano |
| a1-48 | F | Cl | C—F | Cl | CF3 | cyano |
| a1-49 | H | CF3 | C—H | H | CF3 | cyano |
| a1-50 | H | CF3 | C—F | H | CF3 | cyano |
| a1-51 | H | CF3 | C—H | F | CF3 | cyano |
| a1-52 | H | CF3 | C—Cl | H | CF3 | cyano |
| a1-53 | H | CF3 | C—H | Cl | CF3 | cyano |
| a1-54 | H | CF3 | C—Cl | Cl | CF3 | cyano |

TABLE a3

Compounds of Formula (Int.)

| Ex. No. | X¹ | X² | A | X⁴ | Y² | T |
|---|---|---|---|---|---|---|
| a3-1 | H | Cl | C—H | Cl | Cl | aminomethyl |
| a3-2 | H | Cl | C—Cl | Cl | Cl | aminomethyl |
| a3-3 | H | CF3 | C—H | CF3 | Cl | aminomethyl |
| a3-4 | H | Cl | C—H | Cl | Br | aminomethyl |
| a3-5 | H | Cl | C—Cl | Cl | Br | aminomethyl |
| a3-6 | H | CF3 | C—H | CF3 | Br | aminomethyl |
| a3-7 | H | Cl | C—H | Cl | CF3 | aminomethyl |
| a3-8 | H | Cl | C—Cl | Cl | CF3 | aminomethyl |
| a3-9 | H | CF3 | C—H | CF3 | CF3 | aminomethyl |
| a3-10 | H | Cl | C—H | Cl | CH3 | aminomethyl |
| a3-11 | H | Cl | C—Cl | Cl | CH3 | aminomethyl |

TABLE a3-continued

Compounds of Formula (Int.)

| Ex. No. | X¹ | X² | A | X⁴ | Y² | T |
|---|---|---|---|---|---|---|
| a3-12 | H | CF3 | C—H | CF3 | CH3 | aminomethyl |
| a3-13 | H | Cl | C—H | Cl | ethyl | aminomethyl |
| a3-14 | H | Cl | C—Cl | Cl | ethyl | aminomethyl |
| a3-15 | H | CF3 | C—H | CF3 | ethyl | aminomethyl |
| a3-16 | H | F | C—H | Cl | CF3 | aminomethyl |
| a3-17 | H | Br | C—H | Br | CF3 | aminomethyl |
| a3-18 | H | F | C—F | F | CF3 | aminomethyl |
| a3-19 | H | Cl | C—F | Cl | CF3 | aminomethyl |
| a3-20 | F | Cl | C—F | Cl | CF3 | aminomethyl |
| a3-21 | H | CF3 | C—H | H | CF3 | aminomethyl |
| a3-22 | H | CF3 | C—F | H | CF3 | aminomethyl |
| a3-23 | H | CF3 | C—H | F | CF3 | aminomethyl |
| a3-24 | H | CF3 | C—Cl | H | CF3 | aminomethyl |
| a3-25 | H | CF3 | C—H | Cl | CF3 | aminomethyl |
| a3-26 | H | CF3 | C—Cl | Cl | CF3 | aminomethyl |

TABLE b1

Compounds of Formula (Int.)

| Ex. No. | X¹ | X² | A | X⁴ | Y² | T |
|---|---|---|---|---|---|---|
| b1-1 | H | Cl | C—H | Cl | Cl | cyano |
| b1-2 | H | Cl | C—H | Cl | Cl | aminomethyl |
| b1-3 | H | Cl | C—Cl | Cl | Cl | cyano |
| b1-4 | H | Cl | C—Cl | Cl | Cl | aminomethyl |
| b1-5 | H | CF3 | C—H | CF3 | Cl | cyano |
| b1-6 | H | CF3 | C—H | CF3 | Cl | aminomethyl |
| b1-7 | H | Cl | C—H | Cl | CF3 | cyano |
| b1-8 | H | Cl | C—H | Cl | CF3 | aminomethyl |
| b1-9 | H | Cl | C—Cl | Cl | CF3 | cyano |
| b1-10 | H | Cl | C—Cl | Cl | CF3 | aminomethyl |
| b1-11 | H | CF3 | C—H | CF3 | CF3 | cyano |
| b1-12 | H | CF3 | C—H | CF3 | CF3 | aminomethyl |
| b1-13 | H | Cl | C—H | Cl | Cl | hydroxycarbonyl |
| b1-14 | H | Cl | C—H | Cl | Cl | methoxycarbonyl |
| b1-15 | H | Cl | C—Cl | Cl | Cl | hydroxycarbonyl |
| b1-16 | H | Cl | C—Cl | Cl | Cl | methoxycarbonyl |
| b1-17 | H | CF3 | C—H | CF3 | Cl | hydroxycarbonyl |
| b1-18 | H | CF3 | C—H | CF3 | Cl | methoxycarbonyl |
| b1-19 | H | Cl | C—H | Cl | CF3 | hydroxycarbonyl |
| b1-20 | H | Cl | C—H | Cl | CF3 | ethoxycarbonyl |
| b1-21 | H | Cl | C—Cl | Cl | CF3 | hydroxycarbonyl |
| b1-22 | H | Cl | C—Cl | Cl | CF3 | ethoxycarbonyl |
| b1-23 | H | CF3 | C—H | CF3 | CF3 | hydroxycarbonyl |
| b1-24 | H | CF3 | C—H | CF3 | CF3 | ethoxycarbonyl |

TABLE c1

Compounds of Formula (Int.)

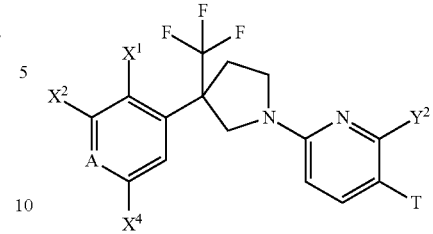

| Ex. No. | $X^1$ | $X^2$ | A | $X^4$ | $Y^2$ | T |
|---|---|---|---|---|---|---|
| c1-1 | H | Cl | C—H | Cl | Cl | cyano |
| c1-2 | H | Cl | C—H | Cl | Cl | aminomethyl |
| c1-3 | H | Cl | C—Cl | Cl | Cl | cyano |
| c1-4 | H | Cl | C—Cl | Cl | Cl | aminomethyl |
| c1-5 | H | CF3 | C—H | CF3 | Cl | cyano |
| c1-6 | H | CF3 | C—H | CF3 | Cl | aminomethyl |
| c1-7 | H | Cl | C—H | Cl | CF3 | cyano |
| c1-8 | H | Cl | C—H | Cl | CF3 | aminomethyl |
| c1-9 | H | Cl | C—Cl | Cl | CF3 | cyano |
| c1-10 | H | Cl | C—Cl | Cl | CF3 | aminomethyl |
| c1-11 | H | CF3 | C—H | CF3 | CF3 | cyano |
| c1-12 | H | CF3 | C—H | CF3 | CF3 | aminomethyl |
| c1-13 | H | Cl | C—H | Cl | Cl | hydroxycarbonyl |
| c1-14 | H | Cl | C—H | Cl | Cl | methoxycarbonyl |
| c1-15 | H | Cl | C—Cl | Cl | Cl | hydroxycarbonyl |
| c1-16 | H | Cl | C—Cl | Cl | Cl | methoxycarbonyl |
| c1-17 | H | CF3 | C—H | CF3 | Cl | hydroxycarbonyl |
| c1-18 | H | CF3 | C—H | CF3 | Cl | methoxycarbonyl |
| c1-19 | H | Cl | C—H | Cl | CF3 | hydroxycarbonyl |
| c1-20 | H | Cl | C—H | Cl | CF3 | ethoxycarbonyl |
| c1-21 | H | Cl | C—Cl | Cl | CF3 | hydroxycarbonyl |
| c1-22 | H | Cl | C—Cl | Cl | CF3 | ethoxycarbonyl |
| c1-23 | H | CF3 | C—H | CF3 | CF3 | hydroxycarbonyl |
| c1-24 | H | CF3 | C—H | CF3 | CF3 | ethoxycarbonyl |

TABLE i

| Ex. No. | $X^1$ | $X^2$ | A | $X^4$ | $Y^2$ | T |
|---|---|---|---|---|---|---|
| i-1 | H | Cl | C—H | Cl | Br | H |
| i-2 | H | Cl | C—Cl | Cl | Br | H |
| i-3 | H | CF3 | C—H | CF3 | Br | H |
| i-4 | H | Cl | C—H | Cl | I | H |
| i-5 | H | Cl | C—Cl | Cl | I | H |
| i-6 | H | CF3 | C—H | CF3 | I | H |
| i-7 | H | Cl | C—H | Cl | Br | formyl |
| i-8 | H | Cl | C—Cl | Cl | Br | formyl |
| i-9 | H | CF3 | C—H | CF3 | Br | formyl |
| i-10 | H | Cl | C—H | Cl | I | formyl |
| i-11 | H | Cl | C—Cl | Cl | I | formyl |
| i-12 | H | CF3 | C—H | CF3 | I | formyl |

TABLE iii

| Ex. No. | $X^1$ | $X^2$ | A | $X^4$ | $Y^2$ | T |
|---|---|---|---|---|---|---|
| iii-1 | H | Cl | C—H | Cl | CH3 | H |
| iii-2 | H | Cl | C—Cl | Cl | CH3 | H |
| iii-3 | H | CF3 | C—H | CF3 | CH3 | H |
| iii-4 | H | Cl | C—H | Cl | ethyl | H |
| iii-5 | H | Cl | C—Cl | Cl | ethyl | H |
| iii-6 | H | CF3 | C—H | CF3 | ethyl | H |
| iii-7 | H | Cl | C—H | Cl | Br | H |
| iii-8 | H | Cl | C—Cl | Cl | Br | H |
| iii-9 | H | CF3 | C—H | CF3 | Br | H |
| iii-10 | H | Cl | C—H | Cl | CH3 | Br |
| iii-11 | H | Cl | C—Cl | Cl | CH3 | Br |
| iii-12 | H | CF3 | C—H | CF3 | CH3 | Br |
| iii-13 | H | Cl | C—H | Cl | ethyl | Br |
| iii-14 | H | Cl | C—Cl | Cl | ethyl | Br |
| iii-15 | H | CF3 | C—H | CF3 | ethyl | Br |
| iii-16 | H | Cl | C—H | Cl | Br | formyl |
| iii-17 | H | Cl | C—Cl | Cl | Br | formyl |
| iii-18 | H | CF3 | C—H | CF3 | Br | formyl |

TABLE A1a

Compounds of Formula (II) for the preparation of compounds as given under the respective 3-digit number in table A1

| Ex. No. | $X^1$ | $X^2$ | A | $X^4$ | $Y^1$ | $Y^2$ | $Y^4$ | $R^3$ | $R^7$ |
|---|---|---|---|---|---|---|---|---|---|
| A1a-85 | H | Cl | C—H | Cl | H | ethyl | H | H | ethyl |
| A1a-140 | H | Cl | C—Cl | Cl | H | ethyl | H | H | ethyl |
| A1a-176 | H | Cl | C—Cl | Cl | H | I | H | H | cyclopropyl |
| A1a-195 | H | CF3 | C—H | CF3 | H | ethyl | H | H | ethyl |
| A1a-198 | H | CF3 | C—H | CF3 | H | ethyl | H | H | cyclopropyl |
| A1a-286 | F | Cl | C—F | Cl | H | CF3 | H | H | cyclopropyl |
| A1a-316 | H | CF3 | C—H | F | H | CF3 | H | H | ethyl |
| A1a-319 | H | CF3 | C—H | F | H | CF3 | H | H | cyclopropyl |
| A1a-348 | H | CF3 | C—Cl | Cl | H | CF3 | H | H | CH3 |
| A1a-349 | H | CF3 | C—Cl | Cl | H | CF3 | H | H | ethyl |
| A1a-352 | H | CF3 | C—Cl | Cl | H | CF3 | H | H | cyclopropyl |
| A1a-367 | H | CF3 | C—H | Cl | H | CF3 | H | H | methylamino |
| A1a-377 | H | Cl | C—H | Cl | H | H | H | H | cyclopropyl-methyl |
| A1a-398 | H | CF3 | C—H | CF3 | H | H | H | H | cyclopropyl |
| A1a-405 | F | Cl | C—H | Cl | H | CF3 | H | H | CH3 |
| A1a-481 | H | Cl | C—Cl | Cl | H | Cl | F | H | cyclopropyl |
| A1a-505 | H | Cl | C—Cl | Cl | H | CH3 | F | H | cyclopropyl |
| A1a-518 | H | Cl | C—Cl | Cl | F | CF3 | H | H | cyclopropyl-methyl |
| A1a-176 | H | Cl | C—Cl | Cl | H | I | H | H | cyclopropyl |
| A1a-264 | H | F | C—F | F | H | CF3 | H | H | cyclopropyl |
| A1a-376 | H | Cl | C—H | Cl | H | H | H | H | cyclopropyl |
| A1a-387 | H | Cl | C—Cl | Cl | H | H | H | H | cyclopropyl |
| A1a-388 | H | Cl | C—Cl | Cl | H | H | H | H | cyclopropyl- |

TABLE A1a-continued

Compounds of Formula (II) for the preparation of compounds as given under the respective 3-digit number in table A1

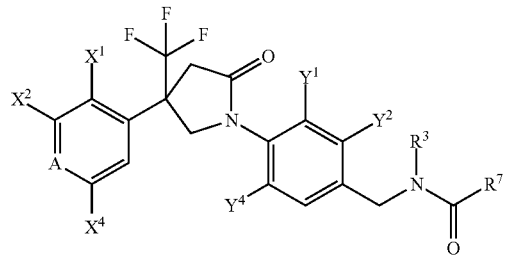

| Ex. No. | X¹ | X² | A | X⁴ | Y¹ | Y² | Y⁴ | R³ | R⁷ |
|---|---|---|---|---|---|---|---|---|---|
| A1a-555 | F | Cl | C—F | Cl | H | H | H | H | methyl n-propyl |
| A1a-557 | F | Cl | C—F | Cl | H | H | H | H | cyclopropyl |
| A1a-558 | F | Cl | C—F | Cl | H | H | H | H | cyclopropylmethyl |

TABLE A2a

Compounds of Formula (II) for the preparation of compounds as given under the respective 3-digit number in table A2

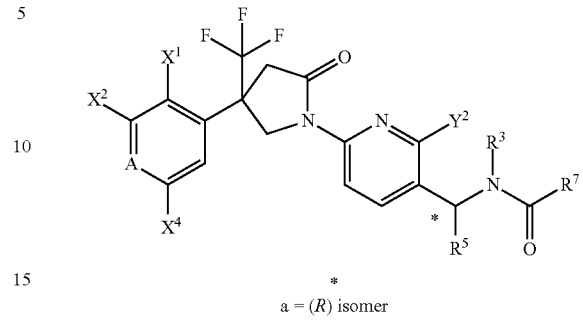

a = (R) isomer
b = (S) isomer

| Ex. No. | X¹ | X² | A | X⁴ | R³ | R⁵ | R⁷ |
|---|---|---|---|---|---|---|---|
| A2a-5 | H | Cl | C—H | Cl | H | CH3 | cyclopropyl |
| A2a-6 | H | Cl | C—H | Cl | H | CH3 | cyclopropylmethyl |
| A2a-16 | H | Cl | C—Cl | Cl | H | CH3 | cyclopropyl |
| A2a-49 | F | Cl | C—F | Cl | H | CH3 | cyclopropyl |
| A2a-50 | F | Cl | C—F | Cl | H | CH3 | cyclopropylmethyl |

TABLE A3a

Compounds of Formula (II) for the preparation of compounds as given under the respective 3-digit number in table A3

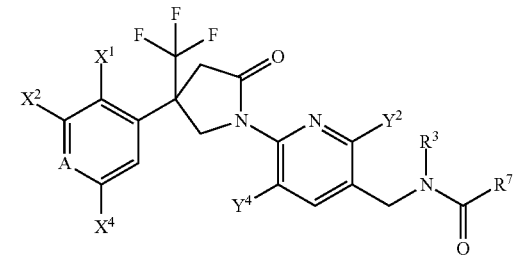

| Ex. No. | X¹ | X² | A | X⁴ | Y² | Y⁴ | R³ | R² |
|---|---|---|---|---|---|---|---|---|
| A3a-1 | H | Cl | C—H | Cl | CF3 | H | H | CH3 |
| A3a-6 | H | Cl | C—H | Cl | CF3 | H | H | cyclopropylmethyl |
| A3a-7 | H | Cl | C—H | Cl | CF3 | H | H | 2,2,2-trifluoroethyl |
| A3a-11 | H | Cl | C—H | Cl | CF3 | H | H | (methylsulfonyl)methyl |
| A3a-12 | H | Cl | C—Cl | Cl | CF3 | H | H | CH3 |
| A3a-14 | H | Cl | C—Cl | Cl | CF3 | H | H | n-propyl |
| A3a-15 | H | Cl | C—Cl | Cl | CF3 | H | H | isopropyl |
| A3a-16 | H | Cl | C—Cl | Cl | CF3 | H | H | cyclopropyl |
| A3a-19 | H | Cl | C—Cl | Cl | CF3 | H | H | 2-methoxyethyl |
| A3a-23 | H | CF3 | C—H | CF3 | CF3 | H | H | CH3 |
| A3a-33 | H | CF3 | C—H | CF3 | CF3 | H | H | (methylsulfonyl)methyl |
| A3a-79 | H | Cl | C—Cl | Cl | CH3 | H | H | ethyl |
| A3a-82 | H | Cl | C—Cl | Cl | CH3 | H | H | cyclopropyl |
| A3a-84 | H | Cl | C—Cl | Cl | CH3 | H | H | 2,2,2-trifluoroethyl |
| A3a-93 | H | Cl | C—Cl | Cl | ethyl | H | H | cyclopropyl |
| A3a-100 | H | Cl | C—Cl | Cl | Cl | H | H | CH3 |
| A3a-102 | H | Cl | C—Cl | Cl | Cl | H | H | n-propyl |
| A3a-104 | H | Cl | C—Cl | Cl | Cl | H | H | cyclopropyl |
| A3a-106 | H | Cl | C—Cl | Cl | Cl | H | H | 2,2,2-trifluoroethyl |
| A3a-108 | H | Cl | C—Cl | Cl | Cl | H | H | (methylsulfanyl)methyl |
| A3a-109 | H | Cl | C—Cl | Cl | Cl | H | H | (methylsulfinyl)methyl |
| A3a-110 | H | Cl | C—Cl | Cl | Cl | H | H | (methylsulfonyl)methyl |
| A3a-115 | H | Cl | C—Cl | Cl | Br | H | H | cyclopropyl |
| A3a-120 | H | Cl | C—Cl | Cl | Br | H | H | (methylsulfinyl)methyl |
| A3a-121 | H | Cl | C—Cl | Cl | Br | H | H | (methylsulfonyl)methyl |
| A3a-122 | H | CF3 | C—H | CF3 | CH3 | H | H | CH3 |
| A3a-123 | H | CF3 | C—H | CF3 | CH3 | H | H | ethyl |
| A3a-126 | H | CF3 | C—H | CF3 | CH3 | H | H | cyclopropyl |
| A3a-127 | H | CF3 | C—H | CF3 | CH3 | H | H | cyclopropylmethyl |
| A3a-128 | H | CF3 | C—H | CF3 | CH3 | H | H | 2,2,2-trifluoroethyl |

TABLE A3a-continued

Compounds of Formula (II) for the preparation of compounds as given under the respective 3-digit number in table A3

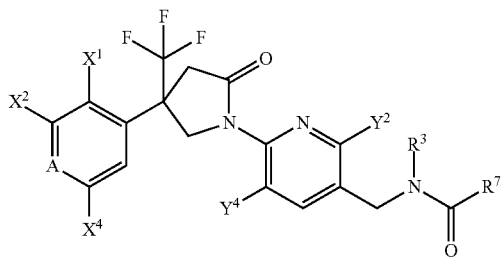

| Ex. No. | X$^1$ | X$^2$ | A | X$^4$ | Y$^2$ | Y$^4$ | R$^3$ | R$^2$ |
|---|---|---|---|---|---|---|---|---|
| A3a-130 | H | CF3 | C—H | CF3 | CH3 | H | H | (methylsulfanyl)methyl |
| A3a-131 | H | CF3 | C—H | CF3 | CH3 | H | H | (methylsulfinyl)methyl |
| A3a-132 | H | CF3 | C—H | CF3 | CH3 | H | H | (methylsulfonyl)methyl |
| A3a-133 | H | CF3 | C—H | CF3 | ethyl | H | H | CH3 |
| A3a-134 | H | CF3 | C—H | CF3 | ethyl | H | H | ethyl |
| A3a-137 | H | CF3 | C—H | CF3 | ethyl | H | H | cyclopropyl |
| A3a-138 | H | CF3 | C—H | CF3 | ethyl | H | H | cyclopropylmethyl |
| A3a-141 | H | CF3 | C—H | CF3 | ethyl | H | H | (methylsulfanyl)methyl |
| A3a-142 | H | CF3 | C—H | CF3 | ethyl | H | H | (methylsulfinyl)methyl |
| A3a-143 | H | CF3 | C—H | CF3 | ethyl | H | H | (methylsulfonyl)methyl |
| A3a-154 | H | CF3 | C—H | CF3 | Cl | H | H | (methylsulfonyl)methyl |
| A3a-157 | H | CF3 | C—H | CF3 | Br | H | H | n-propyl |
| A3a-160 | H | CF3 | C—H | CF3 | Br | H | H | cyclopropylmethyl |
| A3a-167 | H | F | C—H | Cl | CF3 | H | H | ethyl |
| A3a-170 | H | F | C—H | Cl | CF3 | H | H | cyclopropyl |
| A3a-210 | F | Cl | C—F | Cl | CF3 | H | H | CH3 |
| A3a-211 | F | Cl | C—F | Cl | CF3 | H | H | ethyl |
| A3a-214 | F | Cl | C—F | Cl | CF3 | H | H | cyclopropyl |
| A3a-226 | H | CF3 | C—H | H | CF3 | H | H | cyclopropylmethyl |
| A3a-233 | H | CF3 | C—F | H | CF3 | H | H | ethyl |
| A3a-244 | H | CF3 | C—H | F | CF3 | H | H | ethyl |
| A3a-265 | H | CF3 | C—H | Cl | CF3 | H | H | CH3 |
| A3a-271 | H | CF3 | C—H | Cl | CF3 | H | H | 2,2,2-trifluoroethyl |
| A3a-275 | H | CF3 | C—H | Cl | CF3 | H | H | (methylsulfonyl)methyl |
| A3a-288 | H | Cl | C—Cl | Cl | CF3 | H | H | iso-butyl |
| A3a-297 | H | Cl | C—Cl | Cl | CF3 | H | H | ethylamino |
| A3a-322 | F | Cl | C—F | Cl | Br | H | H | CH3 |
| A3a-323 | F | Cl | C—F | Cl | Br | H | H | ethyl |
| A3a-326 | F | Cl | C—F | Cl | Br | H | H | cyclopropyl |
| A3a-355 | H | Cl | C—H | Cl | Cl | F | H | CH3 |
| Aa3-366 | H | Cl | C—Cl | Cl | Cl | F | H | CH3 |
| A3a-371 | H | Cl | C—Cl | Cl | Cl | F | H | cyclopropylmethyl |
| A3a-373 | H | Cl | C—Cl | Cl | Cl | F | H | 2-methoxyethyl |
| A3a-421 | H | Cl | C—Cl | Cl | CF3 | H | H | cyanomethyl |
| A3a-424 | H | Cl | C—Cl | Cl | CF3 | H | prop-1-en-2-yl | cyclopropyl |
| A3a-425 | H | Cl | C—Cl | Cl | CF3 | H | H | 2-(2,6-Cl$_2$-phenyl)-ethyl |
| A3a-426 | H | Cl | C—Cl | Cl | CF3 | H | prop-1-en-2-yl | 1-CF$_3$-cyclopropyl |

TABLE A4a

Compounds of Formula (II) for the preparation of compounds as given under the respective 3-digit number in table A4

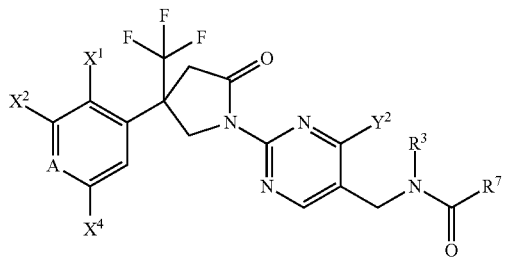

| Ex. No. | X⁴ | X² | A | X⁴ | Y² | R³ | R⁷ |
|---|---|---|---|---|---|---|---|
| A4a-30 | H | CF3 | C—H | CF3 | CF3 | H | 2-methoxyethyl |
| A4a-111 | F | Cl | C—F | Cl | CF3 | H | CH₃ |
| A4a-112 | F | Cl | C—F | Cl | CF3 | H | ethyl |
| A4a-115 | F | Cl | C—F | Cl | CF3 | H | cyclopropyl |
| A4a-201 | H | Cl | C—H | Cl | CF3 | H | (dimethylamino)methyl |
| A4a-203 | H | Cl | C—H | Cl | CF3 | H | 1-(tert-butoxycarbonyl)pyrrolidin-2-yl |
| A4a-216 | H | Cl | C—Cl | Cl | CHF2 | H | ethyl |
| A4a-219 | H | Cl | C—Cl | Cl | CHF2 | H | cyclopropyl |
| A4a-221 | H | Cl | C—Cl | Cl | CHF2 | H | 2,2,2-trifluoroethyl |
| A4a-252 | H | CF3 | C—H | CF3 | Cl | H | cyclopropyl |
| A4a-435 | H | Cl | C—H | Cl | CF3 | H | cyanomethyl |

TABLE A5a

Compounds of Formula (II) for the preparation of compounds as given under the respective 3-digit number in table A5

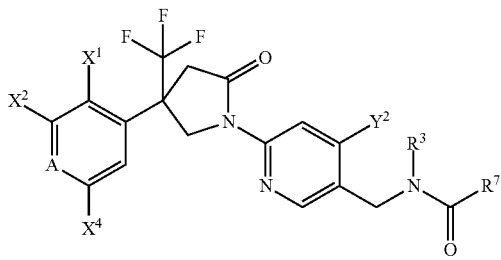

| Ex. No. | X¹ | X² | A | X⁴ | Y² | R³ | R⁷ |
|---|---|---|---|---|---|---|---|
| A5a-29 | H | CF3 | C—H | CF3 | CF3 | H | 2,2,2-trifluoroethyl |
| A5a-33 | H | CF3 | C—H | CF3 | CF3 | H | (methylsulfonyl)methyl |
| A5a-78 | F | Cl | C—F | Cl | CF3 | H | CH₃ |

TABLE A5a-continued

Compounds of Formula (II) for the preparation of compounds as given under the respective 3-digit number in table A5

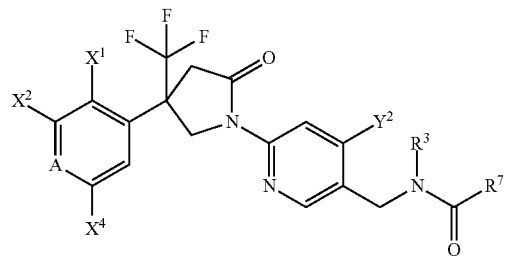

| Ex. No. | X¹ | X² | A | X⁴ | Y² | R³ | R⁷ |
|---|---|---|---|---|---|---|---|
| A5a-79 | F | Cl | C—F | Cl | CF3 | H | ethyl |
| A5a-82 | F | Cl | C—F | Cl | CF3 | H | cyclopropyl |

NMR Table:

The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1-002 | $^1$H-NMR (CDCl$_3$) δ: 1.14 (3H, t), 2.19 (2H, q), 2.76-2.82 (2H, m), 3.44-3.60 (3H, m), 4.34-4.50 (2H, m), 5.70-5.90 (2H, m), 6.60-7.42 (6H, m). |
| a1-004 | $^1$H-NMR (CDCl$_3$) δ: 1.92 (2H, br s), 2.53-2.63 (1H, m), 2.84-2.98 (1H, m), 3.50-4.18 (6H, m), 6.70-7.67 (6H, m). |
| A1-005 | $^1$H-NMR (CDCl$_3$) δ: 0.68-0.74 (2H, m), 0.89-0.98 (2H, m), 1.25-1.34 (1H, m), 2.75-4.51 (7H, m), 5.70-6.08 (2H, m), 6.66-7.60 (6H, m). |
| A1-007 | $^1$H-NMR (CDCl$_3$) δ: 2.73-3.14 (4H, m), 3.58-3.63 (2H, m), 4.40-4.54 (3H, m), 5.70-6.18 (2H, m), 6.67-7.59 (6H, m). |
| A1-008 | $^1$H-NMR (CDCl$_3$) δ: 2.41-4.49 (14H, m), 5.70-5.85 (1H, m), 6.68-7.42 (7H, m). |
| A1-012 | $^1$H-NMR (CDCl$_3$) δ: 1.94 (3H, s), 2.74-2.90 (2H, m), 3.56-3.59 (2H, m), 4.39 (2H, d), 5.85 (1H, d), 5.97 (1H, d), 6.72 (1H, dd), 6.80 (1H, d), 7.19 (1H, dd), 7.46 (2H, s). |
| A1-013 | $^1$H-NMR (CDCl$_3$) δ: 1.13 (3H, t), 2.18 (2H, q), 2.77-2.80 (2H, m), 3.60-3.61 (2H, m), 4.42 (2H, d), 5.84 (1H, s), 6.70 (1H, dd), 6.83 (1H, d), 7.21-7.26 (1H, m), 7.47 (2H, s). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1-016 | $^1$H NMR (CDCl$_3$) δ: 0.71-0.74 (2H, m), 0.89-0.94 (2H, m), 1.30-1.35 (1H, m), 2.78-2.81 (2H, m), 3.58-3.61 (2H, m), 4.43 (2H, d), 5.81 (1H, s), 6.03 (1H, t, J = 10.0 Hz), 6.66-6.72 (1H, m), 6.83 (1H, d), 7.24-7.26 (1H, m), 7.45 (2H, s). |
| A1-018 | $^1$H NMR (CDCl$_3$)δ: 2.75-2.81 (1H, m), 3.05-3.17 (3H, m), 3.53-3.65 (2H, m), 4.42 (2H, d), 5.83 (1H, s), 6.26 (1H, t), 6.67-6.70 (1H, m), 6.86 (1H, dd), 7.22 (1H, d), 7.45 (2H, s). |
| A1-023 | $^1$H-NMR (CDCl$_3$) δ: 1.91 (3H, s), 2.79-2.99 (2H, m), 3.61-3.66 (2H, m), 4.39 (2H, d), 5.98-6.03 (2H, m), 6.77 (1H, dd), 6.81 (1H, d), 7.22 (1H, d), 7.89 (3H, s). |
| A1-024 | $^1$H-NMR (acetone-d$_6$) δ: 1.07 (3H, t), 2.20 (2H, q), 2.93-3.04 (1H, m), 3.14-3.21 (1H, m), 3.63-3.68 (2H, m), 4.36 (2H, d), 5.16 (1H, d), 6.27 (1H, d), 6.81 (1H, dd), 6.94 (1H, d), 7.27-7.21 (2H, m), 8.08 (1H, s), 8.21 (2H, s). |
| A1-027 | $^1$H-NMR (CDCl$_3$) δ: 0.66-0.73 (2H, m), 0.81-0.86 (2H, m), 1.28-1.36 (1H, m), 2.79-2.98 (2H, m), 3.59-3.65 (2H, m), 4.39 (2H, d), 5.92 (1H, d), 6.11 (1H, t), 6.68 (1H, dd), 6.82 (1H, d), 7.17 (1H, d), 7.88 (3H, s). |
| A1-030 | $^1$H-NMR (CDCl$_3$) δ: 2.36 (3H, t), 2.84-2.97 (2H, m), 3.30 (3H, s), 3.52 (2H, t), 3.59-3.64 (2H, m), 4.36 (2H, d), 4.84 (1H, d), 5.97 (1H, d), 6.70 (1H, dd), 6.81 (1H, d), 6.86 (1H, t), 7.12 (1H, d), 7.88 (1H, s), 7.90 (2H, s). |
| A1-031 | $^1$H-NMR (CDCl$_3$) δ: 2.06 (3H, s), 2.77-3.01 (2H, m), 3.15 (2H, s), 3.63-3.68 (2H, m), 4.44 (2H, d), 5.96 (1H, d), 6.72 (1H, dd), 6.86 (1H, d), 7.23 (1H, d), 7.34 (1H, t), 7.88-7.90 (4H, m). |
| A1-032 | $^1$H-NMR (CDCl$_3$) δ: 2.58 (3H, s), 2.76-2.98 (2H, m), 3.18-3.24 (2H, m), 3.57-3.65 (2H, m), 4.43 (2H, d), 5.91 (1H, d), 6.66 (1H, dd), 6.85 (1H, t), 7.18 (1H, t), 7.24 (1H, d), 7.88 (3H, d). |
| A1-033 | $^1$H-NMR (CDCl$_3$) δ: 2.75-3.00 (5H, m), 3.47 (1H, d), 3.58-3.64 (2H, m), 3.74 (2H, s), 4.40 (2H, d), 5.93 (1H, d), 6.68 (1H, dd), 6.84 (1H, d), 7.02 (1H, t), 7.21 (1H, d), 7.87-7.89 (3H, m). |
| A1-034 | $^1$H-NMR (CDCl$_3$) δ: 1.96 (3H, s), 2.80-2.85 (2H, m), 3.63-3.70 (3H, m), 4.44-4.51 (2H, m), 5.74-5.92 (2H, m), 6.93-7.46 (6H, m). |
| A1-035 | $^1$H-NMR (CDCl$_3$) δ: 1.08 (3H, t), 2.17 (2H, q), 2.78-2.85 (2H, m), 3.62-3.68 (3H, m), 4.43-4.50 (2H, m), 5.75-5.92 (2H, m), 6.91-7.43 (6H, m). |
| A1-036 | $^1$H-NMR (CDCl$_3$) δ: 0.91 (3H, t), 156-1.64 (2H, m), 2.10-2.16 (2H, m), 2.81-4.50 (7H, m), 5.76-5.91 (3H, m), 6.80-7.43 (6H, m). |
| A1-038 | $^1$H-NMR (CDCl$_3$) δ: 0.69-0.75 (2H, m), 0.88-0.94 (2H, m), 1.32-1.61 (1H, m), 2.78-4.49 (6H, m), 5.71-5.98 (3H, m), 6.85-7.43 (6H, m). |
| a1-038 | $^1$H-NMR (CDCl$_3$) δ: 2.83-3.15 (2H, m), 3.76-3.82 (2H, m), 6.03 (1H, d), 7.03 (1H, dd), 7.16 (1H, d), 7.67 (1H, d), 7.88 (2H, s), 7.93 (1H, s). |
| A1-039 | $^1$H-NMR (CDCl$_3$) δ: 0.12-0.16 (2H, m), 0.54-0.60 (2H, m), 0.80-0.90 (1H, m), 2.04-2.14 (2H, m), 2.81-2.85 (1H, m), 3.63-3.70 (2H, m), 4.47-4.54 (2H, m), 5.75-6.35 (2H, m), 6.93-7.43 (6H, m) |
| A1-040 | $^1$H-NMR (CDCl$_3$) δ: 2.50-3.30 (5H, m), 3.62-3.69 (2H, m), 4.49-4.54 (2H, m), 5.71-6.10 (2H, m), 6.88-7.42 (6H, m). |
| A1-041 | $^1$H-NMR (CDCl$_3$) δ: 2.43-2.90 (4H, m), 3.31-3.66 (8H, m), 4.52 (1H, d), 5.88 (1H, d), 6.60-7.48 (7H, m). |
| A1-042 | $^1$H-NMR (CDCl$_3$) δ: 2.04 (3H, s), 2.65-2.85 (2H, m), 3.14-3.17 (3H, m), 3.63-3.69 (2H, m), 4.47-4.54 (2H, m), 5.75-7.43 (7H, m). |
| a1-042 | $^1$H-NMR (CDCl$_3$) δ: 2.72-2.89 (2H, m), 3.63-3.69 (2H, m), 5.85 (1H, s), 6.57-6.65 (2H, m), 7.44-7.39 (3H, m). |
| A1-043 | $^1$H-NMR (CDCl$_3$) δ: 2.58-2.63 (5H, m), 2.75-2.83 (1H, m), 3.22-3.25 (1H, m), 3.55-3.76 (3H, m), 4.51-4.55 (2H, m), 5.70-5.86 (2H, m), 6.89-7.43 (6H, m). |
| a1-043 | $^1$H-NMR (CDCl$_3$) δ: 2.51 (3H, s), 2.81-2.90 (2H, m), 3.68-3.74 (2H, m), 6.00 (1H, d), 6.74-6.69 (2H, m), 7.48 (1H, d), 7.87 (2H, s), 7.91 (1H, s). |
| A1-044 | $^1$H-NMR (CDCl$_3$) δ: 2.65-3.04 (5H, m), 3.63-3.83 (4H, m), 4.55-4.58 (3H, m), 5.65-5.80 (1H, m), 6.69-7.46 (6H, m). |
| a1-044 | $^1$H-NMR (CDCl$_3$) δ: 2.80-2.91 (1H, m), 2.97-3.06 (1H, m), 3.38 (1H, d), 3.67-3.73 (2H, m), 5.97 (1H, d), 6.70-6.60 (2H, m), 7.43 (1H, t), 7.86 (2H, s), 7.92 (1H, s). |
| A1-045 | $^1$H-NMR (CDCl$_3$) δ: 1.95 (3H, s), 2.77-2.83 (2H, m), 3.63-3.66 (3H, m), 4.49 (2H, d), 5.74-5.91 (2H, m), 7.01-7.03 (2H, m), 7.37-7.57 (3H, m). |
| A1-046 | $^1$H-NMR (DMSO-d$_6$) δ: 1.02 (3H, t), 2.15 (2H, q), 2.72-2.75 (1H, m), 2.89-2.92 (1H, m), 3.47-3.51 (2H, m), 4.31 (2H, d), 5.98-6.01 (2H, m), 7.02 (1H, d), 7.10 (1H, s), 7.34 (1H, d), 7.79 (2H, s), 8.16 (1H, br s). |
| a1-046 | $^1$H-NMR (CDCl$_3$) δ: 2.66-3.03 (2H, m), 3.21 (1H, d), 3.67-3.74 (2H, m), 5.87 (1H, d), 6.86-7.24 (4H, m), 7.63 (1H, d). |
| a1-047 | $^1$H-NMR (CDCl$_3$) δ: 2.59 (1H, d), 2.73-2.95 (2H, m), 3.72 (2H, dd), 5.88 (1H, d), 6.99 (1H, dd), 7.13 (1H, d), 7.39 (2H, d), 7.66 (1H, d). |
| a1-048 | $^1$H-NMR (CDCl$_3$) δ: 2.77-3.02 (3H, m), 3.72-3.67 (2H, m), 6.09 (1H, dd), 6.99 (1H, dd), 7.09 (1H, d), 7.30 (1H, t), 7.67 (1H, d). |
| A1-049 | $^1$H-NMR (CDCl$_3$) δ: 0.71-0.75 (2H, m), 0.88-0.93 (2H, m), 1.25-1.31 (1H, m), 2.80-2.82 (2H, m), 3.63-3.66 (2H, m), 4.51 (2H, d), 5.85 (1H, s), 5.92-5.96 (1H, m), 6.95 (1H, d), 7.02 (1H, s), 7.42 (1H, d), 7.46 (2H, s). |
| a1-049 | $^1$H-NMR (CDCl$_3$) δ: 2.59 (1H, d), 2.80-3.06 (2H, m), 3.69-3.78 (2H, m), 5.98 (1H, d), 7.01 (1H, dd), 7.15 (1H, d), 7.55-7.78 (5H, m). |
| a1-050 | $^1$H-NMR (CDCl$_3$) δ: 2.69-3.04 (2H, m), 3.28 (1H, d, J = 7.7 Hz), 3.70-3.74 (2H, m), 5.79-5.95 (1H, m), 6.89-7.03 (1H, m), 7.10-7.16 (1H, m), 7.24-7.30 (1H, m), 7.52-7.66 (3H, m). |
| A1-051 | $^1$H-NMR (CDCl$_3$) δ: 2.73-2.82 (2H, m), 3.06 (2H, q), 3.64-3.67 (2H, m), 4.55 (2H, d), 5.85 (1H, d), 6.00-6.03 (1H, m), 6.96 (1H, d), 7.06 (1H, s), 7.43-7.46 (3H, m). |
| a1-053 | $^1$H-NMR (CDCl$_3$) δ: 2.79-3.05 (3H, m), 3.71-3.77 (2H, m), 5.96 (1H, d), 7.01 (1H, dd), 7.14 (1H, d), 7.57-7.67 (4H, m). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1-055 | $^1$H-NMR (CDCl$_3$) δ: 2.77-2.83 (2H, m), 3.03 (3H, s), 3.63-3.66 (2H, m), 3.82 (2H, s), 4.56 (2H, d), 5.85 (1H, d), 6.69-6.72 (1H, m), 6.95 (1H, d), 7.06 (1H, s), 7.43-7.46 (3H, m). |
| A1-056 | $^1$H NMR (CDCl$_3$) δ: 1.93 (3H, s), 2.87-2.99 (2H, m), 3.68-3.74 (2H, m), 4.29 (1H, d), 4.49-4.51 (2H, m), 5.86 (1H, t), 6.05 (1H, d), 7.02-7.07 (2H, m), 7.44 (1H, d), 7.88-7.91 (3H, m). |
| A1-057 | $^1$H NMR (CDCl$_3$)δ: 1.26 (3H, t), 2.17 (2H, q), 2.89-2.98 (2H, m), 3.65-3.73 (2H, m), 3.95 (1H, d), 4.50 (2H, d), 5.83 (1H, t), 6.03 (1H, d), 7.02-7.03 (2H, m), 7.39-7.40 (1H, m), 7.88-7.91 (3H, m). |
| A1-060 | $^1$H NMR (CDCl$_3$) δ: 0.69-0.73 (2H, m), 0.89-0.93 (2H, m), 1.25-1.31 (1H, m), 2.86-2.99 (2H, m), 3.68 (2H, d), 4.50 (2H, d), 5.95-5.98 (2H, m), 6.92-7.03 (2H, m), 7.39 (1H, d), 7.87-7.90 (3H, m). |
| A1-068 | $^1$H NMR (CDCl$_3$) δ: 1.42 (9H, s), 2.67-2.86 (2H, m), 3.59-3.61 (2H, m), 4.25 (2H, d), 4.92 (1H, t), 5.79 (1H, d), 6.66 (1H, d), 6.82 (1H, s), 7.20 (1H, d), 7.46 (2H, s). |
| A1-069 | $^1$H-NMR (CDCl$_3$) δ: 1.33 (9H, s), 2.85-2.97 (2H, m), 3.62 (2H, br s), 4.12 (2H, d), 4.92 (1H, br s), 5.89 (1H, d), 6.62 (1H, d), 6.81 (1H, s), 7.04 (1H, d), 7.89 (3H, s). |
| A1-070 | $^1$H-NMR (CDCl$_3$) δ: 1.45 (9H, s), 2.78-4.80 (8H, m), 5.86 (1H, d), 6.94-7.43 (6H, m). |
| A1-072 | $^1$H NMR (CDCl$_3$) δ: 1.39 (9H, s), 2.85-3.08 (2H, m), 3.70-3.77 (2H, m), 4.25 (2H, d), 4.86 (1H, s), 5.94-6.04 (1H, m), 6.92-7.02 (2H, m), 7.15 (1H, d), 7.62 (1H, d), 7.87-7.94 (3H, m). |
| A1-085 | $^1$H NMR (CDCl$_3$) δ: 1.14-1.25 (6H, m), 2.18-2.20 (2H, m), 2.68-2.79 (4H, m), 3.64-3.76 (2H, m), 4.38 (2H, d), 5.44 (1H, br s), 5.89 (1H, s), 6.67-6.68 (2H, m), 7.16 (1H, d), 7.29-7.40 (3H, m). |
| A1-096 | $^1$H NMR (CDCl$_3$) δ: 1.19 (3H, t), 2.17 (2H, q), 2.74-3.59 (4H, m), 4.30-4.37 (3H, m), 5.67-5.84 (2H, m), 6.45-7.41 (6H, m) |
| A1-101 | $^1$H NMR (CDCl$_3$) δ: 2.24 1H, d), 2.65-2.90 (2H, m), 3.00-3.10 (2H, m), 3.57-3.60 (2H, m), 4.35-4.42 (2H, m), 5.65-6.10 (2H, m), 6.45-7.45 (6H, m) |
| A1-110 | $^1$H NMR (CDCl$_3$) δ: 0.55-1.20 (5H, m), 2.55-4.35 (6H, m), 5.50-7.24 (8H, m) |
| A1-112 | $^1$H NMR (CDCl$_3$) δ: 2.27 (1H, bs), 2.65-2.90 (2H, m), 3.00-3.10 (2H, m), 3.57-3.60 (2H, m), 3.38-4.45 (2H, m), 5.65-6.20 (2H, m), 6.65-7.40 (6H, m) |
| A1-132 | $^1$H-NMR (CDCl$_3$) δ: 0.69-0.74 (2H, m), 0.94-0.99 (2H, m), 1.26-1.33 (15H, m), 2.30 (3H, s), 2.72-2.85 (2H, m), 3.59-3.65 (2H, m), 4.32 (2H, d), 5.68 (1H, br s), 5.86 (1H, d), 6.61-6.68 (2H, m), 7.12 (1H, d), 7.47 (3H, s). |
| A1-140 | $^1$H NMR (CDCl$_3$) δ: 1.16-1.25 (6H, m), 2.23-2.32 (2H, m), 2.68-2.78 (4H, m), 3.75-3.77 (2H, m), 4.39 (2H, d), 5.44 (1H, br s), 5.87 (1H, s), 6.68-6.71 (2H, m), 7.18 (1H, d), 7.47-7.57 (3H, m). |
| A1-151 | $^1$H-NMR (CDCl$_3$) δ: 1.11 (3H, t), 2.19 (2H, q), 2.75-2.84 (2H, m), 3.57-3.66 (2H, m), 4.35 (2H, d), 5.79-5.86 (2H, m), 6.48-6.60 (2H, m), 7.16 (1H, t), 7.46 (2H, s). |
| A1-154 | $^1$H-NMR (CDCl$_3$) δ: 0.67-0.74 (3H, m), 0.85-0.90 (3H, m), 1.26-1.35 (1H, m), 2.75-2.80 (2H, m), 3.54-3.60 (2H, m), 3.86 (1H, t), 4.33 (2H, d), 5.80 (1H, d), 6.03 (1H, t), 6.55-6.46 (2H, m), 7.10 (1H, t), 7.45 (2H, s). |
| A1-161 | $^1$H-NMR (CDCl$_3$) δ: 1.97 (3H, s), 2.68-2.81 (2H, m), 3.55-3.61 (2H, m), 4.41 (2H, d), 5.65-5.91 (2H, m), 6.76 (1H, dd), 7.04 (1H, dd), 7.23-7.30 (1H, m), 7.47 (2H, s). |
| A1-162 | $^1$H-NMR (CDCl$_3$) δ: 1.13 (3H, t), 2.21 (2H, q), 2.78-2.81 (2H, m), 3.59-3.61 (2H, m), 4.41 (2H, d), 5.83 (1H, d), 5.90 (1H, s), 6.75 (1H, dd), 7.00 (1H, d), 7.22-7.28 (1H, m), 7.46 (2H, s). |
| A1-165 | $^1$H-NMR (CDCl$_3$) δ: 0.70-0.73 (2H, m), 0.89-0.90 (2H, m), 1.20-1.36 (1H, m), 2.78-2.80 (2H, m), 3.56-3.59 (2H, m), 4.39 (2H, d), 5.80 (1H, d), 6.14 (1H, s), 6.70 (1H, dd), 6.98 (1H, d), 7.18 (1H, d), 7.45 (2H, s). |
| A1-176 | $^1$H-NMR (CDCl$_3$) δ: 0.70-0.74 (2H, m), 0.86-0.91 (2H, m), 1.27-1.34 (1H, m), 2.67-2.76 (2H, m), 3.57-3.78 (2H, m), 4.27-4.33 (2H, m), 5.80 (1H, s), 6.12-6.14 (1H, m), 6.73-6.75 (1H, m), 7.02-7.17 (1H, m), 7.24-7.29 (2H, m), 7.48-7.53 (2H, m) |
| A1-183 | $^1$H-NMR (CDCl$_3$) δ: 1.97 (3H, s), 2.32 (3H, s), 2.76-3.01 (2H, m), 3.64-3.69 (2H, m), 4.33 (2H, d), 5.50 (1H, s), 5.98 (1H, d), 6.71-6.65 (2H, m), 7.14 (1H, d), 7.89 (3H, s). |
| A1-184 | $^1$H-NMR (CDCl$_3$) δ: 1.11 (3H, t), 2.17 (2H, q), 2.27 (3H, s), 2.78-2.99 (2H, m), 3.58-3.70 (2H, m), 4.27 (2H, d), 5.53 (1H, s), 5.99 (1H, d), 6.69-6.63 (2H, m), 7.06 (1H, d), 7.90 (3H, s). |
| A1-187 | $^1$H-NMR (CDCl$_3$) δ: 0.66-0.73 (2H, m), 0.86-0.92 (2H, m), 1.24-1.32 (1H, m), 2.27 (3H, s), 2.81-2.97 (2H, m), 3.22 (1H, d), 3.60-3.69 (2H, m), 4.27 (2H, d), 5.71 (1H, br s), 5.96 (1H, d), 6.68-6.62 (2H, m), 7.08 (1H, d), 7.89 (3H, s). |
| A1-190 | $^1$H-NMR (CDCl$_3$) δ: 2.39 (2H, t), 2.81-2.98 (2H, m), 3.30 (2H, s), 3.56-3.68 (4H, m), 4.27 (2H, d), 5.98 (1H, d), 6.24 (1H, br s), 6.62-6.68 (2H, m), 7.06 (1H, d), 7.89 (1H, s), 7.90 (2H, s). |
| A1-195 | $^1$H NMR (CDCl$_3$) δ: 1.18-1.26 (6H, m), 2.19-2.21 (2H, m), 2.65-2.67 (2H, m), 2.88-2.98 (2H, m), 3.70-3.75 (2H, m), 4.40 (2H, d), 5.45 (1H, br s), 5.99 (1H, s), 6.70-6.73 (2H, m), 7.20 (1H, d), 7.83-7.92 (3H, m). |
| A1-205 | $^1$H-NMR (CDCl$_3$) δ: 2.17 (3H, s), 2.83-2.97 (2H, m), 3.59-3.64 (2H, m), 4.33 (2H, d), 4.90 (1H, br s), 6.03-5.98 (2H, m), 6.52 (1H, d), 6.62 (1H, d), 7.16 (1H, t), 7.89 (3H, s). |
| A1-206 | $^1$H-NMR (CDCl$_3$) δ: 1.03 (3H, t), 2.14 (2H, q), 2.86-2.97 (2H, m), 3.59-3.64 (2H, m), 4.32 (2H, d), 5.93-6.00 (2H, m), 6.49-6.62 (2H, m), 7.10 (1H, t), 7.88 (1H, s), 7.90 (2H, s). |
| A1-209 | $^1$H-NMR (CDCl$_3$) δ: 0.65-0.72 (2H, m), 0.80-0.85 (2H, m), 1.24-1.33 (1H, m), 2.80-2.97 (2H, m), 3.59-3.64 (2H, m), 4.33 (2H, d), 5.92 (1H, d), 6.05 (1H, t), 6.49-6.57 (2H, m), 7.10 (1H, t), 7.88 (3H, s). |
| A1-216 | $^1$H NMR (CDCl$_3$) δ: 1.94 (3H, s), 2.81-3.21 (2H, m), 3.64-3.66 (2H, m), 4.41 (2H, d), 5.96-5.98 (2H, m), 6.81 (1H, dd), 7.01 (1H, d), 7.25-7.27 (1H, m), 7.87-7.90 (3H, m). |
| A1-217 | $^1$H NMR (CDCl$_3$) δ: 1.08 (3H, t), 2.18 (2H, q), 2.83-2.99 (2H, m), 3.62-3.65 (2H, m), 4.40 (2H, d), 5.94-5.97 (2H, m), 6.78 (1H, dd), 7.01 (1H, d), 7.21 (1H, d), 7.87-7.91 (3H, m). |
| A1-220 | $^1$H NMR (CDCl$_3$) δ: 0.69-0.73 (2H, m), 0.85-0.92 (2H, m), 1.30-1.38 (1H, m), 2.81-3.01 (2H, m), 3.60-3.66 (2H, m), 4.40 (2H, d), 5.92 (1H, d), 6.08-6.11 (1H, m), 6.74 (1H, dd), 7.01 (1H, d), 7.21 (1H, d), 7.88-7.90 (3H, m). |
| A1-239 | $^1$H NMR (CDCl$_3$) δ: 7.43 (1H, d), 7.24 (1H, s), 7.12-7.07 (3H, m), 6.94 (1H, d), 5.93 (1H, t), 5.84 (1H, d), 5.16 (1H, d), 4.50 (2H, d), 3.65-3.56 (2H, m), 2.88-2.79 (2H, m), 2.20 (2H, q), 1.14 (3H, t). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1-242 | $^1$H NMR (CDCl$_3$) δ: 7.44 (1H, d), 7.37 (1H, d), 7.14-7.10 (3H, m), 6.95 (1H, d), 6.64 (1H, s), 5.84 (1H, dd), 5.66 (1H, dd), 4.52 (2H, d), 3.65-3.57 (2H, m), 2.89-2.77 (2H, m), 1.48-1.41 (1H, m), 0.93-0.99 (2H, m), 0.69-0.76 (2H, m). |
| A1-250 | $^1$H-NMR (CDCl$_3$) δ: 1.08 (3H, t), 2.18 (2H, q), 2.75-2.89 (2H, m), 3.58-3.69 (2H, m), 4.22 (1H, d), 4.48 (2H, d), 5.84-5.94 (2H, m), 6.90-7.05 (2H, m), 7.36-7.67 (4H, m). |
| A1-253 | $^1$H-NMR (CDCl$_3$) δ: 0.67-0.76 (2H, m), 0.86-0.94 (2H, m), 1.25-1.35 (1H, m), 2.75-2.89 (2H, m), 3.26 (1H, d), 3.56-3.66 (2H, m), 4.49 (2H, d), 5.72-5.96 (2H, m), 6.85-7.03 (2H, m), 7.29-7.69 (4H, m). |
| A1-261 | $^1$H-NMR (CDCl$_3$) δ: 1.07 (3H, t), 2.17 (2H, q), 2.76-2.84 (2H, m), 3.57-3.69 (2H, m), 4.45 (2H, d), 4.57 (1H, d), 5.71-5.92 (2H, m), 6.88-7.31 (5H, m). |
| A1-264 | $^1$H-NMR (CDCl$_3$) δ: 0.69-0.77 (2H, m), 0.85-0.92 (2H, m), 1.23-1.35 (1H, m), 2.74-2.84 (2H, m), 3.58-3.67 (2H, m), 4.46 (2H, d), 5.83 (1H, d), 5.98 (1H, t), 6.78-7.32 (5H, m). |
| A1-271 | $^1$H-NMR (ACETONE-D6) δ: 7.70-7.68 (3H, m), 7.42 (1H, d), 7.14 (1H, d), 7.05 (1H, dd), 6.03 (1H, s), 4.40 (2H, d), 3.61 (2H, dd), 3.02-2.82 (2H, m), 1.89 (3H, s). |
| A1-272 | $^1$H-NMR (CD3OD) δ: 1.16 (3H, t), 2.25 (2H, q), 2.78-2.87 (2H, m), 3.66-3.57 (2H, m), 4.48 (2H, d), 5.80 (1H, s), 6.97 (1H, dd), 7.07 (1H, d), 7.37-7.47 (4H, m). |
| A1-275 | $^1$H-NMR (CD3OD) δ: 0.72-0.90 (4H, m), 1.59-1.66 (1H, m), 2.74-2.93 (2H, m), 3.51-3.64 (2H, m), 4.46 (2H, s), 5.87 (1H, s), 7.01-7.12 (2H, m), 7.39 (1H, d), 7.60-7.56 (2H, m). |
| A1-282 | $^1$H NMR (CDCl$_3$) δ: 7.40-7.31 (2H, m), 7.06 (1H, d), 6.98 (1H, s), 6.08-5.86 (2H, m), 4.52-4.41 (3H, m), 3.69-3.56 (2H, m), 2.96-2.77 (2H, m), 1.93 (3H, s). |
| A1-283 | $^1$H-NMR (CDCl$_3$) δ: 1.06 (3H, t), 2.16 (2H, q), 2.74-2.98 (2H, m), 3.55-3.67 (2H, m), 4.37-4.50 (2H, m), 4.67 (1H, d), 5.86 (1H, t), 6.08 (1H, dd), 7.05-6.98 (2H, m), 7.35-7.30 (2H, m). |
| A1-286 | $^1$H-NMR (CDCl$_3$) δ: 0.67-0.76 (2H, m), 0.82-0.89 (2H, m), 1.24-1.34 (1H, m), 2.75-2.94 (2H, m), 3.51-3.66 (2H, m), 4.43 (2H, d), 5.98-6.05 (2H, m), 6.91-6.99 (2H, m), 7.35-7.21 (2H, m). |
| A1-294 | $^1$H-NMR (CDCl$_3$) δ: 1.06 (3H, t), 2.15 (2H, q), 2.81-3.00 (2H, m), 3.61-3.69 (2H, m), 3.89 (1H, d), 4.46 (2H, d), 5.81-6.00 (2H, m), 6.97-7.04 (2H, m), 7.35 (1H, d), 7.49-7.69 (4H, m). |
| A1-297 | $^1$H-NMR (CDCl$_3$) δ: 0.66-0.73 (2H, m), 0.83-0.92 (2H, m), 1.23-1.34 (1H, m), 2.76-3.05 (2H, m), 3.57-3.72 (2H, m), 4.46 (2H, d), 5.81-6.00 (2H, m), 6.83-7.04 (2H, m), 7.32-7.78 (5H, m). |
| A1-303 | $^1$H-NMR (CDCl$_3$) δ: 2.76-2.99 (5H, m), 3.59-3.77 (4H, m), 4.52 (2H, d), 5.93 (1H, d), 6.81-7.08 (3H, m), 7.39-7.77 (5H, m). |
| A1-305 | $^1$H-NMR (CDCl$_3$) δ: 1.06 (3H, t), 2.16 (2H, q), 2.78-3.03 (2H, m), 3.63-3.69 (2H, m), 3.98 (1H, d), 4.46 (2H, d), 5.75-5.84 (1H, m), 5.95 (1H, d), 6.89-7.02 (2H, m), 7.21-7.30 (1H, m), 7.34 (1H, d), 7.67 (2H, d). |
| A1-308 | $^1$H-NMR (CDCl$_3$) δ: 0.66-0.72 (2H, m), 0.77-0.84 (2H, m), 1.23-1.34 (1H, m), 2.82-2.93 (2H, m), 3.58-3.67 (2H, m), 4.43 (2H, d), 5.89 (1H, s), 6.07 (1H, t), 6.81-7.01 (2H, m), 7.18-7.25 (2H, m), 7.62-7.68 (2H, m). |
| A1-316 | $^1$H-NMR (CDCl$_3$) δ: 1.04 (3H, t), 2.15 (2H, q), 2.83-2.94 (2H, m), 3.59-3.71 (2H, m), 4.45 (1H, d), 4.87 (1H, d), 5.90-6.00 (2H, m), 6.88-7.02 (2H, m), 7.24-7.60 (4H, m). |
| A1-319 | $^1$H-NMR (CDCl$_3$) δ: 0.66-0.84 (4H, m), 1.25-1.34 (1H, m), 2.82-2.90 (2H, m), 3.56-3.69 (2H, m), 4.32 (1H, d), 4.43 (2H, d,), 5.91 (1H, d), 6.05 (1H, t), 6.83-7.00 (2H, m), 7.25 (1H, d), 7.32-7.40 (2H, m), 7.49 (1H, s). |
| A1-338 | $^1$H-NMR (CDCl$_3$) δ: 1.05 (3H, t), 2.16 (2H, q), 2.83-2.90 (2H, m), 3.61-3.69 (2H, m), 4.38-4.54 (3H, m), 5.80-6.00 (2H, m), 6.89-7.04 (2H, m), 7.35 (1H, d), 7.74-7.59 (3H, m). |
| A1-341 | $^1$H-NMR (CDCl$_3$) δ: 0.66-0.76 (2H, m), 0.79-0.84 (2H, m), 1.24-1.34 (1H, m), 2.82-2.90 (2H, m), 3.59-3.68 (2H, m), 4.44 (2H, d), 5.92 (1H, s), 6.02-6.08 (1H, m), 6.81-7.05 (2H, m), 7.74-7.55 (4H, m). |
| A1-347 | $^1$H-NMR (CDCl$_3$) δ: 2.67-2.99 (5H, m), 3.14 (1H, d), 3.60-3.69 (2H, m), 3.77 (2H, s), 4.52 (2H, d), 5.91 (1H, d), 6.88-7.05 (3H, m), 7.38-7.74 (4H, m). |
| A1-348 | $^1$H NMR (CDCl$_3$) δ: 7.74 (1H, s), 7.67 (1H, s), 7.42 (1H, d), 7.06 (1H, dd), 6.99 (1H, d), 5.98 (1H, d), 5.86 (1H, t), 4.49 (2H, t), 4.40 (1H, d), 3.72-3.63 (2H, m), 2.93-2.79 (2H, m), 1.93 (3H, s). |
| A1-349 | $^1$H NMR (CDCl$_3$) δ: 7.75 (1H, s), 7.67 (1H, s), 7.41 (1H, d), 7.02 (2H, d), 5.95 (1H, d), 5.81 (1H, t), 4.50 (2H, dd), 3.77-3.61 (3H, m), 2.93-2.79 (2H, m), 2.19 (2H, q), 1.09 (3H, t). |
| A1-352 | $^1$H NMR (CDCl$_3$) δ: 7.74 (1H, s), 7.66 (1H, s), 7.39 (1H, d), 7.02 (1H, d), 6.96 (1H, dd), 5.96 (1H, t), 5.89 (1H, d), 4.50 (2H, d), 3.70-3.62 (2H, m), 3.23 (1H, d), 2.94-2.74 (2H, m), 1.34-1.29 (1H, m), 0.90-0.87 (2H, m), 0.75-0.70 (2H, m). |
| A1-361 | $^1$H-NMR (CDCl$_3$) δ: 1.63-2.25 (7H, m), 2.83-3.02 (3H, m), 3.62-3.65 (2H, m), 4.42-4.48 (2H, m), 5.64-5.92 (2H, m), 6.91-7.60 (6H, m). |
| A1-373 | $^1$H-NMR (CDCl$_3$) δ: 1.15-1.18 (3H, m), 2.18-2.29 (2H, m), 2.80-2.83 (2H, m), 3.60-3.62 (2H, m), 4.32-4.44 (2H, m), 5.24 (1H, d), 5.72 (1H, br s), 5.88 (1H, s), 6.80 (2H, d), 7.14-7.46 (5H, m). |
| A1-376 | $^1$H-NMR (CD3CN) δ: 0.65-0.78 (4H, 2m), 1.44-1.48 (1H, m), 2.68-2.78 (1H, m), 2.81-2.89 (1H, m), 3.47-3.59 (2H, m), 3.69-3.71 (1H, d), 4.23-4.25 (2H, d), 5.90-5.92 (1H, d), 6.77-6.80 (2H, m), 6.87 (1H, br), 7.47 (2H, s) 7.50 (1H, s). |
| A1-377 | $^1$H-NMR (CD3CN) δ: 0.11-0.17 (2H, m), 0.47-0.52 (2H, m), 0.98 (1H, cm), 2.04-2.06 (2H, d), 2.68-2.77 (1H, m), 2.82-88 (1H, m), 3.48-3.59 (2H, m), 3.68-3.70 (1H, d), 4.18-4.20 (2H, d), 5.90-5.92 (1H, d), 6.70 (1H, br), 6.77-6.79 (2H, m), 7.18-7.20 (2H, d), 7.47 (2H, s), 7.50 (1H, s). |
| A1-384 | $^1$H NMR (CDCl$_3$) δ: 1.12-1.15 (3H, m), 2.19-2.21 (2H, m), 2.79-2.81 (2H, m), 3.61-3.63 (2H, m), 4.30 (2H, d), 5.69 (1H, br s), 5.88 (1H, s), 6.80 (2H, d), 7.16 (2H, d), 7.47 (2H, s). |
| A1-387 | $^1$H-NMR (CD3CN) δ: 0.65-0.78 (4H, 2m), 1.43-1.48 (1H, m), 2.67-2.77 (1H, m), 2.80-2.87 (1H, m), 3.48-3.59 (2H, m), 3.83-3.85 (1H, d), 4.23-4.25 (2H, d), 5.89-5.91 (1H, d), 6.77-6.79 (2H, m), 6.89 (1H, br), 7.17-7.19 (2H, d) 7.63 (2H, s). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1-388 | $^1$H-NMR (CD3CN) δ: 0.11-0.16 (2H, m), 0.46-0.52 (2H, m), 0.95-0.99 (1H, m), 2.04-2.06 (2H, d) 2.65-2.73 (1H, m), 2.83-2.88 (1H, m), 3.48-3.58 (2H, m), 3.73-3.75 (1H, d), 4.24-4.26 (2H, m), 5.89-5.91 (1H, d), 6.60 (1H, s, br), 6.77-6.79 (2H, d), 7.17-7.19 (2H, d), 7.63 (2H, s). |
| A1-395 | $^1$H-NMR (CDCl$_3$) δ: 1.14-1.19 (3H, m), 2.20-2.29 (2H, m), 2.94-2.97 (2H, m), 3.64-3.68 (2H, m), 4.39 (2H, dd), 5.70 (1H, br s), 5.99 (1H, d), 6.83 (2H, d), 7.20 (2H, d), 7.89 (3H, s). |
| A1-398 | $^1$H-NMR (CD$_3$CN) δ: 0.64-0.78 (4H, 2m), 1.46 (1H, cm), 2.76-2.85 (1H, m), 2.95-3.05 (1H, m), 3.52-3.65 (2H, m), 3.78 (1H, br), 4.24-4.25 (2H, d), 6.04 (1H, d, br), 6.80-6.83 (2H, m), 6.89 (1H, br), 7.18-7.20 (1H, d) 8.04-8.05 (2H, d). |
| A1-399 | $^1$H-NMR (CD$_3$CN) δ: 0.11-0.17 (2H, m), 0.46-0.52 (2H, m), 0.98 (1H, cm), 2.05-2.07 (2H, d), 2.77-2.84 (1H, m), 2.95-3.04 (1H, m), 3.55-3.63 (2H, m), 3.96-3.98 (1H, m), 4.25-4.26 (2H, d), 6.02-6.04 (1H, d), 6.75 (1H, br), 6.80-6.82 (2H, d), 7.19-7.21 (2H, d), 8.04 (1H, s), 8.06 (2H, s). |
| A1-405 | $^1$H NMR (CDCl$_3$) δ: 7.45 (1H, dd), 7.40 (1H, d), 7.24 (1H, dd), 7.06 (1H, dd), 6.98 (1H, d), 6.10 (1H, t), 5.91 (1H, d), 4.57-4.39 (3H, m), 3.66-3.54 (2H, m), 2.94-2.77 (2H, m), 1.93 (3H, s). |
| A1-406 | $^1$H NMR (CDCl$_3$) δ: 7.46 (1H, dd), 7.37 (1H, d), 7.24 (1H, dd), 7.03 (1H, dd), 6.99 (1H, d), 6.09 (1H, dd), 5.80 (1H, s), 4.52-4.41 (2H, m), 3.66-3.57 (2H, m), 2.97-2.78 (2H, m), 2.17 (2H, q), 1.08 (3H, t). |
| A1-409 | $^1$H NMR (CDCl$_3$) δ: 7.47 (1H, dd), 7.32 (1H, d), 7.23 (1H, dd), 6.99-6.94 (2H, m), 6.06 (1H, dd), 5.97 (1H, t), 4.53-4.40 (2H, m), 3.67-3.55 (2H, m), 2.96-2.75 (2H, m), 1.33-1.29 (1H, m), 0.92-0.86 (2H, m), 0.76-0.67 (2H, m). |
| A1-429 | $^1$H NMR (CDCl$_3$) δ: 7.32 (1H, t), 7.19 (1H, d), 6.98 (1H, d), 6.78 (1H, dd), 6.05-5.98 (2H, m), 4.52 (1H, d), 4.36 (2H, d), 3.60-3.49 (2H, m), 2.92-2.74 (2H, m), 1.93 (3H, s). |
| A1-430 | $^1$H NMR (CDCl$_3$) δ: 7.33 (1H, t), 7.12 (1H, d), 6.98 (1H, d), 6.75 (1H, dd), 6.08-5.95 (2H, m), 4.78 (1H, br s), 4.33 (2H, d), 3.60-3.50 (2H, m), 2.91-2.77 (2H, m), 2.16 (2H, q), 1.07 (3H, t). |
| A1-433 | $^1$H NMR (CDCl$_3$) δ: 7.31 (1H, t), 7.16 (1H, d), 6.98 (1H, d), 6.71 (1H, dd), 6.09 (1H, t), 5.98 (1H, dd), 4.37 (2H, d), 3.63-3.44 (2H, m), 2.97-2.72 (2H, m), 1.35-1.29 (1H, m), 0.92-0.86 (2H, m), 0.74-0.68 (2H, m). |
| A1-453 | $^1$H NMR (CDCl$_3$) δ: 1.99 (3H, s), 2.74-2.77 (2H, m), 3.14 (1H, br s), 3.60-3.62 (1H, m), 3.71-3.73 (1H, m), 4.35 (2H, d), 5.81 (1H, t), 6.06 (1H, s), 6.52 (1H), 7.08 (1H, dd), 7.42 (2H, s). |
| A1-454 | $^1$H NMR (CDCl$_3$) δ: 1.11 (3H, t), 2.20 (2H, q), 2.74-2.75 (2H, m), 3.63-3.74 (2H, m), 4.31 (2H, d), 5.95-6.10 (2H, m), 6.50-6.56 (1H, m), 6.97-7.01 (1H, m), 7.44 (2H, s). |
| A1-457 | $^1$H NMR (CDCl$_3$) δ: 0.72-0.74 (2H, m), 0.90-0.94 (2H, m), 1.30-1.37 (1H, m), 2.72-2.76 (2H, m), 3.62-3.72 (2H, m), 4.32 (2H, d), 6.06-6.12 (2H, m), 6.51-6.54 (1H, m), 6.98-7.01 (1H, m), 7.42 (2H, s). |
| A1-464 | $^1$H NMR (CDCl$_3$) δ: 1.46 (9H, s), 2.68-2.77 (2H, m), 3.56-3.63 (1H, m), 3.71-3.73 (1H, m), 4.24 (2H, d), 4.85 (1H, s), 6.04 (1H, s), 6.49-6.53 (1H, m), 7.05-7.08 (1H, m), 7.41 (2H, s). |
| A1-481 | $^1$H NMR (CDCl$_3$) δ: 0.73-0.77 (2H, m), 0.95-1.00 (2H, m), 1.28-1.37 (1H, m), 2.63-2.76 (2H, m), 3.62-3.65 (1H, m), 3.74-3.76 (1H, m), 4.42 (2H, d), 6.04 (2H, s), 6.81 (1H, d), 7.14 (1H, d), 7.41 (2H, s). |
| A1-493 | $^1$H NMR (CDCl$_3$) δ: 0.71-0.77 (2H, m), 0.96-1.01 (2H, m), 1.29-1.34 (1H, m), 2.25 (3H, s), 2.71-2.80 (2H, m), 3.60-3.80 (2H, m), 4.38 (2H, d), 5.65 (1H, br s), 6.06 (1H, s), 6.61-6.71 (1H, m), 6.97 (1H, d), 7.43 (2H, s). |
| A1-505 | $^1$H NMR (CDCl$_3$) δ: 0.75-0.77 (2H, m), 0.97-1.03 (2H, m), 1.30-1.36 (1H, m), 2.27 (3H, s), 2.63-2.76 (2H, m), 3.62-3.64 (1H, m), 3.76-3.78 (1H, m), 4.35 (2H, d), 5.69 (1H, br s), 6.04 (1H, d), 6.64 (1H, d), 6.99 (1H, d), 7.43 (2H, s). |
| A1-525 | $^1$H NMR (CDCl$_3$) δ: 2.68-2.89 (2H, m), 3.37 (2H, s), 3.59-3.64 (2H, m), 4.48 (2H, d), 5.81 (1H, d), 6.50 (1H, br s), 6.75 (1H, dd), 7.05 (1H, d), 7.31 (1H, d), 7.45 (2H, s). |
| A1-528 | $^1$H NMR (CDCl$_3$) δ: 2.76-3.10 (2H, m), 3.38 (2H, s), 3.69-3.75 (2H, m), 4.58 (2H, d), 5.96 (1H, d), 6.32 (1H, br s), 7.01 (1H, d), 7.11 (1H, s), 7.49 (1H, d), 7.88-7.92 (3H, m). |
| A1-557 | $^1$H-NMR (DMSO, 600 Mhz) δ: 0.65-0.69 (4H, m), 1.56-1.59 (1H, m), 2.71-2.78 (1H, m), 3.41-3.43 (2H, m), 4.16-4.17 (2H, m), 5.82 (1H, m), 6.76-6.77 (2H, m), 7.12-7.14 (2H, m), 7.84 (1H, t), 8.39 (1H, m). |
| A1-558 | $^1$H-NMR (DMSO) δ: 0.12-0.14 (2H, m), 0.42-0.45 (2H, m), 0.96-1.01 (2H, m), 2.01 (2H, d), 2.67-2.78 (1H, m), 2.96-3.00 (1H, m), 3.41-3.43 (2H, m), 4.16 (2H, m), 5.80-5.83 (1H, m), 6.04 (1H, d), 6.75-6.77 (2H, m), 7.12-7.18 (2H, m), 7.84 (1H, t), 8.10 (1H, m). |
| A1a-085 | $^1$H-NMR (DMSO, 399.95 MHz) d: 0.99 (3H, t), 1.15 (3H, t), 2.08 (2H, q), 2.58 (2H, q), 2.59-2.68 (1H, m), 2.85-2.91 (1H, m), 3.33-3.40 (2H, m), 3.75-3.77 (1H, m), 4.08-4.10 (1H, m), 4.15 (2H, d), 6.45-6.52 (2H, m), 7.02-7.04 (1H, m), 7.65-7.76 (3H, m), 7.94 (1H, m). |
| A1a-140 | $^1$H-NMR (DMSO, 399.95 MHz) d: 0.98 (3H, t), 1.15 (3H, t), 2.08 (2H, q), 2.59 (2H, q), 2.61-2.68 (1H, m), 2.85-2.92 (1H, m), 3.33-3.42 (2H, m), 3.77 (1H, m), 4.10 (1H, m), 4.15 (2H, d), 6.45-6.47 (1H, m), 6.50 (1H, m), 7.03 (1H, d), 7.90 (2H, s), 7.94 (1H, m). |
| A1a-176 | $^1$H-NMR (CDCl3) d: 0.71-0.76 (2H, m), 1.02-1.08 (2H, m), 1.60-1.65 (1H, m), 2.46-2.63 (1H, m), 2.80-2.87 (1H, m), 3.43-3.56 (m, 2H), 3.70-3.74 (1H, m), 3.98-4.01 (1H, m), 4.42 (2H, m), 5.99 (1H, m), 6.53-6.57 (1H, m), 7.03 (1H, m), 7.28 (1H, m), 7.42 (2H, m). |
| A1a-195 | $^1$H-NMR (CDCl3) d: 1.13-1.28 (6H, m), 2.22 (2H, m), 2.65 (3H, m), 2.94-3.01 (1H, m), 3.50-3.61 (2H, m), 3.82-3.86 (2H, m), 4.10-4.18 (1H, m), 4.38 (2H, m), 5.53 (1H, m), 6.45-6.48 (2H, m), 7.14-7.17 (1H, m), 7.87 (2H, m), 7.92 (1H, s). |
| A1a-198 | $^1$H-NMR (DMSO, 399.95 MHz) d: 0.67-0.72 (4H, m), 1.16 (3H, t), 1.59 (1H, m), 2.57 (2H, q), 2.67-2.75 (1H, m), 3.04-3.09 (1H, m), 3.38-3.51 (2H, m), 3.82 (1H, m), 4.18 (2H, d), 4.29 (1H, m), 6.50-653 (1H, m), 7.06 (1H, m), 8.15-8.25 (4H, m). |
| A1a-264 | $^1$H-NMR (DMSO, 399.95 MHz) d: 0.66-0.71 (4H, m), 1.61-1.67 (1H, m), 2.60-2.68 (1H, m), 2.84-2.90 (1H, m), 3.39-3.51 (2H, m), 3.84-3.87 (1H, m), 4.12-4.15 (1H, m), 4.31-4.32 (2H, d), 6.87-6.89 (2H, m), 7.31-7.33 (1H, m), 7.68 (2H, m), 8.42 (1H, m). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A1a-286 | $^1$H-NMR (CDCl3) δ: 0.68-0.75 (2H, m), 0.92-0.99 (2H, m), 1.30-1.36 (m, 1H), 2.49-2.62 (1H, m), 2.96-3.04 (1H, m), 3.49-3.59 (2H, m), 3.75-3.80 (1H, m), 4.20-4.27 (1H, m), 4.51 (2H, d), 5.87 (1H, br s), 6.68-6.81 (2H, m), 7.29-7.33 (1H, m), 7.44 (1H, d). |
| A1a-316 | $^1$H-NMR (DMSO, 399.95 MHz) d: 1.02 (3H, t), 2.14 (2H, q), 2.65-2.72 (1H, m), 2.96-3.02 (1H, m), 3.44-3.51 (2H, m), 3.85-3.88 (1H, m), 4.26-4.30 (2H, m), 6.90-6.92 (2H, m), 7.29-7.32 (1H, m), 7.79-7.81 (2H, m), 7.87-7.90 (1H, m), 8.15 (1H, m). |
| A1a-319 | $^1$H-NMR (CDCl3) δ: 0.70-0.76 (2H, m), 0.95-1.01 (2H, m), 1.28-1.39 (1H, m), 2.55-2.65 (1H, m), 2.81-2.99 (1H, m), 3.49-3.61 (2H, m), 3.82 (1H, d), 4.13 (1H, d), 4.50-4.54 (2H, m), 5.86 (1H, br s), 6.70-6.75 (1H, m), 6.80-6.83 (1H, m), 7.30-7.5 (4H, m). |
| A1a-348 | $^1$H-NMR (CDCl3) δ: 1.96 (3H, s), 2.50-2.71 (1H, m), 2.83-2.97 (1H, m), 3.45-3.62 (2H, m), 3.78 (1H, d), 4.09 (1H, d), 4.45-4.55 (2H, m), 5.69 (1H, br s), 6.60-6.85 (2H, m), 7.42-7.48 (1H, m), 7.57-7.74 (2H, m). |
| A1a-349 | $^1$H-NMR (CDCl3) δ: 1.12 (3H, t), 2.17 (2H, q), 2.49-2.65 (1H, m), 2.84-2.96 (1H, m), 3.47-3.60 (2H, m), 3.75-3.82 (1H, m), 4.05-4.12 (1H, m), 4.46-4.52 (2H, m), 5.67 (1H, br s), 6.67-6.81 (2H, m), 7.41-7.48 (1H, d), 7.61 (1H, s), 7.69 (1H, s). |
| A1a-352 | $^1$H-NMR (CDCl3) δ: 0.68-0.75 (2H, m), 0.93-0.99 (2H, m), 1.25-1.45 (1H, m), 2.50-2.70 (1H, m), 2.80-2.98 (1H, m), 3.45-3.75 (2H, m), 3.75-3.85 (1H, m), 4.05-4.13 (1H, m), 4.49-4.52 (2H, m), 5.85 (1H, br s), 6.67-6.83 (2H, m), 7.40-7.49 (1H, m), 7.59-7.73 (2H, m). |
| A1a-367 | $^1$H-NMR (CDCl3) d: 2.36-2.44 (1H, m), 2.61 (3H, m), 2.68-2.75 (1H, m), 3.30-3.45 (2H, m), 3.61-3.64 (1H, m), 3.89-3.91 (1H, m), 4.05 (1H, m), 4.29 (2H, m), 4.42 (1H, m), 6.54-6.56 (1H, m), 6.63-6.64 (1H, m), 7.11 (2H, s), 7.24 (1H, m), 7.34-7.36 (1H, m). |
| A1a-376 | $^1$H-NMR (d6-DMSO) δ: 0.60-0.69 (4H, m), 1.54-1.60 (1H, m), 2.61-2.68 (2H, m), 2.86-2.92 (2H, m), 3.30-3.40 (2H, m), 3.76-3.79 (1H, d), 4.09-4.12 81H, d), 4.14-4.15 (2H, d), 6.62-6.64 (2H, d), 7.08-7.10 (2H, d), 7.66 (2H, s), 7.69 (1H, d), 837 (1H, t) |
| A1a-377 | $^1$H-NMR (d6-DMSO) d: 0.10-0.13 (2H, m), 0.41-0.45 (2H, m), 0.95-0.99 (1H, m), 1.99-2.01 (2H, d), 2.60-2.67 (1H, m) 2.85-2.91 (1H, m), 3.30-3.40 (2H, m), 3.76-3.78 (1H, d), 4.02-4.04 (1H, d), 4.14-4.16 (2H, d), 6.62-6.64 (2H, d), 7.08-7.19 (2H, d), 7.66 (2H, s), 7.69-7.70 (1H, d), 8.07 (1H, t). |
| A1a-387 | $^1$H-NMR (d3-CD3CN) δ: 0.64-0.69 (2H, m), 0.73-0.77 (2H, m), 1.42-1.48 (1H, m), 2.54-2.61 (1H, m), 2.82-2.88 (1H, m), 3.39-3.49 (2H, 2m), 3.77-3.80 (1H, d), 4.04-4.07 (1H, d), 4.21-4.22 (2H, d), 6.59-6.61 (2H, d), 6.83 (1H, br), 7.13-7.15 (2H, d), 7.66 2H, s). |
| A1a-388 | $^1$H-NMR (d3-CD3CN) δ: 0.12-0.16 (2H, m), 0.47-0.52 (2H, m), 0.94-0.99 (1H, m), 2.04-2.05 (2H, d), 2.53-2.61 (1H, m), 2.82-2.88 (1H, m), 3.38-3.48 (2H, 2m) 3.77-3.80 (1H, d), 4.04-4.06 (1H, d), 4.22-4.23 (2H, d), 6.59-6.61 (2H, d), 6.69 (1H, br), 7.14-7.16 (2H, d), 7.66 (2H, s). |
| A1a-398 | $^1$H-NMR (d6-DMSO) d: 0.60-0.70 (4H, m), 1.54-1.60 (1H, m), 2.67-2.75 (1H, m), 3.03-3.09 (1H, m), 3.39-3.44 (1H, m), 3.82-3.85 (1H, d), 4.15-4.16 (2H, d), 4.27-4.30 (1H, d), 6.66-6.68 (2 H, d), 7.10-7.12 (2 H, d), 8.21 (1H, s), 8.24 (2H, s), 8.38 (1H, tr). |
| A1a-405 | $^1$H-NMR (CDCl3) δ: 1.96 (3H, s), 2.50-2.59 (1H, m), 2.95-3.04 (1H, m), 3.49-3.57 (2H, m), 3.70-3.78 (1H, m), 4.30-4.28 (1H, m), 4.48 (2H, d), 5.69 (br s), 6.68-6.72 (1H, m), 6.78-6.80 (1H, m), 7.30-7.34 (1H, m), 7.44 (1H, d). |
| A1a-481 | $^1$H-NMR (DMSO, 399.95 MHz) d: 8.48 (1H, t), 7.88 (2H, s), 7.03 1H, d), 6.95 (1H, d), 4.21 (2H, d), 4.11 (1H, d), 3.66-3.60 (1H, m), 3.50-3.40 (1H, m), 2.84-2.78 (1H, m), 2.63-2.58 (1H, m), 1.65-1.59 (1H, m), 0.85-0.63 (4H, m). |
| A1a-505 | $^1$H-NMR (DMSO, 399.95 MHz) d: 8.33 (1H, bt), 7.88 (2H, s), 6.90 (1H, d), 6.71 (1H, d), 4.12 (2H, d), 4.05 (1H, d), 3.83 (1H, d), 3.59-3.55 (1H, m), 2.80-2.73 (1H, m), 2.57-2.66 (1H, m), 2.20 (3H, s), 1.62-1.56 (1H, m), 0.69-0.64 (4H, m). |
| A1a-518 | $^1$H-NMR (DMSO, 399.95 MHz) d: 8.49 (1H, t), 7.91 (2H, d), 7.18-7.12 (2H, m), 4.32 (1H, bs), 4.14 (1H, d), 3.91 (1H, d), 3.70-3.60 (1H, m), 3.50-3.40 (1H, m), 2.85-2.79 (1H, m), 2.67-2.58 (1H, m), 1.67-1.61 (1H, m), 0.70*-0.65 (4H, m). |
| A1a-555 | $^1$H-NMR (DMSO) δ: 1.01 (3H, t), 2.10 (2H, q) 2.61-2.69 (1H, m), 3.00-3.05 (1H, m), 3.38-3.41 (2H, m), 3.71-3.74 (1H, m), 4.13 (2H, d), 4.21-4.24 (1H, d), 6.61-6.63 (2H, m), 7.09-7.11 (2H, m), 7.96 (1H, t), 8.11 (1H, m). |
| A1a-557 | $^1$H-NMR (DMSO) δ: 0.65-0.70 (4H, m), 1.54-1.61 (1H, m), 2.63-2.69 (1H, m), 3.01-3.05 (1H, m), 3.39-3.41 (2H, m), 3.71-3.74 (1H, m), 4.15 (2H, d), 4.21-4.25 (1H, m), 6.62-6.64 (2H, m), 7.10-7.12 (2H, m), 7.96 (1H, m), 8.39 (1H, m). |
| A1a-558 | $^1$H-NMR (DMSO) δ: 0.11-0.13 (2H, m), 0.41-0.44 (2H, m), 0.84-1.01 (1H, m), 2.00 (2H, d), 2.60-2.69 (1H, m), 3.00-3.05 (1H, m), 3.39-3.41 (2H, m), 3.72 (1H, m), 4.15 (2H, d), 4.23 (1H, m), 6.61-6.63 (2H, m), 7.10-7.12 (2H, d), 7.96 (1H, m), 8.08 (1H, m). |
| A2-003-b | $^1$H-NMR (CD$_3$CN) δ: 1.04 (3H, t), 1.36-1.38 (2H, d), 2.09-2.15 (2H, q), 2.67-2.75 (1H, m), 2.81-2.89 (1H, m), 3.48-3.59 (2H, m), 3.67-3.68 (1H, dbr), 4.88 (1H, cm), 5.90-5.92 (1H, d), 6.57-6.58 (1H, d, br), 6.77-6.79 (2H, m), 7.20-7.22 (2H, d), 7.47 (2H, s), 7.50 (1H, s). |
| A2-005-b | $^1$H-NMR (CD3CN) δ: 0.62-0.75 (4H, m), 1.38-1.40 (2H, d), 1.41-1.48 (1H, m), 2.66-2.78 (1H, m), 2.81-2.89 (1H, m), 3.47-3.59 (2H, m), 3.73-3.75 (1H, d, br), 4.89 (1H, cm), 5.90-5.92 (1H, d), 6.77-6.80 (2H, m), 6.88 (1H, br), 7.21-7.23 (2H, d), 7.47 (2H, s), 7.50 (1H, s). |
| A2-006-b | $^1$H-NMR (CD3CN) δ: 0.11-0.16 (2H, m), 0.45-0.50 (2H, m), 0.94-0.98 (1H, m), 1.37-1.39 (2H, d), 2.01-2.03 (2H, d) 2.68-2.77 (1H, m), 2.71-2.79 (1H, m), 3.47-3.59 (2H, m), 3.78 (1H, br), 4.90 (1H, cm), 5.90-5.92 (1H, d), 6.58 (1H, br), 6.77-6.79 (2H, m), 7.21-7.23 (2H, d), 7.47 (2H, s), 7.50 (1H, s). |
| A2-012 | $^1$H-NMR (CDCl$_3$) δ: 1.46 (3H, d), 1.93 (3H, s), 2.75-2.78 (2H, m), 3.57-3.60 (2H, m), 5.03-5.06 (1H, m), 5.73-5.76 (1H, m), 5.86 (1H, s), 6.78-6.81 (2H, m), 7.17-7.24 (2H, m), 7.44-7.46 (2H, m). |
| A2-013 | $^1$H-NMR (CDCl$_3$) δ: 0.66-0.75 (2H, m), 0.84-0.91 (2H, m), 1.23-1.32 (1H, m), 1.47 (3H, d), 2.81-2.97 (2H, m), 3.22-3.23 (1H, m), 3.65-3.75 (2H, m), 5.03-5.06 (1H, m), 5.80-5.98 (2H, m), 6.68-6.84 (2H, m), 7.11-7.26 (2H, m), 7.89-7.99 (3H, m). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A2-014-b | $^1$H-NMR (CD$_3$CN) δ: 1.04 (3H, t), 1.36-1.38 (2H, d), 2.09-2.14 (1H, q), 2.67-2.76 (1H, m), 2.82-2.89 (1H, m), 3.48-3.59 (2H, m), 3.75 (1H, br), 4.89 (1H, cm), 5.89-5.91 (1H, d), 6.58-6.60 (1H, d, br), 6.77-6.79 (2H, d), 7.20-7.22 (2H, d), 7.63 (2H, s). |
| A2-016 | $^1$H-NMR (CDCl$_3$) δ: 0.68-0.73 (2H, m), 0.87-0.93 (2H, m), 1.27-1.31 (1H, m), 1.43 (3H, d), 2.62-2.79 (2H, m), 3.26-3.32 (1H, m), 3.62-3.73 (2H, m), 5.00-5.04 (1H, m), 5.86-5.88 (2H, m), 6.67-6.79 (2H, m), 7.16-7.21 (2H, m), 7.40-7.49 (2H, m). |
| A2-017-b | $^1$H-NMR (CD3CN) δ: 0.11-0.16 (2H, m), 0.46-0.51 (2H, m), 0.96 (1H, cm), 1.37-1.39 (2H, d), 2.01-2.03 (2H, d) 2.66-2.74 (1H, m), 2.80-2.88 (1H, m), 3.49-3.60 (2H, m), 3.69-3.72 (1H, m), 4.9 (1H, cm), 5.89-5.91 (1H, d), 6.60-6.62 (1H, d, br), 6.77-6.79 (2H, d), 7.12-7.14 (2H, d), 7.63 (2H, s). |
| A2-027-b | 1H-NMR (CD3CN) δ: 0.62-0.74 (4H, m), 1.38-1.40 (2H, d), 1.45-1.48 (1H, m), 2.76-2.84 (1H, m), 2.95-3.03 (1H, m), 3.55-3.63 (2H, m), 3.80 (1H, br), 4.89 (1H, cm), 6.04 (1H, br), 6.80-6.83 (2H, d), 6.87-6.89 (1H, d, br), 7.22-7.24 (2H, d), 8.04 (1H, s), 8.06 (2H, s). |
| A2-036-b | $^1$H-NMR (CD3CN) δ: 1.04 (3H, t), 1.36-1.38 (2H, d), 2.09-2.14 (1H, q), 2.67-2.77 (1H, m), 2.93-3.02 (1H, m), 3.55-3.63 (2H, m), 3.85 (1H, br), 4.88 (1H, cm), 6.03-6.04 (1H, d, br), 6.80-6.82 (2H, d), 7.21-7.23 (2H, d), 8.04 (1H, s), 8.05 (2H, s). |
| A2-038-b | $^1$H-NMR (CDCl$_3$) δ: 0.64-0.75 (2H, m), 0.77-0.82 (2H, m), 1.26-1.31 (1H, m), 1.46 (3H, d), 2.81-2.97 (2H, m), 3.63-3.76 (2H, m), 5.00 (1H, dd), 5.86-5.89 (2H, m), 6.76 (2H, dd), 7.16 (2H, dd), 7.93 (2H, d) |
| A2-049-b | $^1$H-NMR (DMSO) δ: 0.59-0.64 (4H, m), 1.32 (3H, d), 1.56-1.62 (1H, m), 2.71-2.76 (1H, m), 2.95-3.02 (1H, m), 3.41-3.43 (2H, m), 4.82-4.88 (1H, m), 5.81-5.84 (1H, m), 6.75-6.77 (2H, m), 7.16-7.18 (2H, m), 7.84 (1H, t), 8.37 (1H, d). |
| A2-050-b | $^1$H-NMR (DMSO) δ: 0.11-0.13 (2H, m), 0.39-0.43 (2H, m), 0.93-0.95 (1H, m), 1.30 (3H, d), 1.98-2.00 (2H, m), 2.71-2.78 (1H, m), 2.96-3.01 (1H, m), 3.41-3.43 (2H, m), 4.84 (1H, m), 5.82-5.85 (1H, m), 6.01-6.04 (1H, m), 6.74-6.76 (2H, m), 7.16-7.18 (2H, m), 7.84 (1H, t), 8.01 (1H, d). |
| A2a-005 | $^1$H-NMR (d6-DMSO) d: 0.57-0.66 (4h, m), 1.30, 1.32 (3H, 2s), 1.45-1.60 (1H, m), 2.61-2.68 (1H, m), 2.85-2.91 (1H, m), 3.31-3.40 (2H, m), 3.76-3.79 (1H, d), 4.08-4.11 (1H, d), 4.81-4.85 (1H, m), 6.61-6.63 (2H, d), 7.13-7.15 (2H, d), 7.66 (2H, s), 7.69-7.70 (1H, d), 8.32-8.34 (1H, d). |
| A2a-006 | $^1$H-NMR (d6-DMSO) δ: 0.11-0.13 (2H, m), 0.39-0.43 (2H, m), 0.93-0.96 (1H, m), 1.29-1.30 (3H, d), 1.97-2.00 (2H, m), 2.53-2.64 (1H, m), 2.85-2.90 (1H, m), 3.35-3.41 (1H, m) 3.75-3.78 (1H, d), 4.09-4.11 (1H, d), 4.81-4.85 (1H, m), 6.61-6.63 (2H, d), 7.13-7.15 (2H, d), 7.66 (2H, d) (1H, s), 7.69 (1H, s), 7.98-8.00 (1H, d) |
| A2a-016 | $^1$H-NMR (d3-CD3CN) δ: 0.62-0.75 (4H, m), 1.38-1.40 (2H, d), 1.41-1.48 (1H, m), 2.68-2.78 (1H, m), 2.83-2.85 (1H, m), 3.48-3.59 (2H, m) 3.73-3.75 (1H, d), 4.89 (1H, m), 5.90-5.93 (1H, d), 6.77-6.80 (2H, d), 6.88 (1H, br), 7.21-7.23 (2H, d), 7.47 (2H, s), 7.49 (1H, d) |
| A2a-049 | $^1$H-NMR (DMSO) δ: 0.62-0.67 (4H, m), 1.31 (3H, d), 1.55-1.61 (1H, m), 2.63-2.69 (1H, m), 3.01-3.05 (1H, m), 3.39-3.41 (2H, m), 3.71-3.74 (1H, m), 4.21-4.24 (1H, m), 4.84 (1H, m), 6.61-6.63 (2H, m), 7.14-7.17 (2H, m), 7.97 (1H, t), 8.34 (1H, d). |
| A2a-050 | $^1$H-NMR (DMSO) δ: 0.10-0.13 (2H, m), 0.39-0.43 (2H, m), 0.92-0.98 (1H, m), 1.30 (3H, d), 1.94-2.03 (2H, m), 2.60-2.68 (1H, m), 3.01-3.04 (1H, m), 3.39-3.41 (2H, m), 3.70-3.73 (1H, m), 4.22-4.24 (1H, m), 4.84 (1H, m), 6.60-6.63 (2H, m), 7.14-7.16 (2H, m), 7.95-8.01 (2H, m). |
| A3-001 | $^1$H-NMR (CDCl$_3$) δ: 1.96 (3H, s), 2.83-2.92 (2H, m), 3.65-3.75 (2H, m), 4.38-4.47 (3H, m), 5.93-5.95 (1H, m), 6.28 (1H, d), 6.57-6.64 (1H, m), 7.34-7.39 (3H, m), 7.78-7.81 (1H, m). |
| A3-002 | $^1$H-NMR (CDCl$_3$) δ: 1.14 (3H, t), 2.16 (2H, q), 2.81-2.84 (2H, m), 3.75-3.76 (2H, m), 4.49-4.54 (3H, m), 5.88-5.95 (1H, m), 6.30 (1H, s), 6.83 (1H, d), 7.31-7.44 (3H, m), 7.84 (1H, m). |
| A3-005 | $^1$H-NMR (CDCl$_3$) δ: 0.75-0.79 (2H, m), 0.91-0.95 (2H, m), 1.23-1.35 (1H, m), 2.79-2.84 (2H, m), 3.74-3.77 (2H, m), 4.52-4.57 (3H, m), 6.02-6.05 (1H, m), 6.32 (1H, s), 6.81 (1H, d), 7.35-7.39 (3H, m), 7.87 (1H, d). |
| A3-006 | $^1$H-NMR (CDCl$_3$) δ: 0.13-0.20 (2H, m), 0.56-0.63 (2H, m), 0.88-0.96 (1H, m), 2.11-2.23 (2H, m), 2.84-2.87 (2H, m), 3.68-3.74 (2H, m), 4.48 (2H, d), 6.30-6.33 (1H, m), 6.57-6.64 (1H, m), 7.35-7.38 (3H, m), 7.81-7.84 (1H, m). |
| a3-006 | $^1$H-NMR (CDCl$_3$) δ: 2.46 (2H, br s), 2.84-3.01 (2H, m), 3.56-4.16 (5H, m), 6.35-6.45 (2H, m), 7.55-8.08 (4H, m). |
| A3-007 | $^1$H-NMR (CDCl$_3$) δ: 2.85-2.88 (2H, m), 3.08 (2H, q), 3.68-3.73 (2H, m), 4.54 (2H, d), 6.05-6.08 (1H, m), 6.29-6.30 (1H, m), 6.63 (1H, d), 7.34-7.38 (3H, m), 7.81 (1H, d). |
| A3-011 | $^1$H-NMR (CDCl$_3$) δ: 2.84-2.87 (2H, m), 3.03 (3H, s), 3.65-3.77 (2H, m), 3.87 (2H, s), 4.55 (2H, d), 6.29 (1H, m), 6.56-6.68 (1H, m), 6.86-6.88 (1H, m), 7.33-7.39 (3H, m), 7.76-7.79 (1H, m). |
| A3-012 | $^1$H-NMR (CDCl3) δ: 1.99 (3H, s), 2.84-2.86 (2H, m), 3.67-3.78 (2H, m), 4.38-4.47 (3H, m), 5.87-5.89 (1H, m), 6.27 (1H, d), 6.56-6.64 (1H, m), 7.47 (2H, s), 7.80-7.83 (1H, m). |
| A3-013 | $^1$H-NMR (CDCl$_3$) δ: 1.15 (3H, t), 2.21 (2H, q), 2.83-2.86 (2H, m), 3.66-3.73 (2H, m), 4.39-4.49 (3H, m), 5.80-5.84 (1H, m), 6.28 (1H, s), 6.63 (1H, d), 7.45 (2H, s), 7.82 (1H, d). |
| A3-014 | $^1$H-NMR (CDCl$_3$) δ: 0.90 (3H, t), 1.62-1.66 (2H, m), 2.11-2.15 (2H, m), 2.83-2.86 (2H, m), 3.67-3.77 (2H, m), 4.34-4.46 (3H, m), 5.80-5.82 (1H, m), 6.56-6.63 (1H, m), 7.49 (2H, s), 7.80-7.83 (1H, m). |
| A3-015 | $^1$H-NMR (CDCl$_3$) δ: 1.12 (6H, d), 2.32-2.38 (1H, m), 2.73-2.87 (2H, m), 3.66-3.77 (2H, m), 4.28 (1H, d), 4.45 (2H, d), 5.81-5.83 (1H, m), 6.27 (1H, d), 6.56-6.62 (1H, m), 7.47 (2H, s), 7.79-7.82 (1H, m). |
| A3-016 | $^1$H-NMR (CDCl$_3$) δ: 0.74-0.77 (2H, m), 0.96-0.99 (2H, m), 1.22-1.36 (1H, m), 2.85-2.86 (2H, m), 3.67-3.72 (2H, m), 4.16-4.24 (1H, m), 4.50 (2H, d), 5.96-6.00 (1H, m), 6.28 (1H, s), 6.60 (1H, d), 7.45 (2H, s), 7.82 (1H, d). |
| A'3-016 | $^1$H-NMR (CDCl3) δ: 0.75-0.79 (2H, m), 0.88-1.04 (2H, m), 1.32-1.35 (1H, m), 2.54-3.15 (2H, m), 3.96 (1H, d), 4.25 (1H, d), 4.42-4.56 (3H, m), 5.89-6.03 (2H, m), 6.68 (1H, d), 7.45 (2H, s), 7.78 (1H, d). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A3-017 | $^1$H-NMR (CDCl$_3$) δ: 0.13-0.19 (2H, m), 0.57-0.61 (2H, m), 0.87-0.94 (1H, m), 2.19 (2H, d), 2.83-2.86 (2H, m), 3.68-3.78 (2H, m), 4.45-4.51 (3H, m), 6.31-6.35 (2H, m), 6.57-6.65 (1H, m), 7.48 (2H, s), 7.80-7.83 (1H, m). |
| A3-018 | $^1$H-NMR (CDCl$_3$) δ: 2.85-3.13 (4H, m), 3.65-3.78 (2H, m), 4.52-4.54 (3H, m), 6.18-6.25 (2H, m), 6.57-6.63 (1H, m), 7.45 (2H, s), 7.78-7.81 (1H, m). |
| A3-019 | $^1$H-NMR (CDCl$_3$) δ: 2.83-2.86 (2H, m), 3.36 (3H, s), 3.56-3.77 (4H, m), 4.37-4.49 (3H, m), 6.27 (1H, s), 6.54-6.70 (1H, m), 6.76-6.78 (1H, m), 7.48 (2H, s), 7.79-7.82 (1H, m). |
| A3-022 | $^1$H-NMR (CDCl$_3$) δ: 2.85-2.87 (2H, m), 3.06 (3H, s), 3.72-3.74 (2H, m), 3.87 (2H, s), 4.56-4.58 (3H, m), 6.28 (1H, s), 6.65-6.70 (2H, m), 7.47 (2H, s), 7.80-7.83 (1H, m). |
| A3-023 | $^1$H-NMR (CDCl$_3$) δ: 1.97 (3H, s), 2.94-3.00 (2H, m), 3.66-3.83 (2H, m), 4.38-4.47 (3H, m), 5.82-5.84 (1H, m), 6.39 (1H, s), 6.64-6.67 (1H, m), 7.83-7.87 (3H, m). |
| A3-024 | $^1$H-NMR (CDCl$_3$) δ: 1.15 (3H, t), 2.23 (2H, q), 2.92-2.97 (2H, m), 3.69-3.79 (2H, m), 4.30-4.34 (1H, m), 4.49 (2H, d), 5.80-5.83 (1H, m), 6.39 (1H, s), 6.65 (1H, d), 7.81-7.96 (4H, m) |
| A'3-024 | $^1$H-NMR (CDCl$_3$) δ: 1.14 (3H, t), 2.22 (2H, q), 2.62-2.67 (1H, m), 3.23-3.28 (1H, m), 4.01 (1H, d), 4.35 (1H, d), 4.50-4.54 (3H, m), 5.70-5.79 (1H, m), 5.96-5.99 (1H, m), 6.72-6.76 (1H, m), 7.88-7.90 (4H, m). |
| A3-027 | $^1$H-NMR (CDCl$_3$) δ: 0.72-0.86 (2H, m), 0.94-0.98 (2H, m), 1.28-1.32 (1H, m), 2.92-2.97 (2H, m), 3.66-3.79 (2H, m), 4.32 (1H, s), 4.51 (2H, d), 6.00-6.04 (1H, m), 6.39 (1H, s), 6.65 (1H, d), 7.80-7.92 (4H, m). |
| A3-028 | $^1$H-NMR (CDCl$_3$) δ: 0.17-0.18 (2H, m), 0.58-0.64 (2H, m), 0.89-0.92 (1H, m), 2.14 (2H, d), 2.87-3.03 (2H, m), 3.70-3.80 (2H, m), 4.44-4.52 (3H, m), 6.35-6.38 (2H, m), 6.59-6.67 (1H, m), 7.81-7.92 (4H, m). |
| A3-029 | $^1$H-NMR (CDCl$_3$) δ: 2.86-3.13 (4H, m), 3.70-3.79 (2H, m), 4.34-4.50 (3H, m), 6.31-6.39 (2H, m), 6.59-6.66 (1H, m), 7.80-7.96 (4H, m). |
| A3-033 | $^1$H-NMR (CDCl$_3$) δ: 2.94-3.04 (5H, m), 3.66-3.94 (4H, m), 4.56-4.58 (3H, m), 6.39 (1H, s), 6.60-6.67 (1H, m), 6.86-6.88 (1H, m), 7.77-7.93 (4H, m). |
| A3-079 | $^1$H-NMR (CDCl$_3$) δ: 1.17 (3H, t), 2.23 (2H, q), 2.44 (3H, s), 2.79-2.82 (2H, m), 3.58-3.72 (2H, m), 4.32-4.41 (3H, m), 5.58-5.61 (1H, m), 6.19-6.29 (2H, m), 7.35-7.55 (3H, m). |
| A3-082 | $^1$H-NMR (CDCl$_3$) δ: 0.73-0.77 (2H, m), 0.97-1.02 (2H, m), 1.20-1.37 (1H, m), 2.45 (3H, s), 2.80-2.82 (2H, m), 3.59-3.73 (2H, m), 4.34-4.36 (2H, m), 5.70-5.74 (1H, m), 6.19-6.29 (2H, m), 7.33-7.55 (3H, m). |
| A3-084 | $^1$H-NMR (CDCl$_3$) δ: 2.43 (3H, s), 2.80-2.83 (2H, m), 3.05-3.12 (2H, m), 3.63-3.66 (2H, m), 4.37-4.39 (3H, m), 5.81-5.84 (1H, m), 6.20-6.30 (2H, m), 7.35-7.48 (3H, m). |
| A3-093 | $^1$H-NMR (ACETONE-D6) δ: 0.62-0.64 (2H, m), 0.77-0.78 (2H, m), 1.23 (3H, t), 1.57-1.59 (1H, m), 2.72 (2H, q), 2.81-3.01 (2H, m), 3.71-3.73 (2H, m), 4.31 (2H, d), 6.44 (1H, s), 6.52 (1H, d), 7.46-7.48 (2H, m), 7.75 (2H, s). |
| A3-101 | $^1$H NMR (CDCl$_3$) δ: 1.14 (3H, t,), 2.22 (2H, q), 2.80-2.84 (2H, m), 3.60-3.71 (2H, m), 4.37 (2H, d), 6.05 (1H, t), 6.26 (1H, d), 6.37 (1H, d), 7.45 (2H, s), 7.60 (1H, d). |
| A3-104 | $^1$H NMR (CDCl$_3$) δ: 0.72-0.77 (2H, m), 0.92-0.97 (2H, m), 1.33-1.39 (1H, m), 2.80-2.84 (2H, m), 3.58-3.71 (2H, m), 4.24 (1H, d), 4.38 (2H, d), 6.20 (1H, t), 6.26 (1H, d), 6.35 (1H, d), 7.45 (2H, s), 7.60 (1H, d). |
| A3-112 | $^1$H-NMR (CDCl$_3$) δ: 1.11 (3H, t), 2.16-2.83 (3H, m), 2.79-2.83 (2H, m), 3.62-3.70 (2H, m), 4.32-4.51 (2H, m), 5.96-6.36 (3H, m), 7.44-7.66 (3H, m). |
| A3-115 | $^1$H-NMR (CDCl$_3$) δ: 0.71-0.80 (2H, m), 0.93-0.99 (2H, m), 1.28-1.38 (1H, m), 2.80-2.85 (2H, m), 3.60-3.70 (2H, m), 4.35-4.41 (3H, m), 6.10-6.37 (3H, m), 7.43-7.64 (3H, m). |
| A3-117 | $^1$H-NMR (CDCl$_3$) δ: 2.81-3.03 (2H, m), 3.04-3.14 (3H, m), 3.60-3.70 (2H, m), 4.39-4.50 (2H, m), 6.24-6.38 (3H, m), 7.44-7.64 (3H, m). |
| A3-122 | $^1$H-NMR (CDCl$_3$) δ: 2.02 (3H, s), 2.46 (3H, s), 2.89-2.93 (2H, m), 3.61-3.75 (2H, m), 4.33-4.35 (3H, m), 5.51-5.54 (1H, m), 6.31-6.36 (2H, m), 7.41-7.45 (1H, m), 7.89-7.92 (3H, m). |
| A3-123 | $^1$H-NMR (CDCl$_3$) δ: 1.16 (3H, t), 2.22 (2H, q), 2.46 (3H, s), 2.91-3.00 (2H, m), 3.58-3.77 (2H, m), 4.32-4.35 (3H, m), 5.57-5.60 (1H, m), 6.21-6.39 (2H, m), 7.41-7.44 (1H, m), 7.7.90 (3H, s). |
| A3-126 | $^1$H-NMR (CDCl$_3$) δ: 0.74-0.79 (2H, m), 0.92-1.01 (2H, m), 1.32-1.36 (1H, m), 2.44 (3H, s), 2.83-2.98 (2H, m), 3.58-3.76 (2H, m), 4.31-4.44 (2H, m), 5.85-5.88 (1H, m), 6.21-6.39 (2H, m), 7.41-7.44 (1H, m), 7.90 (3H, s). |
| A3-127 | $^1$H-NMR (CDCl$_3$) δ: 0.07-0.21 (2H, m), 0.59-0.62 (2H, m), 0.91-0.96 (1H, m), 2.18 (2H, d), 2.49 (3H, s), 2.83-2.99 (2H, m), 3.59-3.78 (2H, m), 4.34-4.47 (2H, m), 6.01-6.03 (1H, m), 6.22-6.39 (2H, m), 7.42-7.45 (1H, m), 7.90 (3H, s). |
| A3-128 | $^1$H-NMR (CDCl$_3$) δ: 2.44 (3H, s), 2.89-2.94 (2H, m), 3.09 (2H, q), 3.59-3.78 (2H, m), 4.38-4.40 (2H, m), 5.81-5.84 (1H, m), 6.28-6.36 (2H, m), 7.42 (1H, s), 7.90 (3H, s). |
| A3-132 | $^1$H-NMR (CDCl$_3$) δ: 2.46 (3H, s), 2.87-2.99 (2H, m), 3.06 (3H, s), 3.58-3.76 (2H, m), 3.87 (2H, s), 4.37-4.39 (2H, m), 6.22-6.39 (2H, m), 6.63-6.66 (1H, m), 7.43-7.46 (1H, m), 7.89 (3H, s). |
| A3-137 | $^1$H-NMR (CDCl$_3$) δ: 0.73-0.76 (2H, m), 0.92-0.99 (2H, m), 1.23-1.37 (4H, m), 2.71-2.99 (4H, m), 3.62-3.76 (2H, m), 4.36-4.38 (2H, m), 5.73-5.76 (1H, m), 6.22-6.37 (2H, m), 7.44-7.47 (1H, m), 7.87-7.94 (3H, m). |
| A3-155 | $^1$H-NMR (CDCl$_3$) δ: 2.00 (3H, s), 2.80-2.98 (2H, m), 3.62-3.74 (2H, m), 4.02-4.41 (3H, m), 5.95 (1H, br s), 6.36-7.88 (6H, m). |
| A3-156 | $^1$H-NMR (CDCl$_3$) δ: 1.51 (3H, t), 2.20 (2H, q), 2.88-3.01 (2H, m), 3.62-3.78 (2H, m), 4.15-4.40 (3H, m), 5.97 (1H, br s), 6.30-6.41 (2H, m), 7.60-8.07 (4H, m). |
| A3-159 | $^1$H-NMR (CDCl$_3$) δ: 0.71-0.78 (2H, m), 0.90-0.99 (2H, m), 1.32-1.40 (1H, m), 2.80-2.98 (2H, m), 3.65-3.74 (2H, m), 4.10-4.42 (3H, m), 6.15 (1H, br s), 6.28-8.07 (6H, m) |
| A3-161 | $^1$H-NMR (CDCl$_3$) δ: 2.80-3.11 (4H, m), 3.62-3.74 (2H, m), 4.08-4.46 (3H, m), 6.27-8.07 (7H, m). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A3-163 | $^1$H-NMR (CDCl$_3$) δ: 2.15 (3H, s), 2.80-3.01 (2H, m), 3.23 (2H, s), 3.62-3.77 (2H, m), 4.18-4.45 (3H, m), 6.33-8.07 (7H, m). |
| A3-164 | $^1$H-NMR (CDCl$_3$) δ: 2.66-3.76 (10H, m), 4.37-4.48 (2H, m), 6.29-8.07 (7H, m). |
| A3-165 | $^1$H-NMR (CDCl$_3$) δ: 2.80-3.07 (5H, m), 3.62-3.75 (2H, m), 3.86-4.09 (3H, m), 4.44-4.49 (2H, m), 6.33-8.07 (7H, m). |
| A3-167 | $^1$H-NMR (CDCl$_3$) δ: 9.69-8.95 (4H, m), 8.49 (1H, d), 8.14 (1H, d), 7.71 (1H, t), 6.33 (2H, d), 6.15 (1H, d), 5.64-5.47 (2H, m), 4.74-4.68 (2H, m), 4.07 (2H, q), 3.00 (3H, t). |
| A3-170 | $^1$H-NMR (CDCl$_3$) δ: 7.81-7.03 (4H, m), 6.61 (1H, d), 6.27 (1H, d), 6.04-5.96 (1H, m), 4.48 (2H, d), 4.24 (1H, d), 3.77-3.59 (2H, m), 2.90-2.80 (2H, m), 1.35-1.27 (1H, m), 0.97-0.91 (2H, m), 0.75-0.71 (2H, m). |
| A3-178 | $^1$H-NMR (CDCl$_3$) δ: 1.15 (3H, t), 2.22 (2H, q), 2.72-2.88 (2H, m), 3.58-3.73 (2H, m), 4.49 (2H, d), 5.79-5.85 (1H, m), 6.26 (1H, s), 6.64 (1H, d), 7.44 (2H, s), 7.66 (1H, t), 7.80 (1H, d). |
| A3-181 | $^1$H-NMR (CDCl$_3$) δ: 0.71-0.78 (2H, m), 0.92-1.01 (2H, m), 1.26-1.38 (1H, m), 2.75-2.87 (2H, m), 3.60-3.71 (2H, m), 4.51 (2H, d), 5.97 (1H, t), 6.26 (1H, s), 6.64 (1H, d), 7.44 (2H, s), 7.67 (1H, t), 7.79 (1H, d). |
| A3-189 | $^1$H-NMR (CDCl$_3$) δ: 7.82-7.07 (3H, m), 6.61 (1H, d), 6.23 (1H, d), 5.85 (1H, br s), 4.48-4.35 (3H, m), 3.75-3.64 (2H, m), 2.84-2.77 (2H, m), 2.18 (2H, q), 1.12 (3H, t). |
| A3-192 | $^1$H-NMR (CDCl$_3$) δ: 7.77-7.06 (3H, m), 6.61 (1H, d), 6.22-6.10 (2H, m), 4.58-4.36 (3H, m), 3.81-3.61 (2H, m), 2.90-2.74 (2H, m), 1.36-1.30 (1H, m), 0.98-0.88 (2H, m), 0.77-0.69 (2H, m). |
| A3-200 | $^1$H-NMR (CDCl$_3$) δ: 1.12 (3H, t), 2.20 (2H, q), 2.80-2.87 (2H, m), 3.61-3.71 (2H, m), 4.43-4.48 (3H, m), 5.90 (1H, t), 6.25 (1H, d), 6.63 (1H, d), 7.40 (2H, d), 7.80 (1H, d). |
| A3-203 | $^1$H-NMR (CDCl$_3$) δ: 0.72-0.78 (2H, m), 0.92-0.99 (2H, m), 1.25-1.37 (1H, m), 2.80-2.88 (2H, m), 3.60-3.80 (2H, m), 4.27 (1H, d), 4.50 (2H, d), 5.99 (1H, d), 6.26 (1H, d), 6.62 (1H, d), 7.39 (1H, s), 7.41 (1H, s), 7.83 (1H, d). |
| A3-210 | $^1$H-NMR (CDCl$_3$) δ: 7.83 (1H, d), 7.32 (1H, t), 6.65 (1H, d), 6.45 (1H, br s), 5.86 (1H, t), 4.48 (2H, d), 4.22 (1H, br s), 3.77-3.60 (2H, m), 2.98-2.80 (2H, m), 1.99 (3H, s). |
| A3-211 | $^1$H-NMR (CDCl$_3$) δ: 1.14 (3H, t), 2.21 (2H, q), 2.77-3.00 (2H, m), 3.58-3.75 (2H, m), 4.11 (2H, q), 4.48 (2H, d), 5.80 (1H, t,), 6.44 (1H, t), 6.63 (1H, d), 7.31 (1H, t), 7.83 (1H, d). |
| A3-214 | $^1$H-NMR (CDCl$_3$) δ: 0.69-0.80 (2H, m), 0.88-1.01 (2H, m), 1.28-1.38 (1H, m), 2.77-2.97 (2H, m), 3.58-3.76 (2H, m), 4.15 (1H, d), 4.49 (2H, d), 6.02 (1H, t), 6.44 (1H, t), 6.62 (1H, d), 7.31 (1H, t), 7.81 (1H, d). |
| A3-221 | $^1$H-NMR (CDCl$_3$) δ: 1.97 (3H, s), 2.94-2.96 (2H, m), 3.69-3.75 (2H, m), 4.49-4.54 (3H, m), 5.80-5.83 (1H, m), 6.37 (1H, d), 6.63-6.66 (1H, m), 7.51-7.67 (4H, m), 7.82-7.85 (1H, m). |
| A3-222 | $^1$H-NMR (CDCl$_3$) δ: 1.15 (3H, t), 2.23 (2H, q), 2.94-2.95 (2H, m), 3.70-3.74 (2H, m), 4.44-4.48 (3H, m), 5.77-5.81 (1H, m), 6.37 (1H, d), 6.63-6.65 (1H, m), 7.54-7.67 (4H, m), 7.83-7.86 (1H, m). |
| A3-225 | $^1$H-NMR (CDCl$_3$) δ: 0.75-0.82 (2H, m), 0.91-0.97 (2H, m), 1.28-1.33 (1H, m), 2.92-2.94 (2H, m), 3.66-3.81 (2H, m), 4.43-4.58 (2H, m), 6.00-6.08 (1H, m), 6.37 (1H, s), 6.55-6.64 (1H, m), 7.54-7.66 (4H, m), 7.79-7.88 (1H, m). |
| A3-226 | $^1$H-NMR (CDCl$_3$) δ: 0.16-0.19 (2H, m), 0.58-0.61 (2H, m), 0.85-0.97 (1H, m), 2.14 (2H, d), 2.93-3.00 (2H, m), 3.67-3.78 (2H, m), 4.22 (1H, s), 4.48 (2H, d), 6.34-6.36 (2H, m), 6.56-6.65 (1H, m), 7.54-7.66 (4H, m), 7.82-7.87 (1H, m). |
| A3-227 | $^1$H-NMR (CDCl$_3$) δ: 2.95-2.96 (2H, m), 3.08 (2H, q), 3.75-3.78 (2H, m), 4.09 (1H, s), 4.54 (2H, d), 6.05-6.08 (1H, m), 6.38 (1H, d), 6.64-6.67 (1H, m), 7.55-7.65 (4H, m), 7.80-7.83 (1H, m). |
| A3-231 | $^1$H-NMR (CDCl$_3$) δ: 2.99-3.07 (5H, m), 3.66-3.77 (2H, m), 3.88 (2H, s), 4.54-4.56 (3H, m), 6.37 (1H, d), 6.57-6.65 (1H, m), 6.85-6.88 (1H, m), 7.51-7.69 (4H, m), 7.73-7.90 (1H, m). |
| A3-233 | $^1$H-NMR (CDCl$_3$) δ: 1.14 (3H, t), 2.21 (2H, q), 2.85-2.96 (2H, m), 3.63-3.80 (2H, m), 4.27 (1H, d), 4.48 (2H, d), 5.81 (1H, br S), 6.32 (1H, d), 6.63 (1H, d), 7.21-7.24 (1H, m), 7.52-7.87 (3H, m). |
| A3-236 | $^1$H-NMR (CDCl$_3$) δ: 0.70-0.78 (2H, m), 0.88-0.98 (2H, m), 1.26-1.38 (1H, m), 2.81-2.96 (2H, m), 3.63-3.79 (2H, m), 4.32 (1H, d), 4.49 (2H, d), 6.02 (1H, br s), 6.32 (1H, d), 6.63 (1H, d), 7.23 (1H, t), 7.63-7.84 (3H, m). |
| A3-244 | $^1$H-NMR (CDCl$_3$) δ: 1.13 (3H, t), 2.21 (2H, q), 2.86-2.96 (2H, m), 3.65-3.81 (2H, m), 4.39-4.49 (3H, m), 5.87 (1H, s), 6.33 (1H, d), 6.65 (1H, d), 7.33-7.84 (4H, m). |
| A3-247 | $^1$H-NMR (CDCl$_3$) δ: 0.71-0.79 (2H, m), 0.90-0.98 (2H, m), 1.30-1.38 (1H, m), 2.84-2.94 (2H, m), 3.63-3.82 (2H, m), 4.38-4.52 (3H, m), 6.06 (1H, br s), 6.32 (1H, d), 6.64 (1H, d), 7.33-7.83 (4H, m). |
| A3-265 | $^1$H-NMR (CDCl$_3$) δ: 1.94 (3H, s), 2.85-2.92 (2H, m), 3.68-3.80 (2H, m), 4.43-4.53 (3H, m), 5.96-6.17 (1H, m), 6.33 (1H, d), 6.56-6.72 (1H, m), 7.60-7.67 (3H, m), 7.74-7.85 (1H, m). |
| A3-266 | $^1$H-NMR (CDCl$_3$) δ: 1.13 (3H, t), 2.19 (2H, q), 2.92-2.95 (2H, m), 3.69-3.77 (2H, m), 4.33-4.49 (3H, m), 5.82-5.84 (1H, m), 6.32-6.33 (1H, d), 6.58-6.63 (1H, m), 7.57-7.63 (3H, m), 7.74-7.86 (1H, m). |
| A3-269 | $^1$H-NMR (CDCl$_3$) δ: 0.75-0.79 (2H, m), 0.88-1.05 (2H, m), 1.30-1.38 (1H, m), 2.87-2.96 (2H, m), 3.69-3.77 (2H, m), 4.33-4.51 (2H, m), 6.03-6.05 (1H, m), 6.33 (1H, s), 6.56-6.64 (1H, m), 7.59-7.62 (3H, m), 7.74-7.86 (1H, m). |
| A3-270 | $^1$H-NMR (CDCl$_3$) δ: 0.07-0.20 (2H, m), 0.58-0.61 (2H, m), 0.89-0.96 (1H, m), 2.18 (2H, d), 2.91-2.98 (2H, m), 3.68-3.81 (2H, m), 4.39-4.52 (3H, m), 6.33-6.36 (2H, m), 6.58-6.66 (1H, m), 7.59-7.63 (3H, m), 7.77-7.84 (1H, m). |
| A3-271 | $^1$H-NMR (CDCl$_3$) δ: 2.89-2.93 (2H, m), 3.05 (2H), 3.70-3.78 (2H, m), 4.51 (2H, d), 6.17-6.18 (1H, m), 6.34 (1H, d), 6.58-6.65 (1H, m), 7.57-7.63 (3H, m), 7.74-7.86 (1H, m). |
| A3-275 | $^1$H-NMR (CDCl$_3$) δ: 2.89-2.92 (2H, m), 3.06 (3H, s), 3.70-3.73 (2H, m), 3.87 (2H, s), 4.56-4.58 (3H, m), 6.30-6.34 (1H, m), 6.67-6.72 (2H, m), 7.57-7.64 (3H, m), 7.76-7.83 (1H, m). |
| A3-288 | $^1$H-NMR (CDCl$_3$) δ: 0.95 (6H, d), 2.06-2.13 (3H, m), 2.83-2.86 (2H, m), 3.66-3.77 (2H, m), 4.30 (1H, s), 4.46 (2H, d), 5.78-5.80 (1H, m), 6.27 (1H, s), 6.56-6.63 (1H, m), 7.44 (2H, s), 7.81-7.84 (1H, m). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A3-297 | $^1$H-NMR (CDCl$_3$) δ: 1.09 (3H, t), 2.82-2.85 (2H, m), 3.14-3.18 (2H, m), 3.66-3.77 (2H, m), 4.40-4.43 (4H, m), 4.79-4.81 (1H, m), 6.25 (1H, s), 6.55-6.62 (1H, m), 7.45 (2H, s), 7.82-7.84 (1H, m). |
| A3-321 | $^1$H-NMR (CDCl$_3$) δ: 1.45 (9H, s), 2.88-3.01 (2H, m), 3.65-3.77 (2H, m), 4.13-4.29 (3H, m), 5.02 (1H, br s), 6.29-6.40 (2H, m), 7.62-8.08 (4H, m) |
| A3-322 | $^1$H NMR (CDCl$_3$) δ: 7.65 (1H, d), 7.30 (1H, t), 6.43 (1H, t), 6.35 (1H, d), 5.93 (1H, t), 4.38 (2H, d), 3.94 (1H, d), 3.69-3.54 (2H, m), 2.95-2.81 (2H, m), 2.00 (3H, s). |
| A3-323 | $^1$H NMR (CDCl$_3$) δ: 7.63 (1H, d), 7.31 (1H, t), 6.42 (1H, t), 6.36 (1H, d), 5.97 (1H, t), 4.38 (2H, d), 3.67-3.58 (2H, m), 2.95-2.77 (2H, m), 2.22 (2H, q), 1.15 (3H, t). |
| A3-326 | $^1$H NMR (CDCl$_3$) δ: 7.60 (1H, d), 7.30 (1H, dd), 6.41 (1H, d), 6.37 (1H, d), 6.24 (1H, t), 4.39 (2H, d), 3.69-3.57 (2H, m), 3.00-2.77 (2H, m), 1.40-1.34 (1H, m), 0.97-0.93 (2H, m), 0.77-0.72 (2H, m). |
| A3-344 | $^1$H NMR (CDCl$_3$) δ: 7.83 (1H, d), 7.47 (1H, dd), 7.23 (1H, dd), 6.65 (1H, d), 6.47 (1H, t), 5.85 (1H, t), 4.48 (2H, dd), 3.77-3.59 (2H, m), 2.97-2.82 (2H, m), 1.99 (3H, s). |
| A3-345 | $^1$H NMR (CDCl$_3$) δ: 7.83 (1H, d), 7.47 (1H, dd), 7.23 (1H, dd) 6.64 (1H, d), 6.47 (1H, t), 5.83 (1H), 4.49 (2H, d), 4.12 (1H, d), 3.79-3.59 (2H, m), 2.97-2.83 (2H, m), 2.22 (2H, q), 1.15 (3H, t). |
| A3-348 | $^1$H NMR (CDCl$_3$) δ: 7.76 (1H, d), 7.45 (1H, dd), 7.23 (1H, dd), 6.71-6.61 (1H, m), 6.44 (1H, br s), 6.18 (1H, br s), 4.47 (2H, d), 4.35 (1H, br s), 3.74-3.60 (2H, m), 2.95-2.81 (2H, m), 1.38-1.32 (1H, m), 0.91-0.96 (2H, m), 0.71-0.76 (2H, m). |
| A3-355 | $^1$H-NMR (DMSO-D6) δ: 1.88 (3H, s), 2.61-2.70 (1H, m), 2.84-2.90 (1H, m), 3.64-3.71 (1H, m), 3.89-3.84 (1H, m), 4.17 (2H, d), 6.28 (1H, d), 6.37 (1H, d), 7.51 (2H, d), 7.53 (1H, d), 7.66 (1H, t), 8.33 (1H, t). |
| A3-366 | $^1$H-NMR (DMSO-D6) δ: 1.88 (3H, s), 2.61-2.68 (1H, m), 2.85-2.91 (1H, m), 3.63-3.70 (1H, m), 3.84-3.90 (1H, m), 4.17 (2H, d), 6.30 (1H, d), 6.40 (1H, d), 7.53 (1H, d), 7.74 (2H, d), 8.33 (1H, t). |
| A3-367 | $^1$H-NMR (ACETONE-D6) δ: 1.07 (3H, t), 2.23 (2H, q), 2.78-2.87 (1H, m), 2.94-3.00 (1H, m), 3.84-4.01 (1H, m), 4.31 (1H, d), 5.59 (1H, d), 6.52 (1H, d), 7.47-7.50 (2H, m), 7.75 (2H, s). |
| A3-370 | $^1$H-NMR (DMSO-D6) δ: 0.66-0.71 (4H, m), 1.58-1.64 (1H, m), 2.60-2.68 (1H, m), 2.85-2.91 (1H, m), 3.64-3.71 (1H, m), 3.90-3.84 (1H, m), 4.20 (2H, d), 6.30 (1H, d), 6.40 (1H, d), 7.52 (1H, d), 7.74 (2H, s), 8.54 (1H, t). |
| A3-377 | $^1$H-NMR (DMSO-D6) δ: 1.88 (3H, s), 2.68-2.77 (1H, m), 3.03-3.09 (1H, m), 3.69-3.76 (1H, m), 3.88-3.94 (1H, m), 4.17-4.19 (2H, m), 6.42-6.49 (2H, m), 7.55 (1H, d), 8.10 (2H, s), 8.17 (1H, s), 8.33 (1H, br s). |
| A3-378 | $^1$H-NMR (DMSO-D6) δ: 1.02 (3H, t), 2.16 (2H, q), 2.67-2.77 (1H, m), 3.02-3.10 (1H, m), 3.68-3.76 (1H, m), 3.87-3.94 (1H, m), 4.19 (2H, d), 6.42-6.49 (2H, m), 7.52 (1H, d), 8.10 (2H, s), 8.17 (1H, s), 8.26 (1H, br s). |
| A3-381 | $^1$H-NMR (CDCl$_3$) δ: 0.75-0.80 (2H, m), 0.96-1.00 (2H, m), 1.34-1.40 (1H, m), 2.81-2.96 (2H, m), 3.91 (1H, br s), 4.12 (1H, br s), 4.33 (1H, d), 4.39 (2H, d), 6.15 (1H, t), 6.33 (1H, d), 7.44 (1H, d), 7.86 (2H, s), 7.89 (1H, s). |
| A3-421 | $^1$H NMR (CDCl$_3$) δ: 2.84-2.88 (2H, m), 3.38 (2H, s), 3.68-3.75 (2H, m), 4.50-4.54 (2H, m), 6.29 (1H, d), 6.40-6.45 (1H, m), 6.61 (1H, d), 7.48 (2H, s), 7.79 (1H, d). |
| A3-424 | $^1$H NMR (CDCl$_3$) δ: 0.77-0.81 (2H, m), 1.04-1.06 (2H, m), 1.93-1.97 (4H, m), 2.83-2.85 (2H, m), 3.71-3.73 (2H, m), 4.36 (1H, d), 4.77-4.79 (3H, m), 6.25-6.26 (1H, m), 6.62 (1H, d), 7.47 (2H, s), 7.70 (1H, d) |
| A3a-001 | $^1$H-NMR (CDCl$_3$) δ: 7.73 (1H, d), 7.39 (2H, s), 6.51 (2H, d), 5.75 (1H, bs), 4.47-4.39 (3H, m), 3.97 (1H, d), 3.75-3.50 (2H, m), 2.99-2.89 (1H, m), 2.57-2.47 (1H, m), 1.98 (3H, s). |
| A3a-006 | $^1$H-NMR (CDCl3) δ: 7.75 (1H, d), 7.40 (1H, s), 7.31 (3H, s), 6.52 (1H, d), 6.29 (1H, bs), 4.49 (2H, d), 4.35 (1H, d), 3.96 (1H, d), 3.70-3.52, 2H, m), 2.99-2.80 (1H, m), 2.60-2.50 (1H, m), 2.15 (2H, d), 0.95-0.87 (1H, m), 0.62-0.56 (2H, m), 0.19-0.14 (2H, m). |
| A3a-007 | $^1$H-NMR (DMSO, 399.95 MHz) d: 8.65 (1H, bt), 7.71-7.62 (4H, m), 6.92 (1H, d), 4.31-4.39 (3H, m), 3.92-3.89 (1H, m), 3.59-3.50 (2H, m), 2.33-2.26 (2H, m), 2.68-2.63 (1H, m). |
| A3a-011 | $^1$H-NMR (CDCl3) δ: 7.69 (1H, d), 7.39 (1H, s), 7.30 (2H, s), 6.70-6.51 (2H, m), 4.54 (2H, d), 4.40 (1H, d), 3.97-3.86 (3H, m), 3.68-3.50 "H, m), 3.05 (3H, s), 2.92-2.85 (1H, m), 2.62-2.58 (1H, m), 1.55 (3H, s). |
| A3a-012 | $^1$H-NMR (CDCl3) δ: 7.71 (1H, d), 7.44 (2H, s), 6.51 (2H, d), 5.81 (1H, bs), 4.48-4.32 (3H, m) 4.12 (1H, q), 3.96 (1H, d), 3.70-3.52 (2H, m), 2.92-2.82 (1H, m), 2.59-2.49 (1H, m), 1.98 (/3H, s). |
| A3a-014 | $^1$H-NMR (CDCl3) δ: 7.74 (1H, d), 7.44 (2H, s), 6.51 (1H, d), 4.50-4.35 (3H, m), 3.96 (1H, d), 3.70-3.55 (2H, m), 2.93-2.80 (1H, m), 2.60-2.48 (1H, m), 2.15 (2H, t), 1.71-1.59 (2H, m), 0.92 (3H, t). |
| A3a-015 | $^1$H-NMR (CDCl3) δ: 7.72 (1H, d), 7.44 (2H, s), 6.51 (1H, d), 5.77 (1H, bs), 4.47-4.35 (3H, m), 3.96 (1H, d), 3.70-3.52 (2H, m), 2.90-2.80 (1H, m), 2.62-2.48 (1H, m), 2.38-2.29 (1H, m), 1.14 (6H, d). |
| A3a-016 | $^1$H-NMR (DMSO, 399.95 MHz) d: 8.47 (1H, bt), 7.86 (2H, s), 7.66 (1H, d), 6.90 (1H, d), 4.38 (1H, d), 4.29 (2H, d), 3.93 (1H, d), 3.56 (2H, m), 3.03-2.89 (1H, m), 2.69-2.61 (1H, m), 1.64-1.58 (1H, m), 0.70-0.65 (4H, m). |
| A3a-019 | $^1$H-NMR (DMSO, 399.95 MHz) d: 8.31 (1H, t), 7.86 (2H, s), 7.66 (1H, d), 6.88 (1H, d), 4.37 (1H, d), 4.29 (1H, d), 3.93-3.90 (1H, m), 3.58-3.52 (2H, m), 3.21 (3H, s), 2.94-2.90 (1H, m), 2.63-2.67 (1H, m). |
| A3a-023 | $^1$H-NMR (CDCl3) δ: 7.92-7.85 (2H, m), 7.74 (2H, d), 6.54 (2H, d), 5.81 (1H, bt), 4.50-4.45 (3H, m) 4.06 (1H, t), 3.72-3.51 (2H, m), 3.05-2.98 (1H, m), 2.70-2.50 (1H, m), 1.98 (3H, s). |
| A3a-079 | $^1$H-NMR (CDCl3) δ: 7.46 (2H, s), 7.34 (1H, d), 6.20 (1H, d), 5.43 (1H, bs), 4.39-4.33 (3H, m), 3.96 (1H, s), 3.65-3.48 2H, m), 2.87-2.79 (1H, m), 2.60-2.42 (4H, m), 2.21 (2H, q), 1.17 (3H, t). |
| A3a-082 | $^1$H-NMR (DMSO, 399.95 MHz) d: 8.29 (1H, bs), 7.85 (2H, m), 7.35 (1H, d), 6.39 (1H, d), 4.35 (1H, d), 4.13 (2H, d), 3.85 (1H, d), 3.51-3.48 (2H, m), 2.92-2.86 (1H, m), 2.67-2.58 (1H, m), 2.33 (3H, s), 1.59-1.53 (1H, m), 0.68-0.64 (4H, m). |
| A3a-084 | $^1$H-NMR (CDCl3) δ: 7.45 (2H, s), 7.33 (1H, d), 6.21 (1H, d), 5.72 (1H, bs), 4.40-4.33 (3H, m), 3.96 (1H, s), 3.65-3.48 (2H, m), 3.07 (2H, q), 2.87-2.80 (1H, m), 2.60-2.44 (4H, m). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A3a-093 | $^1$H-NMR (DMSO, 399.95 MHz) d: 8.29 (1H, bs), 7.85 (2H, s), 7.34 (1H, d), 6.39 (1H, d), 4.31 (1H, d), 4.15 (2H, d), 3.52-3.50 (1H, m), 2.91-2.85 (1H, m), 2.67-2.61 (2H, m), 1.59-1.53 (1H, m), 1.18 (3H, t), 0.68-0.64 (4H, m). |
| A3a-102 | $^1$H-NMR (CDCl3) d: 1.15 (3H, t), 2.22 (2H, q), 2.50-2.58 (1H, m), 2.85-2.89 (1H, m), 3.50-3.66 (2H, m), 3.90-3.93 (1H, m), 4.37-4.40 (3H, m), 5.92 (1H, m), 6.27 (1H, d), 7.44 (2H, s), 7.57 (1H, d). |
| A3a-104 | $^1$H-NMR (CDCl3) d: 0.07-0.77 (2H, m), 0.95-0.99 (2H, m), 1.30-1.39 (1H, m), 2.47-2.55 (1H, m), 2.85-2.90 (1H, m), 3.54-3.63 (2H, m), 3.90-3.94 (1H, d), 4.36-4.40 (3H, m), 6.11 (1H, m), 6.27 (1H, d), 7.44 (2H, m), 7.56 (1H, d). |
| A3a-106 | $^1$H-NMR (CDCl3) d: 2.50-2.55 (1H, m), 2.83-2.90 (1H, m), 3.07 (2H, q), 3.55-3.65 (2H, m), 3.90-3.94 (1H, m), 4.37-4.43 (3H, m), 6.21 (1H, m), 6.28 (1H, d), 7.44 (2H, s), 7.55 (1H, d). |
| A3a-108 | $^1$H-NMR (CDCl3) d: 2.10 (3H, s), 2.45-2.55 (1H, m), 2.84-2.89 (1H, m), 3.20 (2H, s), 3.55-3.65 (2H, m), 3.90-3.94 (1H, m), 4.36-4.43 (3H, m), 6.28 (1H, d), 7.35 (1H, m), 7.44 (2H, s), 7.56 (1H, d). |
| A3a-109 | $^1$H-NMR (CDCl3) d: 2.50-2.55 (1H, m), 2.67 (s, 3H), 2.82-2.89 (1H, m), 3.24-3.29 (1H, m), 3.58-3.71 (3H, m), 3.90-3.94 (1H, m), 4.36-4.40 (2H, m), 4.45-4.47 (2H, m), 6.28 (1H, d), 7.28 (1H, m), 7.44 (2H, s), 7.58 (1H, d). |
| A3a-110 | $^1$H-NMR (CDCl3) d: 2.46-2.57 (1H, m), 2.84-2.91 (2H, m), 3.88-3.93 (3H, m), 4.37-4.40 (1H, m), 4.45 (2H, d), 6.29 (1H, d), 6.84 (1H, m), 7.44 (2H, s), 7.55 (1H, d). |
| A3a-115 | $^1$H-NMR (CDCl3) d: 0.72-0.75 (2H, m), 0.95-0.97 (2H, m), 1.29-1.35 (1H, m), 2.96-2.57 (1H, m), 2.81-2.90 (1H, m), 3.51-3.64 (2H, m), 3.90-3.94 (1H, m), 4.36-4.41 (3H, m), 6.06 (1H, m), 6.27 (1H, d), 7.44 (2H, s), 7.57 (1H, d). |
| A3a-120 | $^1$H-NMR (CDCl3) d: 2.50-2.57 (1H, m), 2.67 (3H, m), 2.84-2.91 (2H, m), 3.24-3.29 (1H, m), 3.48-3.60 (2H, m), 3.66-3.71 (1H, m), 3.88-3.94 (2H, m), 4.36-4.40 (1H, m), 4.47 (2H, m), 6.28 (1H, d), 7.28 (1H, m), 7.44 (2H, s), 7.58 (1H, d). |
| A3a-121 | $^1$H-NMR (CDCl3) d: 2.50-2.55 (1H, m), 2.84-2.89 (1H, m), 3.07 (3H, s), 3.55-3.63 (2H, m), 3.88-3.91 (3H, m), 4.36-4.4 (1H, m), 4.44 (2H, d), 6.28 (1H, d), 6.89 (1H, m), 7.44 (2H, s), 7.55 (1H, d). |
| A3a-122 | $^1$H-NMR (CDCl3) δ: 7.93-7.85 (3H, m), 7.35 (1H, d), 6.22 (1H, d), 5.60 (1H, bs), 4.51 (1H, d), 4.32 (2H, d), 4.02 (1H, d), 3.70-3.48 (2H, m), 3.10-2.90 (1H, m), 2.82-2.43 (4H, m), 2.46 (3H, s), 1.99 (3H, s). |
| A3a-123 | $^1$H-NMR (CDCl3) δ: 7.92-7.85 (3H, m), 7.35 (1H, d), 6.22 (1H, d), 5.51 (1H, m), 4.51 (1H, d), 4.34 (2H, d), 4.05 (1H, d), 3.72-3.50 (2H, m), 3.10-2.90 (1H, m), 2.70-2.50 1H, m), 2.46 (3H, s) 2.22 (2H, q), 1.17 (3H, t). |
| A3a-126 | $^1$H-NMR (CDCl3) δ: 7.90-7.85 (3H, m), 7.37 (1H, d), 6.23 (1H, d), 5.61 (1H, m), 4.51 (1H, d), 4.36 (2H, d), 4.05 (1H, d), 3.20-2.95 (2H, m), 2.74-2.50 (1H, m), 2.47 (3H, s) 1.33-1.26 (1H, m), 1.04-0.95 (2H, m), 0.80-0.70 (2H, m). |
| A3a-127 | $^1$H-NMR (CDCl3) δ: 7.92-7.85 (3H, m), 7.38 (1H, d), 6.23 (1H, d), 5.96 (1H, m), 4.52 (1H, d), 4.38 (2H, d), 4.07 (1H, d), 3.70-3.50 (2H, m), 3.06-2.90 (1H, m), 2.70-2.40 (4H, m), 2.19 (2H, m), 1.00-0.90 (1H, m), 0.63-0.54 (2H, m), 0.20 (2H, q). |
| A3a-128 | $^1$H-NMR (DMSO, 399.95 MHz) d: 8.49 (1H, bs), 8.20 (3H, m), 7.37 (1H, d), 6.44 (1H, d), 4.52 (1H, d), 4.17 (2H, d), 3.92-3.89 (1H, m), 3.56-3.51 (2H, m), 3.27-3.22 (2H, m), 3.09-3.03 (1H, m), 2.74-2.67 (2H, m), 2.33 (3H, s). |
| A3a-130 | $^1$H-NMR (CDCl3) δ: 7.92-7.85 (3H, m), 7.37 (1H, d), 6.93 (1H, d), 6.23 (1H, d), 4.52 (1H, d), 4.38 (2H, d), 4.05 (1H, d), 3.74-3.50 (2H, m), 3.23 (2, s), 3.05-2.95 (1H, s), 2.62-2.50 (1H, m), 2.47 (3H, s), 2.10 (3H, s). |
| A3a-131 | $^1$H-NMR (CDCl3) δ: 7.92-7.85 (3H, m), 7.42 (1H, d), 7.04 (1H, bs), 6.22 (1H, d), 4.51 (1H, d), 4.41 (1H, d), 4.03 (1H, d), 3.69-3.48 (3H, m), 3.24 (1H, s), 3.10-2.85 (1H, m), 2.65-2.48 (7H, m). |
| A3a-132 | $^1$H-NMR (CDCl3) δ: 7.91-7.81 (3H, m), 7.37 (1H, d), 6.53 (1H, bs), 6.22 (1H, d), 4.51 (1H, d), 4.39 (2H, d), 4.02 (1H, d), 3.86 (2H, s), 3.70-3.50 (2H, m), 3.06-2.75 (4H, m), 2.70-2.46 (4H, m). |
| A3a-133 | $^1$H-NMR (CDCl3) δ: 7.93-7.85 (3H, m), 7.35 (1H, d), 6.21 (1H, d), 5.55 (1H, m), 4.46 (1H, d), 4.34 (2H, d), 4.09 (1H, d), 3.70-3.47 (2H, m), 3.05-2.90 (1H, m), 2.73 (2H, q), 2.68-2.55 (1H, m), 1.99 (3H, s), 1.29 (3H, t). |
| A3a-134 | $^1$H-NMR (CDCl3) δ: 7.92-7.85 (3H, m) 7.36 (1H, d), 6.22 (1H, d), 5.45 (1H, bs), 4.46 (1H, d), 4.35 (2H, d), 4.13-4.09 (1H, m), 3.71-3.50 (2H, m), 3.01-2.90 (1H, m), 2.73 (2H, q), 2.70-2.54 (1H, m), 2.21 (2H, q), 1.29 (3H, t), 1.16 (3H, t). |
| A3a-137 | $^1$H-NMR (CDCl3) δ: 7.92-7.85 (3H, m) 7.38 (1H, d), 6.22 (1H, d), 5.66 (1H, bs), 4.46 (1H, d), 4.37 (2H, d), 4.16-4.09 (1H, m), 3.71-3.50 (2H, m), 3.01-2.90 (1H, m), 2.75 (2H, q), 2.68-2.55 (1H, m), 1.55-1.60 (1H, m), 1.29 (3H, t), 1.10-0.99 (2H, m), 0.70-.80 (2H, m). |
| A3a-138 | $^1$H-NMR (CDCl3) δ: 7.92-7.85 (3H, m) 7.37 (1H, d), 6.22 (1H, d), 5.94 (1H, bs), 4.46 (1H, d), 4.38 (2H, d), 4.16-4.06 (1H, m), 3.71-3.50 (2H, m), 3.01-2.90 (1H, m), 2.74 (2H, q), 2.69-2.55 (1H, m), 2.18 (2H, d), 1.30 (3H, t), 0.87-0.98 (1H, m), 0.61-0.53 (2H, m), 0.20-0.15 (2H, m). |
| A3a-141 | $^1$H-NMR (CDCl3) δ: 7.91-7.85 (3H, m), 7.37 (1H, d), 6.90 (1H, bs), 6.23 (1H, d), 4.49-4.37 (3H, m), 4.16-4.09 (2H, m), 3.75-3.48 (2H, m), 3.22 (2H, s), 3.05-2.90 (1H, m), 2.74 (2H, q), 2.67-2.57 (1H, m), 2.10 (3H, s), 1.31 (3H, t). |
| A3a-142 | $^1$H-NMR (CDCl3) δ: 7.91-7.85 (3H, m), 7.41 (1H, d), 7.03 (1H, bs), 6.22 (1H, d), 4.49-4.37 (3H, m), 4.16-4.05 (2H, m), 3.72-3.50 (2H, m), 3.25 (2H, d), 3.01-2.80 (1H, m), 2.77 (2H, q), 2.80-2.57 (4H, m), 1.30 (3H, t). |
| A3a-143 | $^1$H-NMR (CDCl3) δ: 7.91-7.85 (3H, m), 7.37 (1H, d), 6.49 (1H, bs), 6.21 (1H, d), 4.49-4.37 (3H, m), 4.16-4.05 (1H, m), 3.85 (2H, s), 3.72-3.48 (2H, m), 3.12-2.92 (4H, m), 2.77-2.54 (3H, m), 1.30 (3H, t). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A3a-154 | $^1$H-NMR (CDCl3) d: 2.56-2.65 (1H, m), 2.96-3.06 (4H, m), 3.54-3.69 (2H, m), 3.88 (2H, s), 3.95-4.00 (1H, m), 4.46 (2H, d), 4.52-4.56 (1H, m), 6.32 (1H, d), 6.84 (1H, m), 7.57 (1H, d), 7.85 (2H, s), 7.92 (1H, s). |
| A3a-157 | $^1$H-NMR (CDCl3) d: 1.85 (3H, m), 2.55-2.70 (1H, m), 3.57-3.67 (2H, m), 3.98 (1H, m), 4.44 (2H, m), 4.53 (1H, m), 5.80 (1H, dm), 5.91 (1H, m), 6.29 (1H, d), 6.84 (1H, dq), 7.60 (1H, d), 7.85 (2H, s), 7.92 (1H, s). |
| A3a-160 | $^1$H-NMR (CDCl3) d: 0.17-0.22 (2H, m), 0.54-0.64 (2H, m), 0.90-0.97 (1H, m), 2.17 (2H, d), 2.55-2.65 (1H, m), 2.97-3.05 (1H, m), 3.58-3.68 (2H, m), 3.97-4.01 (1H, m), 4.41 (d, 2H), 4.52-4.56 (1H, m), 6.31 (1H, d), 6.46 (1H, m), 7.59 (1H, d), 7.85 (2H, s), 7.92 (1H, s). |
| A3a-167 | $^1$H-NMR (DMSO, 399.95 MHz) d: 1.01 (3H, t), 2.13 (2H, q), 2.61-2.69 (1H, m), 2.87-3.03 (1H, m), 3.54-3.58 (2H, m), 3.90-3.94 (1H, m), 4.27 (2H, d), 4.34-4.37 (1H, m), 6.88-6.90 (1H, m), 7.47-7.56 (3H, m), 7.64-7.66 (1H, m), 8.19 (1H, m). |
| A3a-170 | $^1$H-NMR (CDCl3) δ: 0.70-0.75 (2H, m), 0.93-0.97 (2H, m), 1.50-1.80 (1H, m), 2.47-2.59 (1H, m), 2.80-2.90 (1H, m), 3.52-3.68 (2H, m), 3.95 (1H, d), 4.35 (1H, d), 4.44-4.49 (2H, m), 5.91-5.97 (1H, m), 6.49 (1H, d), 7.01-7.06 (1H, m), 7.08-7.13 (1H, m), 7.20 (1H, s), 7.70 (1H, d). |
| A3a-210 | $^1$H-NMR (CDCl3) δ: 1.96 (3H, s), 2.50-2.62 (1H, m), 2.98-3.06 (1H, m), 3.60-3.85 (3H, m), 4.42-4.46 (2H, m), 4.57-4.64 (1H, m), 5.80-5.84 (1H, m), 6.52 (1H, d), 7.28-7.35 (1H, m), 7.71 (1H, d). |
| A3a-211 | $^1$H-NMR (CDCl3) δ: 1.12 (3H, t), 2.18 (2H, q), 2.48-2.60 (1H, m), 2.98-3.10 (1H, m), 3.59-3.75 (2H, m), 3.78-3.83 (1H, m), 4.40-4.47 (2H, m), 4.57-4.64 (1H, m), 5.74-5.82 (1H, m), 6.52 (1H, d), 7.28-7.33 (1H, m), 7.72 (1H, d). |
| A3a-214 | $^1$H-NMR (CDCl3) δ: 0.69-0.75 (2H, m), 0.92-0.98 (2H, m), 1.25-1.40 (1H, m), 2.49-2.60 (1H, m), 2.99-3.10 (1H, m), 3.57-3.70 (2H, m), 3.82 (1H, d), 4.46 (2H, d), 4.57-4.64 (1H, m), 5.97 (1H, br s), 6.52 (1H, d), 7.29-7.34 (1H, m), 7.70 (1H, d). |
| A3a-226 | $^1$H-NMR (CDCl3) δ: 7.75-7.52 5H, m), 6.52 (1H, d), 6.28 (1H, bs), 4.50-4.44 (3H, m), 4.04 (1H, d), 3.70-3.52. 2H, m), 3.9-2.90 (1H, m), 2.70-2.50 (1H, m), 2.15 (2H, d), 0.95-0.87 (1H, m), 0.62-0.56 (2H, m), 0.19-0.14 (2H, m). |
| A3a-233 | $^1$H-NMR (CDCl3) δ: 1.13 (3H, t), 2.20 (2H, q), 2.52-2.64 (1H, m), 2.89-2-97 (1H, m), 3.50-3.74 (2H, m), 3.96-4.05 (1H, m), 4.36-4.48 (3H, m), 5.76 (1H, br s), 6.47-6.53 (1H, m), 7.21-7.29 (1H, m), 7.60-7.66 (2H, m), 7.71-7.75 (1H, m). |
| A3a-265 | $^1$H-NMR (CDCl3) δ: 7.74 (1H, d), 7.64-7.54 (3H, m), 6.53 (1H, d), 5.78 (1H, bs), 4.48-4.40 (3H, m), 4.00 (1H, d), 3.75-3.50 (2H, m), 3.00-2.90 (1H, m), 2.65-2.50 (1H, m), 1.98 (3H, s). |
| A3a-271 | $^1$H-NMR (CDCl3) δ: 7.72-7.54 (4H, m), 6.53 (1H, d), 5.99 (1H, bs), 4.52-4.43 (3H, m), 4.01 (1H, d), 3.68-3.50 (2H, m), 3.12-2.76 (3H, m), 2.70-2.50 (1H, m). |
| A3a-275 | $^1$H-NMR (CDCl3) δ: 7.72-7.54 (4H, m), 6.67-6.53 (2H, m), 4.55-4.43 3H, m), 4.01-1H, m), 3.86 (2H, s), 3.70-3.50 (2H, m), 3.05-2.85 (4H, m), 2.87-2.52 (1H, m), 1.55 (3H, s). |
| A3a-288 | $^1$H-NMR (CDCl3) δ: 7.75 (1H, d), 7.44 (2H, s), 6.51 (1H, d), 5.72 (1H, bs), 4.46 (1H, d), 4.37 (1H, d), 3.96 (1H, d), 3.70-3.50 (2H, m), 2.90-2.80 (1H, m), 2.30-2.20 (1H, m), 2.15-2.02 (4H, m), 0.92 (6H, d). |
| A3a-297 | $^1$H-NMR (CDCl3) δ: 7.78 (1H, d), 7.44 (2H, s), 6.51 (1H, d), 4.68-4.58 (1H, m), 4.42-4.22 4H, m), 3.96 (1H, d), 3.70-3.50 (2H, m), 3.23-3.14 (2H, m), 2.92-2.83 (1H, m), 2.60-2.48 (1H, m), 1.11 (3H, t). |
| A3a-322 | $^1$H-NMR (CDCl3) δ: 2.50-2.61 (1H, m), 3.01-3.12 (1H, m), 3.64-3.70 (2H, m), 3.82-3.90 (1H, m), 4.43 (2H, d), 4.58-4.66 (1H, m), 5.98 (1H, br s), 6.33 (1H, d), 7.30-7.37 (1H, m), 7.61 (1H, d). |
| A3a-323 | $^1$H-NMR (CDCl3) δ: 1.10 (3H, t), 2.17 (2H, q), 2.40-2.55 (1H, m), 2.95-3.03 (1H, m), 3.50-3.65 (2H, m), 3.72-3.80 (1H, m), 4.33 (2H, d), 4.50-4.57 (1H, m), 5.89 (1H, br s), 6.29 (1H, s), 7.28-7.34 (1H, m), 7.56 (1H, d). |
| A3a-326 | $^1$H-NMR (CDCl3) δ: 0.75-0.86 (2H, m), 1.03-1.10 (2H, m), 1.40-1.46 (1H, m), 2.50-2.65 (1H, m), 2.95-3.19 (1H, m), 3.60-3.71 (2H, m), 3.87-3.93 (1H, m), 4.44-4.48 (2H, m), 4.61-4.89 (1H, m), 6.14 (1H, br s), 6.28 (1H, d), 7.36-7.41 (1H, m), 7.41 (1H, d). |
| A3a-355 | $^1$H-NMR (CDCl3) d: 1.97 (3H, s), 2.42-2.47 (1H, m), 2.74-2.79 (1H, m), 3.74-3.85 (2H, m), 3.97-4.00 (1H, m), 4.28 (2H, m), 4.36-4.39 (1H, m), 6.26 (1H, m), 7.25-7.35 (4H, m). |
| A3a-366 | $^1$H-NMR (CDCl3) d: 2.01 (3H, s), 2.43-2.51 (1H, m), 2.76-2.83 (1H, m), 3.78-3.90 (2H, m), 4.03 (1H, m), 4.34 (2H, m), 4.40 (1H, m), 5.97 (1H, m), 7.36 (1H, d), 7.44 (2H, s). |
| A3a-371 | $^1$H-NMR (CDCl3) d: 0.20 (2H, m), 0.64 (2H, m), 0.95 (1H, m), 2.18 (2H, d), 2.41-2.50 (1H, m), 2.74-2.83 (1H, m), 3.75-3.95 (2H, m), 4.04 (1H, m), 4.38 (2H, m), 4.41 (1H, m), 6.46 (1H, m), 7.34 (1H. D), 7.44 (1H, s). |
| A3a-373 | $^1$H-NMR (CDCl3) d: 2.44-2.50 (m, 3H), 2.77-2.85 (2H, m), 3.38 (3H, s), 3.64 (2H, t), 3.70-3.90 (2H, m), 4.03 (1H, m), 4.35 (2H, m), 4.39 (1H, m), 6.77 (1H, m), 7.34 (d, 1H), 7.44 (1H, m). |
| A3a-421 | $^1$H-NMR (DMSO, 399.95 MHz) d: 2.62-2.69 (1H, m), 2.90-2.96 (1H, m), 3.56-3.59 (2H, m), 3.68 (2H, m), 3.90-3.94 (1H, m), 4.31 (2H, d), 4.37-4.40 (1H, m), 6.89-6.91 (1H, m), 7.69-7.72 (1H, m), 7.87 (2H, s), 8.65 (1H, m). |
| A3a-425 | $^1$H-NMR (CD3CN) δ: 2.40 (2H, m), 2.60 (1H, m), 2.89 (1H, m), 3.18 (2H, m), 3.61 (2H, m), 3.93 (1H, d), 4.37 (3H, m), 6.69 (1H, d), 6.75 (1H, m), 7.19 (1H, t), 7.35 (2H, m), 5.04-5.13 (1H, m), 7.65 (3H, m). |
| A3a-426 | $^1$H-NMR (CD3CN) δ: 1.2-1.35 (4H, m), 2.60 (1H, m), 2.89 (1H, m), 3.60 (2H, m), 3.94 (1H, d), 4.35 (1H, d), 4.43 (2H, dd), 6.69 (1H, d), 7.62 (1H, d), 7.64 (3H, m). |
| A4-002 | $^1$H-NMR (CDCl3) δ: 1.26 (t, 3H), 2.22 (q, 2H), 2.73-2.90 (m, 2H), 3.81-4.03 (m, 2H), 4.44 (d, 2H), 5.77-6.03 (m, 2H), 6.33 (s, 1H), 7.30-7.42 (m, 3H), 8.63-8.76 (m, 1H). |
| A4-005 | $^1$H-NMR (CDCl$_3$) δ: 0.68-0.85 (m, 2H), 0.89-1.07 (m, 2H), 1.30-1.43 (m, 1H), 2.74-2.94 (m, 2H), 3.81-3.97 (m, 2H), 4.46 (s, 2H), 6.12 (br s, 1H), 6.34 (br s, 1H), 7.26-7.50 (m, 3H), 8.59-8.76 (m, 1H). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
| --- | --- |
| A4-007 | ¹H-NMR (CDCl₃) δ: 2.76-2.92 (m, 2H), 3.08 (q, 2H), 3.84-4.03 (m, 2H), 4.49 (d, 2H), 6.19-6.41 (m, 2H), 7.30-7.48 (m, 3H), 8.58-8.77 (m, 1H). |
| A4-011 | ¹H-NMR (CDCl₃) δ: 2.77-2.90 (m, 2H), 3.08 (s, 3H), 3.80-4.03 (m, 4H), 4.52 (s, 2H), 6.28-6.43 (m, 1H), 6.99-7.15 (m, 1H), 7.28-7.48 (m, 3H), 8.56-8.78 (m, 1H). |
| A4-012 | ¹H-NMR (CDCl₃) δ: 1.99 (s, 3H), 2.74-2.87 (m, 2H), 3.82-4.04 (m, 2H), 4.43 (d, 2H), 5.87 (s, 1H), 6.29 (d, 1H), 7.46 (s, 2H), 8.65-8.79 (m, 1H). |
| A4-013 | ¹H-NMR (CDCl₃) d: 1.14 (t, 3H), 2.21 (q, 2H), 2.71-2.88 (m, 2H), 3.78-4.00 (m, 2H), 4.44 (s, 2H), 5.89 (bs, 1H), 6.31 (bs, 1H), 7.46 (s, 2H), 8.69 (bs, 1H) |
| A4-016 | ¹H-NMR (CDCl₃) d: 0.68-0.81 (m, 2H), 0.91-1.02 (m, 2H), 1.28-1.40 (m, 1H), 2.72-2.88 (m, 2H), 3.81-3.95 (m, 2H), 4.18 (bs, 1H), 4.46 (d, 2H), 6.06 (bs, 1H), 6.30 (bs, 1H), 7.46 (s, 2H), 8.70 (bs, 1H) |
| A4-018 | ¹H-NMR (CDCl₃) d: 2.68-2.89 (m, 2H), 3.08 (q, 2H), 3.77-4.02 (m, 3H), 4.48 (d, 2H), 6.13-6.37 (m, 2H), 7.45 (s, 2H), 8.69 (bs, 1H) |
| A4-020 | ¹H-NMR (CDCl₃) d: 2.04 (s, 3H), 2.71-2.89 (m, 2H), 3.20 (s, 2H), 3.70-4.02 (m, 3H), 4.49 (d, 2H), 6.31 (bs, 1H), 7.30 (bs, 1H), 7.46 (s, 2H), 8.68 (bs, 1H) |
| A4-021 | ¹H-NMR (CDCl₃) d: 1.81 (bs, 1H), 2.67 (s, 3H), 2.74-2.86 (m, 2H), 3.30 (d, 1H), 3.67 (d, 1H), 3.80-3.95 (m, 2H), 4.51 (s, 2H), 6.31 (s, 1H), 7.46 (s, 2H), 7.51 (s, 1H), 8.70 (bs, 1H) |
| A4-022 | ¹H-NMR (CDCl₃) d: 1.68 (s, 1H), 2.71-2.89 (m, 2H), 3.07 (s, 3H), 3.81-3.97 (m, 4H), 4.51 (d, 2H), 6.31 (bs, 2H), 7.02 (bs, 1H), 7.45 (s, 2H), 8.64 (bs, 1H) |
| A4-024 | ¹H-NMR (CDCl₃) d: 1.14 (t, 3H), 2.00 (bs, 1H), 2.21 (q, 2H), 2.76-3.04 (m, 2H), 3.85-4.00 (m, 2H), 4.44 (s, 2H), 5.88 (bs, 1H), 6.43 (bs, 1H), 7.81-7.95 (m, 3H), 8.73 (bs, 1H) |
| A4-027 | ¹H-NMR (CDCl₃) d: 0.70-0.81 (m, 2H), 0.90-1.00 (m, 2H), 1.28-1.40 (m, 1H), 2.77-3.03 (m, 2H), 3.85-4.02 (m, 2H), 4.18 (bs, 1H), 4.46 (d, 2H), 6.08 (bs, 1H), 6.40 (bs, 1H), 7.81-7.95 (m, 3H), 8.70 (bs, 1H) |
| A4-029 | ¹H NMR (CDCl₃) d: 1.79 (bs, 1H), 2.76-3.20 (m, 4H), 3.82-4.01 (m, 2H), 4.48 (d, 2H), 6.34-6.55 (m, 2H), 7.81-7.97 (m, 3H), 8.67 (bs, 1H) |
| A4-030 | ¹H NMR (CDCl₃) d: 1.67 (bs, 1H), 2.47 (t, 2H), 2.75-3.05 (m, 2H), 3.37 (s, 3H), 3.60 (t, 2H), 3.82-3.99 (m, 2H), 4.44 (d, 2H), 6.40 (bs, 1H), 6.88 (bs, 1H), 7.76-7.94 (m, 3H), 8.70 (bs, 1H) |
| A4-031 | ¹H NMR (CDCl₃) d: 2.10 (s, 3H), 2.77-3.06 (m, 2H), 3.20 (s, 2H), 3.83-4.04 (m, 2H), 4.50 (d, 2H), 6.42 (bs, 1H), 7.33 (bs, 1H), 7.77-7.98 (m, 3H), 8.72 (bs, 1H) |
| A4-032 | ¹H NMR (CDCl₃) d: 2.67 (s, 3H), 2.78-3.05 (m, 2H), 3.28 (d, 1H), 3.67 (d, 1H), 3.80-3.99 (m, 2H), 4.26 (bs, 1H), 4.52 (s, 1H), 6.42 (bs, 1H), 7.43 (bs, 1H), 7.80-8.00 (m, 3H), 8.72 (bs, 1H) |
| A4-033 | ¹H NMR (CD3CN) d: 2.71-3.11 (m, 5H), 3.72-3.95 (m, 4H), 4.33-4.55 (m, 3H), 6.57 (bs, 1H), 7.23 (bs, 1H), 7.79-8.08 (m, 3H), 8.68 (bs, 1H) |
| A4-049 | ¹H NMR (CDCl₃) d: 0.69-0.79 (m, 2H), 0.92-1.03 (m, 2H), 1.27-1.39 (m, 1H), 2.42 (s, 3H), 2.69-2.84 (m, 2H), 3.73-3.93 (m, 2H), 4.32 (s, 2H), 4.42 (bs, 1H), 5.94 (bs, 1H), 6.28 (s, 1H), 7.47 (s, 2H), 8.14 (bs, 1H) |
| A4-101 | ¹H-NMR (CDCl₃) δ: 8.70-7.32 (3H, m), 6.37-5.91 (2H, m), 4.52-4.28 (3H, m), 3.89-3.78 (2H, m), 2.99-2.66 (2H, m), 2.19 (2H, q), 1.11 (3H, t). |
| A4-104 | ¹H-NMR (CDCl₃) δ: 8.36-7.63 (3H, m), 6.29-6.15 (2H, m), 4.37-4.53 (2H, m), 3.79-3.95 (2H, m), 2.72-2.91 (2H, m), 1.28-1.40 (1H, m), 0.88-1.03 (2H, m), 0.69-0.82 (2H, m). |
| A4-111 | ¹H-NMR (CDCl₃) δ: 10.62-9.12 (2H, m), 8.45-8.25 (1H, m), 7.80-7.60 (1H, m), 6.41-6.22 (2H, m), 5.85-5.65 (3H, m), 4.82-4.61 (2H, m), 1.88 (3H, s). |
| A4-112 | ¹H-NMR (CDCl₃) δ: 8.70 (1H, d), 7.32-7.27 (1H, m), 6.50 (1H, br s), 5.98 (1H, br s), 4.51-4.30 (3H, m), 3.92-3.77 (2H, m), 2.97-2.74 (2H, m), 2.22 (2H, q), 1.14 (3H, t). |
| A4-115 | ¹H-NMR (acetone-d₆) δ: 8.74-8.65 (1H, m), 7.84-7.68 (2H, m), 6.67 (1H, d, J = 4.1 Hz), 4.42 (2H, d, J = 5.5 Hz), 3.87-3.73 (2H, m), 3.14-2.87 (2H, m), 1.64-1.57 (1H, m), 0.78-0.63 (4H, m). |
| A4-201 | ¹H NMR (CDCl₃) δ: 2.26 (s, 6H), 2.75-2.87 (m, 2H), 2.96 (s, 2H), 3.81-4.01 (m, 2H), 4.47 (d, 2H), 6.25-6.38 (m, 1H), 7.29-7.41 (m, 3H), 7.54-7.63 (m, 1H), 8.62-8.77 (m, 1H). |
| A4-202 | ¹H-NMR (CDCl3) δ: 1.66-1.73 (m, 2H), 1.81-1.96 (m, 1H), 2.06-2.21 (m, 1H), 2.79-3.04 (m, 4H), 3.66-3.97 (m, 3H), 4.44 (d, 2H), 6.24-6.38 (m, 1H), 7.29-7.42 (m, 3H), 8.09 (s, 1H), 8.58-8.72 (m, 1H). |
| A4-203 | ¹H-NMR (CDCl3) δ: 1.26-1.53 (m, 11H), 1.78-1.95 (m, 2H), 2.73-2.89 (m, 2H), 3.24-3.48 (m, 2H), 3.80-3.95 (m, 2H), 4.18-4.34 (m, 1H), 4.43 (s, 2H), 6.32 (s, 1H), 7.28-7.42 (m, 2H), 7.50 (s, 1H), 8.56-8.75 (m, 1H). |
| A4-216 | ¹H-NMR (CDCl3) δ: 1.13 (t, 3H), 2.20 (q, 2H), 2.73-2.86 (m, 2H), 3.80-3.92 (m, 2H), 4.47 (d, 2H), 5.87-5.96 (m, 1H), 6.31 (d, 1H), 6.33-6.72 (m, 1H), 7.45 (s, 2H), 8.57-8.66 (m, 1H). |
| A4-219 | ¹H-NMR (CDCl3) δ: 0.68-0.79 (m, 2H), 0.89-1.01 (m, 2H), 1.26-1.37 (m, 1H), 2.72-2.88 (m, 2H), 3.77-3.96 (m, 2H), 4.49 (d, 2H), 6.03-6.14 (m, 1H), 6.30 (s, 1H), 6.54 (t, 1H), 7.45 (s, 2H), 8.52-8.65 (m, 1H). |
| A4-221 | ¹H-NMR (CDCl3) δ: 2.72-2.86 (m, 2H), 3.07 (q, 2H), 3.79-3.93 (m, 2H), 4.53 (d, 2H), 6.12-6.72 (m, 3H), 7.46 (s, 2H), 8.51-8.71 (m, 1H). |
| A4-252 | ¹H-NMR (CDCl3) δ: 0.69-0.82 (m, 2H), 0.91-1.03 (m, 2H), 1.30-1.43 (m, 1H), 2.77-3.01 (m, 2H), 3.84-3.99 (m, 2H), 4.38 (d, 2H), 6.08-6.23 (m, 1H), 6.37-6.42 (m, 1H), 7.82-7.94 (m, 3H), 8.32-8.47 (m, 1H). |
| A4-435 | ¹H-NMR (CDCl3) δ: 2.78-2.90 (m, 1H), 3.38 (s, 2H), 3.78-3.98 (m, 2H), 4.50 (d, 2H), 6.27-6.38 (m, 1H), 6.50 (br s, 1H), 7.29-7.44 (m, 3H), 8.61-8.78 (m, 1H). |
| A4a-030 | ¹H-NMR (CDCl3) δ: 2.47 (2H, t), 2.51-2.66 (1H, m), 2.93-3.09 (1H, m), 3.36 (3H, s), 3.60 (2H, t), 3.80-3.90 (2H, m), 4.05-4.20 (1H, m), 4.40-4.46 (2H, m), 4.55-4.70 (1H, m), 6.80 (1H, br s), 7.85 (2H, s), 7.92 (1H, s), 8.64 (1H, s). |
| A4a-111 | ¹H-NMR (DMSO, 399.95 MHz) d: 1.84 (3H, s), 2.65-2.68 (1H, m), 3.08-3.17 (1H, m), 3.62 (1H, m), 3.76 (1H, m), 3.92-3.96 (1H, m), 4.23 (2H, d), 4.61-4.75 (2H, m), 7.95 (1H, t), 8.30 (1H, m), 8.63 (1H, s). |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| A4a-112 | $^1$H-NMR (CDCl3) δ: 1.12 (3H, t), 2.19 (2H, q), 2.45-2.58 (1H, m), 2.96-3.04 (1H, m), 3.70-3.89 (3H, m), 4.30-4.49 (2H, m), 4.70-4.78 (1H, m), 5.80 (1H, br s), 7.28-7.32 (1H, m), 8.62 (1H, s). |
| A4a-115 | $^1$H-NMR (CDCl3) δ: 0.70-0.77 (2H, m), 0.93-0.99 (2H, m), 1.28-1.36 (1H, m), 2.48-2.55 (1H, m), 2.98-3.05 (1H, m), 3.70-3.91 (3H, m), 4.40-4.46 (2H, m), 4.69-4.77 (1H, m), 5.92 (1H, br s), 7.28-7.32 (1H, t), 8.61 (1H, s). |
| A4a-201 | $^1$H-NMR (CDCl3) δ: 2.24 (6H, s), 2.47-2.52 (1H, m), 2.70-2.99 (3H, m), 3.65-3.85 (2H, m), 3.99 (1H, d), 4.40-4.49 2H, m), 7.28 (2H, s), 7.38 (1H, s), 7.51 (1H, bs), 8.60 (1H, s). |
| A4a-203 | $^1$H-NMR (CDCl3) δ: 1.25-1.50 (11H, m), 1.75-1.87 (2H, m), 2.47-2.54 (1H, m), 2.81-2.91 (1H, m), 3.25-3.50 (2H, m), 3.75-3.80 (2H, m), 3.96-3.99 (1H, m), 4.24-4.30 (1H, m), 4.31-4.49 (3H, m), 7.27 (2H, s), 7.37 (1H, s), 8.56 (1H, br s). |
| A4a-216 | $^1$H-NMR (CDCl3) δ: 0.98 (3H, t), 2.04 (2H, q), 2.28-2.41 (1H, m), 2.70-2.75 (1H, m), 3.55-3·70 (2H, m), 3.78-3.85 (1H, m), 4.29-4.38 (3H, m), 5.64 (1H, br s), 6.35 (1H, t), 7.11 (2H, s), 8.41 (1H, s). |
| A4a-219 | $^1$H-NMR (CDCl3) δ: 0.57-0.61 (2H, m), 0.80-0.83 (2H, m), 1.09-1.20 (1H, m), 2.30-2.41 (1H, m), 2.61-2.75 (1H, m), 3.55-3.70 (2H, m), 3.80-3.88 (1H, m), 4.25-4.35 (3H, m), 5.81 (1H, br s), 6.34 (1H, t) 7.11 (2H, s), 8.40 (1H, s). |
| A4a-221 | $^1$H-NMR (CDCl3) δ: 2.04 (1H, s), 2.36-2.44 (1H, m), 2.30-2.53 (1H, m), 2.90 (2H, q), 3.64-3.70 (1H, m), 3.80-3.91 (1H, m), 4.50-4.69 (3H, m), 5.93 (1H, br s), 6.31 (1H, t), 7.11 (2H, s), 8.44 (1H, s). |
| A4a-252 | $^1$H-NMR (CDCl3) δ: 8.19 (1H, s), 7.76 (1H, s), 7.69 (2H, s), 5.88 (1H, br s), 4.46 (1H, d), 4.21 (2H, d), 3.89 (1H, d), 3.75-3.60 (2H, m), 2.93-2.79 (1H, m), 2.45-2.30 (1H, m), 1.5-1.39 (1H, m), 0.85-0.80 (2H, H), 0.70-0.55 (2H, m). |
| A4a-435 | $^1$H-NMR (CDCl3) δ: 2.30-2.45 (1H, m), 2.70-2.85 (1H, m), 3.22 (2H, s), 3.60-3.75 (2H, m), 3.80-3.85 (1H, m), 4.76-4.93 (3H, m), 6.27 (br s, 1H), 7.14 (2H, s), 7.24 (1H, s), 8.44 (1H, s). |
| A5-013 | $^1$H-NMR (CDCl3) δ: 1.12 (t, 3H), 2.19 (q, 2H), 2.82-2.90 (m, 2H), 3.62-3.81 (m, 2H), 4.46 (d, 2H), 5.88-6.00 (m, 1H), 6.27-6.35 (m, 1H), 6.67 (s, 1H), 7.46 (s, 2H), 8.34 (s, 1H). |
| A5-016 | $^1$H-NMR (CDCl3) δ: 0.67-0.79 (m, 2H), 0.91-1.01 (m, 2H), 1.27-1.39 (m, 1H), 2.80-2.92 (m, 2H), 3.62-3.81 (m, 2H), 4.50 (d, 2H), 5.95-6.10 (m, 1H), 6.32 (s, 1H), 6.65 (s, 1H), 7.45 (s, 2H), 8.37 (s, 1H). |
| A5-018 | $^1$H-NMR (CDCl3) δ: 0.67-0.79 (m, 2H), 0.91-1.01 (m, 2H), 1.27-1.39 (m, 1H), 2.80-2.92 (m, 2H), 3.62-3.81 (m, 2H), 4.50 (d, 2H), 5.95-6.10 (m, 1H), 6.32 (s, 1H), 6.65 (s, 1H), 7.45 (s, 2H), 8.37 (s, 1H). |
| A5-022 | $^1$H-NMR (CDCl3) δ: 2.79-2.92 (m, 2H), 3.05 (s, 3H), 3.60-3.78 (m, 2H), 3.90 (s, 2H), 4.53 (d, 2H), 6.33 (s, 1H), 6.66 (s, 1H), 6.95-7.07 (m, 1H), 7.44 (s, 2H), 8.36 (s, 1H). |
| A5-024 | $^1$H NMR (CDCl$_3$) d: 1.13 (t, 3H), 2.20 (q, 2H), 2.85-3.07 (m, 2H), 3.65-3.88 (m, 2H), 4.45-4.55 (m, 3H), 5.82 (bs, 1H), 6.44 (bs, 1H), 6.68 (s, 1H), 7.82-7.93 (m, 3H), 8.39 (s, 1H) |
| A5-027 | $^1$H NMR (CDCl$_3$) d: 0.66-0.80 (m, 2H), 0.90-1.01 (m, 2H), 1.27-1.38 (m, 1H), 2.84-3.07 (m, 2H), 3.64-3.86 (m, 2H), 4.40 (bs, 2H), 4.51 (d, 1H), 5.98 (bs, 1H), 6.43 (bs, 1H), 6.67 (s, 1H), 7.80-7.95 (m, 3H), 8.39 (s, 1H) |
| A5-029 | $^1$H NMR (CDCl$_3$) d: 2.85-3.17 (m, 4H), 3.64-3.89 (m, 2H), 4.35 (bs, 1H), 4.53 (d, 2H), 6.15 (bs, 1H), 6.44 (bs, 1H), 6.69 (s, 1H), 7.81-7.97 (m, 3H), 8.39 (s, 1H) |
| A5-033 | $^1$H NMR (CDCl$_3$) d: 2.85-3.12 (m, 5H), 3.61-3.83 (m, 2H), 3.89 (s, 2H), 4.39 (bs, 1H), 4.55 (d, 2H), 6.45 (bs, 1H), 6.68 (s, 1H), 6.88 (bs, 1H), 7.77-7.94 (m, 3H), 8.38 (s, 1H) |
| A5-078 | $^1$H-NMR (CDCl$_3$) δ: 8.38 (1H, s), 7.30 (1H, t), 6.65 (1H, s), 6.49 (1H, t), 5.87 (1H, t), 4.47 (3H, d), 3.75-3.62 (2H, m), 2.98-2.85 (2H, m), 1.98 (3H, s). |
| A5-079 | $^1$H-NMR (CDCl3) δ: 8.37 (1H, s), 7.30 (1H, t), 6.65 (1H, s), 6.49 (1H, t), 5.82 (1H, s), 4.48 (2H, d), 4.40 (1H, s), 3.77-3.60 (2H, m), 2.82-3.00 (2H, m), 2.21 (2H, q), 1.14 (3H, t). |
| A5-082 | $^1$H-NMR (CDCl$_3$) δ: 8.36 (1H, s), 7.29 (1H, t, J = 7.3 Hz), 6.63 (1H, s), 6.47 (1H, t, J = 3.2 Hz), 5.97 (1H, t, J = 5.5 Hz), 4.49 (2H, d, J = 6.0 Hz), 4.29 (1H, s), 3.77-3.57 (2H, m), 2.99-2.79 (2H, m), 1.35-1.28 (1H, m), 0.98-0.94 (2H, m), 0.75-0.71 (2H, m). |
| A5a-33 | $^1$H-NMR (CDCl3) δ: 2.60-2.69 (1H, m), 3.0-3.10 (1H, m), 3.04 (3H, s), 3.62-3.75 (2H, m), 3.87 (2H, s), 4.03 (1H, d), 4.51-4.65 (3H, m), 6.61-6.67 (1H, m), 7.86 (2H, s), 7.93 (1H, s), 8.39 (1H, s). |
| A5a-078 | $^1$H-NMR (CDCl3) δ: 1.96 (3H, s), 2.50-2.70 (1H, m), 3.02-3.21 (1H, m), 3.65-3.95 (3H, m), 4.45-4.55 (2H, m), 4.68-4.73 (1H, m), 5.85 (1H, br s), 7.40-7.54 (1H, m), 8.44 (1H, s) |
| A5a-079 | $^1$H-NMR (CDCl3) δ: 1.26 (3H, t), 2.29 (2H, q), 2.50-2.72 (1H, m), 3.06-3.24 (1H, m), 3.66-3.81 (2H, m), 3.87-3.98 (1H, m), 4.47-4.61 (2H, m), 4.74-4.79 (1H, m), 5.76 (1H, br s), 6.68 (1H, s), 7.29-7.46 (1H, m), 8.49 (1H, s). |
| A5a-082 | $^1$H-NMR (CDCl3) δ: 0.75-0.86 (2H, m), 1.03-1.10 (2H, m), 1.40-1.46 (1H, m), 2.60-2.71 (1H, m), 3.10-3.19 (1H, m), 3.70-3.81 (2H, m), 3.91-3.96 (1H, m), 4.50-4.59 (2H, m), 4.69-4.78 (1H, m), 6.19 (1H, br s), 7.29-7.40 (1H, m), 8.21 (1H, s). |
| A6-012 | $^1$H-NMR (CDCl3) δ: 2.00 (3H, s), 2.81-2.91 (2H, m), 3.53-3.71 (2H, m), 4.47-4.56 (2H, m), 4.82-4.83 (1H, m), 6.15-6.21 (2H, m), 7.40 (2H, s) |
| A6-016 | $^1$H-NMR (CDCl3) δ: 0.77-0.79 (2H, m), 0.97-0.98 (2H, m), 1.35-1.37 (1H, m), 2.82-2.84 (2H, m), 3.63-3.64 (2H, m), 4.58-4.60 (3H, m), 6.14-6.26 (2H, m), 7.40 (2H, s) |
| A7-004 | $^1$H-NMR (CDCl3) δ: 2.74-2.92 (2H, m), 3.58-3.68 (2H, m), 3.76 (1H, d), 5.82 (1H, d), 7.09-7.14 (2H, m), 7.34 (1H, s), 7.43 (1H, t), 7.51 (1H, d), 8.02 (1H, s), 8.49 (1H, s). |
| b1-005 | $^1$H-NMR (CDCl$_3$) δ: 2.85-2.94 (1H, m), 3.04-3.14 (1H, m), 3.78-3.86 (1H, m), 3.99-4.06 (1H, m), 7.71 (2H, d), 7.95 (1H, dd), 7.97 (1H, s), 8.23 (2H, s). |
| b1-007 | $^1$H-NMR (CDCl$_3$) δ: 2.78-3.01 (2H, m), 3.76-4.01 (2H, m), 7.45-8.15 (6H, m). |
| b1-013 | $^1$H-NMR (acetone-d$_6$) δ: 3.01-3.04 (1H, m), 3.13-3.17 (1H, m), 3.98-4.02 (1H, m), 4.14-4.19 (1H, m), 7.61 (1H, t), 7.78 (1H, dd), 7.81 (2H, s), 8.01 (2H, dd) |

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| b1-014 | $^1$H-NMR (CDCl$_3$) δ: 2.75-2.82 (1H, m), 2.89-2.95 (1H, m), 3.71-3.79 (1H, m), 3.87-3.94 (4H, m), 7.42 (1H, t), 7.59-7.60 (2H, m), 7.65-7.67 (1H, m), 7.80 (1H, d), 7.92 (1H, d) |
| b1-020 | $^1$H-NMR (CDCl$_3$) δ: 1.38 (3H, t), 2.78-2.82 (1H, m), 2.92-2.97 (1H, m), 3.77-3.83 (1H, m), 3.95-3.99 (1H, m), 4.39 (2H, q), 7.43 (1H, t), 7.60-7.60 (2H, m), 7.89-7.94 (2H, m), 8.04-8.05 (1H, m) |
| B1-027 | $^1$H-NMR (CDCl$_3$) δ: 0.72-0.78 (2H, m), 0.95-1.00 (2H, m), 1.33-1.41 (1H, m), 2.78-2.87 (1H, m), 3.00-3.08 (1H, m), 3.73-3.81 (1H, m), 3.92-4.00 (1H, m), 4.52 (2H, d), 6.10 (1H, t), 7.40 (1H, dd), 7.45 (1H, d), 7.81 (1H, d), 7.95 (1H, s), 8.25 (2H, s). |
| B1-035 | $^1$H-NMR (CDCl$_3$) δ: 1.16 (3H, t), 2.24 (2H, q), 2.72-2.80 (1H, m), 2.87-2.97 (1H, m), 3.72-3.80 (1H, m), 3.87-3.94 (1H, m), 4.60 (2H, d), 5.80 (1H, br s), 7.42 (1H, t), 7.60-7.65 (3H, m), 7.74 (1H, dd), 8.00 (1H, d). |
| B1-046 | $^1$H-NMR (CDCl$_3$) δ: 1.16 (3H, t), 2.24 (2H, q), 2.71-2.79 (1H, m), 2.88-2.98 (1H, m), 3.73-3.81 (1H, m), 3.89-3.96 (1H, m), 4.60 (2H, d), 5.80 (1H, t), 7.64 (1H, d), 7.72 (1H, dd), 7.76 (2H, s), 7.99 (1H, d). |
| B1-069 | $^1$H-NMR (acetone-d$_6$) δ: 1.41 (9H, s), 3.10-3.31 (2H, m), 3.96-4.04 (1H, m), 4.10-4.18 (1H, m), 4.34 (2H, d), 6.51 (1H, br s), 7.45 (1H, d), 7.61 (1H, d), 7.88 (1H, d), 8.17 (1H, s), 8.52 (2H, s). |
| B1-070 | $^1$H-NMR (CDCl$_3$) δ: 1.45 (9H, s), 2.65-3.01 (2H, m), 3.70-4.00 (2H, m), 4.48 (2H, d), 4.95 (1H, t), 7.41-7.93 (6H, m). |
| B1-071 | $^1$H-NMR (CDCl$_3$) δ: 1.45 (9H, s), 2.68-2.75 (1H, m), 2.88-2.98 (1H, m), 3.75-3.81 (1H, m), 3.91-3.94 (1H, m), 4.48 (2H, d), 4.94 (1H, br s), 7.63 (1H, d), 7.76-7.80 (3H, m), 7.93 (1H, s). |
| B1-074 | $^1$H-NMR (CDCl$_3$) δ: 1.13-1.21 (3H, m), 2.18-2.28 (2H, m), 2.71-2.76 (1H, m), 2.86-2.91 (1H, m), 3.71-3.74 (1H, m), 3.85-3.87 (1H, m), 4.41 (2H, d), 5.85 (1H, br s), 7.30-7.43 (3H, m), 7.56-7.60 (4H, m). |
| B1-085 | $^1$H-NMR (CDCl$_3$) δ: 1.16-1.18 (3H, m), 2.23-2.27 (2H, m), 2.71-2.72 (1H, m), 2.86-2.93 (1H, m), 3.72-3.76 (1H, m), 3.87-3.88 (1H, m), 4.43 (2H, d), 5.77 (1H, br s), 7.32 (2H, d), 7.55 (2H, d), 7.77 (2H, d). |
| B1-096 | $^1$H-NMR (CDCl$_3$) δ: 1.13-1.21 (3H, m), 2.24-2.26 (2H, m), 2.83-2.85 (1H, m), 3.02-3.05 (1H, m), 3.77-3.80 (1H, m), 3.94-3.97 (1H, m), 4.43 (2H, d), 5.82 (1H, br s), 7.33 (2H, d), 7.55 (2H, d), 7.94 (1H, s), 8.27 (2H, s). |
| B2-027-b | $^1$H-NMR (CDCl$_3$) δ: 0.69-0.74 (2H, m), 0.90-0.93 (2H, m), 1.24-1.35 (1H, m), 1.46 (3H, d), 2.79-2.85 (1H, m), 3.01-3.04 (1H, m), 3.76-3.79 (1H, m), 3.93-3.99 (1H, m), 5.10 (1H, t), 5.91 (1H, d), 7.37 (2H, d), 7.55 (2H, d), 7.94 (1H, s), 8.27 (2H, s). |
| B3-002 | $^1$H-NMR (CDCl$_3$) δ: 1.14 (3H, t), 2.24 (2H, q), 2.68-2.91 (2H, m), 3.83-3.87 (1H, m), 4.26-4.34 (1H, m), 4.59 (2H, d), 5.85-5.88 (1H, m), 7.41 (1H, s), 7.59 (2H, s), 8.02 (1H, d), 8.61 (1H, d). |
| B3-005 | $^1$H-NMR (CDCl$_3$) δ: 0.75-0.83 (2H, m), 0.95-1.00 (2H, m), 1.19-1.24 (1H, m), 2.68-2.91 (2H, m), 3.83-3.87 (1H, m), 4.26-4.34 (1H, m), 4.60 (2H, d), 6.04-6.07 (1H, m), 7.41 (1H, s), 7.59 (2H, s), 8.01 (1H, d), 8.60 (1H, d). |
| B3-013 | $^1$H-NMR (CDCl$_3$) δ: 1.16 (3H, t), 2.23 (2H, q), 2.67-2.92 (2H, m), 3.86-3.91 (1H, m), 4.26-4.33 (1H, m), 4.59 (2H, d), 5.83-5.87 (1H, m), 7.75 (2H, s), 8.03 (1H, d), 8.60 (1H, d). |
| B3-016 | $^1$H-NMR (CDCl$_3$) δ: 0.75-0.83 (2H, m), 0.93-1.02 (2H, m), 1.17-1.22 (1H, m), 2.67-2.92 (2H, m), 3.86-3.91 (1H, m), 4.26-4.34 (1H, m), 4.61 (2H, d), 6.03-6.05 (1H, m), 7.73 (2H, s), 8.02 (1H, d), 8.59 (1H, d). |
| B3-024 | $^1$H-NMR (CDCl$_3$) δ: 1.17 (3H, t), 2.25 (2H, q), 2.83-3.00 (2H, m), 3.93-4.02 (1H, m), 4.28-4.36 (1H, m), 4.60 (2H, m), 5.87-5.91 (1H, m), 7.98-8.03 (2H, m), 8.23 (2H, s), 8.61 (1H, d). |
| B3-027 | $^1$H-NMR (CDCl$_3$) δ: 0.76-0.81 (2H, m), 0.86-1.05 (2H, m), 1.24-1.28 (1H, m), 2.78-3.05 (2H, m), 3.95-4.00 (1H, m), 4.28-4.37 (1H, m), 4.61 (2H, d), 6.07-6.09 (1H, m), 7.99-8.03 (2H, m), 8.18 (2H, s), 8.57 (1H, d). |
| B3-035 | $^1$H-NMR (CDCl$_3$) δ: 1.19 (3H, t), 2.25 (2H, q), 2.48 (3H, s), 2.73-2.82 (1H, m), 2.92-3.02 (1H, m), 3.92-3.97 (1H, m), 4.25-4.33 (1H, m), 4.43 (2H, d), 5.67-5.70 (1H, m), 7.58 (1H, d), 7.90 (1H, s), 8.13-8.24 (3H, m). |
| B3-049 | $^1$H-NMR (CDCl$_3$) δ: 0.73-0.82 (2H, m), 0.85-1.03 (2H, m), 1.26 (3H, t), 1.33-1.38 (1H, m), 2.74-2.84 (3H, m), 2.95-3.00 (1H, m), 3.94-3.99 (1H, m), 4.29-4.37 (1H, m), 4.46 (2H, d), 5.83-5.87 (1H, m), 7.63 (1H, d), 7.94 (1H, s), 8.20-8.27 (3H, m). |
| c1-003 | $^1$H-NMR (CDCl$_3$) δ: 3.20 (1H, d), 3.38 (1H, d), 4.26 (1H, d), 4.51 (1H, d), 7.38-7.40 (2H, m), 7.70 (2H, d), 7.90 (1H, d). |
| c1-007 | $^1$H-NMR (CDCl$_3$) δ: 3.23 (1H, d), 3.41 (1H, d), 4.31 (1H, d), 4.55 (1H, d), 7.25-8.12 (6H, m). |
| c1-014 | $^1$H-NMR (CDCl$_3$) δ: 3.27 (2H, dd), 3.93 (3H, s), 4.27 (1H, d), 4.51 (1H, d), 7.25-7.27 (2H, m), 7.45-7.45 (1H, m), 7.65-7.68 (1H, m), 7.75 (1H, d), 7.92 (1H, d) |
| C1-027 | $^1$H-NMR (CDCl$_3$) δ: 0.72-0.78 (2H, m), 0.96-0.98 (3H, m), 1.30-1.42 (1H, m), 3.24 (1H, d), 3.44 (1H, d), 4.31 (1H, d), 4.51 (2H, d), 4.58 (1H, d), 6.15 (1H, br s), 7.42-7.43 (2H, m), 7.73 (1H, d), 7.79 (2H, s), 7.98 (1H, s). |
| C1-035 | $^1$H-NMR (CDCl$_3$) δ: 1.16 (3H, t), 2.25 (2H, q), 3.18 (1H, d), 3.35 (1H, d), 4.29 (1H, d), 4.49 (1H, d), 4.60 (2H, d), 5.87 (1H, t), 7.25 (2H, s), 7.45 (1H, t), 7.62 (1H, d), 7.73 (1H, dd), 7.91 (1H, d). |
| C1-046 | $^1$H-NMR (CDCl$_3$) δ: 1.16 (3H, t), 2.24 (2H, q), 3.16 (1H, d), 3.35 (1H, d), 4.27 (1H, d), 4.48 (1H, d), 4.60 (2H, d), 5.81 (1H, t), 7.38 (2H, s), 7.63 (1H, d), 7.72 (1H, dd), 7.90 (1H, d). |
| C1-069 | $^1$H-NMR (CDCl$_3$) δ: 1.45 (9H, s), 3.24 (1H, d), 3.45 (1H, d), 4.38 (2H, d), 4.59 (1H, d), 5.03 (1H, br s), 7.43-7.47 (2H, m), 7.70 (1H, s), 7.79 (2H, s), 7.98 (1H, s). |
| C1-074 | $^1$H-NMR (CDCl$_3$) δ: 1.17 (3H, t), 2.24 (2H, q), 2.34 (3H, s), 3.09 (1H, d), 3.29 (1H, d), 4.24 (1H, d), 4.40-4.45 (3H, m), 5.77 (1H, br s), 7.24 (1H, d), 7.37-7.31 (4H, m). |
| C2-027-b | $^1$H-NMR (CDCl$_3$) δ: 0.71-0.74 (2H, m), 0.91-0.94 (2H, m), 1.26-1.32 (1H, m), 1.49 (3H, d), 3.22 (1H, d), 3.43 (1H, d), 4.33 (1H, d), 4.58 (1H, d), 5.05-5.14 (1H, m), 5.81-5.85 (1H, m), 7.38 (2H, d), 7.55 (2H, d), 7.78 (2H, s), 7.98 (1H, s). |

-continued

NMR Table:
The Example Number (Ex. No.) given in the NMR Table as for example A1-002 refers to Ex. No. A1-2 in table A1, the same applies to the numbering of all other compounds (e.g. Ex. No. A1-005 refers to Ex. No. A1-5 in table A1, or A3-002 refers to Ex. No. A3-2 given in table A3).

| Ex. No. | NMR |
|---|---|
| C3-002 | $^1$H-NMR (CDCl$_3$) δ: 1.12 (3H, t), 2.22 (2H, q), 3.22 (1H, dz), 3.42 (1H, d), 4.40 (1H, d), 4.58 (2H, d), 4.92 (1H, d), 5.91-5.93 (1H, m), 7.17-7.50 (3H, m), 7.97 (1H, d), 8.52 (1H, d). |
| C3-005 | $^1$H-NMR (CDCl$_3$) δ: 0.74-0.86 (2H, m), 0.98-1.01 (2H, m), 1.33-1.41 (1H, m), 3.22 (1H, d), 3.39 (1H, d), 4.38 (1H, d), 4.61 (2H, d), 4.92 (1H, d), 6.04-6.07 (1H, m), 7.27 (2H, s), 7.41 (1H, s), 7.99 (1H, d), 8.52 (1H, d). |
| C3-016 | $^1$H-NMR (CDCl$_3$) δ: 0.76-0.82 (2H, m), 0.94-1.02 (2H, m), 1.32-1.41 (1H, m), 3.21 (1H, d), 3.39 (1H, d), 4.37 (1H, d), 4.61 (2H, d), 4.91 (1H, d), 6.02-6.06 (1H, m), 7.40 (2H, s), 7.99 (1H, d), 8.52 (1H, d). |
| C3-024 | $^1$H-NMR (CDCl$_3$) δ: 1.16 (3H, t), 2.25 (2H, q), 3.30 (1H, d), 3.51 (1H, d), 4.45 (1H, d), 4.60 (2H, d), 5.04 (1H, d), 5.88-5.90 (1H, m), 7.86 (2H, s), 7.99-8.01 (2H, m), 8.53 (1H, d). |
| C3-027 | $^1$H-NMR (CDCl$_3$) δ: 0.68-0.72 (2H, m), 0.89-0.94 (2H, m), 1.28-1.33 (1H, m), 3.26 (1H, d), 3.46 (1H, d), 4.41-4.56 (3H, m), 4.96 (1H, d), 6.05-6.07 (1H, m), 7.66-7.80 (2H, m), 7.87-7.96 (2H, m), 8.44 (1H, d). |
| i-002 | $^1$H-NMR (CDCl$_3$)δ: 2.42-2.52 (1H, m), 2.79-2.88 (1H, m), 3.47-3.54 (2H, m), 3.74 (1H, d), 4.01 (1H, d), 6.51 (1H, dd), 6.73 (1H, s), 6.87 (1H, d), 7.11 (1H, dd), 7.42 (2H, s). |
| i-008 | $^1$H-NMR (CDCl$_3$)δ: 2.54-2.59 (1H, m), 2.87-2.96 (1H, m), 3.54-3.70 (2H, m), 3.82 (1H, d), 4.15 (1H, d), 6.59 (1H, dd), 6.76 (1H, d), 7.41 (2H, s), 7.85 (1H, d), 10.13 (1H, s). |
| iii-002 | $^1$H-NMR (CDCl$_3$) δ: 2.40-2.54 (4H, m), 2.79-2.87 (1H, m), 3.55-3.63 (2H, m), 3.96 (1H, d), 4.36 (1H, d), 6.18 (1H, d), 6.49 (1H, d), 7.36 (1H, t), 7.49 (2H, s). |
| iii-009 | $^1$H-NMR (CDCl$_3$)δ: 2.55-2.65 (1H, m), 2.96-3.05 (1H, m), 3.58-3.97 (2H, m), 3.98 (1H, d), 4.53 (1H, d), 6.30-7.91 (6H, m). |

Measurement of log P values was performed according EEC directive 79/831 Annex V.A8 by HPLC (High Performance Liquid Chromatography) on reversed phase columns at pH 2,7 with 0.1% formic acid in water and with acetonitrile (contains 0.1% formic acid) as eluent with a linear gradient from 10% acetonitrile to 95% acetonitrile. Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

The compounds according to the invention can be formulated in a known manner, as for example given in the below preparation methods without restricting the present invention to the examples.

Preparation Example 1

Granules

To a mixture containing 10 parts of the compound of the present invention (No. A1-23), 30 parts of bentonite (montmorillonite), 58 parts of talc and 2 parts of lignin sulfonate is added 25 parts of water, and the mixture was well kneaded and granulated with 10 to 40 meshes by an extruding granulator and dried at 40 to 50° C. to obtain granules.

Preparation Example 2

Granules 95 parts of clay mineral granules having particle diameter distribution within the range of 0.2 to 2 mm are put into a rotary mixer, and then wetted evenly by spraying of 5 parts of the compound of the present invention (No. A1-23) together with a liquid diluent under rotating condition and dried at 40 to 50° C. to obtain granules.

Preparation Example 3

Emulsion 30 parts of the compound of the present invention (No. A1-23), 55 parts of xylene, 8 parts of polyoxyethylene alkyl phenyl ether and 7 parts of calcium alkylbenzenesulfonate are mixed together to obtain the emulsion.

Preparation Example 4

Wettable Agent 15 parts of the compound of the present invention (No. A1-23), 80 parts of a mixture of white carbon (hydrated amorphous silicon oxide fine powder) and powdered clay (1:5), formalin condensate of 2 parts of sodium alkylbenzenesulfonate and 3 parts of sodium alkylnaphthalenesulfonate is mixed together and the mixture is crushed to obtain a wettable agent.

Preparation Example 5

Wettable Granules 20 parts of the active compound (No. A1-23) of the present invention, 30 parts of lignin sodium sulfonate, 15 parts of bentonite and 35 parts of calcined diatomaceous earth powder are well mixed, and after addition of water, the mixture is then extruded with a screen of 0.3 mm and dried to obtain wettable granules.

As mentioned herein, the compounds according to the invention can be used as actives (active ingredients) for combating/controlling unwanted pests (such as e.g. unwanted insects, acari, helminthes and nematodes). The invention is in particular focussed on combating/controlling pests which occur in the agriculture, and in the non-agricultural field such as horticulture, greens and ornamentals and in the veterinary field, which is demonstrated through the following examples without restricting the invention to the examples.

BIOLOGICAL EXAMPLES

Unless not mentioned otherwise, the test solutions were prepared as follows:
Solvent: 3 parts by weight Dimethylformamide
Emulsifier: 1 part by weight Polyoxyethylene alkyl phenyl ether In order to make an appropriate formulation of an active compound, 1 part by weight of the active compound is mixed with the above mentioned amount of solvent and emulsifier and the mixture is diluted with water to a prescribed concentration. Ammonium salt or ammonium salt and penetration enhancer in a dosage of 1000 ppm are added to the desired concentration if necessary.

Biological Test Example 1

Tobacco Cutworm (*Spodoptera litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C. After 2 days and 4 days more sweet potato leaves were added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each treatment were averaged.

In the biological test example 1, the compound Nos. A1-27, A2-13, A3-13, A3-16, A3-27, B1-27, B3-16, C1-27, C1-46, C2-27-b, C3-16, C3-27 and A3-162 showed an insecticidal activity of 100% at an active compound concentration of 20 ppm.

In this test the following compounds showed an insecticidal activity of 100% at an active compound concentration of 4 ppm: A4-5, A4-7, A4-11, A4-2, A5-16, A5-18, A5-22, A4-12, A1-384, A1-195, A1-140, A1-99, A1-112, A1-110, A5-13, A1-369, A3-101, A3-104, A1-242, A3-170, A3-192, A4-104, A4-101, A4-111, A4-115, A4-112, A1-282, A1-271, A3-210, A5-82, A5-79, A5-78, A1-352, A1-349, A1-348, A3-93, A'3-16

In this test the following compounds showed an insecticidal activity of 80% at an active compound concentration of 4 ppm: A1-101, A3-167, A3-189.

Biological Test Example 2

Two-Spotted Spider Mite (*Tetranychus urticae*)

50 to 100 adult mites of *Tetranychus urticae* were inoculated to leaves of kidney bean at two-leaf stage planted in a pot of 6 cm in diameter. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed.

In this test the following compounds showed an acaricidal activity of 100% at an active compound concentration of 100 ppm: A1-68, A1-369 and A1-368

In this test the following compounds showed an acaricidal activity of 98% at an active compound concentration of 100 ppm: A5-13, A1-575, A3-378

In the biological test example 2, the compound Nos. A1-2, A1-5, A1-7, A1-8, A1-12, A1-13, A1-23, A1-24, A1-27, A1-30, A1-31, A1-32, A1-33, A1-35, A1-36, A1-38, A1-39, A1-40, A1-41, A1-42, A1-43, A1-44, A1-45, A1-46, A1-49, A1-51, A1-55, A1-132, A1-151, A1-154, A1-161, A1-162, A1-165, A1-176, A1-184, A1-187, A1-190, A1-205, A1-206, A1-209, A1-250, A1-253, A1-261, A1-264, A1-272, A1-275, A1-283, A1-286, A1-294, A1-297, A1-303, A1-305, A1-308, A1-316, A1-319, A1-338, A1-341, A1-347, A1-361, A2-12, A2-13, A2-16, A3-1, A3-5, A3-6, A3-7, A3-11, A3-12, A3-13, A3-14, A3-15, A3-16, A3-17, A3-18, A3-19, A3-22, A3-23, A3-24, A3-27, A3-28, A3-29, A3-33, A3-79, A3-82, A3-84, A3-112, A3-115, A3-117, A3-123, A3-127, A3-128, A3-137, A3-159, A3-161, A3-163, A3-200, A3-203, A3-211, A3-214, A3-222, A3-225, A3-226, A3-227, A3-231, A3-247, A3-265, A3-266, A3-269, A3-270, A3-271, A3-275, A3-288, A3-297, A4-13, A4-16, A4-18, A4-20, A4-21, A4-22, A4-24, A4-27, A4-29, A4-30, A4-31, A4-32, A4-33, A5-24, A5-27, A5-29, C1-46, C2-27-b, A5-16, A5-18, A5-22, A1-239, A3-170, A1-352, A1-349, A1-348 and A3-93, A1-60, A1-261, A1-264, A1-429, A1-430, A1-454, A3-163, A3-265, A3-326, A3-344, A3-345, A3-421, A4-13, A4-435, A5-13, A5-24, A5-27, A5-29 showed an acaricidal activity of 100% at an active compound concentration of 20 ppm.

In this test the following compounds showed an insecticidal activity of 98% at an active compound concentration of 20 ppm: A3-164, A3-322, A5-33

In this test the following compounds showed an acaricidal activity of 90% at an active compound concentration of 20 ppm: A1-85, A3-162, A3-167

In this test the following compounds showed an acaricidal activity of 100% at an active compound concentration of 4 ppm: A4-5, A4-7, A4-11, A4-12, A1-195, A1-101, A1-112, A1-110, A3-101, A3-104, A1-242, A4-104, A4-101, A4-111, A4-115, A4-112, A1-282, A1-271, A3-210, A5-82, A5-79 and A5-78, A1-16, A1-18, A1-56, A1-57, A1-176, A1-217, A1-220, A1-250, A1-253, A1-316, A1-319, A1-405, A1-406, A1-409, A1-433, A1-525, A3-6, A3-11, A3-14, A3-15, A3-17, A3-18, A3-19, A3-127, A3-211, A3-214, A3-226, A3-231, A3-236, A3-247, A3-270, A3-271, A3-275, A3-288, A3-297, A3-348, A4-216, A4-219, A4-221.

In this test the following compounds showed an acaricidal activity of 98% at an active compound concentration of 4 ppm: A1-384, A1-528, A1-140 and A4-49.

In this test the following compounds showed an acaricidal activity of 90% at an active compound concentration of 4 ppm: A1-99, A1-216, A3-165, A3-244.

Biological Test Example 3

Cucurbit Leaf Beetle (*Aulacophora femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and thus the insecticidal activity was calculated. An insecticidal activity of 100% means that all larvae were killed, whereas an insecticidal activity of 0% means that no larva was killed.

In the biological test example 3, the compound Nos. A1-2, A1-5, A1-7, A1-8, A1-13, A1-23, A1-24, A1-27, A1-30, A1-31, A1-32, A1-33, A1-34, A1-35, A1-38, A1-39, A1-40, A1-42, A1-44, A1-46, A1-49, A1-51, A1-55, A1-69, A1-132, A1-151, A1-154, A1-161, A1-162, A1-165, A1-176, A1-183, A1-184, A1-187, A1-190, A1-205, A1-206, A1-209, A1-250, A1-253, A1-261, A1-264, A1-272, A1-275, A1-283, A1-286, A1-294, A1-297, A1-303, A1-305, A1-308, A1-316, A1-319, A1-338, A1-341, A1-347, A1-361, A1-373, A1-395, A1-454, A2-16, A3-1, A3-2, A3-5, A3-6, A3-7, A3-11, A3-12, A3-13, A3-14, A3-16, A3-18, A3-19, A3-22, A3-23, A3-24, A3-27, A3-28, A3-29, A3-33, A3-82, A3-84, A3-112, A3-115, A3-117, A3-123, A3-126, A3-127, A3-128, A3-137, A3-155, A3-156, A3-159, A3-161, A3-163, A3-164, A3-165, A3-178, A3-181, A3-200, A3-203, A3-211, A3-214, A3-221, A3-222, A3-225, A3-226, A3-227, A3-231, A3-233, A3-236, A3-244, A3-247, A3-265, A3-266, A3-269, A3-270, A3-271, A3-275, A3-356, A3-381, A4-16, A4-18, A4-20, A4-21, A4-22, A4-24, A4-27, A4-29, A4-30, A4-31, A4-32, A4-33, A4-49, A4-216, A5-24, A5-27, A5-29, A5-33, B1-96, C1-27, C2-27-b, A'3-24, a1-42, a1-43, a1-48, A5-13, A4-5, A4-7, A5-16, A5-18, A5-22, A1-384, A1-195, A1-96, A1-99, A1-101, A1-112, A1-110, A3-101, A3-104, A1-242, A3-170, A3-192, A3-189, A4-104, A4-101, A4-111, A4-115, A4-112, A1-282, A3-210, A5-82, A5-78, A1-352, A1-349, A1-348, A3-93 and A'3-16 showed an insecticidal activity of 100% at an active compound concentration of 20 ppm.

In this test the following compounds showed an insecticidal activity of 100% at an active compound concentration of 100 ppm: A1-72, A1-575.

In this test the following compounds showed an insecticidal activity of 100% at an active compound concentration of 4 ppm: A1-16, A1-18, A1-56, A1-57, A1-60, A1-216, A1-217, A1-220, A1-250, A1-253, A1-264, A1-316, A1-319, A1-405, A1-406, A1-409, A1-429, A1-430, A1-433, A1-457, A1-481, A1-493, A1-528, A3-11, A3-14, A3-18, A3-19, A3-127, A3-148, A3-155, A3-163, A3-164, A3-165, A3-6, A3-211, A3-214, A3-226, A3-231, A3-233, A3-236, A3-244, A3-247, A3-265, A3-270, A3-271, A3-275, A3-323, A3-326, A3-344, A3-345, A3-348, A3-370, A3-377, A3-378, A3-381, A3-424, A4-219, A4-221, A4-252, A5-24, A5-27, A5-29, A5-33.

Biological Test Example 4

Larvae of Spodoptera litura

[A Method Using Artificial Feeds (Trade Name: Insecta LFM, Manufactured by Nosan Corporation)]

Powdery artificial feeds (2.3 g) were added to a plastic cup (diameter: 7.5 cm, height: 4 cm) to achieve a certain thickness. Water-diluted liquid (5 ml) of the active compound prepared above having predetermined concentration was evenly poured thereto and allowed to stand until the feeds were solidified. Five of the 3rd-instar larvae of Spodoptera litura were released in respective cups, and covered. The cups were put in a temperature controlled room at 25° C. and humidity of 50 to 60%, and the number of dead larvae after 7 days was determined to calculate the pesticidal ratio. 100% pesticidal ratio means death of all the larvae, while 0% pesticidal ratio means no dead larvae.

In this test the following compounds showed an insecticidal activity of 80% at an active compound concentration of 100 ppm: A1-575, A4-203.

In this test the following compounds showed an insecticidal activity of 100% at an active compound concentration of 100 ppm: A1-72, A4-201, A4-202.

In the biological test example 3, the compounds Nos. A1-5, A1-7, A1-12, A1-13, A1-23, A1-24, A1-27, A1-30, A1-31, A1-32, A1-33, A1-34, A1-35, A1-36, A1-38, A1-40, A1-41, A1-42, A1-43, A1-44, A1-45, A1-46, A1-49, A1-51, A1-55, A1-132, A1-151, A1-154, A1-161, A1-162, A1-165, A1-176, A1-183, A1-184, A1-187, A1-205, A1-206, A1-209, A1-250, A1-253, A1-261, A1-272, A1-275, A1-283, A1-286, A1-294, A1-297, A1-305, A1-308, A1-316, A1-319, A1-338, A1-341, A1-347, A1-361, A1-373, A1-395, A1-454, A2-12, A2-13, A2-16, A3-1, A3-2, A3-5, A3-6, A3-7, A3-11, A3-12, A3-13, A3-14, A3-15, A3-16, A3-17, A3-18, A3-19, A3-22, A3-23, A3-24, A3-27, A3-28, A3-29, A3-33, A3-79, A3-82, A3-84, A3-112, A3-115, A3-117, A3-122, A3-123, A3-126, A3-128, A3-132, A3-137, A3-155, A3-156, A3-159, A3-161, A3-163, A3-164, A3-165, A3-178, A3-181, A3-200, A3-203, A3-211, A3-214, A3-222, A3-225, A3-227, A3-233, A3-236, A3-244, A3-247, A3-265, A3-266, A3-269, A3-270, A3-271, A3-275, A3-288, A3-297, A3-381, A4-13, A4-16, A4-18, A4-20, A4-21, A4-22, A4-24, A4-27, A4-29, A4-30, A4-31, A4-32, A4-33, A4-49, A5-24, A5-27, A5-29, A5-33, B1-27, B1-96, B3-16, C1-27, C1-46, C1-74, C2-27-b, C3-2, C3-5, C3-16, C3-27, A'3-24, a1-42, a1-44 and a1-47 showed an insecticidal activity of 100% at an active compound concentration of 20 ppm.

In this test the following compounds showed an insecticidal activity of 80% at an active compound concentration of 4 ppm: A1-264, A1-453, A3-127, A3-231.

In this test the following compounds showed an insecticidal activity of 100% at an active compound concentration of 4 ppm: A1-16, A1-18, A1-56, A1-57, A1-60, A1-176, A1-216, A1-217, A1-220, A1-250, A1-253, A1-261, A1-316, A1-319, A1-405, A1-406, A1-409, A1-429, A1-430, A1-433, A1-457, A1-481, A1-493, A1-525, A1-528, A3-6, A3-11, A3-14, A3-15, A3-17, A3-18, A3-19, A3-122, A3-132, A3-148, A3-155, A3-163, A3-164, A3-165, A3-211, A3-214, A3-233, A3-236, A3-244, A3-247, A3-265, A3-270, A3-271, A3-275, A3-288, A3-297, A3-322, A3-323, A3-326, A3-344, A3-345, A3-348, A3-366, A3-367, A3-370, A3-377, A3-378, A3-421, A3-424, A4-49, A4-216, A4-219, A4-221, A4-252, A5-13, A5-24, A5-27, A5-29, A5-33.

Biological Test Example 5

Myzus persicae-Spray Test (MYZUPE)

1 day before treatment, green peach aphids (Myzus persicae) are inoculated onto the testing plants, about 50 heads per leaf, 100 for 1 pot. A paper label is placed on each pot. Solutions are sprayed directly onto both insects and plants. After drying, the pots are placed in the greenhouse at 20° C.-25° C. After 6 days mortality in % is determined. An insecticidal activity of 100% means that all aphids were killed, whereas an insecticidal activity of 0% means that no aphid was killed.

In this test the following compounds showed an insecticidal activity of 90% at an active compound concentration of 100 ppm: A4-13.

In this test the following compounds showed an insecticidal activity of 98% at an active compound concentration of 100 ppm: A3-381.

In this test the following compounds showed an insecticidal activity of 100% at an active compound concentration of 100 ppm: A1-16, A1-18.

In this test the following compounds showed an insecticidal activity of 100% at an active compound concentration of 20 ppm: A3-104, A3-214, A3-247, A4-101 and A4-115.

In this test the following compounds showed an insecticidal activity of 98% at an active compound concentration of 20 ppm: A3-211, A3-236, A3-244, A4-112, A4-216, A5-82, A4-5, A4-7, A1-384, and A4-104.

In this test the following compounds showed an insecticidal activity of 90% at an active compound concentration of 20 ppm: A1-264, A3-14, A3-18, A3-326, A3-348, A3-378, A4-111, A3-424, A4-49, A4-221.

Biological Test Example 6

*Thrips Palmi*—Spraytest (THRIPL)

The compound solutions are sprayed to a cucumber seedling (*Cucumis sativus*). After drying, the treated plant is placed in a plastic stand. About 100 *thrips*-eggs (*Thrips palmi*) on a piece of filter paper are attached to the plant and covered with a cage to keep 100% humidity. The plant is kept in a room at 23° C. After 6 days activity in % is evaluated by feeding damage degree. An insecticidal activity of 100 means that there was no feeding damage, whereas an insecticidal activity of 0% means that there is no difference to the untreated control.

In this test the following compounds showed an insecticidal activity of 100% at an active compound concentration of 100 ppm: A5-13, A5-16, A5-18.

In this test the following compounds showed an insecticidal activity of 98% at an active compound concentration of 100 ppm: A1-16, A5-22, A3-381, A4-13.

In this test the following compounds showed an insecticidal activity of 90% at an active compound concentration of 100 ppm: A1-18, A3-148, A3-378, A5-13.

In this test the following compounds showed an insecticidal activity of 100% at an active compound concentration of 20 ppm: A1-57.

In this test the following compounds showed an insecticidal activity of 98% at an active compound concentration of 20 ppm: A1-112, A1-110, A3-101, A3-104, A4-13, A4-104, A4-101, A4-115, A4-112, A1-56, A1-60, A1-409, A3-11, A3-18, A3-236, A3-271, A3-275, A3-366, A4-49.

In this test the following compounds showed an insecticidal activity of 90% at an active compound concentration of 20 ppm: A4-5, A4-7, A4-11, A4-12, A1-384, A1-96, A1-242, A5-82, A5-79, A1-176, A1-216, A1-217, A1-220, A1-250, A1-253, A1-316, A1-319, A1-433, A3-6, A3-15, A3-17, A3-231, A3-233, A3-265, A3-270, A3-348, A3-367, A4-219, A4-221, A5-24, A5-27, A5-29, A5-33.

In this test the following compounds showed an insecticidal activity of 90% at an active compound concentration of 4 ppm: A3-214.

Biological Test Example 7

*Amblyomma Hebraeum*—Test (AMBYHE)

Solvent: Dimethyl sulfoxide

To produce a suitable preparation of active compound, 10 mg of active compound are dissolved in 0.5 ml solvent, and the concentrate is diluted with water to the desired concentration. Nymphs of the tick *Amblyomma hebraeum* are placed in perforated plastic beakers and immersed in aqueous compound solution for one minute. Ticks are transferred to a filter paper in a petridish and incubated in a climate chamber for 42 days. After the specified period of time, mortality in % is determined. 100% means that all the ticks have been killed; 0% means that none of the ticks have been killed.

In this test, for example, the following compounds from the preparation examples showed good activity of 100% at an application rate of 100 ppm: A4-104, A4-115, A5-82, A3-236, A3-244, A3-247 and A3-271.

Biological Test Example 8

*Boophilus microplus* (Injection)

Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 µl compound solution into the abdomen. Ticks are transferred into replica plates and incubated in a climate chamber for a period of time. Egg deposition of fertile eggs is monitored. After 7 days mortality in % is determined. 100% means that all eggs are infertile; 0% means that all eggs are fertile.

In this test for example, the following compounds from the preparation examples showed good activity of 100% at application rate of 20 µg/animal: A1-23, A1-24, A1-27, A1-31, A1-33, A1-34, A1-35, A1-40, A2-13, A3-12, A3-13, A3-16, A3-24, A3-27, A3-112, A3-115, A3-117, A3-137, B1-27, B3-16, C1-27, C1-46, C2-27-b, C3-16, C3-27, A4-7, A5-16, A5-18, A1-384, A1-112, A1-110, A1-242, A3-170, A4-104, A4-115, A4-112, A3-210, A5-82, A1-16, A1-18, A1-56, A1-57, A1-60, A1-176, A1-216, A1-217, A1-220, A1-250, A1-253, A1-264, A1-316, A1-319, A1-405, A1-406, A1-409, A1-430, A1-433, A3-14, A3-18, A3-148, A3-163, A3-164, A3-165, A3-211, A3-214, A3-236, A3-244, A3-247, A3-265, A3-271, A3-326, A3-344, A3-348, A3-381, A4-13, A4-216, A4-221, A5-13, A5-24, A5-27, A5-29.

Biological Test Example 9

Test Against *Boophilus microplus* (Dip)

Solvent: dimethyl sulfoxide

To produce a suitable preparation of active compound, 10 mg of active compound are dissolved in 0.5 ml solvent, and the concentrate is diluted with water to the desired concentration. Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined. 100% means that all the ticks have been killed; 0% means that none of the ticks have been killed.

In this test for example, the following compounds from the preparation examples showed good activity of 100% at an application rate of 100 ppm: A1-16, A1-18, A4-7, A5-16, A5-18, A1-384, A1-101, A1-112, A1-220, A1-242, A1-253, A1-264, A1-316, A1-405, A1-406, A3-14, A3-18, A3-148, A3-163, A3-164, A3-170, A3-211, A3-214, A3-236, A3-244, A3-247, A3-265, A3-271, A3-326, A3-344, A3-348, A4-13, A4-104, A4-101, A4-111, A4-115, A4-112, A4-216, A4-221, A3-210, A5-13, A5-27, A5-82 and A5-78.

In this test for example, the following compounds from the preparation examples showed good activity of 95% at an application rate of 100 ppm: A1-282.

In this test for example, the following compounds from the preparation examples showed good activity of 90% at an application rate of 100 ppm: A1-110, A1-57, A1-409, A3-165.

In this test for example, the following compounds from the preparation examples showed good activity of 95% at an application rate of 20 ppm: A 1-32.

In this test for example, the following compound from the preparation examples showed good activity of 100% at application rate of 20 ppm: A1-23, A1-24, A1-31, A1-33, A1-35, A2-13, A3-13, A3-16, A3-27, A3-112, A3-115 and A3-117.

In this test, for example, the following compounds from the preparation examples showed good activity of 80% at an application rate of 100 ppm: A3-381.

Biological Test 10

Test Against *Ctenocephalides felis* (CTECFE)

Solvent: dimethyl sulfoxide

To produce a suitable preparation of active compound, 10 mg of active compound are dissolved in 0.5 ml solvent, and the concentrate is diluted with cattle blood to the desired concentration. Approximately 20 adult unfed (*Ctenocepahlides felis*) are placed in flea chambers. The blood chamber, sealed with parafilm on the bottom, are filled with cattle blood supplied with compound solution and placed on top of the flea chamber, so that the fleas are able to suck the blood. The blood chamber is heated to 37° C. whereas the flea chamber is kept at room temperature.

After 2 days mortality in % is determined. 100% means that all the fleas have been killed; 0% means that none of the fleas have been killed.

In this test for example, the following compounds from the preparation examples showed good activity of 100% at application rate of 100 ppm: A1-18, A1-23, A1-24, A1-27, A1-31, A1-33, A1-34, A1-35, A1-40, A1-56, A1-57, A1-60, A1-216, A1-217, A1-220, A1-250, A1-253, A1-264, A1-316, A1-319, A1-405, A1-406, A1-409, A1-430, A1-433 A2-13, A3-12, A3-13, A3-16, A3-18, A3-24, A3-27, A3-112, A3-115, A3-117, A3-137, A3-148, A3-163, A3-164, A3-165, A3-211, A3-214, A3-236, A3-244, A3-265, A3-271, A3-326, A3-344, A3-348, A3-381, A4-13, A4-216, A4-221, A5-13, A5-24, A5-27, A5-29, C1-27, C 1-46, C 2-27-b, A4-7, A5-16, A1-384, A1-112, A1-110, A1-242, A3-170, A4-104, A4-112 and A3-210.

In this test for example, the following compounds from the preparation examples showed good activity of 95% at an application rate of 100 ppm: A3-14, A3-247, A5-82.

In this test for example, the following compounds from the preparation examples showed good activity of 90% at an application rate of 100 ppm: A1-16, A5-18, A4-115.

Biological Test Example 11

Test Against *Lucilia Cuprina*

Solvent: dimethyl sulfoxide 10 mg active compound are dissolve in 0.5 mL dimethyl sulfoxide. Serial dilutions are made to obtain the desired rates.

Approximately 20 *Lucilia cuprina* $1^{st}$ instar larvae are transferred into a test tube containing 1 cm³ of minced horse meat and 0.5 ml aqueous dilution of test compound. After 48 hrs percentage of larval mortality are recorded. 100% efficacy=all larvae are killed, % efficacy=normally developed larvae after 48 hrs.

In this test for example, the following compounds from the preparation examples showed good activity of 100% at application rate of 100 ppm: A1-16, A1-18, A 1-23, A 1-24, A 1-27, A 1-31, A 1-33, A 1-34, A 1-35, A 1-40, A1-56, A1-57, A1-60, A1-176, A1-216, A1-217, A1-220, A1-250, A1-253, A1-264, A1-316, A1-319, A1-405, A1-406, A1-409, A1-430, A1-433, A 2-13, A 3-12, A 3-13, A 3-14, A 3-16, A 3-18, A 3-24, A 3-27, A 3-112, A 3-115, A 3-117, A 3-137, A3-148, A3-163, A3-164, A3-165, A3-211, A3-214, A3-236, A3-244, A3-247, A3-265, A3-271, A3-326, A3-344, A3-348, A3-381, A4-13, A4-216, A4-221, A5-13, A5-24, A5-27, A5-29, B 3-16, C 1-27, C 1-46, C 2-27-b, C 3-16, C 3-27, A4-7, A5-16, A5-18, A1-384, A1-112, A1-110, A1-242, A3-170, A4-104, A4-115, A4-112, A3-210 and A5-82.

Biological Test Example 12

Test Against *Musca domestica*

Solvent: dimethyl sulfoxide

To produce a suitable preparation of active compound, 10 mg of active compound are dissolved in 0.5 ml solvent, and the concentrate is diluted with water to the desired concentration. Prior to the assay, a piece of kitchen sponge is soaked with a mixture of sugar and compound solution and placed into a container. 10 adults (*Musca domestica*) are placed into the container and closed with a perforated lid. After 2 days mortality in % is determined. 100% means that all the flies have been killed; 0% means that none of the flies have been killed.

In this test, for example, the following compounds from the preparation examples showed activity of 80% at an application rate of 100 ppm: A1-16, A1-176.

In this test, for example, the following compounds from the preparation examples showed good activity of 80% at an application rate of 100 ppm: A1-16, A1-176.

In this test for example, the following compounds from the preparation examples showed good activity of 90% at an application rate of 100 ppm: A1-253, A 3-112, C 3-27, A3-170.

In this test for example, the following compounds from the preparation examples showed good activity of 100% at an application rate of 100 ppm: A1-16, A 1-23, A 1-24, A 1-27, A 1-31, A 1-33, A 1-34, A 1-40, A1-56, A1-57, A1-60, A1-216, A1-217, A1-220, A1-264, A1-316, A1-319, A1-405, A1-406, A1-409, A1-430, A1-433, A 3-12, A 3-13, A3-14, A3-16, A3-18, A 3-24, A 3-27, A 3-115, A 3-117, A 3-137, A3-148, A3-163, A3-164, A3-165, A3-211, A3-214, A3-236, A3-244, A3-247, A3-265, A3-271, A3-326, A3-344, A3-348, A3-381, A4-216, A4-221, A5-13, A5-24, A5-27, A5-29 C 2-27-b, A4-7, A5-16, A5-18, A4-104, A4-115, A4-112, A3-210, A5-82.

Biological Test Example 13

*Phaedon Cochleariae*—Test (PHAECO Spray Application)

| Solvent: | 78.0 parts by weight of acetone |
| --- | --- |
|  | 1.5 parts by weight of dimethylformamide |
| Emulsifier: | 0.5 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks are sprayed with a preparation of the active ingredient of the desired concentration. Once dry, the leaf disks are infested with mustard beetle larvae (*Phaedon cochleariae*). After 7 days mortality in % is determined. 100% means that all beetle larvae have been killed and 0% means that none of the beetle larvae have been killed.

In this test, for example, the following compounds from the preparation examples showed activity of 100% at an application rate of 500 g/ha: A1-77, A1-79, A3-356, A3-359.

Biological Test Example 14

Spodoptera frugiperda—Test (SPODFR Spray Application)

| Solvent: | 78.0 parts by weight acetone |
| --- | --- |
| | 1.5 parts by weight dimethylformamide |
| Emulsifier: | 0.5 parts by weight alkylarylpolyglycolether |

To produce a suitable preparation of the active compound, 1 part by weight of active compound is mixed with the stated amount of solvent and emulsifier, and the concentrate is diluted with emulsifier-containing water to the desired concentration. Maize (Zea mais) leaf sections are sprayed with a preparation of the active ingredient of the desired concentration. Once dry, the leaf sections are infested with fall armyworm larvae (Spodoptera frugiperda). After 7 days mortality in % is determined. 100% means that all caterpillars have been killed and 0% means that none of the caterpillars have been killed.

In this test, for example, the following compounds from the preparation examples showed activity of 83% at an application rate of 500 g/ha: A1-79.

In this test, for example, the following compounds from the preparation examples showed activity of 100% at an application rate of 500 g/ha: A1-77, A3-356, A3-359.

Biological Test Example 15

Tetranychus urticae—Test OP-Resistant (TETRUR Spray Application)

| Solvent: | 78.0 parts by weight acetone |
| --- | --- |
| | 1.5 parts by weight dimethylformamide |
| Emulsifier: | 0.5 parts by weight alkylarylpolyglycolether |

To produce a suitable preparation of active compound, 1 part by weight of active compound is mixed with the stated amount of solvent and emulsifier, and the concentrate is diluted with emulsifier-containing water to the desired concentration. French beans (Phaseolus vulgaris) which are heavily infested with all stages of the two spotted spidermite (Tetranychus urticae), are sprayed with a preparation of the active ingredient at the desired concentration. After 6 days mortality in % is determined. 100% means that all spider mites have been killed and 0% means that none of the spider mites have been killed.

In this test, for example, the following compounds from the preparation examples showed activity of 90% at an application rate of 500 g/ha: A1-79.

In this test, for example, the following compounds from the preparation examples showed activity of 100% at an application rate of 500 g/ha: A3-356, A3-359.

The invention claimed is:

1. An arylpyrrolidine compound of Formula (I)

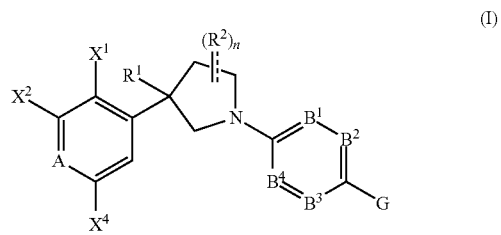

wherein $R^1$ is $CF_3$;

$R^2$ is hydroxy;

n is 1;

A is C—$X^3$;

$X^1$, $X^2$, $X^3$ and $X^4$ each independently are hydrogen, fluoro, chloro, bromo, iodo or $C_{1-4}$ haloalkyl;

$B^1$ is C—H or C—F;

$B^2$ is C—H, C—F, C—Cl, C—Br, C—I, C—$CH_3$, C—$CH_2CH_3$, C—$CF_2H$, C—$CF_3$, C—$OCF_2H$ or C—$OCF_3$;

$B^3$ is C—H;

$B^4$ is C—H or C—F;

G is a chemical moiety (ε)

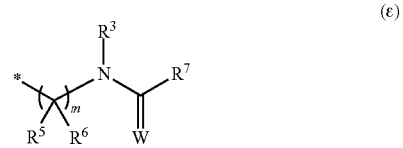

wherein $R^3$ is hydrogen, $C_{1-4}$ alkyl, $C_{1-4}$ haloalkyl, $C_{3-4}$ alkenyl, $C_{1-6}$ alkyl-carbonyl, $C_{1-6}$ alkoxy-carbonyl or $C_{1-12}$ haloalkoxy-carbonyl;

$R^5$ and $R^6$ each independently are hydrogen, cyano, $C_{1-4}$ alkyl, $C_{1-4}$ haloalkyl or cyclopropyl;

$R^7$ is $C_{1-6}$ alkyl, $C_{1-6}$ cyanoalkyl, $C_{1-6}$ haloalkyl, $C_{3-6}$ cycloalkyl that is optionally substituted with 1 to 5 fluorine, chlorine, or $C_{1-4}$ haloalkyl, $C_{3-6}$ cycloalkyl-$C_{1-4}$ alkyl that is optionally substituted with 1 to 5 fluorine or chlorine, $C_{3-6}$ halocycloalkyl-$C_{1-6}$ alkyl, $C_{2-6}$ alkenyl, $C_{2-6}$ haloalkenyl, $C_{1-4}$ alkoxy, $C_{1-4}$ haloalkoxy, $C_{1-4}$ alkoxy-$C_{1-4}$ alkyl, $C_{1-4}$ alkoxy-$C_{1-4}$ haloalkyl, $C_{1-4}$ alkyl-S—$C_{1-4}$ alkyl that is optionally substituted with fluorine or chlorine, $C_{1-4}$ alkyl-S(O)—$C_{1-4}$ alkyl that is optionally substituted with fluorine or chlorine, $C_{1-4}$ alkyl-S(O)$_2$-$C_{1-4}$ alkyl that is optionally substituted with fluorine or chlorine, phenyl, phenyl-$C_{1-6}$ alkyl, methylamino that is optionally substituted with 1 to 3 fluorine or chlorine, dimethylamino that is optionally substituted with 1 to 5 fluorine or chlorine, ethylamino that is optionally substituted with 1 to 5 fluorine or chlorine, cyclopropylamino that is optionally substituted with 1 to 4 fluorine or chlorine, or prop-2-yn-1-ylamino that is optionally substituted with 1 to 3 fluorine or chlorine;

W is oxygen or sulfur; and m is 1.

2. A method of controlling insects, arachnids, helminths, nematodes and/or molluscs, which are encountered in agriculture, in horticulture, in animal husbandry, in forests, in gardens and leisure facilities, in protection of stored products and of materials, and/or in the hygiene sector, the method comprising applying a compound according to claim 1 to said insects, arachnids, helminths, nematodes and/or molluscs or their surroundings, their habitats, or places to be protected.

3. Seeds treated with a compound according to claim 1.

4. The compound according to claim 1, wherein $X^1$, $X^2$, $X^3$ and $X^4$ each independently are hydrogen, fluoro, chloro, bromo or trifluoromethyl;

$R^3$ is hydrogen;

$R^5$ and $R^6$ each independently are hydrogen, trifluoromethyl or methyl; and $R^7$ is $C_{1-6}$ alkyl, $C_{1-6}$ cyanoalkyl, $C_{1-6}$ haloalkyl, $C_{3-6}$ cycloalkyl that is optionally substituted with 1 to 5 fluorine, chlorine, or $C_{1-4}$ haloalkyl, $C_{1-4}$ alkoxy, $C_{1-4}$ haloalkoxy, $C_{1-4}$ alkoxy-$C_{1-4}$ alkyl, $C_{1-4}$ alkoxy-$C_{1-4}$ haloalkyl, $C_{1-4}$ alkyl-S—$C_{1-4}$ alkyl that is optionally substituted with fluorine or chlorine, $C_{1-4}$ alkyl-S(O)—$C_{1-4}$ alkyl that is optionally substituted with fluorine or chlorine, $C_{1-4}$ alkyl-S(O)$_2$-$C_{1-4}$ alkyl that is optionally substituted with fluorine or chlorine, methylamino that is optionally substituted with 1 to 3 fluorine or chlorine, dimethylamino that is optionally substituted with 1 to 5 fluorine or chlorine, ethylamino that is optionally substituted with 1 to 5 fluorine or chlorine, cyclopropylamino that is optionally substituted with 1 to 4 fluorine or chlorine, or prop-2-yn-1-ylamino that is optionally substituted with 1 to 3 fluorine or chlorine.

5. The compound according to claim 1, having the structure

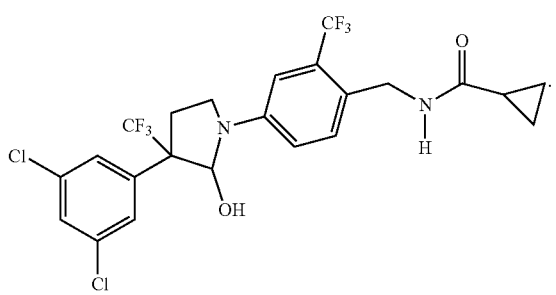 [SMILES: O=C(NCc1ccc(N2CCC(c3cc(Cl)cc(Cl)c3)(C(F)(F)F)C2O)cc1C(F)(F)F)C1CC1]

6. The compound according to claim 1, having the structure

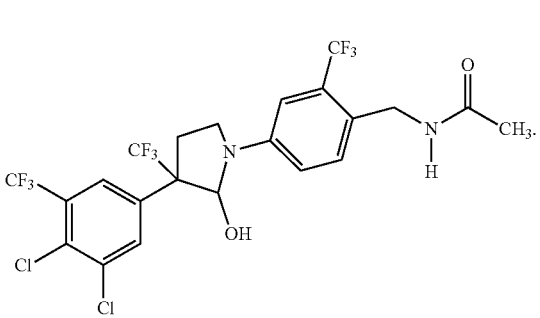 [SMILES: CC(=O)NCc1ccc(N2CCC(c3cc(Cl)c(Cl)c(C(F)(F)F)c3)(C(F)(F)F)C2O)cc1C(F)(F)F]

7. The compound according to claim 1, having the structure

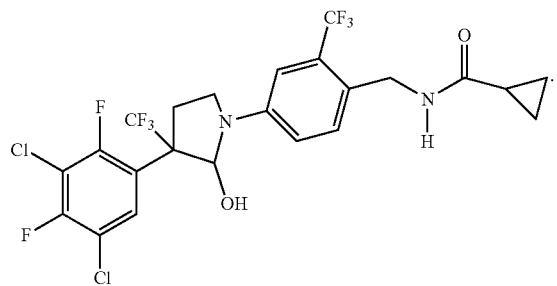 [SMILES: O=C(NCc1ccc(N2CCC(c3cc(Cl)c(F)c(Cl)c3F)(C(F)(F)F)C2O)cc1C(F)(F)F)C1CC1]

8. The compound according to claim 1, having the structure

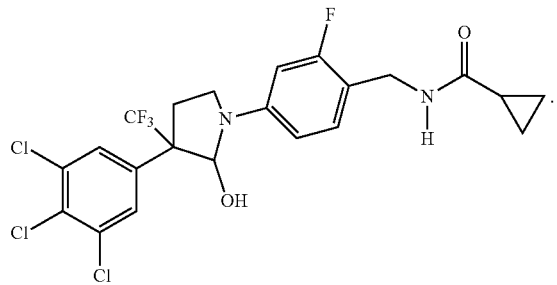 [SMILES: O=C(NCc1ccc(N2CCC(c3cc(Cl)c(Cl)c(Cl)c3)(C(F)(F)F)C2O)cc1F)C1CC1]

9. The compound according to claim 1, having the structure

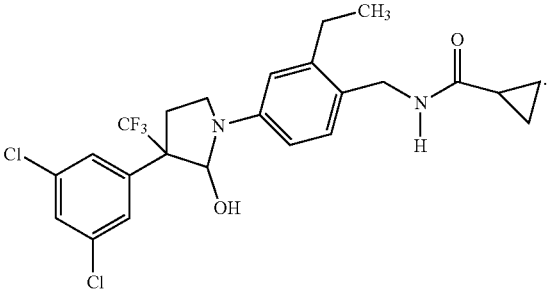 [SMILES: CCc1cc(N2CCC(c3cc(Cl)cc(Cl)c3)(C(F)(F)F)C2O)ccc1CNC(=O)C1CC1]

10. The compound according to claim 1, having the structure
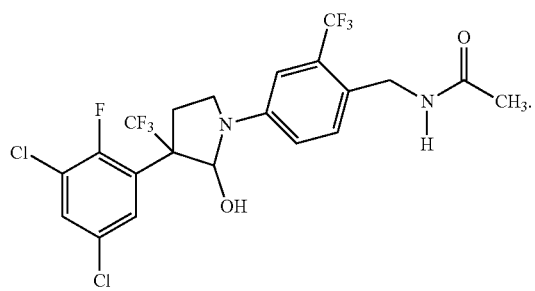 [SMILES: CC(=O)NCc1ccc(N2CCC(c3cc(Cl)cc(Cl)c3F)(C(F)(F)F)C2O)cc1C(F)(F)F]
11. The compound according to claim 1, having the structure
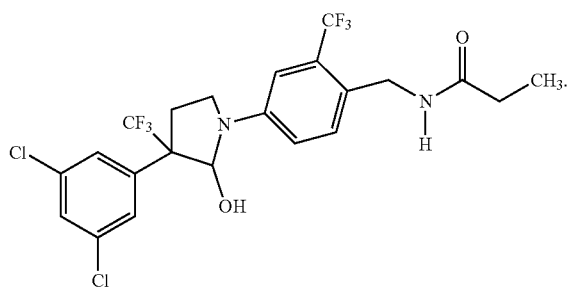 [SMILES: CCC(=O)NCc1ccc(N2CCC(c3cc(Cl)cc(Cl)c3)(C(F)(F)F)C2O)cc1C(F)(F)F]
12. The compound according to claim 1, having the structure
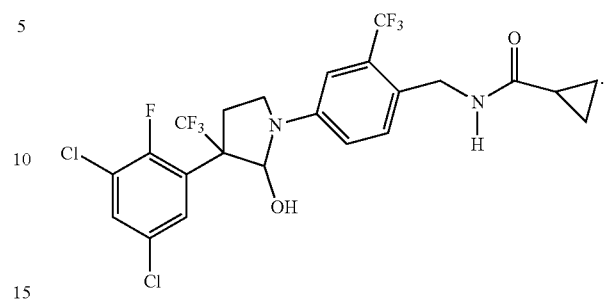
13. The compound according to claim 1, having the structure
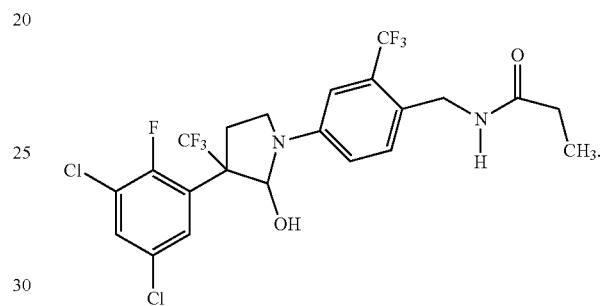
* * * * *